(12) United States Patent
Bhattacharjee et al.

(10) Patent No.: US 8,278,281 B2
(45) Date of Patent: Oct. 2, 2012

(54) TRIAZOLE COMPOUNDS AND METHODS OF MAKING AND USING THE SAME

(75) Inventors: Ashoke Bhattacharjee, Cheshire, CT (US); Zoltan F. Kanyo, North Haven, CT (US); Edward C. Sherer, Manville, NJ (US)

(73) Assignee: Rib-X Pharmaceuticals, Inc., New Haven, CT (US)

( * ) Notice: Subject to any disclaimer, the term of this patent is extended or adjusted under 35 U.S.C. 154(b) by 595 days.

(21) Appl. No.: 11/990,883

(22) PCT Filed: Aug. 24, 2006

(86) PCT No.: PCT/US2006/033645
§ 371 (c)(1),
(2), (4) Date: Sep. 17, 2009

(87) PCT Pub. No.: WO2007/025284
PCT Pub. Date: Mar. 1, 2007

(65) Prior Publication Data
US 2010/0016956 A1    Jan. 21, 2010

Related U.S. Application Data

(60) Provisional application No. 60/711,443, filed on Aug. 24, 2005, provisional application No. 60/762,907, filed on Jan. 26, 2006.

(51) Int. Cl.
*A61K 31/70* (2006.01)
*C07H 17/08* (2006.01)

(52) U.S. Cl. .............. 514/29; 536/7.2; 536/7.4
(58) Field of Classification Search .......... None
See application file for complete search history.

(56) References Cited

U.S. PATENT DOCUMENTS

| | | | |
|---|---|---|---|
| 5,792,765 A | 8/1998 | Riedl et al. | |
| 2008/0045585 A1* | 2/2008 | Farmer et al. | 514/450 |

FOREIGN PATENT DOCUMENTS

| | | |
|---|---|---|
| EP | 0643068 A1 | 3/1995 |
| WO | WO-9916779 A1 | 4/1999 |
| WO | WO-9922722 A2 | 5/1999 |
| WO | WO-9963937 A2 | 12/1999 |
| WO | WO-0006606 A2 | 2/2000 |
| WO | WO-0021960 A1 | 4/2000 |
| WO | WO-0040589 A2 | 7/2000 |
| WO | WO-0140222 A1 | 6/2001 |
| WO | WO-0142242 A1 | 6/2001 |
| WO | WO-0158885 A1 | 8/2001 |
| WO | WO-0181350 A1 | 11/2001 |
| WO | WO-02051855 | 7/2002 |
| WO | WO-03022824 A1 | 3/2003 |
| WO | WO-03035073 A1 | 5/2003 |
| WO | WO-2004013153 A2 | 2/2004 |
| WO | WO-2004029066 A2 | 4/2004 |
| WO | WO-2005042554 A1 | 5/2005 |
| WO | WO-2005049632 A1 | 6/2005 |
| WO | WO2005/085266 * | 9/2005 |
| WO | WO-2007025089 A2 | 3/2007 |

OTHER PUBLICATIONS

Wolff, Manfred E. "Burger's Medicinal Chemistry, 5ed, Part I", John Wiley & Sons, 1995, pp. 975-977.*
Banker, G.S. et al, "Modern Pharmaceutics, 3ed.", Marcel Dekker, New York, 1996, p. 596.*
Hwang et al. "1,3-Dipolar Cycloaddition of Nitrile Oxides to 1-phenylsulfonyl-1,3-butadienes: Synthesis of 3-(4,5-dihydroisoxazol-5-yl)pyrroles." *Tetrahed. Lett.* 43.1(2002):53-56.

* cited by examiner

*Primary Examiner* — Traviss C McIntosh, III
(74) *Attorney, Agent, or Firm* — Mintz Levin Cohn Ferris Glovsky and Popeo, P.C.; Ivor R. Elrifi; Jennifer L. Loebach

(57) ABSTRACT

The present invention provides triazole macrocyclic compounds useful as therapeutic agents. More particularly, these compounds are useful as anti-infective, anti-proliferative, anti-inflammatory, and prokinetic agents. The compounds have the following structure: wherein T is the macrocyclic part.

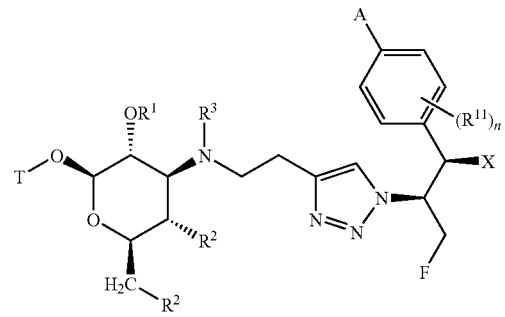

25 Claims, No Drawings

TRIAZOLE COMPOUNDS AND METHODS OF MAKING AND USING THE SAME

RELATED APPLICATIONS

This application is a national stage application, filed under 35 U.S.C. 371, of International Application No. PCT/US2006/033645, filed on Aug. 24, 2006, which claims the benefit of and priority to U.S. Patent Application Ser. No. 60/711,443, filed Aug. 24, 2005 and U.S. Patent Application Ser. No. 60/762,907, filed Jan. 26, 2006, the disclosure of each is incorporated by reference herein.

FIELD OF THE INVENTION

The present invention relates generally to the field of anti-infective, anti-proliferative, anti-inflammatory, and prokinetic agents. More particularly, the invention relates to a family of triazole macrocyclic compounds that are useful as such agents.

BACKGROUND

Since the discovery of penicillin in the 1920s and streptomycin in the 1940s, many new compounds have been discovered or specifically designed for use as antibiotic agents. It was once believed that infectious diseases could be completely controlled or eradicated with the use of such therapeutic agents. However, such beliefs have been shaken because strains of cells or microorganisms resistant to currently effective therapeutic agents continue to evolve. In fact, virtually every antibiotic agent developed for clinical use has ultimately encountered problems with the emergence of resistant bacteria. For example, resistant strains of Gram-positive bacteria such as methicillin-resistant staphylococci, penicillin-resistant streptococci, and vancomycin-resistant enterococci have developed. These resistant bacteria can cause serious and even fatal results for patients infected with such resistant bacteria. Bacteria that are resistant to macrolide antibiotics have emerged. Also, resistant strains of Gram-negative bacteria such as *H. influenzae* and *M. catarrhalis* have been identified. See, e.g., F. D. Lowry, "Antimicrobial Resistance: The Example of *Staphylococcus aureus*," *J. Clin. Invest.*, vol. 111, no. 9, pp. 1265-1273 (2003); and Gold; H. S. and Moellering, R. C., Jr., "Antimicrobial-Drug Resistance," *N. Engl. J. Med.*, vol. 335, pp. 1445-53 (1996).

The problem of resistance is not limited to the area of anti-infective agents. Resistance has also been encountered with anti-proliferative agents used in cancer chemotherapy. Therefore, the need exists for new anti-infective and anti-proliferative agents that are both effective against resistant bacteria and resistant strains of cancer cells.

Despite the problem of increasing antibiotic resistance, no new major classes of antibiotics have been developed for clinical use since the approval in the United States in 2000 of the oxazolidinone ring-containing antibiotic, linezolid, which is sold under the trade name Zyvox®. See, R. C. Moellering, Jr., "Linezolid: The First Oxazolidinone Antimicrobial," *Annals of Internal Medicine*, vol. 138, no. 2, pp. 135-142 (2003). Linezolid was approved for use as an antibacterial agent active against Gram-positive organisms. However, linezolid-resistant strains of organisms are already being reported. See, Tsiodras et al., *Lancet*, vol. 358, p. 207 (2001); Gonzales et al., *Lancet*, vol 357, p. 1179 (2001); Zurenko et al., *Proceedings Of The 39th Annual Interscience Conference On Antibacterial Agents And Chemotherapy (ICAAC)*, San Francisco, Calif., USA (Sep. 26-29, 1999).

Another class of antibiotics is the macrolides, so named for their characteristic 14- to 16-membered ring. The macrolides also often have one or more 6-membered sugar-derived rings attached to the main macrolide ring. The first macrolide antibiotic to be developed was erythromycin, which was isolated from a soil sample from the Philippines in 1952. Even though erythromycin has been one of the most widely prescribed antibiotics, its disadvantages are relatively low bioavailability, gastrointestinal side effects, and a limited spectrum of activity. Another macrolide is the compound, azithromycin, which is an azolide derivative of erythromycin incorporating a methyl-substituted nitrogen in the macrolide ring. Azithromycin is sold under the trade name Zithromax®. A more recently introduced macrolide is telithromycin, which is sold under the trade name Ketek®. Telithromycin is a semisynthetic macrolide in which a hydroxyl group of the macrolide ring has been oxidized to a ketone group. See Yong-Ji Wu, Highlights of Semi-synthetic Developments from Erythromycin A, *Current Pharm. Design*, vol. 6, pp. 181-223 (2000), and Yong-Ji Wu and Wei-uo Su, Recent Developments on Ketolides and Macrolides, *Curr. Med. Chem.*, vol. 8, no. 14, pp. 1727-1758 (2001).

In the search for new therapeutic agents, researchers have tried combining or linking various portions of antibiotic molecules to create multifunctional or hybrid compounds Other researches have tried making macrolide derivatives by adding further substituents to the large macrolide ring or associated sugar rings. However, this approach for making macrolide derivatives has also met with limited success.

Notwithstanding the foregoing, there is an ongoing need for new anti-infective and anti-proliferative agents. Furthermore, because many anti-infective and anti-proliferative agents have utility as anti-inflammatory agents and prokinetic agents, there is also an ongoing need for new compounds useful as anti-inflammatory and prokinetic agents. The present invention provides compounds that meet these needs.

SUMMARY OF THE INVENTION

The invention provides compounds useful as anti-infective agents and/or anti-proliferative agents, for example, anti-biotic agents, anti-microbial agents, anti-bacterial agents, anti-fungal agents, anti-parasitic agents, anti-viral agents, and chemotherapeutic agents. The present invention also provides compounds useful as anti-inflammatory agents, and/or pro-kinetic (gastrointestinal modulatory) agents. The present invention also provides pharmaceutically acceptable salts, esters, N-oxides, or prodrugs thereof.

The present invention provides compounds having the structure:

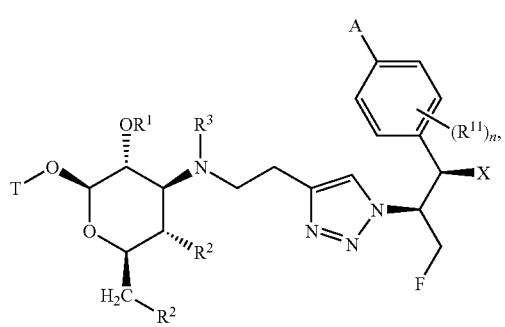

or a stereoisomer, pharmaceutically acceptable salt, ester, N-oxide, or prodrug thereof. In the formula, variables A, T, X, $R^1$, $R^2$, $R^3$, $R^{11}$, and n can be selected from the respective groups of chemical moieties later defined in the detailed description. In addition, the invention provides methods of synthesizing the foregoing compounds. Following synthesis, a therapeutically effective amount of one or more of the compounds can be formulated with a pharmaceutically acceptable carrier for administration to a mammal, particularly humans, for use as an anti-cancer, anti-biotic, anti-microbial, anti-bacterial, anti-fungal, anti-parasitic or anti-viral agent, or to treat a proliferative disease, an inflammatory disease or a gastrointestinal motility disorder, or to suppress disease states or conditions caused or mediated by nonsense or missense mutations. Accordingly, the compounds or the formulations can be administered, for example, via oral, parenteral, or topical routes, to provide an effective amount of the compound to the mammal.

The foregoing and other aspects and embodiments of the invention can be more fully understood by reference to the following detailed description and claims.

DETAILED DESCRIPTION OF THE INVENTION

The present invention provides a family of compounds that can be used as anti-proliferative agents and/or anti-infective agents. The compounds can be used without limitation, for example, as anti-cancer, anti-microbial, anti-bacterial, anti-fungal, anti-parasitic and/or anti-viral agents. Further, the present invention provides a family of compounds that can be used without limitation as anti-inflammatory agents, for example, for use in treating chronic inflammatory airway diseases, and/or as prokinetic agents, for example, for use in treating gastrointestinal motility disorders such as gastroesophageal reflux disease, gastroparesis (diabetic and post surgical), irritable bowel syndrome, and constipation. Further, the compounds can be used to treat or prevent a disease state in a mammal caused or mediated by a nonsense or missense mutation.

The compounds described herein can have asymmetric centers. Compounds of the present invention containing an asymmetrically substituted atom can be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and can be isolated as a mixture of isomers or as separate isomeric forms. All chiral, diastereomeric, racemic, and geometric isomeric forms of a structure are intended, unless specific stereochemistry or isomeric form is specifically indicated. All processes used to prepare compounds of the present invention and intermediates made therein are considered to be part of the present invention. All tautomers of shown or described compounds are also considered to be part of the present invention.

1. DEFINITIONS

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Ring double bonds, as used herein, are double bonds that are formed between two adjacent ring atoms (e.g., C=C, C=N, or N=N).

The present invention is intended to include all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

When any variable (e.g., $R^3$) occurs more than one time in any constituent or formula for a compound, its definition at each occurrence is independent of its definition at every other occurrence. Thus, for example, if a group is shown to be substituted with one or more $R^3$ moieties, then the group can optionally be substituted with one, two, three, four, five, or more $R^3$ moieties, and $R^3$ at each occurrence is selected independently from the definition of $R^3$. Also, combinations of substituents and/or variables are permissible, but only if such combinations result in stable compounds.

A chemical structure showing a dotted line representation for a chemical bond indicates that the bond is optionally present. For example, a dotted line drawn next to a solid single bond indicates that the bond can be either a single bond or a double bond.

When a bond to a substituent is shown to cross a bond connecting two atoms in a ring, then such substituent can be bonded to any atom on the ring. When a substituent is listed without indicating the atom via which such substituent is bonded to the rest of the compound of a given formula, then such substituent can be bonded via any atom in such substituent. Combinations of substituents and/or variables are permissible, but only if such combinations result in stable compounds.

In cases wherein there are nitrogens in the compounds of the present invention, these can be converted to N-oxides by treatment with an oxidizing agent (e.g., MCPBA and/or hydrogen peroxides) to afford other compounds of the present invention. Thus, all shown and claimed nitrogens are considered to cover both the shown nitrogen and its N-oxide (N→O) derivative.

As used herein, the term "anomeric carbon" means the acetal carbon of a glycoside.

As used herein, the term "glycoside" is a cyclic acetal.

As used herein, "alkyl" is intended to include both branched and straight-chain saturated aliphatic hydrocarbon groups having the specified number of carbon atoms. $C_{1-6}$ alkyl is intended to include $C_1$, $C_2$, $C_3$, $C_4$, $C_5$, and $C_6$ alkyl groups. $C_{1-8}$ alkyl is intended to include $C_1$, $C_2$, $C_3$, $C_4$, $C_5$, $C_6$, $C_7$, and $C_8$ alkyl groups. Examples of alkyl include, but are not limited to, methyl, ethyl, n-propyl, i-propyl, n-butyl, s-butyl, t-butyl, n-pentyl, s-pentyl, n-hexyl, n-heptyl, and n-octyl.

As used herein, "alkenyl" is intended to include hydrocarbon chains of either straight or branched configuration and one or more unsaturated carbon-carbon bonds that can occur in any stable point along the chain, such as ethenyl and propenyl. $C_{2-6}$ alkenyl is intended to include $C_2$, $C_3$, $C_4$, $C_5$, and $C_6$ alkenyl groups. $C_{2-8}$ alkenyl is intended to include $C_2$, $C_3$, $C_4$, $C_5$, $C_6$, $C_7$, and $C_8$ alkenyl groups.

As used herein, "alkynyl" is intended to include hydrocarbon chains of either straight or branched configuration and one or more triple carbon-carbon bonds that can occur in any stable point along the chain, such as ethynyl and propynyl. $C_{2-6}$ alkynyl is intended to include $C_2$, $C_3$, $C_4$, $C_5$, and $C_6$ alkynyl groups. $C_{2-8}$ alkynyl is intended to include $C_2$, $C_3$, $C_4$, $C_5$, $C_6$, $C_7$, and $C_8$ alkynyl groups.

Furthermore, "alkyl", "alkenyl", and "alkynyl" are intended to include moieties which are diradicals, i.e., having two points of attachment, an example of which in the present invention is when D is selected from these chemical groups. A nonlimiting example of such an alkyl moiety that is a diradical is —CH$_2$CH$_2$—, i.e., a C$_2$ alkyl group that is covalently bonded via each terminal carbon atom to the remainder of the molecule.

As used herein, the terms used to describe various carbon-containing moieties, including, for example, "alkyl," "alkenyl," "alkynyl," "phenyl," and any variations thereof, are intended to include univalent, bivalent, or multivalent species. For example, "C$_{1-6}$ alkyl-R$^3$" is intended to represent a univalent C$_{1-6}$ alkyl group substituted with a R$^3$ group, and "O—C$_{1-6}$ alkyl-R$^3$" is intended to represent a bivalent C$_{1-6}$ alkyl group, i.e., an "alkylene" group, substituted with an oxygen atom and a R$^3$ group.

As used herein, "cycloalkyl" is intended to include saturated ring groups, such as cyclopropyl, cyclobutyl, or cyclopentyl. C$_{3-8}$ cycloalkyl is intended to include C$_3$, C$_4$, C$_5$, C$_6$, C$_7$, and C$_8$ cycloalkyl groups.

As used herein, "halo" or "halogen" refers to fluoro, chloro, bromo, and iodo. "Counterion" is used to represent a small, negatively charged species such as chloride, bromide, hydroxide, acetate, and sulfate.

As used herein, "haloalkyl" is intended to include both branched and straight-chain saturated aliphatic hydrocarbon groups having the specified number of carbon atoms, substituted with 1 or more halogen (for example —C$_v$F$_w$ where v=1 to 3 and w=1 to (2v+1)). Examples of haloalkyl include, but are not limited to, trifluoromethyl, trichloromethyl, pentafluoroethyl, and pentachloroethyl.

As used herein, "alkoxy" refers to an alkyl group as defined above with the indicated number of carbon atoms attached through an oxygen bridge. C$_{1-6}$ alkoxy, is intended to include C$_1$, C$_2$, C$_3$, C$_4$, C$_5$, and C$_6$ alkoxy groups. C$_{1-8}$ alkoxy, is intended to include C$_1$, C$_2$, C$_3$, C$_4$, C$_5$, C$_6$, C$_7$, and C$_8$ alkoxy groups. Examples of alkoxy include, but are not limited to, methoxy, ethoxy, n-propoxy, i-propoxy, n-butoxy, s-butoxy, t-butoxy, n-pentoxy, s-pentoxy, n-heptoxy, and n-octoxy.

As used herein, "alkylthio" refers to an alkyl group as defined above with the indicated number of carbon atoms attached through an sulfur bridge. C$_{1-6}$ alkylthio, is intended to include C$_1$, C$_2$, C$_3$, C$_4$, C$_5$, and C$_6$ alkylthio groups. C$_{1-8}$ alkylthio, is intended to include C$_1$, C$_2$, C$_3$, C$_4$, C$_5$, CO$_6$, C$_7$, and C$_8$ alkylthio groups.

As used herein, "carbocycle" or "carbocyclic ring" is intended to mean, unless otherwise specified, any stable 3, 4, 5, 6, 7, 8, 9, 10, 11, or 12-membered monocyclic, bicyclic or tricyclic ring, any of which can be saturated, unsaturated (including partially and fully unsaturated), or aromatic, recognizing that rings with certain numbers of members cannot be bicyclic or tricyclic, e.g., a 3-membered ring can only be a monocyclic ring. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane, [2.2.2]bicyclooctane, fluorenyl, phenyl, naphthyl, indanyl, adamantyl, and tetrahydronaphthyl. As shown above, bridged rings are also included in the definition of carbocycle (e.g., [2.2.2]bicyclooctane). A bridged ring occurs when one or more carbon atoms link two non-adjacent carbon atoms. Preferred bridges are one or two carbon atoms. It is noted that a bridge always converts a monocyclic ring into a tricyclic ring. When a ring is bridged, the substituents recited for the ring can also be present on the bridge. Fused (e.g., naphthyl and tetrahydronaphthyl) and spiro rings are also included.

As used herein, the term "heterocycle" means, unless otherwise stated, a stable 3, 4, 5, 6, 7, 8, 9, 10, 11, or 12-membered monocyclic, bicyclic or tricyclic ring (recognizing that rings with certain numbers of members cannot be bicyclic or tricyclic, e.g., a 3-membered ring can only be a monocyclic ring), which is saturated, unsaturated (including partially and fully unsaturated), or aromatic, and consists of carbon atoms and one or more ring heteroatoms, e.g., 1 or 1-2 or 1-3 or 1-4 or 1-5 or 1-6 heteroatoms, independently selected from nitrogen, oxygen, and sulfur, and including any bicyclic or tricyclic group in which any of the above-defined heterocyclic rings is fused to a second ring (e.g., a benzene ring). The nitrogen and sulfur heteroatoms can optionally be oxidized (i.e., N→O and S(O)$_p$, where p=1 or 2). When a nitrogen atom is included in the ring it is either N or NH, depending on whether or not it is attached to a double bond in the ring (i.e., a hydrogen is present if needed to maintain the tri-valency of the nitrogen atom). The nitrogen atom can be substituted or unsubstituted (i.e., N or NR wherein R is H or another substituent, as defined). The heterocyclic ring can be attached to its pendant group at any heteroatom or carbon atom that results in a stable structure. The heterocyclic rings described herein can be substituted on carbon or on a nitrogen atom if the resulting compound is stable. A nitrogen in the heterocycle can optionally be quaternized. Bridged rings are also included in the definition of heterocycle. A bridged ring occurs when one or more atoms (i.e., C, O, N, or S) link two non-adjacent carbon or nitrogen atoms. Preferred bridges include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring can also be present on the bridge. Spiro and fused rings are also included.

As used herein, the term "aromatic heterocycle" or "heteroaryl" is intended to mean a stable 5, 6, 7, 8, 9, 10, 11, or 12-membered monocyclic or bicyclic aromatic ring (recognizing that rings with certain numbers of members cannot be a bicyclic aromatic, e.g., a 5-membered ring can only be a monocyclic aromatic ring), which consists of carbon atoms and one or more heteroatoms, e.g., 1 or 1-2 or 1-3 or 1-4 or 1-5 or 1-6 heteroatoms, independently selected from nitrogen, oxygen, and sulfur. In the case of bicyclic heterocyclic aromatic rings, only one of the two rings needs to be aromatic (e.g., 2,3-dihydroindole), though both can be (e.g., quinoline). The second ring can also be fused or bridged as defined above for heterocycles. The nitrogen atom can be substituted or unsubstituted (i.e., N or NR wherein R is H or another substituent, as defined). The nitrogen and sulfur heteroatoms can optionally be oxidized (i.e., N→O and S(O)$_p$, where p=1 or 2). In some compounds, the total number of S and O atoms in the aromatic heterocycle is not more than 1.

Examples of heterocycles include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

As used herein, the phrase "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, ethane sulfonic, fumaric, glucoheptonic, gluconic, glutamic, glycolic, glycollyarsanilic, hexylresorcinic, hydrabamic, hydrobromic, hydrochloric, hydroiodide, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicylic, stearic, subacetic, succinic, sulfamic, sulfanilic, sulfuric, tannic, tartaric, and toluene sulfonic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences,* 18th ed., Mack Publishing Company, Easton, Pa., USA, p. 1445 (1990).

Since prodrugs are known to enhance numerous desirable qualities of pharmaceuticals (e.g., solubility, bioavailability, manufacturing, etc.) the compounds of the present invention can be delivered in prodrug form. Thus, the present invention is intended to cover prodrugs of the presently claimed compounds, methods of delivering the same and compositions containing the same. "Prodrugs" are intended to include any covalently bonded carriers that release an active parent drug of the present invention in vivo when such prodrug is administered to a mammalian subject. Prodrugs the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate, and benzoate derivatives of alcohol and amine functional groups in the compounds of the present invention.

"Stable compound" and "stable structure" are meant to indicate a compound that is sufficiently robust to survive isolation to a useful degree of purity from a reaction mixture, and formulation into an efficacious therapeutic agent.

As used herein, "treating" or "treatment" means the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting its development; and/or (c) relieving the disease-state, i.e., causing regression of the disease state.

As used herein, "mammal" refers to human and non-human patients.

As used herein, the term "therapeutically effective amount" refers to a compound, or a combination of compounds, of the present invention present in or on a recipient in an amount sufficient to elicit biological activity, for example, anti-microbial activity, anti-fungal activity, anti-viral activity, anti-parasitic activity, and/or anti-proliferative activity. The combination of compounds is preferably a synergistic combination. Synergy, as described, for example, by Chou and Talalay, *Adv. Enzyme Regul.* vol. 22, pp. 27-55 (1984), occurs when the effect of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased anti-proliferative and/or anti-infective effect, or some other beneficial effect of the combination compared with the individual components.

All percentages and ratios used herein, unless otherwise indicated, are by weight.

Throughout the description, where compositions are described as having, including, or comprising specific components, or where processes are described as having, including, or comprising specific process steps, it is contemplated that compositions of the present invention also consist essentially of, or consist of, the recited components, and that the processes of the present invention also consist essentially of, or consist of, the recited processing steps. Further, it should be understood that the order of steps or order for performing certain actions are immaterial so long as the invention remains operable. Moreover, two or more steps or actions can be conducted simultaneously.

2. COMPOUNDS OF THE INVENTION

The invention provides a compound having the structure:

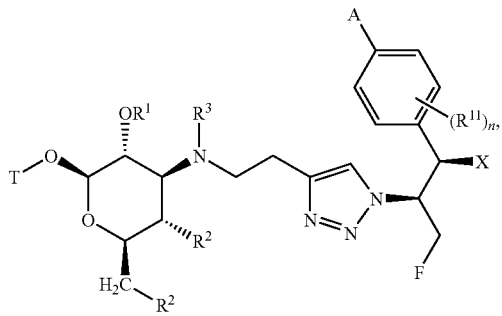

or a pharmaceutically acceptable salt, ester, N-oxide, or prodrug thereof, wherein A is selected from (a) a $C_{1-6}$ alkyl group, (b) a $C_{2-6}$ alkenyl group, (c) a $C_{2-6}$ alkynyl group, (d) a $C_{3-12}$ saturated, unsaturated, or aromatic carbocycle, (e) a 3-12 membered saturated, unsaturated, or aromatic heterocycle containing one or more nitrogen, oxygen or sulfur atoms, (f) H, (g) —OH (h) —SH, (i) F, (j) Cl, (k) Br, (l) I, (m) —CF$_3$, (n) —CN, (o) —N$_3$ (p) —NO$_2$, (q) —NR$^6$(CR$^6$R$^6$)$_r$R$^9$, (r) —OR$^9$, (s) —S(CR$^6$R$^6$)$_r$R$^9$, (t) —S(O)(CR$^6$R$^6$)$_r$R$^9$, (u) —S(O)$_2$ (CR$^6$R$^6$)$_t$R$^9$ (v) —C(O)(CR$^6$R$^6$)$_r$R$^9$, (w) —OC(O)(CR$^6$R$^6$)$_r$ R$^9$, (x) —OC(O)O(CR$^6$R$^6$)$_r$R$^9$, (y) —SC(O)(CR$^6$R$^6$)$_r$R$^9$, (z) —C(O)O(CR$^6$R$^6$)$_r$R$^9$, (aa) —NR$^6$C(O)(CR$^6$R$^6$)$_r$R$^9$, (bb) —C(O)NR$^6$(CR$^6$R$^6$)$_r$R$^9$, (cc) —C(=NR$^6$)(CR$^6$R$^6$)$_r$R$^9$, (dd) —C(=NNR$^6$R$^6$)(CR$^6$R$^6$)$_r$R$^9$, (ee) —C[=NNR$^6$C(O)R$^6$] (CR$^6$R$^6$)$_r$R$^9$, (ff) —NR$^6$C(O)O(CR$^6$R$^6$)$_r$R$^9$, (gg) —OC(O) NR$^6$(CR$^6$R$^6$)$_r$R$^9$, (hh) —NR$^6$C(O)NR$^6$(CR$^6$R$^6$)$_r$R$^9$, (ii) —NR$^6$S(O)$_p$(CR$^6$R$^6$)$_r$R$^9$, (jj) —S(O)$_p$NR$^6$(CR$^6$R$^6$)$_r$R$^9$, (kk) —NR$^6$R$^6$, (ll) —NR$^6$(CR$^6$R$^6$)$_r$R$^9$, (mm) —SR$^6$, (nn) —S(O) R$^6$, (oo) —S(O)$_2$R$^6$, (pp) —NR$^6$C(O)R$^6$, (qq) —Si(R$^{13}$)$_3$, and (rr) —C(=O)H;

wherein (a)-(e) optionally are substituted with one or more R$^{14}$ groups;

T is a 14- or 15-membered macrolide connected via a macrocyclic ring carbon atom;

X is selected from —OR$^{15}$ and —SR$^{15}$,

R$^1$ and R$^3$ independently are selected from: (a) H, (b) a $C_{1-6}$ alkyl group, (c) a $C_{2-6}$ alkenyl group, (d) a $C_{2-6}$ alkynyl group, (e) —C(O)R$^5$, (f) —C(O)OR$^5$, (g) —C(O)—NR$^4$R$^4$, (h) —C(S)R$^5$, (i) —C(S)OR$^5$, (j) —C(O)SR$^5$, or (k) —C(S)—NR$^4$R$^4$;

alternatively R$^1$ and R$^3$ are taken together with the oxygen to which R$^1$ is attached, the nitrogen to which R$^3$ is attached and the two intervening carbons to form a 5 or 6 membered ring, said ring being optionally substituted with one or more R$^5$;

R$^2$ is hydrogen or —OR$^{12}$;

R$^4$, at each occurrence, independently is selected from:
(a) H, (b) a $C_{1-6}$ alkyl group, (c) a $C_{2-6}$ alkenyl group, (d) a $C_{2-6}$ alkynyl group, (e) a $C_{6-10}$ to saturated, unsaturated, or aromatic carbocycle, (f) a 3-12 membered saturated, unsaturated, or aromatic heterocycle containing one or more heteroatoms selected from nitrogen, oxygen, and sulfur, (g) —C(O)—$C_{1-6}$ alkyl, (h) —C(O)—$C_{2-6}$alkenyl, (i) —C(O)—$C_{2-6}$ alkynyl, (j) —C(O)—$C_{6-10}$ saturated, unsaturated, or aromatic carbocycle, (k) —C(O)-3-12 membered saturated, unsaturated, or aromatic heterocycle containing one or more heteroatoms selected from nitrogen, oxygen, and sulfur, (l) —C(O) O—$C_{1-6}$ alkyl, (m) —C(O)O—$C_{2-6}$ alkenyl, (n) —C(O) O—$C_{2-6}$ alkynyl, (o) —C(O)O—$C_{6-10}$ saturated, unsaturated, or aromatic carbocycle, p) —C(O)O-3-12 membered saturated, unsaturated, or aromatic heterocycle containing one or more heteroatoms selected from nitrogen, oxygen, and sulfur, and q) —C(O)NR$^6$R$^6$, wherein any of (b)-(p) optionally is substituted with one or more R$^5$ groups, alternatively, NR$^6$R$^6$ forms a 3-7 membered saturated, unsaturated or aromatic ring including the nitrogen atom to which the R$^6$ groups are attached, wherein said ring is optionally substituted at a position other than the nitrogen atom to which the R$^6$ groups are attached, with one or more substituents selected from O, S(O)$_p$, N, and NR$^8$;

R$^5$ is selected from:
(a) R$^7$, (b) a $C_{1-8}$ alkyl group, (c) a $C_{2-8}$alkenyl group, (d) a $C_{2-8}$ alkynyl group, (e) a $C_{3-12}$ saturated, unsaturated, or aromatic carbocycle, and (f) a 3-12 membered saturated, unsaturated, or aromatic heterocycle containing one or more heteroatoms selected from nitrogen, oxygen, and sulfur, or two R$^5$ groups, when present on the same carbon atom can be taken together with the carbon atom to which they are attached to form a spiro 3-6 membered carbocyclic ring or heterocyclic ring containing one or more heteroatoms selected from nitrogen, oxygen, and sulfur, wherein any of (b)-(f) immediately above optionally is substituted with one or more R$^7$ groups;

R$^6$, at each occurrence, independently is selected from:
(a) H, (b) a $C_{1-6}$ alkyl group, (c) a $C_{2-6}$ alkenyl group, (d) a $C_{2-6}$ alkynyl group, (e) a $C_{3-10}$ saturated, unsaturated, or aromatic carbocycle, and (f) a 3-membered saturated, unsaturated, or aromatic heterocycle containing one or more heteroatoms selected from nitrogen, oxygen, and sulfur, wherein any of (b)-(f) optionally is substituted with one or more moieties selected from:
(aa) a carbonyl group, (bb) a formyl group, (cc) F, (dd) Cl, (ee) Br, (ff) I, (gg) CN, (hh) NO$_2$, (ii) —OR$^8$, (jj) —S(O)$_p$R$^8$, (kk) —C(O)R$^8$, (ll) —C(O)OR$^8$, (mm) —OC(O)R$^8$, (nn) —C(O)NR$^8$R$^8$, (oo) —OC (O)NR$^8$R$^8$, (pp) —C(=NR)R$^8$, (qq) —C(R$^8$)(R$^8$) OR$^8$, (rr) —C(R$^8$)$_2$OC(O)R$^8$, (ss) —C(R$^8$)(OR$^8$) (CH$_2$)$_r$NR$^8$R$^8$, (tt) —NR$^8$R$^8$, (uu) —NR$^8$OR$^8$, (vv) —NR$^8$C(O)R$^8$, (ww) —NR$^8$C(O)OR$^8$, (xx) —NR$^8$C(O)NR$^8$R$^8$, (yy) —NR$^8$S(O)$_r$R$^8$, (zz) —C(OR$^8$)(OR$^8$)R$^8$, (ab) —C(R$^8$)$_2$NR$^8$R$^8$, (ac) =NR$^8$, (ad) —C(S)NR$^8$R$^8$, (ae) —NR$^8$C(S)R$^8$, (af) —OC(S)NR$^8$R$^8$, (ag) —NR$^8$C(S)OR$^8$, (ah) —NR$^8$C(S)NR$^8$R$^8$, (ai) —SC(O)R$^8$, (aj) a $C_{1-8}$ alkyl group, (ak) a $C_{2-8}$ alkenyl group, (al) a $C_{2-8}$ alkynyl group, (am) a $C_{1-8}$ alkoxy group, (an) a $C_{1-8}$ alkylthio group, (ao) a $C_{1-8}$ acyl group, (ap) —CF$_3$, (aq) —SCF$_3$, (ar) a $C_{3-10}$ saturated, unsaturated, or aromatic carbocycle, and (as) a 3-10 membered saturated, unsaturated, or aromatic heterocycle containing one or more heteroatoms selected from nitrogen, oxygen, and sulfur, alternatively, NR$^6$R$^6$ forms a 3-10 membered saturated, unsaturated or aromatic ring including the nitrogen atom to which the R$^6$ groups are attached wherein said ring is optionally substituted at a position other than the nitrogen atom to which the R$^6$ groups are bonded, with one or more moieties selected from O, S(O)$_p$, N, and NR$^8$;

alternatively, CR$^6$R$^6$ forms a carbonyl group;
R$^7$, at each occurrence, is selected from:
(a) H, (b) =O, (c) =S, (d) F, (e) Cl, (f) Br, (g) I, (h) —CF$_3$, (i) —CN, (j) —N$_3$, (k) —NO$_2$, (l) —NR$^6$(CR$^6$R$^6$)$_r$R$^9$, (m) —OR$^9$, (n) —S(O)$_p$C(R$^6$R$^6$)$_r$R$^9$, (o) —C(O)(CR$^6$R$^6$)$_r$R$^9$, (p) —OC(O)(CR$^6$R$^6$)$_r$R$^9$, (q) —SC(O)(CR$^6$R$^6$)$_r$R$^9$, (r) —C(O)O(CR$^6$R$^6$)$_r$R$^9$, (s) —NR$^6$C(O)(CR$^6$R$^6$)$_r$R$^9$, (t) —C(O)NR$^6$(CR$^6$R$^6$)$_r$R$^9$, (u) —C(=NR(CR$^6$R$^6$)$_r$R$^9$, (v) —C(=NNR$^6$R$^6$)(CR$^6$R$^6$)$_r$R$^9$, (w) —C(=NNR$^6$C(O)R$^6$)(CR$^6$R$^6$)$_r$R$^9$, (x) —C(=NOR$^9$)(CR$^6$R$^6$)$_r$R$^9$, (y) —NR$^6$C(O)O(CR$^6$R$^6$)$_r$R$^9$, (z) —OC(O)NR$^6$(CR$^6$R$^6$)$_r$R$^9$, (aa) —NR$^6$C(O)NR$^6$(CR$^6$R$^6$)$_r$R$^9$, (bb) —NR$^6$S(O)$_p$(CR$^6$R$^6$)$_r$R$^9$, (cc) —S(O)$_p$NR$^6$(CR$^6$R$^6$)$_r$R$^9$, (dd) —NR$^6$S(O)$_p$NR$^6$(CR$^6$R$^6$)$_r$R$^9$, (ee) —NR$^6$R$^6$, (ff) —NR$^6$(CR$^6$R$^6$), (gg) —OH, (hh) —NR$^6$R$^6$, (ii) —OCH$_3$, (jj) —S(O)$_p$R$^6$, (kk) —NC(O)R$^6$, (ll) a C$_{1-6}$ alkyl group, (mm) a C$_{2-6}$ alkenyl group, (nn) a C$_{2-6}$ alkynyl group, (oo) —C$_{3-10}$ to saturated, unsaturated, or aromatic carbocycle, and (pp) 3-10 membered saturated, unsaturated, or aromatic heterocycle containing one or more heteroatoms selected from nitrogen, oxygen, and sulfur,
    wherein any of (ll)-(pp) optionally is substituted with one or more R$^9$ groups;
alternatively, two R$^7$ groups can form —O(CH$_2$)$_u$O—;
R$^8$ is selected from:
(a) H, (b) a C$_{1-6}$ alkyl group, (c) a C$_{2-6}$ alkenyl group, (d) a C$_{2-6}$ alkynyl group, (e) a C$_{3-10}$ saturated, unsaturated, or aromatic carbocycle, (f) a 3-10 membered saturated, unsaturated, or aromatic heterocycle containing one or more heteroatoms selected from nitrogen, oxygen, and sulfur, (g) —C(O)—C$_{1-6}$ alkyl, (h) —C(O)—C$_{1-6}$ alkenyl, (i) —C(O)—C$_{1-6}$ alkynyl; (j) —C(O)—C$_{3-10}$ saturated, unsaturated, or aromatic carbocycle, and (k) —C(O)-3-10 membered saturated, unsaturated, or aromatic heterocycle containing one or more heteroatoms selected from nitrogen, oxygen, and sulfur,
    wherein any of (c)-(k) optionally is substituted with one or more moieties selected from: (aa) H, (bb) F, (cc) Cl, (dd) Br, (ee) I, (ff) CN, (gg) NO$_2$, (hh) OH, (ii) NH$_2$, (jj) NH(C$_{1-6}$ alkyl), (kk) N(C$_{1-6}$ alkyl)$_2$, (ll) a C$_{1-6}$ alkoxy group, (mm) an aryl group, (nn) a substituted aryl group, (oo) a heteroaryl group, (pp) a substituted heteroaryl group, and qq) a C$_{1-6}$ alkyl group optionally substituted with one or more moieties selected from an aryl group, a substituted aryl group, a heteroaryl group, a substituted heteroaryl group, F, Cl, Br, I, CN, NO$_2$, CF$_3$, SCF$_3$, and OH;
R$^9$, at each occurrence, independently is selected from:
(a) R$^{10}$, (b) a C$_{1-6}$ alkyl group, (c) a C$_{2-6}$ alkenyl group, (d) a C$_{2-6}$ alkynyl group, e) a C$_{3-10}$ saturated, unsaturated, or aromatic carbocycle, and f) a 3-10 membered saturated, unsaturated, or aromatic heterocycle containing one or more heteroatoms selected from nitrogen, oxygen, and sulfur,
    wherein any of (b)-(f) optionally is substituted with one or more R$^{10}$ groups;
R$^{10}$, at each occurrence, independently is selected from:
(a) H, (b) =O, (c) F, (d) Cl, (e) Br, (f) I, (g) —CF$_3$, (h) —CN, (i) —NO$_2$, (j) —NR$^6$R$^6$, (k) —OR$^6$, (l) —S(O)$_p$R$^6$, (m) —C(O)R$^6$, (n) —C(O)OR$^6$, (o) —OC(O)R$^6$, (p) NR$^6$C(O)R$^6$, (q) —C(O)NR$^6$R$^6$, (r) —C(=NR$^6$)R$^6$, (s) —NR$^6$C(O)NR$^6$R$^6$, (t) —NR$^6$S(O)$_p$R$^6$, (u) —S(O)$_p$NR$^6$R$^6$, (v) —NR$^6$S(O)$_p$NR$^6$R$^6$, (w) a C$_{1-6}$ alkyl group, (x) a C$_{2-6}$ alkenyl group, (y) a C$_{2-6}$ alkynyl group, (z) a C$_{3-10}$ saturated, unsaturated, or aromatic carbocycle, and (aa) a 3-10 membered saturated, unsaturated, or aromatic heterocycle containing one or more heteroatoms selected from nitrogen, oxygen, and sulfur,
    wherein any of (w)-(aa) optionally is substituted with one or more moieties selected from R$^6$, F, Cl, Br, I, CN, NO$_2$, —OR$^6$, —NH$_2$, —NH(C$_{1-6}$ alkyl), —N(C$_{1-6}$ alkyl)$_2$, a C$_{1-6}$ alkoxy group, a C$_{1-6}$ alkylthio group, and a C$_{1-6}$ acyl group;
R$^{11}$ at each occurrence, independently is selected from:
(a) H, (b) F, (c) Cl, (d) Br, (e) I, (f) CN, (g) NO$_2$, (h) OR$^8$, (i) —S(O)$_p$R$^8$, (j) —C(O)R$^8$, (k) —C(O)OR$^8$, (l) —OC(O)R$^8$, (m) —C(O)NR$^8$R$^8$, (n) —OC(O)NR$^8$R$^8$, (o) —C(=NR$^8$)R$^8$, (p) —C(R$^8$)(R$^8$)OR$^8$, (q) —C(R$^8$)$_2$OC(O)R$^8$, (r) —C(R$^8$)(OR$^8$)(CH$_2$)$_r$NR$^8$R$^8$, (s) NR$^8$R$^8$, (t) —NR$^8$OR$^8$, (u) —NR$^8$C(O)R$^8$, (v) —NR$^8$C(O)OR$^8$, (w) —NR$^8$C(O)NR$^8$R$^8$, (x) —NR$^8$S(O)$_p$R$^8$, (y) —C(OR$^8$)(OR$^8$)R$^8$, (z) —C(R$^8$)$_2$NR$^8$R$^8$, (aa) —C(S)NR$^8$R$^8$, (bb) —NR$^8$C(S)R$^8$, (cc) —OC(S)NR$^8$R$^8$, (dd) —NR$^8$C(S)OR$^8$, (ee) —NR$^8$C(S)NR$^8$R$^8$, (ff) —SC(O)R$^8$, (gg) —N$_3$, (hh) —Si(R$^{13}$)$_3$, (ii) a C$_{1-8}$ alkyl group, (jj) a C$_{2-8}$ alkenyl group, (kk) a C$_{2-8}$ alkynyl group, (ll) a C$_{3-10}$ saturated, unsaturated, or aromatic carbocycle, and (mm) a 3-10 membered saturated, unsaturated, or aromatic heterocycle containing one or more heteroatoms selected from nitrogen, oxygen, and sulfur, wherein (ii)-(mm) optionally are substituted with one or more R$^5$ groups;
R$^{12}$ is selected from:
(a) H, (b) a C$_{1-6}$ alkyl group, (c) a C$_{2-6}$ alkenyl group, (d) a C$_{2-6}$ alkynyl group, (e) —C(O)R$^5$, (f) —C(O)OR$^5$, (g) —C(O)—NR$^4$R$^4$R$^4$R$^4$, (h) —C(S)R$^5$, (i) —C(S)OR$^5$, (j) —C(O)SR$^5$, (k) —C(S)—NR$^4$R$^4$R$^4$R$^4$, (l) a C$_{3-10}$ saturated, unsaturated, or aromatic carbocycle, or (m) a 3-10 membered saturated, unsaturated, or aromatic heterocycle containing one or more heteroatoms selected from nitrogen, oxygen, and sulfur, (n) a —(C$_{1-6}$ alkyl)-C$_{3-10}$ saturated, unsaturated, or aromatic carbocycle, or (o) a —(C$_{1-6}$ alkyl)-3-10 membered saturated, unsaturated, or aromatic heterocycle containing one or more heteroatoms selected from nitrogen, oxygen, and sulfur, wherein (a)-(d) and (l)-(o) optionally are substituted with one or more R$^5$ groups;
each R$^{13}$ is independently selected from (a) —C$_{1-6}$ alkyl and (b) —O—(C$_{1-6}$ alkyl);
R$^{14}$ at each occurrence is independently selected from:
(a) H, (b) F, (c) Cl, (d) Br, (e) I, (f) CN, (g) NO$_2$ (h) OR$^8$, (i) —S(O)$_p$R$^8$, (j) —C(O)R$^8$, (k) —C(O)OR$^8$, (l) —OC(O)R$^8$, (m) —C(O)NR$^8$R$^8$, (n) —OC(O)NR$^8$R$^8$, (o) —C(=NR$^8$)R$^8$, (p) —C(R$^8$)(R$^8$)OR$^8$, (q) —C(R$^8$)$_2$OC(O)R$^8$, (r) —C(R$^8$)(OR$^8$)(CH$_2$)$_r$NR$^8$R$^8$, (s) —NR$^8$R$^8$, (t) —NR$^8$OR$^8$, (u) —NR$^8$C(O)R$^8$, (v) —NR$^8$C(O)OR$^8$, (w) —NR$^8$C(O)NR$^8$R$^8$, (x) —NR$^8$S(O)$_p$R$^8$, (y) —C(OR$^8$)(OR$^8$)R$^8$, (z) —C(R$^8$)$_2$NR$^8$R$^8$, (aa) —C(S)NR$^8$R$^8$, (bb) —NR$^8$C(S)R$^8$, (cc) —OC(S)NR$^8$R$^8$, (dd) —NR$^8$C(S)OR$^8$, (ee) —NR$^8$C(S)NR$^8$R$^8$, (ff) —SC(O)R$^8$, (gg) —N$_3$, (hh) —Si(R$^{13}$)$_3$, (ii) a C$_{1-8}$ alkyl group, (jj) a C$_{2-8}$ alkenyl group, (kk) a C$_{2-8}$ alkynyl group, (ll) a C$_{3-10}$ saturated, unsaturated, or aromatic carbocycle, and (mm) a 3-10 membered saturated, unsaturated, or aromatic heterocycle containing one or more heteroatoms selected from nitrogen, oxygen, and sulfur, wherein (ii)-(mm) optionally are substituted with one or more R$^5$ groups;
alternatively two R$^{14}$ groups are taken together to form (a) =O, (b) =S, (c) =NR$^8$, (e) =NOR$^8$;
R$^{15}$ is selected from C$_{1-6}$ alkyl, optionally substituted with from 1 to 13 fluorine atoms;

n at each occurrence is 0, 1, 2, 3, or 4;
p at each occurrence is 0, 1, or 2;
r at each occurrence is 0, 1, or 2;
t at each occurrence is 0, 1, or 2;
and u at each occurrence is 1, 2, 3, or 4.

In further embodiments of the present invention, n is 1 or 2.

In further embodiments of the present invention, n is 1.

In further embodiments of the present invention, $R^{11}$ is F.

In further embodiments of the present invention, n is 0.

In further embodiments of the present invention, X is —$OR^{15}$.

In further embodiments of the present invention, X is —$SR^{15}$.

In further embodiments of the present invention, $R^{15}$ is $C_{1-3}$ alkyl, optionally substituted with from 1 to 7 fluorines.

In further embodiments of the present invention, $R^{15}$ is $C_{1-2}$ alkyl, optionally substituted with from 1 to 5 fluorines.

In further embodiments of the present invention, $R^{15}$ is selected from —$CH_3$, —$CH_2F$, —$CHF_2$, and —$CF_3$.

In further embodiments of the present invention, $R^{15}$ is —$CH_3$.

In further embodiments of the present invention, A is selected from (a) a $C_{1-6}$ alkyl group, (b) a $C_{2-6}$ alkenyl group, (c) a $C_{2-6}$ alkynyl group, (d) a $C_{3-12}$ saturated, unsaturated, or aromatic carbocycle, (e) a 3-12 membered saturated; unsaturated, or aromatic heterocycle containing one or more nitrogen, oxygen or sulfur atoms, (f) —$CF_3$, (g) —$NR^6(CR^6R^6)_tR^9$, (h) —$OR^9$, (i) —$S(CR^6R^6)_rR^9$, (j) —$S(O)(CR^6R^6)_rR^9$, (k) —$S(O)_2(CR^6R^6)_rR^9$ (l) —$C(O)(CR^6R^6)_rR^9$, (m) —$OC(O)(CR^6R^6)_rR^9$, (n) $OC(O)O(CR^6R^6)_rR^9$, (o) —$SC(O)(CR^6R^6)_rR^9$, (p) —$C(O)O(CR^6R^6)_rR^9$, (q) —$NR^6C(O)(CR^6R^6)_rR^9$, (r) —$C(O)NR^6(CR^6R^6)_rR^9$, (s) —$C(=NR)(CR^6R^6)_rR^9$, (t) —$C(=NNR^6R^6)(CR^6R^6)_rR^9$, (u) —$C[=NNR^6C(O)R^6](CR^6R^6)_rR^9$, (v) —$NR^6C(O)O(CR^6R^6)_rR^9$, (w) —$OC(O)NR^6(CR^6R^6)_rR^9$, (x) —$NR^6C(O)NR^6(CR^6R^6)_rR^9$, (y) —$NR^6S(O)_p(CR^6R^6)_rR^9$, (z) —$S(O)_pNR^6(CR^6R^6)_rR^9$, (aa) —$NR^6R^6$, (bb) —$NR^6(CR^6R^6)_rR^9$, (cc) —$SR^6$, (dd) —$S(O)R^6$, (ee) —$S(O)_2R^6$, and (ff) —$NR^6C(O)R^6$; wherein (a)-(e) optionally are substituted with one or more $R^{14}$ groups;

In further embodiments of the present invention, A is selected from (a) a $C_{1-6}$ alkyl group, (b) a $C_{2-6}$ alkenyl group, (c) a $C_{2-6}$ alkynyl group, (d) a $C_{3-12}$ saturated, unsaturated, or aromatic carbocycle, (e) a 3-12 membered saturated, unsaturated, or aromatic heterocycle containing one or more nitrogen, oxygen or sulfur atoms; wherein (a)-(e) optionally are substituted with one or more $R^{14}$ groups.

In further embodiments of the present invention, A is selected (a) —$NR^6(CR^6R^6)_tR^9$, (b) —$OR^9$, (c) —$S(CR^6R^6)_tR^9$, (d) —$S(O)(CR^6R^6)_tR^9$, (e) —$S(O)_2(CR^6R^6)_tR^9$ (f) —$C(O)(CR^6R^6)_tR^9$, (g) —$OC(O)(CR^6R^6)_tR^9$, (h) —$OC(O)O(CR^6R^6)_tR^9$, (i) —$SC(O)(CR^6R^6)_tR^9$, (j) —$C(O)O(CR^6R^6)_tR^9$, (k) —$NR^6C(O)(CR^6R^6)_tR^9$, (l) —$C(O)NR^6(CR^6R^6)_tR^9$, (m) —$C(=NR^6)(CR^6R^6)_tR^9$, (n) —$C(=NNR^6R^6)(CR^6R^6)_tR^9$, (o) —$C[=NNR^6C(O)R^6](CR^6R^6)_tR^9$, (p) —$NR^6C(O)O(CR^6R^6)_tR^9$, (q) —$OC(O)NR^6(CR^6R^6)_tR^9$, (r) —$NR^6C(O)NR^6(CR^6R^6)_tR^9$, (s) —$NR^6S(O)_p(CR^6R^6)_tR^9$, (t) —$S(O)_pNR^6(CR^6R^6)_tR^9$, (u) —$NR^6R^6$, (v) —$NR^6(CR^6R^6)_tR^9$, (w) —$SR^6$, (x) —$S(O)R^6$, (y) —$S(O)_2R^6$, and (z) —$NR^6C(O)R^6$.

In further embodiments of the present invention, A is a $C_{1-6}$ alkyl group, optionally substituted with one or more $R^{14}$ groups.

In further embodiments of the present invention, A is a $C_{2-6}$ alkenyl group, optionally substituted with one or more $R^{14}$ groups.

In further embodiments of the present invention, A is a $C_{2-6}$ alkynyl group, optionally substituted with one or more $R^{14}$ groups.

In further embodiments of the present invention, A is a $C_{3-12}$ saturated, unsaturated, or aromatic carbocycle, optionally are substituted with one or more $R^{14}$ groups.

In further embodiments of the present invention, A is a 3-12 membered saturated, unsaturated, or aromatic heterocycle containing one or more nitrogen, oxygen or sulfur atoms, optionally substituted with one or more $R^{14}$ groups.

In further embodiments of the present invention, A is H.

In further embodiments of the present invention, A is —OH.

In further embodiments of the present invention, A is —SH.

In further embodiments of the present invention, A is F.

In further embodiments of the present invention, A is Cl.

In further embodiments of the present invention, A is Br.

In further embodiments of the present invention, A is I.

In further embodiments of the present invention, A is —$CF_3$.

In further embodiments of the present invention, A is —CN.

In further embodiments of the present invention, A is —$N_3$.

In further embodiments of the present invention, A is —$NO_2$.

In further embodiments of the present invention, A is —$NR^6(CR^6R^6)_tR^9$.

In further embodiments of the present invention, A is —$OR^9$.

In further embodiments of the present invention, A is —$S(CR^6R^6)_tR^9$.

In further embodiments of the present invention, A is —$S(O)(CR^6R^6)_tR^9$.

In further embodiments of the present invention, A is —$S(O)_2(CR^6R^6)_tR^9$.

In further embodiments of the present invention, A is —$C(O)(CR^6R^6)_tR^9$.

In further embodiments of the present invention, A is —$OC(O)(CR^6R^6)_tR^9$.

In further embodiments of the present invention, A is —$OC(O)O(CR^6R^6)_tR^9$.

In further embodiments of the present invention, A is —$SC(O)(CR^6R^6)_tR^9$.

In further embodiments of the present invention, A is —$C(O)O(CR^6R^6)_tR^9$.

In further embodiments of the present invention, A is —$NR^6C(O)(CR^6R^6)_tR^9$.

In further embodiments of the present invention, A is —$C(O)NR^6(CR^6R^6)_tR^9$.

In further embodiments of the present invention, A is —$C(=NR^6)(CR^6R^6)_tR^9$.

In further embodiments of the present invention, A is —$C(=NNR^6R^6)(CR^6R^6)_tR^9$.

In further embodiments of the present invention, A is —$C[=NNR^6C(O)R^6](CR^6R^6)_tR^9$.

In further embodiments of the present invention, A is —$NR^6C(O)O(CR^6R^6)_tR^9$.

In further embodiments of the present invention, A is —$OC(O)NR^6(CR^6R^6)_tR^9$.

In further embodiments of the present invention, A is —$NR^6C(O)NR^6(CR^6R^6)_tR^9$.

In further embodiments of the present invention, A is —$NR^6S(O)_p(CR^6R^6)_tR^9$.

In further embodiments of the present invention, A is —$S(O)_pNR^6(CR^6R^6)_tR^9$.

In further embodiments of the present invention, A is —NR$^6$R$^6$.

In further embodiments of the present invention, A is —NR$^6$(CR$^6$R$^6$)$_t$R$^9$.

In further embodiments of the present invention, A is —SR$^6$.

In further embodiments of the present invention, A is —S(O)R$^6$.

In further embodiments of the present invention, A is —S(O)$_2$R$^6$.

In further embodiments of the present invention, A is —NR$^6$C(O)R$^6$.

In further embodiments of the present invention, A is —Si(R$^{13}$)$_3$.

In further embodiments of the present invention, A is and —C(=O)H.

In further embodiments of the present invention, R$^{13}$ is selected from —CH$_3$ and —OCH$_3$.

In further embodiments of the present invention, R$^{13}$ is —CH$_3$.

In further embodiments of the present invention, R$^{13}$ is —OCH$_3$.

In further embodiments, the invention provides a compound having the structure:

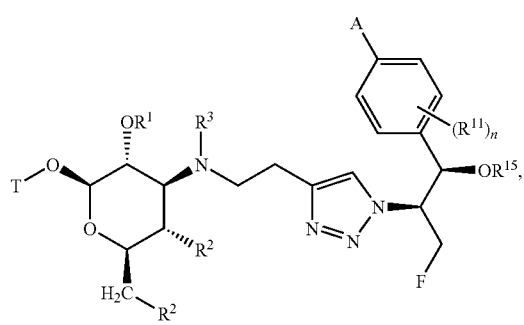

or a pharmaceutically acceptable salt, ester, N-oxide, or prodrug thereof, wherein R$^1$, R$^2$, R$^3$, R$^{11}$, R$^{15}$, n A, and T, are as described herein.

In further embodiments, the invention provides a compound having the structure:

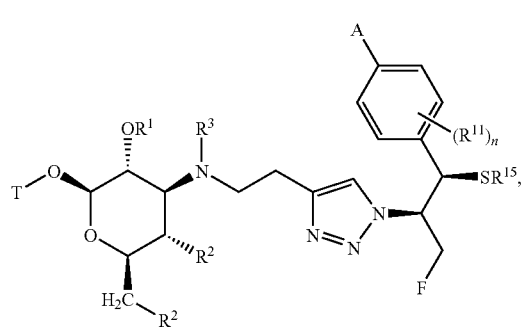

or a pharmaceutically acceptable salt, ester, N-oxide, or prodrug thereof, wherein R$^1$, R$^2$, R$^3$, R$^{11}$, R$^{15}$, n, A, and T, are as described herein.

In further embodiments, the invention provides a compound having the structure:

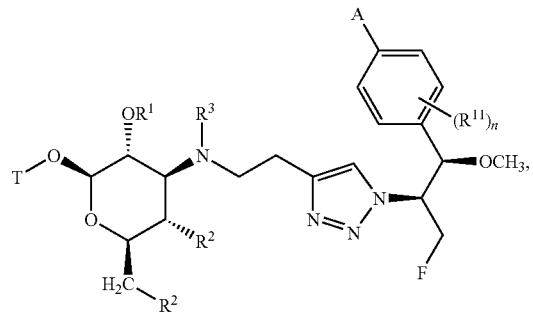

or a pharmaceutically acceptable salt, ester, N-oxide, or prodrug thereof, wherein R$^1$, R$^2$, R$^3$, R$^{11}$, n A, and T, are as described herein.

In further embodiments of the present invention, T is

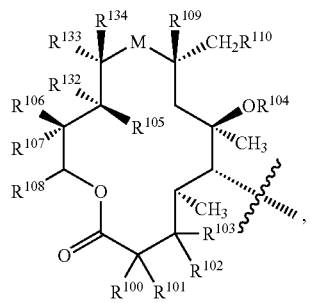

wherein:

M is selected from:

(a) —C((O)—, (b) —CH(—OR$^{114}$)—, (c) —NR$^{114}$—CH$_2$—, (d) —CH$_2$—NR$^{114}$—, (e) —CH(NR$^{114}$R$^{114}$)—, (f) —C(=NNR$^{114}$R$^{114}$)—, (g) —NR$^{114}$—C(O)—, (h) —C(O)NR$^{114}$—, (i) —C(=NR$^{114}$), (j) —CR$^{115}$R$^{115}$—, and (k) —C(=NOR$^{127}$)—;

R$^{100}$ is selected from (a) H, (b) F, (c) Cl, (d) —Br, (e) —SR$^{114}$, and (f) C$_{1-6}$alkyl, wherein (f) optionally is substituted with one or more R$^{115}$ groups;

R$^{101}$ is selected from:

(a) —H, (b) Cl, (c) F, (d) Br, (e) I, (f) —NR$^{114}$R$^{114}$, (g) —NR$^{114}$C(O)R$^{114}$, (h) —OR$^{114}$, (i) —OC(O)R$^{114}$, (j) —OC(O)OR$^{114}$, (k) —OC(O)NR$^{114}$R$^{114}$, (l) —O—C$_{1-6}$ alkyl, (m) —OC(O)—C$_{1-6}$ alkyl, (n) —OC(O)O—C$_{1-6}$ alkyl, (o) —OC(O)NR$^{114}$—C$_{1-6}$ alkyl, (p) C$_{1-6}$ alkyl, (q) C$_{1-6}$ alkenyl, and (r) C$_{1-6}$ alkynyl, wherein any of (l)-(r) optionally is substituted with one or more R$^{115}$ groups;

R$^{102}$ is H, (b) F, (c) Cl, (d) Br, (e) —SR$^{114}$, (f) C$_{1-6}$ alkyl, wherein (f) optionally is substituted with one or more R$^{115}$ groups;

R$^{103}$ is selected from:

(a) H, (b) —OR$^{114}$, (c) —O—C$_{1-6}$ alkyl-R$^{115}$, (d) —OC((O)R$^{114}$, (e) —OC(O)—C$_{1-6}$ alkyl-R$^{115}$, (f) —OC(O)OR$^{114}$, (g) —OC(O)O—C$_{1-6}$ alkyl-R$^{115}$, (h) —OC(O)NR$^{114}$R$^{114}$, (i) —OC(O)NR$^{114}$—C$_{1-6}$ alkyl-R$^{115}$, and

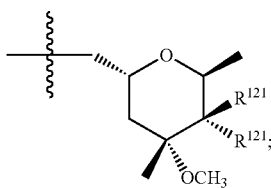

alternatively, $R^{102}$ and $R^{103}$ taken together with the carbon to which they are attached form (a) a carbonyl group or (b) a 3-7 membered saturated, unsaturated or aromatic carbocyclic or heterocyclic ring which can optionally be substituted with one or more $R^{114}$ groups;

alternatively, $R^{101}$ and $R^{103}$ taken together are a single bond between the respective carbons to which these two groups are attached thereby creating a double bond between the carbons to which $R^{100}$ and $R^{102}$ are attached;

alternatively, $R^{101}$ and $R^{103}$ taken together with the carbons to which they are attached form a 3-membered saturated, unsaturated or aromatic carbocyclic or heterocyclic ring which can optionally be substituted with one or more $R^{114}$ groups;

$R^{104}$ is selected from:
(a) H, (b) $R^{114}$, (c) —C(O)$R^{114}$ (d) —C(O)O$R^{114}$ (e) —C(O)N$R^{114}R^{114}$, (f) —C$_{1-6}$ alkyl-K—$R^{114}$, (g) —C$_{2-6}$ alkenyl-K—$R^{114}$, and (h) —C$_{2-6}$ alkynyl-K—$R^{114}$;

K is selected from:
(a) —C(O)—, (b) —C(O)O—, (c) —C(O)N$R^{114}$—, (d) —C(=N$R^{114}$)—, (e) —C(=N$R^{114}$)O—, (f) —C(=N$R^{114}$)N$R^{114}$—, (g) —OC(O)—, (h) —OC(O)O—, (i) —OC(O)N$R^{114}$—, (j) —N$R^{114}$C(O)—, (k) —N$R^{114}$C(O)O—, (l) —N$R^{114}$C(O)N$R^{114}$—, (m) —N$R^{114}$C(=N$R^{114}$)N$R^{114}$ and (o) —S(O)$_p$—;

alternatively $R^{103}$ and $R^{104}$, taken together with the atoms to which they are bonded, form:

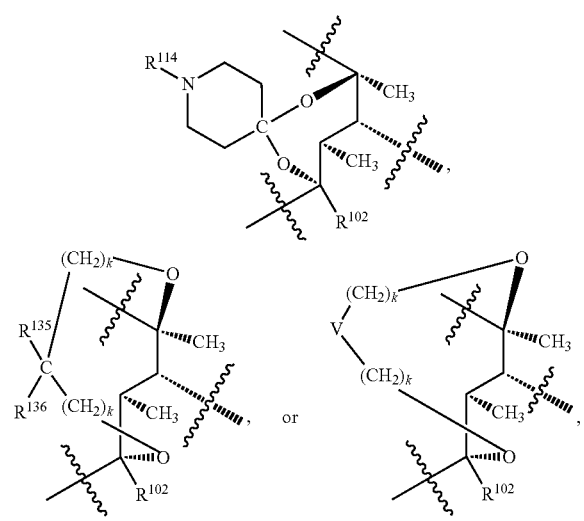

wherein $R^{135}$ and $R^{136}$ are selected from (a) hydrogen, (b) $C_{1-6}$ alkyl, (c) $C_{2-6}$ alkenyl, (d) $C_{2-6}$ alkynyl, (d) $C_{3-14}$ saturated, unsaturated or aromatic carbocycle, (e) 3-14 membered saturated, unsaturated or aromatic heterocycle containing one or more oxygen, nitrogen, or sulfur atoms, (f) F, (g) Br, (h) I, (i) OH, (j) —N$_3$, wherein (b) through (e) are optionally substituted with one or more $R^{117}$; or alternatively, $R^{135}$ and $R^{136}$ are taken together to form =O, =S and =N$R^{114}$, =NO$R^{114}$, =N$R^{114}$, and =N—N$R^{114}$, $R^{114}$];

wherein V is selected from (a) —(C$_4$-alkyl)-, (b) —(C$_4$-alkenyl)-, (c) O, (d) S, and (e) N$R^{114}$, wherein (a) and (b) are optionally further substituted with one or more $R^{117}$;

$R^{105}$ is selected from:
(a) $R^{114}$, (b) —O$R^{114}$, (c) N$R^{114}R^{114}$, (d) —O—C$_{1-6}$ alkyl-$R^{115}$, (e) —C(O)—$R^{114}$, (f) —C(O)—C$_{1-6}$ alkyl-$R^{115}$, (g) —OC(O)—$R^{114}$, (h) —OC(O)—C$_{1-6}$ alkyl-$R^{115}$, (i) —OC(O)O—$R^{114}$, (j) —OC(O)O—C$_{1-6}$ alkyl-$R^{115}$, (k) —OC(O)N$R^{114}R^{114}$, (l) —OC(O)N$R^{114}$—C$_{1-6}$ alkyl-$R^{115}$, (m) —C(O)—C$_{2-6}$ alkenyl-$R^{115}$, and (n) —C(O)—C$_{2-6}$ alkynyl-$R^{115}$;

alternatively, $R^{104}$ and $R^{105}$, taken together with the atoms to which they are bonded, form

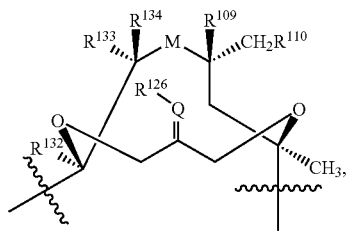

wherein
Q is CH or N, and $R^{126}$ is —O$R^{114}$, —N$R^{114}$ or $R^{114}$;

alternatively, $R^{104}$ and $R^{105}$, taken together with the atoms to which they are bonded, form:

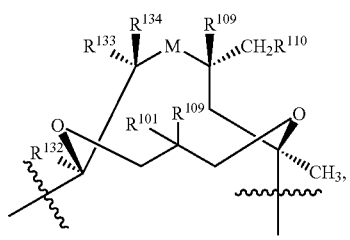

wherein
i) $R^{101}$ is as defined above;
ii) alternately, $R^{101}$ and $R^{109}$ can be taken together with the carbon to which they are attached to form a carbonyl group;
iii) alternately, $R^{101}$ and $R^{109}$ can be taken together to form the group —O(C$R^{116}R^{116}$)$_u$O—;

alternatively, $R^{104}$ and $R^{105}$, taken together with the atoms to which they are bonded, form:

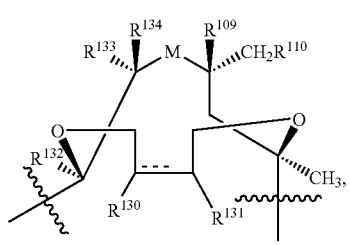

wherein in the preceding structure the dotted line indicates an optional double bond i) $R^{130}$ is —OH, =C(O), or $R^{114}$,
ii) $R^{131}$ is —OH, =C(O), or $R^{114}$,
iii) alternately, $R^{130}$ and $R^{131}$ together with the carbons to which they are attached form a 3-7 membered saturated, unsaturated or aromatic carbocyclic or heterocyclic ring which can optionally be substituted with one or more $R^{114}$ groups;
iv) alternatively, $R^{130}$ and the carbon to which it is attached or $R^{131}$ and the carbon to which it is attached are each independently —C(=O)—, alternatively, $R^{105}$, $R^{132}$ and M, taken together with the atoms to which they are attached, form:

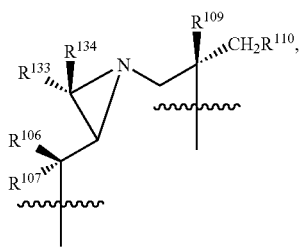

$R^{106}$ is selected from:
(a) —$OR^{114}$, (b) —$C_{1-6}$ alkoxy-$R^{115}$, (c) —C(O)$R^{114}$, (d) —OC(O)$R^{114}$, (e) —OC(O)O$R^{114}$, (f) —OC(O)N$R^{114}R^{114}$, and (g) —N$R^{114}R^{114}$, alternatively, $R^{105}$ and $R^{106}$ taken together with the atoms to which they are attached form a 5-membered ring by attachment to each other through a chemical moiety selected from:
(a) —OC($R^{115}$)$_2$O—, (b) —OC(O)O—, (c) —OC(O)N$R^{114}$—, (d) —N$R^{114}$C(O)O—, (e) —OC(O)NOR$^{114}$, (f) —NOR$^{114}$—C(O)O—, (g) —OC(O)NN$R^{114}R^{114}$—, (h) —NN$R^{114}R^{114}$—C(O)O—, (i) —OC(O)C($R^{115}$)$_2$—, (j) —C($R^{115}$)$_2$C(O)O—, (k) —OC(S)O—, (l) —OC((S)N$R^{114}$—, (m) —N$R^{114}$C(S)O—, (n) —OC(S)NOR$^{114}$—, (o)—NOR$^{114}$—C(S)O—, (p)—OC(S)NN$R^{114}R^{114}$—, (q)—NN$R^{114}R^{114}$—C(S)O—, (r) —OC(S)C($R^{115}$)$_2$—, and (s) —C($R^{115}$)$_2$C(S)O—;

alternatively, $R^{105}$, $R^{106}$, and $R^{133}$ taken together with the atoms to which they are attached form:

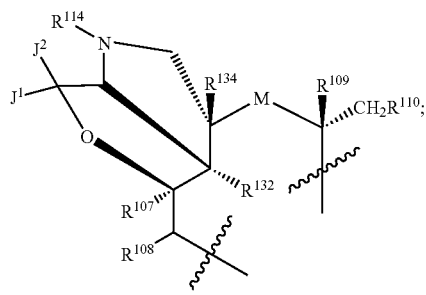

alternatively, M, $R^{105}$, and $R^{106}$ taken together with the atoms to which they are attached form:

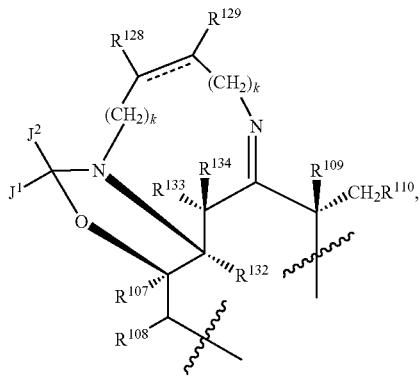

wherein in the preceding structure the dotted line indicates an optional double bond,

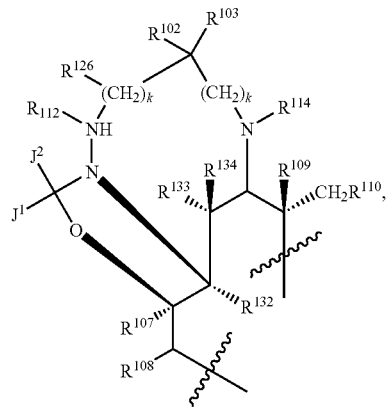

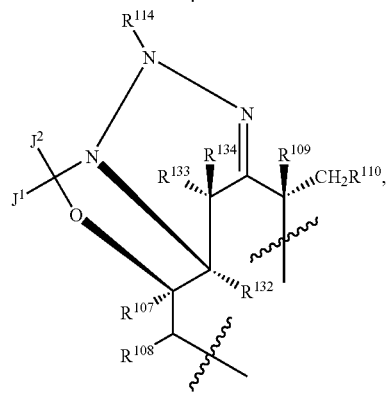

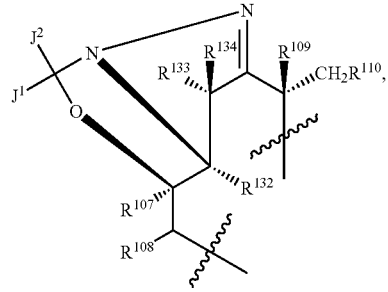

wherein $J^1$ and $J^2$ are selected from hydrogen, Cl, F, Br, I, OH, —$C_{1-6}$ alkyl, and —O($C_{1-6}$alkyl) or are taken together to form =O, =S and =N$R^{114}$, =NOR$^{114}$, =N$R^{114}$, and =N—N$R^{114}$, $R^{114}$;

alternatively, M and R$^{104}$ taken together with the atoms to which they are attached form:

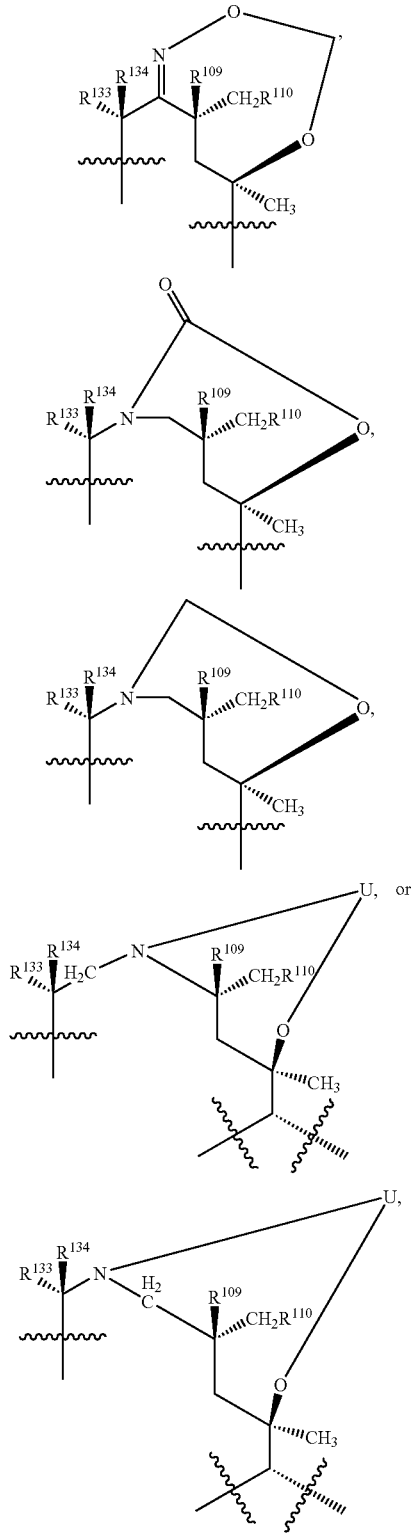

wherein U is selected from (a) —(C$_4$-alkyl)- and (b) —(C$_4$-alkenyl)-, wherein (a) and (b) are optionally further substituted with one or more R$^{117}$;

alternatively, M and R$^{105}$ are taken together with the atoms to which they are attached to form:

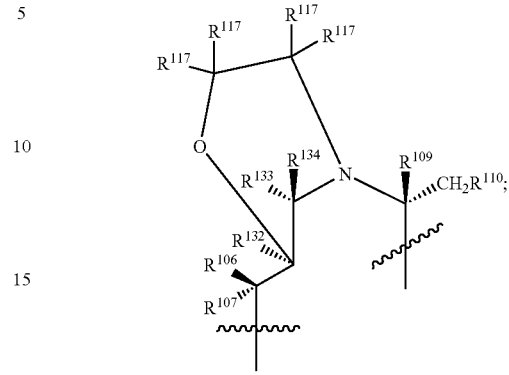

R$^{107}$ is selected from
(a) H, (b) —C$_{1-4}$ alkyl, (c) —C$_{2-4}$ alkenyl, which can be further substituted with C$_{1-12}$ alkyl or one or more halogens, (d) —C$_{2-4}$ alkynyl, which can be further substituted with C$_{1-12}$ alkyl or one or more halogens, (e) aryl or heteroaryl, which can be further substituted with C$_{1-12}$ alkyl or one or more halogens, (f) —C(O)H, (g) —COOH, (h) —CN, (i) —COOR$^{114}$, (j) —C(O)NR$^{114}$R$^{114}$, (k) —C(O)R$^{114}$, and (l) —C(O)SR$^{114}$, wherein (b) is further substituted with one or more substituents selected from (aa) —OR$^{114}$, (bb) halogen, (cc) —SR$^{114}$, (dd) C$_{1-12}$ alkyl, which can be further substituted with halogen, hydroxyl, C$_{1-6}$ alkoxy, or amino, (ee) —OR$^{114}$, (ff) —SR$^{114}$, (gg) —NR$^{114}$R$^{114}$, (hh) —CN, (ii) —NO$_2$, (jj) —NC(O)R$^{114}$, (kk) —COOR$^{114}$, (ll) —N$_3$, (mm) =N—O—R$^{114}$, (nn) =NR$^{114}$, (oo) =N—NR$^{114}$R$^{114}$, (pp) =N—NH—C(O)R$^{114}$, and (qq)=N—NH—C(O)NR$^{114}$R$^{114}$;
alternatively R$^{106}$ and R$^{107}$ are taken together with the atom to which they are attached to form an epoxide, a carbonyl, an olefin, or a substituted olefin, or a C$_3$-C$_7$ carbocyclic, carbonate, or carbamate, wherein the nitrogen of said carbamate can be further substituted with a C$_1$-C$_6$ alkyl;
R$^{108}$ is selected from:
(a) C$_{1-6}$ alkyl, (b) C$_{2-6}$ alkenyl, and (c) C$_{2-6}$ alkynyl, wherein any of (a)-(c) optionally is substituted with one or more R$^{114}$ groups;
R$^{111}$ is selected from H and —C(O)R$^{114}$;
R$^{112}$ is selected from H, OH, and OR$^{114}$;
R$^{113}$ is selected from:
(a) H, (b) R$^{114}$ (C)—C$_{1-6}$ alkyl-K—R$^{114}$, (d) —C$_{2-6}$alkenyl-K—R$^{114}$, and (e) —C$_{2-6}$ alkynyl-K—R$^{114}$, wherein any of (c)-(e) optionally is substituted with one or more R$^{115}$ groups;
R$^{114}$, at each occurrence, independently is selected from:
(a) H, (b) C$_{1-6}$ alkyl, (c) C$_{2-6}$ alkenyl, (d) C$_{2-6}$alkynyl; (e) C$_{6-10}$ saturated, unsaturated, or aromatic carbocycle, (f) 3-12 membered saturated, unsaturated, or aromatic heterocycle containing one or more heteroatoms selected from nitrogen, oxygen, and sulfur, (g) —C(O)—C$_{1-6}$ alkyl, (h) —C(O)—C$_{2-6}$ alkenyl, (i) —C(O)—C$_{2-6}$ alkynyl, (j) —C(O)—C$_{6-10}$ saturated, unsaturated, or aromatic carbocycle, (k) —C(O)-3-12 membered saturated, unsaturated, or aromatic heterocycle containing one or more heteroatoms selected from nitrogen, oxygen, and sulfur, (l) —C(O)O—C$_{1-6}$ alkyl, (m) —C(O)O—C$_{2-6}$ alkenyl, (n) —C(O)O—C$_{2-6}$ alkynyl, (o)—C(O)O—

$C_{6-10}$ saturated, unsaturated, or aromatic carbocycle, (p) —C(O)O-3-12 membered saturated, unsaturated, or aromatic heterocycle containing one or more heteroatoms selected from nitrogen, oxygen, and sulfur, (q) —C(O)NR$^{116}$R$^{116}$, (r) —NR$^{116}$CO—C2-6 alkyl, (s) —NR$^{116}$CO—C$_{6-10}$ saturated, unsaturated, or aromatic carbocycle, and (t) —NR$^{116}$C(O)-3-12 membered saturated, unsaturated, or aromatic heterocycle containing one or more heteroatoms selected from nitrogen, oxygen, and sulfur wherein any of (b)-(t) optionally is substituted with one or more R$^{115}$ groups, wherein one or more non-terminal carbon moieties of any of (b)-(d) optionally is replaced with oxygen, S(O)$_p$, or —NR$^{116}$.

alternatively, NR$^{114}$R$^{114}$R$^{114}$ forms a 3-7 membered saturated, unsaturated or aromatic ring including the nitrogen atom to which the R$^{114}$ groups are bonded and optionally one or more moieties selected from O, S(O)$_p$, N, and NR$^{118}$;

R$^{115}$ is selected from:
(a) R$^{117}$, (b) C$_{1-8}$ alkyl, (c) C$_{2-8}$ alkenyl, (d) C$_{2-8}$ alkynyl, (e) C$_{3-12}$ saturated, unsaturated, or aromatic carbocycle, (f) 3-12 membered saturated, unsaturated, or aromatic heterocycle containing one or more heteroatoms selected from nitrogen, oxygen, and sulfur,
wherein any of (b)-(f) optionally is substituted with one or more R$^{117}$ groups;

R$^{116}$, at each occurrence, independently is selected from:
(a) H, (b) C$_{1-6}$ alkyl, (c) C$_{2-6}$ alkenyl, (d) C$_{2-6}$alkynyl, (e) C$_{3-10}$ saturated, unsaturated, or aromatic carbocycle, and (f) 3-10 membered saturated, unsaturated, or aromatic heterocycle containing one or more heteroatoms selected from nitrogen, oxygen, and sulfur,
wherein one or more non-terminal carbon moieties of any of (b)-(d) optionally is replaced with oxygen, S(O)$_p$, or —NR$^{114}$, wherein any of (b)-(f) optionally is substituted with one or more moieties selected from:
(aa) carbonyl, (bb) formyl, (cc) F, (dd) Cl, (ee) Br, (ff) I, (gg) CN, (hh) N$_3$, (ii) NO$_2$, (jj) OR$^{118}$, (kk) —S(O)$_p$R$^{118}$, (ll) —C(O)R$^{118}$, (mm) —C(O)OR$^{118}$, (nn) —OC(O)R$^{118}$, (oo) —C(O)NR$^{118}$R$^{118}$, (pp) —OC(O)NR$^{118}$R$^{118}$, (qq) —C(=NR$^{118}$)R$^{118}$, (rr) —C(R$^{118}$)(R$^{118}$)OR$^{118}$, (ss) —C(R$^{118}$)$_2$OC(O)R$^{118}$, (tt) —C(R$^{118}$)(OR$^{118}$)(CH$_2$)$_r$NR$^{118}$R$^{118}$, (uu) —NR$^{118}$R$^{118}$, (vv) —NR$^{118}$OR$^{118}$, (ww) —NR$^{118}$C(O)R$^{118}$, (xx) —NR$^{118}$C(O)OR$^{118}$, (yy) —NR$^{118}$C(O)NR$^{118}$R$^{118}$, (zz) —NR$^{118}$S(O)$_r$R$^{118}$, (ab) —C(OR$^{118}$)(OR$^{118}$)R$^{118}$, (ac) —C(R$^{118}$)$_2$NR$^{118}$R$^{118}$, (ad) =NR$^{118}$, (ae) —C(S)NR$^{118}$R$^{118}$, (af) —NR$^{118}$C(S)R$^{118}$, (ag) —OC(S)NR$^{118}$R$^{118}$, (ah) —NR$^{118}$C(S)OR$^{118}$, (ai) —NR$^{118}$C(S)NR$^{118}$R$^{118}$, (aj) —SC(O)R$^{118}$, (ak) C$_{1-8}$ alkyl, (al) C$_{2-8}$ alkenyl, (am) C$_{2-8}$alkynyl, (an) C$_{1-8}$ alkoxy, (ao) C$_{1-8}$ alkylthio, (ap) C$_{1-8}$ acyl, (aq) saturated, unsaturated, or aromatic C$_{3-10}$ carbocycle, and (ar) saturated, unsaturated, or aromatic 3-10 membered heterocycle containing one or more heteroatoms selected from nitrogen, oxygen, and sulfur, alternatively, NR$^{116}$R$^{116}$ forms a 3-10 membered saturated, unsaturated or aromatic ring including the nitrogen atom to which the R$^{116}$ groups are attached and optionally one or more moieties selected from O, S(O)$_p$, N, and NR$^{118}$;
alternatively, CR$^{116}$R$^{116}$ forms a carbonyl group;

R$^{117}$, at each occurrence, is selected from:
(a) H, (b) =O, (c) F, (d) Cl, (e) Br, (f) I, (g) (CR$^{116}$R$^{116}$)$_r$CF$_3$, (h) (CR$^{116}$R$^{116}$)$_r$CN, (i) (CR$^{116}$R$^{116}$)$_r$NO2, (j) (CR$^{116}$R$^{116}$)$_r$NR$^{16}$(CR$^{116}$R$^{116}$)$_r$R$^{119}$, (k) (CR$^{116}$R$^{116}$)$_r$OR$^{119}$, (l) (CR$^{116}$R$^{116}$)$_r$S(O)$_p$(CR$^{116}$R$^{116}$)$_r$R$^9$, (m) (CR$^{116}$R$^{116}$)$_r$C(O)(CR$^{116}$R$^{116}$)$_r$R$^{119}$, (n) (CR$^{116}$R$^{116}$)$_r$OC(O)(CR$^{116}$R$^{116}$)$_r$R$^{119}$, (o) (CR$^{116}$R$^{116}$)$_r$SC(O)(CR$^{116}$R$^{116}$)$_r$R$^{119}$, (p) (CR$^{116}$R$^{116}$)$_r$C(O)O(CR$^{116}$R$^{116}$)$_t$ R$^{119}$, (q) (CR$^{116}$R$^{116}$)$_r$NR$^{116}$C(O)(CR$^{116}$R$^{116}$)$_t$R$^{119}$, (r) (CR$^{116}$R$^{116}$)$_r$C(O)NR$^{116}$(CR$^{116}$R$^{116}$)$_t$R$^{119}$, (s) (CR$^{116}$R$^{116}$)$_r$C(=NR$^{116}$)(CR$^{116}$R$^{116}$)$_t$R$^{119}$, (t) (CR$^{116}$R$^{116}$)$_r$C(=NNR$^{116}$R$^{116}$)(CR$^{116}$R$^{116}$)$_t$R$^9$, (u) (CR$^{116}$R$^{116}$)$_r$C(=NNR$^{116}$C(O)R$^{116}$)(CR$^{116}$R$^{116}$)$_r$R$^{119}$, (v) (CR$^{116}$R$^{116}$)$_r$C(=NOR$^{119}$)(CR$^{116}$R$^{116}$)$_r$R$^{119}$, (w) (CR$^{116}$R$^{116}$)$_r$NR$^{116}$C(O)O(CR$^{116}$R$^{116}$)$_r$R$^{119}$, (x) (CR$^{116}$R$^{116}$)$_r$OC(O)NR$^{116}$(CR$^{116}$R$^{116}$)$_r$R$^{119}$, (y) (CR$^{116}$R$^{116}$)$_r$NR$^{116}$C(O)NR$^{116}$(CR$^{116}$R$^{116}$)$_r$R$^{119}$, (z) (CR$^{116}$R$^{116}$)$_r$NR$^{116}$S(O)$_p$(CR$^{116}$R$^{116}$)$_r$R$^{119}$, (aa) (CR$^{116}$R$^{116}$)$_r$S(O)$_p$NR$^{116}$(CR$^{116}$R$^{116}$)$_r$R$^{119}$, (bb) (CR$^{116}$R$^{116}$)$_r$NR$^{116}$S(O)$_p$NR$^{116}$(CR$^{116}$R$^{116}$)$_r$R$^{119}$, (cc) (CR$^{116}$R$^{116}$)$_r$NR$^{116}$R$^{116}$, (dd) C$_{1-6}$ alkyl, (ee) C$_{2-6}$ alkenyl, (ff) C$_{2-6}$ alkynyl, (gg) (CR$^{116}$R$^{116}$)$_r$—C$_{3-10}$ saturated, unsaturated, or aromatic carbocycle, and (hh) (CR$^{116}$R$^{116}$)$_r$-3-10 membered saturated, unsaturated, or aromatic heterocycle containing one or more heteroatoms selected from nitrogen, oxygen, and sulfur, wherein any of (dd)-(hh) optionally is substituted with one or more R$^{119}$ groups;

alternatively, two R$^{117}$ groups can form —O(CH$_2$)$_u$O—;

R$^{118}$ is selected from:
(a) H, (b) C$_{1-6}$ alkyl, (c) C$_{2-6}$alkenyl, (d) C$_{2-6}$ alkynyl, (e) C$_{3-10}$ saturated, unsaturated, or aromatic carbocycle, (f) 3-10 membered saturated, unsaturated, or aromatic heterocycle containing one or more heteroatoms selected from nitrogen, oxygen, and sulfur, (g) —C(O)—C$_{1-6}$ alkyl, (h) —C(O)—C$_{1-6}$ alkenyl, (g) —C(O)—C$_{1-6}$ alkynyl, (i) —C(O)—C$_{3-10}$ saturated, unsaturated, or aromatic carbocycle, and (j) —C(O)-3-10 membered saturated, unsaturated, or aromatic heterocycle containing one or more heteroatoms selected from nitrogen, oxygen, and sulfur, wherein any of (b)-(j) optionally is substituted with one or more moieties selected from: (aa) H, (bb) F, (cc) Cl, (dd) Br, (ee) I, (ff) CN, (gg) NO$_2$, (hh) OH, (ii) NH$_2$, (jj) NH(C$_{1-6}$alky(l), (kk) N(C$_{1-6}$alky(l)$_2$, (ll) C$_{1-6}$ alkoxy, (mm) aryl, (nn) substituted aryl, (oo) heteroaryl, (pp) substituted heteroaryl, and (qq) C$_{1-6}$ alkyl, optionally substituted with one or more moieties selected from aryl, substituted aryl, heteroaryl, substituted heteroaryl, F, Cl, Br, I, CN, NO$_2$, and OH;

R$^{119}$, at each occurrence, independently is selected from:
(a) R$^{120}$, (b) C$_{1-6}$ alkyl, (c) C$_{2-6}$ alkenyl, (d) C$_{2-6}$ alkynyl, (e) C$_{3-10}$ saturated, unsaturated, or aromatic carbocycle, and (f) 3-10 membered saturated, unsaturated, or aromatic heterocycle containing one or more heteroatoms selected from nitrogen, oxygen, and sulfur,
wherein any of (b)-(f) optionally is substituted with one or more R$^{119}$ groups;

R$^{120}$, at each occurrence, independently is selected from:
(a) H, (b) =O, (c) F, (d) Cl, (e) Br, (f) I, (g) (CR$^{116}$R$^{116}$)$_r$CF$_3$, (h) (CR$^{116}$R$^{116}$)$_r$CN, (i) (CR$^{116}$R$^{116}$)$_r$NO$_2$, (j) (CR$^{116}$R$^{116}$)$_r$NR$^{116}$R$^{116}$, (k) (CR$^{116}$R$^{116}$)$_r$OR$^{114}$, (l) (CR$^{116}$R$^{116}$)$_r$S(O)$_p$R$^{116}$, (m) (CR$^{116}$R$^{116}$)$_r$C(O)R$^{116}$, (n) (CR$^{116}$R$^{116}$)$_r$C(O)OR$^{116}$, (o) (CR$^{116}$R$^{116}$)$_r$OC(O)R$^{116}$, (p) (CR$^{116}$R$^{116}$)$_r$NR$^{116}$C(O)R$^{116}$, (q) (CR$^{116}$R$^{116}$)$_r$C(O)NR$^{116}$R$^{116}$, (r) (CR$^{116}$R$^{116}$)$_r$C(=NR$^{116}$)R$^{116}$, (s) (CR$^{116}$R$^{116}$)$_r$NR$^{116}$C(O)NR$^{116}$R$^{116}$, (t) (CR$^{116}$R$^{116}$)$_r$NR$^{116}$S(O)$_p$R$^{116}$, (u) (CR$^{116}$R$^{116}$)$_r$S(O)$_p$NR$^{116}$R$^{116}$, (v) (CR$^{116}$R$^{116}$)$_r$ $NR^{116}S(O)_pNR^{116}R^{116}$, (w) $C_{1-6}$ alkyl, (x) $C_{2-6}$ alkenyl, (y) $C_{2-6}$ alkynyl, (z) $(CR^{116}R^{116})_r$—$C_{3-10}$ saturated, unsaturated, or aromatic carbocycle, and (aa) $(CR^{116}R^{116})_r$-3-10 membered saturated, unsaturated, or aromatic heterocycle containing one or more heteroatoms selected from nitrogen, oxygen, and sulfur,
wherein any of (w)-(aa) optionally is substituted with one or more moieties selected from $R^{116}$, F, Cl, Br, I, CN, $NO_2$, —$OR^{116}$, —$NH_2$, —$NH(C_{1-6}$ alkyl), —$N(C_{1-6}$ alkyl)$_2$, $C_{1-6}$ alkoxy, $C_{1-6}$ alkylthio, and $C_{1-6}$ acyl;

$R^{121}$, at each occurrence, independently is selected from:
(a) H, (b) —$OR^{118}$, (c) —O—$C_{1-6}$ alkyl-$OC(O)R^{118}$, (d) —O—$C_{1-6}$ alkyl-$OC(O)OR^{118}$, (e) —O—$C_{1-6}$ alkyl-$OC(O)NR^{118}R^{118}$, (f) —O—$C_{1-6}$ alkyl-$C(O)NR^{118}R^{118}$, (g) —O—$C_{1-6}$ alkyl-$NR^{118}C(O)R^{118}$, (h) —O—$C_{1-6}$ alkyl-$NR^{118}C(O)OR^{118}$, (i) —O—$C_{1-6}$ alkyl-$NR^{118}C(O)NR^{118}R^{118}$, (j) —O—$C_{1-6}$ alkyl-$NR^{118}C(=N(H)NR^{118}R^{118}$, (k) —O—$C_{1-6}$ alkyl-$S(O)_pR^{118}$, (l) —O—$C_{2-6}$ alkenyl-$OC(O)R^{118}$, (m) —O—$C_{2-6}$ alkenyl-$OC(O)OR^{118}$, (n) —O—$C_{2-6}$ alkenyl-$OC(O)NR^{118}R^{118}$, (o)—O—$C_{2-6}$ alkenyl-$C(O)NR^{118}R^{118}$, (p)—O—$C_{2-6}$ alkenyl-$NR^{118}C(O)R^{118}$, (q) —O—$C_{2-6}$ alkenyl-$NR^{118}C(O)OR^{118}$, (r) —O—$C_{2-6}$ alkenyl-$NR^{118}C(O)NR^{118}R^{118}$, (s) —O—$C_{2-6}$ alkenyl-$NR^{118}C(=N(H)NR^{118}R^{118}$, (t) —O—$C_{2-6}$ alkenyl-$S(O)_pR^{118}$, (u) —O—$C_{2-6}$ alkynyl-$OC(O)R^{118}$, (v) —O—$C_{2-6}$ alkynyl-$OC(O)OR^{118}$, (w) —O—$C_{2-6}$ alkynyl-$OC(O)NR^{118}R^{118}$, (x) —O—$C_{2-6}$ alkynyl-$C(O)NR^{118}R^{118}$, (y)—O—$C_{2-6}$ alkynyl-$NR^{118}C(O)R^{118}$, (z) —O—$C_{2-6}$ alkynyl-$NR^{118}C(O)OR^{118}$, (aa) —O—$C_{2-6}$ alkynyl-$NR^{118}C(O)NR^{118}R^{118}$, (bb) —O—$C_{2-6}$ alkynyl-$NR^{118}C(=N(H)NR^{118}R^{118}$, (cc) —O—$C_{2-6}$ alkynyl-$S(O)_pR^{118}$; and (dd) —$NR^{118}R^{118}$;
alternatively, two $R^{121}$ groups taken together form =O, =$NOR^{118}$, or =$NNR^{118}R^{118}$; $R^{122}$ is $R^{115}$;

$R^{123}$ is selected from:
(a) $R^{116}$, (b) F, (c) Cl, (d) Br, (e) I, (f) CN, (g) $NO_2$, and (h) —$OR^{114}$;
alternatively, $R^{122}$ and $R^{123}$ taken together are —$O(CH_2)_uO$—;

$R^{124}$, at each occurrence, independently is selected from:
(a) H, (b) F, (c) Cl, (d) Br, (e) I, (f) CN, (g) —$OR^{114}$, (h) —$NO_2$, (i) —$NR^{114}R^{114}$, (j) $C_{1-6}$ alkyl, (k) $C_{1-6}$ acyl, and (l) $C_{1-6}$ alkoxy;

$R^{125}$ is selected from:
(a) $C_{1-6}$ alkyl, (b) $C_{2-6}$ alkenyl, (c) $C_{2-6}$ alkynyl, (d) $C_{1-6}$ acyl, (e) $C_{1-6}$ alkoxy, (f) $C_{1-6}$ alkylthio, (g) saturated, unsaturated, or aromatic $C_{5-10}$ carbocycle, (h) saturated, unsaturated, or aromatic 5-10 membered heterocycle containing one or more heteroatoms selected from nitrogen, oxygen, and sulfur, (i) —O—$C_{1-6}$ alkyl-saturated, unsaturated, or aromatic 5-10 membered heterocycle containing one or more heteroatoms selected from nitrogen, oxygen, and sulfur, (j) —$NR^{114}$—$C_{1-6}$ alkyl-saturated, unsaturated, or aromatic 5-10 membered heterocycle containing one or more heteroatoms selected from nitrogen, oxygen, and sulfur,
(k) saturated, unsaturated, or aromatic 10-membered bicyclic ring system optionally containing one or more heteroatoms selected from nitrogen, oxygen, and sulfur, (l) saturated, unsaturated, or aromatic 13-membered tricyclic ring system optionally containing one or more heteroatoms selected from nitrogen, oxygen, and sulfur, (m) —$OR^{114}$,
(n) —$NR^{114}R^{114}$, (o) —$S(O)_pR^{114}$, and (p) —$R^{124}$,
wherein any of (a)-(l) optionally is substituted with one or more $R^{115}$ groups;
alternatively, $R^{125}$ and one $R^{124}$ group, taken together with the atoms to which they are bonded, form a 5-7 membered saturated or unsaturated carbocycle, optionally substituted with one or more $R^{115}$ groups; or a 5-7 membered saturated or unsaturated heterocycle containing one or more atoms selected from nitrogen, oxygen, and sulfur, and optionally substituted with one or more $R^{115}$ groups;

$R^{126}$ at each occurrence, independently is selected from:
(a) hydrogen, (b) an electron-withdrawing group, (c) aryl, (d) substituted aryl, (e) heteroaryl, (f) substituted heteroaryl, and (g) $C_{1-6}$ alkyl, optionally substituted with one or more $R^{115}$ groups;
alternatively, any $R^{126}$ and any $R^{123}$, taken together with the atoms to which they are bonded, form a 5-7 membered saturated or unsaturated carbocycle, optionally substituted with one or more $R^{115}$ groups; or a 5-7 membered saturated or unsaturated heterocycle containing one or more atoms selected from nitrogen, oxygen, and sulfur, and optionally substituted with one or more $R^{115}$ groups;

$R^{109}$ is H or F;
$R^{127}$ is $R^{114}$, a monosaccharide or disaccharide (including amino sugars and halo sugar(s), —$(CH_2)_n$—(O—$CH_2CH_2$—)$_m$—$O(CH_2)_pCH_3$ or —$(CH_2)_n$—(O—$CH_2CH_2$—)$_m$—OH
$R^{128}$ is $R^{114}$.
$R^{129}$ is $R^{114}$;
$R^{110}$ is $R^{114}$
Alternatively, $R^{109}$ and $R^{110}$ taken together with the carbons to which they are attached form:

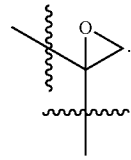

Alternately, $R^{128}$ and $R^{129}$ together with the carbons to which they are attached form a 3-6 membered saturated, unsaturated or aromatic carbocyclic or heterocyclic ring which can optionally be substituted with one or more $R^{114}$ groups;

$R^{132}$, $R^{133}$, and $R^{134}$ are each independently selected from (a) H, (b) F, (c) Cl, (d) Br, (e) —$OR^{114}$, (f) —$SR^{114}$, (g) —$NR^{114}R^{114}$, and (h) $C_{1-6}$ alkyl, wherein (h) optionally is substituted with one or more $R^{115}$ groups;
alternatively, $R^{132}$ and $R^{133}$ are taken together to form a carbon-carbon double;
alternatively, $R^{133}$ and $R^{134}$ are taken together to form =O, =S, =$NOR^{114}$, =$NR^{114}$, and =N—$NR^{114}$, $R^{114}$;
alternatively, $R^{105}$ and $R^{134}$ are taken together with the carbons to which they are attached to form a 3-membered ring, said ring optionally containing an oxygen or nitrogen atom, and said ring being optionally substituted with one or more $R^{114}$ groups;
alternatively when M is a carbon moiety, $R^{134}$ and M are taken together to form a carbon-carbon double bond;
k, at each occurrence is 0, 1, or 2;
m, at each occurrence is 0, 1, 2, 3, 4, or 5;
n, at each occurrence is 1, 2, or 3.

In further embodiments of the present invention, T is selected from:
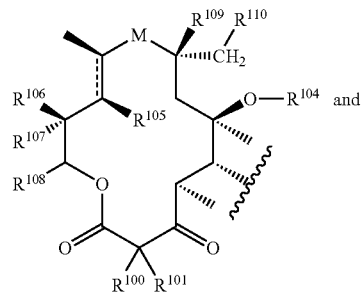 and
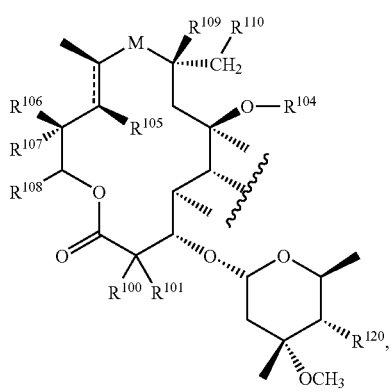
wherein M, $R^{100}$, $R^{101}$, $R^{104}$, $R^{105}$, $R^{106}$, $R^{107}$, $R^{108}$, $R^{109}$, $R^{110}$, and $R^{120}$ are as described above and where the dotted lines indicate optional double bonds.
In further embodiments of the present invention, T is selected from:
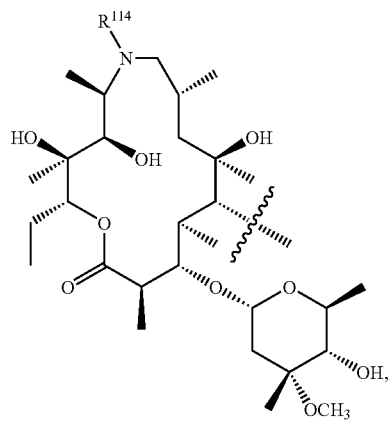
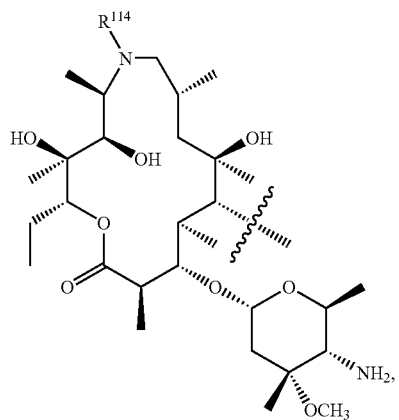
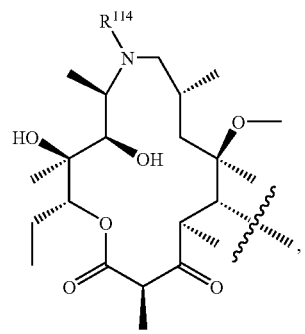
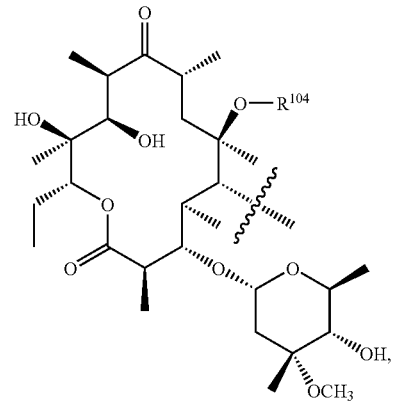
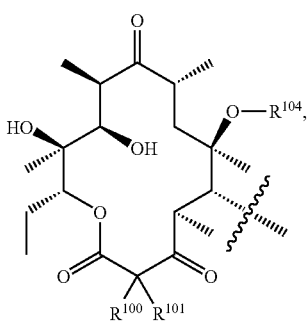

-continued
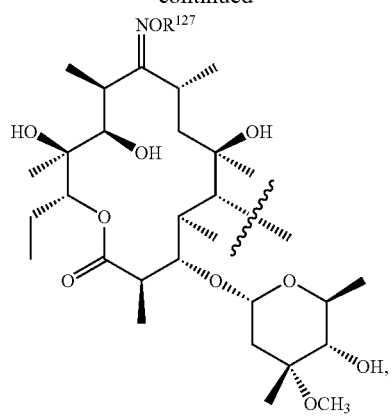
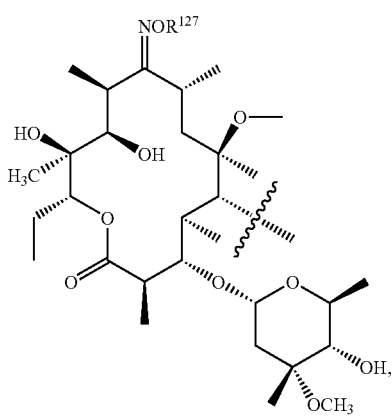
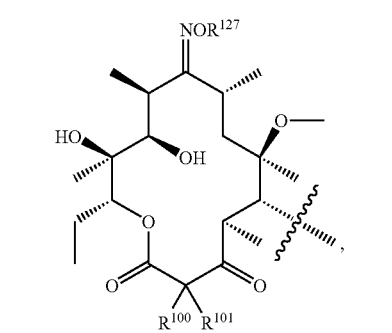
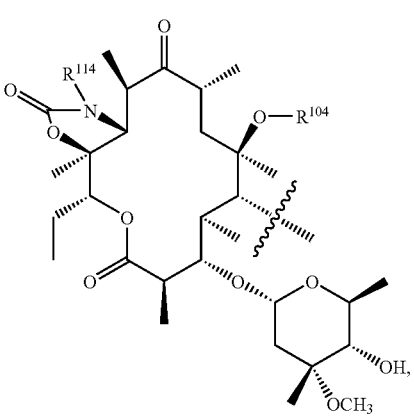
-continued
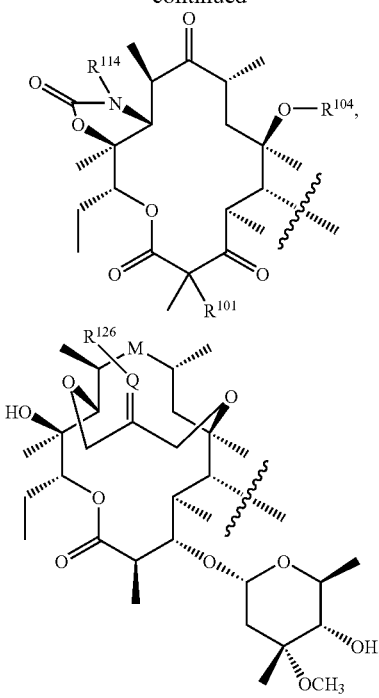
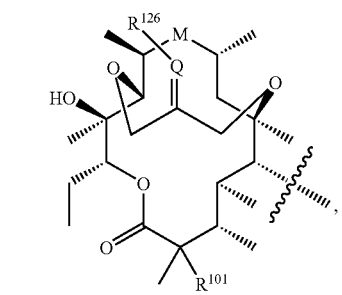
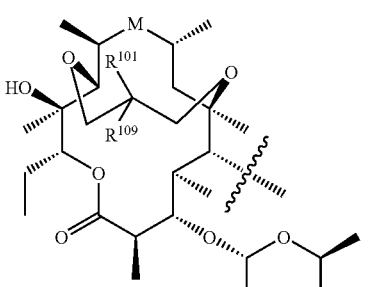
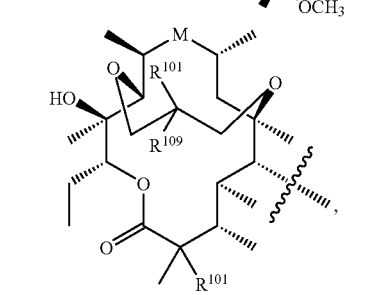

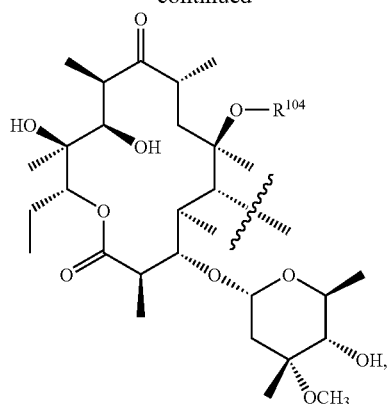
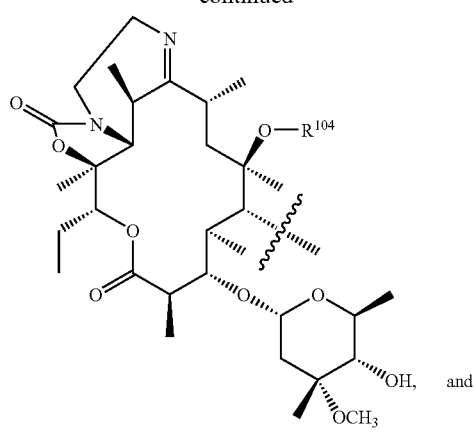
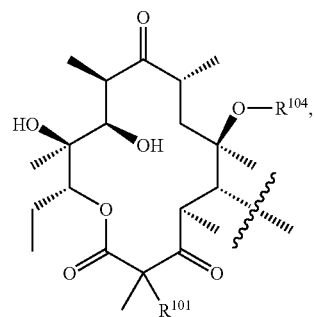
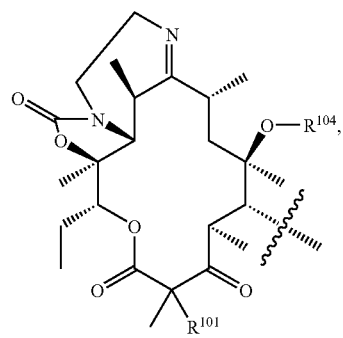
wherein M, $R^{100}$, $R^{101}$, $R^{102}$, $R^{104}$, $R^{109}$, $R^{114}$, $R^{126}$ and $R^{127}$ are as described above.
In further embodiments of the present invention, T is selected from:
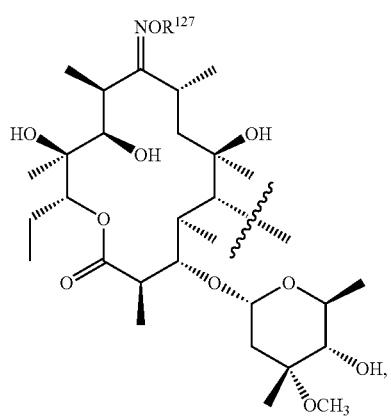
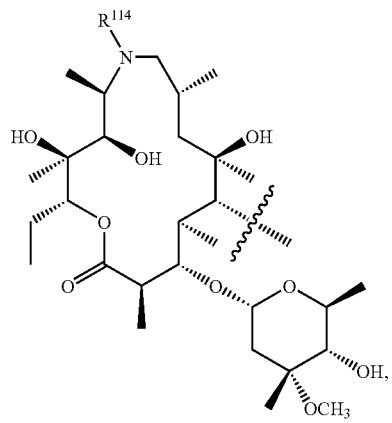
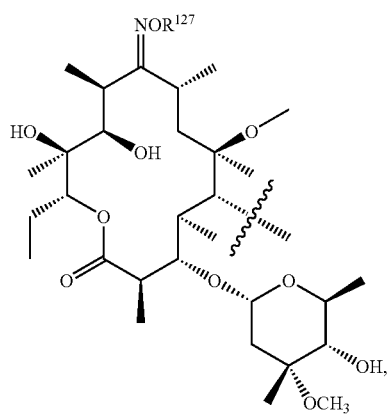
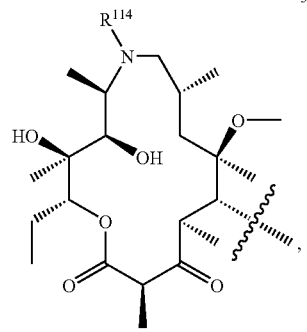

33
-continued
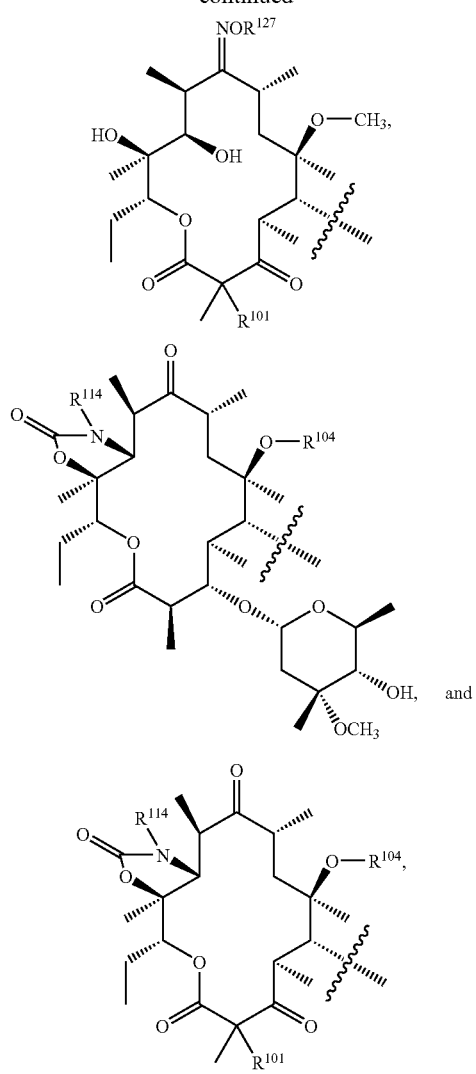
wherein M, $R^1$, $R^2$, $R^{104}$, $R^{114}$, $R^{109}$ and $R^{127}$ are as described above.
In further embodiments of the present invention T is selected from T1 through T33:
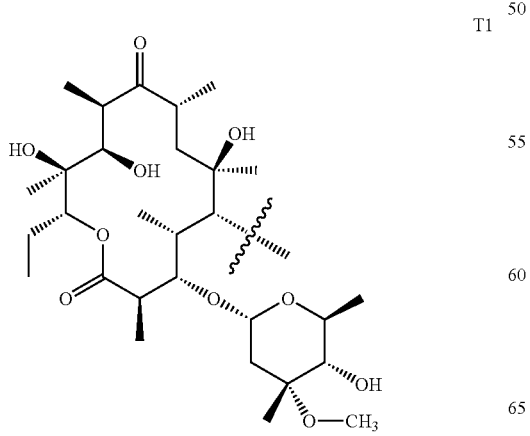
T1
34
-continued
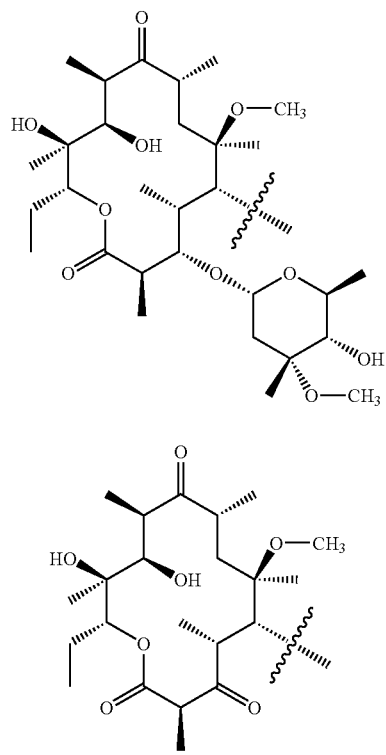
T2
T3
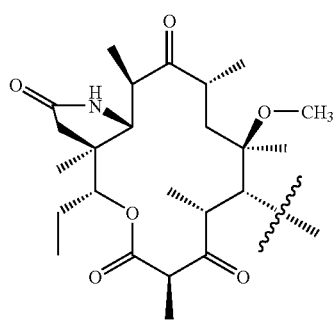
T4
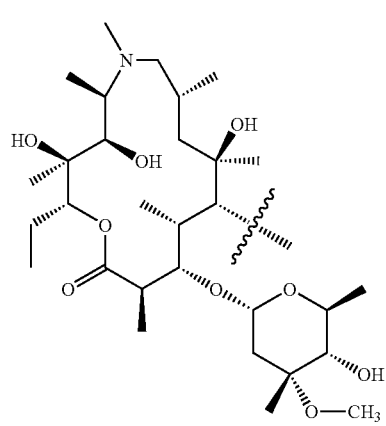
T5

-continued
T6
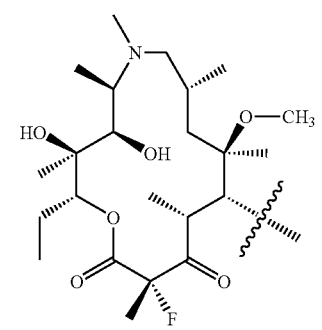
T7
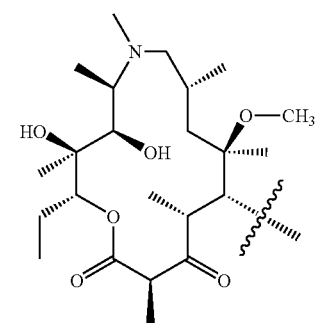
T8
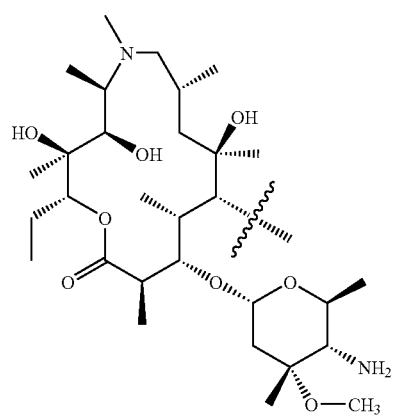
T9
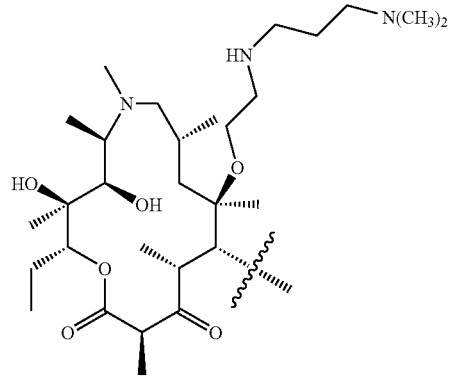
-continued
T10
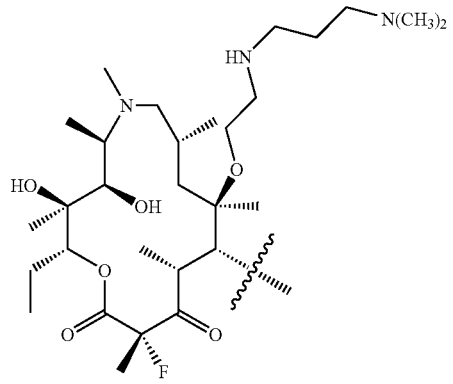
T11
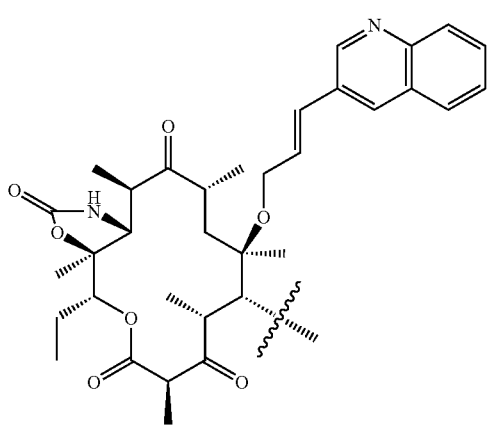
T12
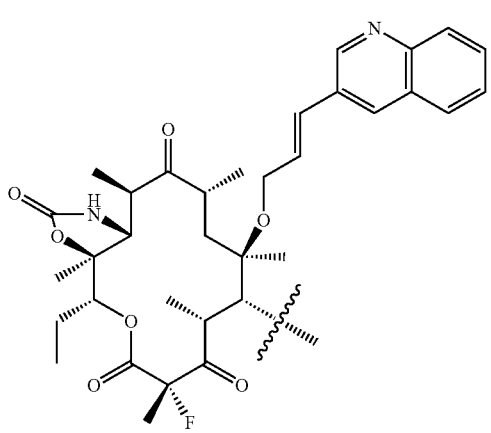
T13
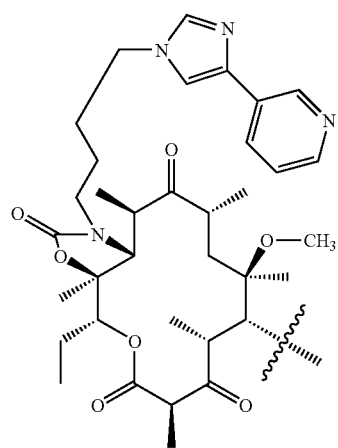

37
-continued
T14
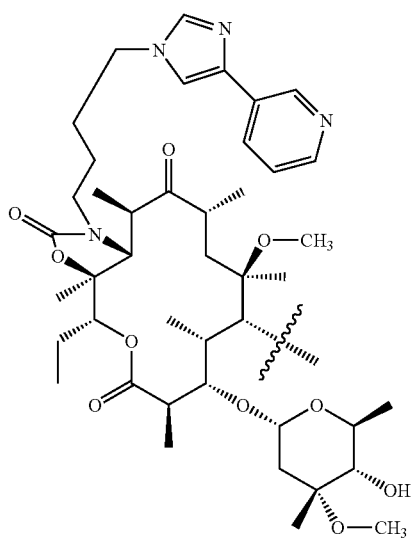
T15
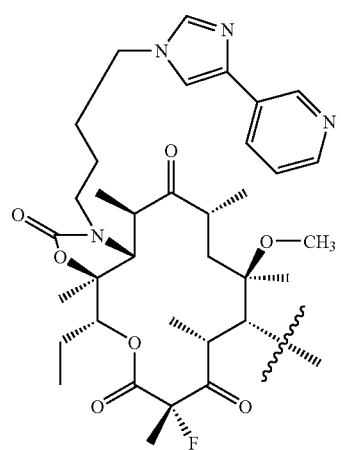
T16
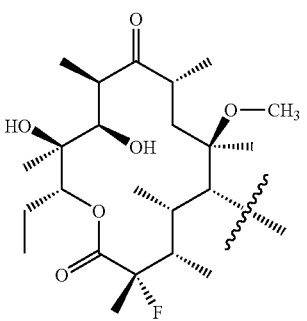
38
-continued
T17
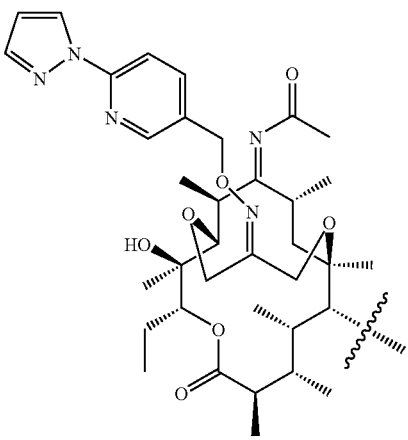
T18
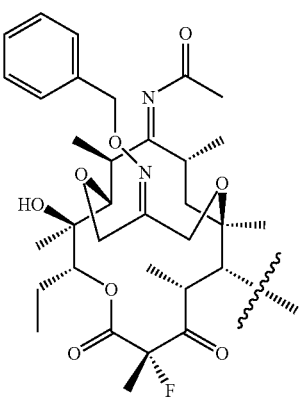
T19
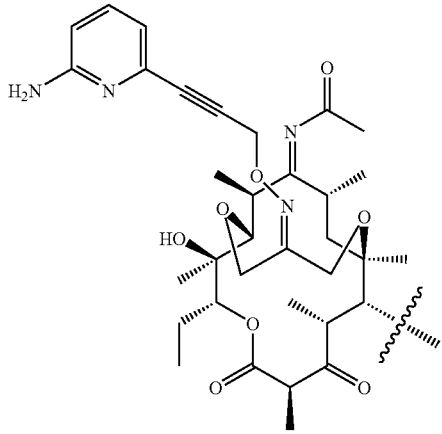
T20
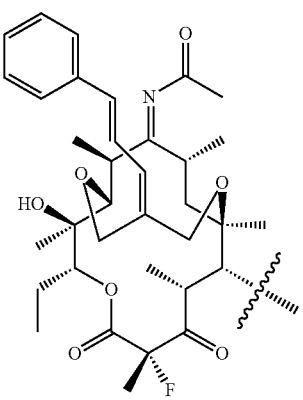

T21
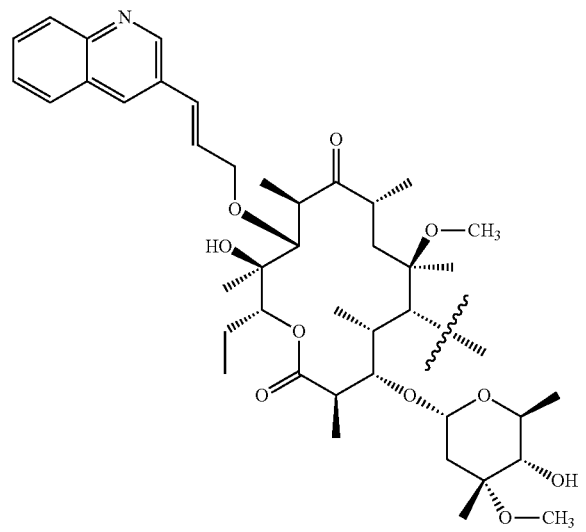
T22
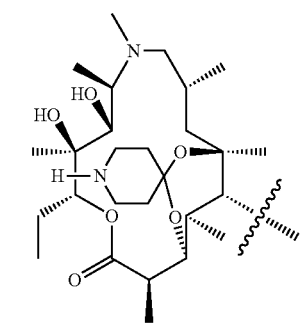
T23
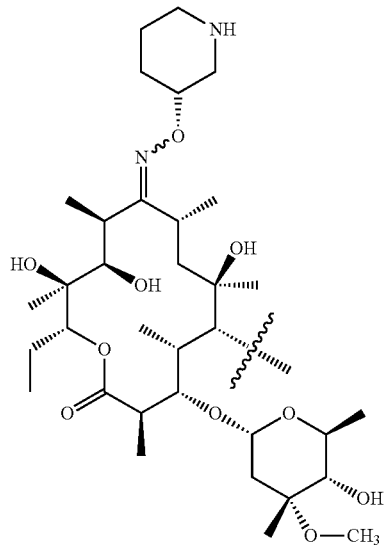
T24
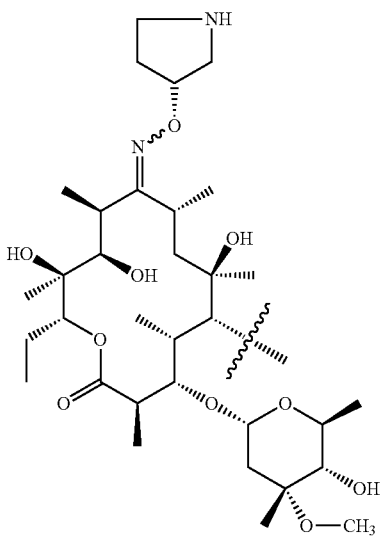
T25
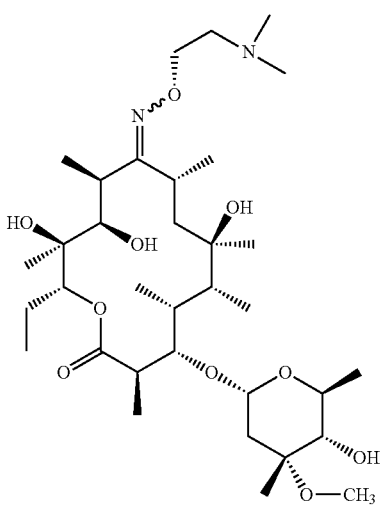
T26
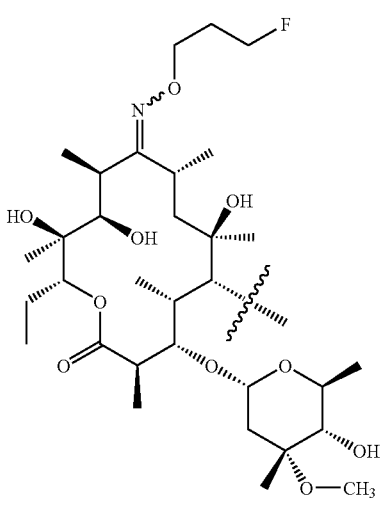

T27
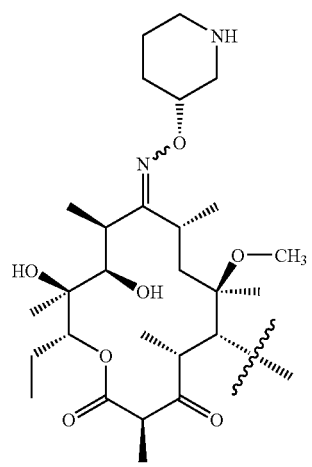
T28
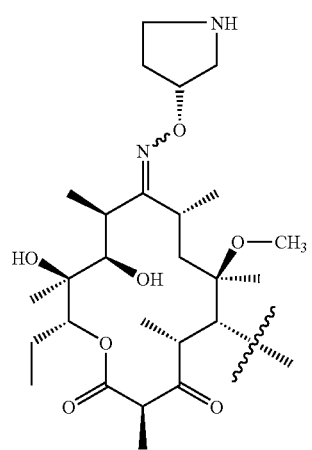
T29
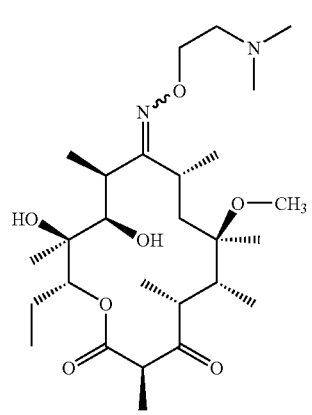
T30
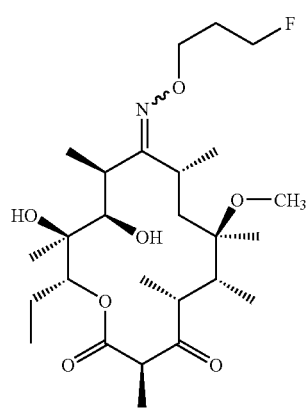
T31
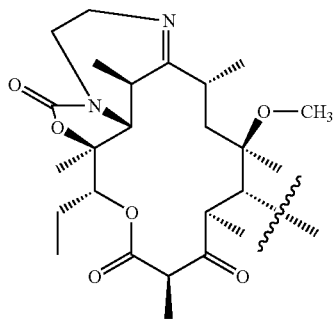
T32
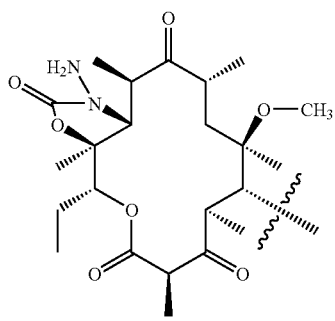
T33
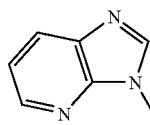
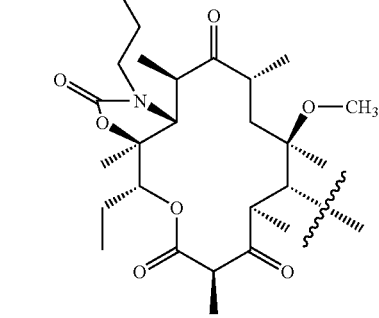
In the present invention, the macrolide, "T" is defined to include various 14- and 15-membered ring systems, which can contain one or more heteroatoms. Also, as defined herein, the macrolide, "T" is connected via a macrocyclic ring carbon atom", which means that the connection or bond is made to a carbon atom on the 14- or 15-membered ring of the macrolide moiety. The macrolide can include further substituents, including ring substituents. For example, the substituent designated as $R^{103}$ can in certain embodiments be a sugar moiety, e.g. a cladinose sugar, or the substituents such as $R^{104}$ and $R^{105}$ are taken together in certain embodiments to form a bridged bicyclic ring system with the macrolide ring, or the substituents $R^{105}$ and $R^{106}$, are taken together in certain embodiments to form a fused bicyclic ring system with the macrolide ring, or the substituents or components M, $R^{105}$, and $R^{106}$ are taken together to form a fused tricyclic ring system with the macrolide ring, etc. It is also recognized in the present invention that "T" is depicted as being connected to a 6-membered ring, for example in certain embodiments a desosamine sugar ring.

As is seen from the foregoing, the macrolide component of the compounds of the present invention can comprise a wide range of structures. Examples of such macrolide components and their syntheses are provided in the following documents, all of which are incorporated by reference in their entirety: PCT application No. WO 2005/118610, published Dec. 15, 2005, to Rib-X Pharmaceuticals, Inc.; PCT application No. WO 2005/085266, published Sep. 15, 2005, to Rib-X Pharmaceuticals, Inc.; PCT application No. WO 2005/049632, published Jun. 2, 2005, to Rib-X Pharmaceuticals, Inc.; PCT application No. WO 2005/042554, published May 12, 2005, to Rib-X Pharmaceuticals, Inc.; PCT application No. WO 2004/078770, published Sep. 16, 2004, to Rib-X Pharmaceuticals, Inc.; PCT application No. WO 2004/029066, published Apr. 8, 2004, to Rib-X Pharmaceuticals, Inc.; U.S. Pat. No. 6,992,069, to Gu et al., issued Jan. 31, 2006; U.S. Pat. No. 6,953,782, to Phan et al., issued Oct. 11, 2005; U.S. Pat. No. 6,939,861, to Ashley et al., issued Sep. 6, 2005; U.S. Pat. No. 6,927,057, to Khosla et al., issued Aug. 9, 2005; U.S. Pat. No. 6,794,366, to Chu et al., issued Sep. 21, 2004; U.S. Pat. No. 6,762,168, to Chu, issued Jul. 13, 2004; U.S. Pat. No. 6,756,359, to Chu et al, issued Jun. 29, 2994; U.S. Pat. No. 6,750,205, to Ashley et al, issued Jun. 15, 2004; U.S. Pat. No. 6,740,642, to Angehrn et al., issued May 25, 2004; U.S. Pat. No. 6,727,352, to Cheng et al., issued Apr. 27, 2004; U.S. Patent Application Publication No. US 2006/0154881, to Or et al., published Jul. 13, 2006; U.S. Patent Application Publication No. US 2006/0142215, to Tang et al., published Jun. 29, 2006; U.S. Patent Application Publication No. US 2006/0142214, to Or et al, published Jun. 29, 2006; U.S. Patent Application Publication No. US 2006/0122128, to Or et al., published Jun. 8, 2006; U.S Patent Application Publication No. US 2006/0069048, to Or et al. published Mar. 30, 2006; U.S. Patent Application Publication No. US 2005/0272672, to Li et al., published Dec. 8, 2005; U.S. Patent Application Publication No US 2005/0009764, to Burger et al, published Jan. 13, 2005; PCT application No. WO 2006/067589, to Pfizer Products Inc., published Jun. 29, 2006; PCT application No. WO 2004/096823, to Chiron Corporation, published Nov. 11, 2004; PCT application No. WO 2004/096822, to Chiron Corporation, published Nov. 11, 2004; PCT application No. WO 2004/080391, to Optimer Pharmaceuticals, Inc., published Sep. 23, 2004; PCT application No. WO 2004/078771, to Taisho Pharmaceutical Co., Ltd., published Sep. 16, 2004; PCT application no. WO 03/061671, to Kosan Biosciences, Inc. published Jul. 31, 2003; and European Patent Document EP 1 256 587 B1, to the Kitasato Institute, granted Mar. 29, 2006.

The invention also provides a compound having the structure corresponding to any one of the structures listed in Table 1, 1A or 1C, or a pharmaceutically acceptable salt, ester, N-oxide, or prodrug thereof.

The invention also provides a pharmaceutical composition that contains one or more of the compounds described above and a pharmaceutically acceptable carrier.

The invention also provides a method for treating or preventing a disease state in a mammal by administering to a mammal in need thereof an effective amount of one or more of the compounds described above.

The invention also provides a method of treating a microbial infection in a mammal by administering to the mammal an effective amount of one or more of the compounds described above.

The invention also provides a method of treating a fungal infection in a mammal by administering to the mammal an effective amount of one or more of the compounds described above.

The invention also provides a method of treating a parasitic disease in a mammal by administering to the mammal an effective amount of one or more of the compounds described above.

The invention also provides a method of treating a proliferative disease in a mammal by administering to the mammal an effective amount of one or more of the compounds described above.

The invention also provides a method of treating a viral infection in a mammal by administering to the mammal an effective amount of one or more of the compounds described above.

The invention also provides a method of treating an inflammatory disease in a mammal by administering to the mammal an effective amount of one or more of the compounds described above.

The invention also provides a method of treating a gastrointestinal motility disorder in a mammal by administering to the mammal an effective amount of one or more of the compounds described above.

The invention also provides a method of treating or preventing a disease state in a mammal caused or mediated by a nonsense or missense mutation by administering to the mammal an effective amount of one or more of the compounds described above to suppress expression of the nonsense or missense mutation.

In the methods described herein, the compound or compounds are administered orally, parentally, or topically.

The invention also provides a method of synthesizing the compounds described above.

The invention also provides a medical device containing one or more of the compounds described above. For example, the device is a stent.

3. SYNTHESIS OF THE COMPOUNDS OF THE INVENTION

The invention provides methods for making the compounds of the invention. The following schemes depict exemplary chemistries available for synthesizing the compounds of the invention.

Scheme 1 illustrates the synthesis of triazole compounds of type 5 and 6. Erythromycin can be N-demethylated as described in the art (U.S. Pat. No. 3,725,385; Flynn et al. (1954) J. AM. CHEM. SOC. 76: 3121; Ku et al. (1997) BIOORG. MED. CHEM. LETT. 7: 1203; Stenmark et al. (2000) J. ORG. CHEM. 65: 3875) to afford secondary amine 1. Alkylation of 1 with electrophiles of type 2 yields alkynes of type 3 containing an alkyl chain of appropriate length, generally between one and about four carbon atoms between the nitrogen atom and the alkyne group. Cycloaddition of azides of type 4 with alkynes 3 generates two regioisomeric triazole products. The reaction can be thermally catalyzed, or a number of catalysts could be added to facilitate the reaction (such as, but not limited to, copper (I) iodide: see Tornoe, C. W. et al. (2002) J. ORG. CHEM. 67: 3057). The major isomer (for steric reasons) is the "anti" isomer 5, a 1,4 disubstituted triazole. The minor component is the "syn" isomer 6, a 1,5 disubstituted triazole.

Scheme 1

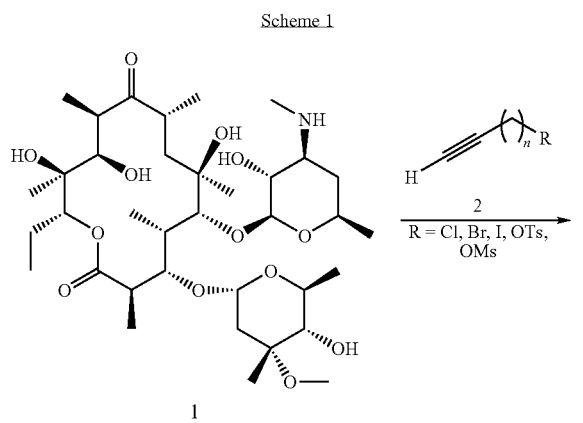

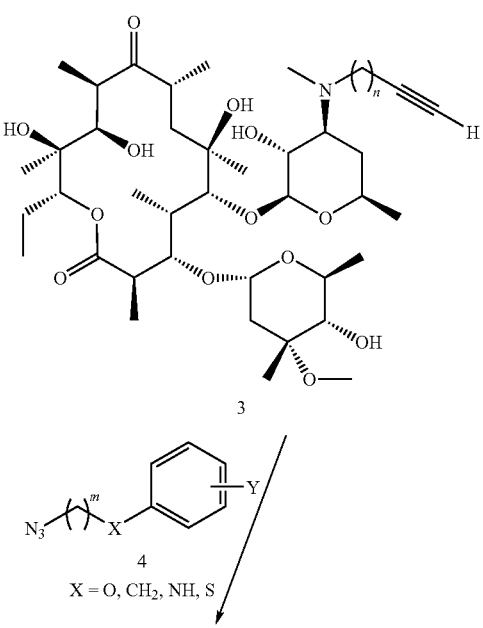

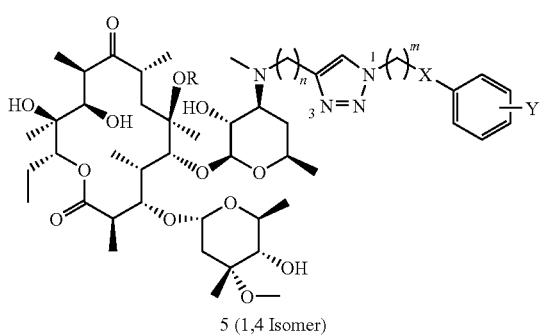

5 (1,4 Isomer)

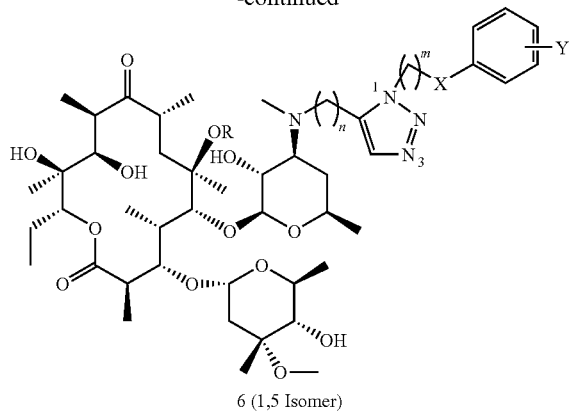

6 (1,5 Isomer)

It is to be understood that other macrolide compounds such as, but not limited to, azithromycin and clarithromycin, could be N-demethylated and serve as starting materials for the chemistry exemplified in Scheme 1. Target compounds derived from such alternate macrolide precursors are to be considered within the scope of the present invention.

An alternate approach to derivatives of type 5 and 6 is illustrated by Scheme 2. Acetylenic alcohols of type 14 can be treated with azides 4 to yield intermediate alcohol 15 (along with a minor amount of the regioisomeric triazole). Tosylation of 15 will provide tosylates 16 which can serve as alkylating agents for macrolide amines of type 1 to afford targets 5 (and its isomer 6). It will be appreciated that other sulfonate derivatives or halides could be formed from intermediate alcohol 15, and these would be useful as electrophiles for the alkylation of macrolide amines such as 1 to afford compounds of the invention.

Scheme 2

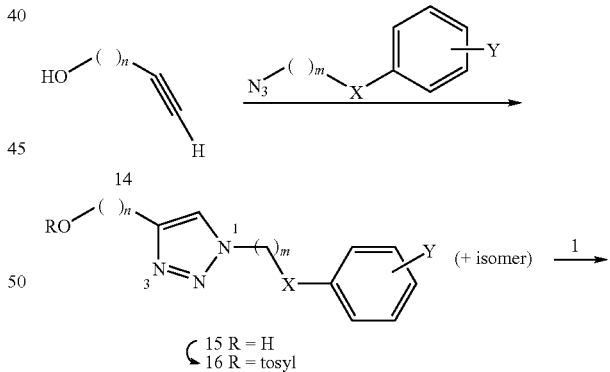

Other starting materials for the synthesis of compounds of the present invention are readily synthesizable.

4. CHARACTERIZATION OF COMPOUNDS OF THE INVENTION

Compounds designed, selected and/or optimized by methods described above, once produced, can be characterized using a variety of assays known to those skilled in the art to determine whether the compounds have biological activity. For example, the molecules can be characterized by conventional assays, including but not limited to those assays described below, to determine whether they have a predicted activity, binding activity and/or binding specificity.

Furthermore, high-throughput screening can be used to speed up analysis using such assays. As a result, it can be possible to rapidly screen the molecules described herein for activity, for example, as anti-cancer, anti-bacterial, anti-fungal, anti-parasitic or anti-viral agents. Also, it can be possible to assay how the compounds interact with a ribosome or ribosomal subunit and/or are effective as modulators (for example, inhibitors) of protein synthesis using techniques known in the art. General methodologies for performing high-throughput screening are described, for example, in Devlin (1998) *High Throughput Screening*, Marcel Dekker, and U.S. Pat. No. 5,763,263. High-throughput assays can use one or more different assay techniques including, but not limited to, those described below.

(1) Surface Binding Studies.

A variety of binding assays can be useful in screening new molecules for their binding activity. One approach includes surface plasmon resonance (SPR) that can be used to evaluate the binding properties of molecules of interest with respect to a ribosome, ribosomal subunit or a fragment thereof.

SPR methodologies measure the interaction between two or more macromolecules in real-time through the generation of a quantum-mechanical surface plasmon. One device, (BIAcore Biosensor® from Pharmacia Biosensor, Piscataway, N.J.) provides a focused beam of polychromatic light to the interface between a gold film (provided as a disposable biosensor "chip") and a buffer compartment that can be regulated by the user. A 100 nm thick "hydrogel" composed of carboxylated dextran that provides a matrix for the covalent immobilization of analytes of interest is attached to the gold film. When the focused light interacts with the free electron cloud of the gold film, plasmon resonance is enhanced. The resulting reflected light is spectrally depleted in wavelengths that optimally evolved the resonance. By separating the reflected polychromatic light into its component wavelengths (by means of a prism), and determining the frequencies that are depleted, the BIAcore establishes an optical interface which accurately reports the behavior of the generated surface plasmon resonance. When designed as above, the plasmon resonance (and thus the depletion spectrum) is sensitive to mass in the evanescent field (which corresponds roughly to the thickness of the hydrogel). If one component of an interacting pair is immobilized to the hydrogel, and the interacting partner is provided through the buffer compartment, the interaction between the two components can be measured in real time based on the accumulation of mass in the evanescent field and its corresponding effects of the plasmon resonance as measured by the depletion spectrum. This system permits rapid and sensitive real-time measurement of the molecular interactions without the need to label either component.

(2) Fluorescence Polarization.

Fluorescence polarization (FP) is a measurement technique that can readily be applied to protein-protein, protein-ligand, or RNA-ligand interactions in order to derive $IC_{50}$s and Kds of the association reaction between two molecules. In this technique one of the molecules of interest is conjugated with a fluorophore. This is generally the smaller molecule in the system (in this case, the compound of interest). The sample mixture, containing both the ligand-probe conjugate and the ribosome, ribosomal subunit or fragment thereof, is excited with vertically polarized light. Light is absorbed by the probe fluorophores, and re-emitted a short time later. The degree of polarization of the emitted light is measured. Polarization of the emitted light is dependent on several factors, but most importantly on viscosity of the solution and on the apparent molecular weight of the fluorophore. With proper controls, changes in the degree of polarization of the emitted light depends only on changes in the apparent molecular weight of the fluorophore, which in-turn depends on whether the probe-ligand conjugate is free in solution, or is bound to a receptor. Binding assays based on FP have a number of important advantages, including the measurement of $IC_{50}$s and Kds under true homogenous equilibrium conditions, speed of analysis and amenity to automation, and ability to screen in cloudy suspensions and colored solutions.

(3) Protein Synthesis.

It is contemplated that, in addition to characterization by the foregoing biochemical assays, the compound of interest can also be characterized as a modulator (for example, an inhibitor of protein synthesis) of the functional activity of the ribosome or ribosomal subunit.

Furthermore, more specific protein synthesis inhibition assays can be performed by administering the compound to a whole organism, tissue, organ, organelle, cell, a cellular or subcellular extract, or a purified ribosome preparation and observing its pharmacological and inhibitory properties by determining, for example, its inhibition constant ($IC_{50}$) for inhibiting protein synthesis. Incorporation of $^3$H leucine or $^{35}$S methionine, or similar experiments can be performed to investigate protein synthesis activity. A change in the amount or the rate of protein synthesis in the cell in the presence of a molecule of interest indicates that the molecule is a modulator of protein synthesis. A decrease in the rate or the amount of protein synthesis indicates that the molecule is a inhibitor of protein synthesis.

Furthermore, the compounds can be assayed for anti-proliferative or anti-infective properties on a cellular level. For example, where the target organism is a microorganism, the activity of compounds of interest can be assayed by growing the microorganisms of interest in media either containing or lacking the compound. Growth inhibition can be indicative that the molecule can be acting as a protein synthesis inhibitor. More specifically, the activity of the compounds of interest against bacterial pathogens can be demonstrated by the ability of the compound to inhibit growth of defined strains of human pathogens. For this purpose, a panel of bacterial strains can be assembled to include a variety of target pathogenic species, some containing resistance mechanisms that have been characterized. Use of such a panel of organisms permits the determination of structure-activity relationships not only in regards to potency and spectrum, but also with a view to obviating resistance mechanisms. The assays can be performed in microtiter trays according to conventional methodologies as published by The National Committee for Clinical Laboratory Standards (NCCLS) guidelines (NCCLS. M7-A5-Methods for Dilution Antimicrobial Susceptibility Tests for Bacteria That Grow Aerobically; Approved Standard-Fifth Edition. NCCLS Document M100-S12/M7 (ISBN 1-56238-394-9)).

5. FORMULATION AND ADMINISTRATION

The compounds of the invention can be useful in the prevention or treatment of a variety of human or other animal, including mammalian and non mammalian, disorders, including for example, bacterial infection, fungal infections, viral infections, parasitic diseases, and cancer. It is contemplated that, once identified, the active molecules of the invention can be incorporated into any suitable carrier prior to use. The dose of active molecule, mode of administration and use of suitable carrier will depend upon the intended recipient and target organism. The formulations, both for veterinary and for human medical use, of compounds according to the present invention typically include such compounds in association with a pharmaceutically acceptable carrier.

The carrier(s) should be "acceptable" in the sense of being compatible with the other ingredients of the formulations and not deleterious to the recipient. Pharmaceutically acceptable carriers, in this regard, are intended to include any and all solvents, dispersion media, coatings, anti-bacterial and anti-fungal agents, isotonic and absorption delaying agents, and the like, compatible with pharmaceutical administration. The use of such media and agents for pharmaceutically active substances is known in the art. Except insofar as any conventional media or agent is incompatible with the active compound, use thereof in the compositions is contemplated. Supplementary active compounds (identified or designed according to the invention and/or known in the art) also can be incorporated into the compositions. The formulations can conveniently be presented in dosage unit form and can be prepared by any of the methods well known in the art of pharmacy/microbiology. In general, some formulations are prepared by bringing the compound into association with a liquid carrier or a finely divided solid carrier or both, and then, if necessary, shaping the product into the desired formulation.

A pharmaceutical composition of the invention should be formulated to be compatible with its intended route of administration. Examples of routes of administration include oral or parenteral, for example, intravenous, intradermal, inhalation, transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide.

Useful solutions for oral or parenteral administration can be prepared by any of the methods well known in the pharmaceutical art, described, for example, in Remington's *Pharmaceutical Sciences*, (Gennaro, A., ed.), Mack Pub., (1990). Formulations for parenteral administration can also include glycocholate for buccal administration, methoxysalicylate for rectal administration, or citric acid for vaginal administration. The parenteral preparation can be enclosed in ampoules, disposable syringes or multiple dose vials made of glass or plastic. Suppositories for rectal administration also can be prepared by mixing the drug with a non-irritating excipient such as cocoa butter, other glycerides, or other compositions which are solid at room temperature and liquid at body temperatures. Formulations also can include, for example, polyalkylene glycols such as polyethylene glycol, oils of vegetable origin, and hydrogenated naphthalenes. Formulations for direct administration can include glycerol and other compositions of high viscosity. Other potentially useful parenteral carriers for these drugs include ethylene-vinyl acetate copolymer particles, osmotic pumps, implantable infusion systems, and liposomes. Formulations for inhalation administration can contain as excipients, for example, lactose, or can be aqueous solutions containing, for example, polyoxyethylene-9-lauryl ether, glycocholate and deoxycholate, or oily solutions for administration in the form of nasal drops, or as a gel to be applied intranasally. Retention enemas also can be used for rectal delivery.

Formulations of the present invention suitable for oral administration can be in the form of: discrete units such as capsules, gelatin capsules, sachets, tablets, troches, or lozenges, each containing a predetermined amount of the drug, a powder or granular composition; a solution or a suspension in an aqueous liquid or non-aqueous liquid; or an oil-in-water emulsion or a water-in-oil emulsion. The drug can also be administered in the form of a bolus, electuary or paste. A tablet can be made by compressing or moulding the drug optionally with one or more accessory ingredients. Compressed tablets can be prepared by compressing, in a suitable machine, the drug in a free-flowing form such as a powder or granules, optionally mixed by a binder, lubricant, inert diluent, surface active or dispersing agent. Moulded tablets can be made by moulding, in a suitable machine, a mixture of the powdered drug and suitable carrier moistened with an inert liquid diluent.

Oral compositions generally include an inert diluent or an edible carrier. For the purpose of oral therapeutic administration, the active compound can be incorporated with excipients. Oral compositions prepared using a fluid carrier for use as a mouthwash include the compound in the fluid carrier and are applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose; a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor ELTM (BASF, Parsippany, N.J.) or phosphate buffered saline (PBS). It should be stable under the conditions of manufacture and storage and should be preserved against the contaminating action of microorganisms such as bacteria and fungi. The carrier can be a solvent or dispersion medium containing, for example, water, ethanol, polyol (for example, glycerol, propylene glycol, and liquid polyethylene glycol), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as manitol, sorbitol, or sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filter sterilization. Generally, dispersions are prepared by incorporating the active compound into a sterile vehicle which contains a basic dispersion medium and the required other ingredients from those enumerated above. In the case of sterile powders for the preparation of sterile injectable solutions, methods of preparation include vacuum drying and freeze-drying which yields a powder of the active ingredient plus any additional desired ingredient from a previously sterile-filtered solution thereof.

Formulations suitable for intra-articular administration can be in the form of a sterile aqueous preparation of the drug that can be in microcrystalline form, for example, in the form of an aqueous microcrystalline suspension. Liposomal formulations or biodegradable polymer systems can also be used to present the drug for both intra-articular and ophthalmic administration.

Formulations suitable for topical administration, including eye treatment, include liquid or semi-liquid preparations such as liniments, lotions, gels, applicants, oil-in-water or water-in-oil emulsions such as creams, ointments or pastes; or solutions or suspensions such as drops. Formulations for topical administration to the skin surface can be prepared by dispersing the drug with a dermatologically acceptable carrier such as a lotion, cream, ointment or soap. Particularly useful are carriers capable of forming a film or layer over the skin to localize application and inhibit removal. For topical administration to internal tissue surfaces, the agent can be dispersed in a liquid tissue adhesive or other substance known to enhance adsorption to a tissue surface. For example, hydroxypropylcellulose or fibrinogen/thrombin solutions can be used to advantage. Alternatively, tissue-coating solutions, such as pectin-containing formulations can be used.

For inhalation treatments, inhalation of powder (self-propelling or spray formulations) dispensed with a spray can, a nebulizer, or an atomizer can be used. Such formulations can be in the form of a fine powder for pulmonary administration from a powder inhalation device or self-propelling powder-dispensing formulations. In the case of self-propelling solution and spray formulations, the effect can be achieved either by choice of a valve having the desired spray characteristics (i.e., being capable of producing a spray having the desired particle size) or by incorporating the active ingredient as a suspended powder in controlled particle size. For administration by inhalation, the compounds also can be delivered in the form of an aerosol spray from pressured container or dispenser which contains a suitable propellant, e.g., a gas such as carbon dioxide, or a nebulizer.

Systemic administration also can be by transmucosal or transdermal means. For transmucosal or transdermal administration, penetrants appropriate to the barrier to be permeated are used in the formulation. Such penetrants generally are known in the art, and include, for example, for transmucosal administration, detergents and bile salts. Transmucosal administration can be accomplished through the use of nasal sprays or suppositories. For transdermal administration, the active compounds typically are formulated into ointments, salves, gels, or creams as generally known in the art.

The active compounds can be prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. Liposomal suspensions can also be used as pharmaceutically acceptable carriers. These can be prepared according to methods known to those skilled in the art, for example, as described in U.S. Pat. No. 4,522,811.

Oral or parenteral compositions can be formulated in dosage unit form for ease of administration and uniformity of dosage. Dosage unit form refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals. Furthermore, administration can be by periodic injections of a bolus, or can be made more continuous by intravenous, intramuscular or intraperitoneal administration from an external reservoir (e.g., an intravenous bag).

Where adhesion to a tissue surface is desired the composition can include the drug dispersed in a fibrinogen-thrombin composition or other bioadhesive. The compound then can be painted, sprayed or otherwise applied to the desired tissue surface. Alternatively, the drugs can be formulated for parenteral or oral administration to humans or other mammals, for example, in therapeutically effective amounts, e.g., amounts that provide appropriate concentrations of the drug to target tissue for a time sufficient to induce the desired effect.

Where the active compound is to be used as part of a transplant procedure, it can be provided to the living tissue or organ to be transplanted prior to removal of tissue or organ from the donor. The compound can be provided to the donor host. Alternatively or, in addition, once removed from the donor, the organ or living tissue can be placed in a preservation solution containing the active compound. In all cases, the active compound can be administered directly to the desired tissue, as by injection to the tissue, or it can be provided systemically, either by oral or parenteral administration, using any of the methods and formulations described herein and/or known in the art. Where the drug comprises part of a tissue or organ preservation solution, any commercially available preservation solution can be used to advantage. For example, useful solutions known in the art include Collins solution, Wisconsin solution, Belzer solution, Eurocollins solution and lactated Ringer's solution.

The compounds of the present invention can be administered directly to a tissue locus by applying the compound to a medical device that is placed in contact with the tissue. An example of a medical device is a stent, which contains or is coated with one or more of the compounds of the present invention.

For example, an active compound can be applied to a stent at the site of vascular injury. Stents can be prepared by any of the methods well known in the pharmaceutical art. See, e.g., Fattori, R. and Piva, T., "Drug Eluting Stents in Vascular Intervention," Lancet, 2003, 361, 247-249; Morice, M. C., "A New Era in the Treatment of Coronary Disease?" European Heart Journal, 2003, 24, 209-211; and Toutouzas, K. et al., "Sirolimus-Eluting Stents: A Review of Experimental and Clinical Findings," Z. Kardiol., 2002, 91(3), 49-57. The stent can be fabricated from stainless steel or another bio-compatible metal, or it can be made of a bio-compatible polymer. The active compound can be linked to the stent surface, embedded and released from polymer materials coated on the stent, or surrounded by and released through a carrier which coats or spans the stent. The stent can be used to administer single or multiple active compounds to tissues adjacent to the stent.

Active compound as identified or designed by the methods described herein can be administered to individuals to treat disorders (prophylactically or therapeutically). In conjunction with such treatment, pharmacogenomics (i.e., the study of the relationship between an individual's genotype and that individual's response to a foreign compound or drug) can be considered. Differences in metabolism of therapeutics can lead to severe toxicity or therapeutic failure by altering the relation between dose and blood concentration of the pharmacologically active drug. Thus, a physician or clinician can consider applying knowledge obtained in relevant pharmacogenomics studies in determining whether to administer a drug as well as tailoring the dosage and/or therapeutic regimen of treatment with the drug.

In therapeutic use for treating, or combating, bacterial infections in mammals, the compounds or pharmaceutical compositions thereof will be administered orally, parenterally and/or topically at a dosage to obtain and maintain a concentration, that is, an amount, or blood-level or tissue level of active component in the animal undergoing treatment which will be anti-microbially effective. Generally, an effective amount of dosage of active component will be in the range of from about 0.1 to about 100, more preferably from about 1.0 to about 50 mg/kg of body weight/day. The amount administered will also likely depend on such variables as the type and extent of disease or indication to be treated, the overall health status of the particular patient, the relative biological efficacy of the compound delivered, the formulation of the drug, the presence and types of excipients in the formulation, and the route of administration. Also, it is to be understood that the initial dosage administered can be increased beyond the above upper level in order to rapidly achieve the desired blood-level or tissue level, or the initial dosage can be smaller than the optimum and the daily dosage can be progressively increased during the course of treatment depending on the particular situation. If desired, the daily dose can also be divided into multiple doses for administration, for example, two to four times per day.

Various disease states or conditions in humans and other mammals are found to be caused by or mediated by nonsense or missense mutations. These mutations cause or mediate the disease state or condition by adversely affecting, for example, protein synthesis, folding, trafficking and/or function. Examples of disease states or conditions in which an appreciable percentage of the disease or condition is believed to result from nonsense or missense mutations include hemophilia (factor VIII gene), neurofibromatosis (NF1 and NF2 genes), retinitis pigmentosa (human USH2A gene), bullous skin diseases like Epidermolysis bullosa pruriginosa (COL7A1 gene), cystic fibrosis (cystic fibrosis transmembrane regulator gene), breast and ovarian cancer (BRCA1 and BRCA2 genes), Duchenne muscular dystrophy (dystrophin gene), colon cancer (mismatch repair genes, predominantly in MLH1 and MSH2), and lysosomal storage disorders such as Neimann-Pick disease (acid sphingomyelinase gene). See Sanders C R, Myers J K. Disease-related misassembly of membrane proteins. Annu Rev Biophys Biomol Struct. 2004; 33:25-51; National Center for Biotechnology Information (U.S.) *Genes and disease* Bethesda, Md.: NCBI, NLM ID: 101138560; and Raskó, István; Downes, C S *Genes in medicine: molecular biology and human genetic disorders* 1st ed. London; New York: Chapman & Hall, 1995. NLM ID: 9502404. The compounds of the present invention can be used to treat or prevent a disease state in a mammal caused or mediated by such nonsense or missense mutations by administering to a mammal in need thereof an effective amount of the present invention to suppress the nonsense or missense mutation involved in the disease state.

6. EXAMPLES

Nuclear magnetic resonance (NMR) spectra were obtained on a Bruker Avance 300 or Avance 500 spectrometer, or in some cases a GE-Nicolet 300 spectrometer. Common reaction solvents were either high performance liquid chromatography (HPLC) grade or American Chemical Society (ACS) grade, and anhydrous as obtained from the manufacturer unless otherwise noted. "Chromatography" or "purified by silica gel" refers to flash column chromatography using silica gel (EM Merck, Silica Gel 60, 230-400 mesh) unless otherwise noted.

Some of the abbreviations used in the following experimental details of the synthesis of the examples are defined below:

| | |
|---|---|
| Ac = | acetyl |
| hr = | hour(s) |
| min = | minute(s) |
| mol = | mole(s) |
| mmol = | millimole(s) |
| M = | molar |
| μM = | micromolar |
| g = | gram(s) |
| μg = | microgram(s) |
| rt = | room temperature |
| L = | liter(s) |
| mL = | milliliter(s) |
| $Et_2O$ = | diethyl ether |
| THF = | tetrahydrofuran |
| DMSO = | dimethyl sulfoxide |
| EtOAc = | ethyl acetate |
| $Et_3N$ = | triethylamine |
| i-$Pr_2$NEt = | diisopropylethylamine |
| $CH_2Cl_2$ = | methylene chloride |
| $CHCl_3$ = | chloroform |
| $CDCl_3$ = | deuterated chloroform |
| $CCl_4$ = | carbon tetrachloride |
| MeOH = | methanol |
| $CD_3OD$ = | deuterated methanol |
| EtOH = | ethanol |
| DMF = | dimethylformamide |
| BOC = | t-butoxycarbonyl |
| CBZ = | benzyloxycarbonyl |
| TBS = | t-butyldimethylsilyl |
| TBSCl = | t-butyldimethylsilyl chloride |
| TFA = | trifluoroacetic acid |
| DBU = | diazabicycloundecene |
| TBDPSCl = | t-butyldiphenylchlorosilane |
| Hunig's Base = | N,N-diisopropylethylamine |
| DMAP = | 4-dimethylaminopyridine |
| CuI = | copper (I) iodide |
| MsCl = | methanesulfonyl chloride |
| $NaN_3$ = | sodium azide |
| $Na_2SO_4$ = | sodium sulfate |
| $NaHCO_3$ = | sodium bicarbonate |
| NaOH = | sodium hydroxide |
| $MgSO_4$ = | magnesium sulfate |
| $K_2CO_3$ = | potassium carbonate |
| KOH = | potassium hydroxide |
| $NH_4OH$ = | ammonium hydroxide |
| $NH_4Cl$ = | ammonium chloride |
| $SiO_2$ = | silica |
| Pd—C = | palladium on carbon |
| Pd(dppf)$Cl_2$ = | dichloro[1,1'-bis(diphenylphosphino)ferrocene] palladium (II) |

Exemplary compounds which can be synthesized in accordance with the invention are listed in Table 1, Table 1A, and Table 1C. A bolded or dashed bond is shown to indicate a particular stereochemistry at a chiral center, whereas a wavy bond indicates that the substituent can be in either orientation or that the compound is a mixture thereof. It should also be known that in the interest of space, the chemical structures for some compounds have been condensed, for example the methyl and ethyl group substituents are designated with just a carbon backbone representation, and the unsaturated bonds in the triazole rings might not always be visible.

The compounds of the present invention can be prepared, formulated, and delivered as pharmaceutically acceptable salts, esters, and prodrugs. For convenience, the compounds are generally shown without indicating a particular salt, ester, or prodrug form.

TABLE 1

| Compound No. | Structure |
| --- | --- |
| 100 | 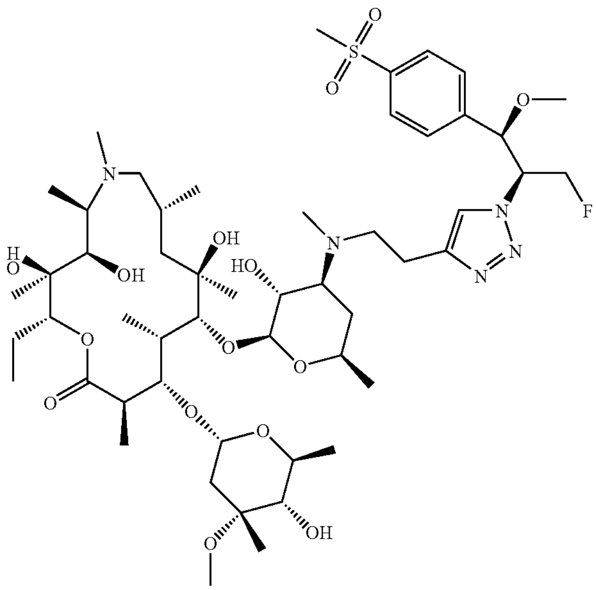 |
| 101 | 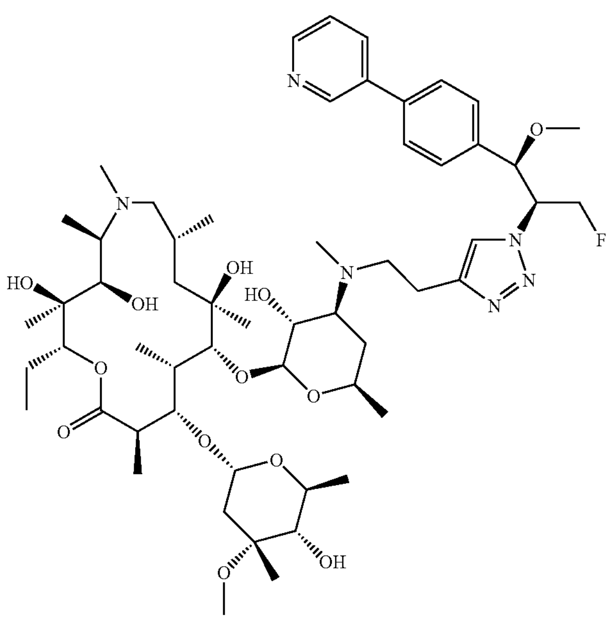 |

TABLE 1-continued
| Compound No. | Structure |
|---|---|
| 102 | 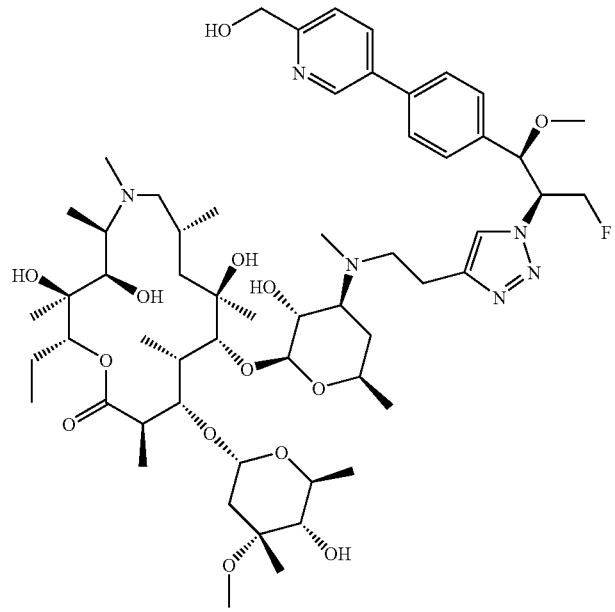 |
| 103 | 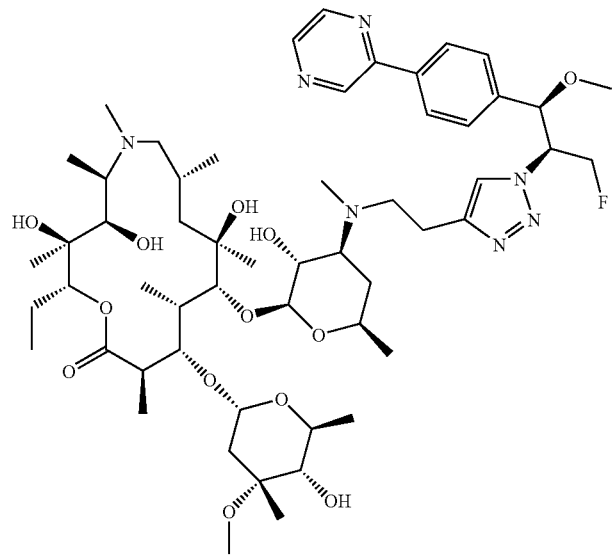 |

TABLE 1-continued
| Compound No. | Structure |
|---|---|
| 104 | 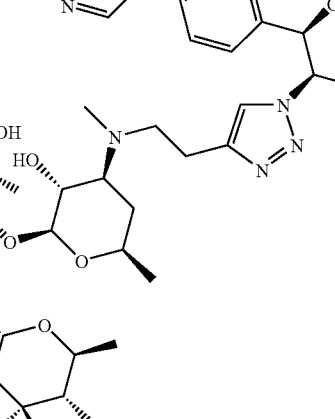 |
| 105 | 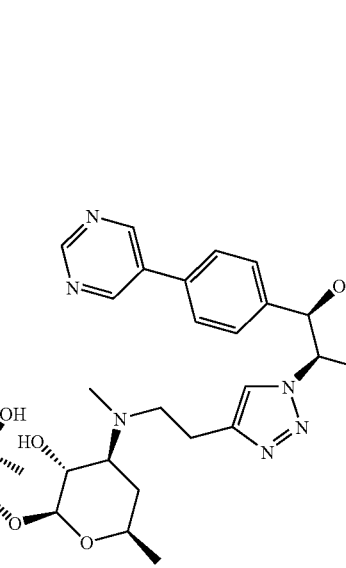 |

US 8,278,281 B2
61
TABLE 1-continued
62
| Compound No. | Structure |
|---|---|
| 106 | 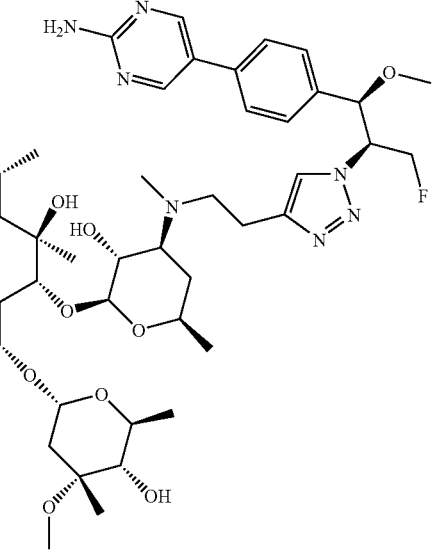 |
| 107 | 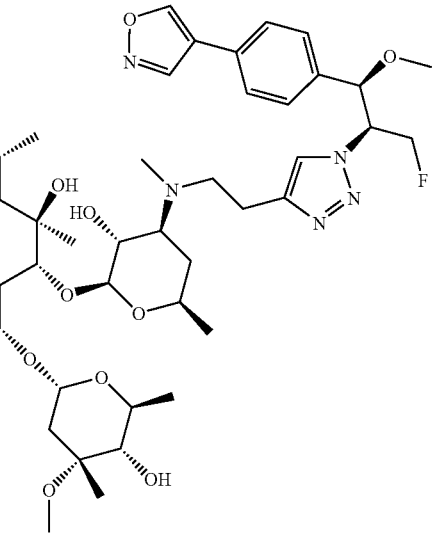 |

TABLE 1-continued
| Compound No. | Structure |
|---|---|
| 108 | 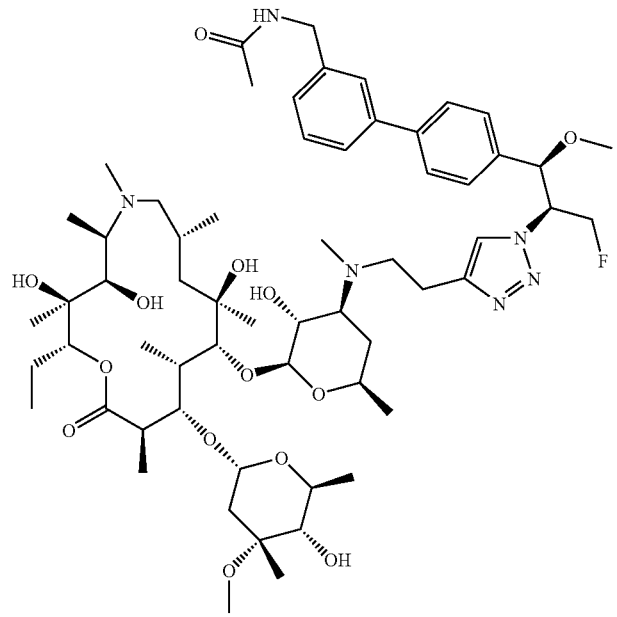 |
| 109 | 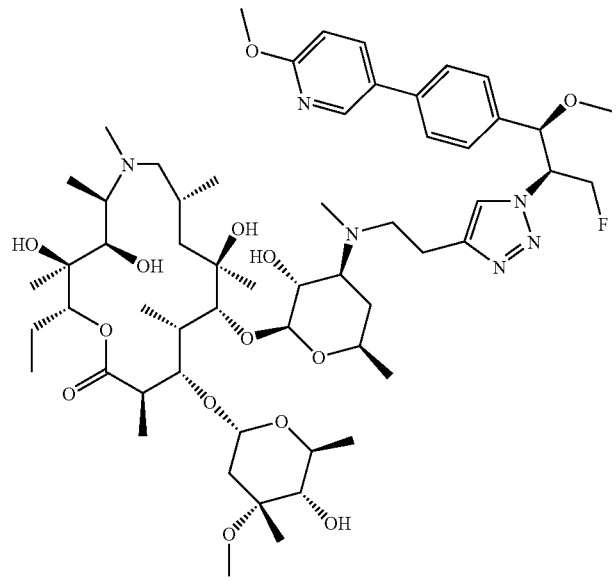 |

TABLE 1-continued

| Compound No. | Structure |
|---|---|
| 110 | 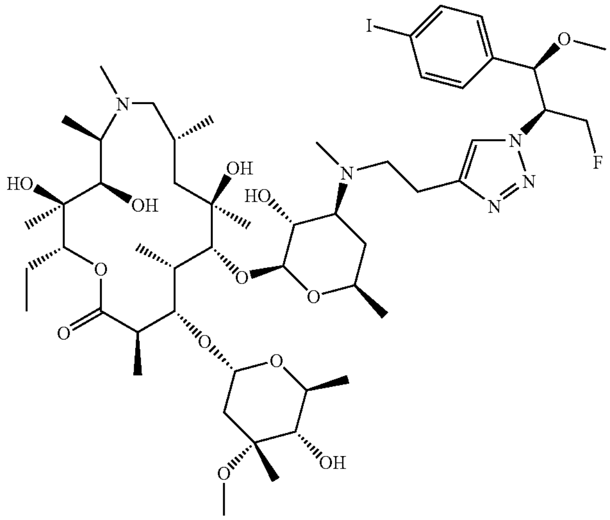 |
| 111 | 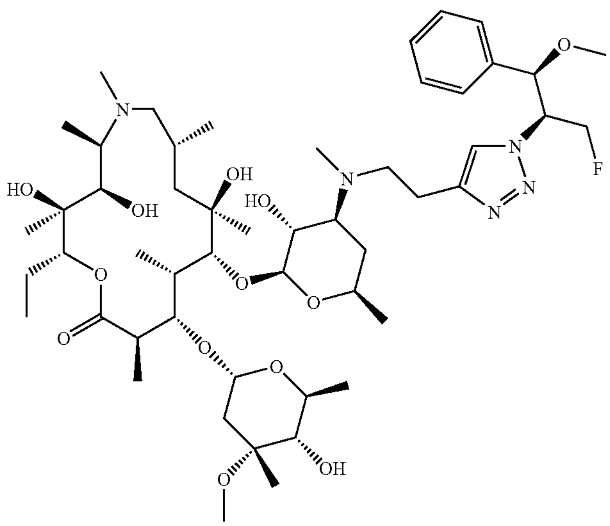 |
| 112 | 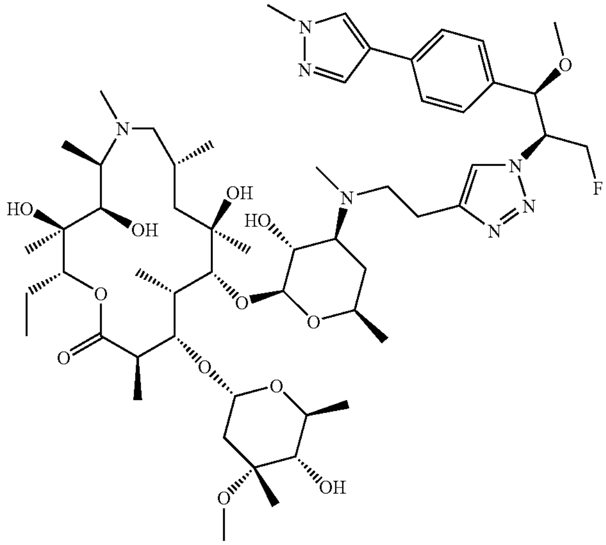 |

TABLE 1-continued
| Compound No. | Structure |
|---|---|
| 113 | 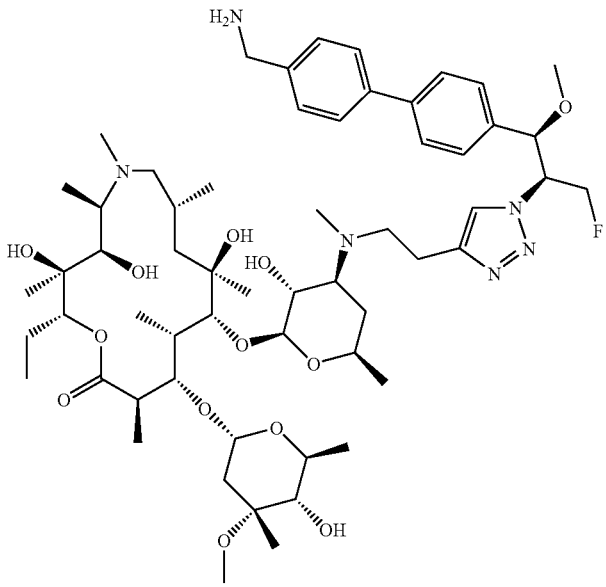 |
| 114 | 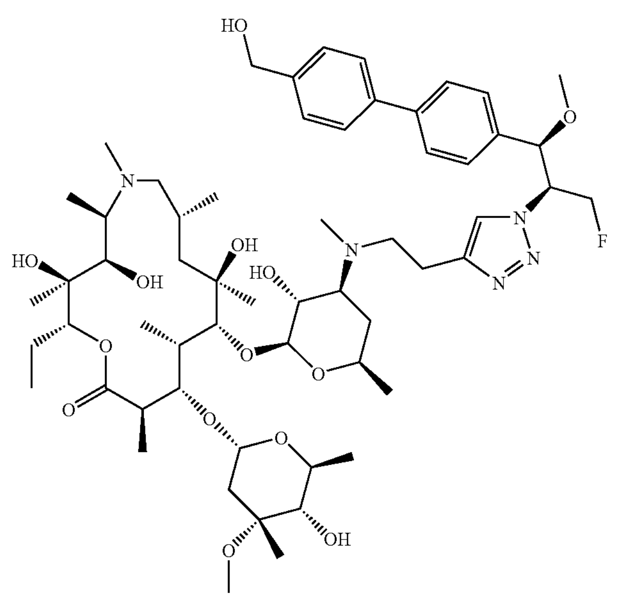 |

TABLE 1-continued

| Compound No. | Structure |
|---|---|
| 115 | 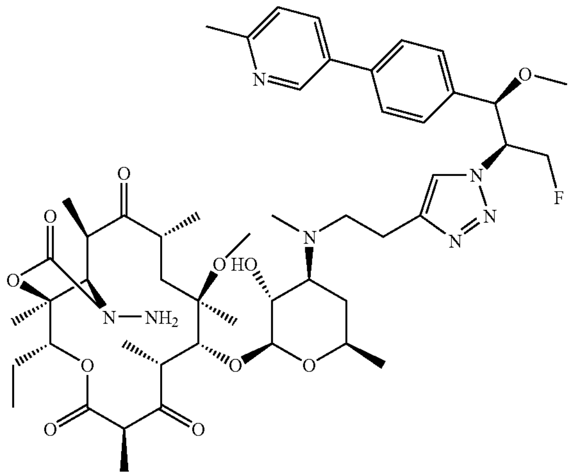 |
| 116 | 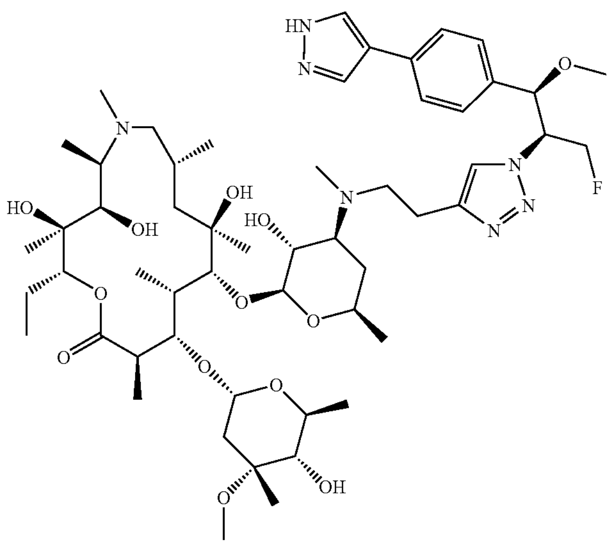 |
| 117 | 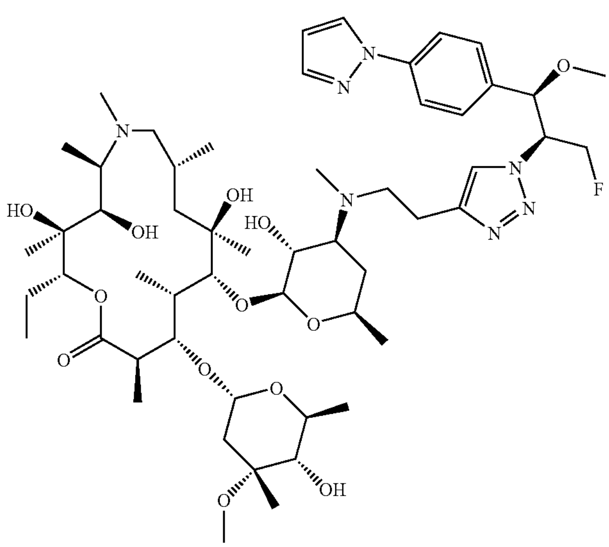 |

TABLE 1-continued

| Compound No. | Structure |
|---|---|
| 118 | 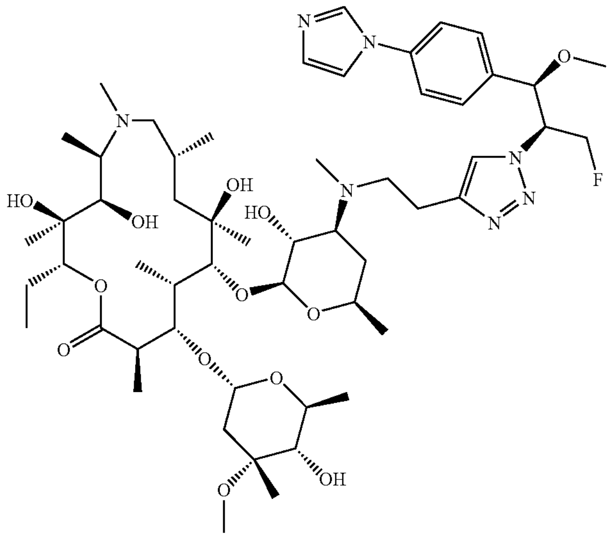 |
| 119 | 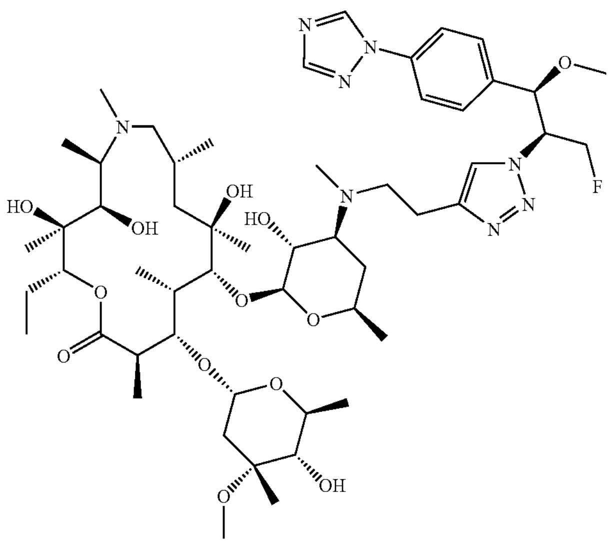 |
| 120 | 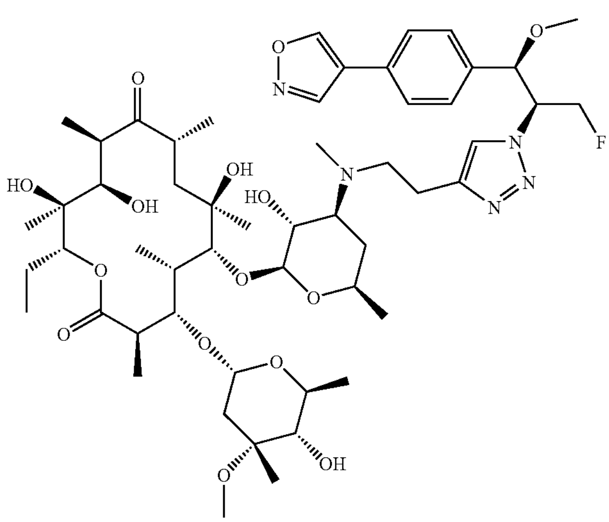 |

TABLE 1-continued
| Compound No. | Structure |
|---|---|
| 121 | 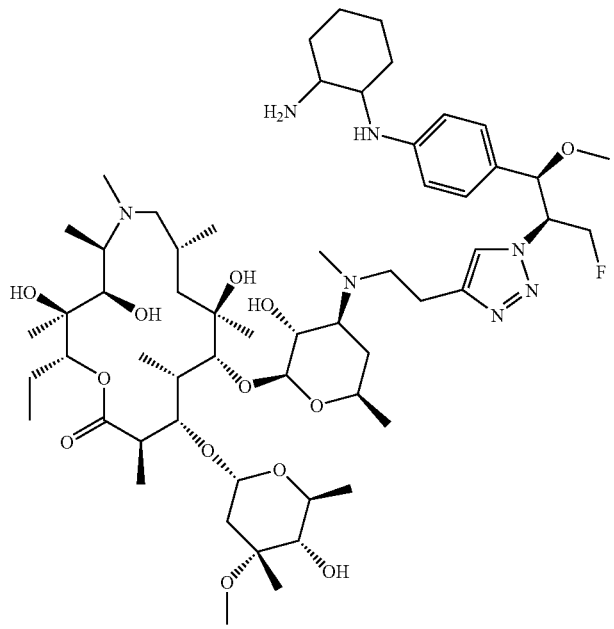 |
| 122 | 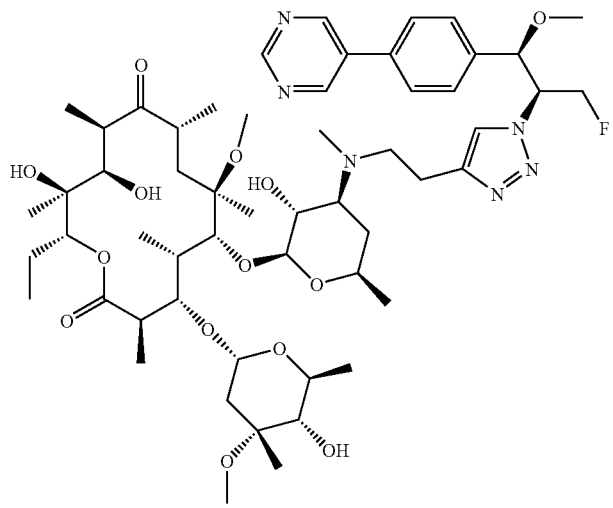 |

TABLE 1-continued

| Compound No. | Structure |
|---|---|
| 123 | 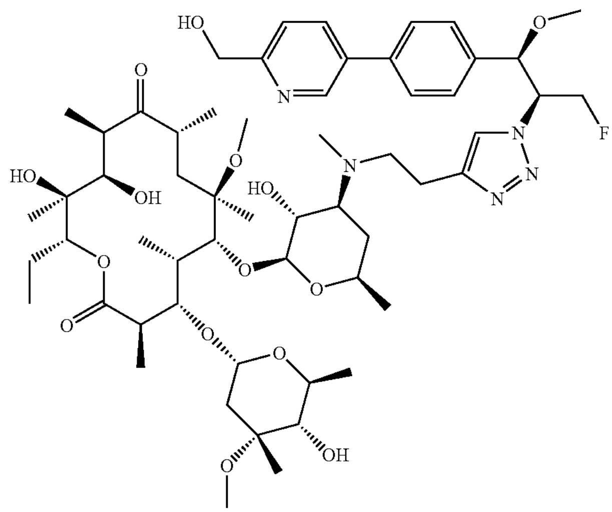 |
| 124 | 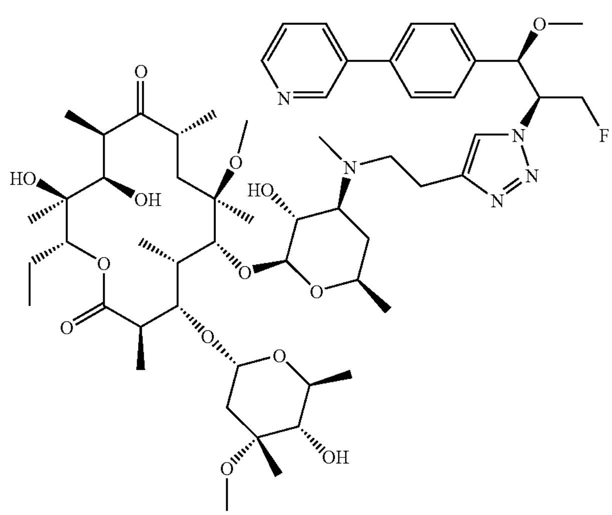 |
| 125 | 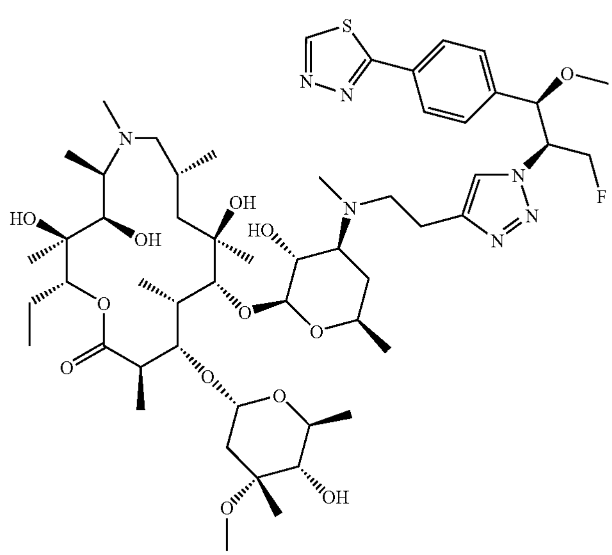 |

US 8,278,281 B2
TABLE 1-continued
| Compound No. | Structure |
|---|---|
| 126 | 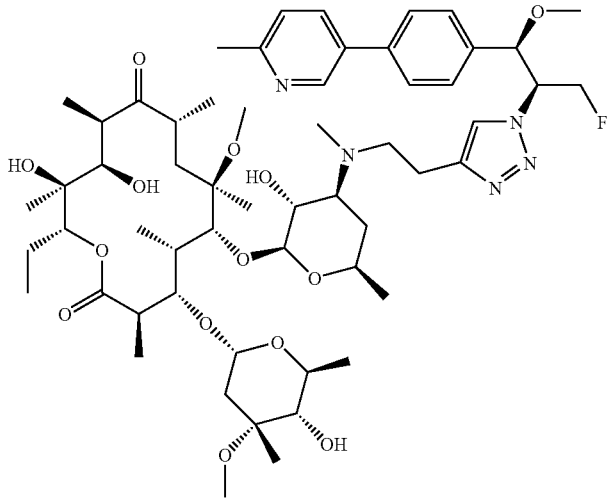 |
| 127 | 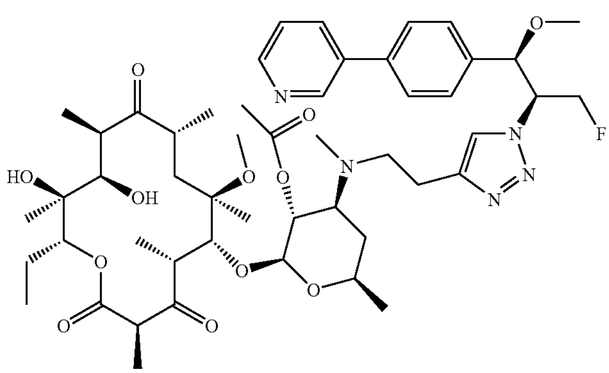 |
| 128 | 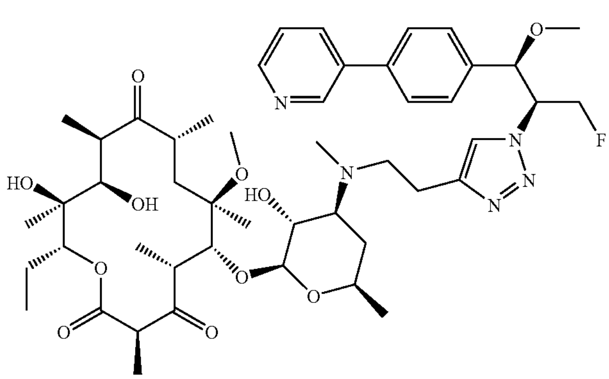 |

TABLE 1-continued
| Compound No. | Structure |
|---|---|
| 129 | 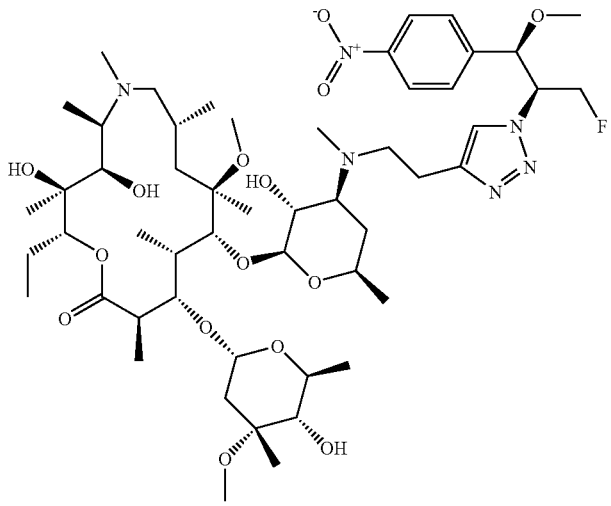 |
| 130 | 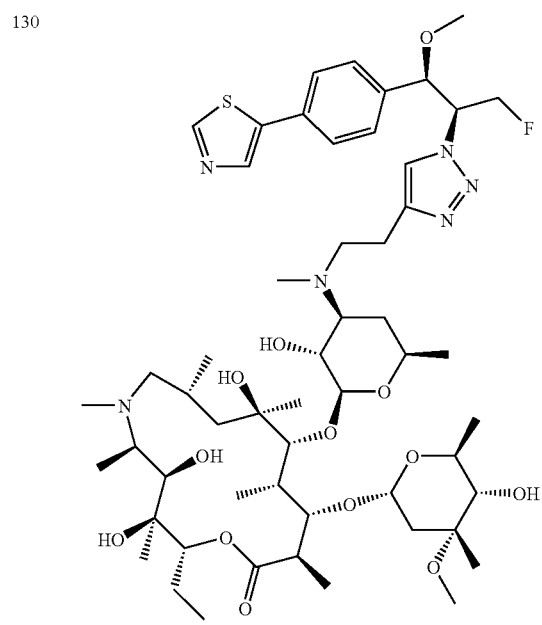 |

TABLE 1-continued
| Compound No. | Structure |
|---|---|
| 131 | 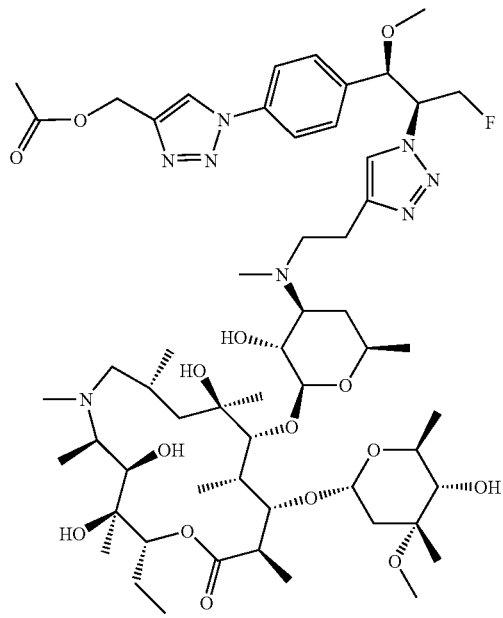 |
| 132 | 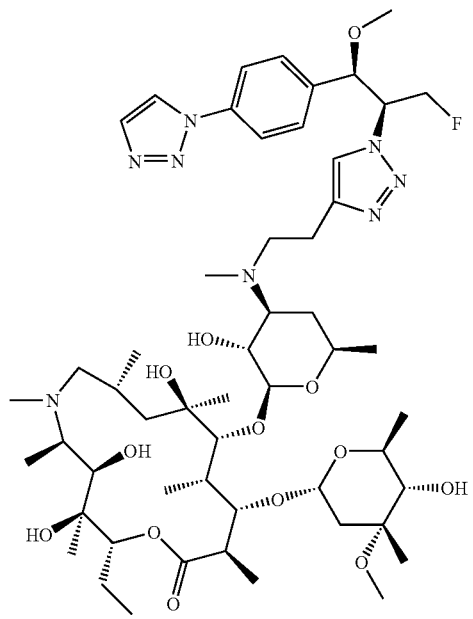 |

TABLE 1-continued
| Compound No. | Structure |
|---|---|
| 133 | 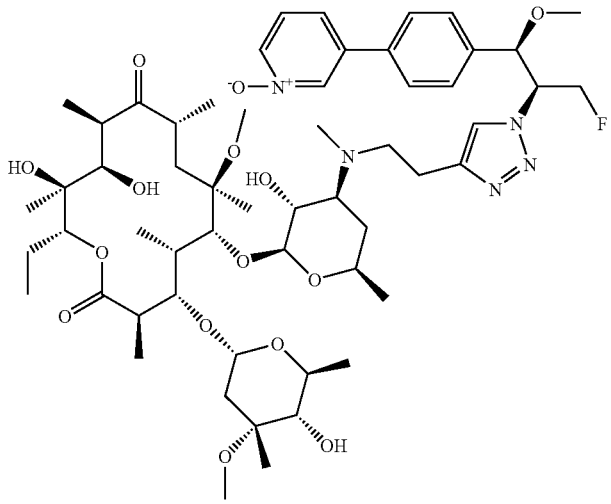 |
| 134 | 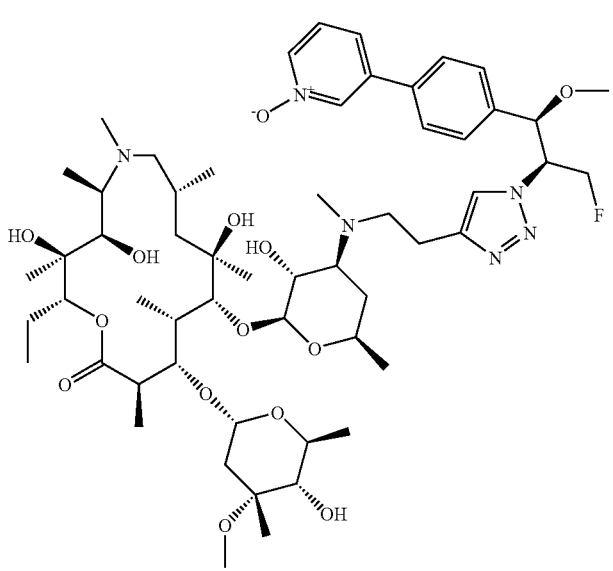 |
| 135 | 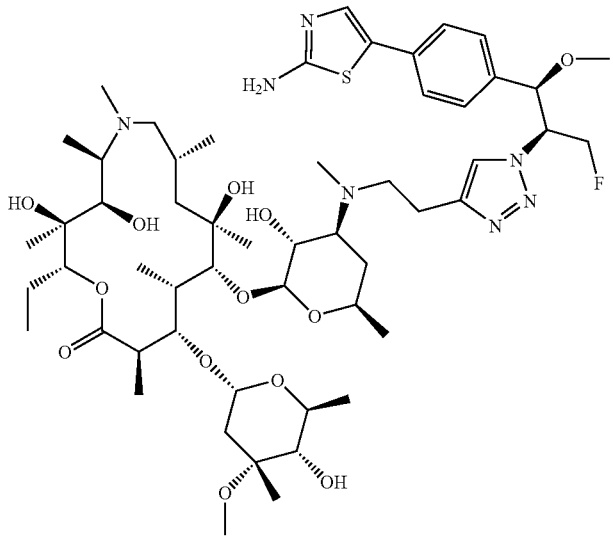 |

TABLE 1-continued
| Compound No. | Structure |
|---|---|
| 136 | 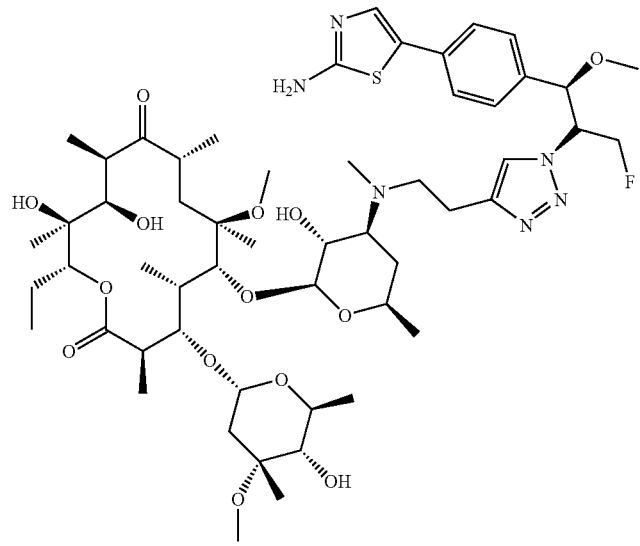 |
| 137 | 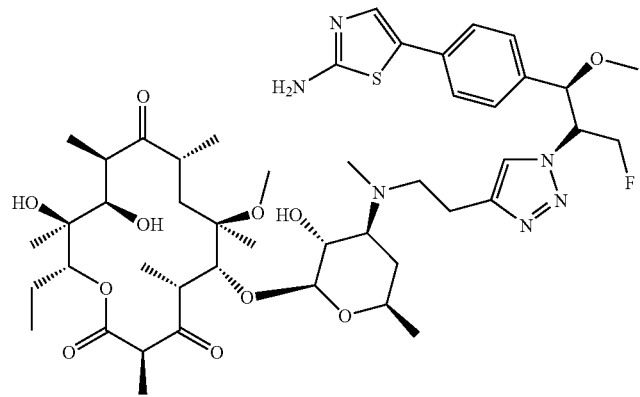 |
| 138 | 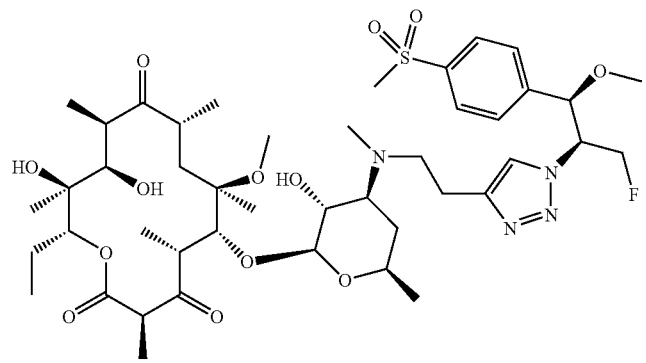 |

TABLE 1-continued
| Compound No. | Structure |
|---|---|
| 139 | 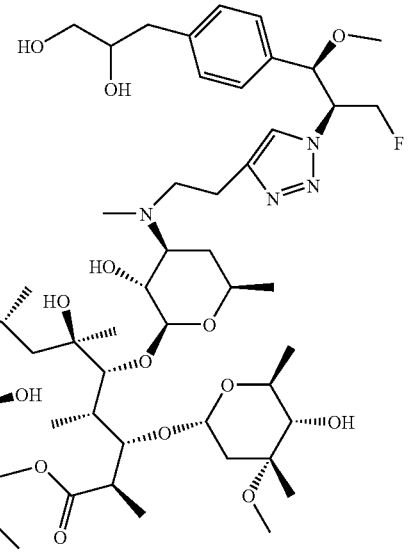 |
| 140 | 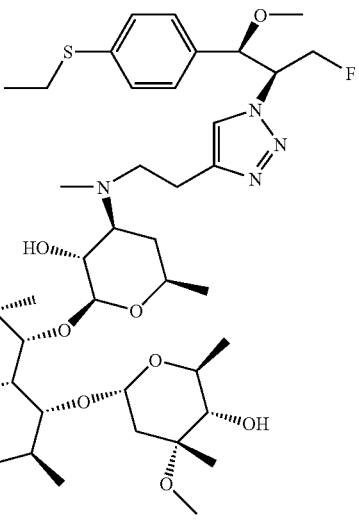 |
| 141 | 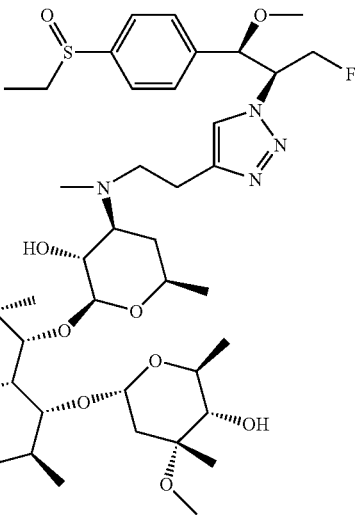 |

TABLE 1-continued
| Compound No. | Structure |
|---|---|
| 142 | 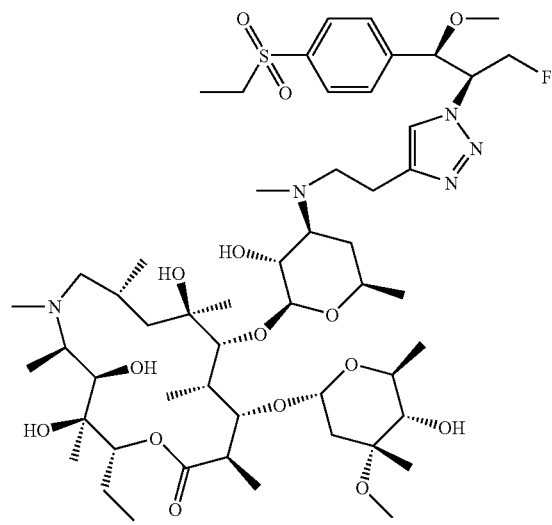 |
| 143 | 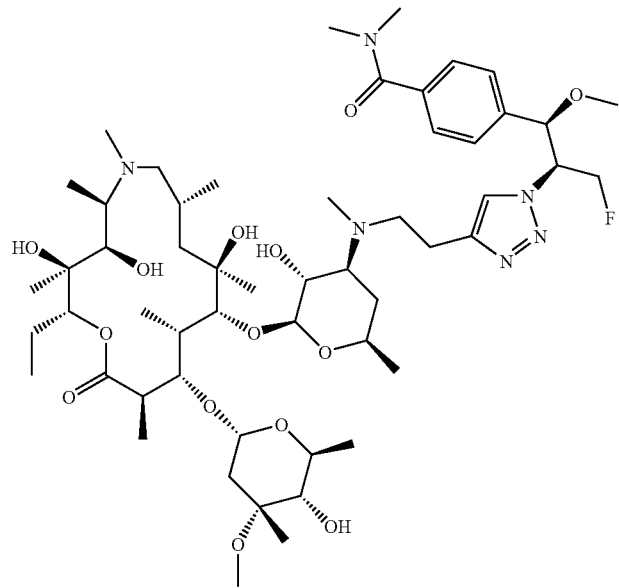 |

TABLE 1-continued
| Compound No. | Structure |
|---|---|
| 144 | 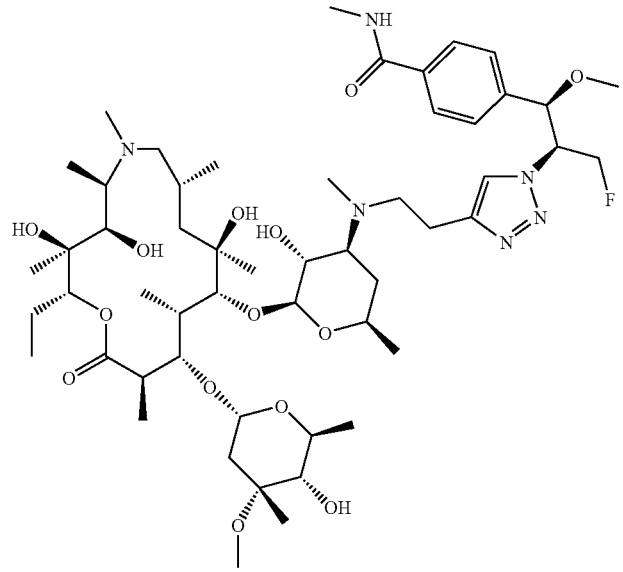 |
| 145 | 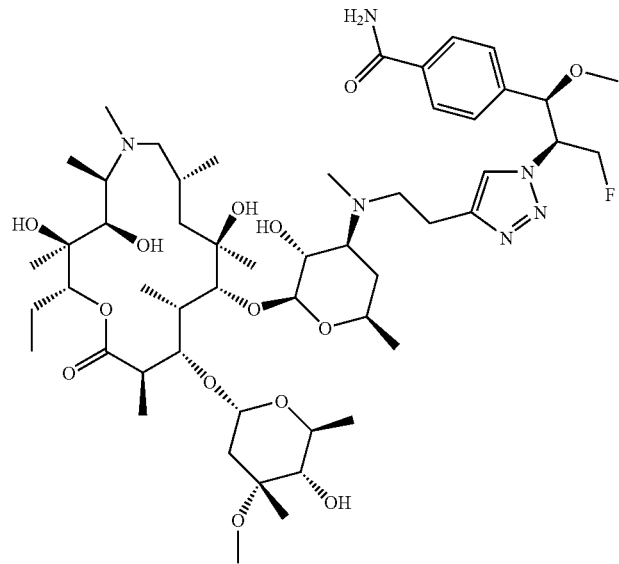 |

TABLE 1-continued
| Compound No. | Structure |
|---|---|
| 146 | 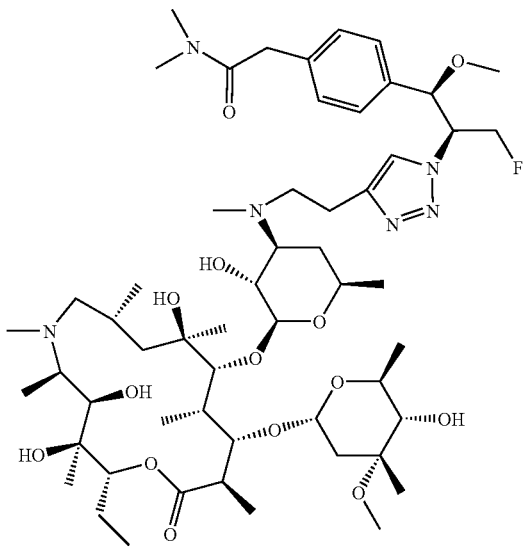 |
| 147 | 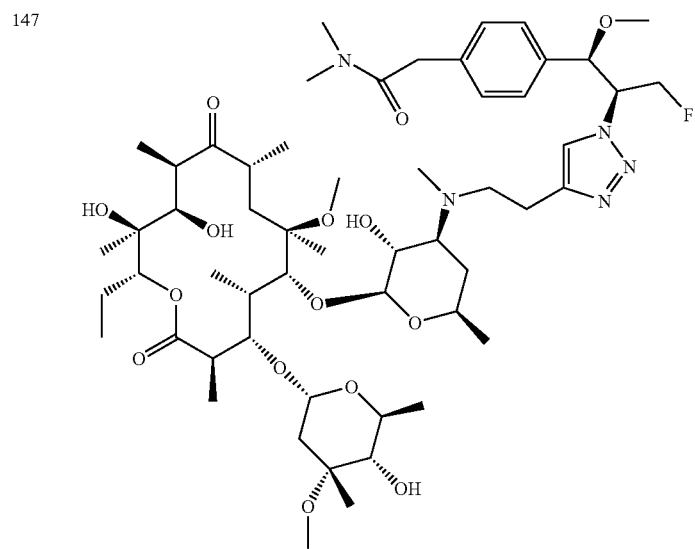 |

TABLE 1-continued
| Compound No. | Structure |
|---|---|
| 148 | 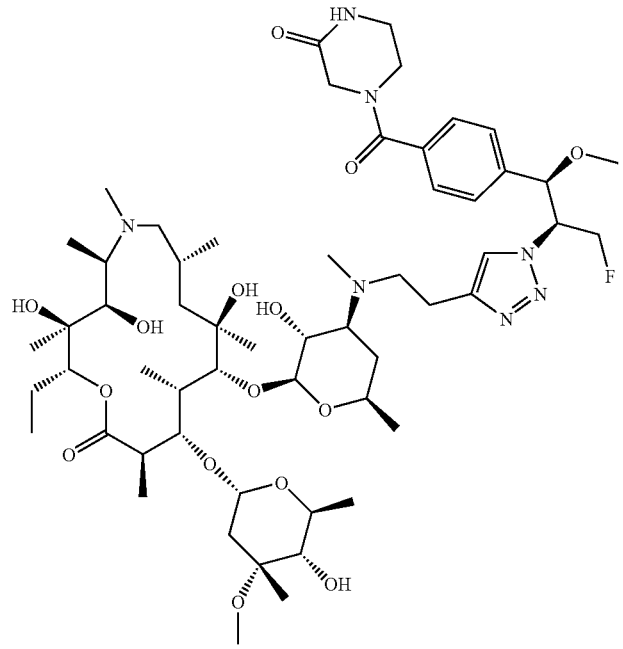 |
| 149 | 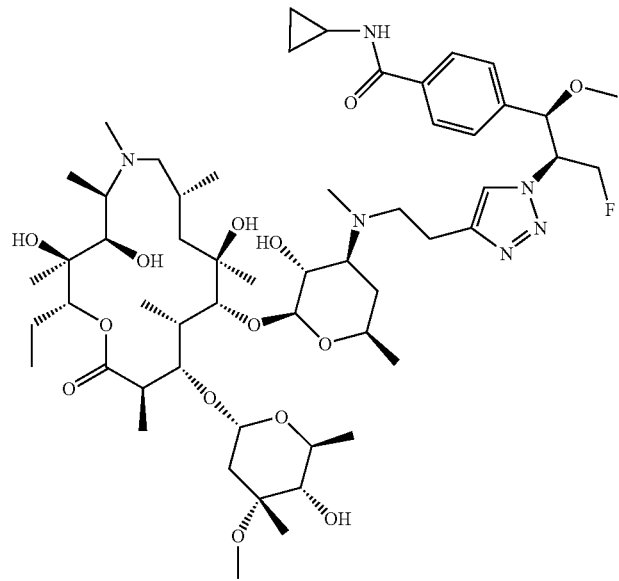 |

//TABLE 1-continued
| Compound No. | Structure |
|---|---|
| 150 | 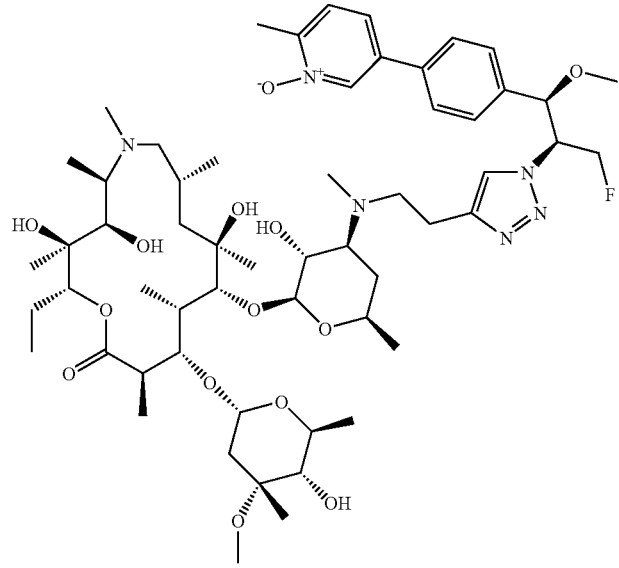 |
| 151 | 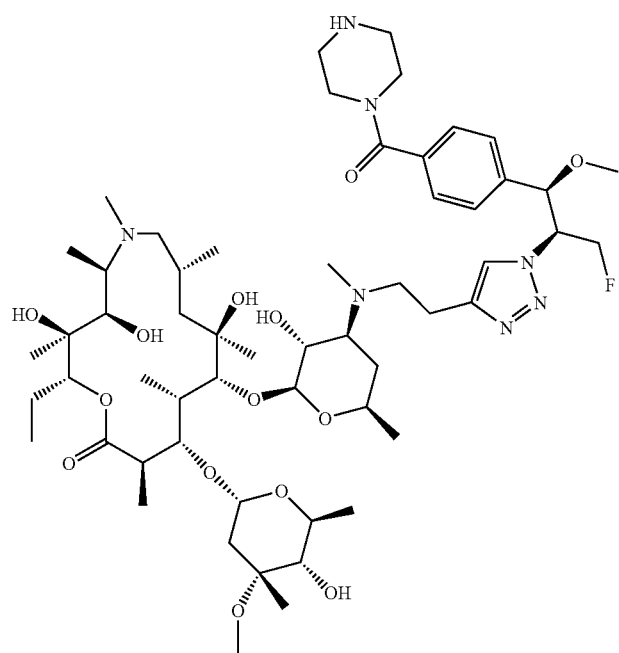 |

TABLE 1-continued
| Compound No. | Structure |
|---|---|
| 152 | 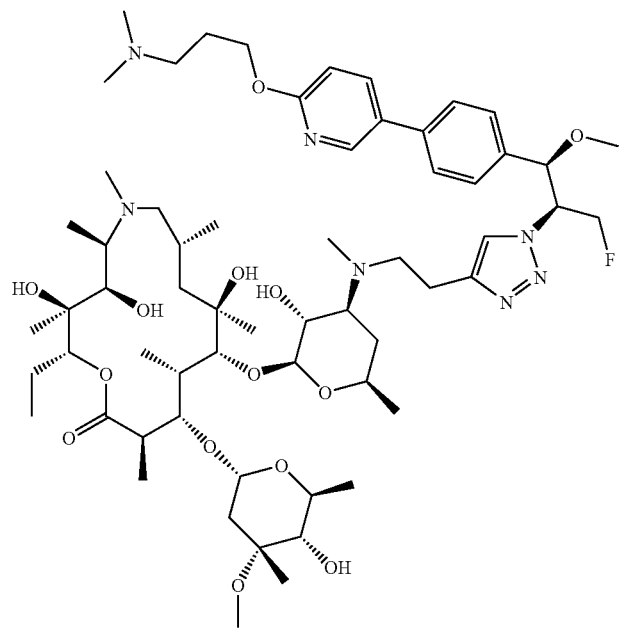 |
| 153 | 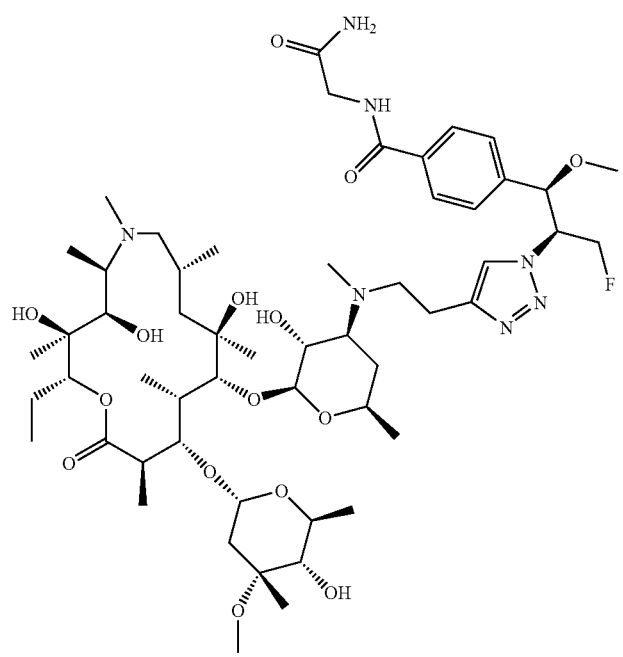 |

TABLE 1-continued
| Compound No. | Structure |
|---|---|
| 154 | 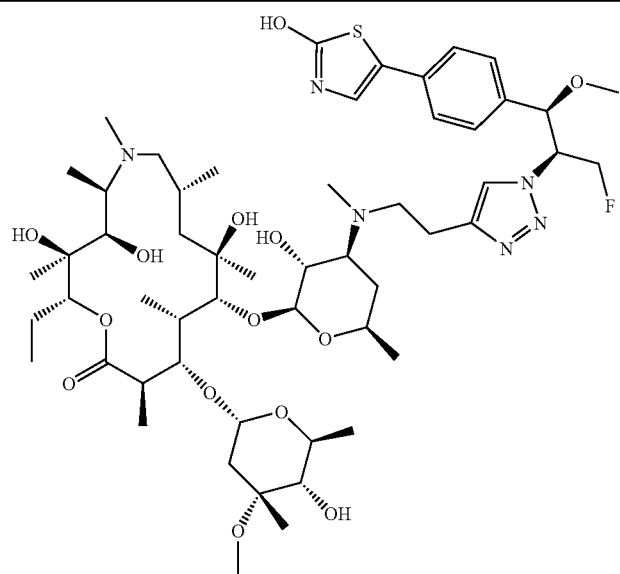 |
| 155 | 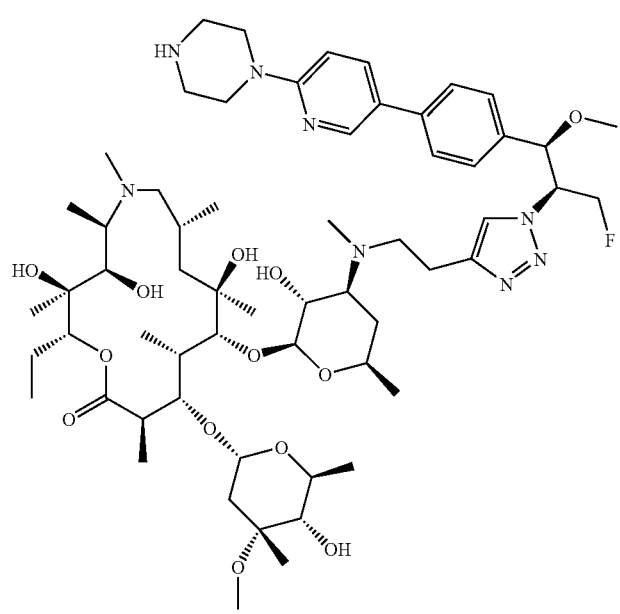 |

TABLE 1-continued
| Compound No. | Structure |
|---|---|
| 156 | 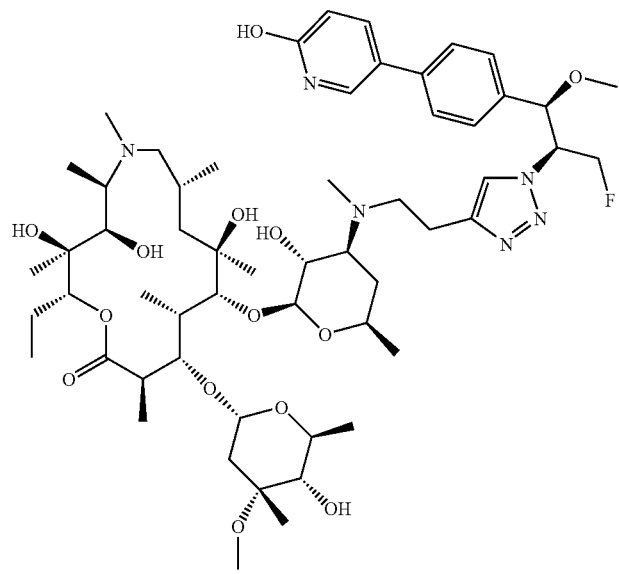 |
| 157 | 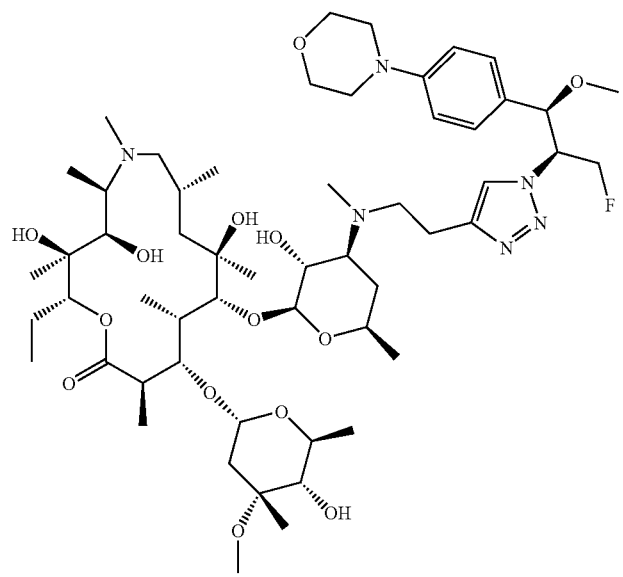 |

TABLE 1-continued
| Compound No. | Structure |
| --- | --- |
| 158 | 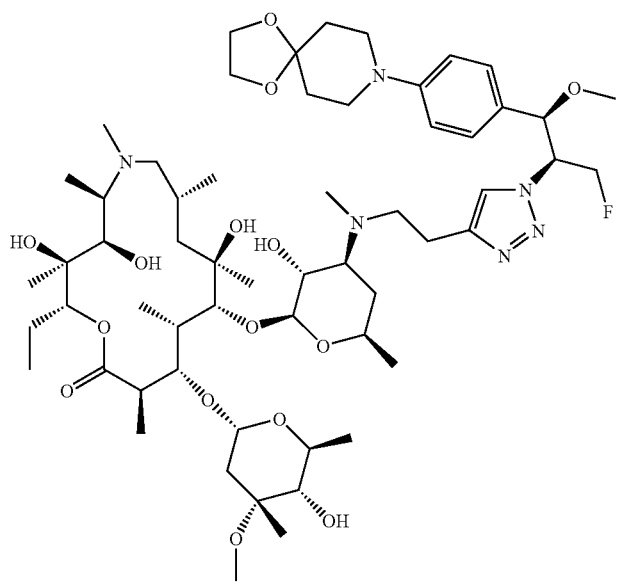 |
| 159 | 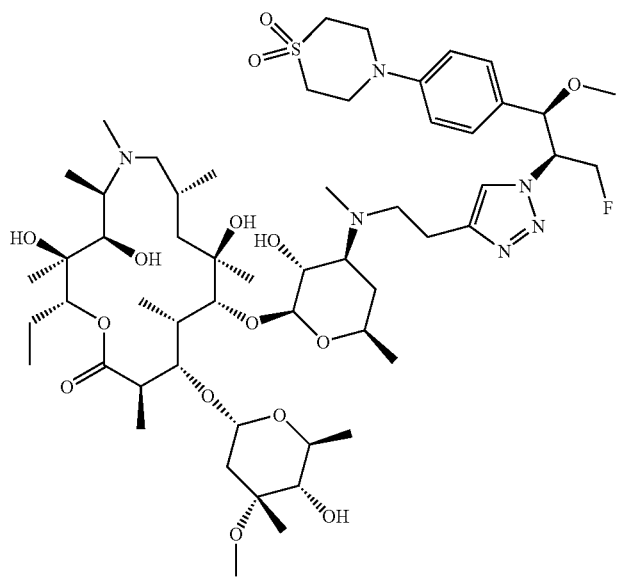 |

TABLE 1-continued
| Compound No. | Structure |
|---|---|
| 160 | 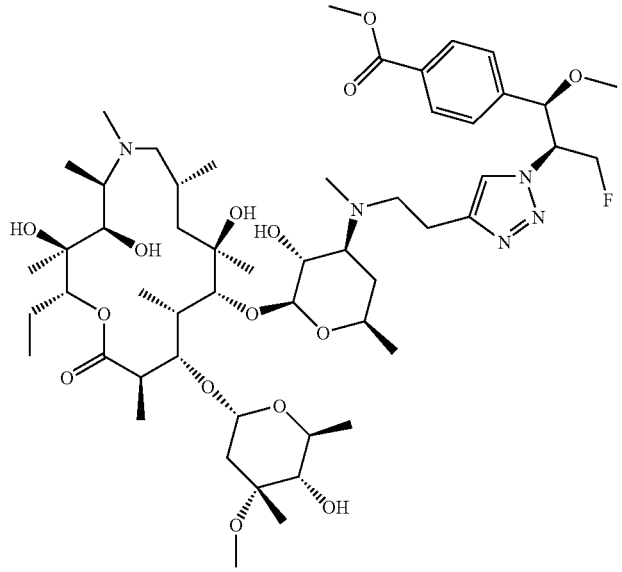 |
| 161 | 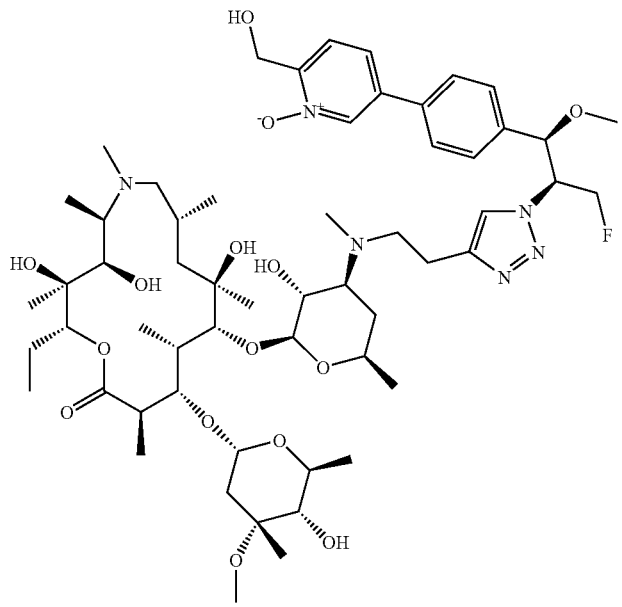 |

TABLE 1-continued
| Compound No. | Structure |
|---|---|
| 162 | 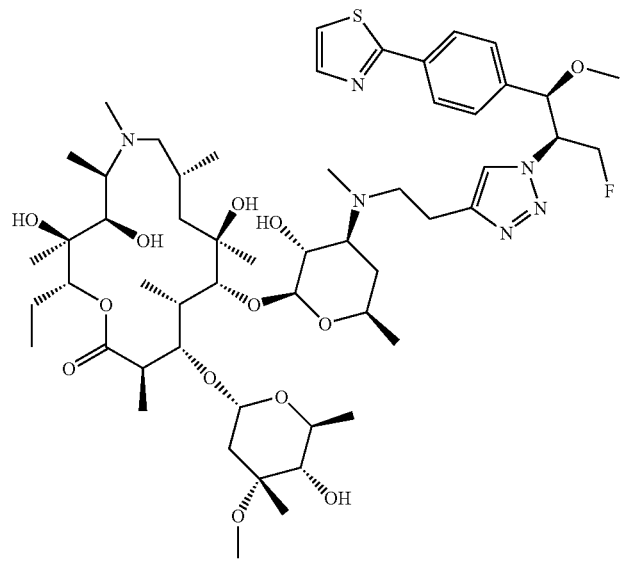 |
| 163 | 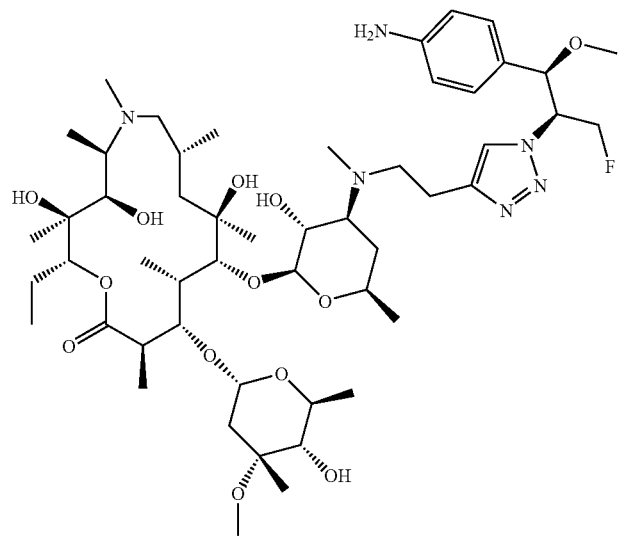 |

TABLE 1-continued
| Compound No. | Structure |
|---|---|
| 164 | 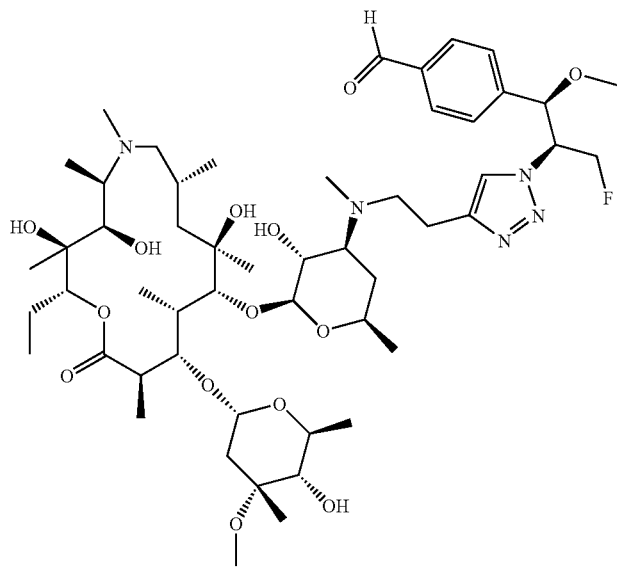 |
| 165 | 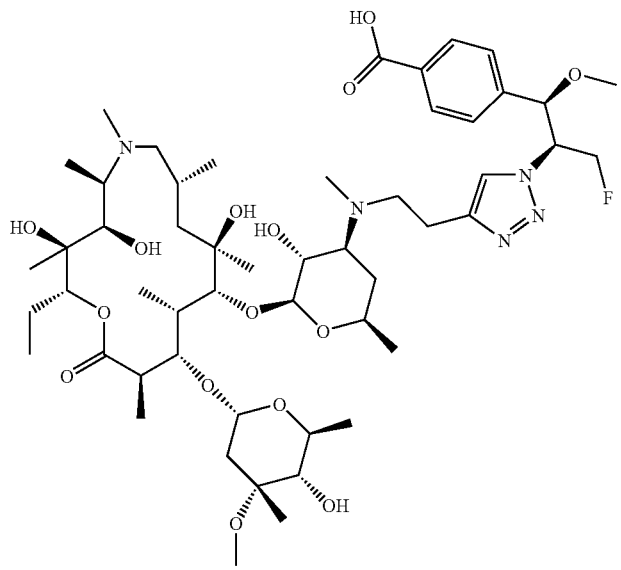 |

TABLE 1-continued
| Compound No. | Structure |
|---|---|
| 166 | 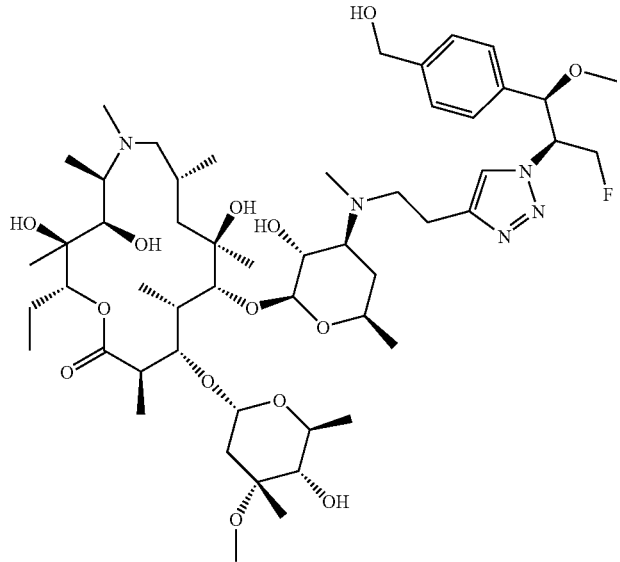 |
| 167 | 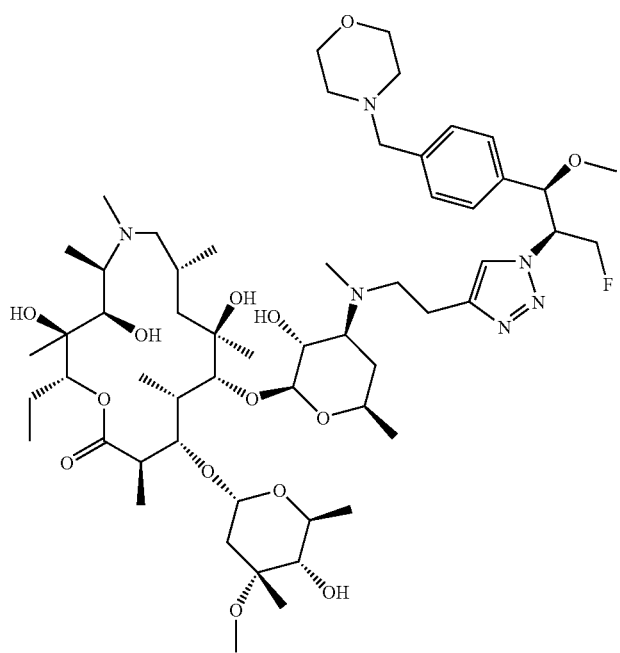 |

TABLE 1-continued
| Compound No. | Structure |
|---|---|
| 168 | 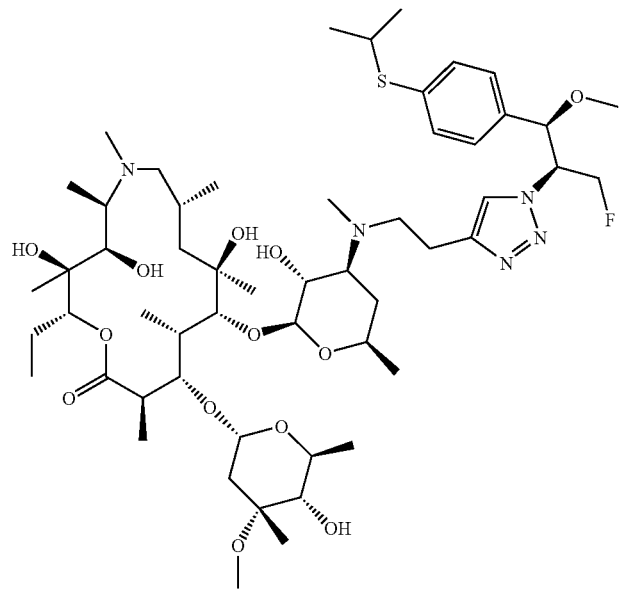 |
| 169 | 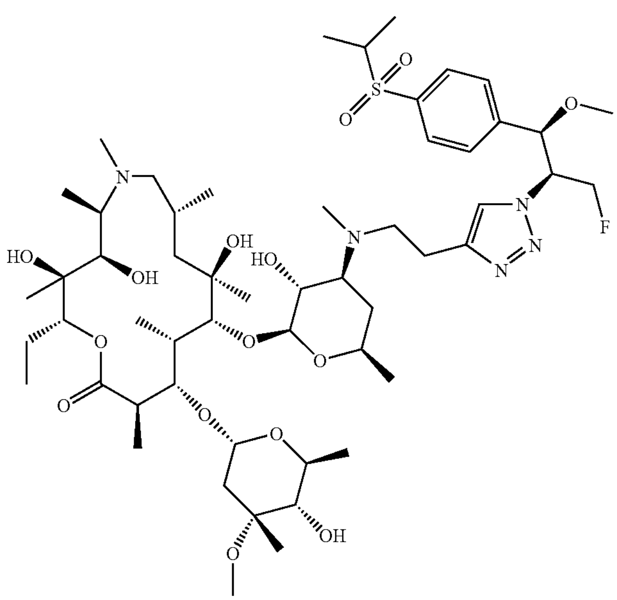 |

TABLE 1-continued
| Compound No. | Structure |
|---|---|
| 170 | 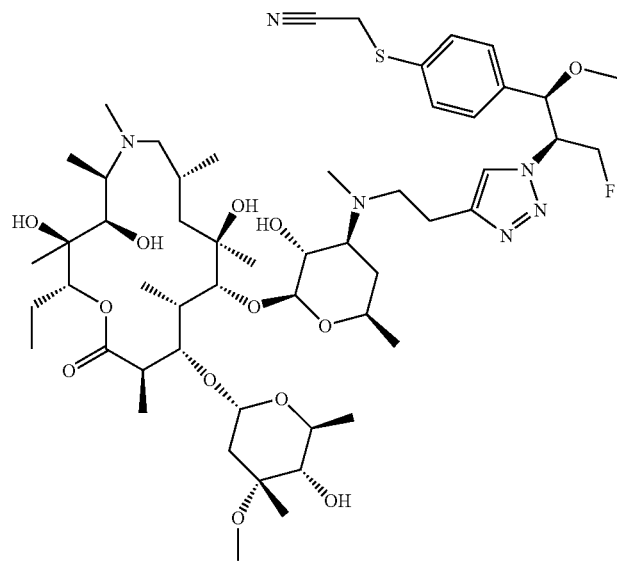 |
| 171 | 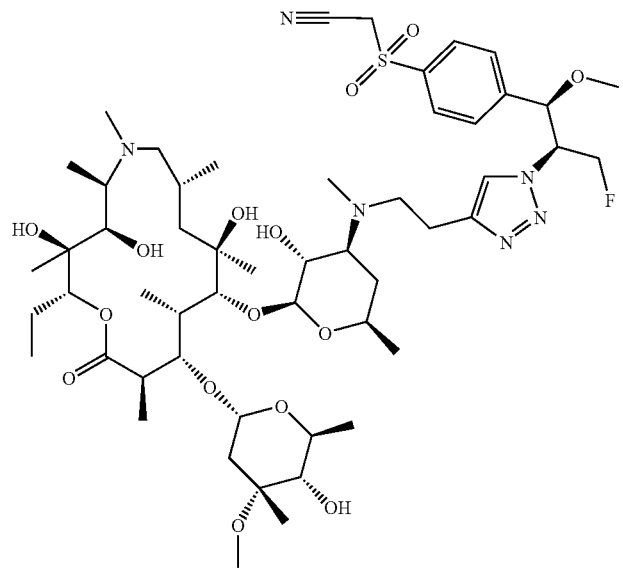 |

TABLE 1-continued
| Compound No. | Structure |
|---|---|
| 172 | 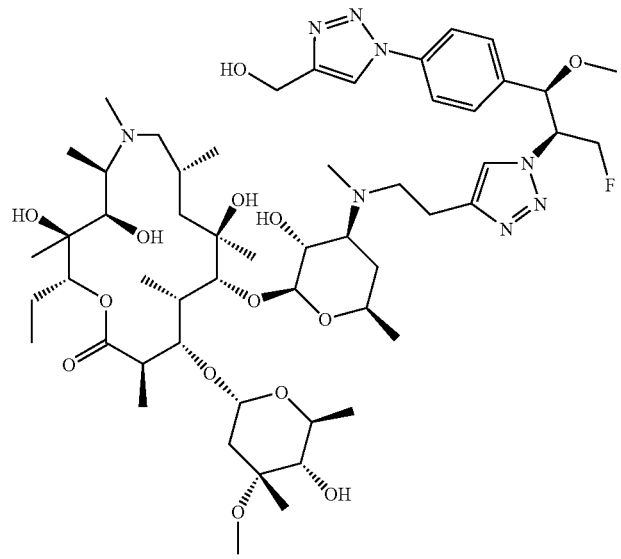 |
| 173 | 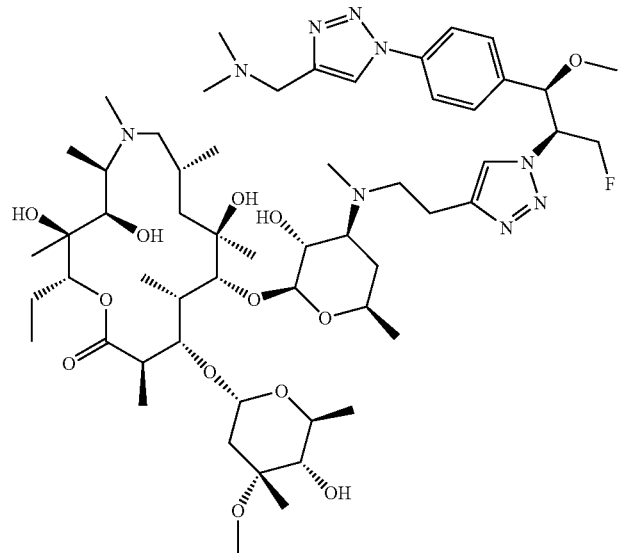 |

TABLE 1-continued
| Compound No. | Structure |
|---|---|
| 174 | 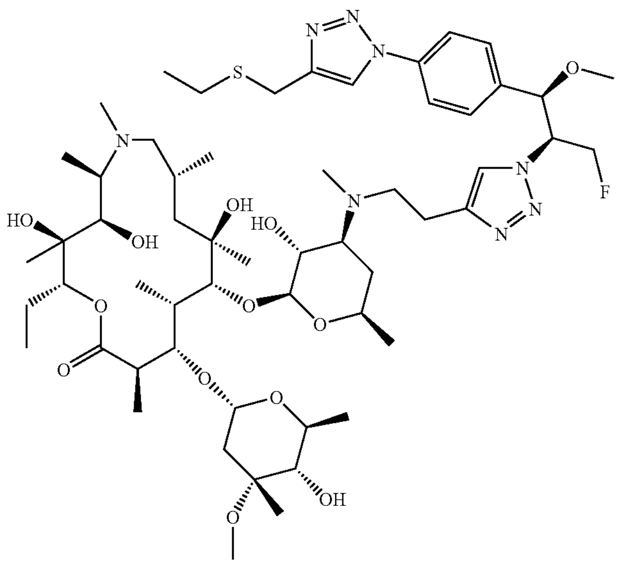 |
| 175 | 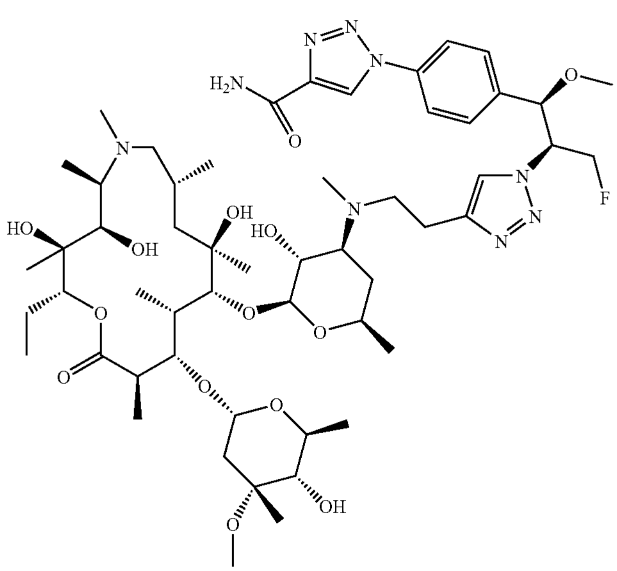 |

TABLE 1-continued
| Compound No. | Structure |
|---|---|
| 176 | 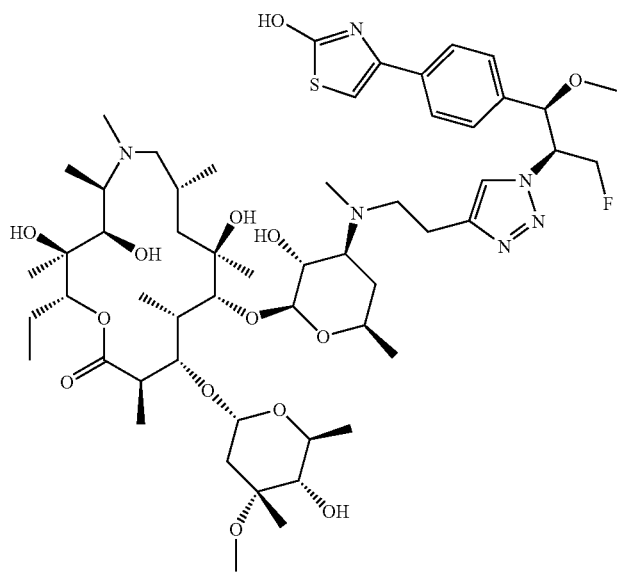 |
| 177 | 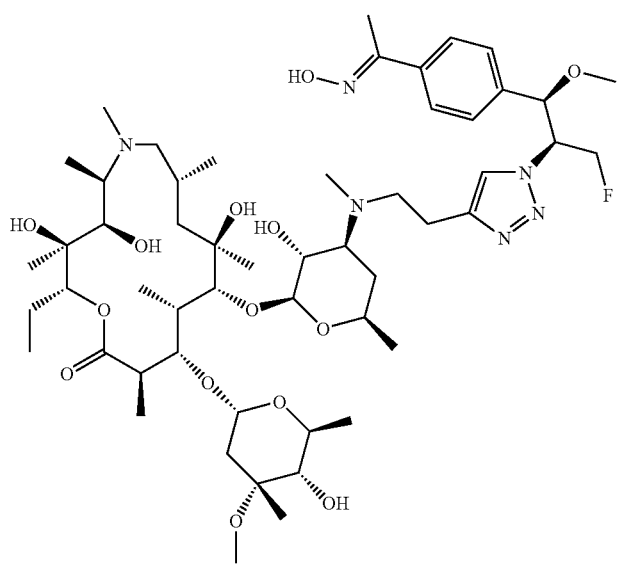 |

TABLE 1-continued
| Compound No. | Structure |
|---|---|
| 178 | 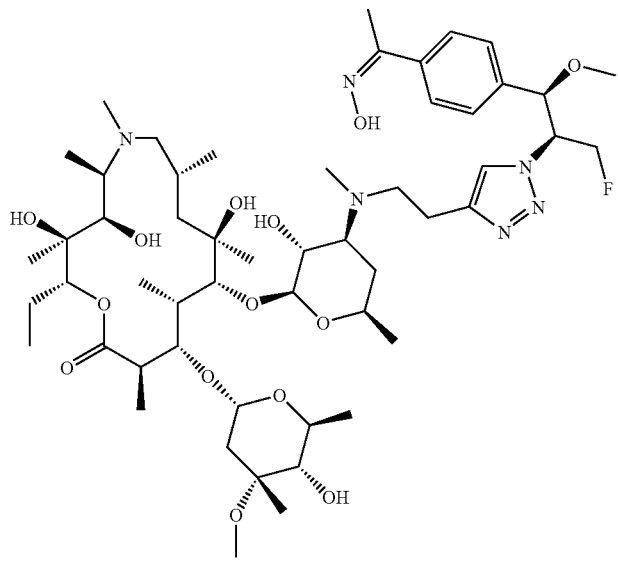 |
| 179 | 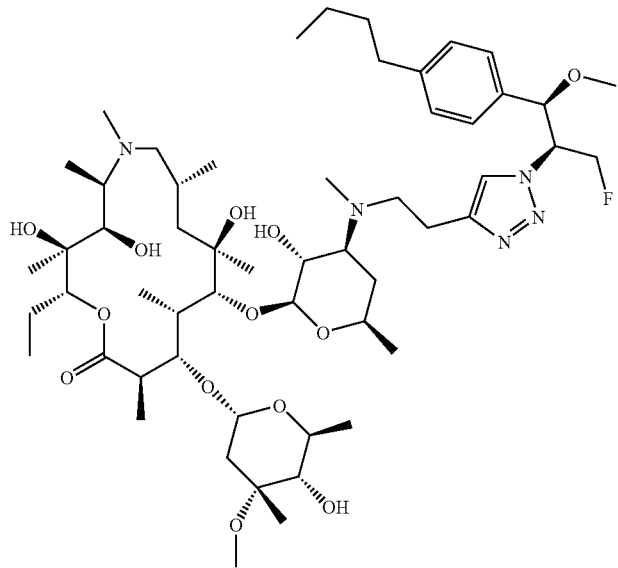 |

TABLE 1-continued
| Compound No. | Structure |
|---|---|
| 180 | 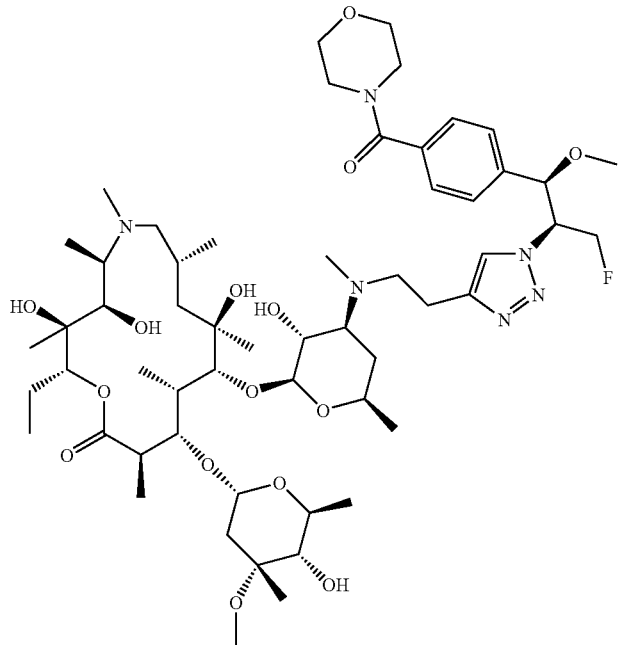 |
| 181 | 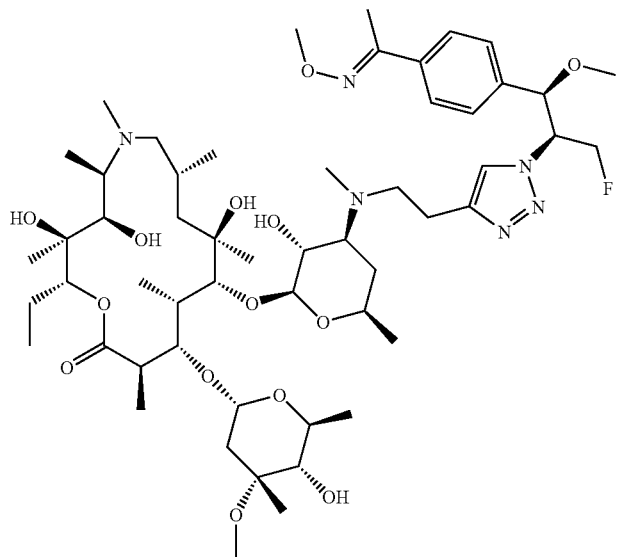 |

TABLE 1-continued
| Compound No. | Structure |
|---|---|
| 182 | 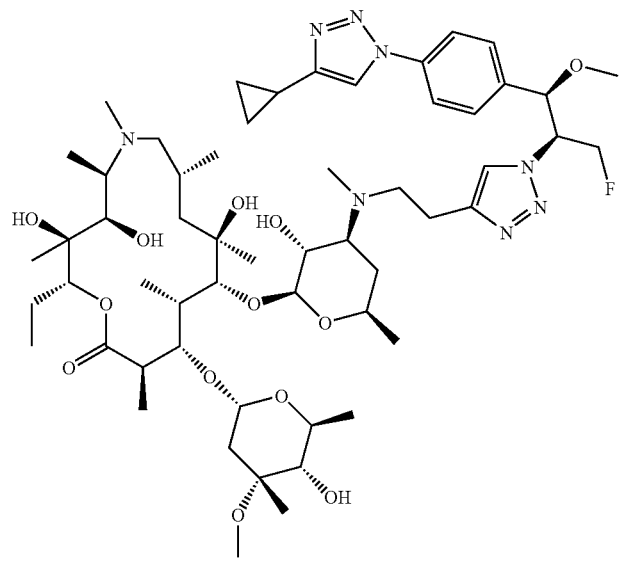 |
| 183 | 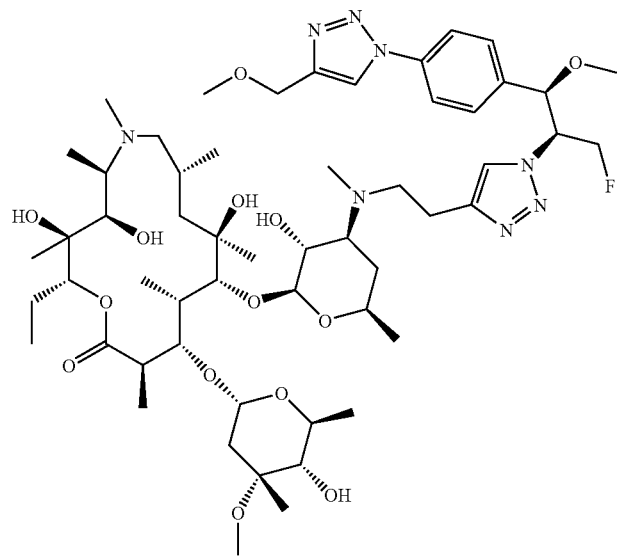 |

TABLE 1-continued
| Compound No. | Structure |
|---|---|
| 184 | 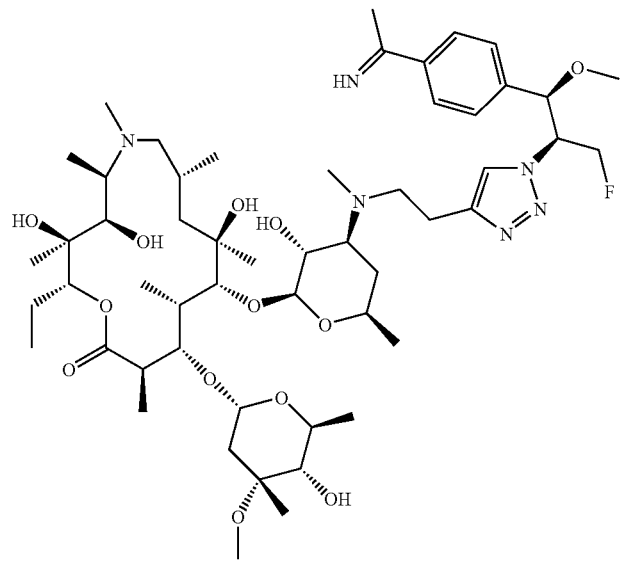 |
| 185 | 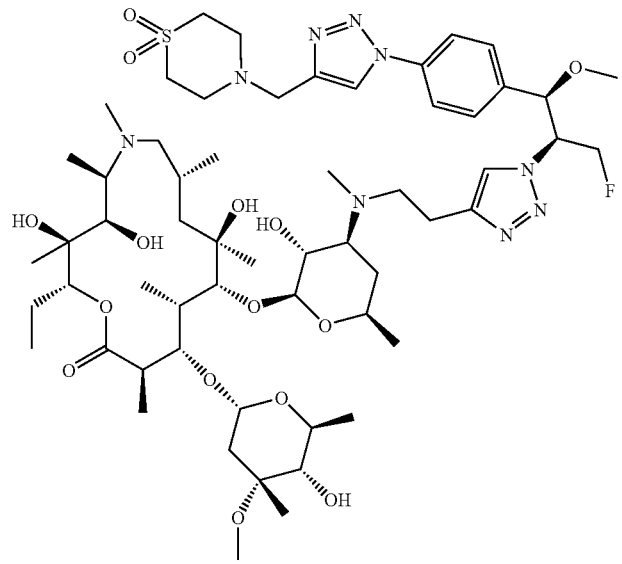 |

TABLE 1-continued
| Compound No. | Structure |
|---|---|
| 186 | 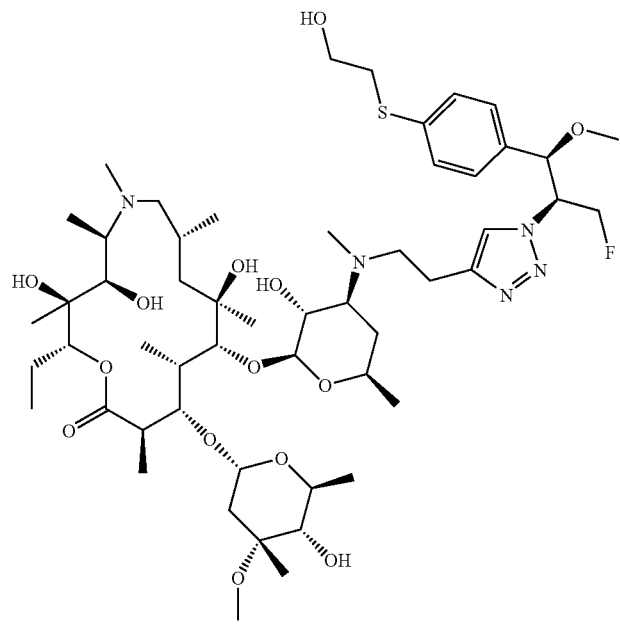 |
| 187 | 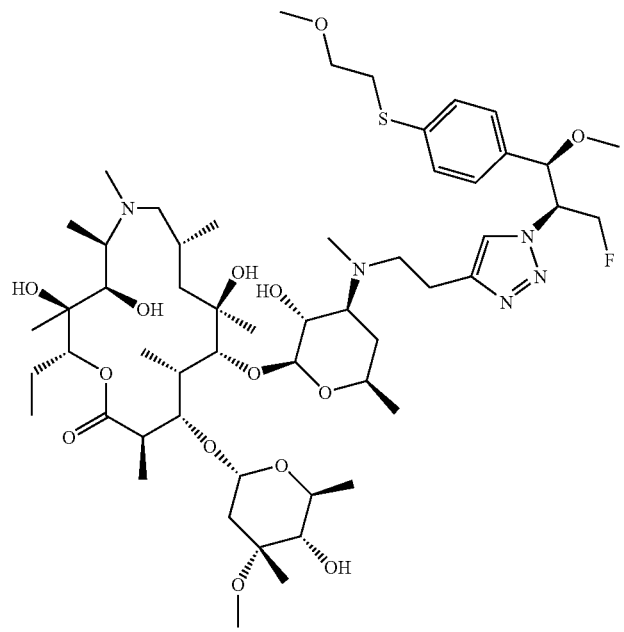 |

TABLE 1-continued
| Compound No. | Structure |
|---|---|
| 188 | 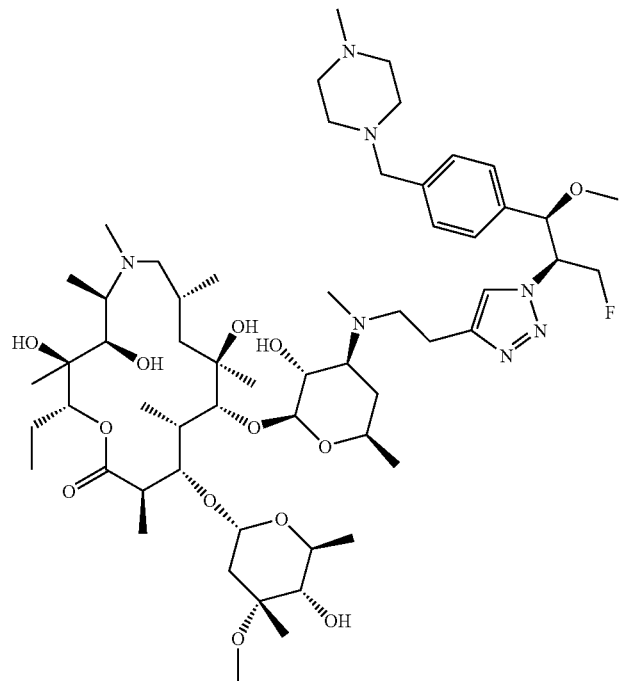 |
| 189 | 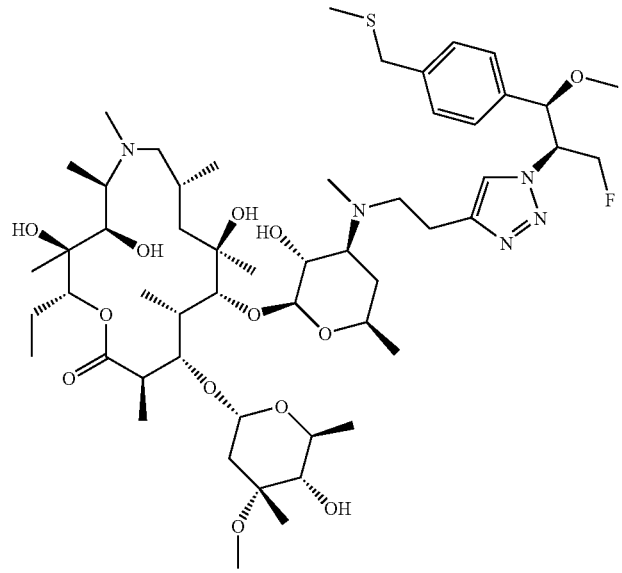 |

TABLE 1-continued
| Compound No. | Structure |
|---|---|
| 190 | 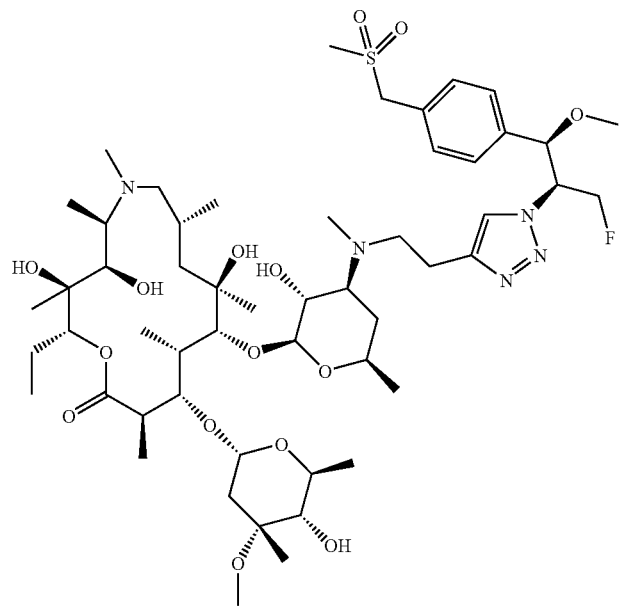 |
| 191 | 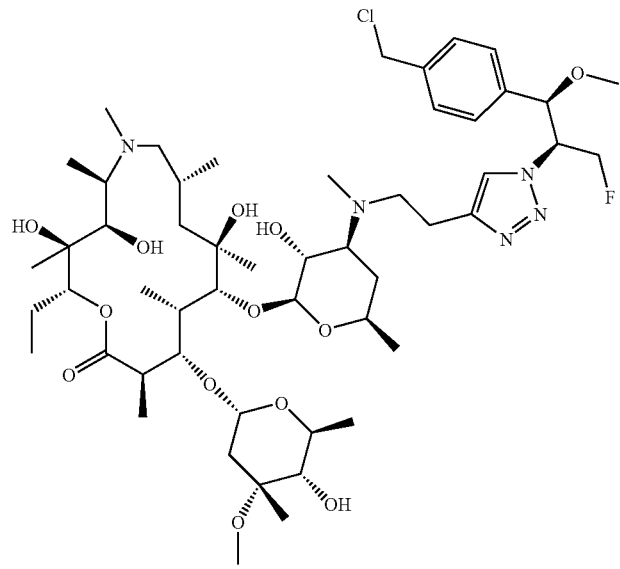 |

TABLE 1-continued
| Compound No. | Structure |
|---|---|
| 192 | 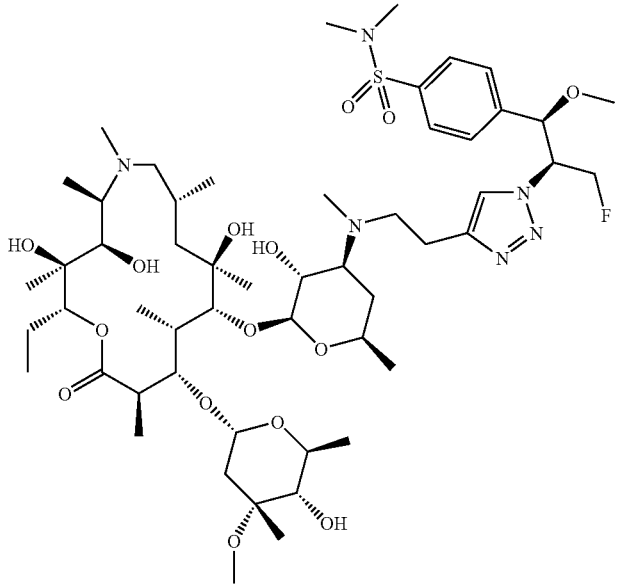 |
| 193 | 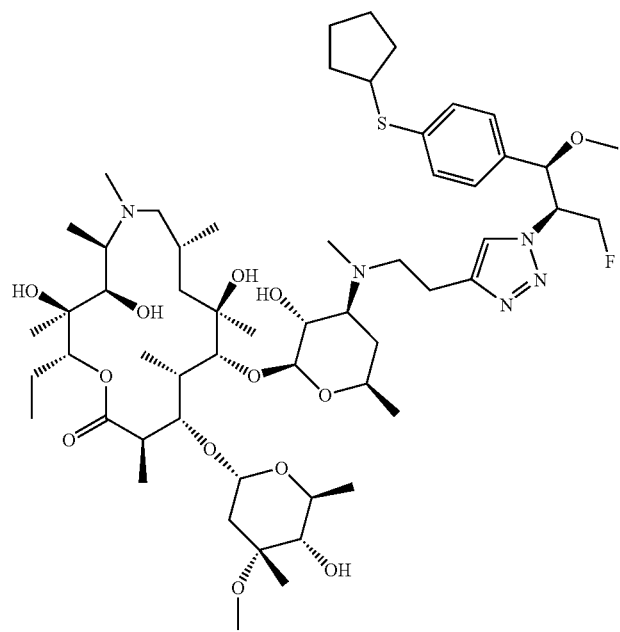 |

TABLE 1-continued
| Compound No. | Structure |
|---|---|
| 194 | 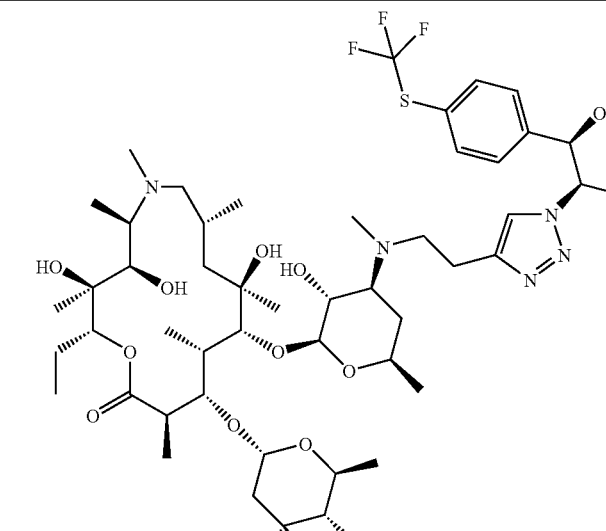 |
| 195 | 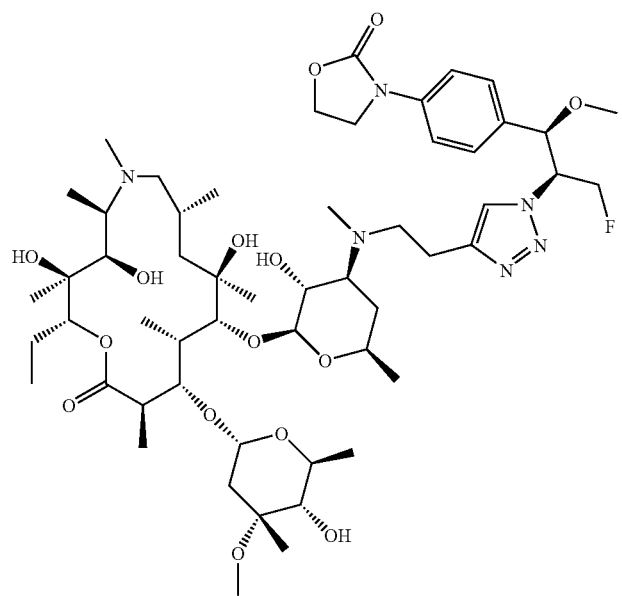 |

TABLE 1-continued
| Compound No. | Structure |
|---|---|
| 196 | 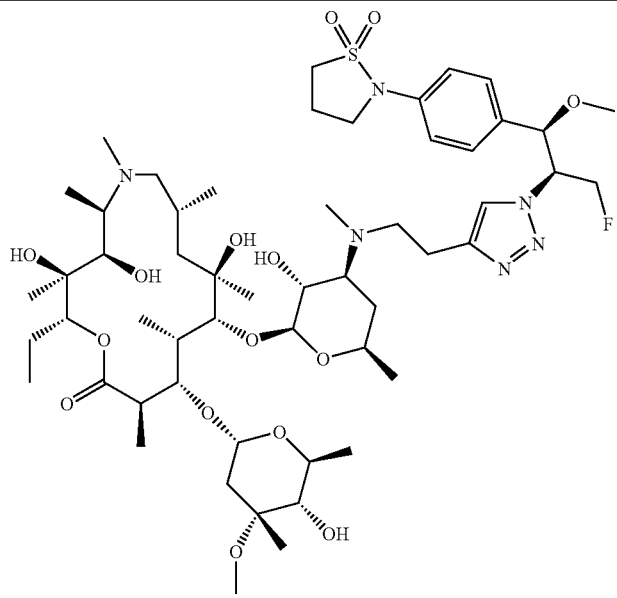 |
| 197 | 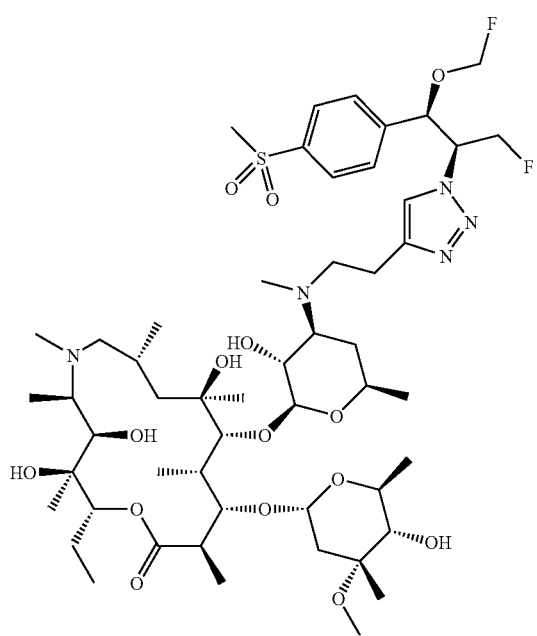 |

TABLE 1-continued
| Compound No. | Structure |
|---|---|
| 198 | 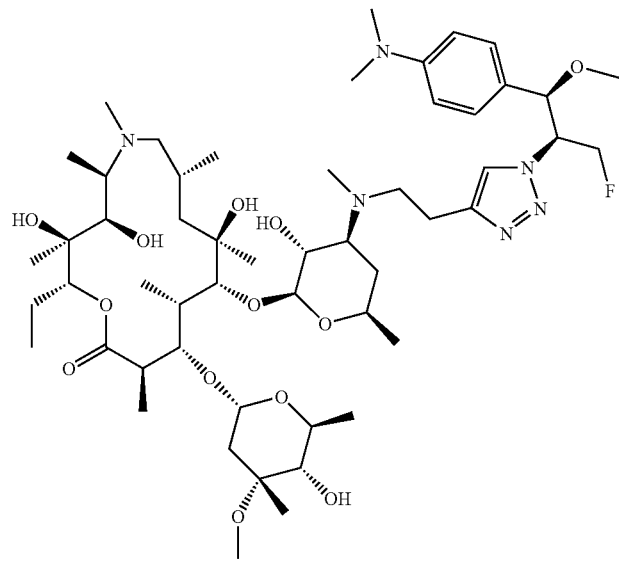 |
| 199 | 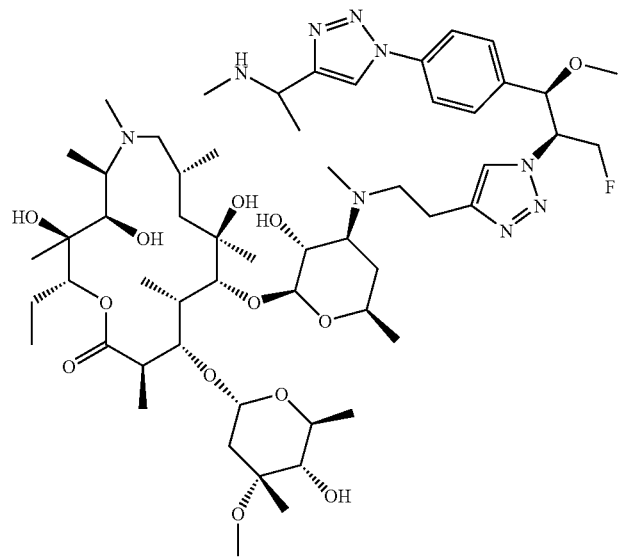 |

TABLE 1-continued
| Compound No. | Structure |
|---|---|
| 200 | 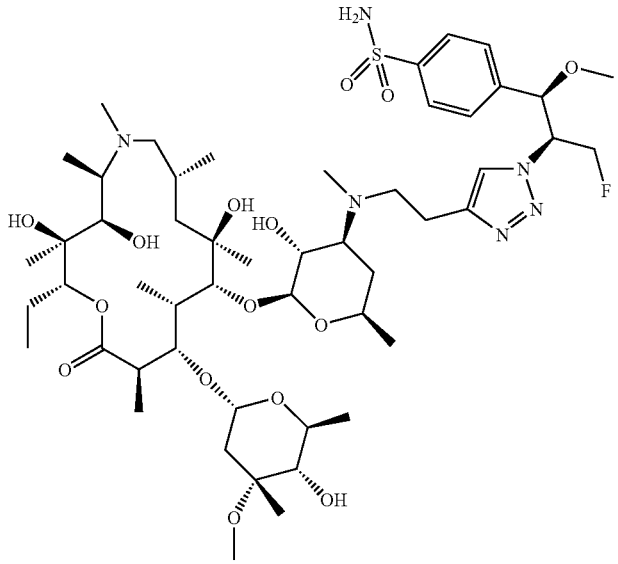 |
| 201 | 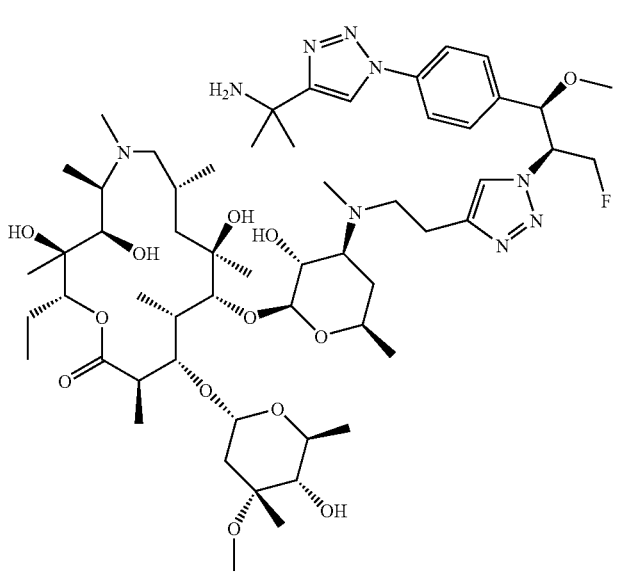 |

TABLE 1-continued
| Compound No. | Structure |
|---|---|
| 202 | 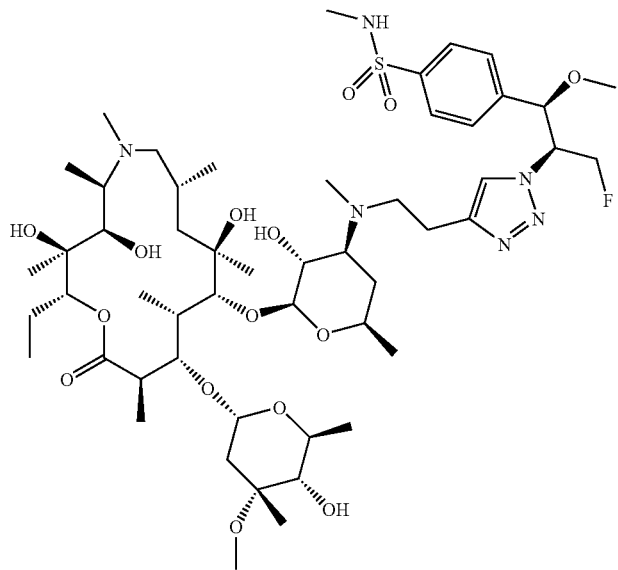 |
| 203 | 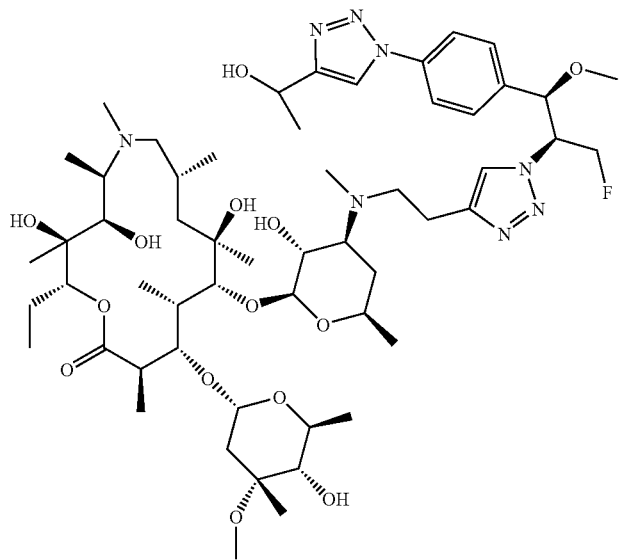 |

TABLE 1-continued
| Compound No. | Structure |
|---|---|
| 204 | 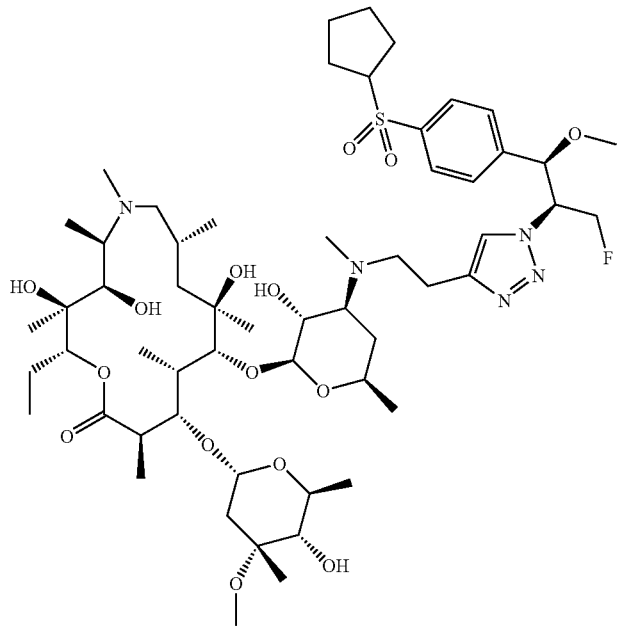 |
| 205 | 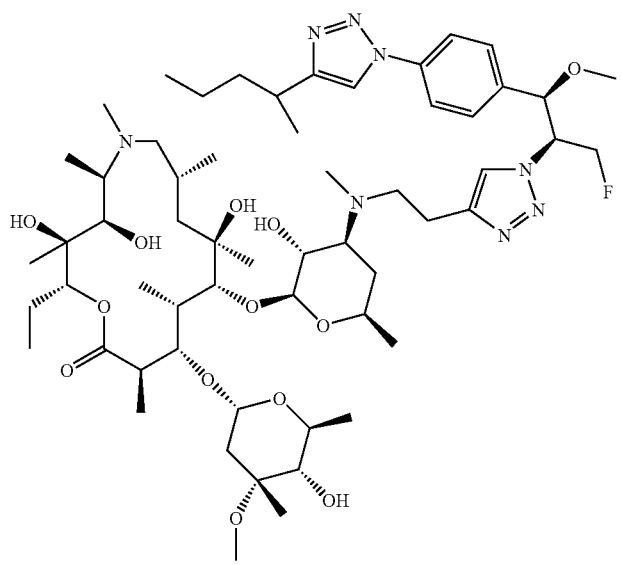 |

TABLE 1-continued
| Compound No. | Structure |
|---|---|
| 206 | 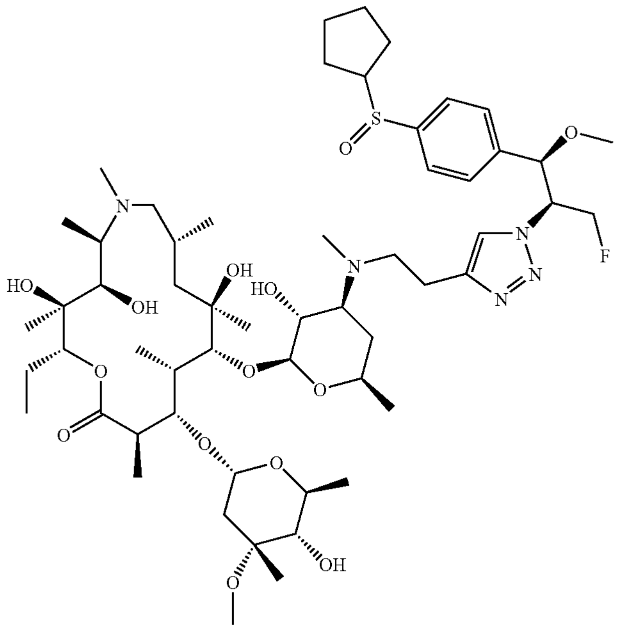 |
| 207 | 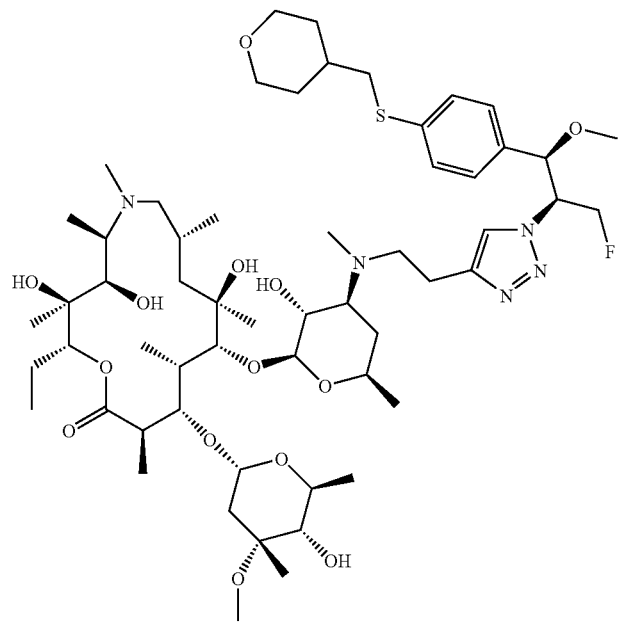 |

TABLE 1-continued
| Compound No. | Structure |
|---|---|
| 208 | 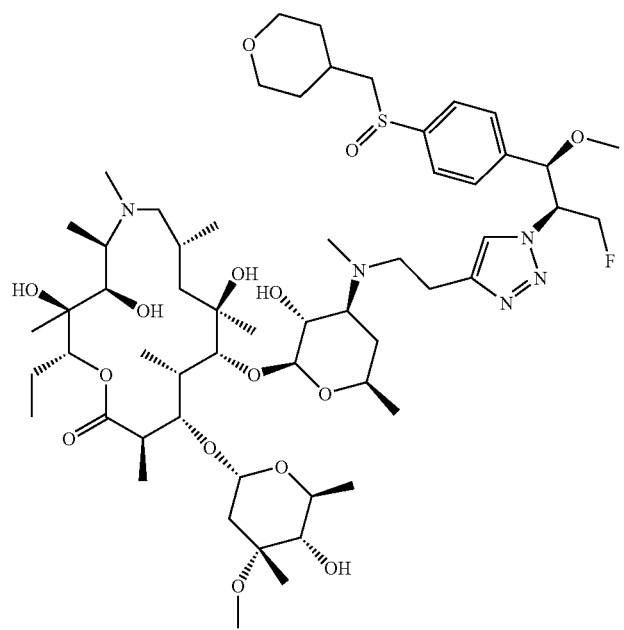 |
| 209 | 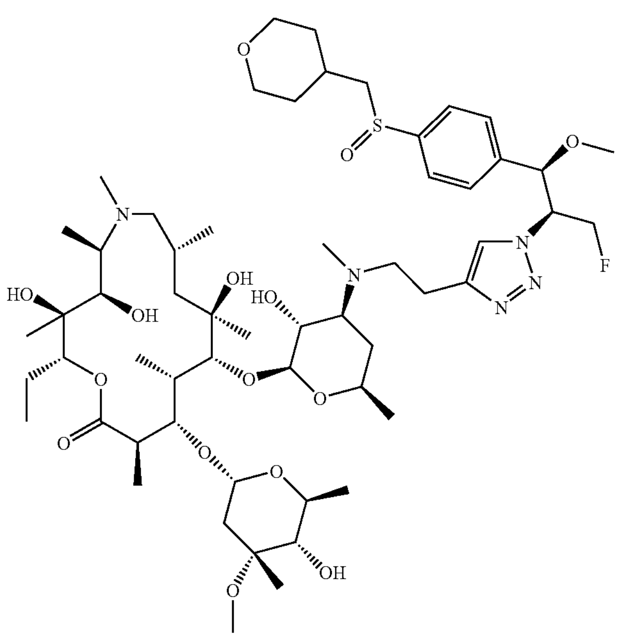 |

TABLE 1-continued
| Compound No. | Structure |
|---|---|
| 210 | 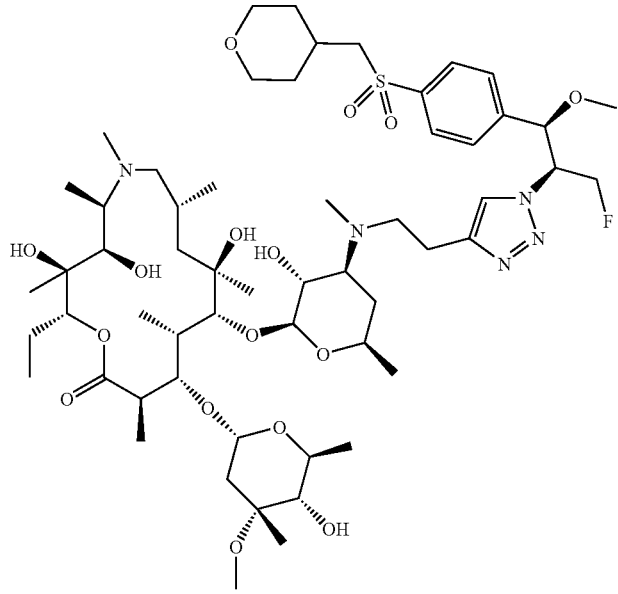 |
| 211 | 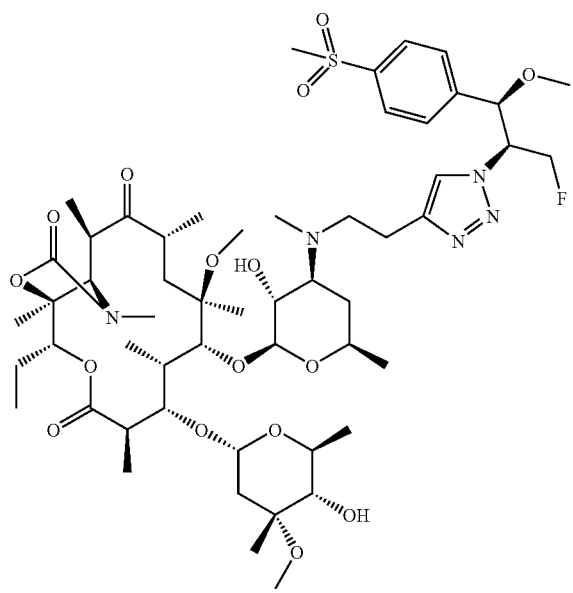 |

TABLE 1-continued
| Compound No. | Structure |
|---|---|
| 212 | 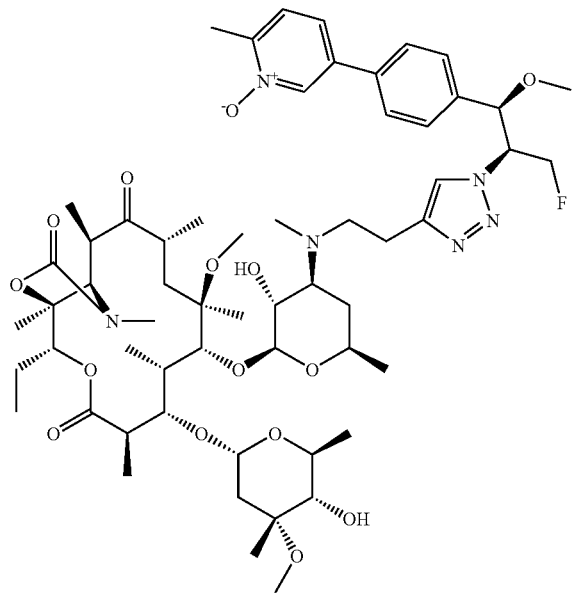 |
| 213 | 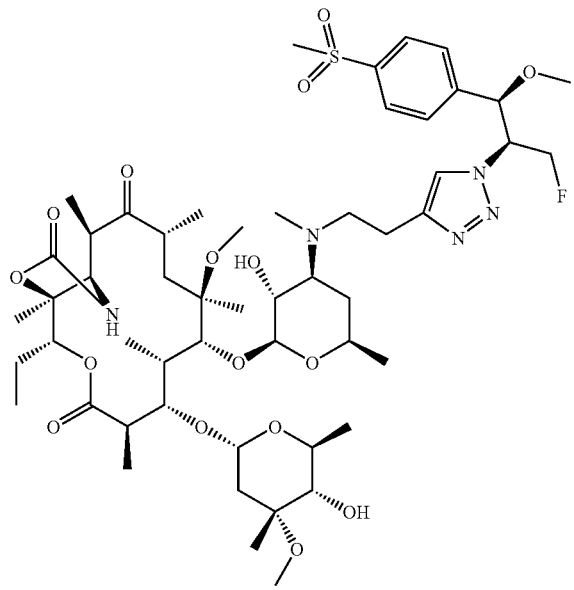 |

TABLE 1-continued
| Compound No. | Structure |
| --- | --- |
| 214 | 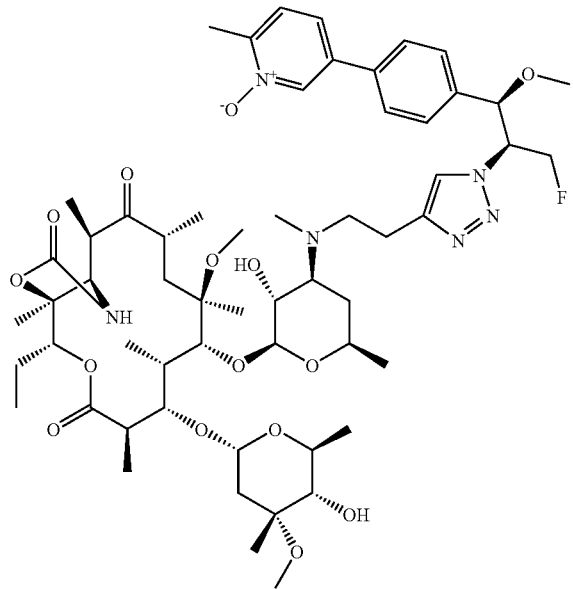 |
| 215 | 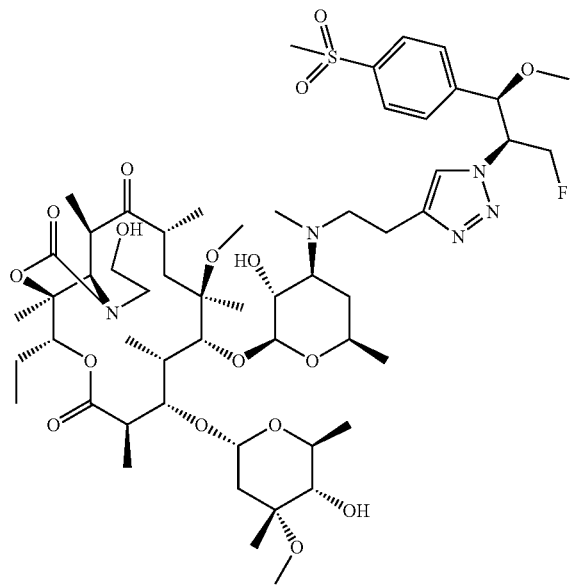 |

TABLE 1-continued
| Compound No. | Structure |
|---|---|
| 216 | 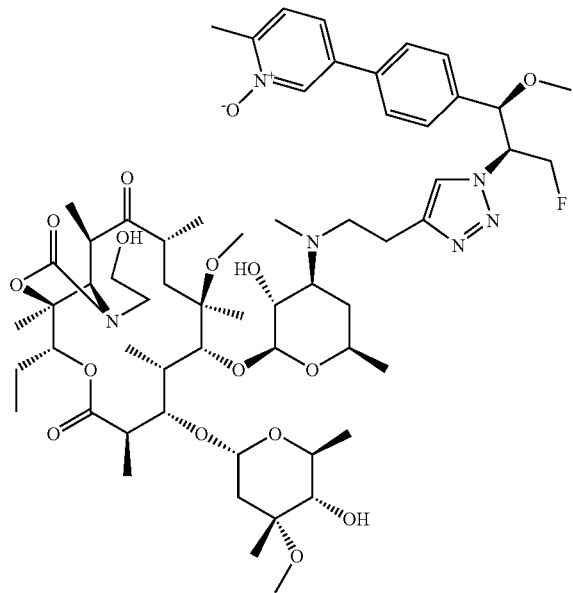 |
| 217 | 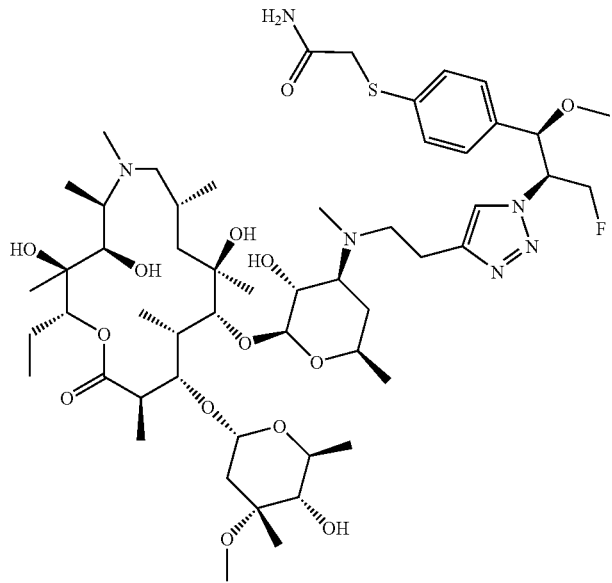 |

TABLE 1-continued
| Compound No. | Structure |
|---|---|
| 218 | 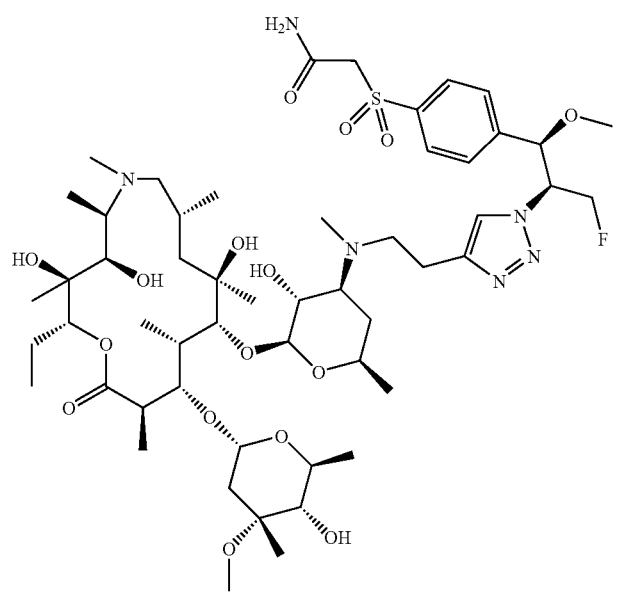 |
| 219 | 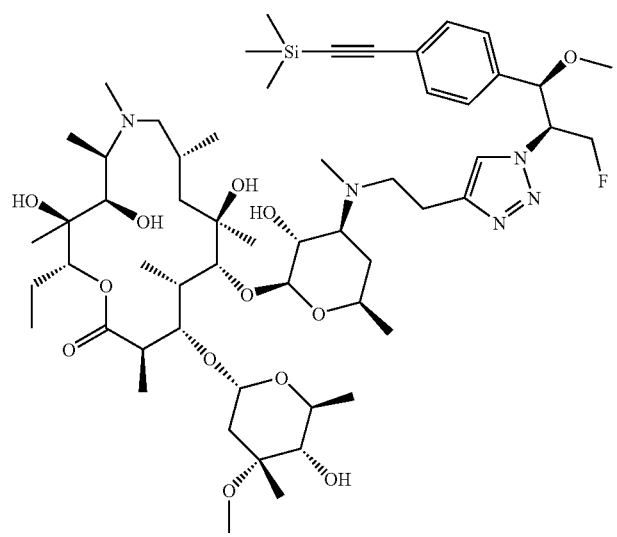 |

TABLE 1-continued

| Compound No. | Structure |
|---|---|
| 220 | 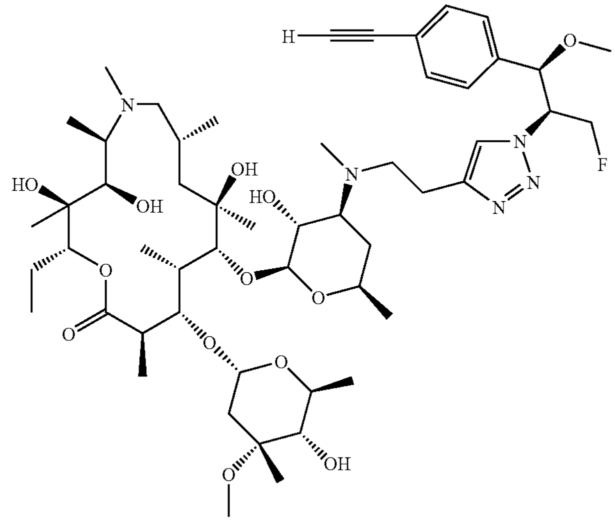 |
| 221 | 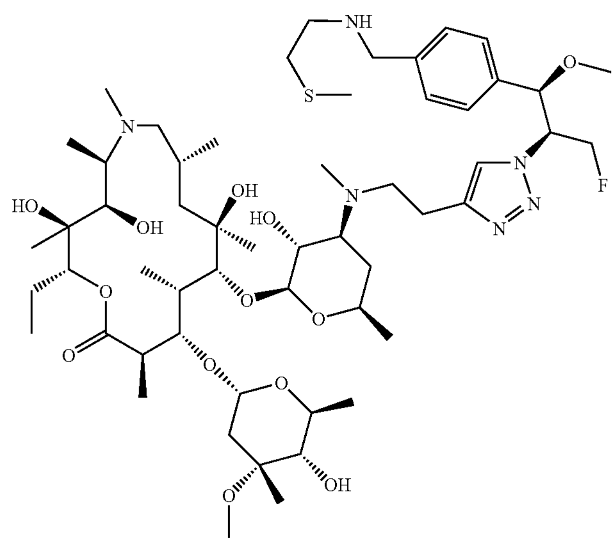 |
| 222 | 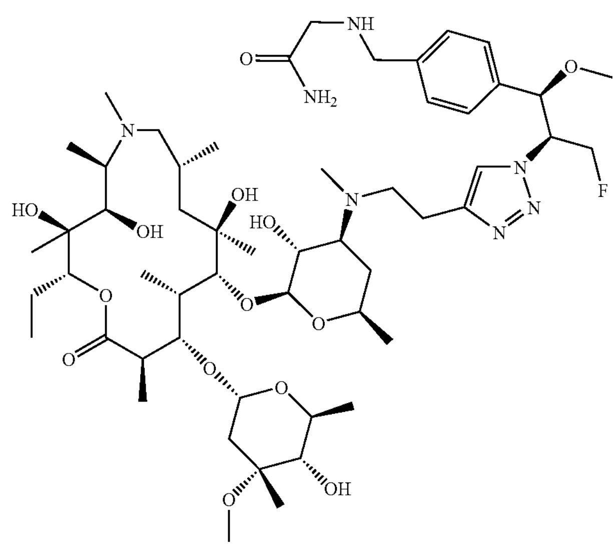 |

TABLE 1-continued
| Compound No. | Structure |
|---|---|
| 223 | 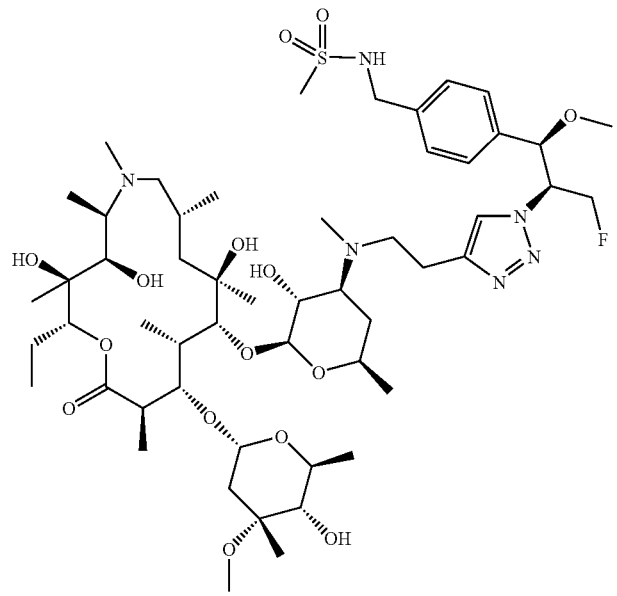 |
| 224 | 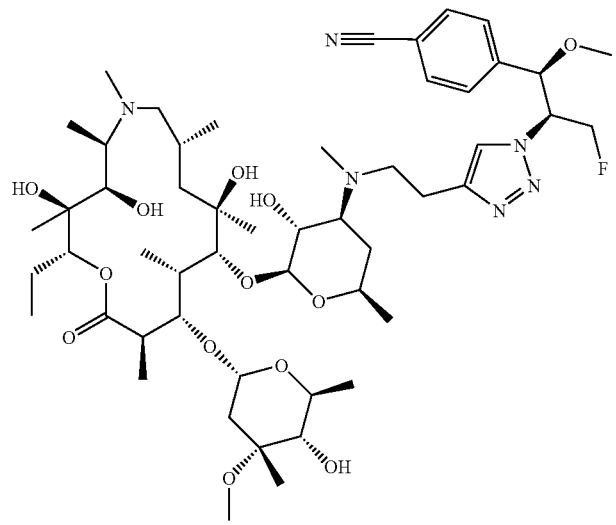 |

TABLE 1-continued
| Compound No. | Structure |
|---|---|
| 225 | 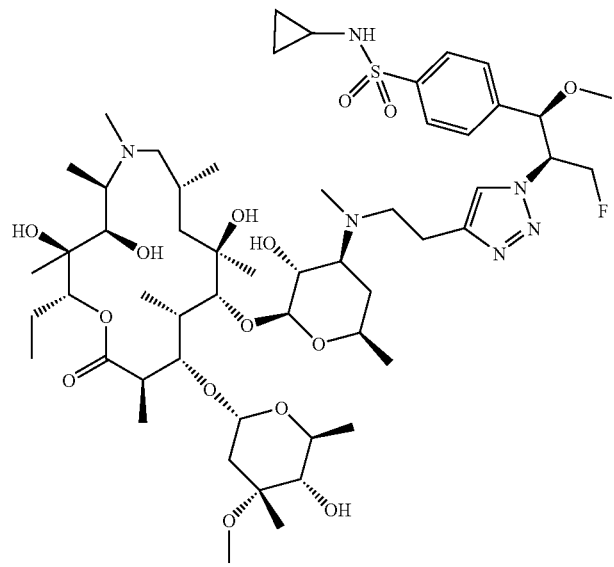 |
| 226 | 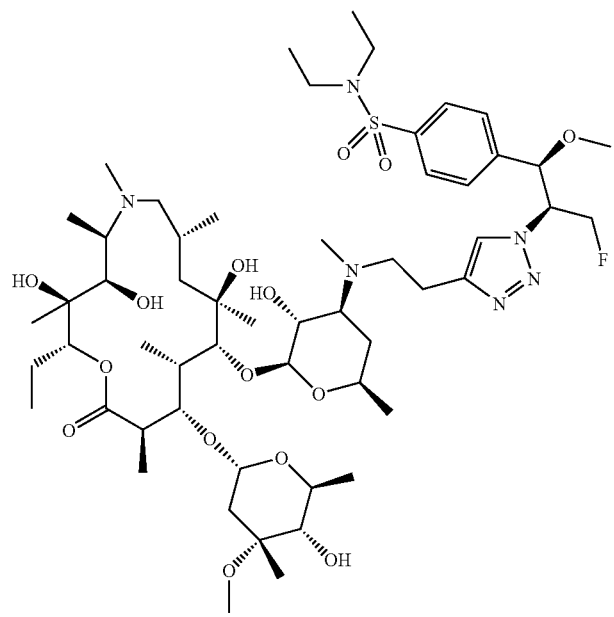 |

TABLE 1-continued
| Compound No. | Structure |
|---|---|
| 227 | 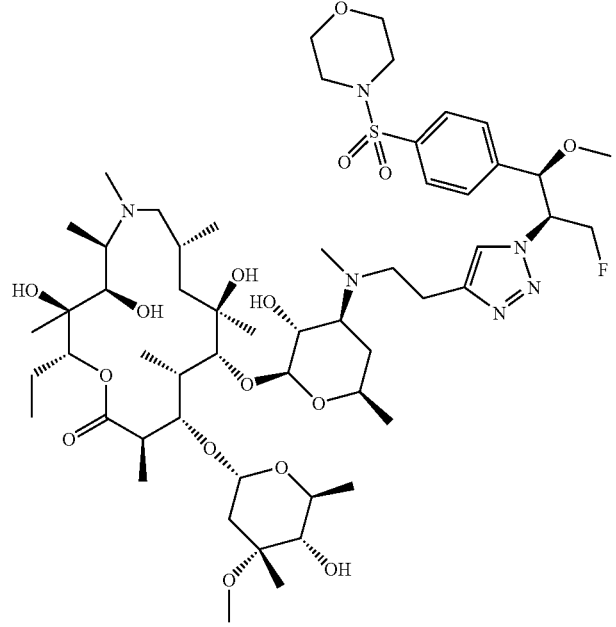 |
| 228 | 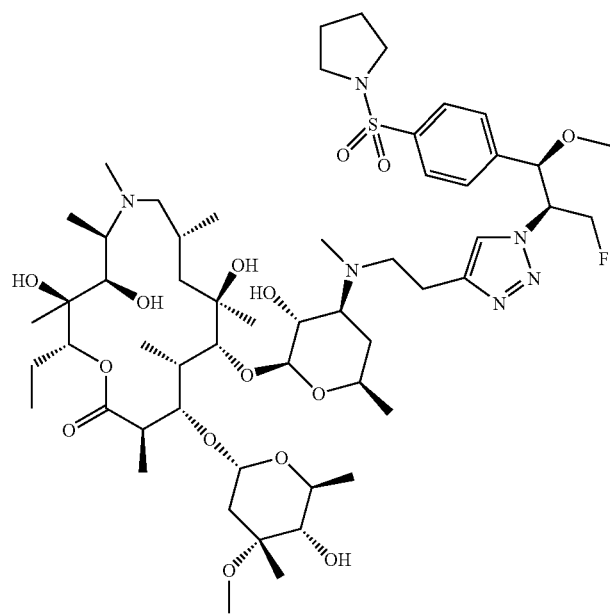 |

TABLE 1-continued
| Compound No. | Structure |
|---|---|
| 229 | 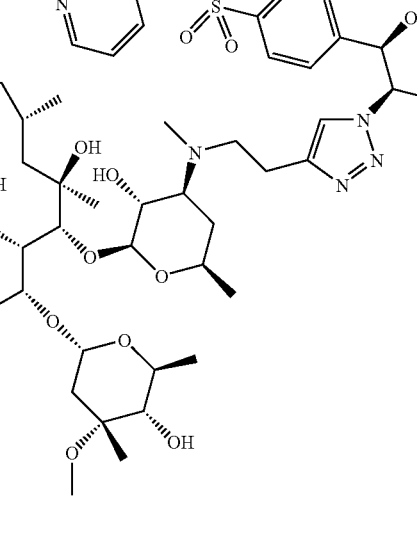 |
| 230 | 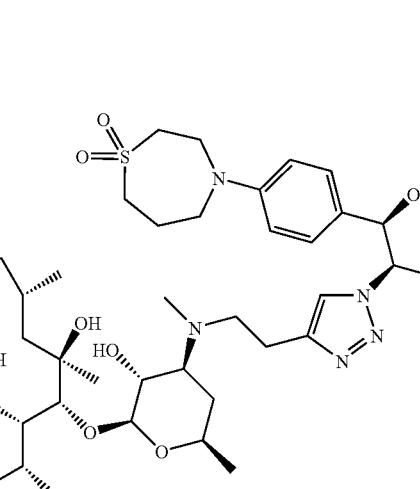 |

TABLE 1-continued
| Compound No. | Structure |
|---|---|
| 231 | 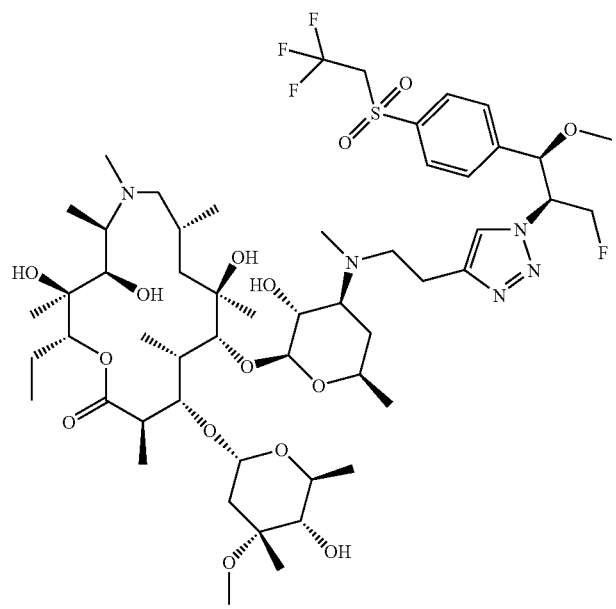 |
| 232 | 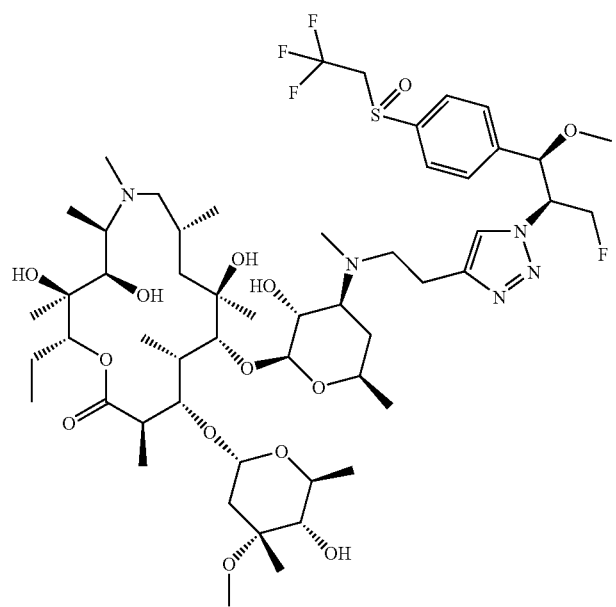 |

TABLE 1-continued
| Compound No. | Structure |
|---|---|
| 233 | 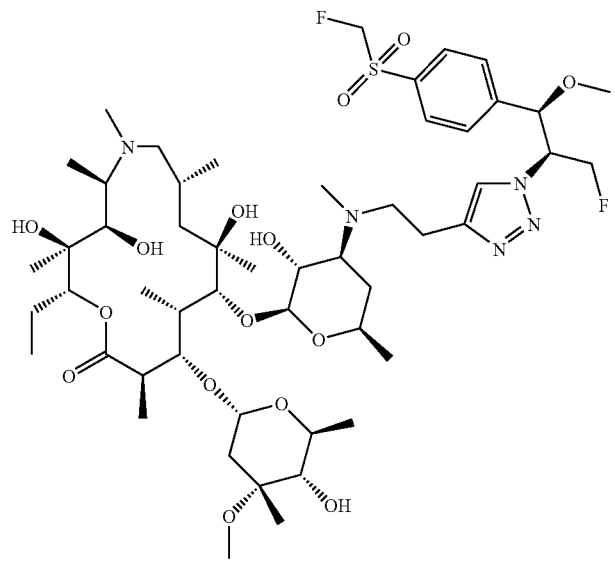 |
| 234 | 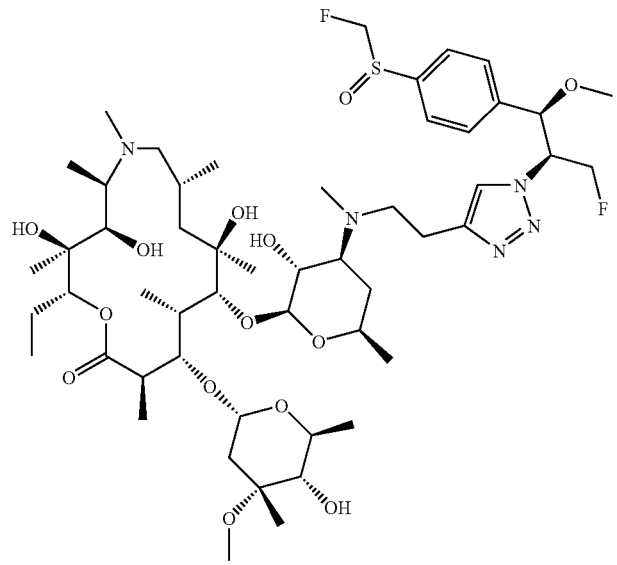 |

TABLE 1-continued
| Compound No. | Structure |
|---|---|
| 235 | 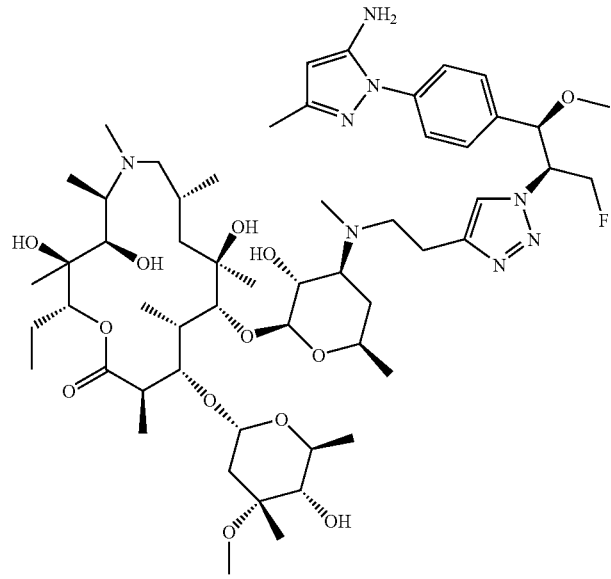 |
| 236 | 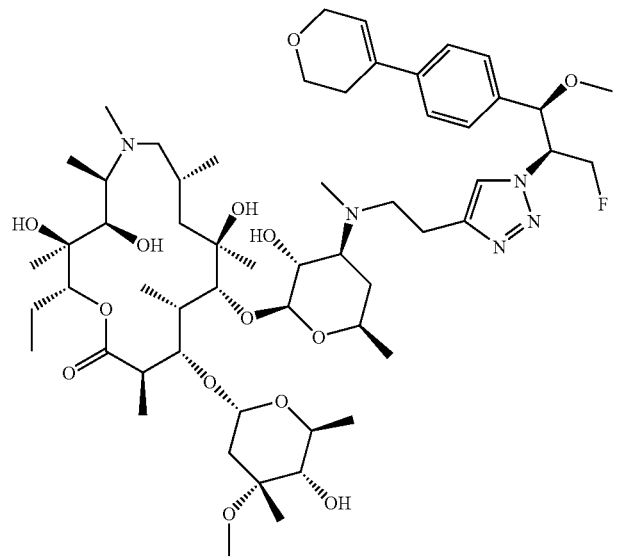 |

TABLE 1-continued
| Compound No. | Structure |
|---|---|
| 237 | 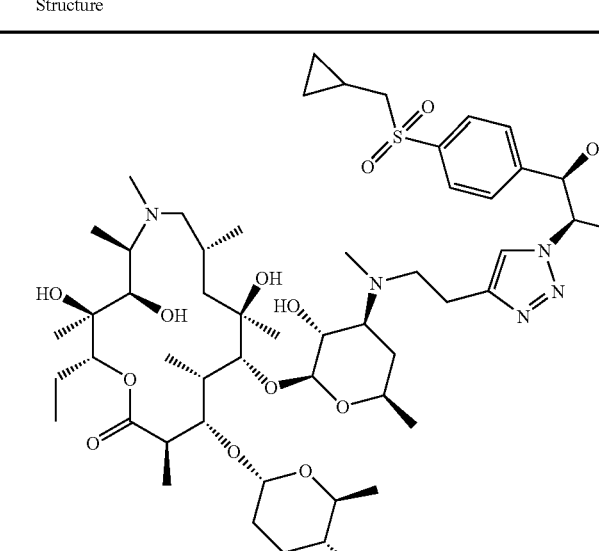 |
| 238 | 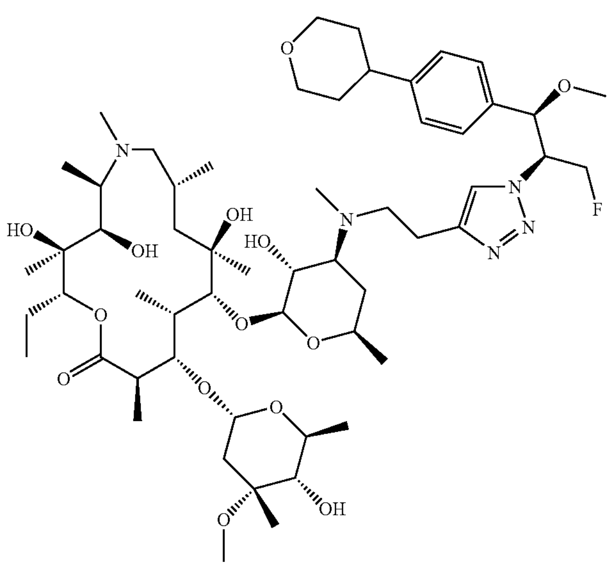 |

TABLE 1-continued
| Compound No. | Structure |
|---|---|
| 239 | 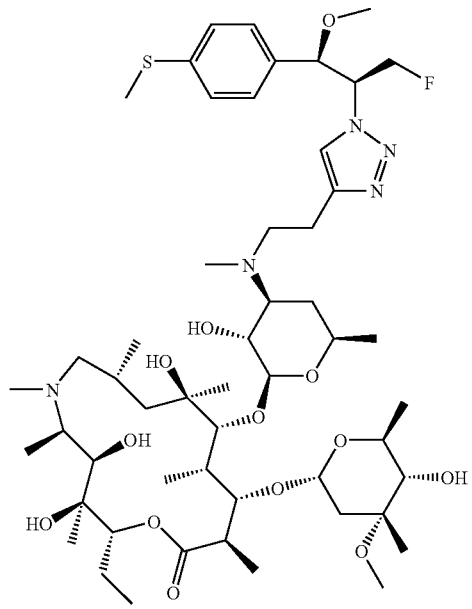 |
| 240 | 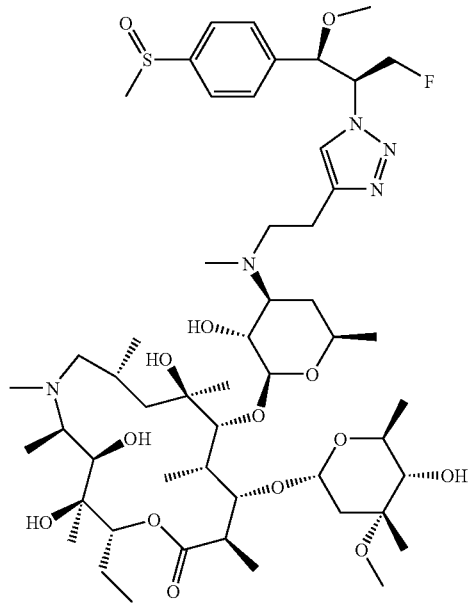 |

TABLE 1-continued
| Compound No. | Structure |
|---|---|
| 241 | 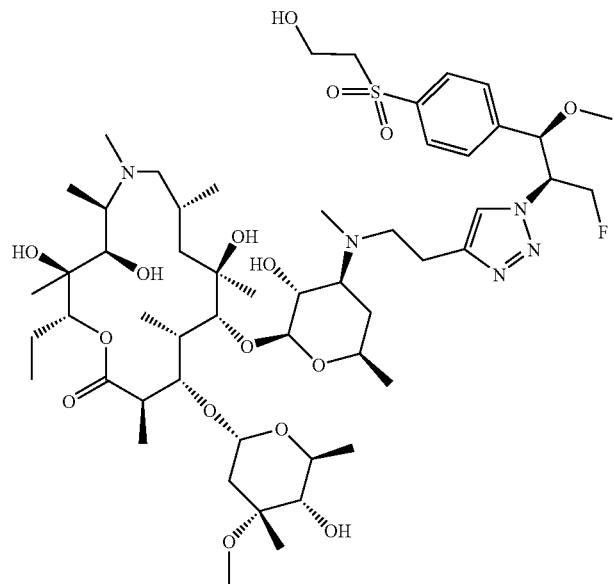 |
| 242 | 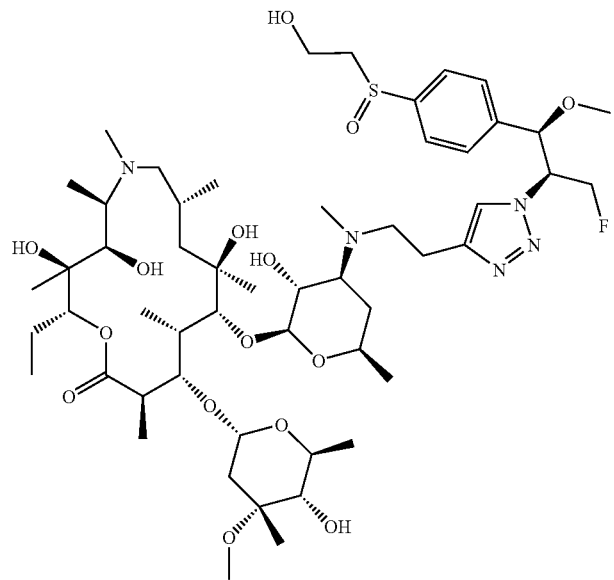 |

TABLE 1-continued
| Compound No. | Structure |
|---|---|
| 243 | 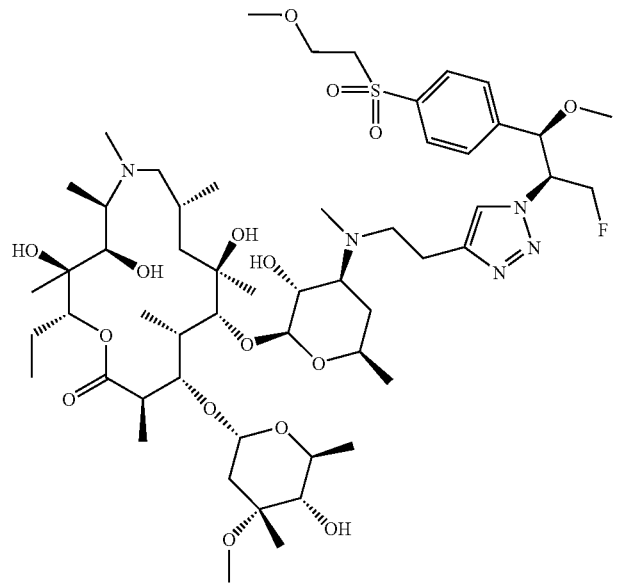 |
| 244 | 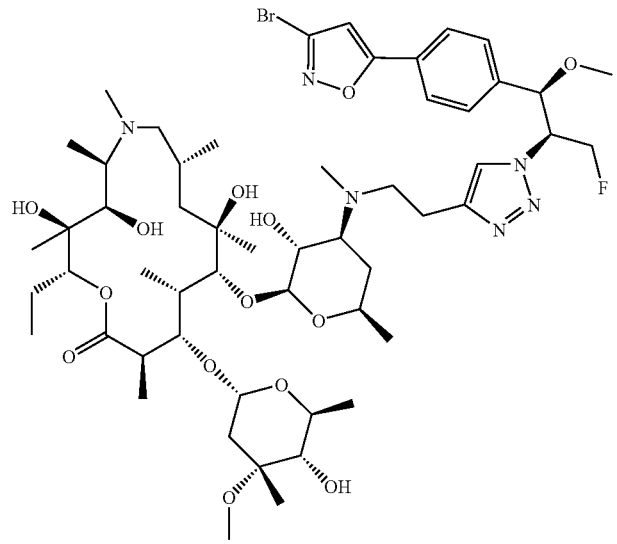 |

TABLE 1-continued
| Compound No. | Structure |
|---|---|
| 245 | 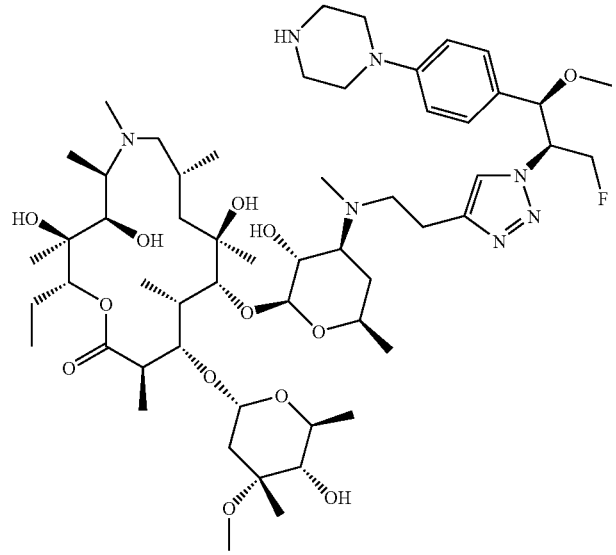 |
| 246 | 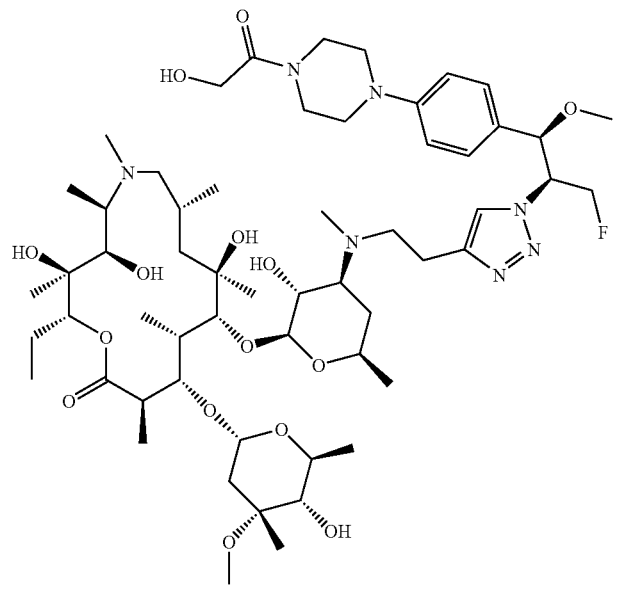 |

TABLE 1-continued
| Compound No. | Structure |
|---|---|
| 247 | 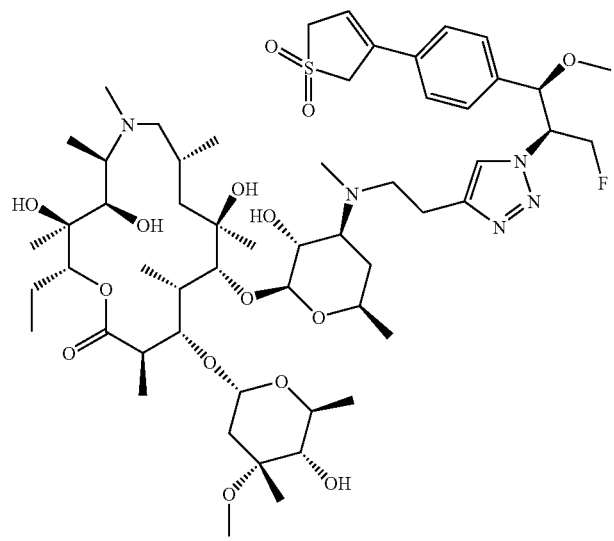 |
| 248 | 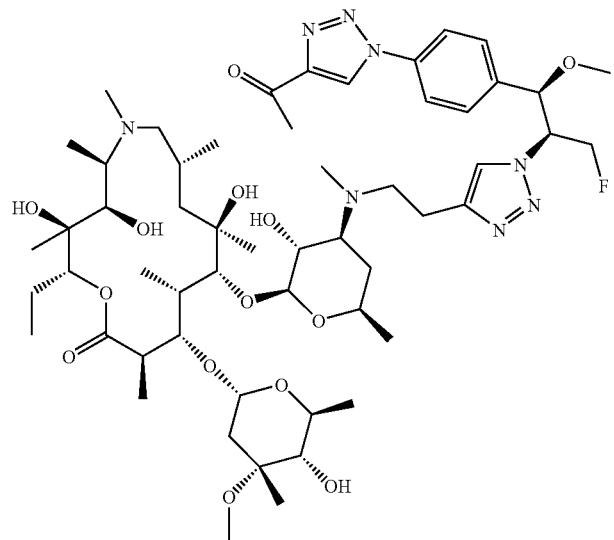 |

TABLE 1-continued
| Compound No. | Structure |
|---|---|
| 249 | 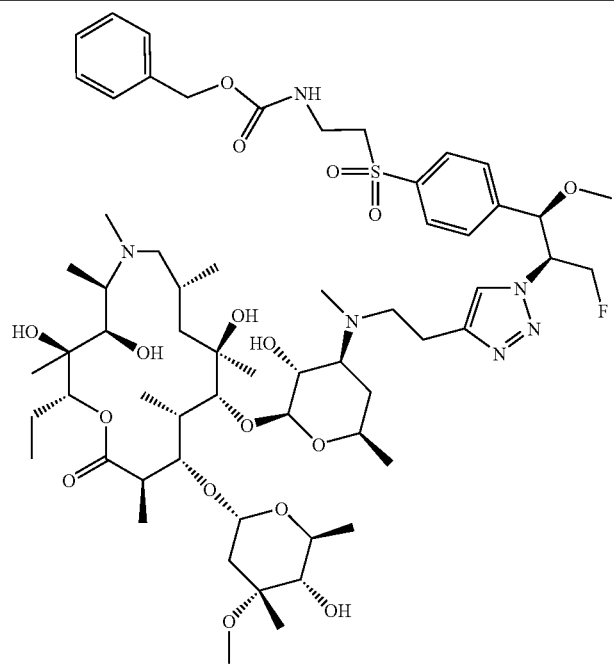 |
| 250 | 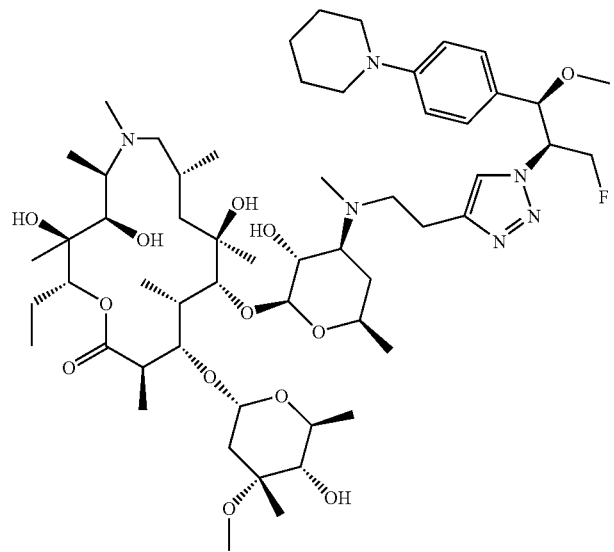 |

TABLE 1-continued
| Compound No. | Structure |
|---|---|
| 251 | 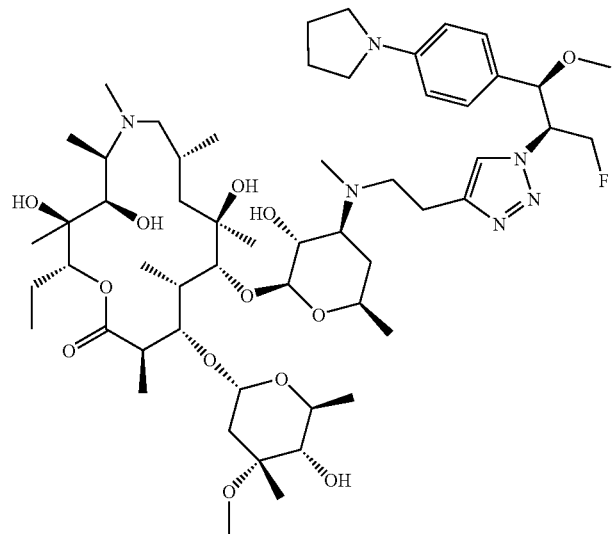 |
| 252 | 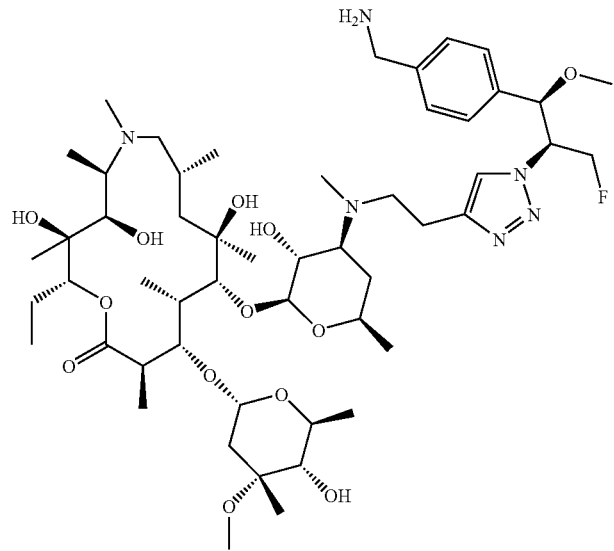 |

TABLE 1-continued
| Compound No. | Structure |
|---|---|
| 253 | 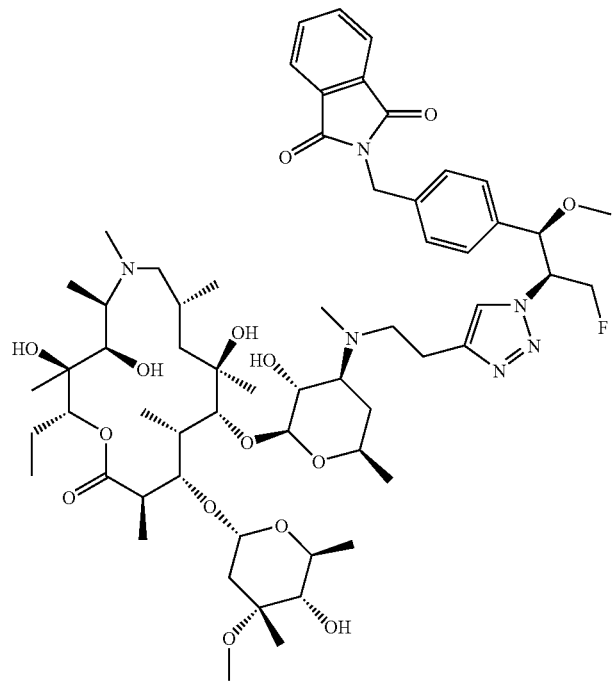 |
| 254 | 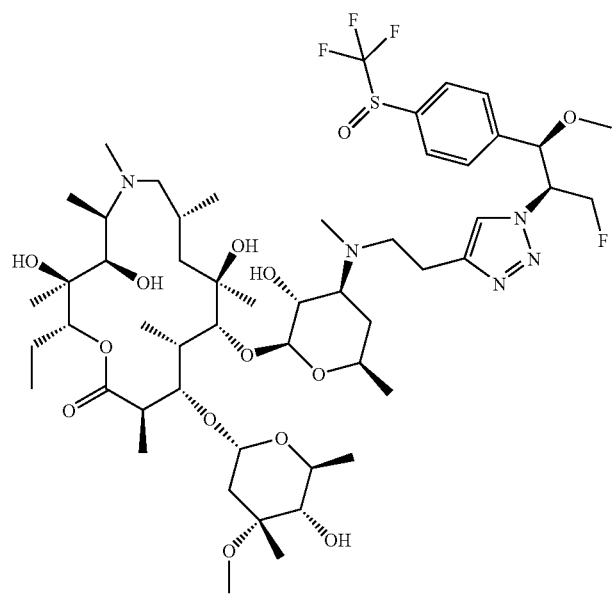 |

TABLE 1-continued

| Compound No. | Structure |
|---|---|
| 255 | 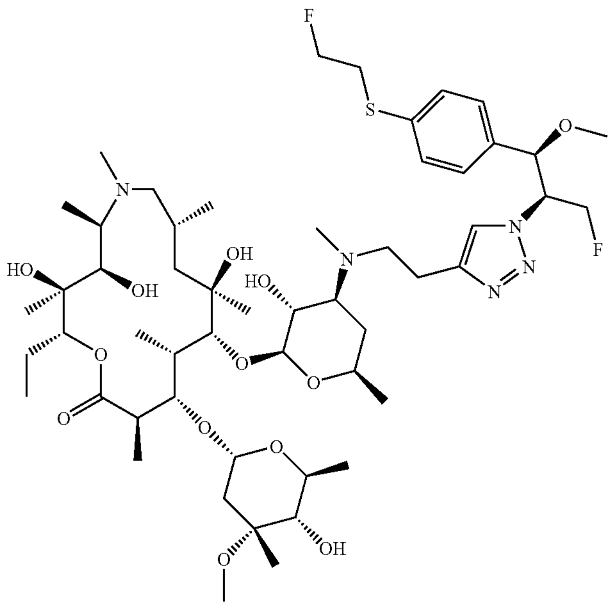 |
| 256 | 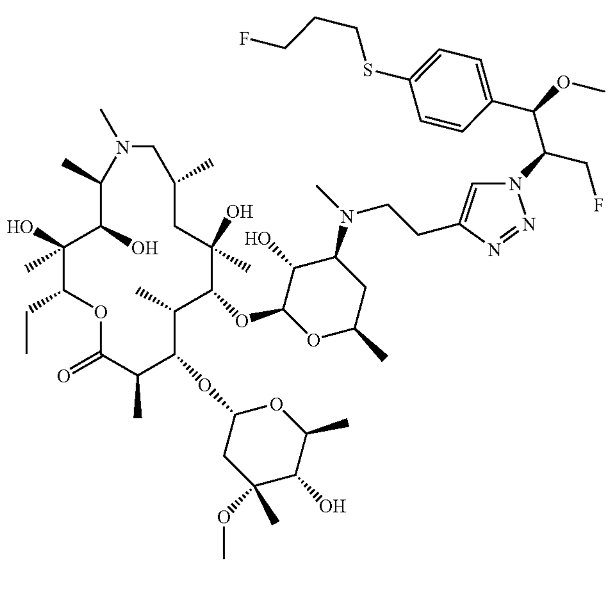 |

TABLE 1-continued
| Compound No. | Structure |
|---|---|
| 257 | 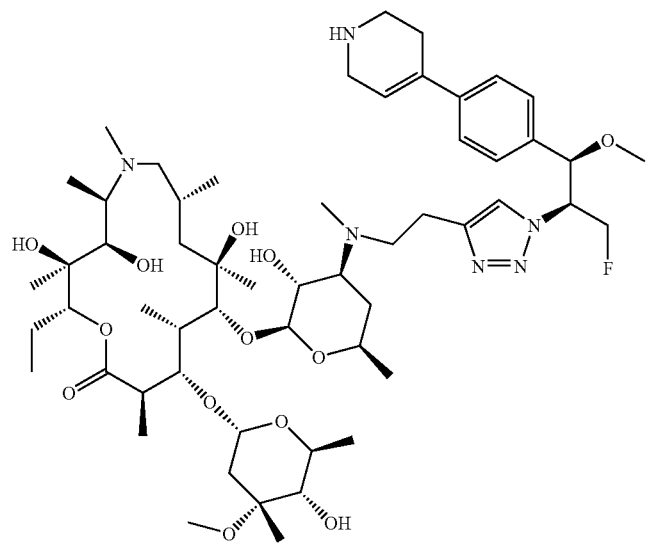 |
| 258 | 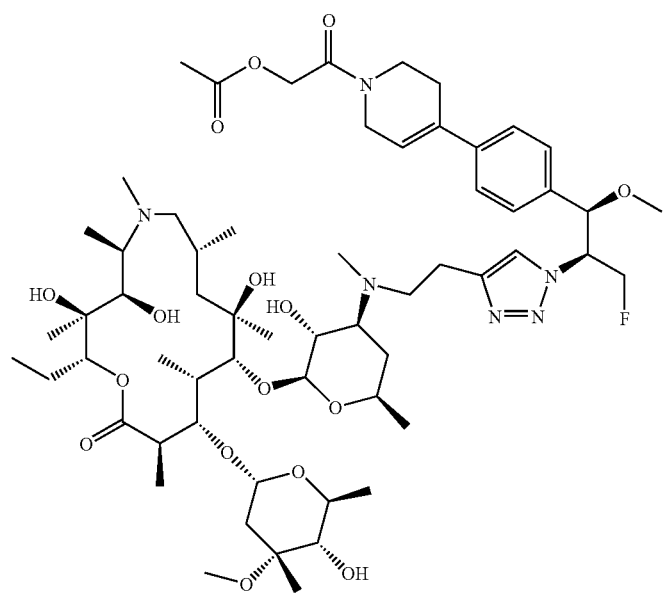 |

TABLE 1-continued
| Compound No. | Structure |
|---|---|
| 259 | 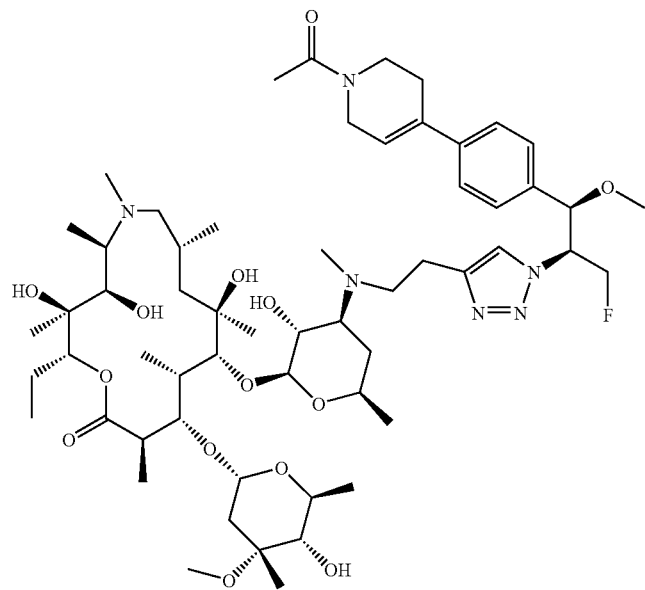 |
| 260 | 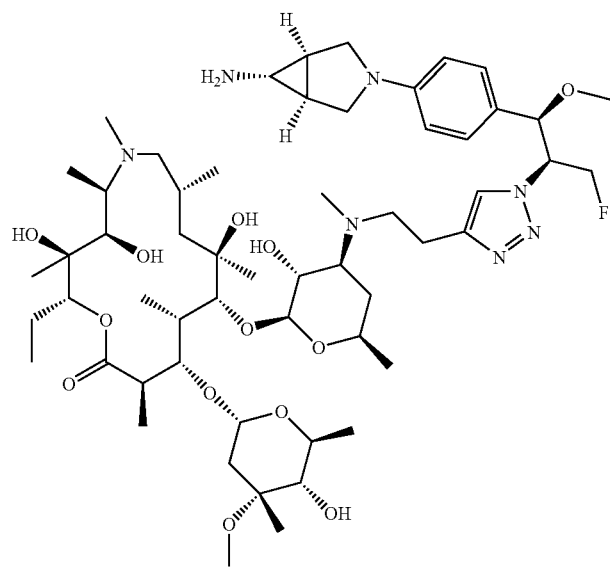 |

TABLE 1-continued
| Compound No. | Structure |
|---|---|
| 261 | 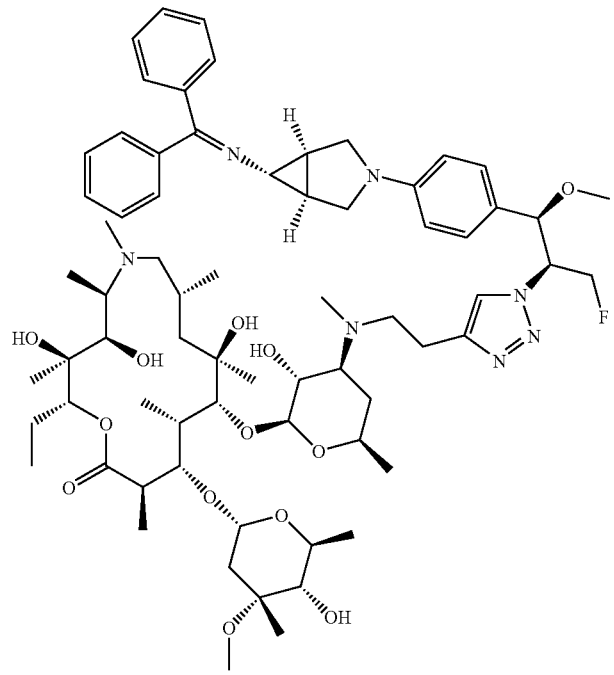 |
| 262 | 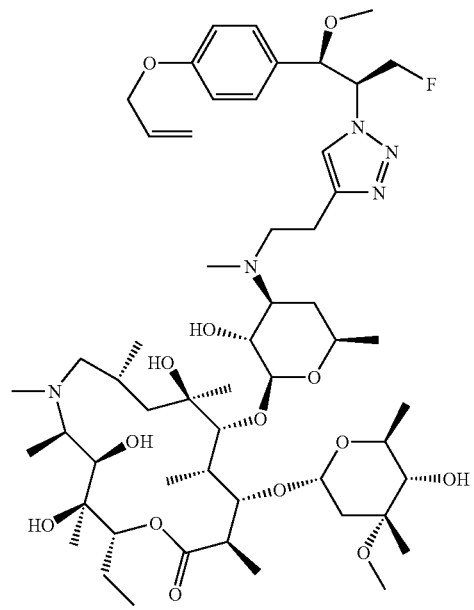 |

TABLE 1-continued
| Compound No. | Structure |
|---|---|
| 263 | 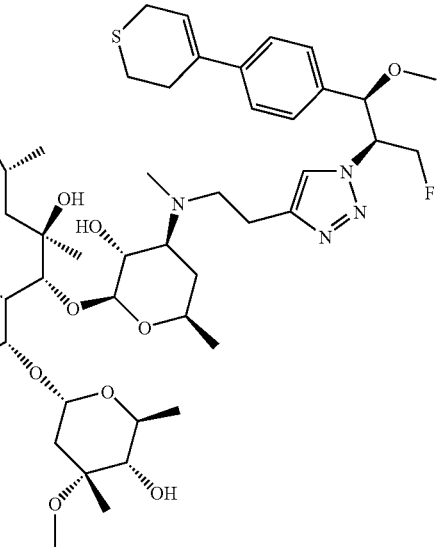 |
| 264 | 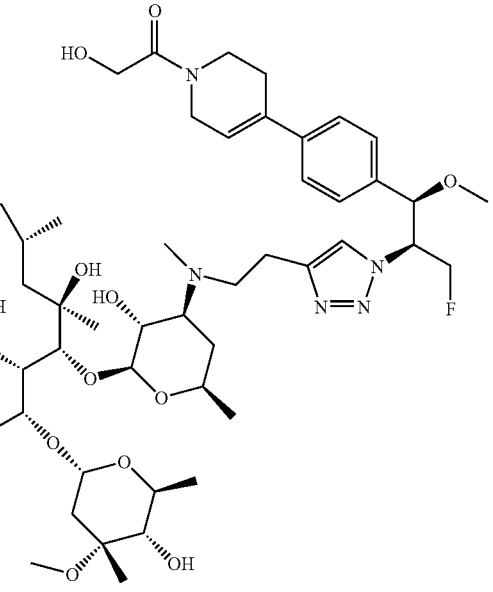 |
| 265 | 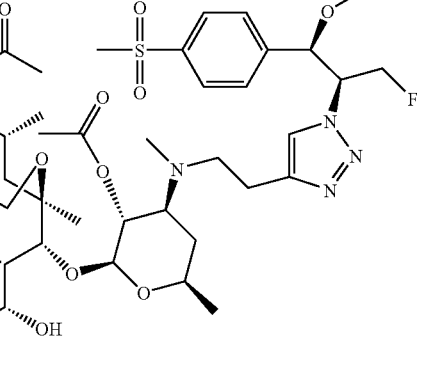 |

TABLE 1-continued
| Compound No. | Structure |
|---|---|
| 266 | 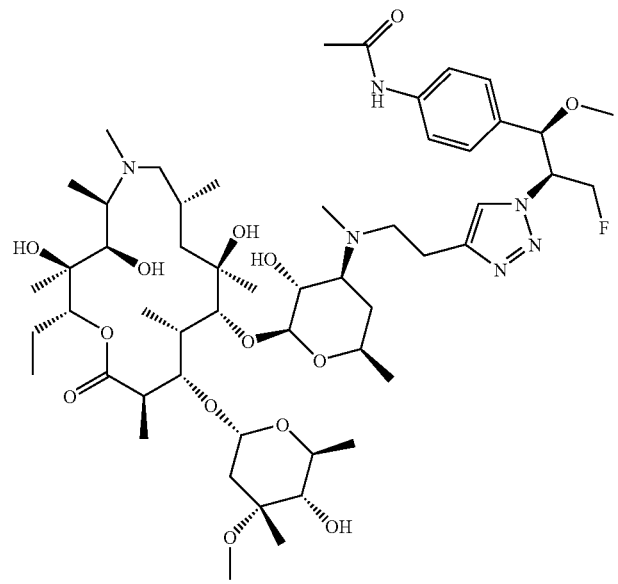 |
| 267 | 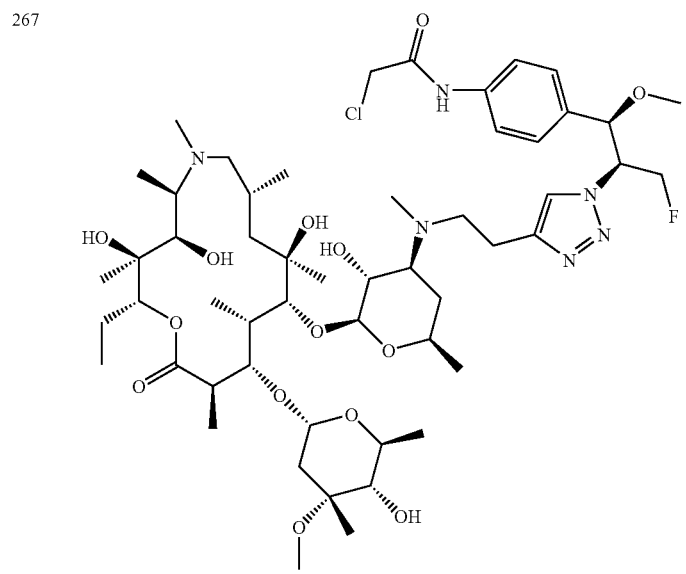 |

TABLE 1-continued
| Compound No. | Structure |
|---|---|
| 268 | 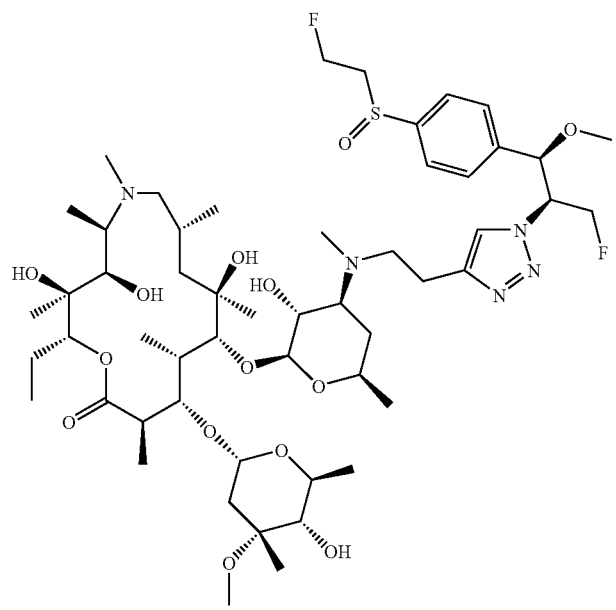 |
| 269 | 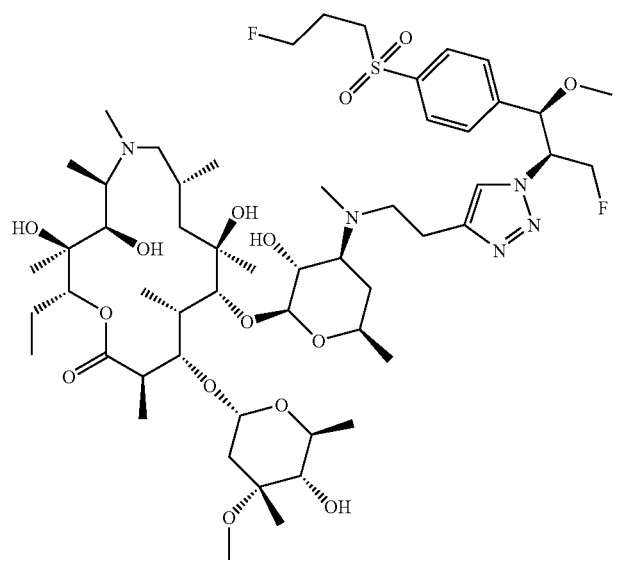 |

TABLE 1-continued
| Compound No. | Structure |
|---|---|
| 270 | 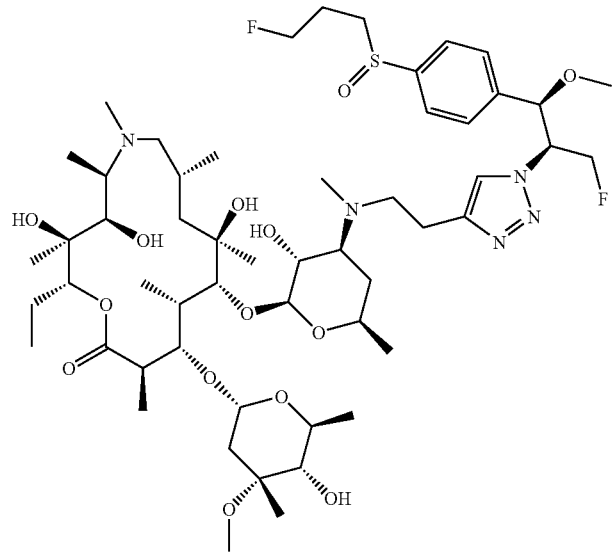 |
| 271 | 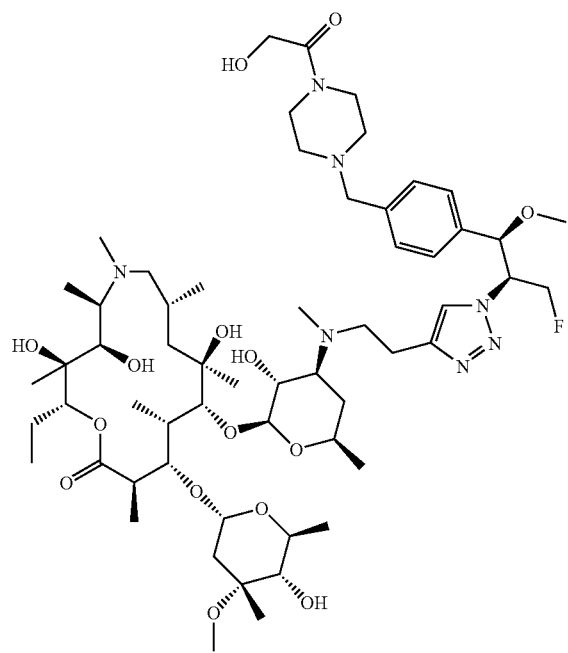 |

TABLE 1-continued
| Compound No. | Structure |
|---|---|
| 272 | 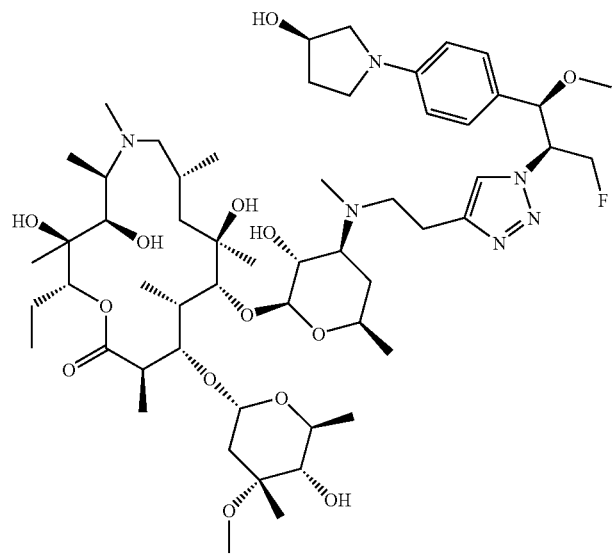 |
| 273 | 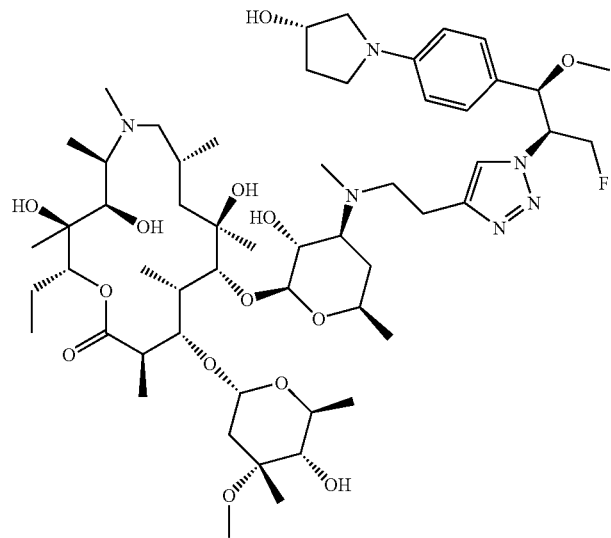 |

TABLE 1-continued
| Compound No. | Structure |
|---|---|
| 274 | 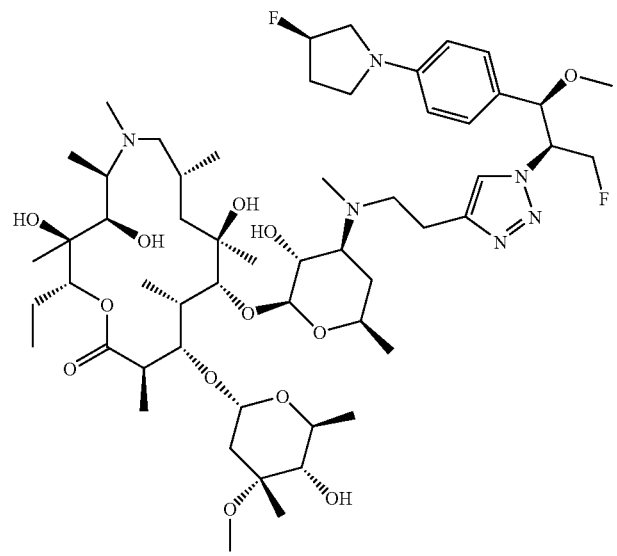 |
| 275 | 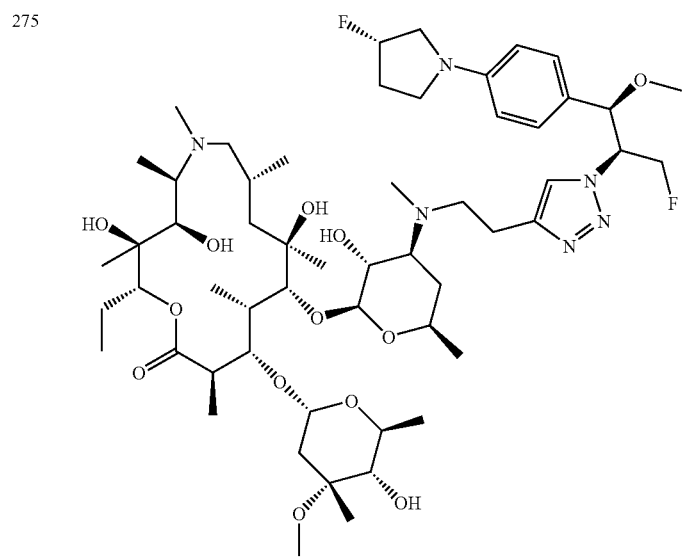 |

TABLE 1-continued
| Compound No. | Structure |
|---|---|
| 276 | 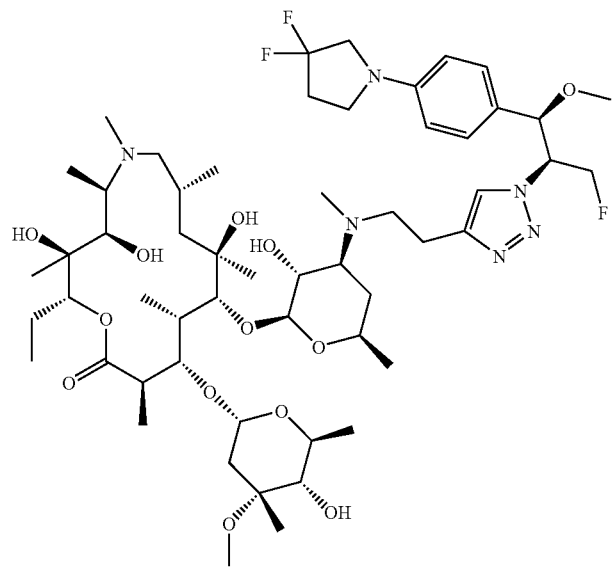 |
| 277 | 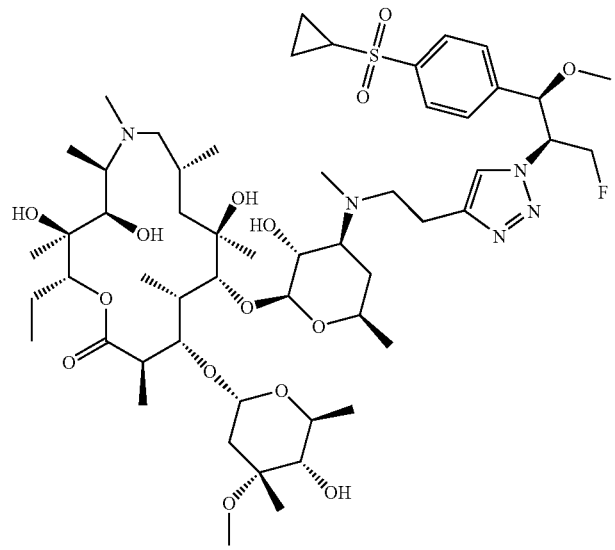 |

TABLE 1-continued
| Compound No. | Structure |
|---|---|
| 278 | 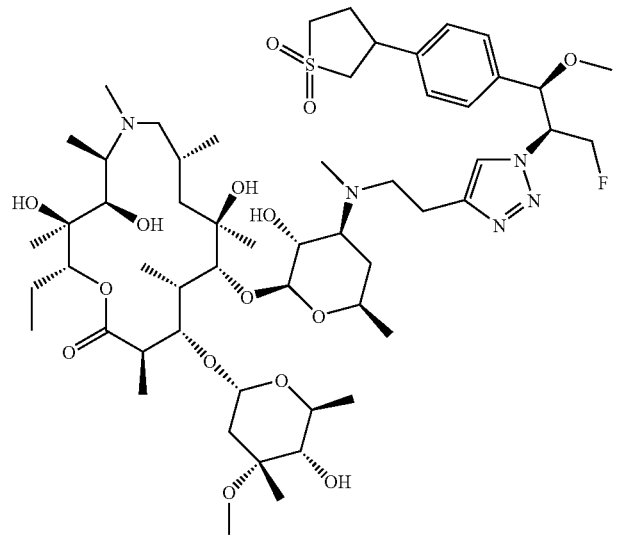 |
| 279 | 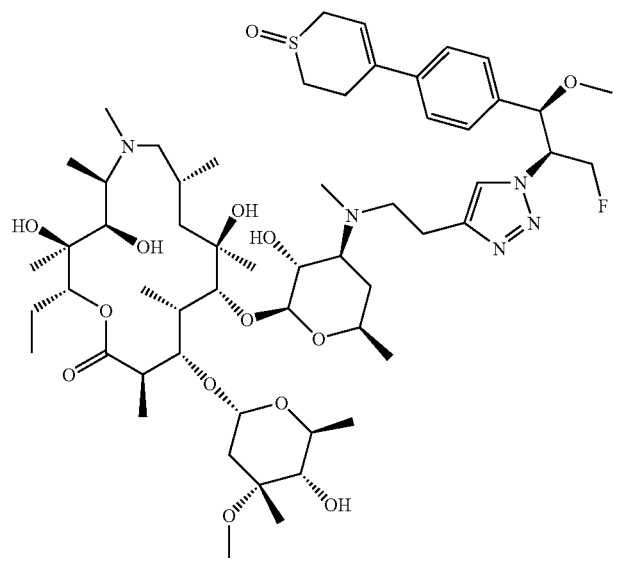 |

TABLE 1-continued
| Compound No. | Structure |
|---|---|
| 280 | 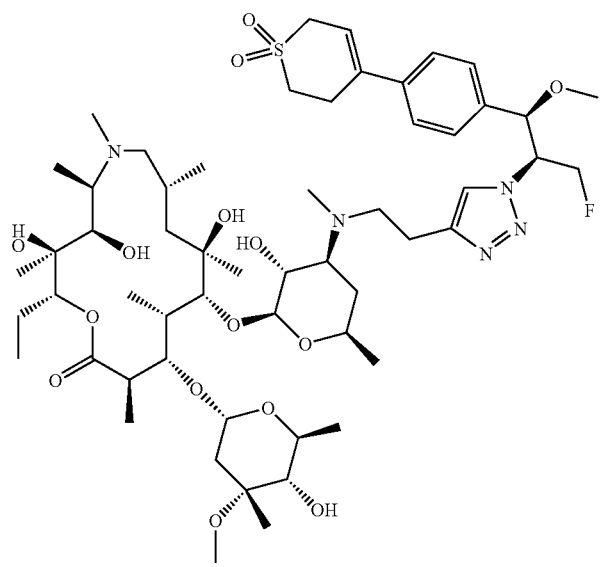 |
| 281 | 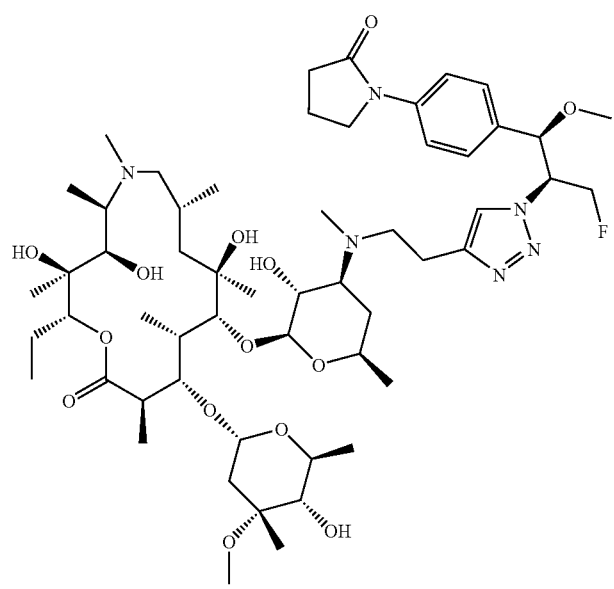 |

TABLE 1-continued
| Compound No. | Structure |
|---|---|
| 282 | 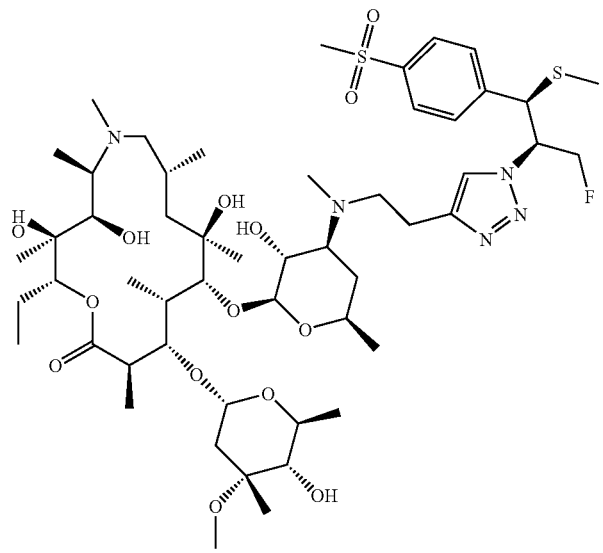 |
| 283 | 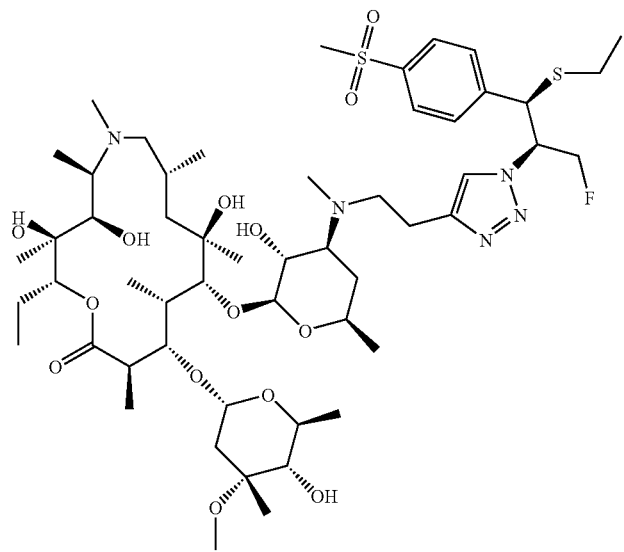 |

TABLE 1-continued

| Compound No. | Structure |
|---|---|
| 284 | 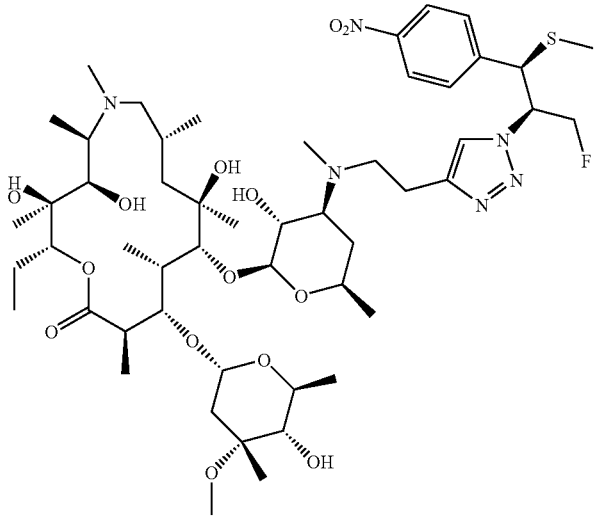 |
| 285 | 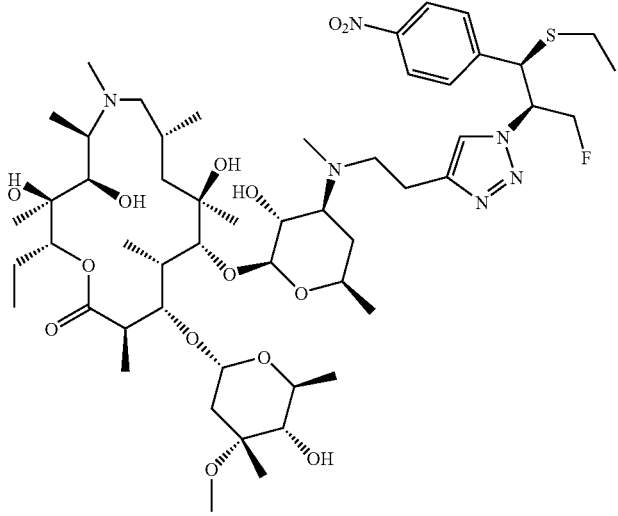 |

Table 1A provides further examples of compounds, compounds 1000a-h through 1051a-h, of the present invention. These compounds correspond to the following structure, wherein "T", "A", and R[11] are as defined below and in Table 1B. Compounds in which, for example, the —OCH$_3$ substituent is replaced with —OCH$_2$F or —SCH$_3$ can also be prepared and are contemplated as within the scope of the present invention.

TABLE 1A

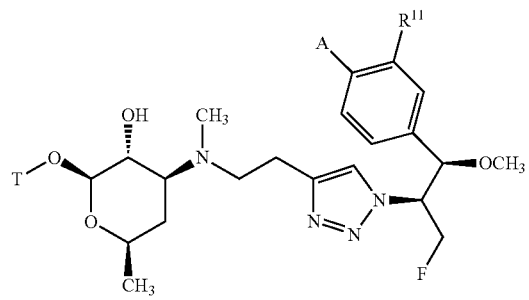

| Compound | T | A | R11 |
|---|---|---|---|
| 1000a | T1 | H | H |
| 1000b | T1 | H | F |
| 1000c | T2 | H | H |
| 1000d | T2 | H | F |
| 1000e | T3 | H | H |
| 1000f | T3 | H | F |
| 1000g | T4 | H | H |
| 1000h | T4 | H | F |
| 1001a | T1 | CH₃CH₂CH₂— | H |
| 1001b | T1 | CH₃CH₂CH₂— | F |
| 1001c | T2 | CH₃CH₂CH₂— | H |
| 1001d | T2 | CH₃CH₂CH₂— | F |
| 1001e | T3 | CH₃CH₂CH₂— | H |
| 1001f | T3 | CH₃CH₂CH₂— | F |
| 1001g | T4 | CH₃CH₂CH₂— | H |
| 1001h | T4 | CH₃CH₂CH₂— | F |
| 1002a | T1 | CH₂=CHCH₂— | H |
| 1002b | T1 | CH₂=CHCH₂— | F |
| 1002c | T2 | CH₂=CHCH₂— | H |
| 1002d | T2 | CH₂=CHCH₂— | F |
| 1002e | T3 | CH₂=CHCH₂— | H |
| 1002f | T3 | CH₂=CHCH₂— | F |
| 1002g | T4 | CH₂=CHCH₂— | H |
| 1002h | T4 | CH₂=CHCH₂— | F |
| 1003a | T1 | HC≡CCH₂— | H |
| 1003b | T1 | HC≡CCH₂— | F |
| 1003c | T2 | HC≡CCH₂— | H |
| 1003d | T2 | HC≡CCH₂— | F |
| 1003e | T3 | HC≡CCH₂— | H |
| 1003f | T3 | HC≡CCH₂— | F |
| 1003g | T4 | HC≡CCH₂— | H |
| 1003h | T4 | HC≡CCH₂— | F |
| 1004a | T1 | cyclohexyl | H |
| 1004b | T1 | cyclohexyl | F |
| 1004c | T2 | cyclohexyl | H |
| 1004d | T2 | cyclohexyl | F |
| 1004e | T3 | cyclohexyl | H |
| 1004f | T3 | cyclohexyl | F |
| 1004g | T4 | cyclohexyl | H |
| 1004h | T4 | cyclohexyl | F |

TABLE 1A-continued

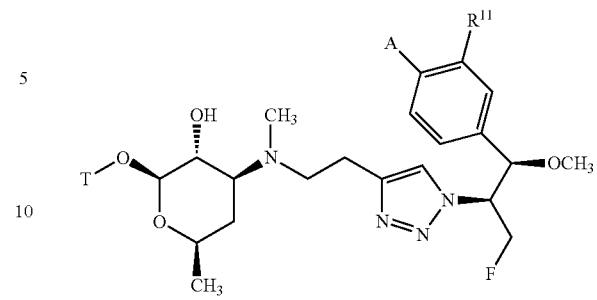

| Compound | T | A | R11 |
|---|---|---|---|
| 1005a | T1 | cyclohexenyl | H |
| 1005b | T1 | cyclohexenyl | F |
| 1005c | T2 | cyclohexenyl | H |
| 1005d | T2 | cyclohexenyl | F |
| 1005e | T3 | cyclohexenyl | H |
| 1005f | T3 | cyclohexenyl | F |
| 1005g | T4 | cyclohexenyl | H |
| 1005h | T4 | cyclohexenyl | F |
| 1006a | T1 | phenyl | H |
| 1006b | T1 | phenyl | F |
| 1006c | T2 | phenyl | H |
| 1006d | T2 | phenyl | F |
| 1006e | T3 | phenyl | H |
| 1006f | T3 | phenyl | F |
| 1006g | T4 | phenyl | H |
| 1006h | T4 | phenyl | F |

TABLE 1A-continued

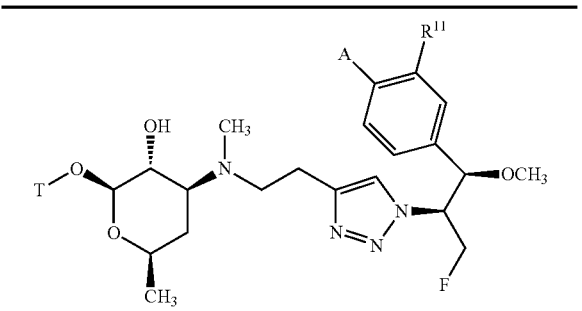

| Compound | T | A | R¹¹ |
|---|---|---|---|
| 1007a | T1 | pyrrolidinyl | H |
| 1007b | T1 | pyrrolidinyl | F |
| 1007c | T2 | pyrrolidinyl | H |
| 1007d | T2 | pyrrolidinyl | F |
| 1007e | T3 | pyrrolidinyl | H |
| 1007f | T3 | pyrrolidinyl | F |
| 1007g | T4 | pyrrolidinyl | H |
| 1007h | T4 | pyrrolidinyl | F |
| 1008a | T1 | cyclopentadienyl | H |
| 1008b | T1 | cyclopentadienyl | F |
| 1008c | T2 | cyclopentadienyl | H |
| 1008d | T2 | cyclopentadienyl | F |
| 1008e | T3 | cyclopentadienyl | H |
| 1008f | T3 | cyclopentadienyl | H |
| 1008g | T4 | cyclopentadienyl | H |
| 1008h | T4 | cyclopentadienyl | F |
| 1009a | T1 | furyl | H |

TABLE 1A-continued

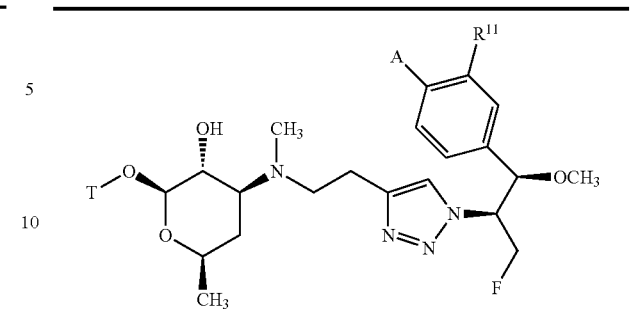

| Compound | T | A | R¹¹ |
|---|---|---|---|
| 1009b | T1 | furyl | F |
| 1009c | T2 | furyl | H |
| 1009d | T2 | furyl | F |
| 1009e | T3 | furyl | H |
| 1009f | T3 | furyl | F |
| 1009g | T4 | furyl | H |
| 1009h | T4 | furyl | F |
| 1010a | T1 | morpholinyl | H |
| 1010b | T1 | morpholinyl | F |
| 1010c | T2 | morpholinyl | H |
| 1010d | T2 | morpholinyl | F |
| 1010e | T3 | morpholinyl | H |
| 1010f | T3 | morpholinyl | F |
| 1010g | T4 | morpholinyl | H |
| 1010h | T4 | morpholinyl | F |
| 1011a | T1 | tetrahydropyridinyl | H |

TABLE 1A-continued

| Compound | T | A | R[11] |
|---|---|---|---|
| 1011b | T1 | pyridine | F |
| 1011c | T2 | pyridine | H |
| 1011d | T2 | pyridine | F |
| 1011e | T3 | pyridine | H |
| 1011f | T3 | pyridine | F |
| 1011g | T4 | pyridine | H |
| 1011h | T4 | pyridine | F |
| 1012a | T1 | triazine | H |
| 1012b | T1 | triazine | F |
| 1012c | T2 | triazine | H |
| 1012d | T2 | triazine | F |
| 1012e | T3 | triazine | H |
| 1012f | T3 | triazine | F |
| 1012g | T4 | triazine | H |
| 1012h | T4 | triazine | F |
| 1013a | T1 | cyclooctyl | H |
| 1013b | T1 | cyclooctyl | F |
| 1013c | T2 | cyclooctyl | H |
| 1013d | T2 | cyclooctyl | F |
| 1013e | T3 | cyclooctyl | H |
| 1013f | T3 | cyclooctyl | F |
| 1013g | T4 | cyclooctyl | H |
| 1013h | T4 | naphthyl | F |
| 1014a | T1 | spiro | H |
| 1014b | T1 | spiro | F |
| 1014c | T2 | spiro | H |
| 1014d | T2 | spiro | F |

TABLE 1A-continued

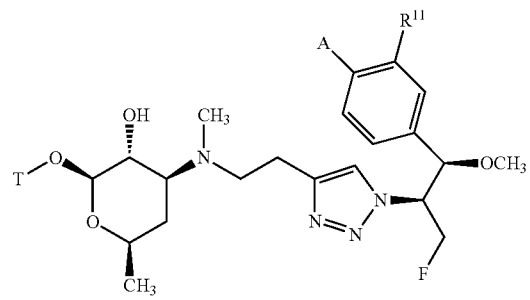

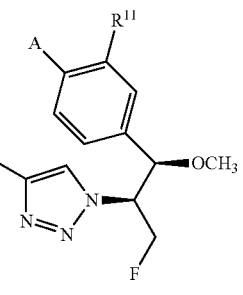

| Compound | T | A | R11 |
|---|---|---|---|
| 1014e | T3 | spirocycle | H |
| 1014f | T3 | spirocycle | F |
| 1014g | T4 | spirocycle | H |
| 1014h | T4 | spirocycle | F |
| 1015a | T1 | naphthyl | H |
| 1015b | T1 | naphthyl | F |
| 1015c | T2 | naphthyl | H |
| 1015d | T2 | naphthyl | F |
| 1015e | T3 | naphthyl | H |
| 1015f | T3 | naphthyl | F |
| 1015g | T4 | naphthyl | H |
| 1015h | T4 | naphthyl | F |
| 1016a | T1 | HO— | H |
| 1016b | T1 | HO— | F |
| 1016c | T2 | HO— | H |
| 1016d | T2 | HO— | F |
| 1016e | T3 | HO— | H |
| 1016f | T3 | HO— | F |
| 1016g | T4 | HO— | H |
| 1016h | T4 | HO— | F |
| 1017a | T1 | HS— | H |
| 1017b | T1 | HS— | F |
| 1017c | T2 | HS— | H |
| 1017d | T2 | HS— | F |
| 1017e | T3 | HS— | H |
| 1017f | T3 | HS— | F |
| 1017g | T4 | HS— | H |
| 1017h | T4 | HS— | F |
| 1018a | T1 | F | H |
| 1018b | T1 | F | F |
| 1018c | T2 | F | H |
| 1018d | T2 | F | F |
| 1018e | T3 | F | H |
| 1018f | T3 | F | F |
| 1018g | T4 | F | H |
| 1018h | T4 | F | F |
| 1019a | T1 | Cl | H |
| 1019b | T1 | Cl | F |
| 1019c | T2 | Cl | H |
| 1019d | T2 | Cl | F |
| 1019e | T3 | Cl | H |
| 1019f | T3 | Cl | F |
| 1019g | T4 | Cl | H |
| 1019h | T4 | Cl | F |
| 1020a | T1 | Br | H |
| 1020b | T1 | Br | F |
| 1020c | T2 | Br | H |
| 1020d | T2 | Br | F |
| 1020e | T3 | Br | H |
| 1020f | T3 | Br | F |
| 1020g | T4 | Br | H |
| 1020h | T4 | Br | F |
| 1021a | T1 | I | H |
| 1021b | T1 | I | F |
| 1021c | T2 | I | H |
| 1021d | T2 | I | F |
| 1021e | T3 | I | H |
| 1021f | T3 | I | F |
| 1021g | T4 | I | H |
| 1021h | T4 | I | F |
| 1022a | T1 | $F_3C$— | H |
| 1022b | T1 | $F_3C$— | F |
| 1022c | T2 | $F_3C$— | H |
| 1022d | T2 | $F_3C$— | F |
| 1022e | T3 | $F_3C$— | H |
| 1022f | T3 | $F_3C$— | F |
| 1022g | T4 | $F_3C$— | H |
| 1022h | T4 | $F_3C$— | F |
| 1023a | T1 | NC— | H |
| 1023b | T1 | NC— | F |
| 1023c | T2 | NC— | H |
| 1023d | T2 | NC— | F |
| 1023e | T3 | NC— | H |
| 1023f | T3 | NC— | F |
| 1023g | T4 | NC— | H |
| 1023h | T4 | NC— | F |
| 1024a | T1 | $N_3$— | H |

TABLE 1A-continued

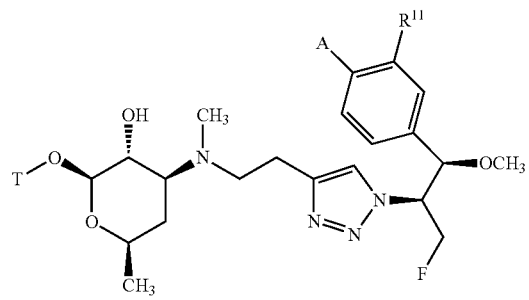

TABLE 1A-continued

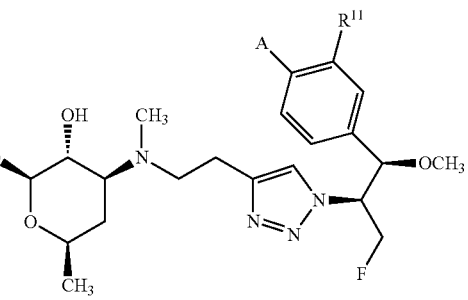

| Compound | T | A | $R^{11}$ |
|---|---|---|---|
| 1024b | T1 | $N_3$— | F |
| 1024c | T2 | $N_3$— | H |
| 1024d | T2 | $N_3$— | F |
| 1024e | T3 | $N_3$— | H |
| 1024f | T3 | $N_3$— | F |
| 1024g | T4 | $N_3$— | H |
| 1024h | T4 | $N_3$— | F |
| 1025a | T1 | $NO_2$— | H |
| 1025b | T1 | $NO_2$— | F |
| 1025c | T2 | $NO_2$— | H |
| 1025d | T2 | $NO_2$— | F |
| 1025e | T3 | $NO_2$— | H |
| 1025f | T3 | $NO_2$— | F |
| 1025g | T4 | $NO_2$— | H |
| 1025h | T4 | $NO_2$— | F |
| 1026a | T1 | $(CH_3)_2N$— | H |
| 1026b | T1 | $(CH_3)_2N$— | F |
| 1026c | T2 | $(CH_3)_2N$— | H |
| 1026d | T2 | $(CH_3)_2N$— | F |
| 1026e | T3 | $(CH_3)_2N$— | H |
| 1026f | T3 | $(CH_3)_2N$— | F |
| 1026g | T4 | $(CH_3)_2N$— | H |
| 1026h | T4 | $(CH_3)_2N$— | F |
| 1027a | T1 | $CH_3O$— | H |
| 1027b | T1 | $CH_3O$— | F |
| 1027c | T2 | $CH_3O$— | H |
| 1027d | T2 | $CH_3O$— | F |
| 1027e | T3 | $CH_3O$— | H |
| 1027f | T3 | $CH_3O$— | F |
| 1027g | T4 | $CH_3O$— | H |
| 1027h | T4 | $CH_3O$— | F |
| 1028a | T1 | $CH_3S$— | H |
| 1028b | T1 | $CH_3S$— | F |
| 1028c | T2 | $CH_3S$— | H |
| 1028d | T2 | $CH_3S$— | F |
| 1028e | T3 | $CH_3S$— | H |
| 1028f | T3 | $CH_3S$— | F |
| 1028g | T4 | $CH_3S$— | H |
| 1028h | T4 | $CH_3S$— | F |
| 1029a | T1 | $CH_3S(=O)$— | H |
| 1029b | T1 | $CH_3S(=O)$— | F |
| 1029c | T2 | $CH_3S(=O)$— | H |
| 1029d | T2 | $CH_3S(=O)$— | F |
| 1029e | T3 | $CH_3S(=O)$— | H |
| 1029f | T3 | $CH_3S(=O)$— | F |
| 1029g | T4 | $CH_3S(=O)$— | H |
| 1029h | T4 | $CH_3S(=O)$— | F |
| 1030a | T1 | $CH_3S(=O)_2$— | H |
| 1030b | T1 | $CH_3S(=O)_2$— | F |
| 1030c | T2 | $CH_3S(=O)_2$— | H |
| 1030d | T2 | $CH_3S(=O)_2$— | F |
| 1030e | T3 | $CH_3S(=O)_2$— | H |
| 1030f | T3 | $CH_3S(=O)_2$— | F |
| 1030g | T4 | $CH_3S(=O)_2$— | H |
| 1030h | T4 | $CH_3S(=O)_2$— | F |
| 1031a | T1 | $HC(=O)$— | H |
| 1031b | T1 | $HC(=O)$— | F |
| 1031c | T2 | $HC(=O)$— | H |
| 1031d | T2 | $HC(=O)$— | F |
| 1031e | T3 | $HC(=O)$— | H |
| 1031f | T3 | $HC(=O)$— | F |
| 1031g | T4 | $HC(=O)$— | H |
| 1031h | T4 | $HC(=O)$— | F |

| Compound | T | A | $R^{11}$ |
|---|---|---|---|
| 1032a | T1 | $CH_3C(=O)$— | H |
| 1032b | T1 | $CH_3C(=O)$— | F |
| 1032c | T2 | $CH_3C(=O)$— | H |
| 1032d | T2 | $CH_3C(=O)$— | F |
| 1032e | T3 | $CH_3C(=O)$— | H |
| 1032f | T3 | $CH_3C(=O)$— | F |
| 1032g | T4 | $CH_3C(=O)$— | H |
| 1032h | T4 | $CH_3C(=O)$— | F |
| 1033a | T1 | $CH_3OC(=O)$— | H |
| 1033b | T1 | $CH_3OC(=O)$— | F |
| 1033c | T2 | $CH_3OC(=O)$— | H |
| 1033d | T2 | $CH_3OC(=O)$— | F |
| 1033e | T3 | $CH_3OC(=O)$— | H |
| 1033f | T3 | $CH_3OC(=O)$— | F |
| 1033g | T4 | $CH_3OC(=O)$— | H |
| 1033h | T4 | $CH_3OC(=O)$— | F |
| 1034a | T1 | $CH_3COO$— | H |
| 1034b | T1 | $CH_3COO$— | F |
| 1034c | T2 | $CH_3COO$— | H |
| 1034d | T2 | $CH_3COO$— | F |
| 1034e | T3 | $CH_3COO$— | H |
| 1034f | T3 | $CH_3COO$— | F |
| 1034g | T4 | $CH_3COO$— | H |
| 1034h | T4 | $CH_3COO$— | F |
| 1035a | T1 | $CH_3OCOO$— | H |
| 1035b | T1 | $CH_3OCOO$— | F |
| 1035c | T2 | $CH_3OCOO$— | H |
| 1035d | T2 | $CH_3OCOO$— | F |
| 1035e | T3 | $CH_3OCOO$— | H |
| 1035f | T3 | $CH_3OCOO$— | F |
| 1035g | T4 | $CH_3OCOO$— | H |
| 1035h | T4 | $CH_3OCOO$— | F |
| 1036a | T1 | $CH_3C(=O)S$— | H |
| 1036b | T1 | $CH_3C(=O)S$— | F |
| 1036c | T2 | $CH_3C(=O)S$— | H |
| 1036d | T2 | $CH_3C(=O)S$— | F |
| 1036e | T3 | $CH_3C(=O)S$— | H |
| 1036f | T3 | $CH_3C(=O)S$— | F |
| 1036g | T4 | $CH_3C(=O)S$— | H |
| 1036h | T4 | $CH_3C(=O)S$— | F |
| 1037a | T1 | $CH_3C(=O)NH$— | H |
| 1037b | T1 | $CH_3C(=O)NH$— | F |
| 1037c | T2 | $CH_3C(=O)NH$— | H |
| 1037d | T2 | $CH_3C(=O)NH$— | F |
| 1037e | T3 | $CH_3C(=O)NH$— | H |
| 1037f | T3 | $CH_3C(=O)NH$— | F |
| 1037g | T4 | $CH_3C(=O)NH$— | H |
| 1037h | T4 | $CH_3C(=O)NH$— | F |
| 1038a | T1 | $CH_3NHC(=O)$— | H |
| 1038b | T1 | $CH_3NHC(=O)$— | F |
| 1038c | T2 | $CH_3NHC(=O)$— | H |
| 1038d | T2 | $CH_3NHC(=O)$— | F |
| 1038e | T3 | $CH_3NHC(=O)$— | H |
| 1038f | T3 | $CH_3NHC(=O)$— | F |
| 1038g | T4 | $CH_3NHC(=O)$— | H |
| 1038h | T4 | $CH_3NHC(=O)$— | F |
| 1039a | T1 | $CH_3C(=NOH)$— | H |
| 1039b | T1 | $CH_3C(=NOH)$— | F |
| 1039c | T2 | $CH_3C(=NOH)$— | H |
| 1039d | T2 | $CH_3C(=NOH)$— | F |
| 1039e | T3 | $CH_3C(=NOH)$— | H |
| 1039f | T3 | $CH_3C(=NOH)$— | F |
| 1039g | T4 | $CH_3C(=NOH)$— | H |

TABLE 1A-continued

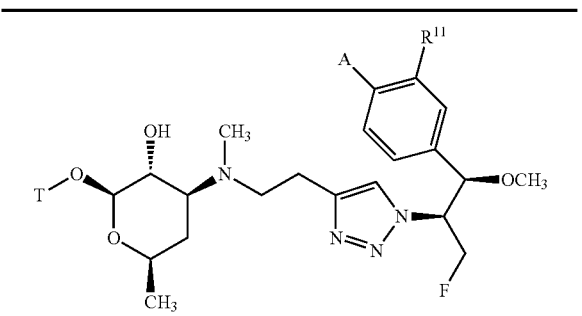

| Compound | T | A | R11 |
|---|---|---|---|
| 1039h | T4 | CH3C(=NOH)— | F |
| 1040a | T1 | CH3C[=N—N(CH3)2]— | H |
| 1040b | T1 | CH3C[=N—N(CH3)2]— | F |
| 1040c | T2 | CH3C[=N—N(CH3)2]— | H |
| 1040d | T2 | CH3C[=N—N(CH3)2]— | F |
| 1040e | T3 | CH3C[=N—N(CH3)2]— | H |
| 1040f | T3 | CH3C[=N—N(CH3)2]— | F |
| 1040g | T4 | CH3C[=N—N(CH3)2]— | H |
| 1040h | T4 | CH3C[=N—N(CH3)2]— | F |
| 1041a | T1 | ![acetyl-methylhydrazone] | H |
| 1041b | T1 | ![acetyl-methylhydrazone] | F |
| 1041c | T2 | ![acetyl-methylhydrazone] | H |
| 1041d | T2 | ![acetyl-methylhydrazone] | F |
| 1041e | T3 | ![acetyl-methylhydrazone] | H |
| 1041f | T3 | ![acetyl-methylhydrazone] | F |
| 10410g | T4 | ![acetyl-methylhydrazone] | H |

TABLE 1A-continued

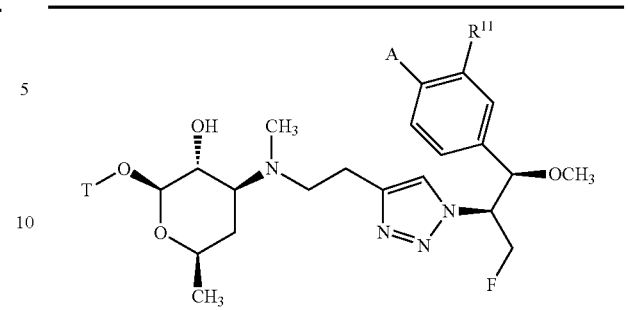

| Compound | T | A | R11 |
|---|---|---|---|
| 1041h | T4 | ![acetyl-methylhydrazone-S] | F |
| 1042a | T1 | CH3C[=N—OCH3]— | H |
| 1042b | T1 | CH3C[=N—OCH3]— | F |
| 1042c | T2 | CH3C[=N—OCH3]— | H |
| 1042d | T2 | CH3C[=N—OCH3]— | F |
| 1042e | T3 | CH3C[=N—OCH3]— | H |
| 1042f | T3 | CH3C[=N—OCH3]— | F |
| 1042g | T4 | CH3C[=N—OCH3]— | H |
| 1042h | T4 | CH3C[=N—OCH3]— | F |
| 1043a | T1 | CH3OC(=O)NH— | H |
| 1043b | T1 | CH3OC(=O)NH— | F |
| 1043c | T2 | CH3OC(=O)NH— | H |
| 1043d | T2 | CH3OC(=O)NH— | F |
| 1043e | T3 | CH3OC(=O)NH— | H |
| 1043f | T3 | CH3OC(=O)NH— | F |
| 1043g | T4 | CH3OC(=O)NH— | H |
| 1043h | T4 | CH3OC(=O)NH— | F |
| 1044a | T1 | CH3NHC(=O)O— | H |
| 1044b | T1 | CH3NHC(=O)O— | F |
| 1044c | T2 | CH3NHC(=O)O— | H |
| 1044d | T2 | CH3NHC(=O)O— | F |
| 1044e | T3 | CH3NHC(=O)O— | H |
| 1044f | T3 | CH3NHC(=O)O— | F |
| 1044g | T4 | CH3NHC(=O)O— | H |
| 1044h | T4 | CH3NHC(=O)O— | F |
| 1045a | T1 | CH3NHC(=O)NH— | H |
| 1045b | T1 | CH3NHC(=O)NH— | F |
| 1045c | T2 | CH3NHC(=O)NH— | H |
| 1045d | T2 | CH3NHC(=O)NH— | F |
| 1045e | T3 | CH3NHC(=O)NH— | H |
| 1045f | T3 | CH3NHC(=O)NH— | F |
| 1045g | T4 | CH3NHC(=O)NH— | H |
| 1045h | T4 | CH3NHC(=O)NH— | F |
| 1046a | T1 | CH3S(=O)2NH— | H |
| 1046b | T1 | CH3S(=O)2NH— | F |
| 1046c | T2 | CH3S(=O)2NH— | H |
| 1046d | T2 | CH3S(=O)2NH— | F |
| 1046e | T3 | CH3S(=O)2NH— | H |
| 1046f | T3 | CH3S(=O)2NH— | F |
| 1046g | T4 | CH3S(=O)2NH— | H |
| 1046h | T4 | CH3S(=O)2NH— | F |
| 1047a | T1 | CH3NHS(=O)2— | H |
| 1047b | T1 | CH3NHS(=O)2— | F |
| 1047c | T2 | CH3NHS(=O)2— | H |
| 1047d | T2 | CH3NHS(=O)2— | F |
| 1047e | T3 | CH3NHS(=O)2— | H |
| 1047f | T3 | CH3NHS(=O)2— | F |
| 1047g | T4 | CH3NHS(=O)2— | H |
| 1047h | T4 | CH3NHS(=O)2— | F |
| 1048a | T1 | NH2— | H |
| 1048b | T1 | NH2— | F |
| 1048c | T2 | NH2— | H |
| 1048d | T2 | NH2— | F |
| 1048e | T3 | NH2— | H |
| 1048f | T3 | NH2— | F |
| 1048g | T4 | NH2— | H |
| 1048h | T4 | NH2— | F |

TABLE 1A-continued

[Structure: sugar-T with OH, CH₃, N(CH₃), ethyl-triazole linker to phenyl ring with A and R¹¹ substituents, with OCH₃ and CH₂F groups]

| Compound | T | A | R¹¹ |
|---|---|---|---|
| 1049a | T1 | (CH₃)₂N— | H |
| 1049b | T1 | (CH₃)₂N— | F |
| 1049c | T2 | (CH₃)₂N— | H |
| 1049d | T2 | (CH₃)₂N— | F |
| 1049e | T3 | (CH₃)₂N— | H |
| 1049f | T3 | (CH₃)₂N— | F |
| 1049g | T4 | (CH₃)₂N— | H |
| 1049h | T4 | (CH₃)₂N— | F |
| 1050a | T1 | (CH₃)₃Si— | H |
| 1050b | T1 | (CH₃)₃Si— | F |
| 1050c | T2 | (CH₃)₃Si— | H |
| 1050d | T2 | (CH₃)₃Si— | F |
| 1050e | T3 | (CH₃)₃Si— | H |
| 1050f | T3 | (CH₃)₃Si— | F |
| 1050g | T4 | (CH₃)₃Si— | H |
| 1050h | T4 | (CH₃)₃Si— | F |
| 1051a | T1 | (CH₃O)₃Si— | H |
| 1051b | T1 | (CH₃O)₃Si— | F |
| 1051c | T2 | (CH₃O)₃Si— | H |
| 1051d | T2 | (CH₃O)₃Si— | F |
| 1051e | T3 | (CH₃O)₃Si— | H |
| 1051f | T3 | (CH₃O)₃Si— | F |
| 1051g | T4 | (CH₃O)₃Si— | H |
| 1051h | T4 | (CH₃O)₃Si— | F |

In the forgoing Table 1A, T1, T2, T3, and T4 correspond to the following structures as defined below in Table 1B:

TABLE 1B

T

T1: [macrolide structure with HO, OH, methoxy, sugar group]

T2: [macrolide structure with ketone groups]

T3: [macrolide structure with NH bridge, sugar group]

T4: [macrolide structure with pyrazole-phenoxy group, N=Ac, imino substituents]

Table 1C provides further examples of compounds of the present invention. These compounds correspond to the following structure, wherein "A" is as defined in Table 1C, below. Note that the fragments for "A" are drawn such that the fragment is bonded to the phenyl ring in the structure below via the bond on the left. For example, the first fragment,

[CF₃-CF₂— fragment structure]

could alternatively be drawn as

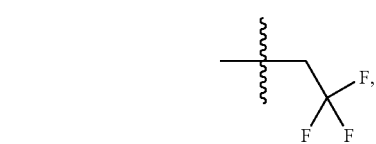
or —CH$_2$—CF$_3$.
TABLE 1C
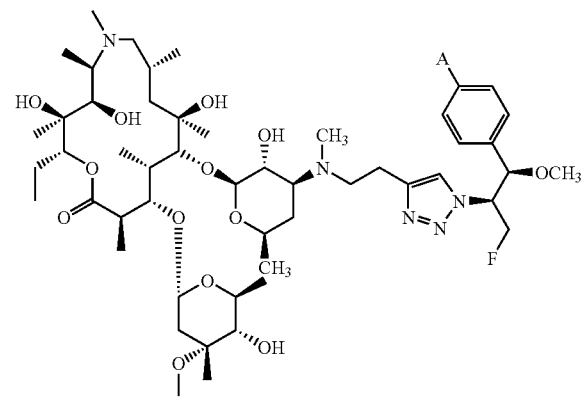
A Groups. Connection is to bond on left.
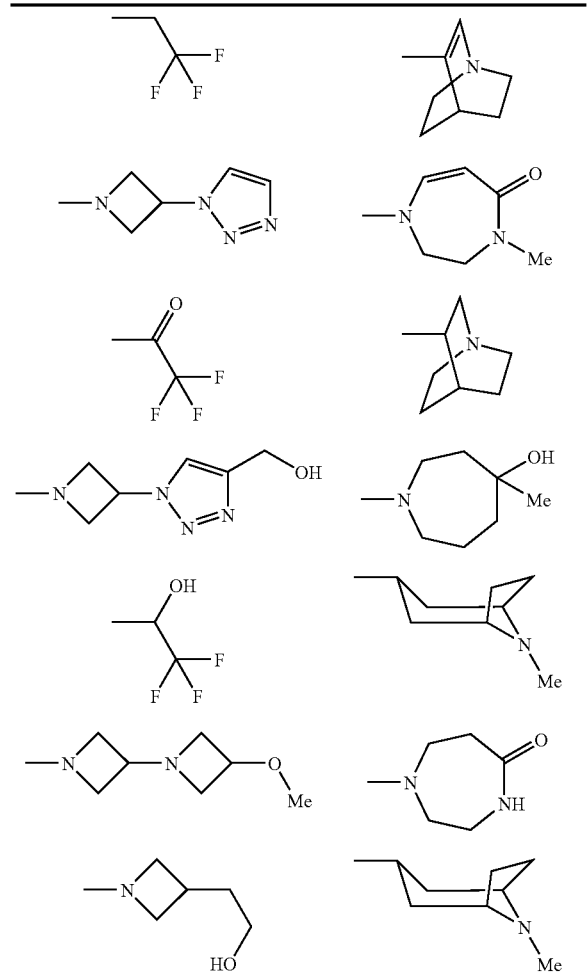
TABLE 1C-continued
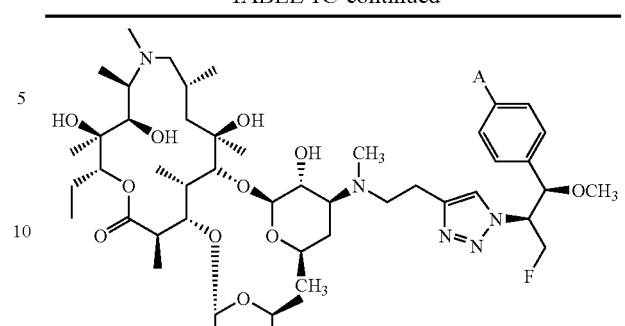
A Groups. Connection is to bond on left.
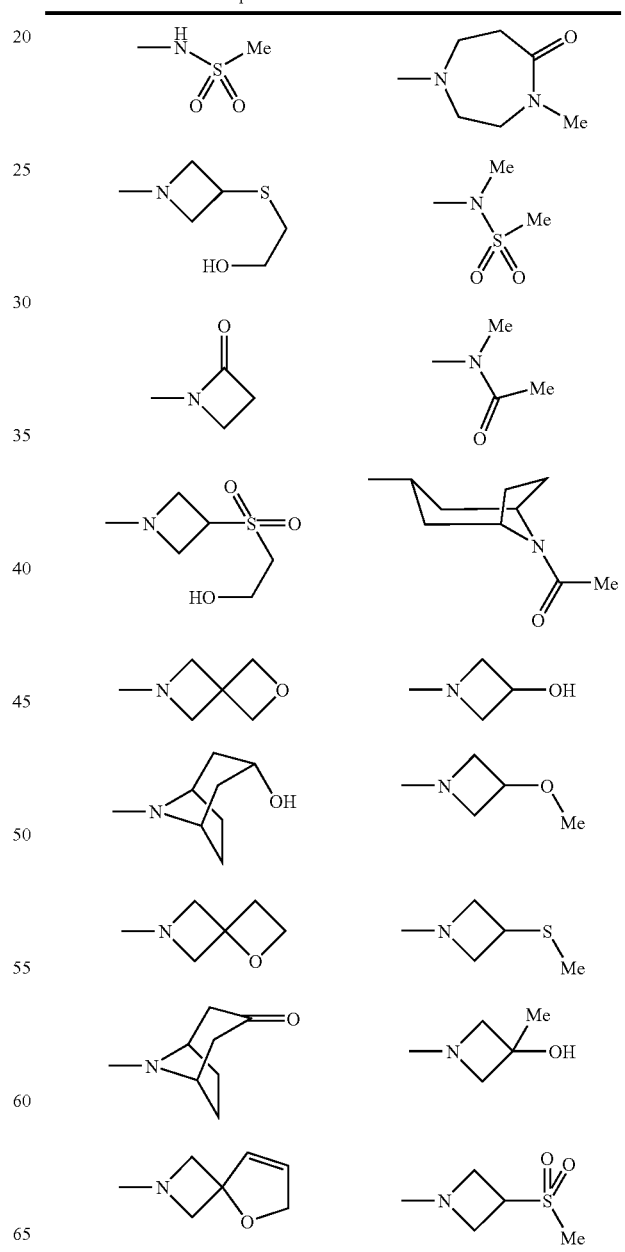

TABLE 1C-continued
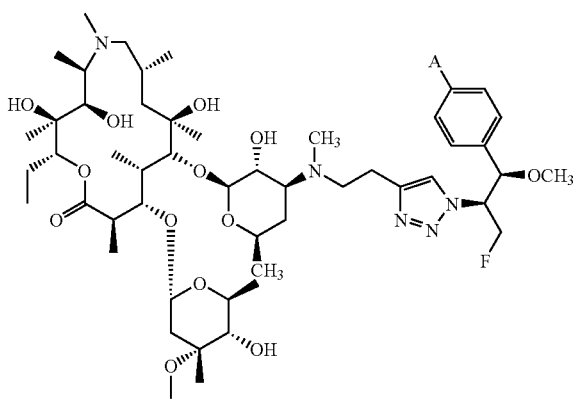
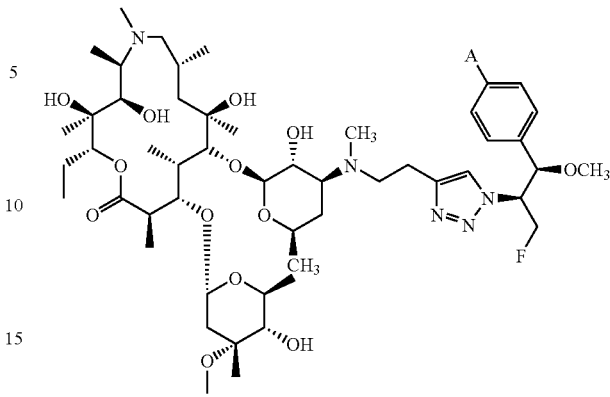
A Groups. Connection is to bond on left.
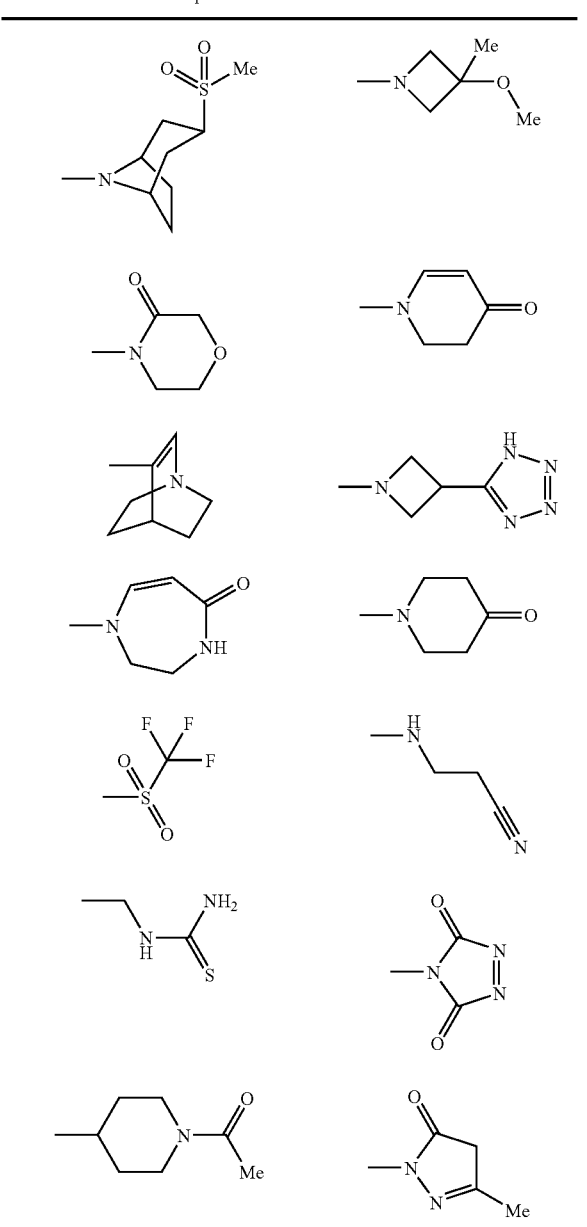
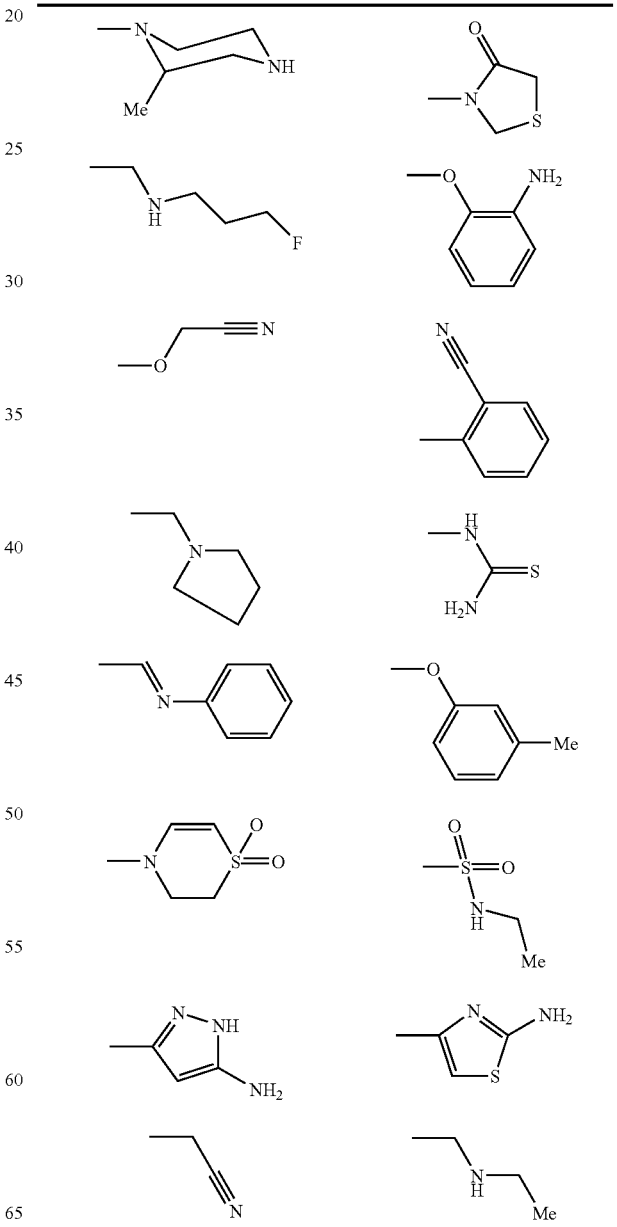

TABLE 1C-continued
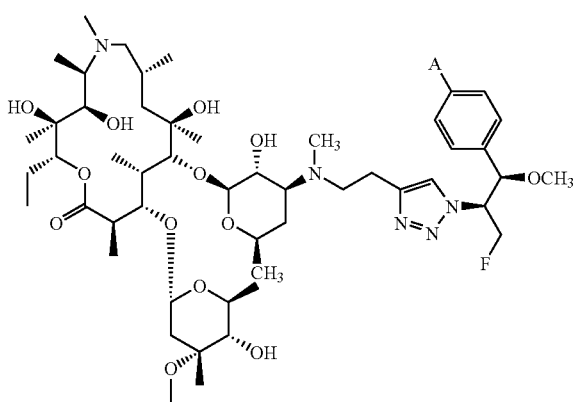
A Groups. Connection is to bond on left.
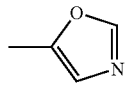 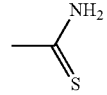
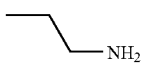 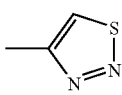
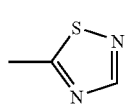 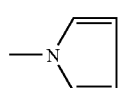
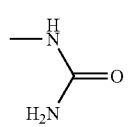 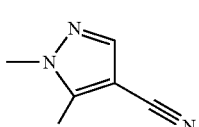
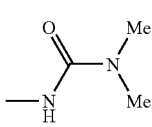 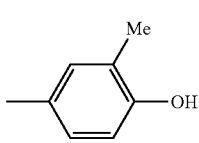
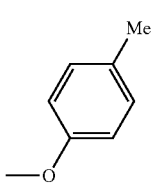 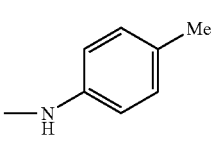
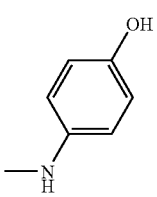 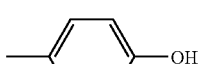
TABLE 1C-continued
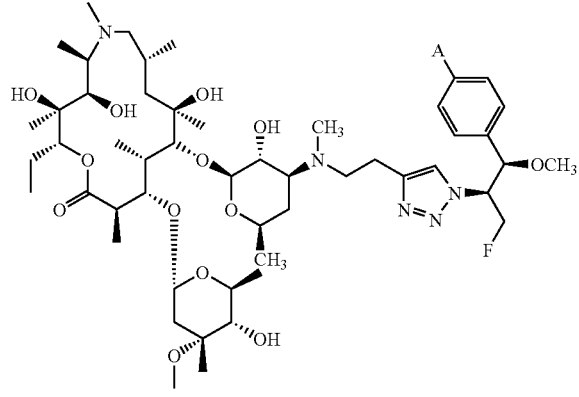
A Groups. Connection is to bond on left.
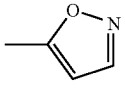 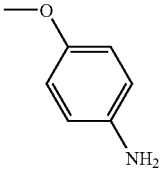
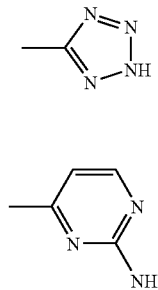
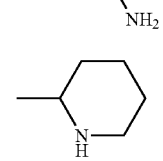
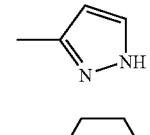
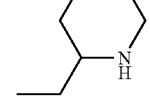
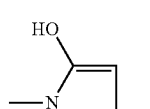
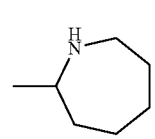

TABLE 1C-continued
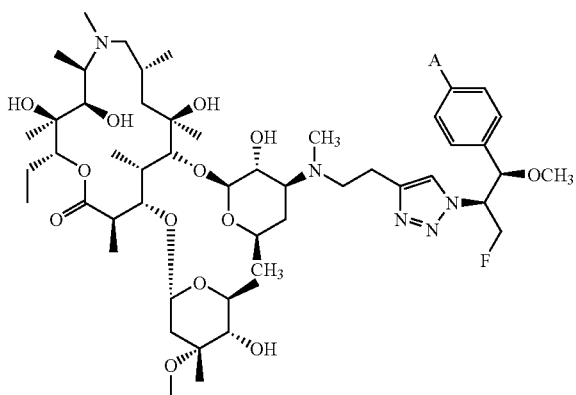
A Groups. Connection is to bond on left.
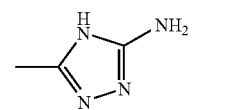 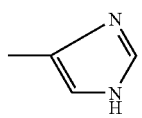
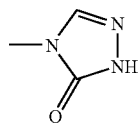 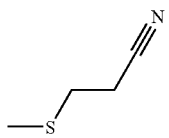
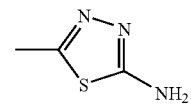 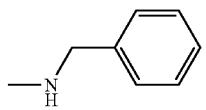
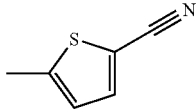 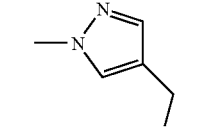
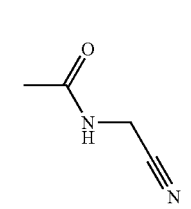 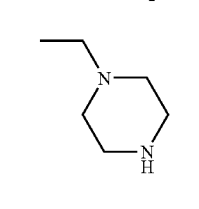
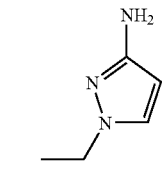 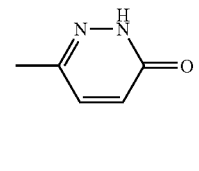
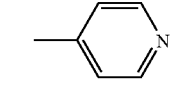
 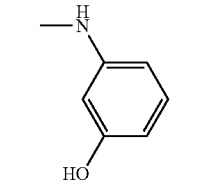
A Groups. Connection is to bond on left.
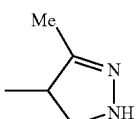 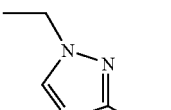
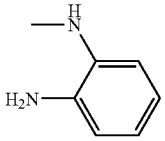 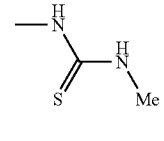
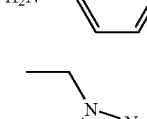 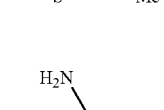
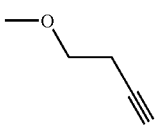 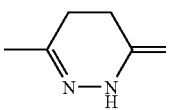
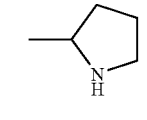 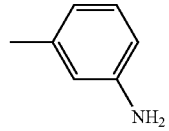
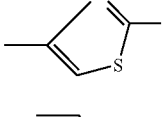 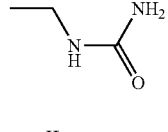
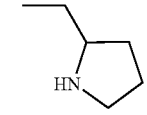 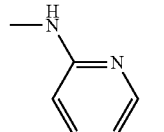

TABLE 1C-continued
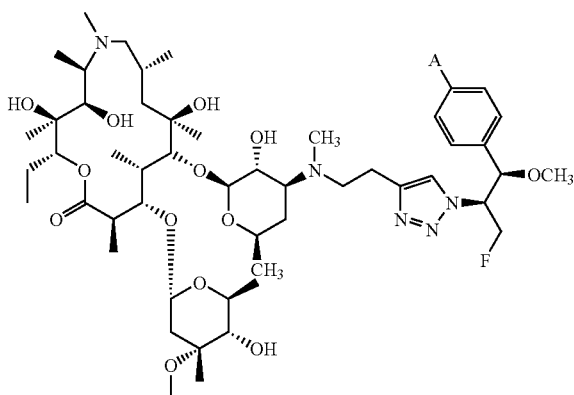
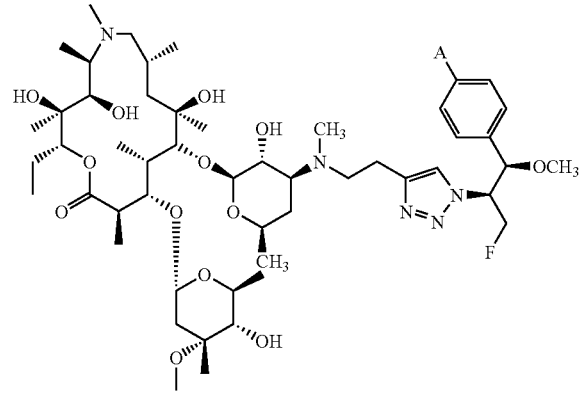
A Groups. Connection is to bond on left.
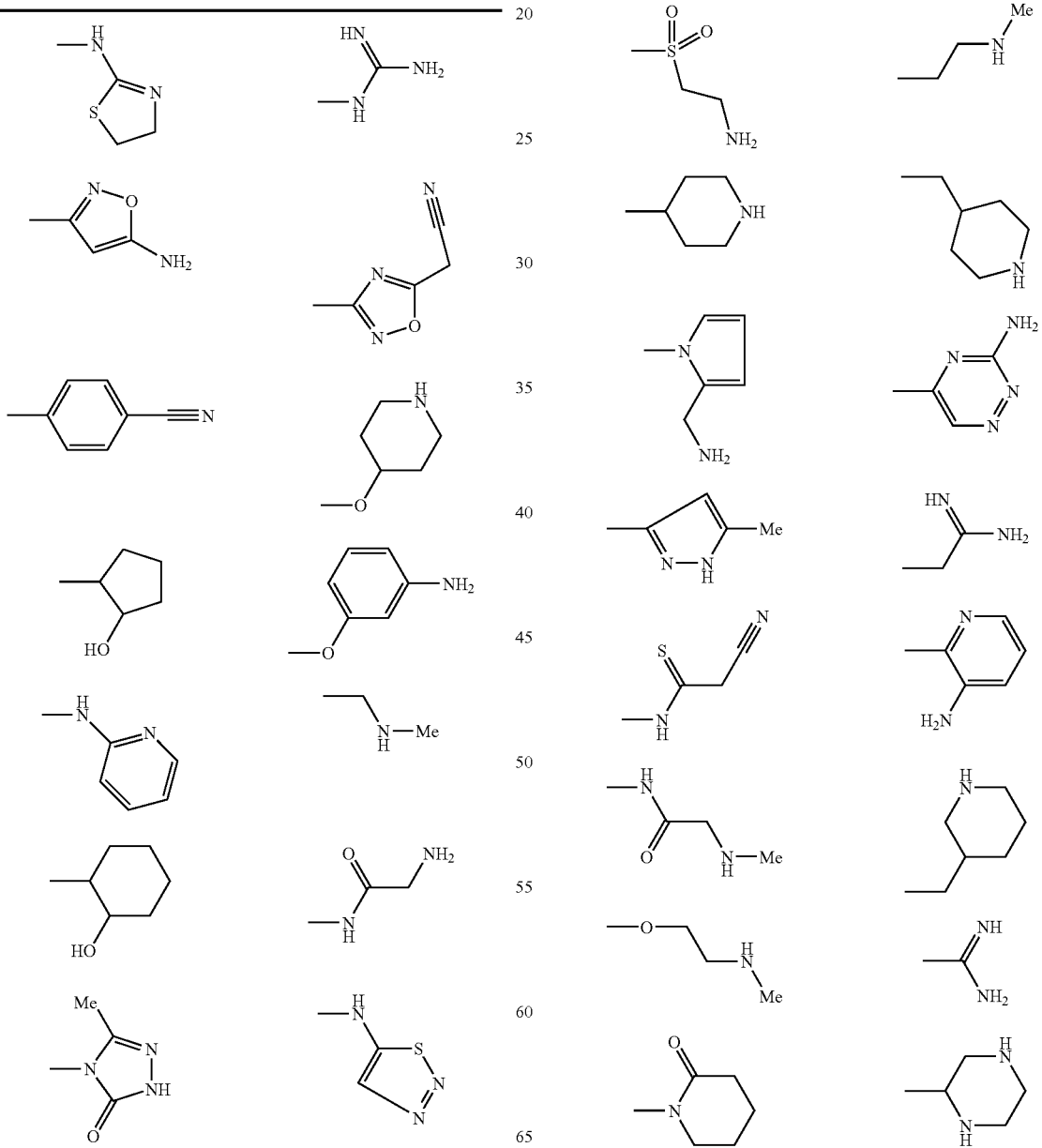

TABLE 1C-continued
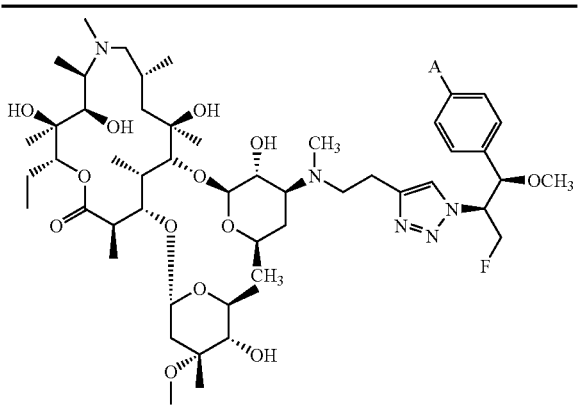
A Groups. Connection is to bond on left.
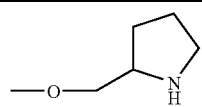 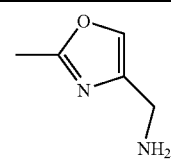
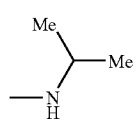 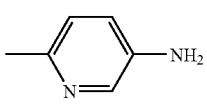
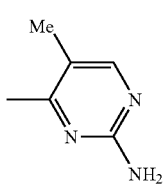 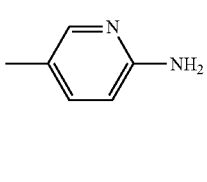
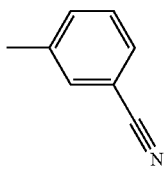 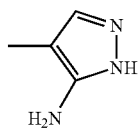
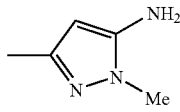 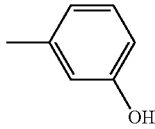
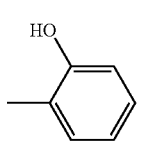 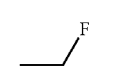
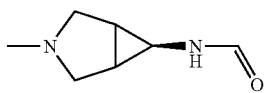 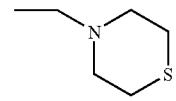
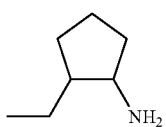 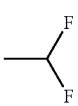
TABLE 1C-continued
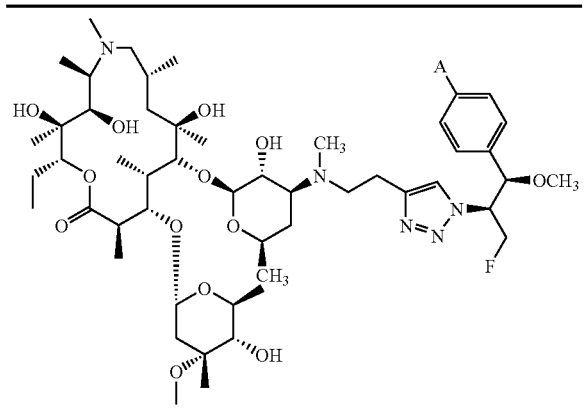
A Groups. Connection is to bond on left.
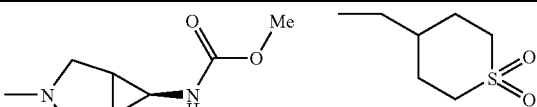
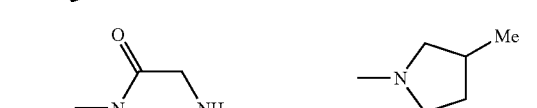
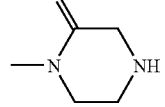 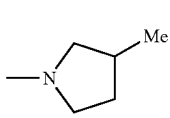
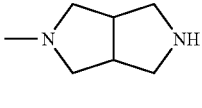 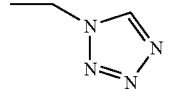
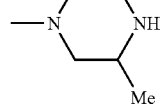 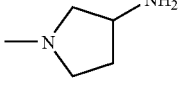
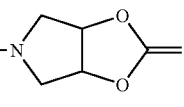 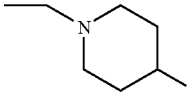
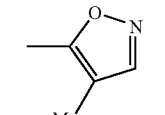 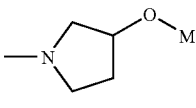
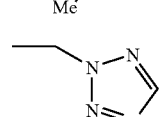 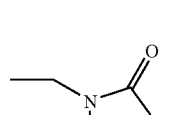
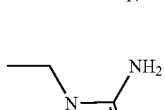 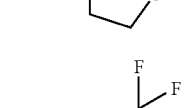
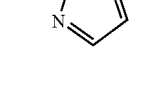 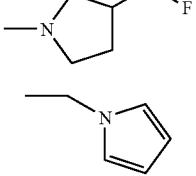
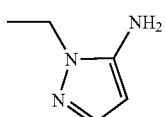
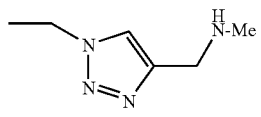
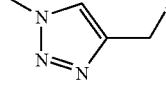 

TABLE 1C-continued
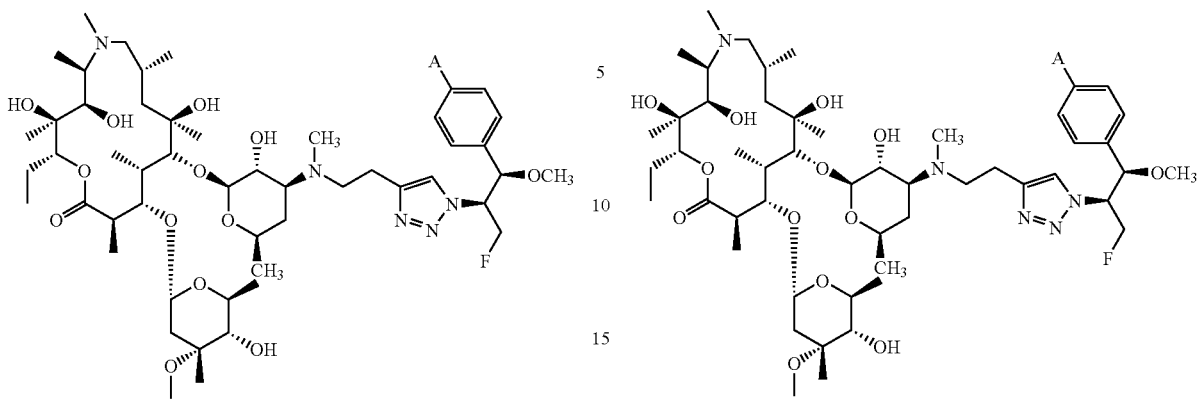
A Groups. Connection is to bond on left.
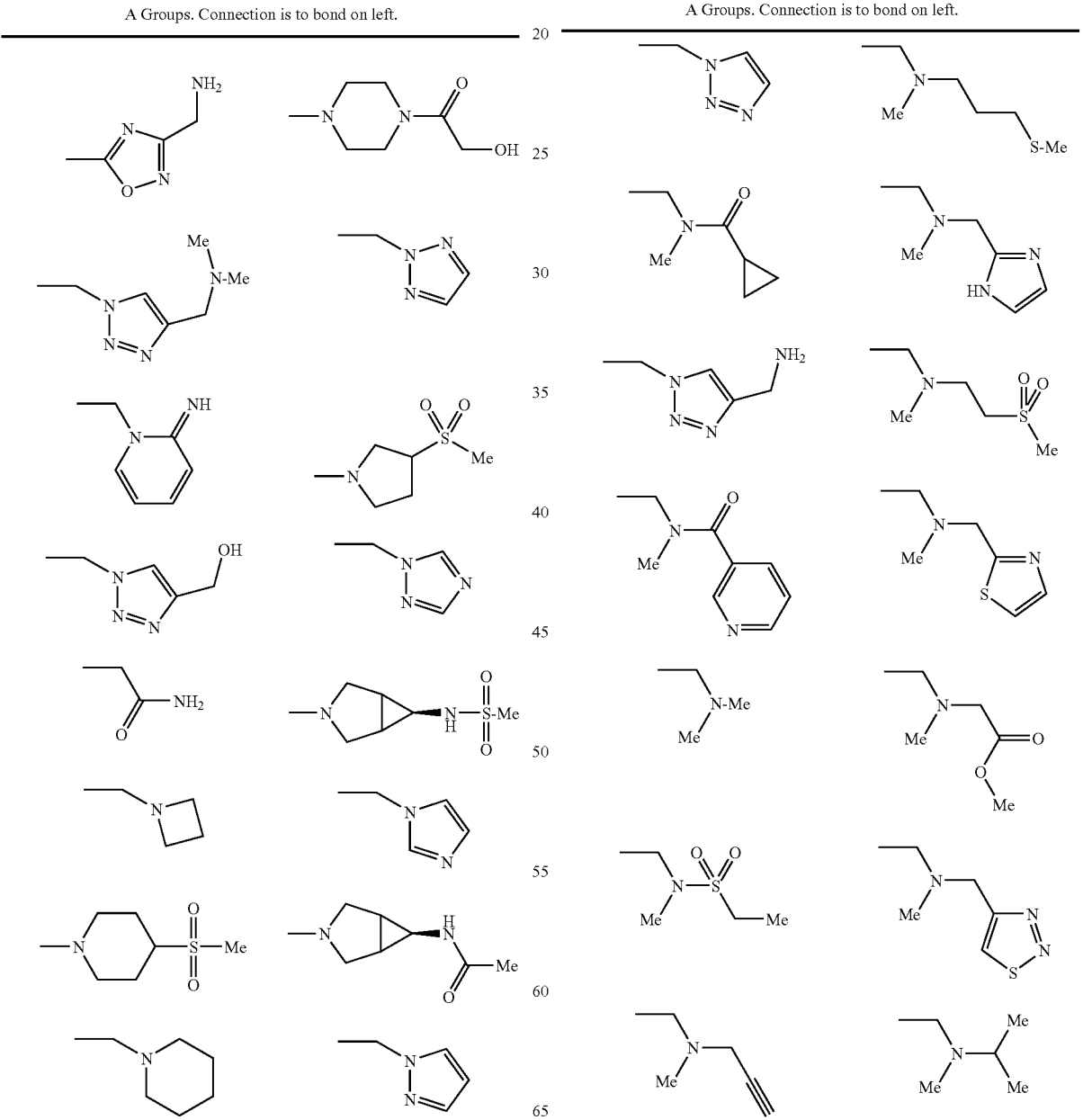

TABLE 1C-continued
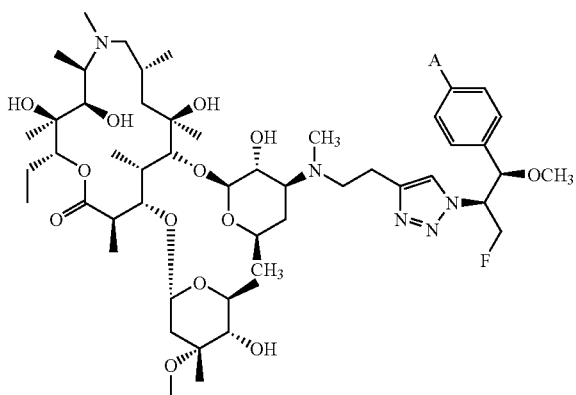
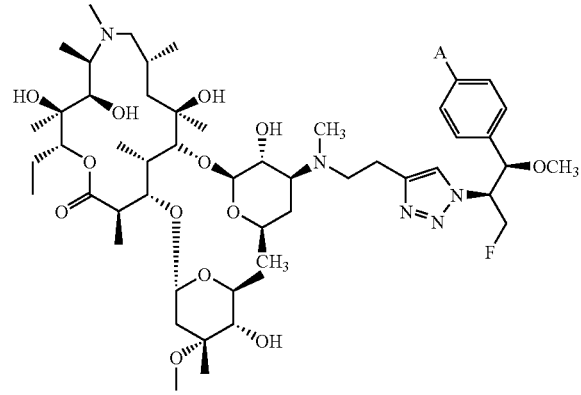
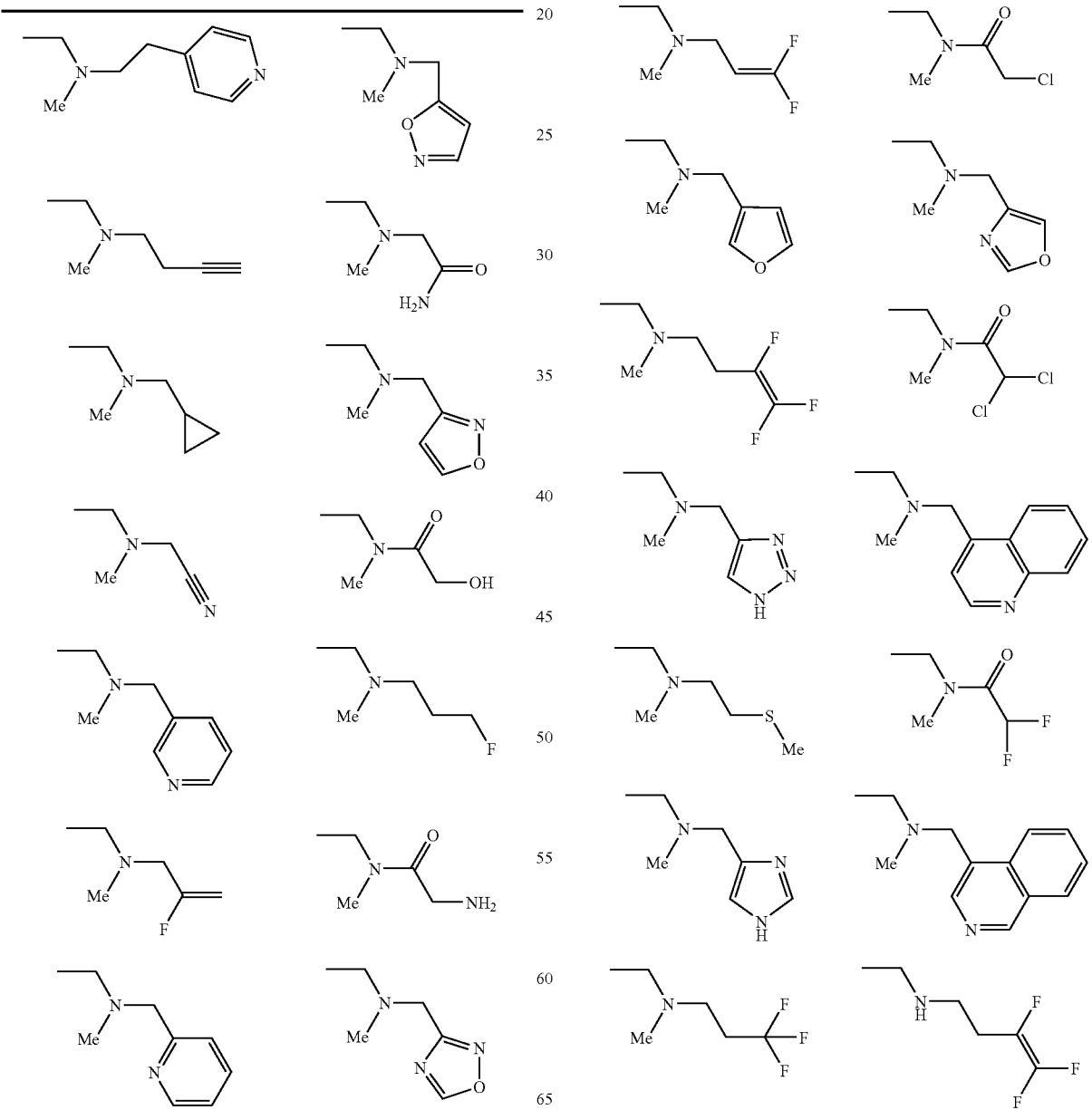

261
TABLE 1C-continued
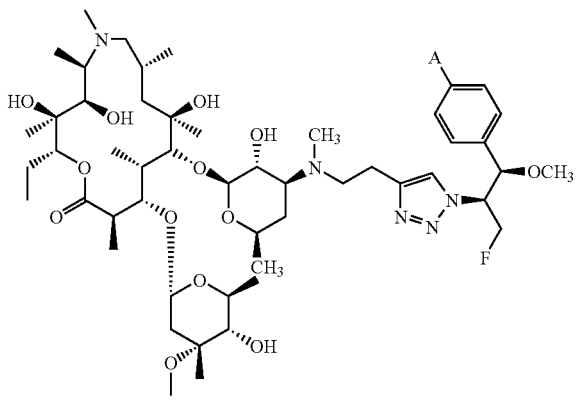
A Groups. Connection is to bond on left.
262
TABLE 1C-continued
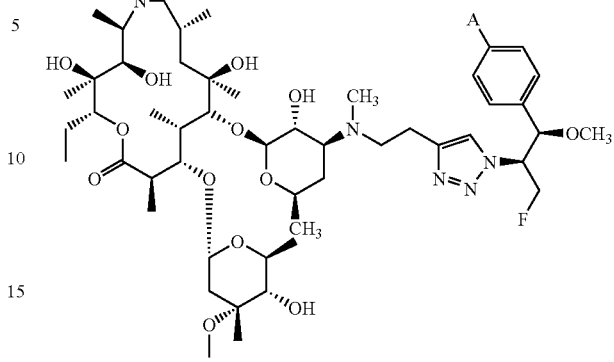
A Groups. Connection is to bond on left.
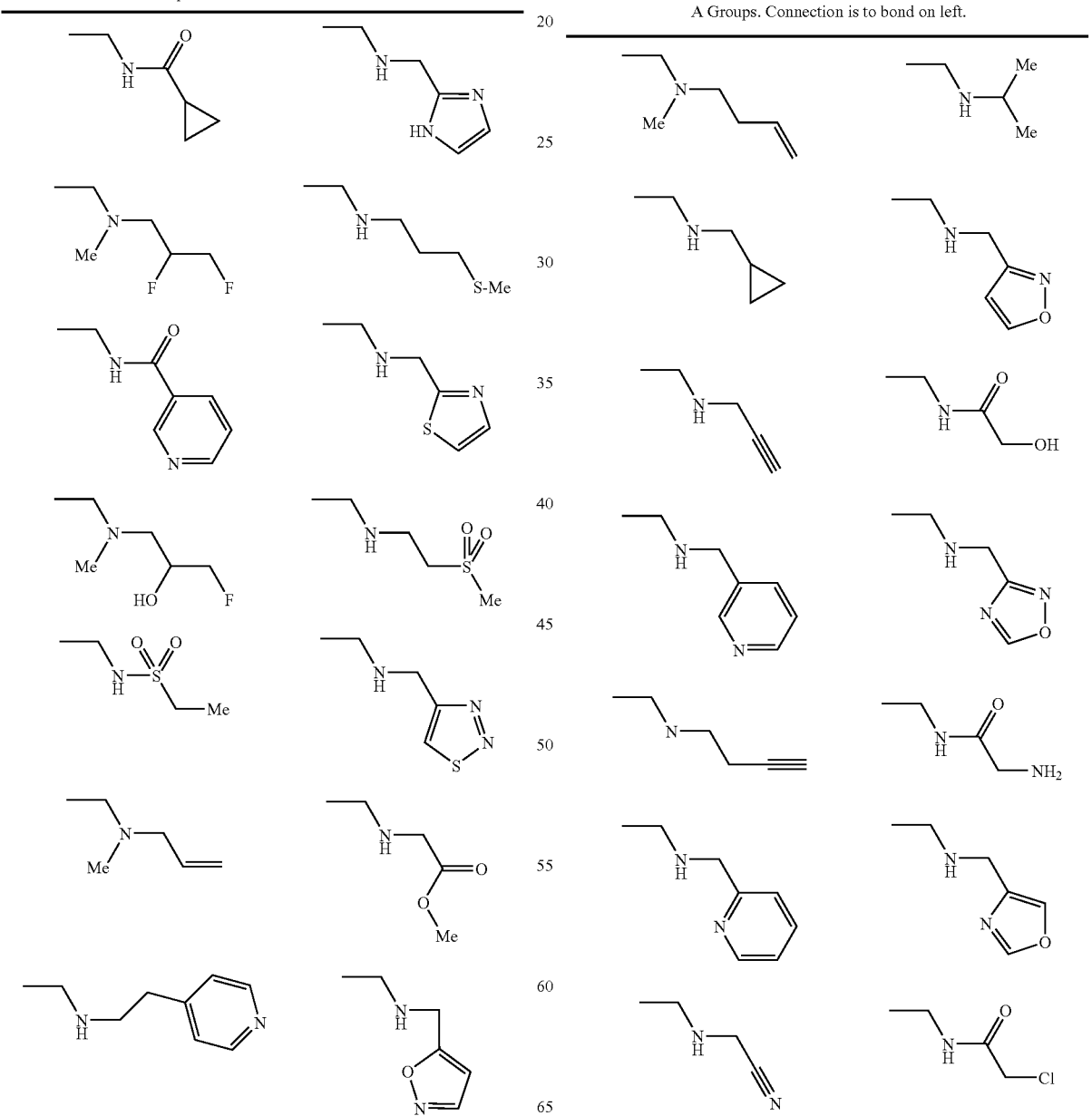

TABLE 1C-continued
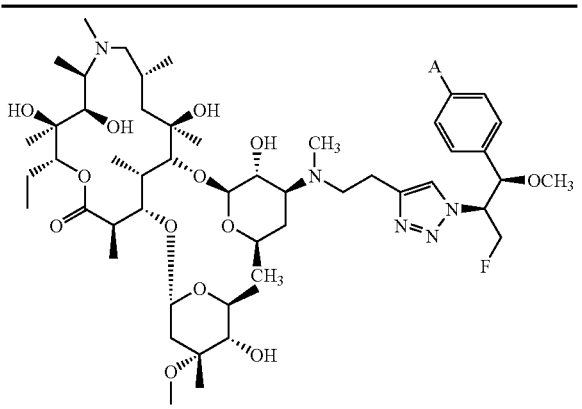
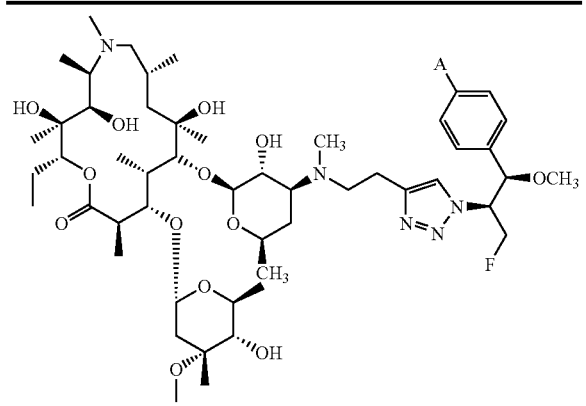
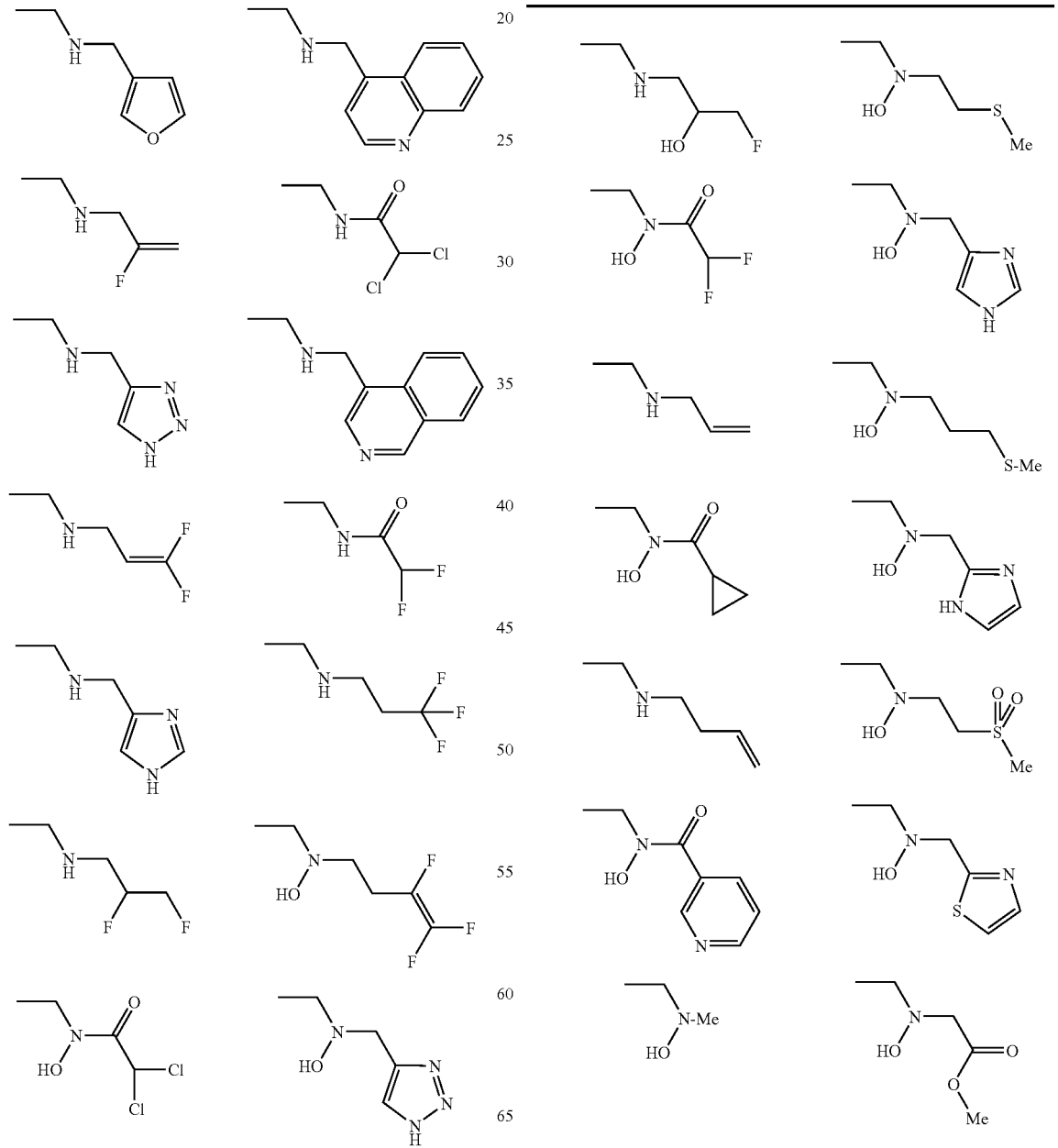

265
TABLE 1C-continued
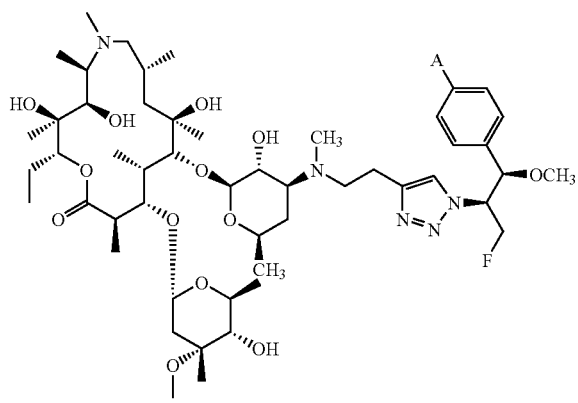
A Groups. Connection is to bond on left.
266
TABLE 1C-continued
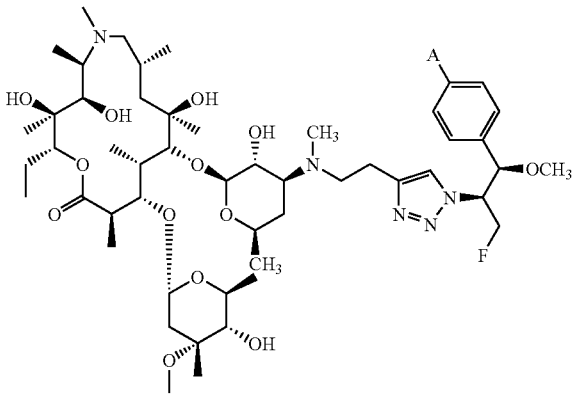
A Groups. Connection is to bond on left.
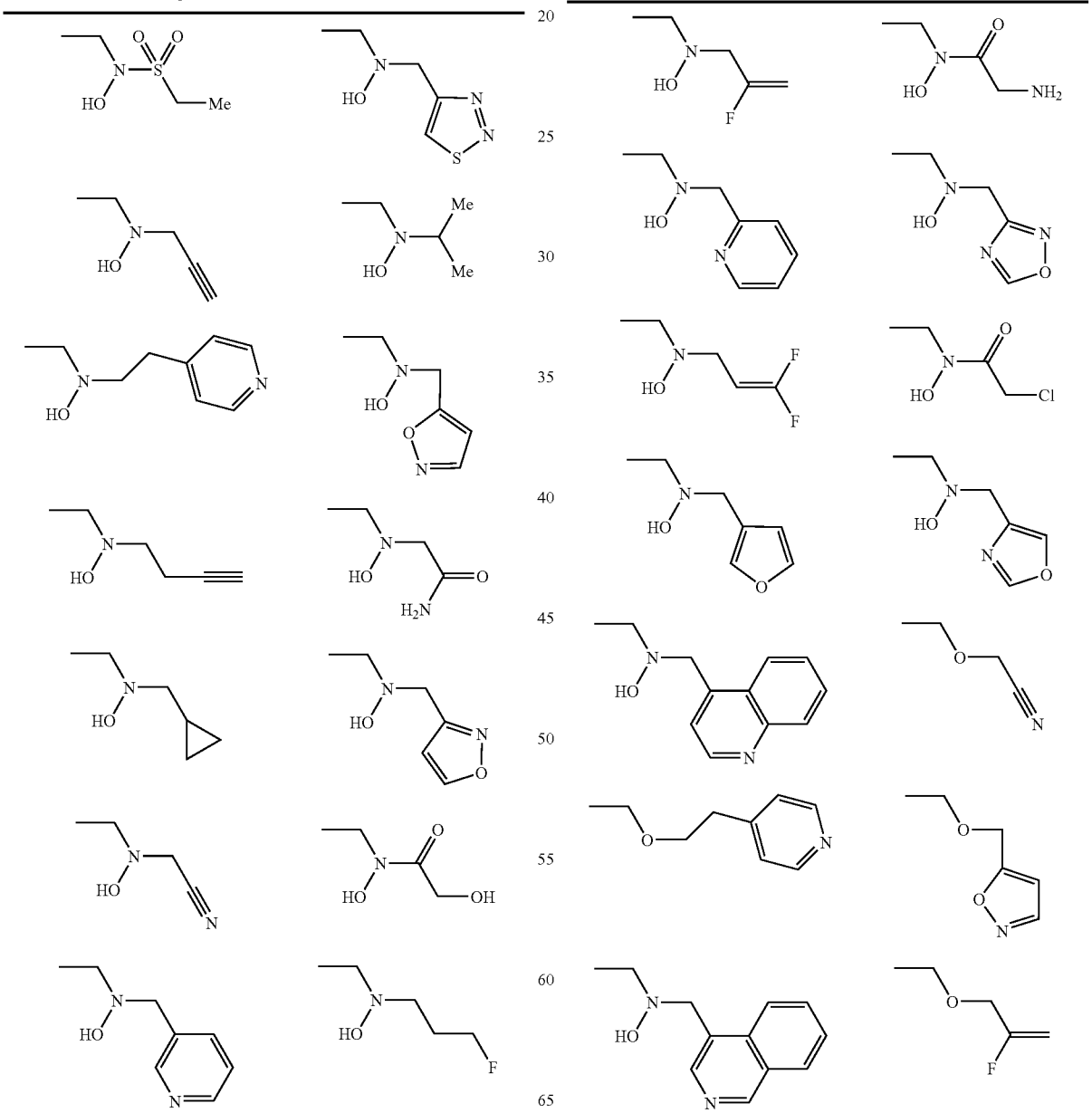

TABLE 1C-continued

A Groups. Connection is to bond on left.

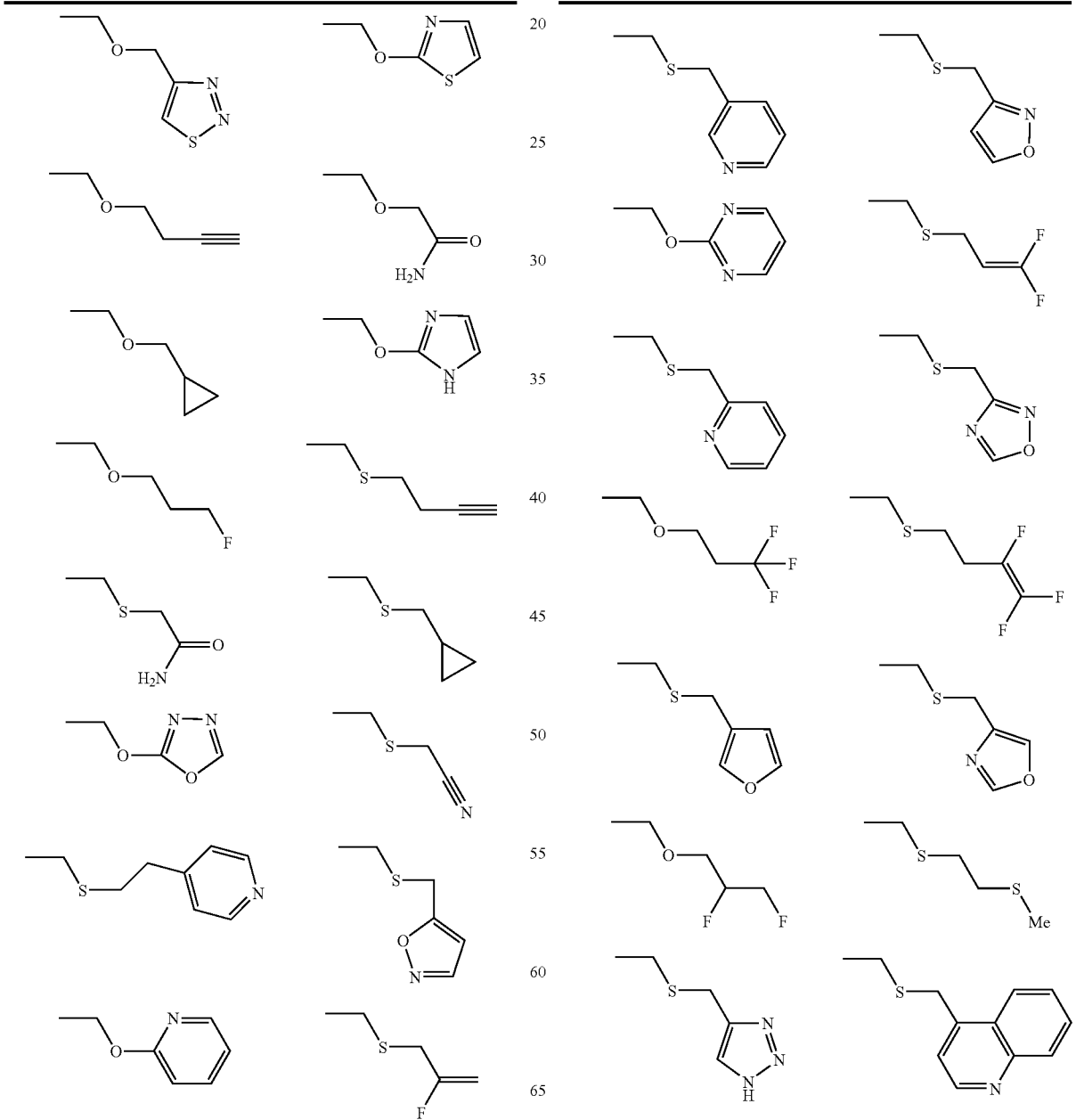

TABLE 1C-continued
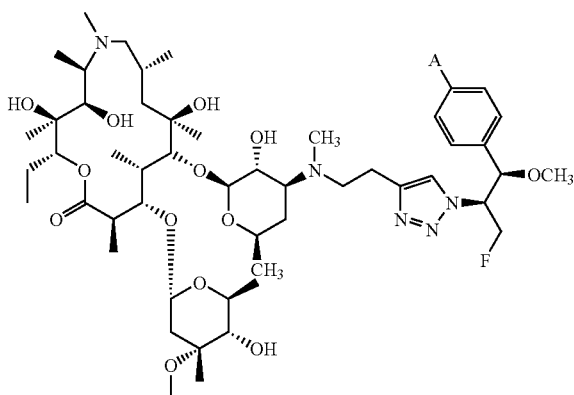
A Groups. Connection is to bond on left.
TABLE 1C-continued
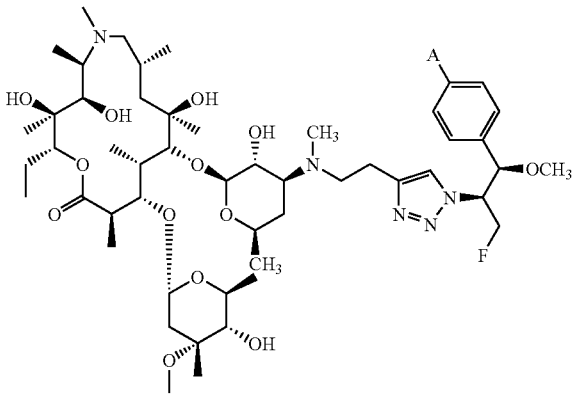
A Groups. Connection is to bond on left.

TABLE 1C-continued
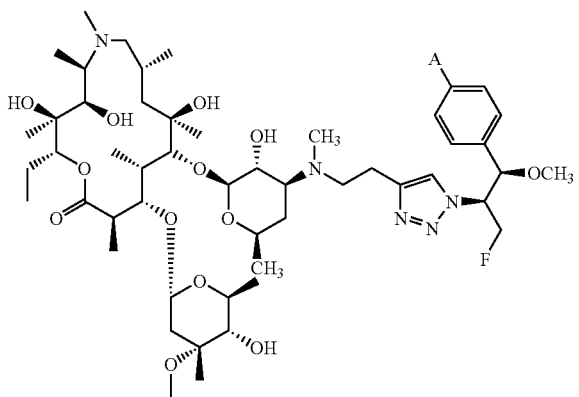
A Groups. Connection is to bond on left.
TABLE 1C-continued
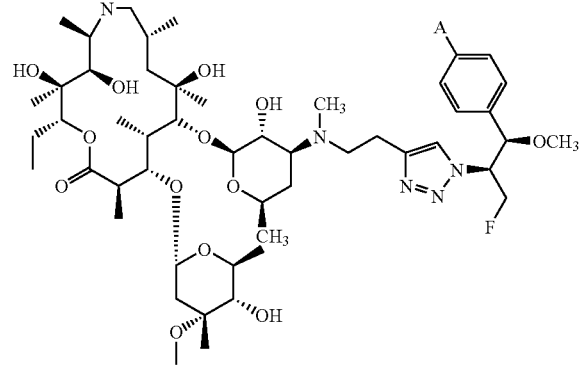
A Groups. Connection is to bond on left.
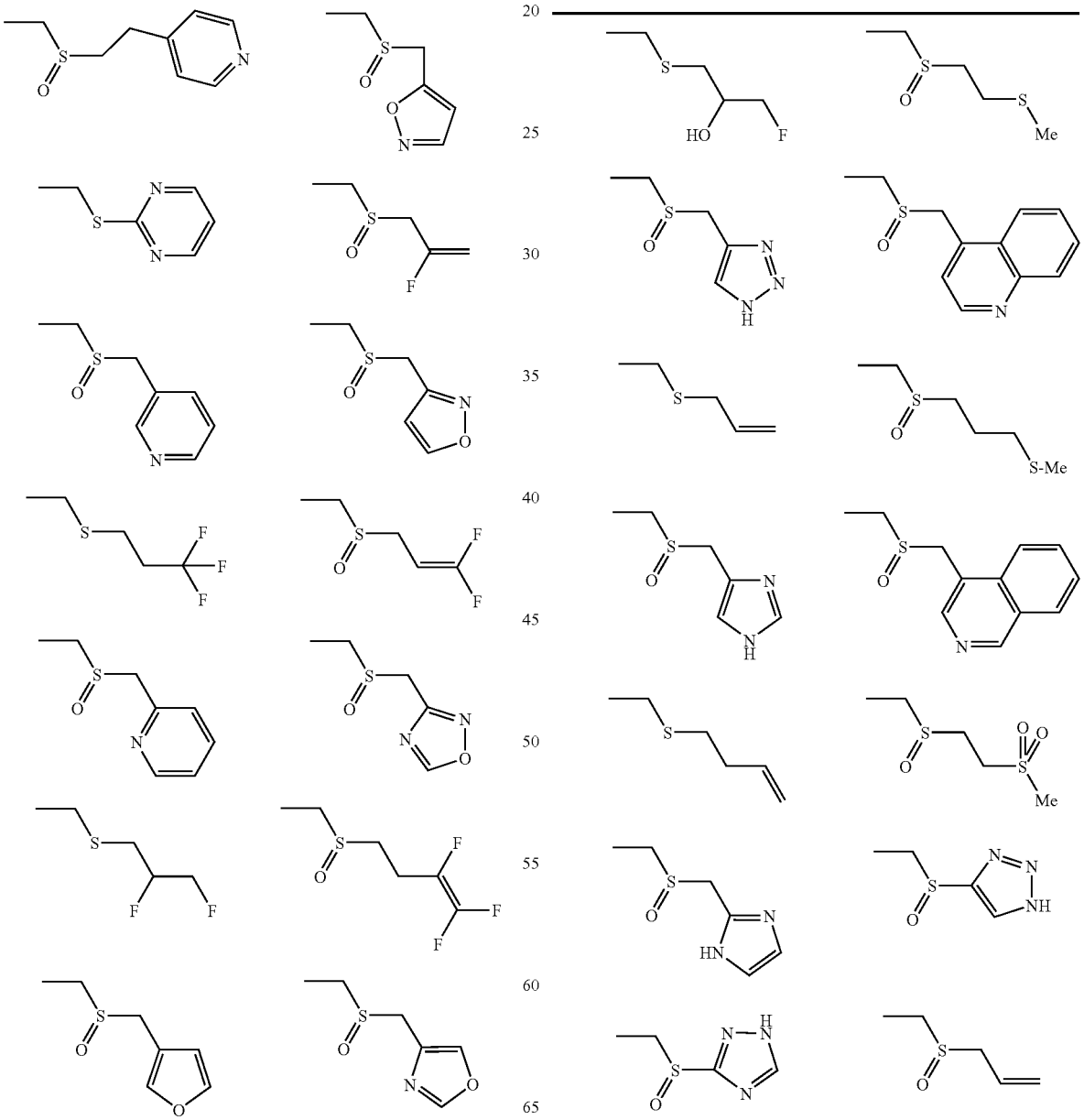

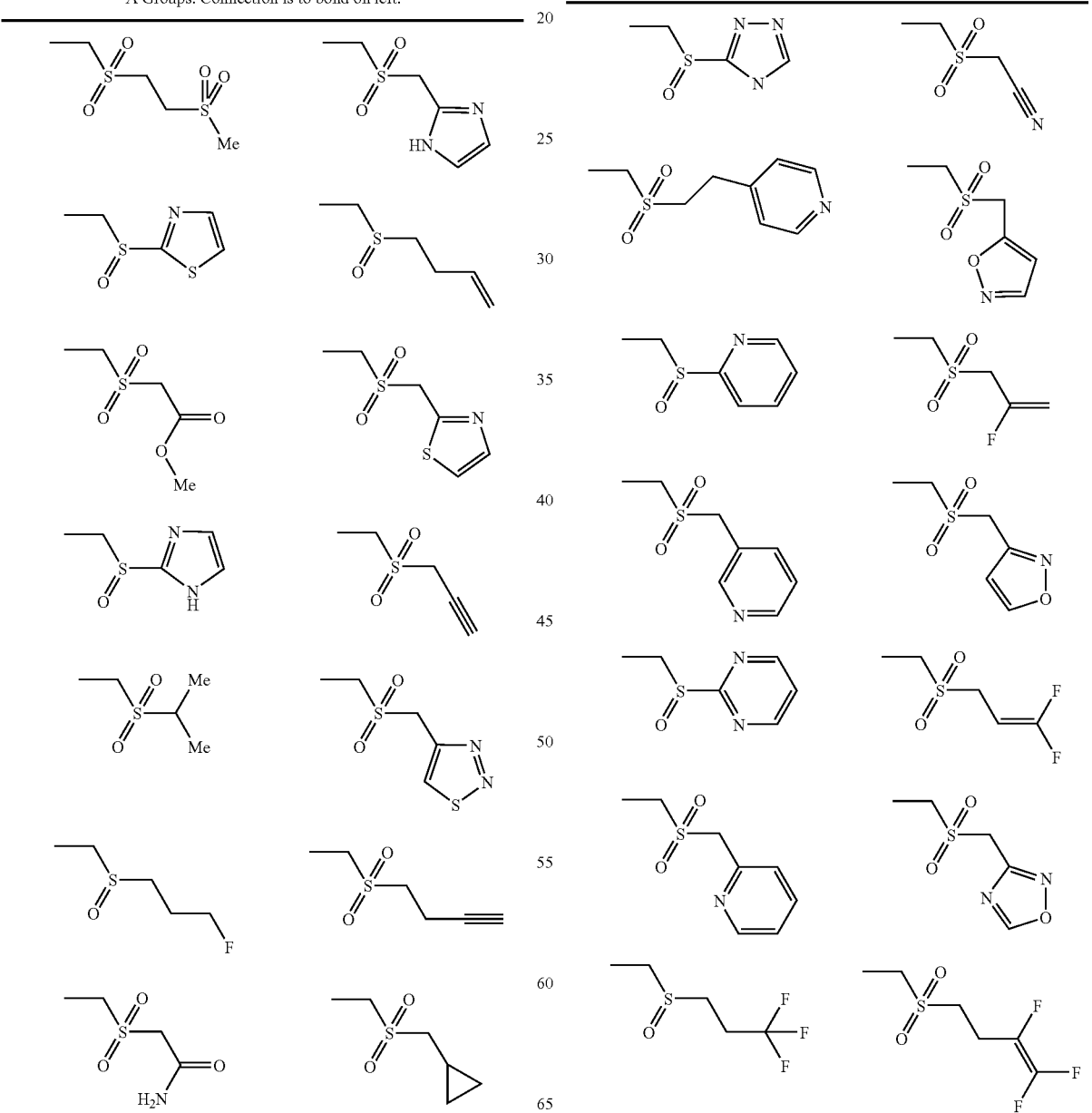

277
TABLE 1C-continued
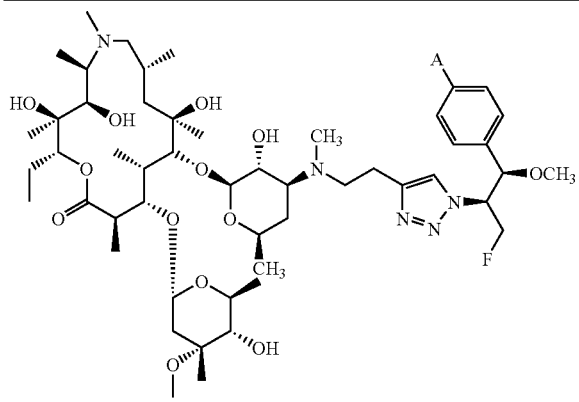
A Groups. Connection is to bond on left.
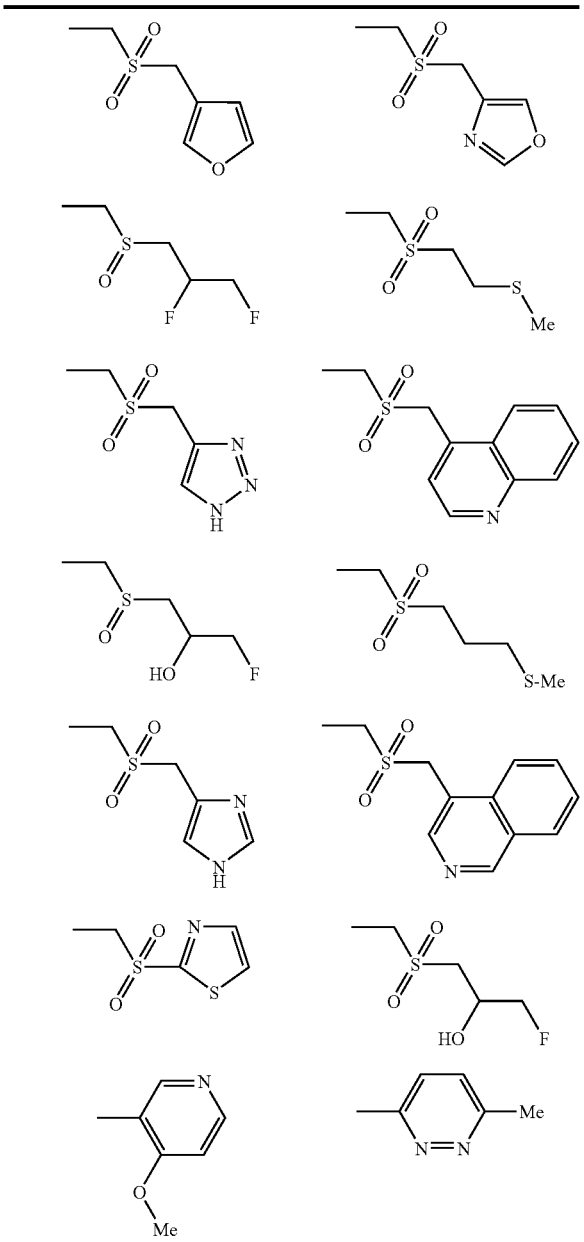
278
TABLE 1C-continued
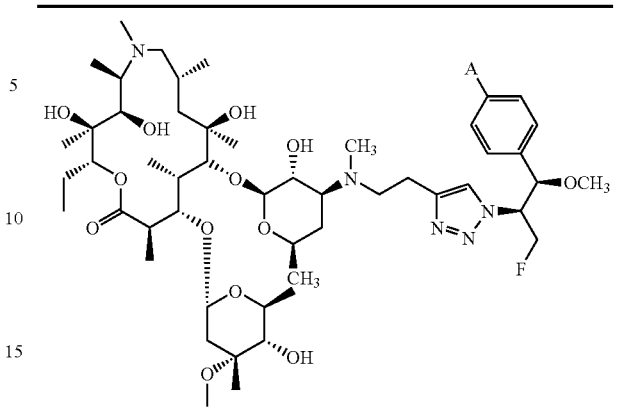
A Groups. Connection is to bond on left.
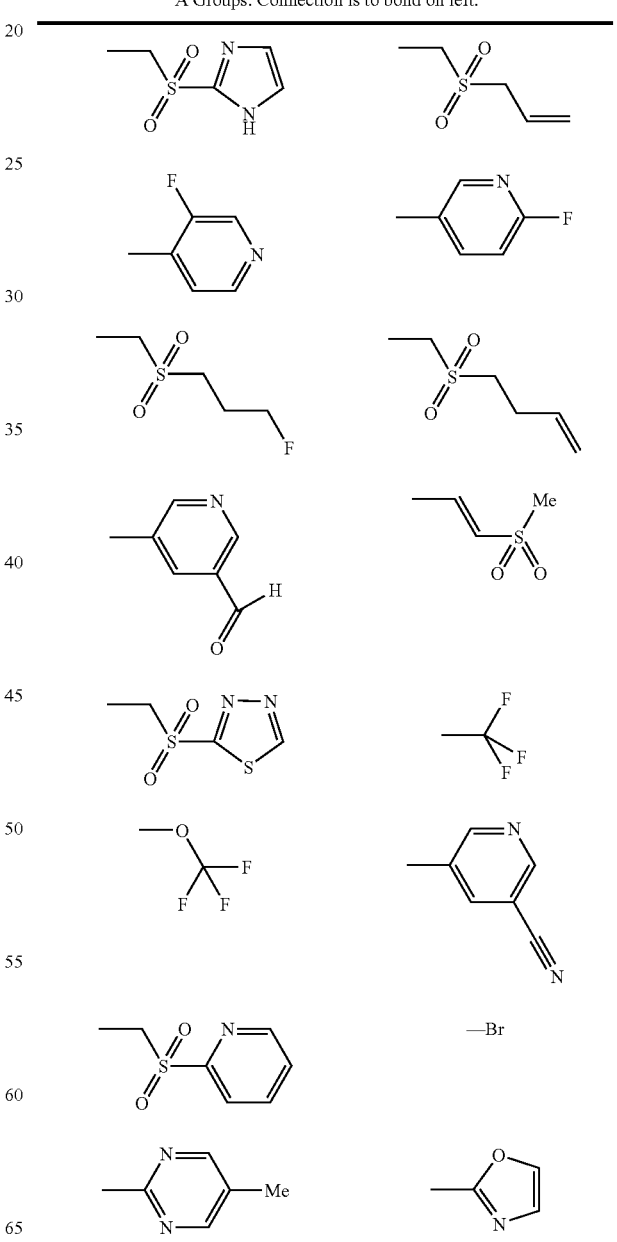

TABLE 1C-continued
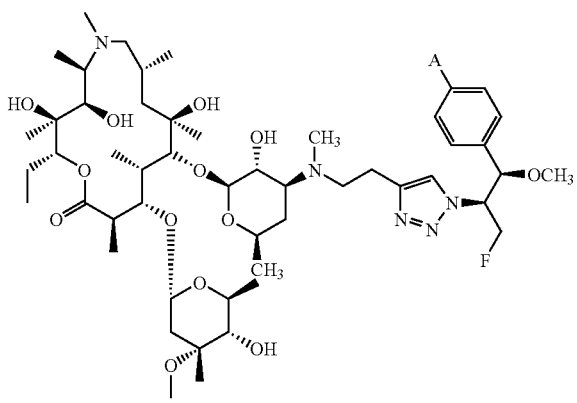
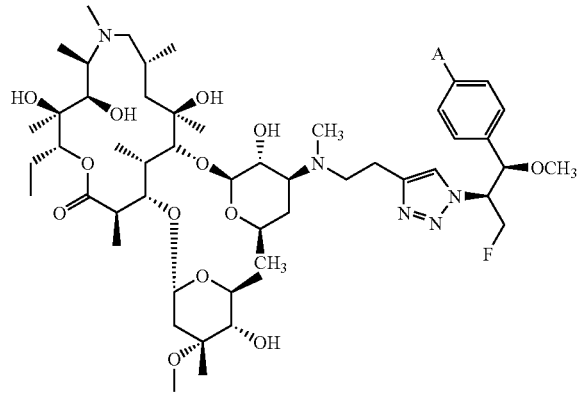
A Groups. Connection is to bond on left.
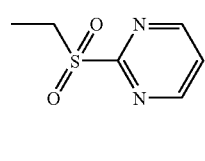 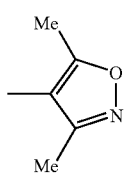
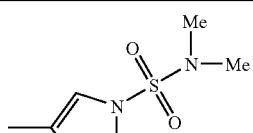 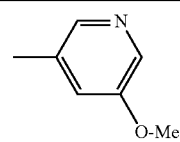
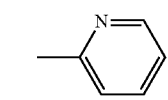 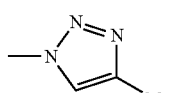
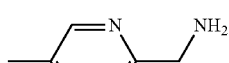 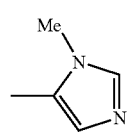
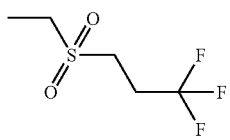 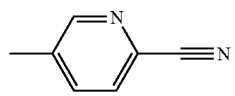
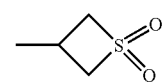 
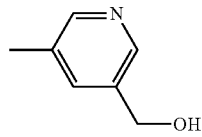 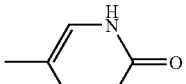
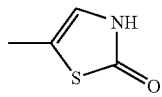 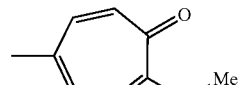
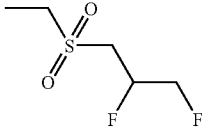 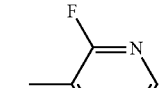
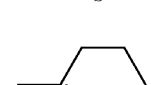 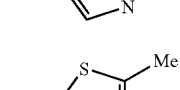
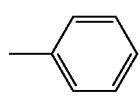 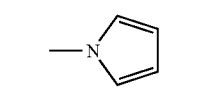
—Cl
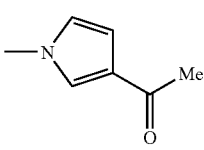
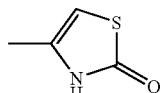 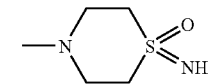
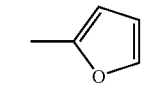 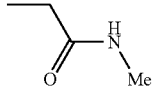

TABLE 1C-continued

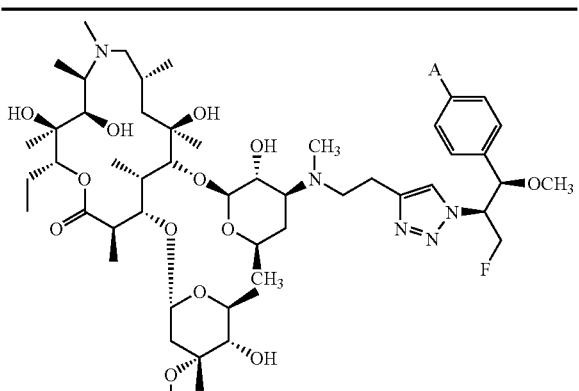

A Groups. Connection is to bond on left.

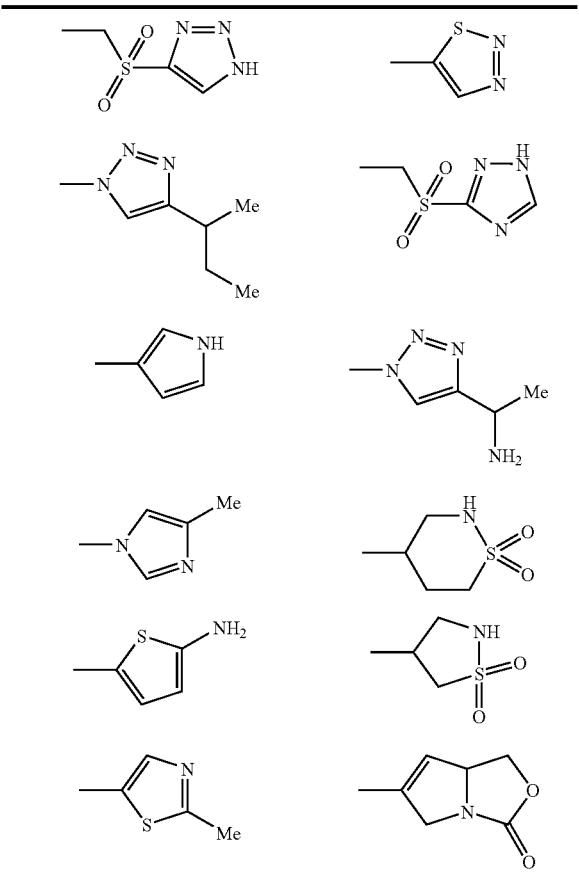

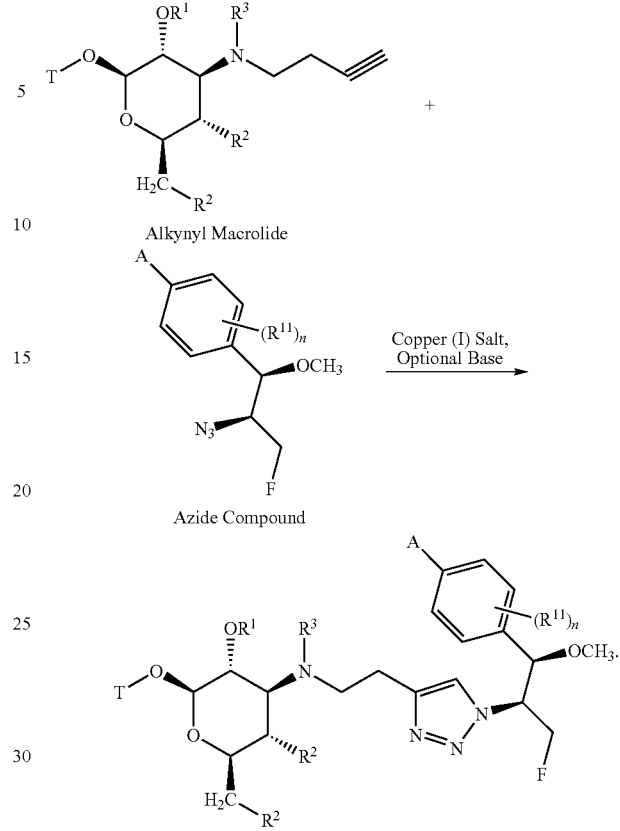

Alkynyl Macrolide

Azide Compound

Synthesis of the Compounds of the Present Invention

Compounds of the present invention can be made, for example, via a cycloaddition reaction of an alkynyl macrolide with an azide compound. In this cycloaddition reaction, the triazole functional group of the resulting compound is formed. Other compounds of the present invention are made by further chemically modifying the resulting compound from the cycloaddition reaction.

The cycloaddition reaction is generally run in the presence of a copper (I) salt such as copper iodide (CuI). A base can also be optionally used, such as Hunig's base (N,N-diisopropylethylamine). The following general reaction scheme outlines the cycloaddition reaction of the alkynyl macrolide and the azide compound.

The time required for the reaction to proceed to completion is variable and is dependent upon several factors including, the specific alkynyl macrolide and azide compounds and their concentrations; the amount of Cu(I) salt used; and the presence or absence of base, such as Hunig's Base (N,N-diisopropylethylamine). Reactions are monitored for the disappearance of the starting materials by TLC and/or LCMS and are typically allowed to run for between about 2 hours to about 72 hours. Reactions are generally stopped when analysis demonstrates that the starting alkynyl macrolide has been substantially consumed. The workup and purification protocols are standard. Modifications to the described workup procedures can be used. Such modifications can include the use of different aqueous wash solutions, different organic solvents for extraction, the use of other anhydrous salts for the drying of organic extracts, and the employment of different solvent mixtures for the chromatographic purification of the compounds. The methods used for the workup of the reaction mixtures, the extraction of products, the drying of organic extracts, and for the isolation and purification of the title compounds are typical of procedures familiar to those trained in the art of organic synthesis. The isolated chemical yields for the synthesis of compounds can be variable and are indicated in Table 2.

Most compounds of the present invention can be prepared from the desired alkynyl macrolide and azide compound under one of several similar reaction conditions as exemplified by Conditions A, B, C, and D below. Use of Conditions A and C, which do not include the step of degassing the reaction mixture, tend to result in the formation of iodinated side-products in addition to the desired product and thereby generally produced lower isolated yields. Additionally, reduction of the amount of copper iodide used in the reaction to 0.5 molar equivalents or less as in conditions B and D also tends to result in reduced formation of iodinated by-products. As demonstrated in Condition D, the presence of Hunig's base is not essential for the success of the triazole formation step; however, it is found preferable that the base be included since it often results in a higher rate of reaction and correspondingly shorter reaction times.

Condition A:

To a stirred solution of the alkynyl macrolide (0.04 mmol), the azide compound (0.07 mmol) and Hunig's base (10 μL) in 0.5 mL tetrahydrofuran (THF) is added CuI (5 mg, 0.03 mmol). The mixture is stirred at ambient temperature for 16 hours then diluted with $CH_2Cl_2$ (10 mL) and washed with a 3:1 mixture of saturated aqueous $NH_4Cl$ and 28% aqueous $NH_4OH$ (10 mL) and with brine (10 mL) the aqueous washes are back-extracted with $CH_2Cl_2$ (2×10 mL). The combined organic extracts are dried over $K_2CO_3$, filtered, and concentrated to afford 52 mg of crude product which is purified by chromatography on silica gel (elution with 40:1 2M $NH_3$ in MeOH and $CH_2Cl_2$) to give the desired compound.

Condition B:

A solution of alkynyl compound (0.10 mmol) and azide compound (0.12 mmol) and Hunig's base in 0.4 mL THF are thoroughly degassed by alternately evacuating the reaction vessel and purging with dry argon. CuI is then added (2 mg, 0.01 mmol) and the mixture is further degassed. The mixture is stirred under argon for 6 h then diluted with $CH_2Cl_2$ (20 mL) and washed with a 3:1 mixture of saturated aqueous $NH_4Cl$ and 28% aqueous $NH_4OH$ (10 mL) and with brine (10 mL) the aqueous washes are back-extracted with $CH_2Cl_2$ (2×15 mL). The combined organic extracts were dried over $K_2CO_3$, filtered, and concentrated to afford 115 mg of crude product which is purified by chromatography on silica gel (eluted with 2M $NH_3$ in MeOH (2.5%) and $CH_2Cl_2$ (97.5%), to give the desired compound.

Condition C:

To a stirred solution of alkynyl compound (0.10 mmol) and Hunig's base (0.2 mL) in 3 mL THF is added the azide compound (0.50 mmol) and CuI (20 mg, 0.10 mmol). The reaction mixture is stirred under argon for 60 hours then poured into saturated aqueous $NH_4Cl$ and extracted with $CH_2Cl_2$. The organic extracts are dried over $Na_2SO_4$, filtered, and concentrated to afford a crude residue which is purified by silica gel chromatography (eluted with 25:1:0.1 $CH_2Cl_2$: MeOH:$NH_4OH$) and then by preparative TLC (elution with 25:1:0.1 $CH_2Cl_2$:MeOH:$NH_4OH$) to afford the desired compound.

Condition D

A solution of alkynyl compound (0.15 mmol) and the azide compound (0.25 mmol) in 2.7 mL THF are thoroughly degassed by alternately evacuating the reaction vessel and purging with dry argon. CuI is then added (10 mg, 0.05 mmol) and the mixture is further degassed. The mixture is stirred under argon for 4 h then concentrated in vacuo, dissolved in $CH_2Cl_2$ (1 mL), and placed directly on a silica gel column. Elution with 2 molar (M) $NH_3$ in MeOH (3%) and $CH_2Cl_2$ (97%) gives the desired compound.

Synthesis of Compounds wherein Substituent "A" Contains a Triazole Ring

Compounds 131, 132, 172, 173, 174, 175, 182, 185, 199, 201, 203, and 205, as well as other similar compounds, correspond to the generic structure wherein substituent A, as defined for the compounds of the present invention, contains a triazole ring. For Compounds 131, 132, 172, 173, 174, 175, 182, 185, 199, 201, 203, and 205, $(R^{11})_n$ is hydrogen, i.e. the phenyl ring is only substituted with A. These compounds are generally prepared from the cycloaddition reaction of the desired alkynyl macrolide and the nitro phenyl azide compound to form the resulting nitro phenyl macrolide compound. This nitro phenyl macrolide compound is then further transformed to yield the desired compound. For compounds 131, 132, 172, 173, 174, 175, 182, 185, 199, 201, 203, and 205, the nitro group is converted to an azide group via an amine. The azide group is then reacted with an appropriately functionalized alkyne in a second cycloaddition reaction to form the desired compound.

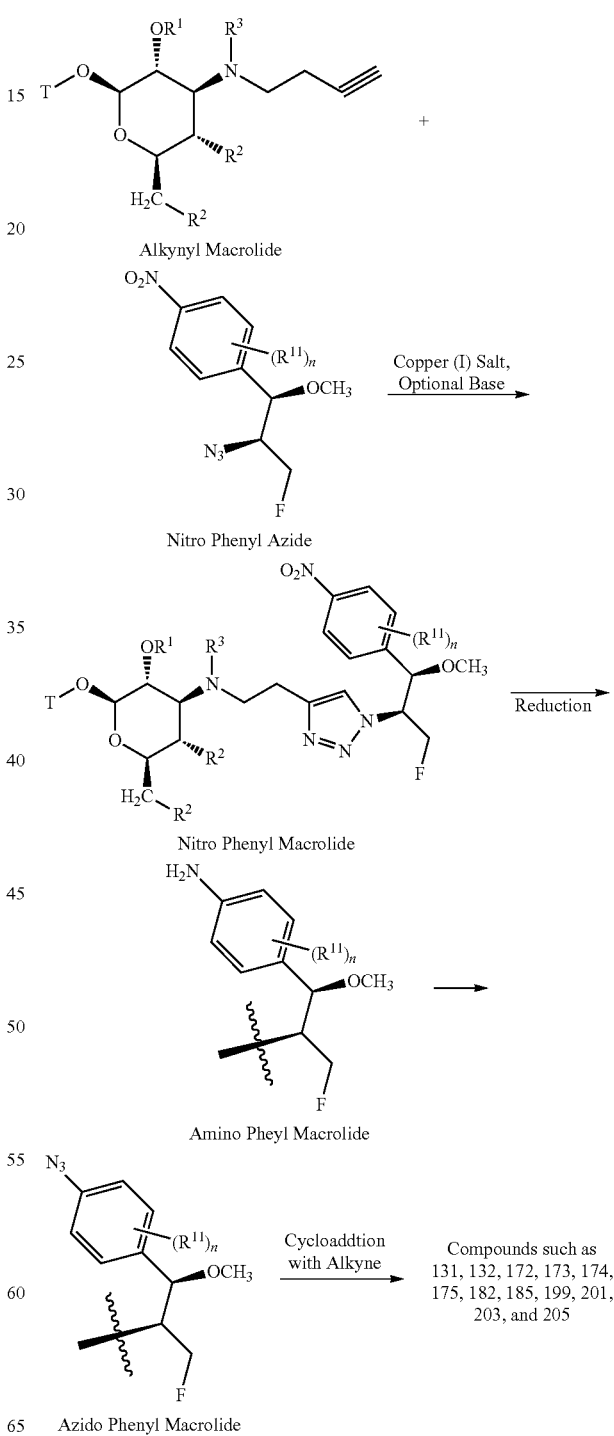

Further detail for some of the compounds of the present invention are provided in Table 2, which are organized as follows:

The first column (labeled "Compound") lists compound numbers corresponding to those of Table 1, above.

The second column (labeled "Alkynyl Macrolide") corresponds to the alkynyl macrolide compounds that can be used in the synthesis of the compounds of the present invention. Nonlimiting examples of alkynyl macrolide compounds, labeled M1 to M28 are separately shown below in Table 3.

The third column (labeled "Azide") corresponds to the azide compounds that can be used in the synthesis of the compounds of the present invention. It should be noted that compounds 131, 132, 172, 173, 174, 175, 182, 185, 199, 201, 203, and 205, as well as other similar compounds, are prepared via a common nitro phenyl azide intermediate, X. The nitro group is further transformed after the cycloaddition reaction to produce the final desired product.

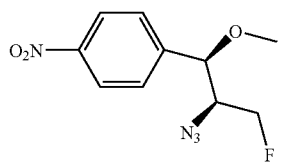

X

The fourth column (labeled "Yield") provides the percent yield corresponding to the cycloaddition reaction of the alkynyl macrolide and the azide compound for the indicated compound. In the case of compounds 131, 132, 172, 173, 174, 175, 182, 185, 199, 201, 203, and 205, the yield is a general average for the reaction of the alkynyl macrolide and nitro phenyl azide X.

The fifth column (labeled "LCMS") provides the liquid chromatography mass spectral data, where available, for the compound.

TABLE 2

| Compound | Alkynyl Macrolide | Azide | LCMS |
|---|---|---|---|
| 100 | M1 | | 538.2 $(M + 2H)^{2+}$ |
| 101 | M1 | | 537.7 $(M + 2H)^{2+}$ |
| 102 | M1 | | 552.6 $(M + 2H)^{2+}$ |
| 103 | M1 | | 538.2 $(M + 2H)^{2+}$ |
| 104 | M1 | | 544.6 $(M + 2H)^{2+}$ |

TABLE 2-continued

| Compound | Alkynyl Macrolide | Azide | LCMS |
|---|---|---|---|
| 105 | M1 | (pyrimidin-5-yl phenyl structure with OMe, N₃, F) | 538.2 (M + 2H)²⁺ |
| 106 | M1 | (2-aminopyrimidin-5-yl phenyl structure with OMe, N₃, F) | 545.675 (M + 2H)²⁺ |
| 107 | M1 | (isoxazol-4-yl phenyl structure with OMe, N₃, F) | 532.6 (M + 2H)²⁺ |
| 108 | M1 | (acetamidomethyl biphenyl structure with OMe, N₃, F) | 572.7 (M + 2H)²⁺ |
| 109 | M1 | (6-methoxypyridin-3-yl phenyl structure with OMe, N₃, F) | 552.6 (M + 2H)²⁺ |
| 110 | M1 | (4-iodophenyl structure with OMe, N₃, F) | 562.1 (M + 2H)²⁺ |
| 111 | M1 | (phenyl structure with OMe, N₃, F) | 499.1 (M + 2H)²⁺ |
| 112 | M1 | (1-methylpyrazol-4-yl phenyl structure with OMe, N₃, F) | 539.2 (M + 2H)²⁺ |
| 113 | M1 | (aminomethyl biphenyl structure with OMe, N₃, F) | 551.7 (M + 2H)²⁺ |

TABLE 2-continued

| Compound | Alkynyl Macrolide | Azide | LCMS |
|---|---|---|---|
| 114 | M1 | | 552.2 (M + 2H)$^{2+}$ |
| 115 | M2 | | — |
| 116 | M1 | | 532.2 (M + 2H)$^{2+}$ |
| 117 | M1 | | 532.2 (M + 2H)$^{2+}$ |
| 118 | M1 | | 532.2 (M + 2H)$^{2+}$ |
| 119 | M1 | | 532.1 (M + 2H)$^{2+}$ |
| 120 | M3 | | 1063.0 (M + H)$^{+}$ |
| 121 | M1 | | 555.2 (M + 2H)$^{2+}$ |
| 122 | M3 | | 1074.1 (M + H)$^{+}$ |

TABLE 2-continued
| Compound | Alkynyl Macrolide | Azide | LCMS |
|---|---|---|---|
| 123 | M3 | 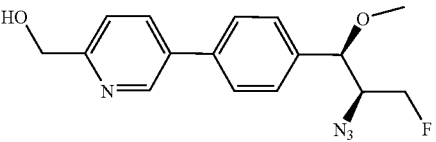 | 552.2 (M + 2H)$^{2+}$ |
| 124 | M3 | 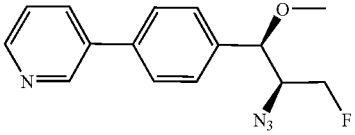 | 1073.3 (M + H)$^+$ |
| 125 | M1 | 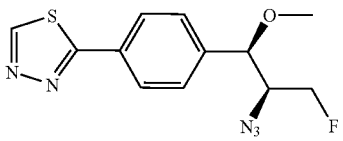 | 541.2 (M + 2H)$^{2+}$ |
| 126 | M3 | 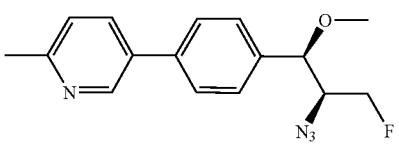 | 1087 (M + H)$^+$ |
| 127 | M4 | 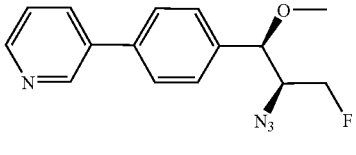 | 955 (M + 2)$^+$ |
| 128 | M5 | 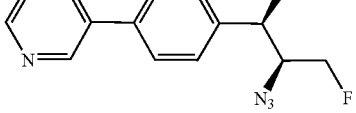 | 913 (M + H)$^+$ |
| 129 | M1 | 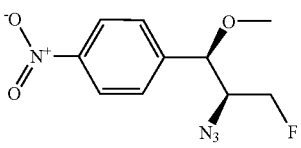 | 521.6 (M + 2H)$^{2+}$ |
| 130 | M1 | 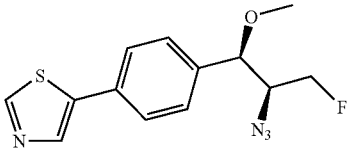 | 540.7 (M + 2H)$^{2+}$ |
| 131 | M1 | 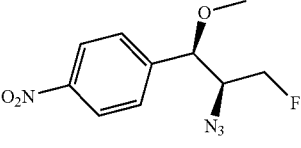 | 568.7 (M + 2H)$^{2+}$ |
| 132 | M1 | 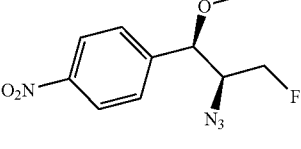 | 532.7 (M + 2H)$^{2+}$ |

TABLE 2-continued

| Compound | Alkynyl Macrolide | Azide | LCMS |
|---|---|---|---|
| 133 | M3 | (pyridine N-oxide-phenyl-CH(OMe)-CH(N3)-CH2F) | 1088.8 (M + H)+ |
| 134 | M1 | (pyridine N-oxide-phenyl-CH(OMe)-CH(N3)-CH2F) | 545.7 (M + 2H)2+ |
| 135 | M1 | (2-aminothiazole-phenyl-CH(OMe)-CH(N3)-CH2F) | 548.2 (M + 2H)2+ |
| 136 | M3 | (2-aminothiazole-phenyl-CH(OMe)-CH(N3)-CH2F) | 1093.8 (M + H)+ |
| 137 | M5 | (2-aminothiazole-phenyl-CH(OMe)-CH(N3)-CH2F) | 934 (M + H)+ |
| 138 | M3 | (methylsulfonyl-phenyl-CH(OMe)-CH(N3)-CH2F) | 914 (M + H)+ |
| 139 | M1 | (HOCH2-CH(OH)-CH2-phenyl-CH(OMe)-CH(N3)-CH2F) | 536.1 (M + 2H)2+ |
| 140 | M1 | (ethylthio-phenyl-CH(OMe)-CH(N3)-CH2F) | 529.2 (M + 2H)2+ |
| 141 | M1 | (ethylsulfinyl-phenyl-CH(OMe)-CH(N3)-CH2F) | 537.2 (M + 2H)2+ |

TABLE 2-continued

| Compound | Alkynyl Macrolide | Azide | LCMS |
|---|---|---|---|
| 142 | M1 | (ethylsulfonyl-phenyl with methoxy, azido, fluoromethyl side chain) | 545.2 (M + 2H)$^{2+}$ |
| 143 | M1 | (N,N-dimethylbenzamide with methoxy, azido, fluoromethyl side chain) | 534.7 (M + 2H)$^{2+}$ |
| 144 | M1 | (N-methylbenzamide with methoxy, azido, fluoromethyl side chain) | 534.7 (M + 2H)$^{2+}$ |
| 145 | M1 | (benzamide with methoxy, azido, fluoromethyl side chain) | 520.6 (M + 2H)$^{2+}$ |
| 146 | M1 | (N,N-dimethylphenylacetamide with methoxy, azido, fluoromethyl side chain) | 541.6 (M + 2H)$^{2+}$ |
| 147 | M3 | (N,N-dimethylphenylacetamide with methoxy, azido, fluoromethyl side chain) | 541.2 (M + 2H)$^{2+}$ |
| 148 | M1 | (oxopiperazinyl-carbonyl-phenyl with methoxy, azido, fluoromethyl side chain) | 562.2 (M + 2H)$^{2+}$ |
| 149 | M1 | (N-cyclopropylbenzamide with methoxy, azido, fluoromethyl side chain) | 540.7 (M + 2H)$^{2+}$ |
| 150 | M1 | (methylpyridine N-oxide-phenyl with methoxy, azido, fluoromethyl side chain) | 552.7 (M + 2H)$^{2+}$ |

TABLE 2-continued
| Compound | Alkynyl Macrolide | Azide | LCMS |
|---|---|---|---|
| 151 | M1 | 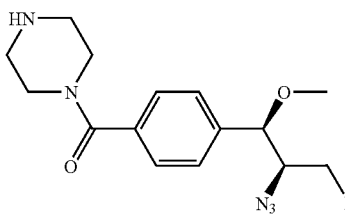 | 555.2 (M + 2H)$^{2+}$ |
| 152 | M1 | 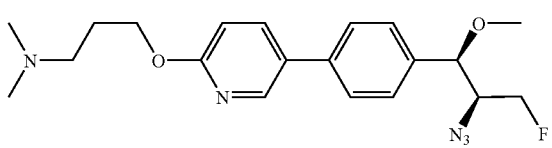 | 588.2 (M + 2H)$^{2+}$ |
| 153 | M1 | 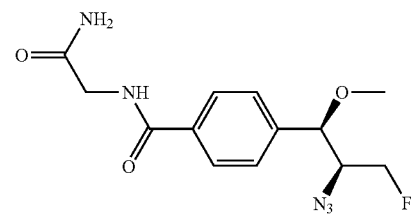 | 549.2 (M + 2H)$^{2+}$ |
| 154 | M1 | 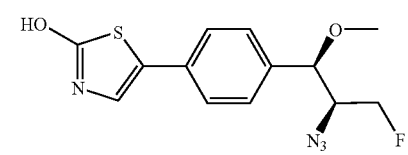 | 548.7 (M + 2H)$^{2+}$ |
| 155 | M1 | 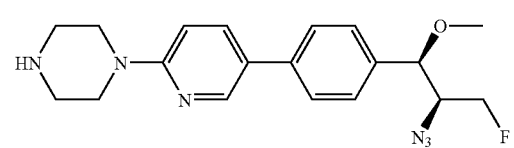 | 579.7 (M + 2H)$^{2+}$ |
| 156 | M1 | 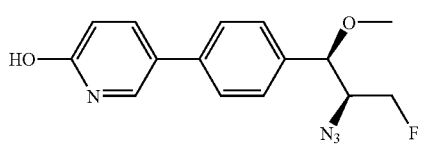 | 545.7 (M + 2H)$^{2+}$ |
| 157 | M1 | 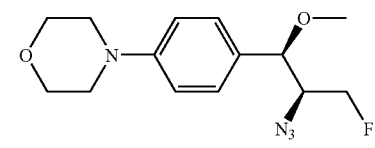 | 541.7 (M + 2H)$^{2+}$ |
| 158 | M1 | 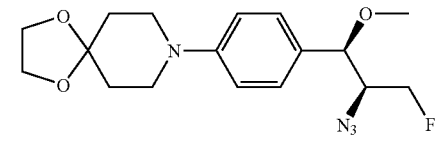 | 569.8 (M + 2H)$^{2+}$ |
| 159 | M1 | 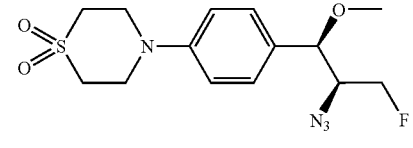 | 565.7 (M + 2H)$^{2+}$ |

TABLE 2-continued

| Compound | Alkynyl Macrolide | Azide | LCMS |
|---|---|---|---|
| 160 | M1 | | 528.2 $(M + 2H)^{2+}$ |
| 161 | M1 | | 560.5 $(M + 2H)^{2+}$ |
| 162 | M1 | | 540.7 $(M + 2H)^{2+}$ |
| 163 | M1 | | 506.6 $(M + 2H)^{2+}$ |
| 164 | M1 | | 513.1 $(M + 2H)^{2+}$ |
| 165 | M1 | | 521.1 $(M + 2H)^{2+}$ |
| 166 | M1 | | 514.1 $(M + 2H)^{2+}$ |
| 167 | M1 | | 548.6 $(M + 2H)^{2+}$ |
| 168 | M1 | | 536 $(M + 2H)^{2+}$ |

TABLE 2-continued

| Compound | Alkynyl Macrolide | Azide | LCMS |
|---|---|---|---|
| 169 | M1 | (isopropylsulfonyl-phenyl with OMe, N₃, F substituents) | 552 (M + 2H)²⁺ |
| 170 | M1 | (NC-CH₂-S-phenyl with OMe, N₃, F substituents) | 534.5 (M + 2H)²⁺ |
| 171 | M1 | (NC-CH₂-SO₂-phenyl with OMe, N₃, F substituents) | 550.5 (M + 2H)²⁺ |
| 172 | M1 | (O₂N-phenyl with OMe, N₃, F substituents) | 547.8 (M + 2H)²⁺ |
| 173 | M1 | (O₂N-phenyl with OMe, N₃, F substituents) | 561.2 (M + 2H)²⁺ |
| 174 | M1 | (O₂N-phenyl with OMe, N₃, F substituents) | 569.8 (M + 2H)²⁺ |
| 175 | M1 | (O₂N-phenyl with OMe, N₃, F substituents) | 554.3 (M + 2H)²⁺ |
| 176 | M1 | (HO-thiazole-phenyl with OMe, N₃, F substituents) | 548.7 (M + 2H)²⁺ |
| 177 | M1 | (HO-N=C(CH₃)-phenyl with OMe, N₃, F substituents) | 527.7 (M + 2H)²⁺ |
| 178 | M1 | (CH₃-C(=N-OH)-phenyl with OMe, N₃, F substituents) | 527.7 (M + 2H)²⁺ |

TABLE 2-continued
| Compound | Alkynyl Macrolide | Azide | LCMS |
|---|---|---|---|
| 179 | M1 | 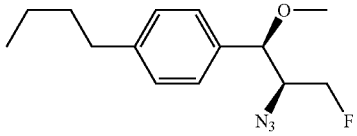 | 527.2 (M + 2H)$^{2+}$ |
| 180 | M1 | 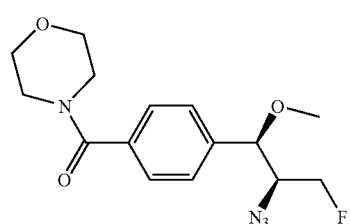 | 555.7 (M + 2H)$^{2+}$ |
| 181 | M1 | 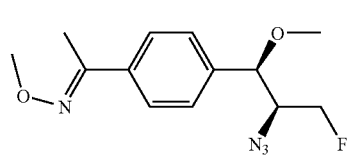 | 534.6 (M + 2H)$^{2+}$ |
| 182 | M1 | 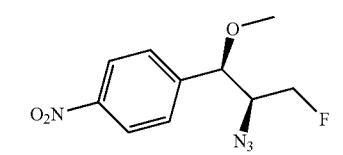 | 552.8 (M + 2H)$^{2+}$ |
| 183 | M1 | 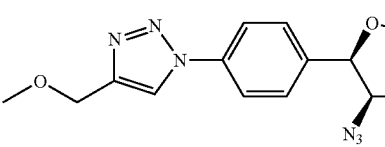 | 554.7 (M + 2H)$^{2+}$ |
| 184 | M1 | 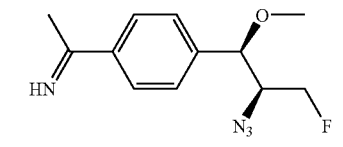 | 519.7 (M + 2H)$^{2+}$ |
| 185 | M1 | 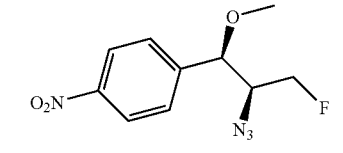 | 606.3 (M + 2H)$^{2+}$ |
| 186 | M1 | 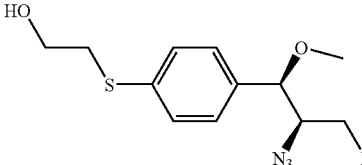 | 537.1 (M + 2H)$^{2+}$ |
| 187 | M1 | 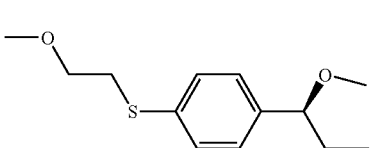 | 544.1 (M + 2H)$^{2+}$ |

TABLE 2-continued

| Compound | Alkynyl Macrolide | Azide | LCMS |
|---|---|---|---|
| 188 | M1 | (4-methylpiperazin-1-ylmethyl phenyl structure with OMe, N₃, F) | 555.1 (M + 2H)²⁺ |
| 189 | M1 | (methylthiomethyl phenyl structure with OMe, N₃, F) | 529.1 (M + 2H)²⁺ |
| 190 | M1 | (methylsulfonylmethyl phenyl structure with OMe, N₃, F) | 545.1 (M + 2H)²⁺ |
| 191 | M1 | (chloromethyl phenyl structure with OMe, N₃, F) | 523.3 (M + 2H)²⁺ |
| 192 | M1 | (N,N-dimethylsulfamoyl phenyl structure with OMe, N₃, F) | 552.7 (M + 2H)²⁺ |
| 193 | M1 | (cyclopentylthio phenyl structure with OMe, N₃, F) | 549.2 (M + 2H)²⁺ |
| 194 | M1 | (trifluoromethylthio phenyl structure with OMe, N₃, F) | 549.1 (M + 2H)²⁺ |
| 195 | M1 | (oxazolidin-2-one phenyl structure with OMe, N₃, F) | 541.8 (M + 2H)²⁺ |

TABLE 2-continued

| Compound | Alkynyl Macrolide | Azide | LCMS |
|---|---|---|---|
| 196 | M1 | | 558.5 (M + 2H)$^{2+}$ |
| 197 | M1 | | 547.1 (M + 2H)$^{2+}$ |
| 198 | M1 | | 520.6 (M + 2H)$^{2+}$ |
| 199 | M1 | | 560.9 (M + 2H)$^{2+}$ |
| 200 | M1 | | 538.5 (M + 2H)$^{2+}$ |
| 201 | M1 | | 561.1 (M + 2H)$^{2+}$ |
| 202 | M1 | | 545.7 (M + 2H)$^{2+}$ |
| 203 | M1 | | 554.8 (M + 2H)$^{2+}$ |
| 204 | M1 | | 565.2 (M + 2H)$^{2+}$ |

TABLE 2-continued
| Compound | Alkynyl Macrolide | Azide | LCMS |
|---|---|---|---|
| 205 | M1 | 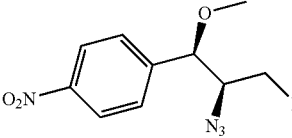 | 567.8 (M + 2H)$^{2+}$ |
| 206 | M1 | 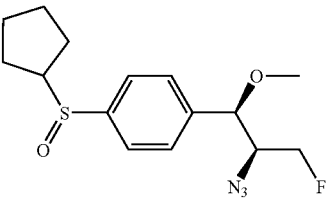 | 557.2 (M + 2H)$^{2+}$ |
| 207 | M1 | 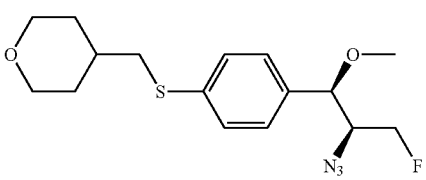 | 564.2 (M + 2H)$^{2+}$ |
| 208 | M1 | 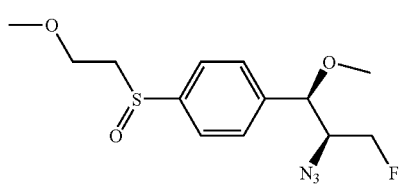 | 552.1 (M + 2H)$^{2+}$ |
| 209 | M1 | 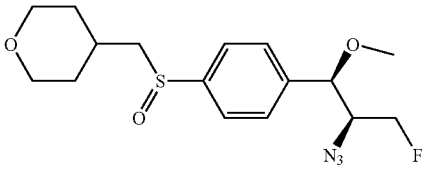 | 572.2 (M + 2H)$^{2+}$ |
| 210 | M1 | 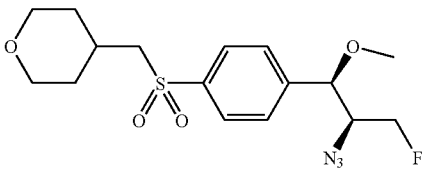 | 580.2 (M + 2H)$^{2+}$ |
| 211 | M6 | 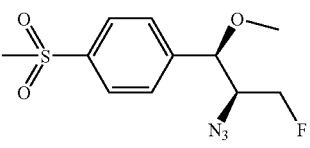 | 1113.4 (M + H)$^+$ |
| 212 | M6 | 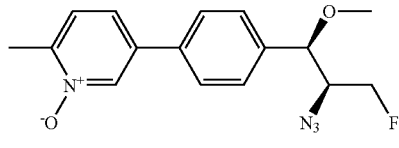 | 1142.4 (M + H)$^+$ |
| 213 | M7 | 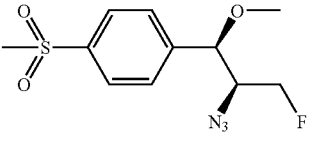 | 1099.4 (M + H)$^+$ |

TABLE 2-continued

| Compound | Alkynyl Macrolide | Azide | LCMS |
|---|---|---|---|
| 214 | M7 | (2-methylpyridine N-oxide-phenyl-CH(OMe)-CH(N3)-CH2F) | 1128.4 (M + H)+ |
| 215 | M8 | (methylsulfonyl-phenyl-CH(OMe)-CH(N3)-CH2F) | 1143.4 (M + H)+ |
| 216 | M8 | (2-methylpyridine N-oxide-phenyl-CH(OMe)-CH(N3)-CH2F) | 1172.4 (M + H)+ |
| 217 | M1 | (H2N-C(O)-CH2-S-phenyl-CH(OMe)-CH(N3)-CH2F) | 543.6 (M + 2H)2+ |
| 218 | M1 | (H2N-C(O)-CH2-SO2-phenyl-CH(OMe)-CH(N3)-CH2F) | 559.8 (M + 2H)2+ |
| 219 | M1 | (TMS-C≡C-phenyl-CH(OMe)-CH(N3)-CH2F) | 547.2 (M + 2H)2+ |
| 220 | M1 | (HC≡C-phenyl-CH(OMe)-CH(N3)-CH2F) | 511.0 (M + 2H)2+ |
| 221 | M1 | (MeS-CH2CH2-NH-CH2-phenyl-CH(OMe)-CH(N3)-CH2F) | 550.5 (M + 2H)2+ |
| 222 | M1 | (H2N-C(O)-CH2-NH-CH2-phenyl-CH(OMe)-CH(N3)-CH2F) | 542.1 (M + 2H)2+ |

TABLE 2-continued

| Compound | Alkynyl Macrolide | Azide | LCMS |
|---|---|---|---|
| 223 | M1 | (methanesulfonamidomethyl phenyl azide structure) | 552.5 $(M + 2H)^{2+}$ |
| 224 | M1 | (4-cyanophenyl azide structure) | 511.6 $(M + 2H)^{2+}$ |
| 225 | M1 | (N-cyclopropyl sulfonamide phenyl azide structure) | 558.7 $(M + 2H)^{2+}$ |
| 226 | M1 | (N,N-diethyl sulfonamide phenyl azide structure) | 566.6 $(M + 2H)^{2+}$ |
| 227 | M1 | (morpholinyl sulfonyl phenyl azide structure) | 573.6 $(M + 2H)^{2+}$ |
| 228 | M1 | (pyrrolidinyl sulfonyl phenyl azide structure) | 565.6 $(M + 2H)^{2+}$ |
| 229 | M1 | (pyridin-3-ylmethyl sulfonamide phenyl azide structure) | 584.1 $(M + 2H)^{2+}$ |
| 230 | M1 | (thiazepane dioxide phenyl azide structure) | 573.1 $(M + 2H)^{2+}$ |

TABLE 2-continued

| Compound | Alkynyl Macrolide | Azide | LCMS |
|---|---|---|---|
| 231 | M1 | (structure) | 572.5 (M + 2H)$^{2+}$ |
| 232 | M1 | (structure) | 564.2 (M + 2H)$^{2+}$ |
| 233 | M1 | (structure) | 547.1 (M + 2H)$^{2+}$ |
| 234 | M1 | (structure) | 539.1 (M + 2H)$^{2+}$ |
| 235 | M1 | (structure) | 546.6 (M + 2H)$^{2+}$ |
| 236 | M1 | (structure) | 540.3 (M + 2H)$^{2+}$ |
| 237 | M1 | (structure) | 558.3 (M + 2H)$^{2+}$ |
| 238 | M1 | (structure) | 541.1 (M + 2H)$^{2+}$ |
| 239 | M1 | (structure) | 522.2 (M + 2H)$^{2+}$ |

TABLE 2-continued
| Compound | Alkynyl Macrolide | Azide | LCMS |
|---|---|---|---|
| 240 | M1 | 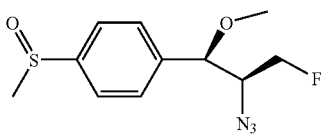 | 530.1 (M + 2H)$^{2+}$ |
| 241 | M1 | 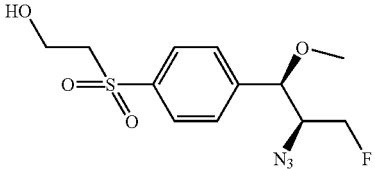 | 553.0 (M + 2H)$^{2+}$ |
| 242 | M1 | 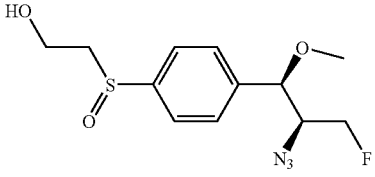 | 545.1 (M + 2H)$^{2+}$ |
| 243 | M1 | 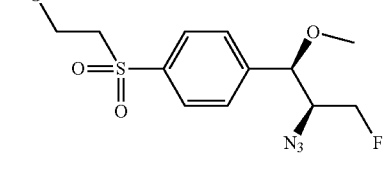 | 560.1 (M + 2H)$^{2+}$ |
| 244 | M1 | 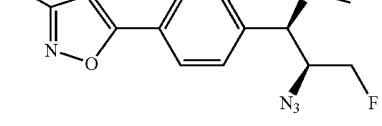 | 572.4 (M + 2H)$^{2+}$ |
| 245 | M1 | 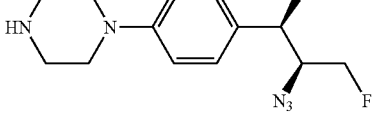 | 541.3 (M + 2H)$^{2+}$ |
| 246 | M1 | 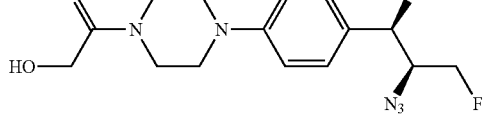 | 570.2 (M + 2H)$^{2+}$ |
| 247 | M1 | 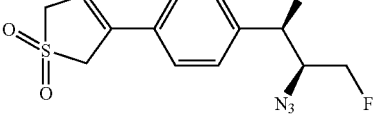 | 557.1 (M + 2H)$^{2+}$ |
| 248 | M1 | 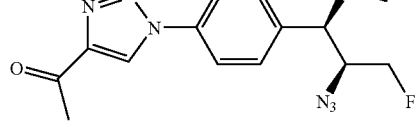 | 553.7 (M + 2H)$^{2+}$ |

TABLE 2-continued

| Compound | Alkynyl Macrolide | Azide | LCMS |
|---|---|---|---|
| 249 | M1 | (benzyl carbamate-NH-ethyl-sulfonyl-phenyl-CH(OMe)-CH(N₃)-CH₂F) | 619.9 (M + 2H)²⁺ |
| 250 | M1 | (piperidinyl-phenyl-CH(OMe)-CH(N₃)-CH₂F) | 540.8 (M + 2H)²⁺ |
| 251 | M1 | (pyrrolidinyl-phenyl-CH(OMe)-CH(N₃)-CH₂F) | 533.7 (M + 2H)²⁺ |
| 252 | M1 | (H₂N-CH₂-phenyl-CH(OMe)-CH(N₃)-CH₂F) | 513.7 (M + 2H)²⁺ |
| 253 | M1 | (phthalimido-CH₂-phenyl-CH(OMe)-CH(N₃)-CH₂F) | 478.8 (M + 2H)²⁺ |
| 254 | M1 | (CF₃-S(O)-phenyl-CH(OMe)-CH(N₃)-CH₂F) | 557.2 (M + 2H)²⁺ |
| 255 | M1 | (F-CH₂CH₂-S-phenyl-CH(OMe)-CH(N₃)-CH₂F) | 538.1 (M + 2H)²⁺ |
| 256 | M1 | (F-CH₂CH₂CH₂-S-phenyl-CH(OMe)-CH(N₃)-CH₂F) | 545.2 (M + 2H)²⁺ |

TABLE 2-continued

| Compound | Alkynyl Macrolide | Azide | LCMS |
|---|---|---|---|
| 257 | M1 | (structure) | 539.8 (M + 2H)$^{2+}$ |
| 258 | M1 | (structure) | 589.8 (M + 2H)$^{2+}$ |
| 259 | M1 | (structure) | 560.7 (M + 2H)$^{2+}$ |
| 260 | M1 | (structure) | 547.1 (M + 2H)$^{2+}$ |
| 261 | M1 | (structure) | 419.9 (M + 3H)$^{3+}$ 629.5 (M + 2H)$^{2+}$ |
| 262 | M1 | (structure) | 527.3 (M + 2H)$^{2+}$ |

TABLE 2-continued

| Compound | Alkynyl Macrolide | Azide | LCMS |
|---|---|---|---|
| 263 | M1 | (thiopyran-phenyl-CH(OMe)-CH(N3)-CH2F) | 548.1 (M + 2H)$^{2+}$ |
| 264 | M1 | (N-hydroxyacetyl-tetrahydropyridinyl-phenyl-CH(OMe)-CH(N3)-CH2F) | 568.6 (M + 2H)$^{2+}$ |
| 265 | M27 | (methylsulfonyl-phenyl-CH(OMe)-CH(N3)-CH2F) | 1039.3 (M + H)$^+$ |
| 266 | M1 | (acetamido-phenyl-CH(OMe)-CH(N3)-CH2F) | 527.7 (M + 2H)$^{2+}$ |
| 267 | M1 | (chloroacetamido-phenyl-CH(OMe)-CH(N3)-CH2F) | 544.8 (M + 2H)$^{2+}$ |
| 268 | M1 | (2-fluoroethylsulfinyl-phenyl-CH(OMe)-CH(N3)-CH2F) | 546.1 (M + 2H)$^{2+}$ |
| 269 | M1 | (3-fluoropropylsulfonyl-phenyl-CH(OMe)-CH(N3)-CH2F) | 561.3 (M + 2H)$^{2+}$ |
| 270 | M1 | (3-fluoropropylsulfinyl-phenyl-CH(OMe)-CH(N3)-CH2F) | 553.1 (M + 2H)$^{2+}$ |

TABLE 2-continued

| Compound | Alkynyl Macrolide | Azide | LCMS |
|---|---|---|---|
| 271 | M1 | (structure) | 577.3 (M + 2H)$^{2+}$ |
| 272 | M1 | (structure) | 541.6 (M + 2H)$^{2+}$ |
| 273 | M1 | (structure) | 541.8 (M + 2H)$^{2+}$ |
| 274 | M1 | (structure) | 542.8 (M + 2H)$^{2+}$ |
| 275 | M1 | (structure) | 542.8 (M + 2H)$^{2+}$ |
| 276 | M1 | (structure) | 551.8 (M + 2H)$^{2+}$ |
| 277 | M1 | (structure) | 551.1 (M + 2H)$^{2+}$ |
| 278 | M1 | (structure) | 558.3 (M + 2H)$^{2+}$ |
| 279 | M1 | (structure) | 556.2 (M + 2H)$^{2+}$ |

TABLE 2-continued

| Compound | Alkynyl Macrolide | Azide | LCMS |
|---|---|---|---|
| 280 | M1 | [structure] | 564.3 (M + 2H)$^{2+}$ |
| 281 | M1 | [structure] | 540.6 (M + 2H)$^{2+}$ |

The alkynyl macrolide compounds that can be used in the synthesis of the compounds of the present invention are shown in the following Table 3. It is appreciated by one of skill in the art that these alkynyl macrolide compounds, M1 to M28, are non-limiting examples and that a wide variety of additional alkynyl macrolides can be used to prepare other compounds of the present invention.

TABLE 3

| Alkynyl Macrolide Compound | Structure |
|---|---|
| M1 | [structure] |
| M2 | [structure] |

TABLE 3-continued
| Alkynyl Macrolide Compound | Structure |
|---|---|
| M3 | 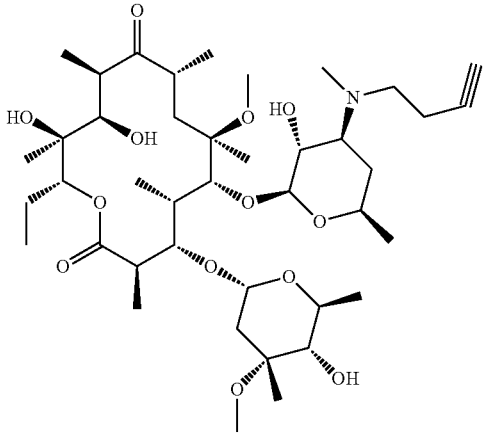 |
| M4 | 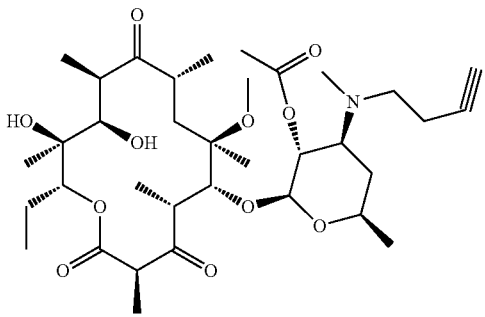 |
| M5 | 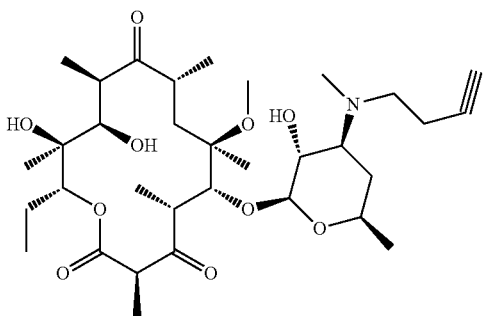 |
| M6 | 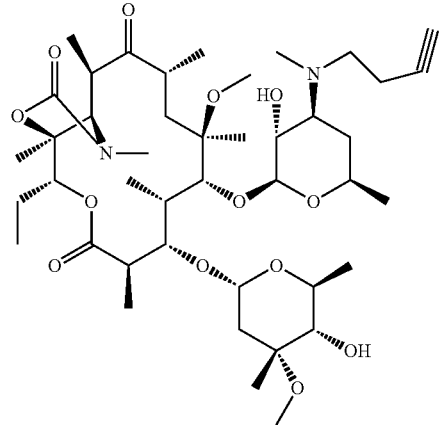 |

TABLE 3-continued

| Alkynyl Macrolide Compound | Structure |
| --- | --- |
| M7 | 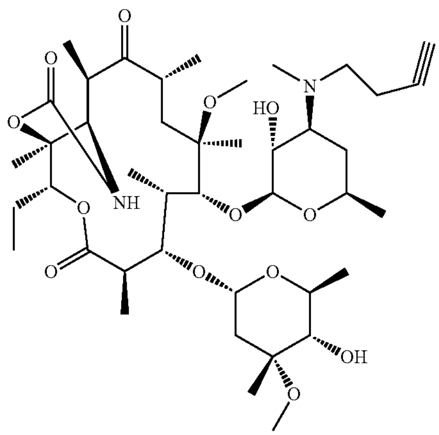 |
| M8 | 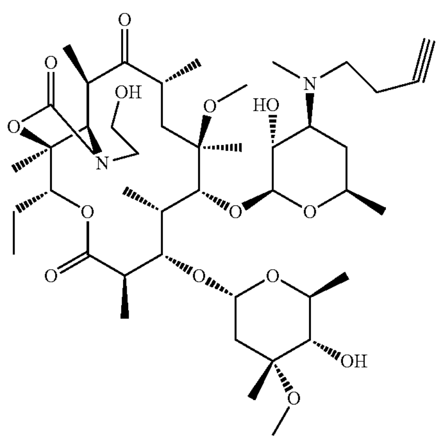 |
| M9 | 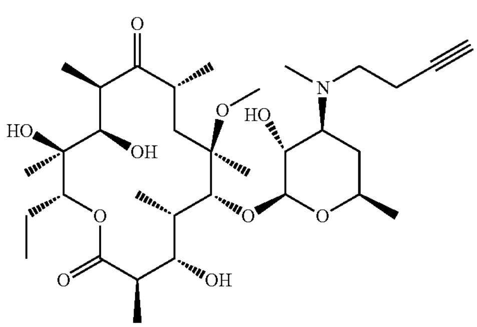 |
| M10 | 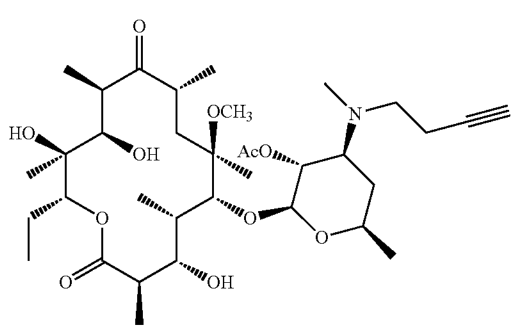 |

TABLE 3-continued
| Alkynyl Macrolide Compound | Structure |
|---|---|
| M11 | 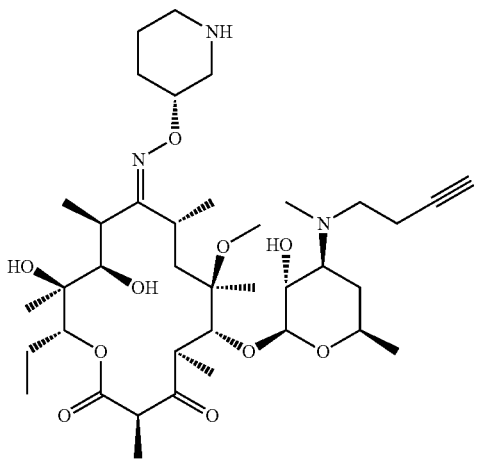 |
| M12 | 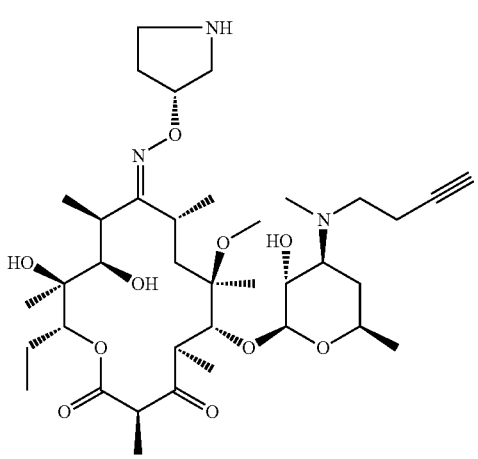 |
| M13 | 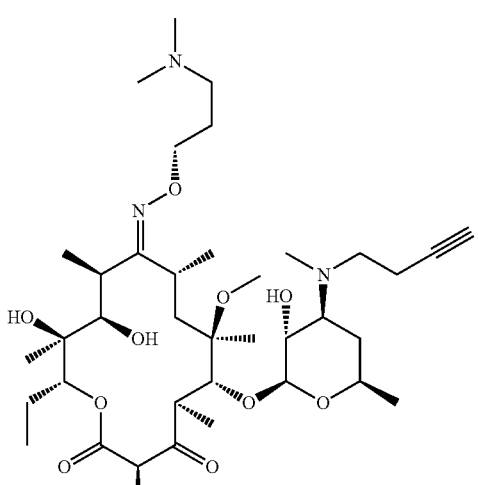 |

TABLE 3-continued

| Alkynyl Macrolide Compound | Structure |
|---|---|
| M14 | 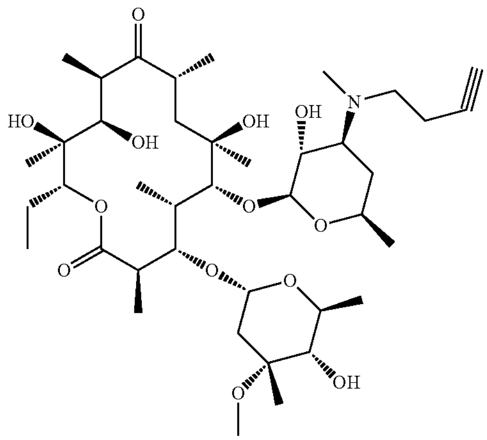 |
| M15 | 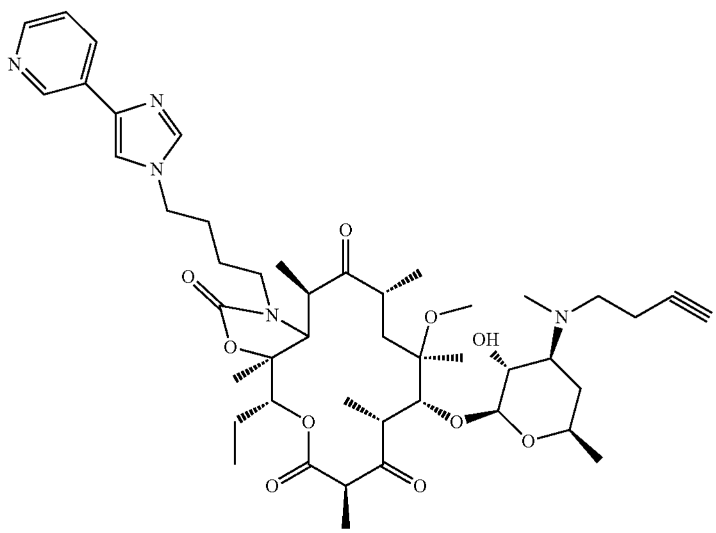 |
| M16 | 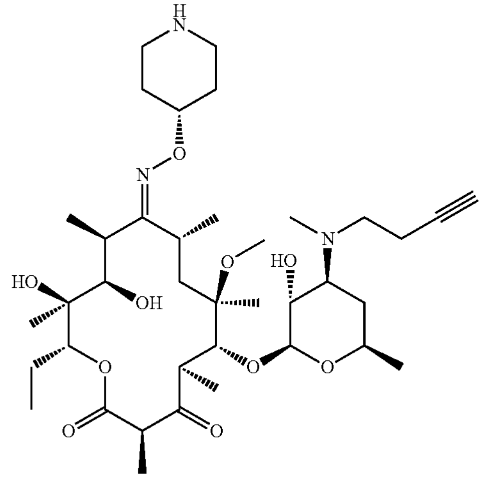 |

TABLE 3-continued
| Alkynyl Macrolide Compound | Structure |
|---|---|
| M17 | 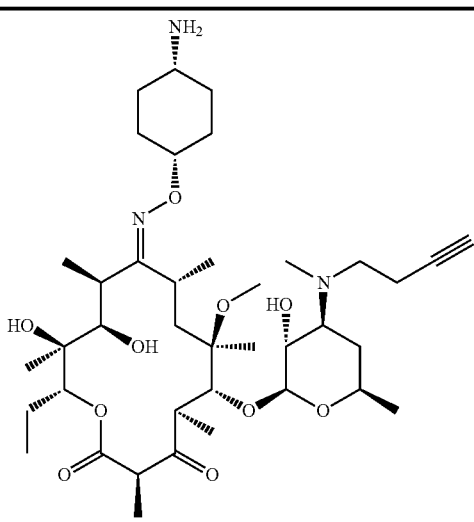 |
| M18 | 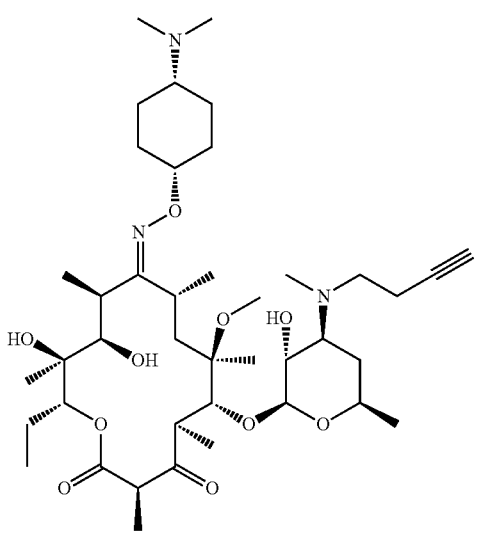 |
| M19 | 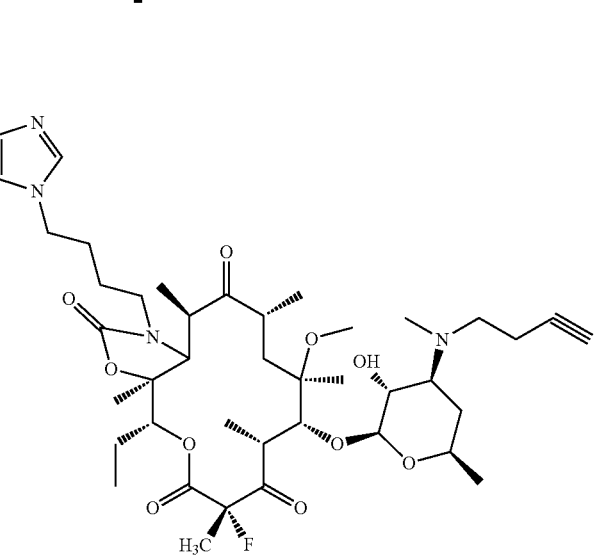 |

TABLE 3-continued

| Alkynyl Macrolide Compound | Structure |
| --- | --- |
| M20 | (structure) |
| M21 | (structure) |
| M22 | (structure) |

TABLE 3-continued
| Alkynyl Macrolide Compound | Structure |
|---|---|
| M23 | 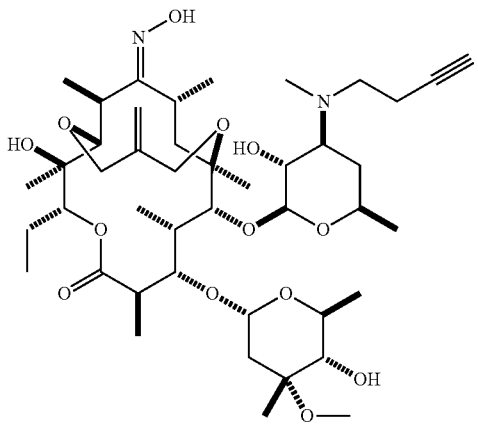 |
| M24 | 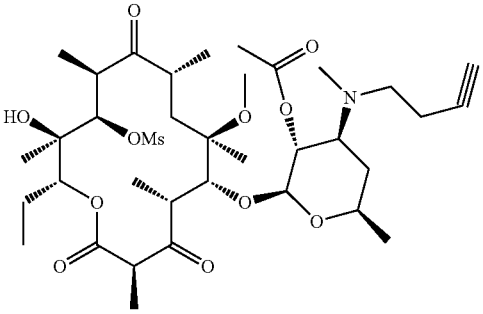 |
| M25 | 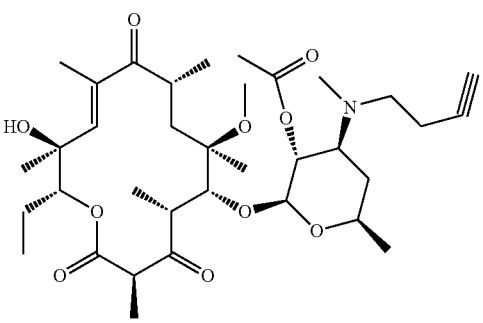 |
| M26 | 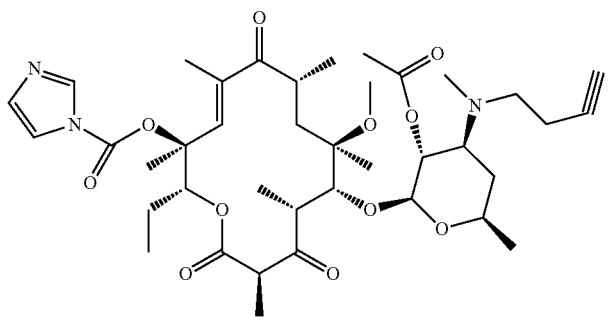 |

TABLE 3-continued

| Alkynyl Macrolide Compound | Structure |
|---|---|
| M27 | (structure shown) |
| M28 | (structure shown) |

Synthesis of Alkynyl Macrolides

The alkynyl macrolide compounds, such as alkynyl macrolide compounds M1 to M28, are generally made by the alkynylation (i.e. the addition of an alkynyl group) to a monomethyl amine macrolide compound. The monomethyl amine macrolide is generally made by the desmethylation of the corresponding macrolide compound. Depending on the macrolide compound and functional groups present, the desmethylation process can involve several steps, including various protection and deprotection steps. The desmethyl macrolide compound is alkynylated with the corresponding alkynyl compound, which is generally an alkynyl halide, tosylate, or mesylate. For the compounds of the present invention, 4-bromo-1-butyne, 4-iodo-1-butyne, or the tosylate or mesylate of 1-butyn-4-ol are generally used. Examples of synthetic procedures for preparing alkynyl macrolides are found in PCT Application No. WO 2005/085266, published Sep. 15, 2005, to Rib-X Pharmaceuticals, Inc. The following general reaction scheme outlines this alkynylation process.

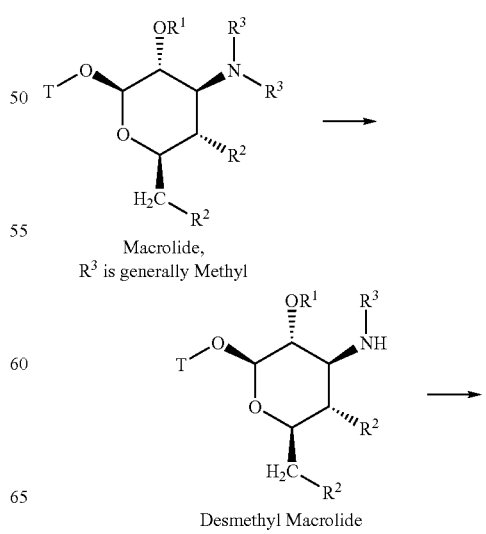

-continued

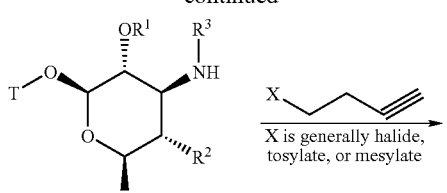

Desmethyl Macrolide

X is generally halide, tosylate, or mesylate

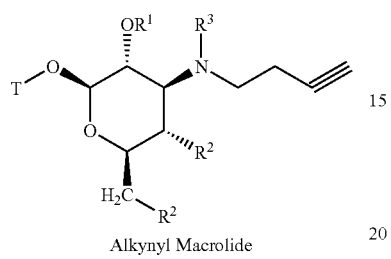

Alkynyl Macrolide

The following procedures outline the synthesis of various alkynyl macrolide compounds of the present invention.

Synthesis of Alkynyl Macrolide M1

Alkynyl macrolide M1 is made by selective demethylation of azithromycin 1 to produce 3'-N-desmethylazithromycin 2. This compound 2 is selectively alkylated with alkynyl tosylate 11 to produce alkynyl macrolide M1.

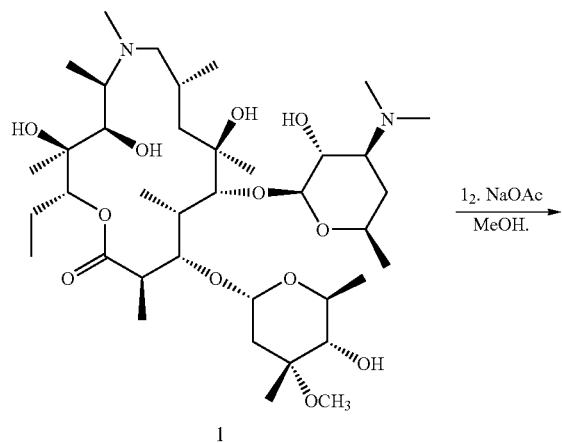

1

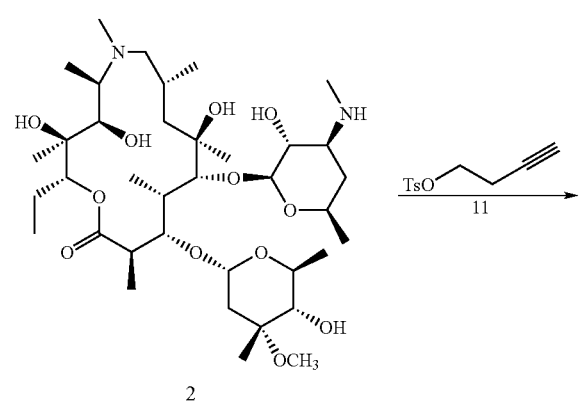

2

-continued

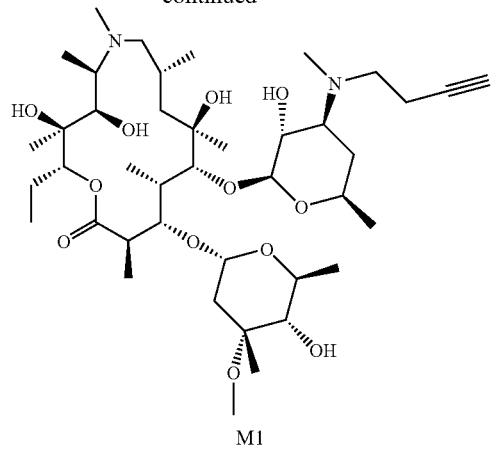

M1

Synthesis of 3'-N-desmethylazithromycin 2

Azithromycin 1 (0.80 g, 1.02 mmol) and sodium acetate (NaOAc) (0.712 g, 8.06 mmol) were dissolved in 80% aqueous MeOH (25 mL). The solution was heated to 50° C. followed by addition of iodine ($I_2$) (0.272 g, 1.07 mmol) in three batches within 3 minutes. The reaction was maintained at a pH between 8 and 9 by adding 1N sodium hydroxide (NaOH) (1 mL) at 10 min and 45 minute intervals. The solution turned colorless within 45 minutes. Stirring was continued for 2 hours. TLC($CH_2Cl_2$/MeOH/$NH_4OH$ 10:1:0.05) after 2 hours showed a single major product (Rf=0.66). The reaction was cooled to room temperature, poured into $H_2O$ (75 mL) containing $NH_4OH$ (1.5 mL) and extracted with $CHCl_3$ (3×30 mL). The combined organic layers were washed with $H_2O$ (30 mL) containing $NH_4OH$ (1.5 mL), dried over $Na_2SO_4$ and the solvent evaporated to give a white residue. The crude was purified on a silica gel column eluting with $CH_2Cl_2$/MeOH/$NH_4OH$ 18:1:0.05 to 10:1:0.05 to provide compound 2 (0.41 g, 55%).

Synthesis of Alkynyl Macrolide M1

A mixture of 3'-N-desmethylazithromycin 2 and tosylate 11 in Hunig's base was stirred. The reaction mixture was diluted to EtOAc and washed with $NaHCO_3$ (aq) and with brine. The organic layer was dried over $K_2CO_3$ and the solvent was evaporated to give product. The crude product was purified on silica gel column to give M1 as a white solid.

Synthesis of Alkynyl Macrolide M3.

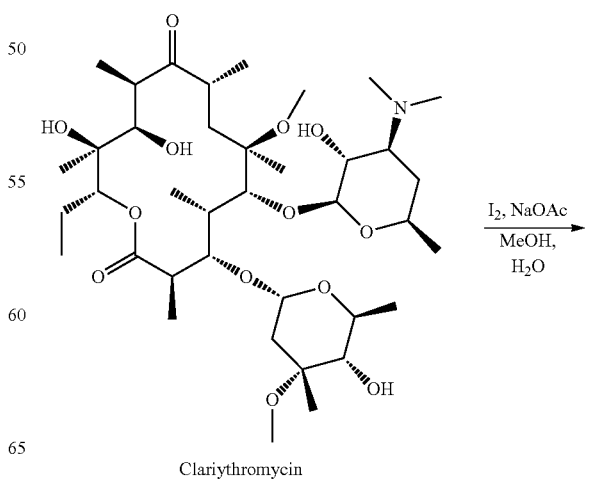

Clariythromycin

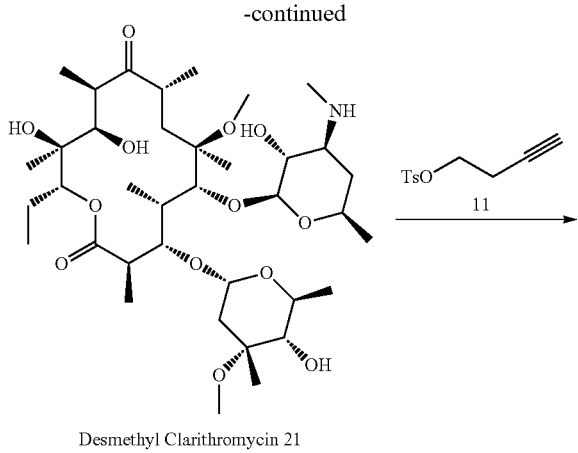

Desmethyl Clarithromycin 21

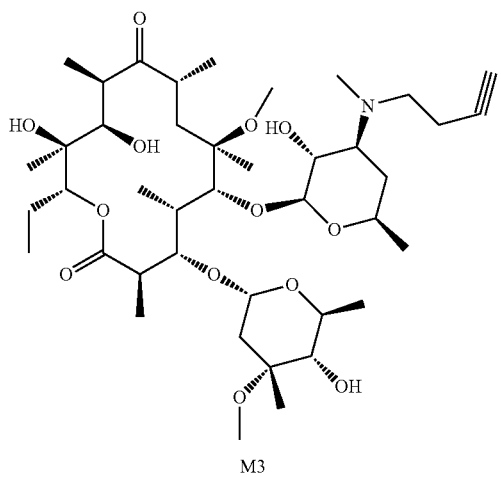

M3

Synthesis of 3'-N-desmethyl-clarithromycin 21

To a mixture of clarithromycin (1.00 g, 1.3 mmol) and NaOAc.3H₂O (0.885 g, 6.5 mmol) was added MeOH—H₂O (20 mL, 4:1), and the mixture heated to 55-60° C. Iodine (0.330 g, 1.3 mmol) was added portion-wise and the reaction stirred at 55-60° C. for 3 h. The reaction mixture was poured into 50 mL CHCl₃ containing 1 mL ammonium hydroxide. It was extracted with CHCl₃ (4×50 mL), washed with water (70 mL) containing 5 mL ammonium hydroxide, dried (anhydrous Na₂SO₄), concentrated, and purified by flash chromatography (silica gel, CHCl₃:MeOH:NH₄OH 100:10:0.1) to afford 21. Yield: 0.9 g (92%).

Synthesis of Alkynyl Macrolide M3

A mixture of 3'-N-desmethyl-clarithromycin 21 and tosylate 11 in anhydrous THF and Hunig's base was stirred. The reaction was poured into CH₂Cl₂, extracted with 2% aqueous NH₄OH and saturated brine. The organic layer was dried over Na₂SO₄ and the solvent was evaporated away. The crude was purified on a silica gel column to give M3.

Synthesis of Alkynyl Macrolide M14

Alkynyl macrolide M14 is made using a procedure analogous to that for making M3, starting from erythromycin A. The 3'-N-desmethyl-erythromycin A intermediate is made using a procedure described in U.S. Pat. No. 3,725,385, to Freiberg, issued Apr. 3, 1973. Alkynyl macrolide M14 can further be used to prepare a variety of macrolides analogous to those already depicted for the clarithromycin core.

A mixture of 3'-N-desmethyl-erythromycin (1.0 g, 1.4 mmol) and the tosylate of 1-butyn-4-ol (1.25 g, 5.6 mmol) in anhydrous THF (15 mL) and Hunig's base (2.2 mL, 11.9 mmol) was kept stirring at 55° C. for 48 hours. The reaction was poured into CH₂Cl₂ (50 mL), extracted with 2% aqueous NH₄OH (3×30 mL) and saturated brine (1×30 mL). The organic layer was dried over Na₂SO₄ and the solvent was evaporated away. The crude was purified on a silica gel column eluting with CH₂Cl₂/MeOH 10:1 to give alkynyl macrolide 14 (0.35 g, 32%).

Synthesis of Alkynyl Macrolides M4, M9, M10, M11 and M12

The synthesis of alkynyl macrolides M4, M9, M10, M11 and M12 are depicted in the scheme below. Alkynyl macrolide M9 is prepared from the removal of the cladinose sugar of alkynyl macrolide M3 under acidic conditions. Alkynyl macrolide M10 is made by the acetylation of macrolide M9. Macrolide M4 is made by the oxidation of the hydroxyl group of macrolide M10. Alkynyl macrolides M11 and M12 are made by converting a keto group of alkynyl macrolide M4 to the desired oximes. The oxime functionality of alkynyl macrolides of precursors with substituted oxime functionality at the 9-position of the macrocyclic ring were prepared from alkyne M3 and as shown below.

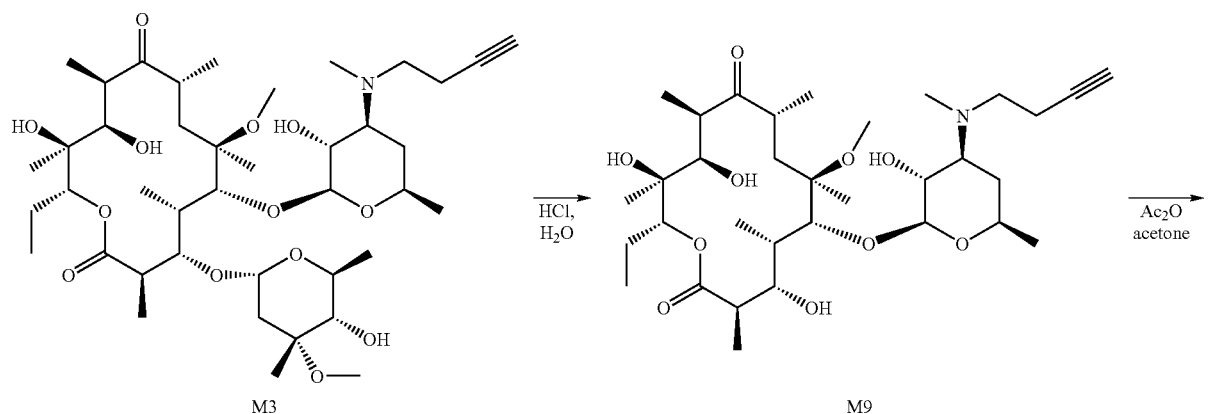

-continued
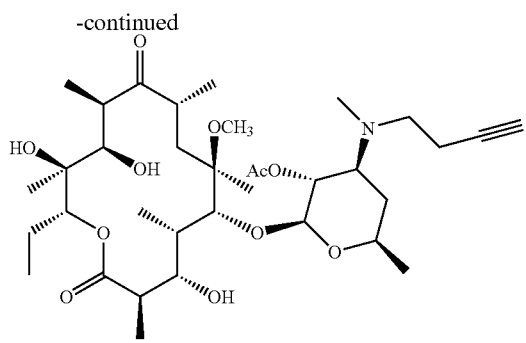
M10
↓ EDC
DMSO
pyrH+CF₃CO₂-
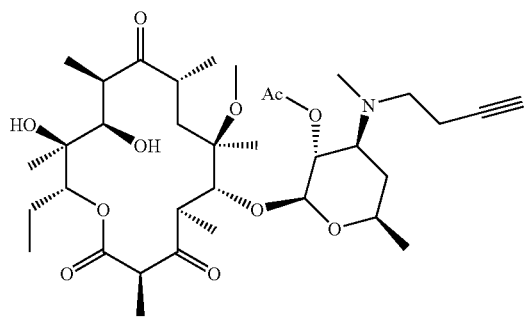
M4
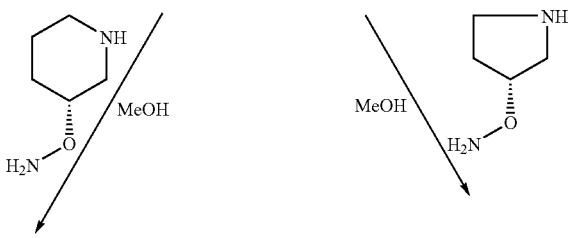
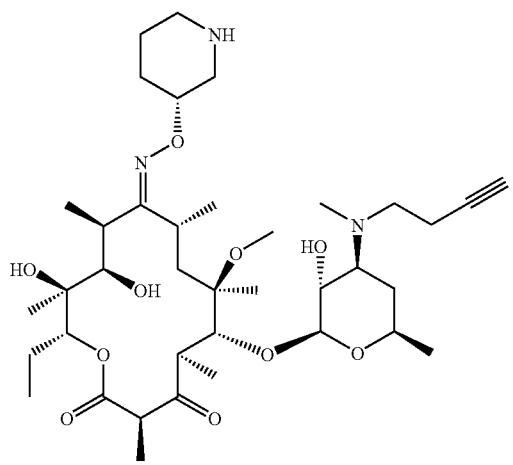
M11
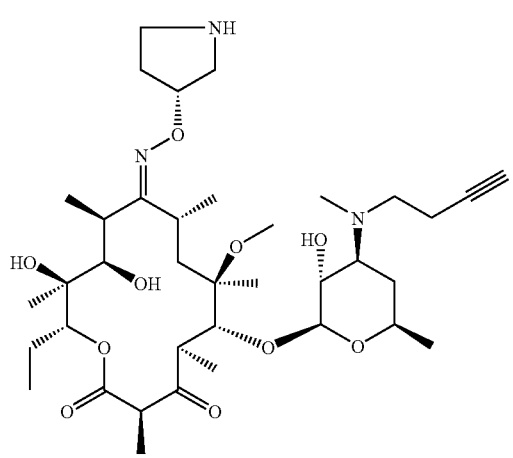
M12

Synthesis of Alkynyl Macrolide M9

To the alkynyl macrolide M3 (0.700 g) was added 10 mL 0.9N HCl and the mixture was stirred for 4 h at room temperature. The reaction mixture was saturated with sodium chloride and was adjusted to pH 8 using aqueous $NH_4OH$ solution. The solution was extracted with ethyl acetate (3×30 mL), dried (with $Na_2SO_4$), and concentrated under reduced pressure. Purification of the crude reaction mixture by flash chromatography (silica gel, 60% ethyl acetate in hexane) afforded 0.200 g (35% yield) of the descladinose alkynyl macrolide M9. Data for M9: $^1$HNMR (300 MHz, $CDCl_3$, partial): δ 0.82 (t, 3H), 2.25 (s, 3H), 3.00 (s, 3H), 3.25 (dd, 1H), 3.55 (m, 2H), 3.70 (s, 1H), 3.85 (s, 1H), 3.95 (s, 1H), 4.40 (d, 1H), 5.15 (dd, 1H).

Synthesis of Alkynyl Macrolide M5

A solution of alkynyl macrolide M4 (1 g, 1.5 mmol) in MeOH (30 mL) was refluxed for 12 h. The solution was concentrated and the crude material was purified by flash chromatography over silica gel (50% ethyl acetate in hexane). Yield: 0.5 g of MS (53%).

Synthesis of Alkynyl Macrolide M10

To a solution of alkynyl macrolide M9 (0.200 g, 0.32 mmol) in acetone (2 mL) was added acetic anhydride (0.050 mL, 0.5 mmol) and the mixture was stirred overnight at room temperature. The reaction was quenched with water and extracted with ethyl acetate (3×50 mL). The combined organic fractions were washed with saturated sodium bicarbonate (3×50 mL), dried (anhydrous $Na_2SO_4$), and concentrated under reduced pressure. The crude reaction mixture was purified by flash chromatography (silica gel, 50% ethyl acetate in hexane) to yield 0.100 g (50% yield) of acetate functionalized alkynyl macrolide M10. Data for M10: $^1$HNMR (300 MHz, $CDCl_3$, partial): δ 0.84 (t, 3H), 2.00 (s, 3H), 2.20 (s, 3H), 2.90 (s, 3H), 3.00 (q, 1H), 3.25 (s, 1H, 3.47 (m, 2H), 3.70 (bs, 1H), 3.82 (bs, 1H), 3.97 (s, 1H), 4.60 (d, 1H), 4.77 (dd, 1H), 5.15 (dd, 1H).

Synthesis of Alkynyl Macrolide M4

To a solution of alkynyl macrolide M10 (0.090 g, 0.134 mmol), EDC.HCl (0.172 g, 0.90 mmol), and DMSO (0.171 mL, 2.41 mmol) in $CH_2Cl_2$ (1.5 mL) was added dropwise a solution of pyridinium trifluoroacetate (0.174 g, 0.90 mmol) in $CH_2Cl_2$ (1 mL) at 15° C. The reaction mixture was slowly warmed up to room temperature and stirred for 3 h. The reaction was quenched with water (2 mL), and allowed to stir for 30 min. The mixture was then poured into $CHCl_3$ (50 mL), and the organic layer was washed with water (2×50 mL), dried (over anhydrous $Na_2SO_4$), and concentrated under reduced pressure. The crude material was purified by flash chromatography (silica gel, 30% ethyl acetate in hexane) to yield 0.070 g (78%) of the alkynyl macrolide M4 (also commonly referred to as a ketolide). Data for M4:M4 MS (ESI) m/e 668 (M+H)$^+$; $^1$HNMR (300 MHz, $CDCl_3$, partial): δ 0.86 (t, 3H), 2.00 (s, 3H), 2.24 (s, 3H), 2.70 (s, 3H), 2.95-3.10 (m, 1H), 3.15-3.05 (m, 1H), 3.45-3.65 (m, 1H), 3.80 (q, 1H), 3.90 (s, 1H), 4.28 (d, 1H), 4.40 (d, 1H), 4.76 (dd, 1H), 5.10 (dd, 1H).

Synthesis of Alkynyl Macrolide M11

To a solution of M4 (2.0 g, 2.9 mmol) in MeOH (10 mL) was added (R)—N-Piperidin-3-yl-hydroxylamine hydrobromide (1.26 g, 4.4 mmol). The reaction mixture was stirred at rt for 14 h. The mixture was then poured into (50 mL) and water (50 mL) the pH was adjusted to 11 by addition of $NH_4OH$ and the organic layer was separated and washed with brine (50 mL), dried (over anhydrous $Na_2SO_4$), and concentrated under reduced pressure. The crude material was purified by flash chromatography (silica gel, 12:1 $CH_2Cl_2$ and 2M methanolic ammonia) to yield 2 g (78%) of the oxime functionalized alkynyl macrolide M11 as a 1:1 mixture of E/Z isomers. Data for M11: MS (ESI) m/e 724.7 (M+H)$^+$.

Synthesis of Alkynyl Macrolide M12

Alkynyl macrolide M12 was synthesized from alkynyl macrolide M4 and (R)—N-Pyrollidin-3-yl-hydroxylamine hydrobromide using the conditions described above for the synthesis of alkynyl macrolide M11. Data for M12: MS (ESI) m/e 710.6 (M+H)$^+$.

Synthesis of Alkynyl Macrolides M13, M16, M17, and M18

Alkynyl macrolides M13, M16, and M17 are also synthesized from alkynyl macrolide M4. Alkynyl macrolide M18 is synthesized from alkynyl macrolide M17. The syntheses are outlined in the following reaction scheme.

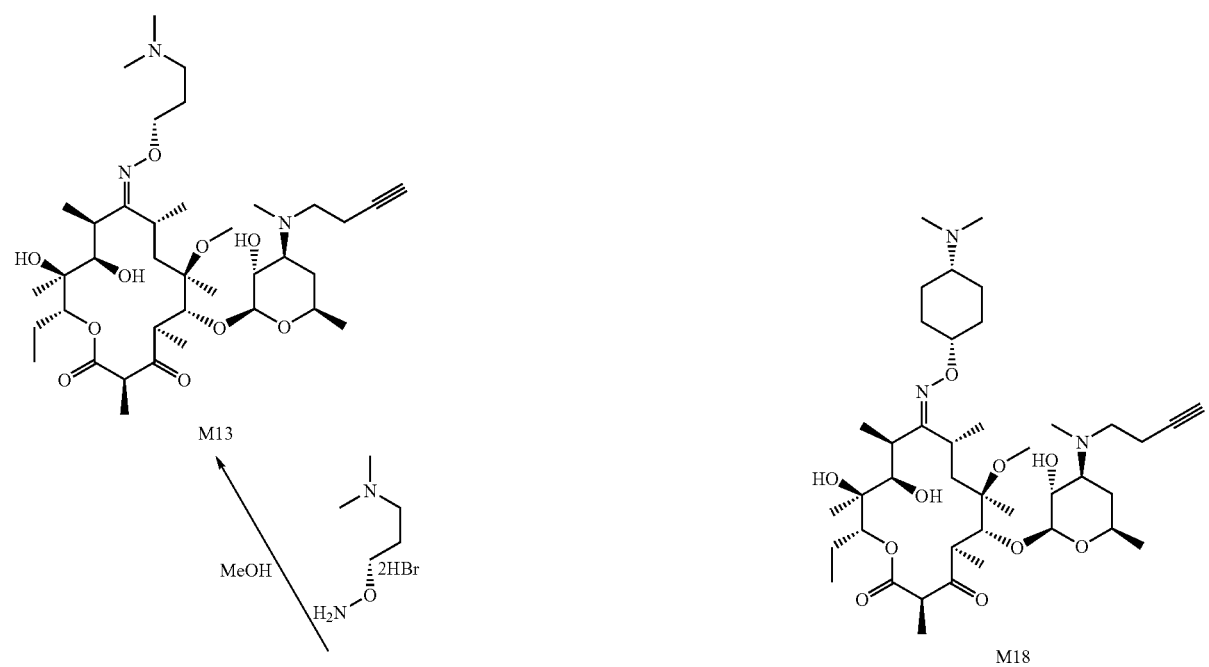

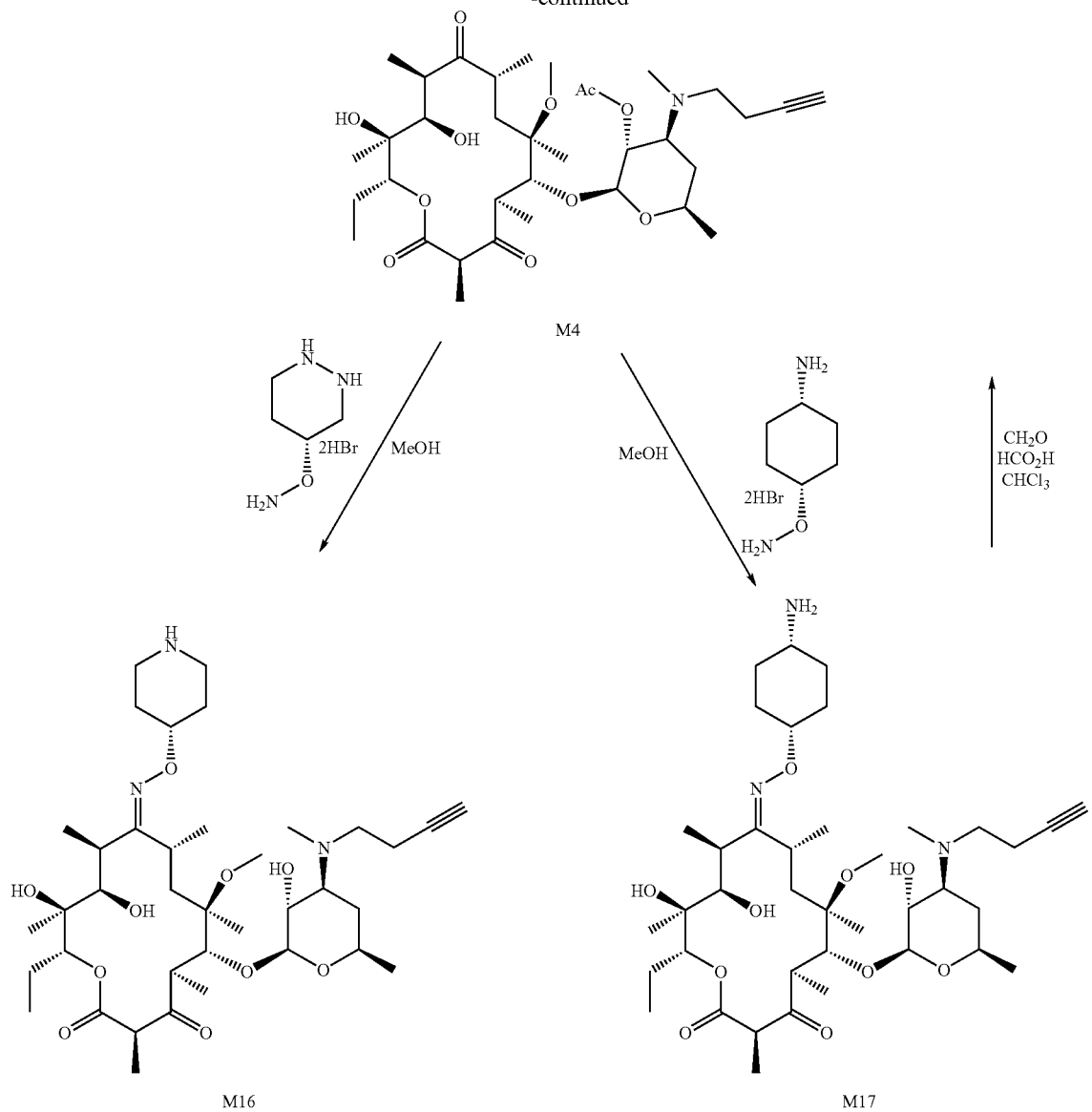

Synthesis of Alkynyl Macrolide M13

Alkynyl macrolide M13 was synthesized from alkynyl macrolide M4 and N-[2-dimethylaminoethyl]-hydroxylamine hydrobromide using the conditions described above for the synthesis of oxime M11. Data for M13: MS (ESI) m/e 726.5 (M+H)$^+$.

Synthesis of Alkynyl Macrolide M16

Alkynyl macrolide M16 was synthesized from alkyne M4 and N-Piperidin-4-yl-hydroxylamine hydrobromide using the conditions described above for the synthesis of oxime M11. Data for M16: MS (ESI) m/e 724.6 (M+H)$^+$.

Synthesis of Alkynyl Macrolide M17

Alkynyl macrolide M17 was synthesized from alkyne M4 and cis-4-aminocyclohexyl-hydroxylamine hydrobromide using the conditions described above for the synthesis of oxime M11. Data for M17: MS (ESI) m/e 738.7 (M+H)$^+$.

Synthesis of Alkynyl Macrolide M18

To a solution of alkynyl macrolide M17 (20 mg, 0.02 mmol) in CHCl$_3$ (0.2 mL) was added formaldehyde (5 mg of 37% aqueous solution, 0.06 mmol) and formic acid (6 mg, 0.12 mmol). The mixture was heated at 50° C. in a sealed tube for 12 h. The reaction mixture was partitioned between aqueous NaHCO$_3$ (10 mL) and chloroform (10 mL) the organic fraction was dried on K$_2$CO$_3$, filtered and concentrated to give alkynyl macrolide M18 as a white solid (18 mg). Data for M18: MS (ESI) m/e 766.7 (M+H)$^+$.

Synthesis of Alkynyl Macrolide M15

Telithromycin was selectively N-demethylated and then alkylated with the tosylate of 1-butyn-4-ol as described for azithromycin, erythromycin and clarithromycin above.

Synthesis of 3'-N-Desmethyl telithromycin 30

To a solution of telithromycin 29 (3.0 g, 3.60 mmol) in anhydrous acetonitrile (70 mL) was added N-iodosuccinimide (NIS) (0.98 g, 4.32 mmol) in two portions within 30 min at 0° C. under argon atmosphere. The mixture was allowed to warm to rt and stirred overnight. CH$_2$Cl$_2$ (250 mL) and 5% Na$_2$S$_2$O$_3$ (80 mL) were added and the two layers separated. The organic layer was extracted with 5% Na$_2$S$_2$O$_3$ (1×80 mL), dilute NH$_4$Cl (1×80 mL) and dried over Na$_2$SO$_4$. Solvent was evaporated and the crude was purified on silica gel eluting with 0-8% methanolic ammonia (2N NH$_3$) in CH$_2$Cl$_2$ to give compound 30 as white solid (1.95 g, 68%). MS (ESI) M/E; M+H$^+$ 798.6.

Scheme 105 Synthesis of Alkynyl Macrolide M15.
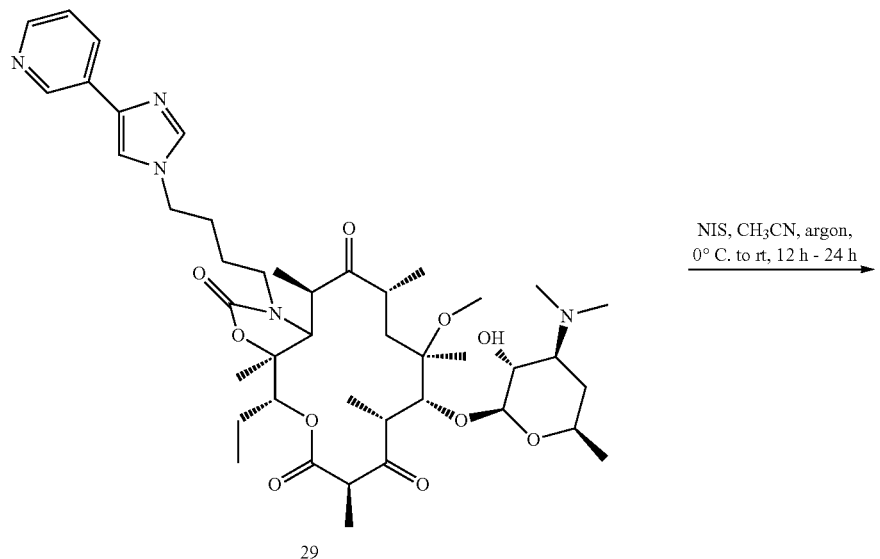
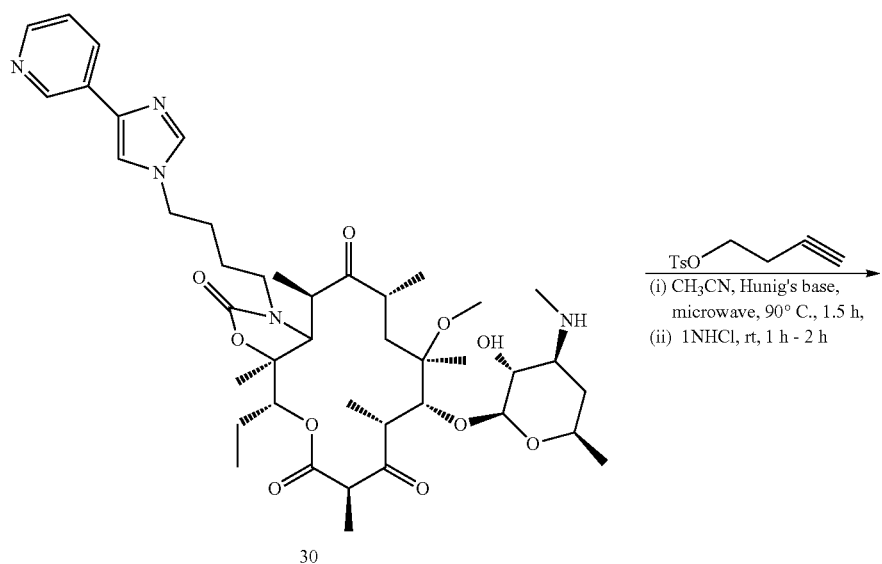
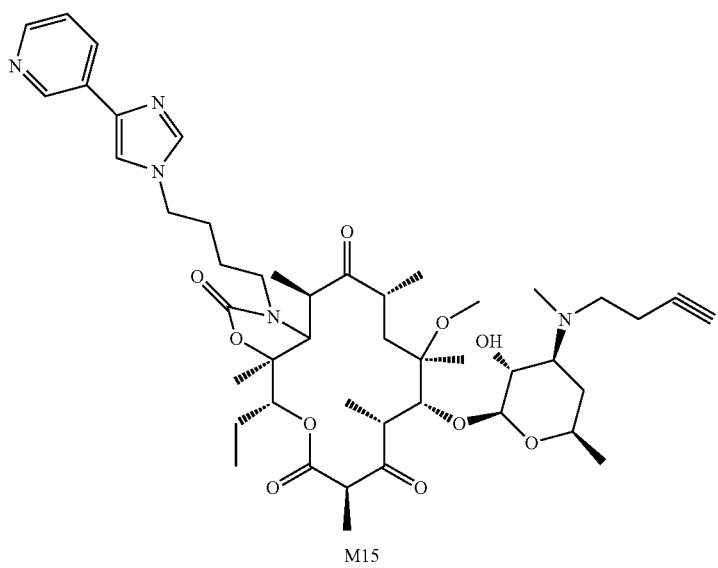

Synthesis of 3'-N-(but-3-ynyl) telithromycin, M15
Protocol A: A mixture of amine 30 (0.66 g, 0.83 mmol) and tosylate 11 (0.33 g, 1.49 mmol) in THF (15 mL) and Hunig's base (3 mL) was heated at 90° C. for 5 days. The solvent was evaporated; the residue was dissolved in 1N HCl (50 mL) and kept stirring at room temperature for about 1 h. CH$_2$Cl$_2$ (30 mL) was added and the two layers were separated. The aqueous layer was extracted with CH$_2$Cl$_2$ (2×30 mL) and basified with NaOH (1N) to form a whitish-suspension. The suspension was extracted with CH$_2$Cl$_2$ (3×30 mL) and the organic layer was dried over Na$_2$SO$_4$. Solvent was evaporated and the crude was purified on silica gel eluting with 0-6% methanolic ammonia (2N NH$_3$) in CH$_2$Cl$_2$ to give compound M15 as white solid (0.12 g, 17%). MS (ESI) m/e 850.8 (M+H)$^+$.
Synthesis of 3'-N-(but-3-ynyl) telithromycin, M15

Protocol B: A mixture of amine 30 (0.66 g, 0.83 mmol), and tosylate 11 (0.40 g, 1.84 mmol) in acetonitrile (10 mL) and Hunig's base (0.18 mL, 1.0 mmol) was microwave heated to 90° C. within 10 min and maintained at 90° C. for 1.5 h. The reaction was vented within 15 min and solvent was evaporated. The residue was dissolved in 1N HCl (60 mL) and kept stirring at room temperature for about 2 h. CH$_2$Cl$_2$ (30 mL) was added and the two layers were separated. The aqueous layer was extracted with CH$_2$Cl$_2$ (2×30 mL) and basified with 50% KOH to form a whitish-suspension. The suspension was extracted with CH$_2$Cl$_2$ (3×30 mL) and the organic layer was dried over Na$_2$SO$_4$. The solvent was evaporated and the crude was purified by preparative TLC (2000 micron plate) eluting with CH$_2$Cl$_2$/methanolic ammonia (2N NH$_3$) 12:1 to give compound M15 as white solid (0.19 g, 27%). MS (ESI) m/e 850.8 (M+H)$^+$.

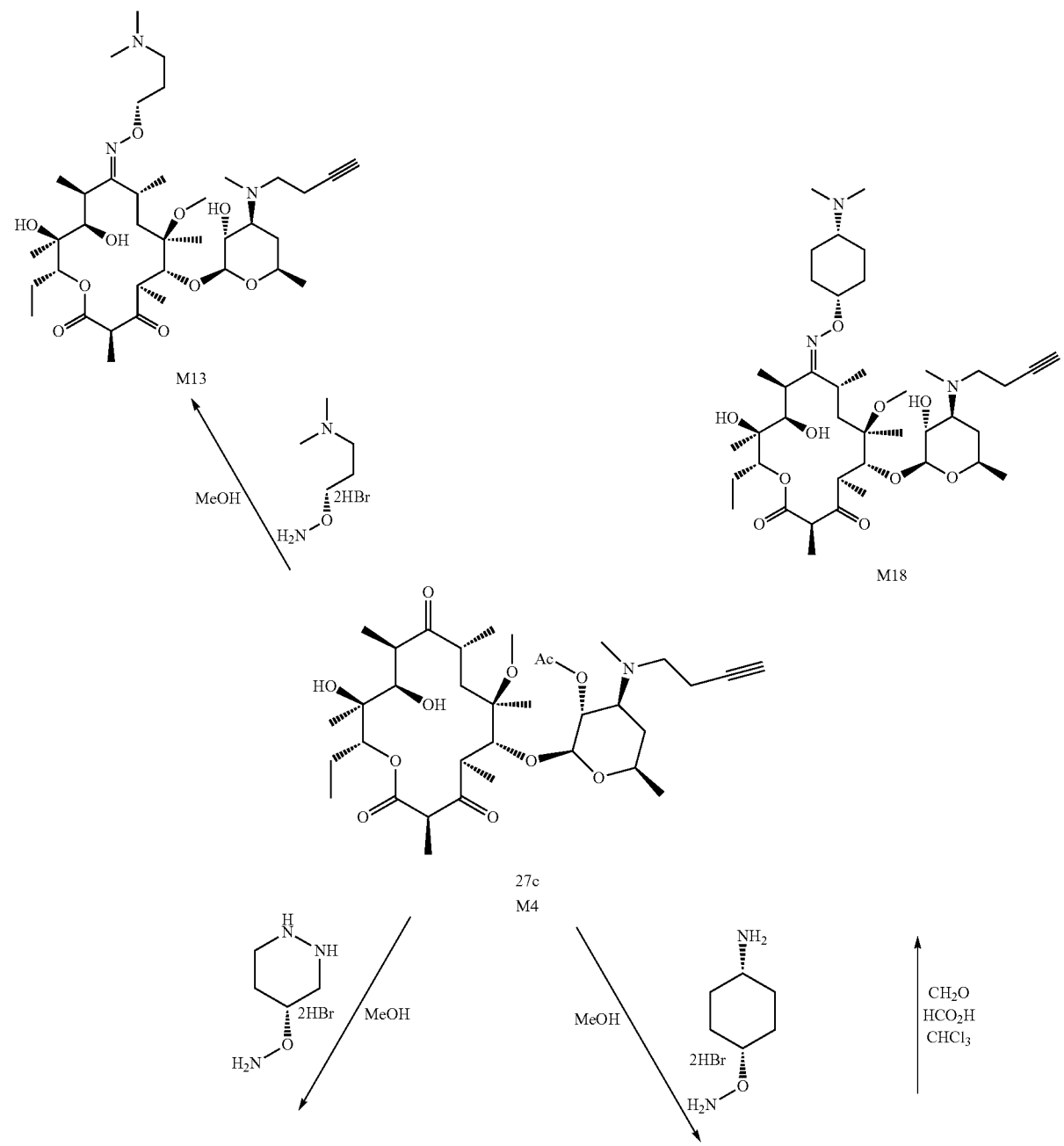

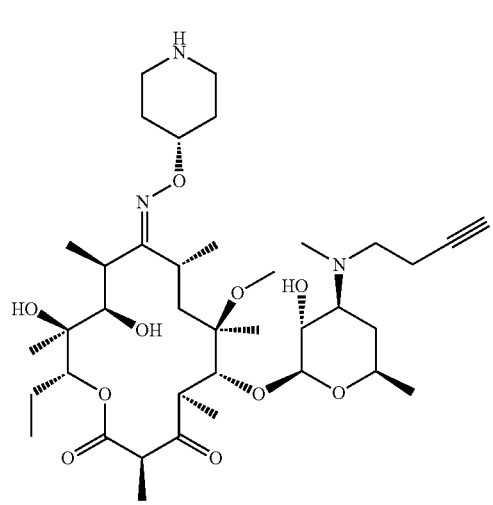
M16
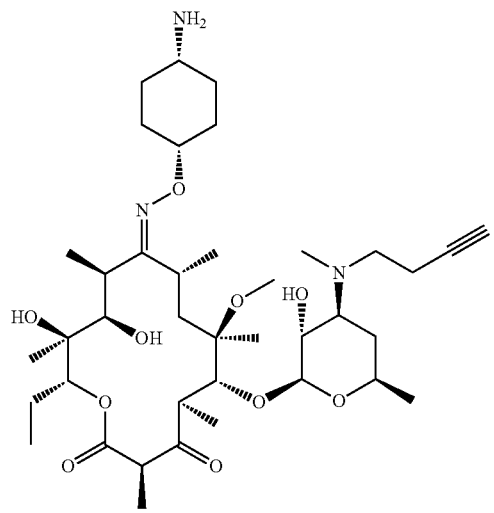
M17
Synthesis of Alkynyl Macrolide M19.
Desmethyl telithromycin 30 was treated according to the procedures of U.S. Pat. No. 6,124,269 to afford the 2-fluoro amine 30a. This was then alkylated with the tosylate of 1-butyn-4-ol under the conditions for making M15 to afford the fluorinated alkynyl macrolide M19. The reactions are outlined in the following scheme.
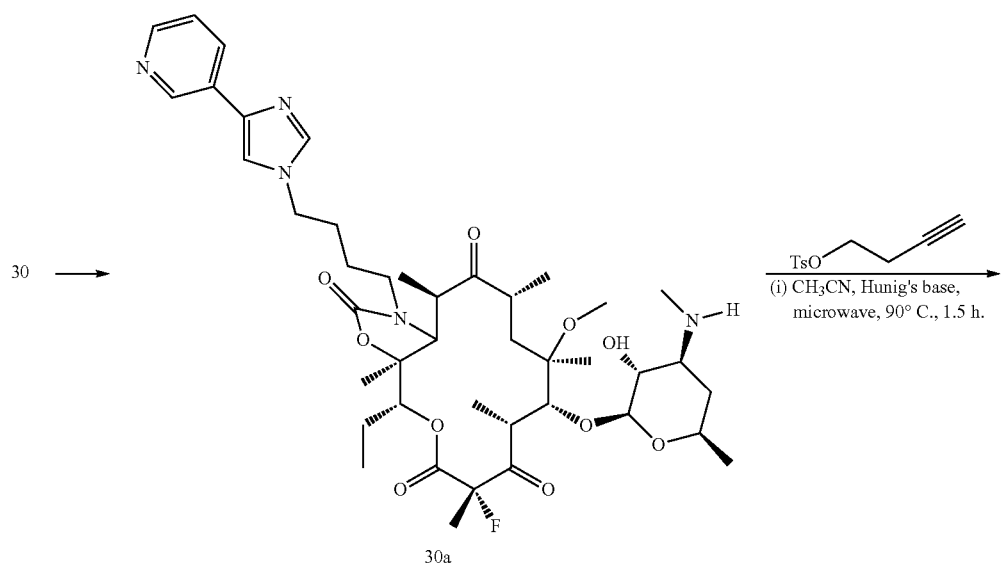

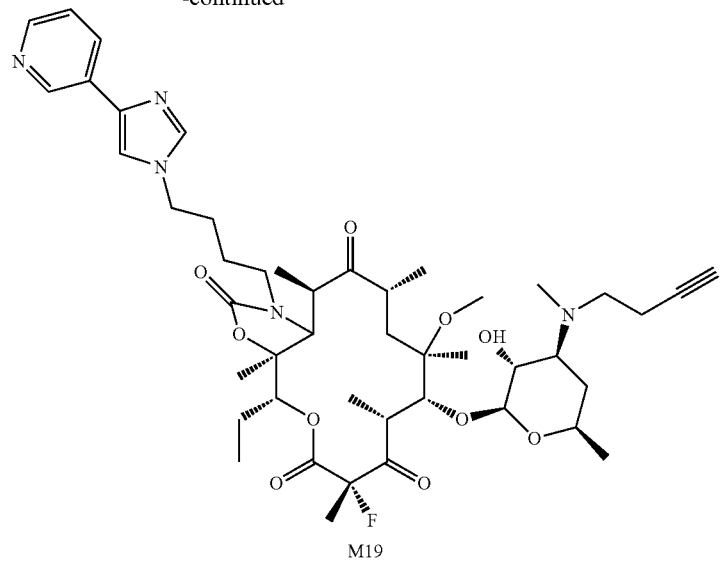
M19
Synthesis of Alkynyl Macrolides M20, M21, M22, and M23
Alkynyl macrolides M21, M22, and M23 are prepared according to the following reaction scheme from alkynyl macrolide M20. Alkynyl macrolide M20 is in turn made from alkynyl macrolide M14.
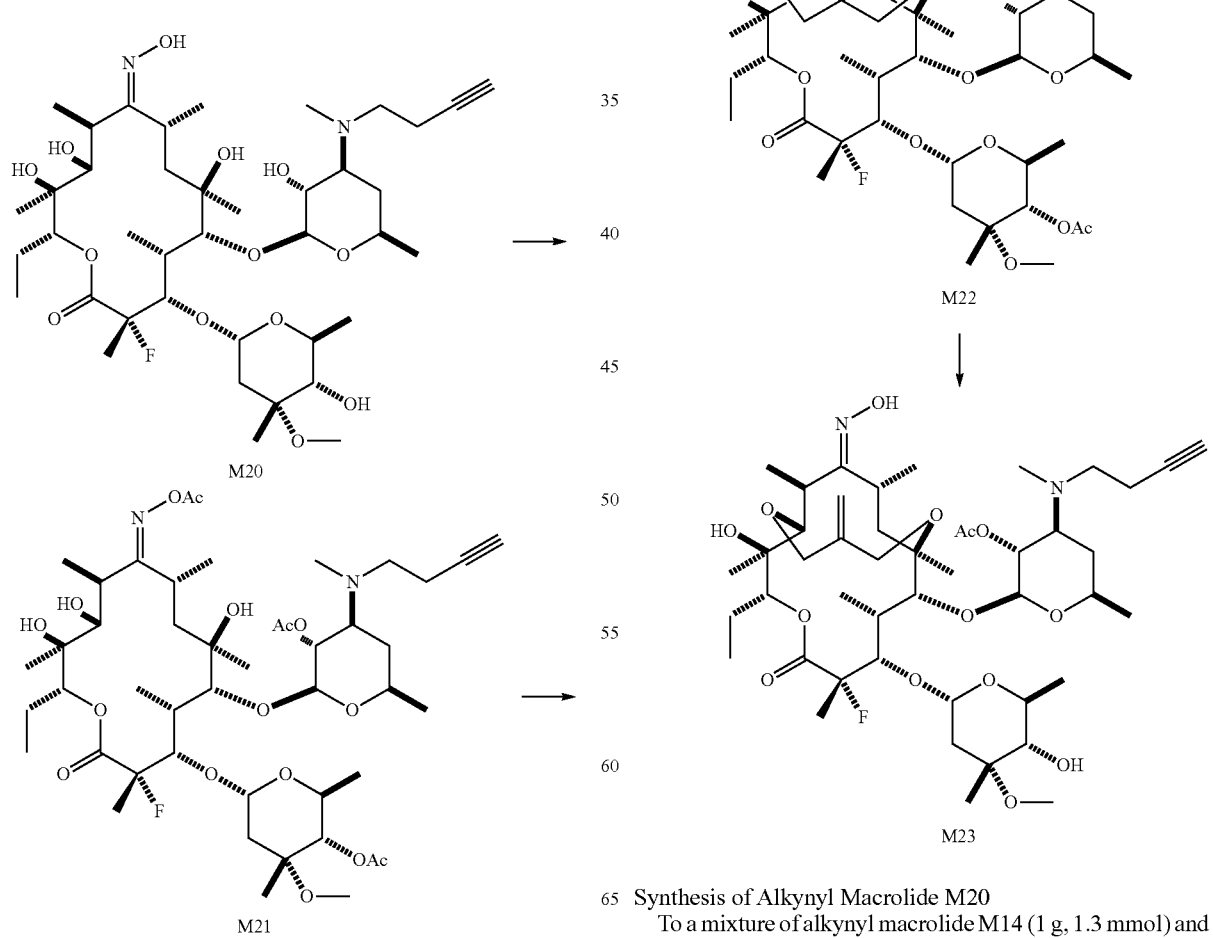
Synthesis of Alkynyl Macrolide M20
To a mixture of alkynyl macrolide M14 (1 g, 1.3 mmol) and hydroxylamine hydrochloride (0.4 g, 6.4 mmol) was added methanol (15 mL) and triethylamine (3.2 mmol). The solution was refluxed for 72 h Cooled to ambient temperature, poured into water (50 mL) and adjusted pH to 11. The resulting solution was extracted with dichloromethane (4×50 mL), dried and concentrated. The crude material was purified by flash chromatography over silica gel to yield M20 ($C_2Cl_2$:2N $NH_3$-MeOH=10:1). Yield: 0.6 g (60%).

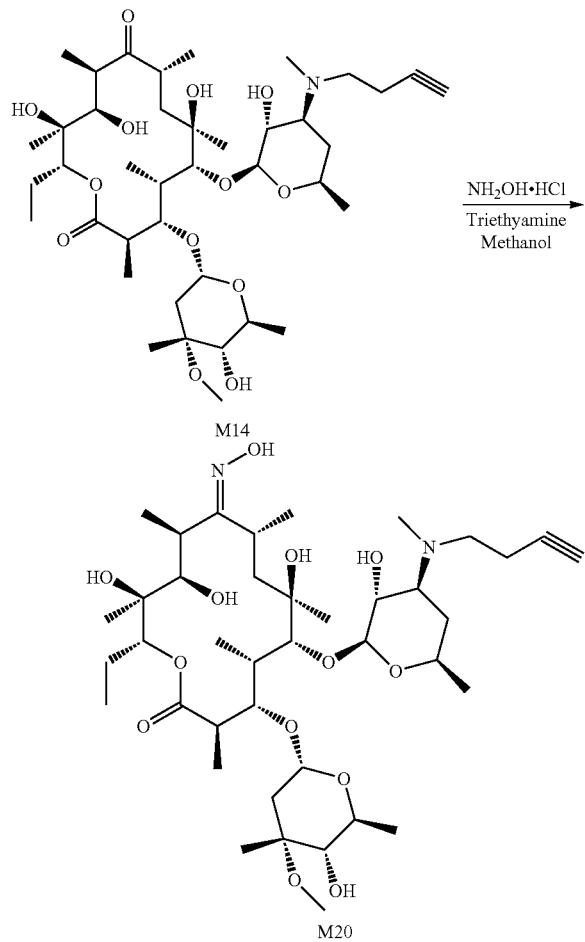

Synthesis of Alkynyl Macrolide M21

To a solution of alkynyl macrolide M20 (2.00 g, 2.54 mmol) in THF (17 mL) at 0° C. was added $Et_3N$ (1.50 mL, 10.67 mmol), followed by addition of acetic anhydride (946 L, 9.91 mmol), then, DMAP (34 mg, 0.25 mmol). The mixture was stirred at 0° C. for 3 h, then, $Et_3N$ (150 μL, 1.07 mmol) and acetic anhydride (95 μL, 0.99 mmol) were added. The mixture was stirred for 3 h, then, MeOH (2.0 ml) was added. The reaction mixture was concentrated and EtOAc (100 mL) was added, washed with saturated $NaHCO_3$ (30.0 mL), then, brine (30.0 mL), dried with $Na_2SO_4$, gave 2.28 g of alkynyl macrolide M21. The residue was used for the next step without further purification. MS (ESI) m/e 913 $(M+H)^+$.

Synthesis of Alkynyl Macrolide M22

To a solution of triacetate alkynyl M21 (913 mg, 1.00 mmol, crude), 2-methylene-1,3-propane-[bis-(tert-butyl)carbonate] (865 mg, 3.00 mmol) and 1,4-bis(diphenylphosphino)-butane (dppb) (305 mg, 0.70 mmol) in THF (10 mL, degassed) was added $Pd_2(dba)_3$ (92 mg, 0.10 mmol) at room temperature. The mixture was refluxed for 12 h, then, the reaction mixture was concentrated and EtOAc (100 mL) was added. Washed with saturated $NaHCO_3$ (30 mL), brine (30 mL), dried with $Na_2SO_4$. The residue was isolated by silica gel chromatography ($CH_2Cl_2$ to 2% MeOH in $CH_2Cl_2$ containing 0.2% $NH_4OH$), gave 340 mg of alkynyl macrolide M22 in 35% yield for two steps. MS (ESI) m/e 966 $(M+H)^+$.

Synthesis of Alkynyl Macrolide M23

Alkynyl macrolide M22 (330 mg, 0.34 mmol) in MeOH (6 mL), was refluxed for 5 days. The residue was isolated by FC($CH_2Cl_2$ to 2% MeOH in $CH_2Cl_2$ containing 0.2% $NH_4OH$), gave 143 mg of alkynyl macrolide M23 in 50% yield.

MS (ESI) m/e 839 $(M+H)^+$.

Synthesis of Alkynyl Macrolide M24

To a solution of alkynyl macrolide M4 (6.4 g, 9.6 mmol) in pyridine (25 mL) was added methanesulfonic anhydride (4.0 g, 22.9 mmol) at 10° C. The reaction was stirred at ambient temperature for 24 h. The solution was concentrated and portioned between ethyl acetate (150 mL) and saturated $NaHCO_3$ solution (150 mL). Organic layer was separated and the aqueous layer was back extracted with ethyl acetate (2×100 mL). The combined organic layer was washed with brine (2×150 mL), dried and concentrated. The crude material was purified by flash chromatography over silica gel (50% ethyl acetate in hexane) to give 5.9 g of M24 (83%).

Synthesis of Alkynyl Macrolide M25

To a solution of alkynyl macrolide M24 (5.9 g, 7.9 mmol) in acetone (25 mL) was added diazabicycloundecene (DBU) (1.4 mL, 9.5 mmol) at ambient temperature. After stirring for 48 h, the reaction was diluted with methylene chloride, washed with water, dried and concentrated in vacuo. The crude material was purified by flash chromatography over silica gel (40% ethyl acetate in hexanes). Yield 3.6 g M25 (70%).

Synthesis of Alkynyl Macrolide M26

To a solution of M25 (3.3 g, 5.0 mmol) in methylene chloride (30 mL) was added DBU (1.0 mL, 6.5 mmol) at 0° C. Then was added carbonyldiimidazole (1.0 g, 6.1 mmol) at once. After stirring for 3 h, the reaction was diluted with methylene chloride, washed with water, dried and concentrated in vacuo. The crude material was purified by flash chromatography over silica gel (70% ethyl acetate in hexanes). Yield 3.4 g M26 (89%).

Synthesis of Alkynyl Macrolide M27

Alkynyl macrolide M27 is made from alkynyl macrolide M23 by reduction of the oxime to the imine followed by acetylation of the compound, which is then oxidized to give the bridged ketone. The cladinose sugar is then hydrolyzed by treatment with dilute hydrochloric acid.

Synthesis of Alkynyl Macrolide M28

Alkynyl macrolide M28 is made by refluxing alkynyl macrolide M27 with the following hydroxylamine compound in methanol.

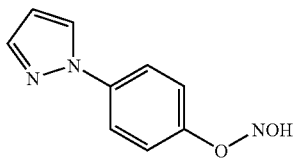

Synthesis of Alkynyl Macrolide M2

A mixture of M26 (1.48 g, 2.0 mmol) and hydrazine (0.65 mL, 20 mmol) in acetonitrile (40 mL) and water (6 mL) was heated to 50° C. After 5 h the solution was concentrated and refluxed with MeOH (100 mL) for 20 h. The solution was concentrated and the crude material was purified by flash chromatography over silica gel (60% ethyl acetate in hexane). Yield: 0.8 g M2 (60%).

Synthesis of Alkynyl Macrolides M6, M7, and M8

Alkynyl macrolides M6, M7, and M8 are made from M26 (using a procedure analogous to that for making M2, in which the hydrazine is replaced with methyl amine, ammonium hydroxide, and ethanol amine respectively).

Synthesis of Azide Compounds

The organic azide compounds used in the synthesis of the compounds of the present invention are generally prepared from the iodo compound 2 or the boronic acid ester compound 3. Typically, the iodo or boronic acid functional groups provide a means for preparing a wide range of compounds using methods available to one skilled in the art.

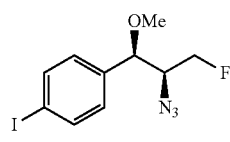

Idodo Compound, 2

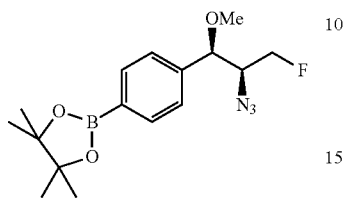

Boronic Acid Ester Compound, 3

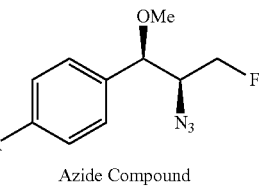

Azide Compound

The iodo compound 2, is prepared according to the following scheme from commercially available (1R,2R)-(−)-2-amino-1-(4-nitrophenyl)-1,3-propanediol. The boronic acid ester compound 3 is prepared from the iodo compound 2.

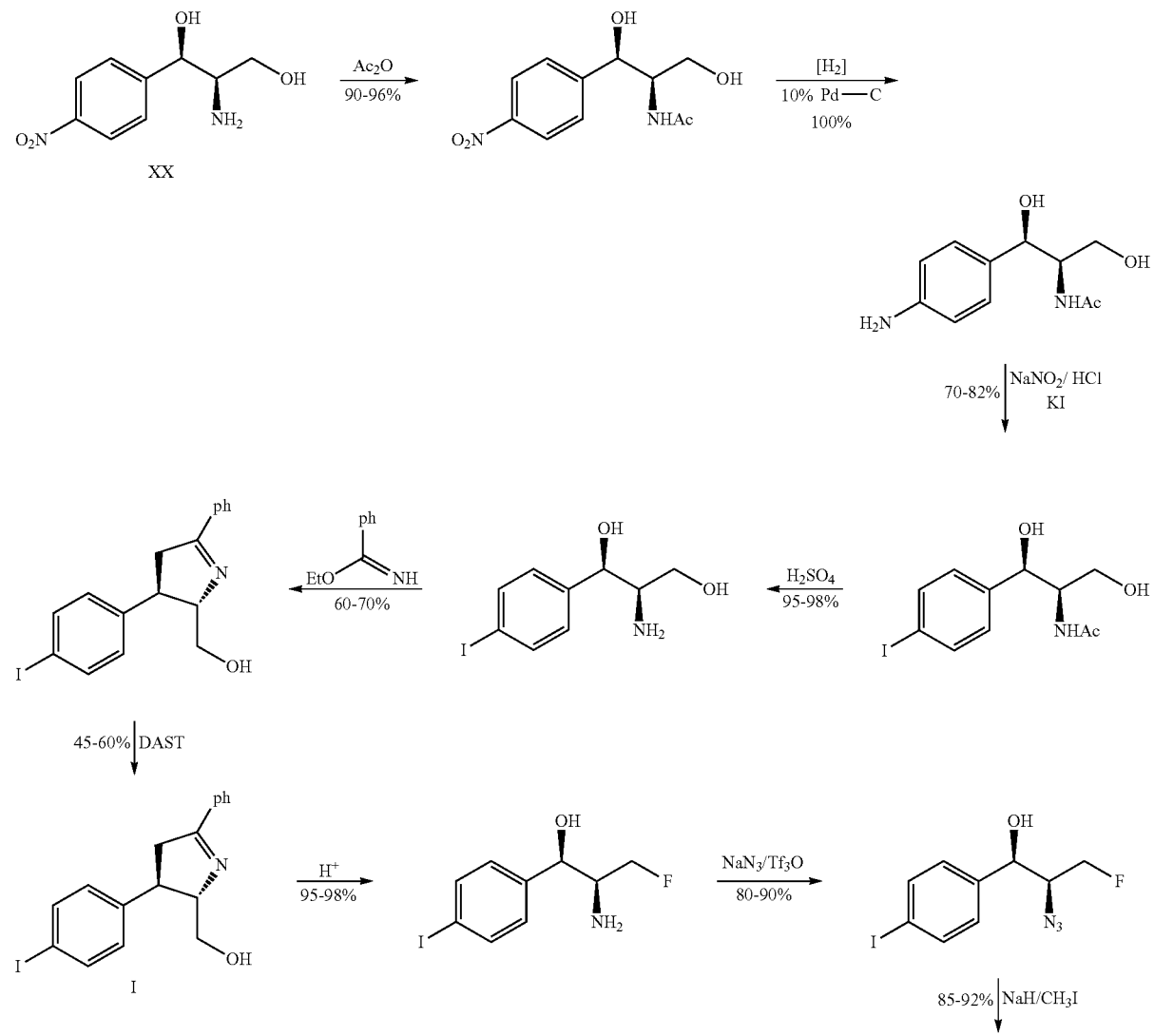

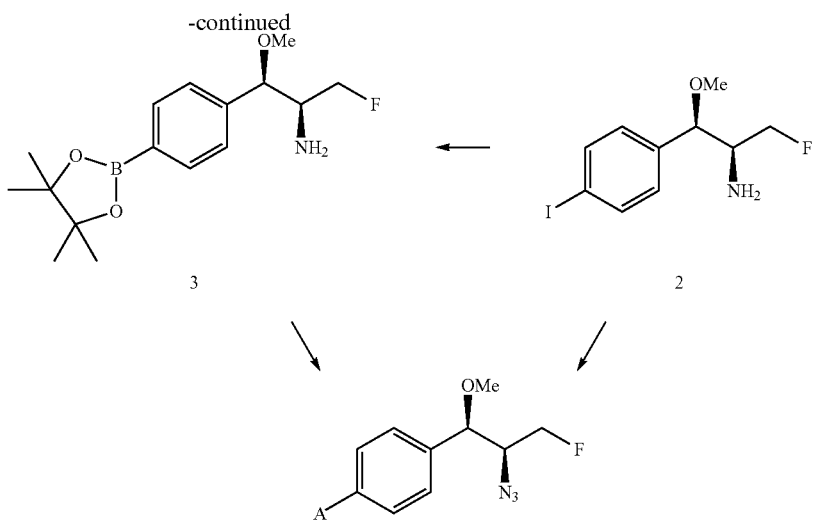
The following reaction scheme illustrates various azide compounds that can be made from iodo compound 2. $R^a$, $R^b$, $R^c$, and $R^d$ represent various alkyl, substituted alkyl, aryl, and substituted aryl groups.
General Scheme for Synthesis of Various Azide Compounds from Iodo Compound 2
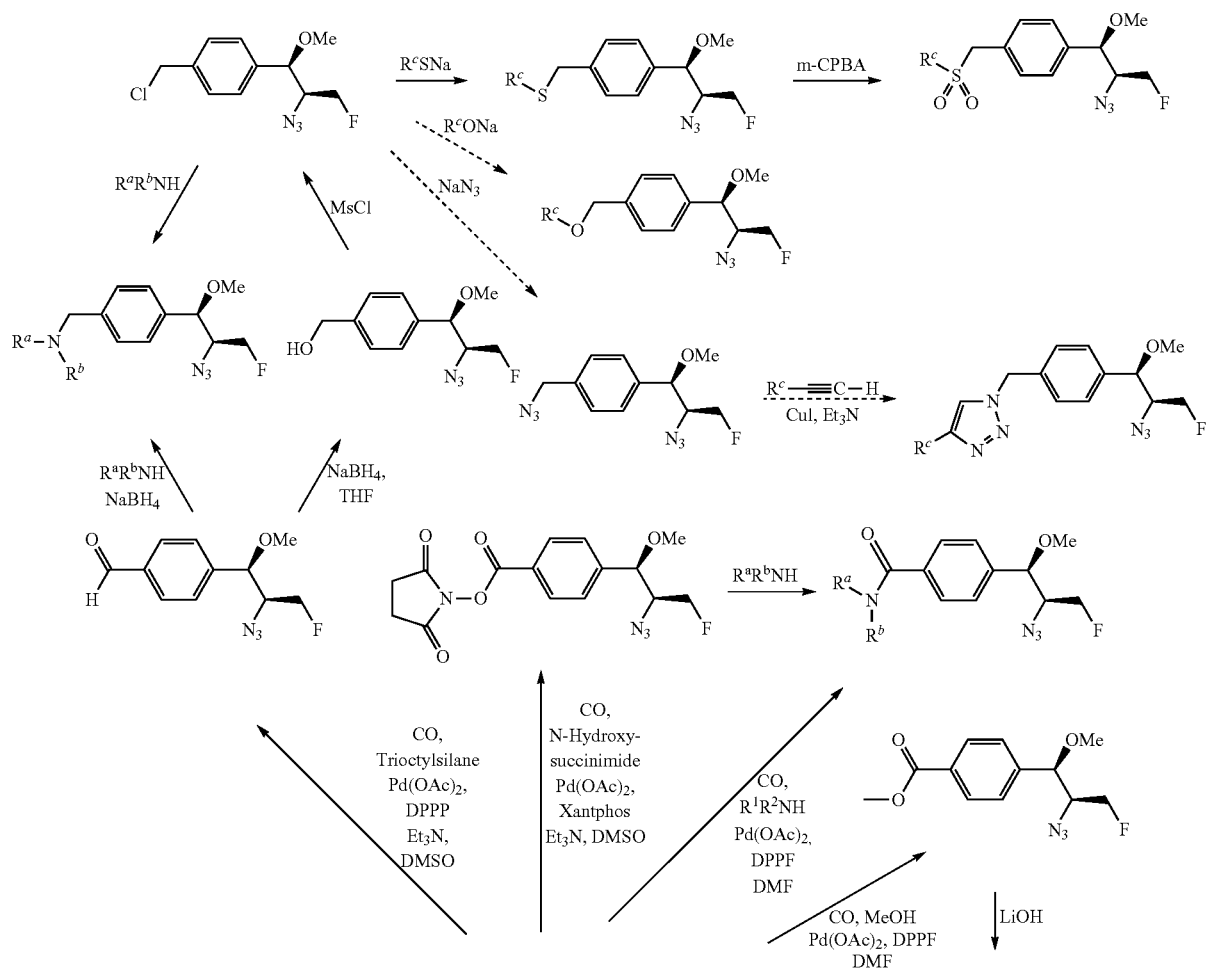

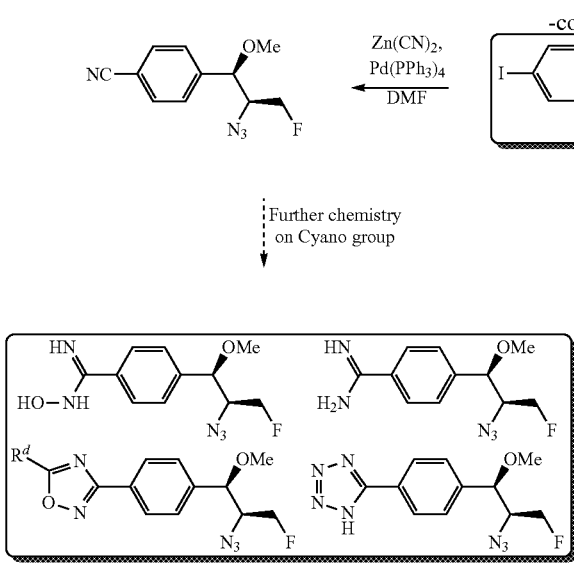

Synthesis of Compounds 131, 132, 172, 173, 174, 175, 182, 185, 199, 201, 203, and 205

As described above, compounds 131, 132, 172, 173, 174, 175, 182, 185, 199, 201, 203, and 205, as well as other similar compounds, are prepared from the cycloaddition reaction of the desired alkynyl macrolide and nitro phenyl azide to form a resulting nitro phenyl macrolide compound. This nitro phenyl macrolide is then further converted to an azide group, via reduction to an amine. The azide is a common intermediate which is then reacted with an appropriately functionalized alkyne in a second cycloaddition reaction to form the desired compound. Table 4, below shows the corresponding alkynes used in the preparation of compounds 131, 132, 172, 173, 174, 175, 182, 185, 199, 201, 203, and 205. It should be noted in the case of compound 132 that the TMS-acetylene is used as the alkyne and the TMS group is then subsequently removed under standard conditions.

TABLE 4

| Compound | Alkyne |
| --- | --- |
| 131 | |
| 132 | |
| 172 | |
| 173 | |
| 174 | |
| 175 | |
| 182 | |
| 185 | |
| 199 | |
| 201 | |
| 203 | |
| 205 | |

INCORPORATION BY REFERENCE

The entire disclosure of each of the patent documents and scientific articles referred to herein is incorporated by reference for all purposes.

EQUIVALENTS

The invention can be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. A compound having the structure:

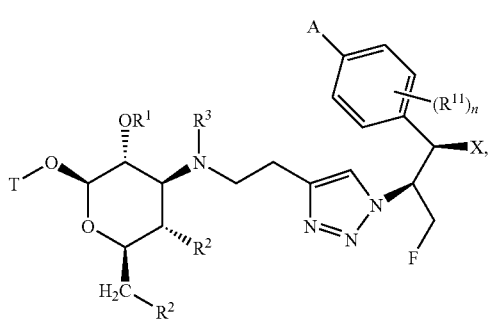

or a pharmaceutically acceptable salt, ester, or N-oxide thereof,
wherein
A is selected from: (a) a $C_{1-6}$ alkyl group, (b) a $C_{2-6}$ alkenyl group, (c) a $C_{2-6}$ alkynyl group, (d) a $C_{3-12}$ saturated, unsaturated, or aromatic carbocycle, (e) a 3-12 membered saturated, unsaturated, or aromatic heterocycle containing one or more nitrogen, oxygen or sulfur atoms, (f) H, (g) —OH, (h) —SH, (i) F, (j) Cl, (k) Br, (l) I, (m) —$CF_3$, (n) —CN, (o) —$N_3$, (p) —$NO_2$, (q) —$NR^6(CR^6R^6)_rR^9$, (r) —$OR^9$, (s) —$S(CR^6R^6)_rR^9$, (t) —$C(O)(CR^6R^6)_rR^9$, (u) —$OC(O)(CR^6R^6)_rR^9$, (v) —$OC(O)O(CR^6R^6)_rR^9$, (w) —$SC(O)(CR^6R^6)_rR^9$, (x) —$C(O)O(CR^6R^6)_rR^9$, (y) —$NR^6C(O)(CR^6R^6)_rR^9$, (z) —$C(O)NR^6(CR^6R^6)_rR^9$, (aa) —$C(=NR^6)(CR^6R^6)_rR^9$, (bb) —$C(=NNR^6R^6)(CR^6R^6)_rR^9$, (cc) —$C[=NNR^6C(O)R^6](CR^6R^6)_rR^9$, (dd) —$NR^6C(O)O(CR^6R^6)_rR^9$, (ee) —$OC(O)NR^6(CR^6R^6)_rR^9$, (ff) —$NR^6C(O)NR^6(CR^6R^6)_rR^9$, (gg) —$NR^6S(O)_p(CR^6R^6)_rR^9$, (hh) —$S(O)_p NR^6(CR^6R^6)_rR^9$, (ii) —$NR^6R^6$, (jj) —$SR^6$, (kk) —$S(O)R^6$, (ll) —$NR^6C(O)R^6$, (mm) —$Si(R^{13})_3$, and (nn) —C(=O)H,
wherein (a)-(e) optionally are substituted with one or more $R^{14}$ groups;
T is a 14- or 15-membered macrolide connected via a macrocyclic ring carbon atom;
X is selected from —$OR^{15}$ and —$SR^{15}$;
$R^1$ and $R^3$ independently are selected from: (a) H, (b) a $C_{1-6}$ alkyl group, (c) a $C_{2-6}$ alkenyl group, (d) a $C_{2-6}$ alkynyl group, (e) —$C(O)R^5$, (f) —$C(O)OR^5$, (g) —$C(O)—NR^4R^4$, (h) —$C(S)R^5$, (i) —$C(S)OR^5$, (j) —$C(O)SR^5$, and (k) —$C(S)—NR^4R^4$;
alternatively, $R^1$ and $R^3$ are taken together with the oxygen to which $R^1$ is attached, the nitrogen to which $R^3$ is attached and the two intervening carbons to form a 5 or 6 membered ring, said ring being optionally substituted with one or more $R^5$;
$R^2$ is hydrogen or —$OR^{12}$;
$R^4$, at each occurrence, independently is selected from:
(a) H, (b) a $C_{1-6}$ alkyl group, (c) a $C_{2-6}$ alkenyl group, (d) a $C_{2-6}$ alkynyl group, (e) a $C_{6-10}$ saturated, unsaturated, or aromatic carbocycle, (f) a 3-12 membered saturated, unsaturated, or aromatic heterocycle containing one or more heteroatoms selected from nitrogen, oxygen, and sulfur, (g) —$C(O)$—$C_{1-6}$ alkyl, (h) —$C(O)$—$C_{2-6}$ alkenyl, (i) —$C(O)$—$C_{2-6}$ alkynyl, (j) —$C(O)$—$C_{6-10}$ saturated, unsaturated, or aromatic carbocycle, (k) —C(O)-3-12 membered saturated, unsaturated, or aromatic heterocycle containing one or more heteroatoms selected from nitrogen, oxygen, and sulfur, (l) —$C(O)O$—$C_{1-6}$ alkyl, (m) —$C(O)O$—$C_{2-6}$ alkenyl, (n) —$C(O)O$—$C_{2-6}$ alkynyl, (o) —$C(O)O$—$C_{6-10}$ saturated, unsaturated, or aromatic carbocycle, (p) —C(O)O-3-12 membered saturated, unsaturated, or aromatic heterocycle containing one or more heteroatoms selected from nitrogen, oxygen, and sulfur, and (q) —$C(O)NR^6R^6$,
wherein any of (b)-(p) optionally is substituted with one or more $R^5$ groups;
alternatively, $NR^6R^6$ forms a 3-7 membered saturated, unsaturated or aromatic ring including the nitrogen atom to which the $R^6$ groups are attached, wherein said ring is optionally substituted at a position other than the nitrogen atom to which the $R^6$ groups are attached, with one or more substituents selected from O, $S(O)_p$, N, and $NR^8$;
$R^5$ is selected from:
(a) $R^7$, (b) a $C_{1-8}$ alkyl group, (c) a $C_{2-8}$ alkenyl group, (d) a $C_{2-8}$ alkynyl group, (e) a $C_{3-12}$ saturated, unsaturated, or aromatic carbocycle, and (f) a 3-12 membered saturated, unsaturated, or aromatic heterocycle containing one or more heteroatoms selected from nitrogen, oxygen, and sulfur, or two $R^5$ groups, when present on the same carbon atom can be taken together with the carbon atom to which they are attached to form a spiro 3-6 membered carbocyclic ring or heterocyclic ring containing one or more heteroatoms selected from nitrogen, oxygen, and sulfur,
wherein any of (b)-(f) immediately above optionally is substituted with one or more $R^7$ groups;
$R^6$, at each occurrence, independently is selected from:
(a) H, (b) a $C_{1-6}$ alkyl group, (c) a $C_{2-6}$ alkenyl group, (d) a $C_{2-6}$ alkynyl group, (e) a $C_{3-10}$ saturated, unsaturated, or aromatic carbocycle, and (f) a 3-10 membered saturated, unsaturated, or aromatic heterocycle containing one or more heteroatoms selected from nitrogen, oxygen, and sulfur,
wherein any of (b)-(f) optionally is substituted with one or more moieties selected from:
(aa) a carbonyl group, (bb) a formyl group, (cc) F, (dd) Cl, (ee) Br, (ff) I, (gg) CN, (hh) $NO_2$, (ii) —$OR^8$, (jj) —$S(O)_pR^8$, (kk) —$C(O)R^8$, (ll) —$C(O)OR^8$, (mm) —$OC(O)R^8$, (nn) —$C(O)NR^8R^8$, (oo) —$OC(O)NR^8R^8$, (pp) —$C(=NR^8)R^8$, (qq) —$C(R^8)(R^8)OR^8$, (rr) —$C(R^8)_2OC(O)R^8$, (ss) —$C(R^8)(OR^8)(CH_2)_rNR^8R^8$, (tt) —$NR^8R^8$, (uu) —$NR^8OR^8$, (vv) —$NR^8C(O)R^8$, (ww) —$NR^8C(O)OR^8$, (xx) —$NR^8C(O)NR^8R^8$, (yy) —$NR^8S(O)_rR^8$, (zz) —$C(OR^8)(OR^8)R^8$, (ab) —$C(R^8)_2NR^8R^8$, (ac) =$NR^8$, (ad) —$C(S)NR^8R^8$, (ae) —$NR^8C(S)R^8$, (af) —$OC(S)NR^8R^8$, (ag) —$NR^8C(S)OR^8$, (ah) —$NR^8C(S)NR^8R^8$, (ai) —$SC(O)R^8$, (aj) a $C_{1-8}$ alkyl group, (ak) a $C_{2-8}$ alkenyl group, (al) a $C_{2-8}$ alkynyl group, (am) a $C_{1-8}$ alkoxy group, (an) a $C_{1-8}$ alkylthio group, (ao) a $C_{1-8}$ acyl group, (ap) —$CF_3$, (aq) —$SCF_3$-, (ar) a $C_{3-10}$ saturated, unsaturated, or aromatic carbocycle, and (as) a 3-10 membered saturated, unsaturated, or aromatic heterocycle containing one or more heteroatoms selected from nitrogen, oxygen, and sulfur;

alternatively, $NR^6R^6$ forms a 3-10 membered saturated, unsaturated or aromatic ring including the nitrogen atom to which the $R^6$ groups are attached wherein said ring is optionally substituted at a position other than the nitrogen atom to which the $R^6$ groups are bonded, with one or more moieties selected from —O, $S(O)_p$, N, and $NR^8$;

alternatively, $CR^6R^6$ forms a carbonyl group;

$R^7$, at each occurrence, is selected from:
  (a) H, (b) =O, (c) =S, (d) F, (e) Cl, (f) Br, (g) I, (h) —$CF_3$, (i) —CN, (j) —$N_3$, (k) —$NO_2$, (l) —$NR^6(CR^6R^6)_rR^9$, (m) —$OR^9$, (n) —$S(O)_pC(R^6R^6)_rR^9$, (o) —$C(O)(CR^6R^6)_rR^9$, (p) —$OC(O)(CR^6R^6)_rR^9$, (q) —$SC(O)(CR^6R^6)_rR^9$, (r) —$C(O)O(CR^6R^6)_rR^9$, (s) —$NR^6C(O)(CR^6R^6)_rR^9$, (t) —$C(O)NR^6(CR^6R^6)_rR^9$, (u) —$C(=NR^6)(CR^6R^6)_rR^9$, (v) —$C(=NNR^6R^6)(CR^6R^6)_rR^9$, (w) —$C(=NNR^6C(O)R^6)(CR^6R^6)_rR^9$, (x) —$C(=NOR^9)(CR^6R^6)_rR^9$, (y) —$NR^6C(O)O(CR^6R^6)_rR^9$, (z) —$OC(O)NR^6(CR^6R^6)_rR^9$, (aa) —$NR^6C(O)NR^6(CR^6R^6)_rR^9$, (bb) —$NR^6S(O)_p(CR^6R^6)_rR^9$, (cc) —$S(O)_pNR^6(CR^6R^6)_rR^9$, (dd) —$NR^6S(O)_pNR^6(CR^6R^6)_rR^9$, (ee) —$NR^6R^6$, (ff) —$NR^6(CR^6R^6)$, (gg) —OH, (hh) —$NR^6R^6$, (ii) —$OCH_3$, (jj) —$S(O)_pR^6$, (kk) —$NC(O)R^6$, (ll) a $C_{1-6}$ alkyl group, (mm) a $C_{2-6}$ alkenyl group, (nn) a $C_{2-6}$ alkynyl group, (oo) —$C_{3-10}$ saturated, unsaturated, or aromatic carbocycle, and (pp) 3-10 membered saturated, unsaturated, or aromatic heterocycle containing one or more heteroatoms selected from nitrogen, oxygen, and sulfur,
    wherein any of (ll)-(pp) optionally is substituted with one or more $R^9$ groups; alternatively, two $R^7$ groups taken together form —$O(CH_2)_uO$—;

$R^8$ is selected from:
  (a) H, (b) a $C_{1-6}$ alkyl group, (c) a $C_{2-6}$ alkenyl group, (d) a $C_{2-6}$ alkynyl group, (e) a $C_{3-10}$ saturated, unsaturated, or aromatic carbocycle, (f) a 3-10 membered saturated, unsaturated, or aromatic heterocycle containing one or more heteroatoms selected from nitrogen, oxygen, and sulfur, (g) —C(O)—$C_{1-6}$ alkyl, (h) —C(O)—$C_{1-6}$ alkenyl, (i) —C(O)—$C_{1-6}$ alkynyl, (j) —C(O)—$C_{3-10}$ saturated, unsaturated, or aromatic carbocycle, and (k) —C(O)-3-10 membered saturated, unsaturated, or aromatic heterocycle containing one or more heteroatoms selected from nitrogen, oxygen, and sulfur,
    wherein any of (c)-(k) optionally is substituted with one or more moieties selected from: (aa) H, (bb) F, (cc) Cl, (dd) Br, (ee) I, (ff) CN, (gg) $NO_2$, (hh) OH, (ii) $NH_2$, (jj) $NH(C_{1-6}$ alkyl), (kk) $N(C_{1-6}$ alkyl$)_2$, (ll) a $C_{1-6}$ alkoxy group, (mm) an aryl group, (nn) a substituted aryl group, (oo) a heteroaryl group, (pp) a substituted heteroaryl group, and (qq) a $C_{1-6}$ alkyl group optionally substituted with one or more moieties selected from an aryl group, a substituted aryl group, a heteroaryl group, a substituted heteroaryl group, F, Cl, Br, I, CN, $NO_2$, $CF_3$, $SCF_3$, and OH;

$R^9$, at each occurrence, independently is selected from:
  (a) $R^{10}$, (b) a $C_{1-6}$ alkyl group, (c) a $C_{2-6}$ alkenyl group, (d) a $C_{2-6}$ alkynyl group, (e) a $C_{3-10}$ saturated, unsaturated, or aromatic carbocycle, and (f) a 3-10 membered saturated, unsaturated, or aromatic heterocycle containing one or more heteroatoms selected from nitrogen, oxygen, and sulfur,
    wherein any of (b)-(f) optionally is substituted with one or more $R^{10}$ groups;

$R^{10}$, at each occurrence, independently is selected from:
  (a) H, (b) =O, (c) F, (d) Cl, (e) Br, (f) I, (g) —$CF_3$, (h) —CN, (i) —$NO_2$, (j) —$NR^6R^6$, (k) —$OR^6$, (l) —$S(O)_p R^6$, (m) —$C(O)R^6$, (n) —$C(O)OR^6$, (o) —$OC(O)R^6$, (p) $NR^6C(O)R^6$, (q) —$C(O)NR^6R^6$, (r) —$C(=NR^6)R^6$, (s) —$NR^6C(O)NR^6R^6$, (t) —$NR^6S(O)_pR^6$, (u) —$S(O)_pNR^6R^6$, (v) —$NR^6S(O)_pNR^6R^6$, (w) a $C_{1-6}$ alkyl group, (x) a $C_{2-6}$ alkenyl group, (y) a $C_{2-6}$ alkynyl group, (z) a $C_{3-10}$ saturated, unsaturated, or aromatic carbocycle, and (aa) a 3-10 membered saturated, unsaturated, or aromatic heterocycle containing one or more heteroatoms selected from nitrogen, oxygen, and sulfur,
    wherein any of (w)-(aa) optionally is substituted with one or more moieties selected from $R^6$, F, Cl, Br, I, CN, $NO_2$, —$OR^6$, —$NH_2$, —$NH(C_{1-6}$ alkyl), —$N(C_{1-6}$ alkyl$)_2$, a $C_{1-6}$ alkoxy group, a $C_{1-6}$ alkylthio group, and a $C_{1-6}$ acyl group;

$R^{11}$ at each occurrence, independently is selected from:
  (a) H, (b) F, (c) Cl, (d) Br, (e) I, (f) CN, (g) $NO_2$, (h) $OR^8$, (i) —$S(O)_pR^8$, (j) —$C(O)R^8$, (k) —$C(O)OR^8$, (l) —$OC(O)R^8$, (m) —$C(O)NR^8R^8$, (n) —$OC(O)NR^8R^8$, (o) —$C(=NR^8)R^8$, (p) —$C(R^8)(R^8)OR^8$, (q) —$C(R^8)_2OC(O)R^8$, (r) —$C(R^8)(OR^8)(CH_2)_rNR^8R^8$, (s) —$NR^8R^8$, (t) —$NR^8OR^8$, (u) —$NR^8C(O)R^8$, (v) —$NR^8C(O)OR^8$, (w) —$NR^8C(O)NR^8R^8$, (x) —$NR^8S(O)_pR^8$, (y) —$C(OR^8)(OR^8)R^8$, (z) —$C(R^8)_2NR^8R^8$, (aa) —$C(S)NR^8R^8$, (bb) —$NR^8C(S)R^8$, (cc) —$OC(S)NR^8R^8$, (dd) —$NR^8C(S)OR^8$, (ee) —$NR^8C(S)NR^8R^8$, (ff) —$SC(O)R^8$, (gg) —$N_3$, (hh) —$Si(R^{13})_3$, (ii) a $C_{1-8}$ alkyl group, (jj) a $C_{2-8}$ alkenyl group, (kk) a $C_{2-8}$ alkynyl group, (ll) a $C_{3-10}$ saturated, unsaturated, or aromatic carbocycle, and (mm) a 3-10 membered saturated, unsaturated, or aromatic heterocycle containing one or more heteroatoms selected from nitrogen, oxygen, and sulfur, wherein (ii)-(mm) optionally are substituted with one or more $R^5$ groups;

$R^{12}$ is selected from:
  (a) H, (b) a $C_{1-6}$ alkyl group, (c) a $C_{2-6}$ alkenyl group, (d) a $C_{2-6}$ alkynyl group, (e) —$C(O)R^5$, (f) —$C(O)OR^5$, (g) —$C(O)$—$NR^4R^4$, (h) —$C(S)R^5$, (i) —$C(S)OR^5$, (j) —$C(O)SR^5$, (k) —$C(S)$—$NR^4R^4$, (l) a $C_{3-10}$ saturated, unsaturated, or aromatic carbocycle, (m) a 3-10 membered saturated, unsaturated, or aromatic heterocycle containing one or more heteroatoms selected from -nitrogen, oxygen, and sulfur, (n) a —$(C_{1-6}$ alkyl$)$-$C_{3-10}$ saturated, unsaturated, or aromatic carbocycle, and (o) a —$(C_{1-6}$ alkyl)-3-10 membered saturated, unsaturated, or aromatic heterocycle containing one or more heteroatoms selected from nitrogen, oxygen, and sulfur,
    wherein (a)-(d) and (l)-(o) optionally are substituted with one or more $R^5$ groups;

$R^{13}$ at each occurrence, is independently selected from (a) —$C_{1-6}$ alkyl and (b) —O—$(C_{1-6}$ alkyl);

$R^{14}$ at each occurrence is independently selected from:
  (a) H, (b) F, (c) Cl, (d) Br, (e) I, (l) CN, (g) $NO_2$, (h) $OR^8$, (i) —$S(O)_pR^8$, (j) —$C(O)R^8$, (k) —$C(O)OR^8$, (l) —$OC(O)R^8$, (m) —$C(O)NR^8R^8$, (n) —$OC(O)NR^8R^8$, (o) —$C(=NR^8)R^8$, (p) —$C(R^8)(R^8)OR^8$, (q) —$C(R^8)_2OC(O)R^8$, (r) —$C(R^8)(OR^8)(CH_2)_rNR^8R^8$, (s) —$NR^8R^8$, (t) —$NR^8OR^8$, (u) —$NR^8C(O)R^8$, (v) —$NR^8C(O)OR^8$, (w) —$NR^8C(O)NR^8R^8$, (x) —$NR^8S(O)_pR^8$, (y) —$C(OR^8)(OR^8)R^8$, (z) —$C(R^8)_2NR^8R^8$, (aa) —$C(S)NR^8R^8$, (bb) —$NR^8C(S)R^8$, (cc)

—OC(S)NR⁸R⁸, (dd) —NR⁸C(S)OR⁸, (ee) —NR⁸C(S)NR⁸R⁸, (ff) —SC(O)R⁸, (gg) —N₃, (hh) —Si(R¹³)₃, (ii) a C$_{1-8}$ alkyl group, (jj) a C$_{2-8}$ alkenyl group, (kk) a C$_{2-8}$ alkynyl group, (ll) a C$_{3-10}$ saturated, unsaturated, or aromatic carbocycle, and (mm) a 3-10 membered saturated, unsaturated, or aromatic heterocycle containing one or more heteroatoms selected from nitrogen, oxygen, and sulfur, wherein (ii)-(mm) optionally are substituted with one or more R⁵ groups;

alternatively, two R¹⁴ groups are taken together to form (a) =O, (b) =S, (c) =NR⁸, (e) =NOR⁸;

R¹⁵ is C$_{1-6}$ alkyl, optionally substituted with from 1 to 13 fluorine atoms;

n at each occurrence is 0, 1, 2, 3, or 4;

p at each occurrence is 0, 1, or 2;

r at each occurrence is 0, 1, or 2;

t at each occurrence is 0, 1, or 2;

and u at each occurrence is 1, 2, 3, or 4.

2. The compound according to claim 1 having the structure:

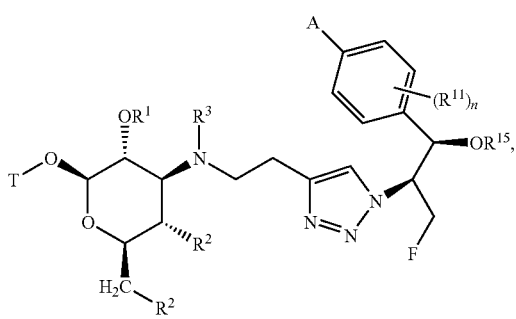

or a pharmaceutically acceptable salt, ester, or N-oxide thereof.

3. The compound according to claim 1 having the structure:

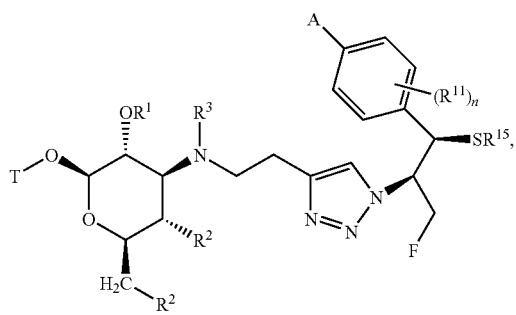

or a pharmaceutically acceptable salt, ester, or N-oxide thereof.

4. The compound according to claim 1, or a pharmaceutically acceptable salt, ester, or N-oxide thereof, wherein R¹⁵ is C$_{1-3}$ alkyl, optionally substituted with from 1 to 7 fluorines.

5. The compound according to claim 1, or a pharmaceutically acceptable salt, ester, or N-oxide thereof, wherein R¹⁵ is C$_{1-2}$ alkyl, optionally substituted with from 1 to 5 fluorines.

6. The compound according to claim 1, or a pharmaceutically acceptable salt, ester, or N-oxide thereof, wherein R¹⁵ is selected from —CH₃, —CH₂F, —CHF₂, and —CF₃.

7. The compound according to claim 6, or a pharmaceutically acceptable salt, ester, or N-oxide thereof, wherein R¹⁵ is —CH₃.

8. The compound according to claim 1 having the structure:

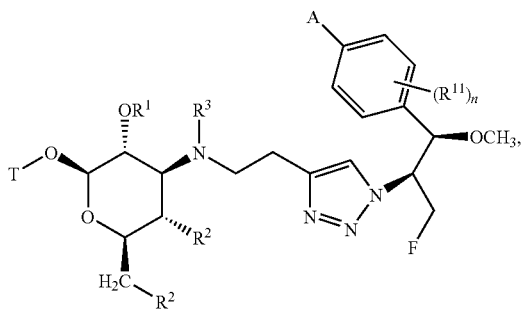

or a pharmaceutically acceptable salt, ester, or N-oxide thereof.

9. The compound according to claim 1, or a pharmaceutically acceptable salt, ester, or N-oxide thereof, wherein n is 1 or 2.

10. The compound according to claim 1, or a pharmaceutically acceptable salt, ester, or N-oxide thereof, wherein n is 1.

11. The compound according to claim 1, or a pharmaceutically acceptable salt, ester, or N-oxide thereof, wherein R¹¹ is F.

12. The compound according to claim 1, or a pharmaceutically acceptable salt, ester, or N-oxide thereof, wherein n is 0.

13. The compound according to claim 1, or a pharmaceutically acceptable salt, ester, or N-oxide thereof, wherein A is selected from: (a) a C$_{1-6}$ alkyl group, (b) a C$_{2-6}$ alkenyl group, (c) a C$_{2-6}$ alkynyl group, (d) a C$_{3-12}$ saturated, unsaturated, or aromatic carbocycle, (e) a 3-12 membered saturated, unsaturated, or aromatic heterocycle containing one or more nitrogen, oxygen or sulfur atoms, (f) —CF₃, (g) —NR⁶(CR⁶R⁶)$_t$R⁹, (h) —OR⁹, (i) —S(CR⁶R⁶)$_r$R⁹, (j) —C(O)(CR⁶R⁶)$_r$R⁹, (k) —OC(O)(CR⁶R⁶)$_r$R⁹, (l) —OC(O)O(CR⁶R⁶)$_r$R⁹, (m) —SC(O)(CR⁶R⁶)$_r$R⁹, (n) —C(O)O(CR⁶R⁶)$_t$R⁹, (o) —NR⁶C(O)(CR⁶R⁶)$_r$R⁹, (p) —C(O)NR⁶(CR⁶R⁶)$_r$R⁹, (q) —C(=NR⁶)(CR⁶R⁶)$_r$R⁹, (r) —C(=NNR⁶R⁶)(CR⁶R⁶)$_r$R⁹, (s) —C[=NNR⁶C(O)R⁶](CR⁶R⁶)$_r$R⁹, (t) —NR⁶C(O)O(CR⁶R⁶)$_r$R⁹, (u) —OC(O)NR⁶(CR⁶R⁶)$_r$R⁹, (v) —NR⁶C(O)NR⁶(CR⁶R⁶)$_r$R⁹, (w) —NR⁶S(O)$_p$(CR⁶R⁶)$_r$R⁹, (x) —S(O)$_p$NR⁶(CR⁶R⁶)$_r$R⁹, (y) —NR⁶R⁶, (z) —SR⁶, (aa) —S(O)R⁶, and (bb) —NR⁶C(O)R⁶, wherein (a)-(e) optionally are substituted with one or more R¹⁴ groups.

14. The compound according to claim 1, or a pharmaceutically acceptable salt, ester, or N-oxide thereof, wherein A is selected from: (a) a C$_{1-6}$ alkyl group, (b) a C$_{2-6}$ alkenyl group, (c) a C$_{2-6}$ alkynyl group, (d) a C$_{3-12}$ saturated, unsaturated, or aromatic carbocycle, (e) a 3-12 membered saturated, unsaturated, or aromatic heterocycle containing one or more nitrogen, oxygen or sulfur atoms, wherein (a)-(e) optionally are substituted with one or more R¹⁴ groups.

15. The compound according to claim 1, or a pharmaceutically acceptable salt, ester, or N-oxide thereof, wherein A is selected from (a) —NR⁶(CR⁶R⁶)$_t$R⁹, (b) —OR⁹, (c) —S(CR⁶R⁶)$_r$R⁹, (d) —C(O)(CR⁶R⁶)$_r$R⁹, (e) —OC(O)(CR⁶R⁶)$_r$R⁹, (f) —OC(O)O(CR⁶R⁶)$_r$R⁹, (g) —SC(O)(CR⁶R⁶)$_r$R⁹, (h) —C(O)O(CR⁶R⁶)$_t$R⁹, (i) —NR⁶C(O)(CR⁶R⁶)$_r$R⁹, (j) —C(O)NR⁶(CR⁶R⁶)$_r$R⁹, (k) —C(=NR⁶)(CR⁶R⁶)$_r$R⁹, (l) —C(=NNR⁶R⁶)(CR⁶R⁶)$_r$R⁹, (m) —C[=NNR⁶C(O)R⁶](CR⁶R⁶)$_r$R⁹, (n) —NR⁶C(O)O(CR⁶R⁶)$_r$R⁹, (o) —OC(O)NR⁶(CR⁶R⁶)$_r$R⁹, (p) —NR⁶C(O)

$NR^6(CR^6R^6)_rR^9$, (q) —$NR^6S(O)_p(CR^6R^6)_rR^9$, (r) —$S(O)_p$ $NR^6(CR^6R^6)_rR^9$, (s) —$NR^6R^6$, (t) —$SR^6$, (u) —$S(O)R^6$, and (v) —$NR^6C(O)R^6$.

16. The compound according to claim 1, or a pharmaceutically acceptable salt, ester, or N-oxide thereof, wherein T is

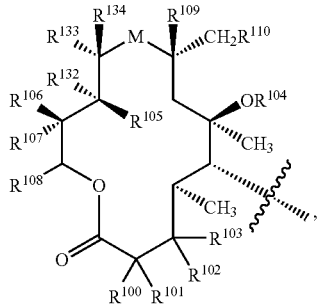

wherein:

M is selected from:
(a) —C(O)—, (b) —CH(—$OR^{114}$)—, (c) —$NR^{114}$—$CH_2$—, (d) (e) —CH($NR^{114}R^{114}$)—, (f) —C(=$NNR^{114}R^{114}$)—, (g) —$NR^{114}$—C(O)—, (h) —C(O)$NR^{114}$—, (i) —C(=$NR^{114}$)—, (j) —$CR^{115}R^{115}$—, and (k) —C(=$NOR^{127}$)—;

$R^{100}$ is selected from (a) H, (b) F, (c) Cl, (d) Br, (e) —$SR^{114}$, and (f) $C_{1-6}$ alkyl, wherein (f) optionally is substituted with one or more $R^{115}$ groups;

$R^{101}$ is selected from:
(a) H, (b) Cl, (c) F, (d) Br, (e) I, (f) —$NR^{114}R^{114}$, (g) —$NR^{114}C(O)R^{114}$, (h) —$OR^{114}$, (i) —$OC(O)R^{114}$, (j) —$OC(O)OR^{114}$, (k) —$OC(O)NR^{114}R^{114}$, (l) —O—$C_{1-6}$ alkyl, (m) —OC(O)—$C_{1-6}$ alkyl, (n) —OC(O)O—$C_{1-6}$ alkyl, (o) —OC(O)$NR^{114}$—$C_{1-6}$ alkyl, (p) $C_{1-6}$ alkyl, (q) $C_{1-6}$ alkenyl, and (r) $C_{1-6}$ alkynyl,
wherein any of (l)-(r) optionally is substituted with one or more $R^{115}$ groups;

$R^{102}$ is (a) H, (b) F, (c) Cl, (d) Br, (e) —$SR^{114}$, (f) $C_{1-6}$ alkyl, wherein (f) optionally is substituted with one or more $R^{115}$ groups;

$R^{103}$ is selected from:
(a) H, (b) —$OR^{114}$, (c) —O—$C_{1-6}$ alkyl-$R^{115}$, (d) —OC(O)$R^{114}$, (e) —OC(O)—$C_{1-6}$ alkyl-$R^{115}$, (f) —OC(O)$OR^{114}$, (g) —OC(O)O—$C_{1-6}$ alkyl-$R^{115}$, (h) —OC(O)$NR^{114}R^{114}$, (i) —OC(O)$NR^{114}$—$C_{1-6}$ alkyl-$R^{115}$, and (j)

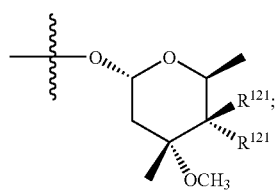

alternatively, $R^{102}$ and $R^{103}$ taken together with the carbon to which they are attached form (a) a carbonyl group or (b) a 3-7 membered saturated, unsaturated or aromatic carbocyclic or heterocyclic ring which can optionally be substituted with one or more $R^{114}$ groups; alternatively, $R^{101}$ and $R^{103}$ taken together are a single bond between the respective carbons to which these two groups are attached thereby creating a double bond between the carbons to which $R^{100}$ and $R^{102}$ are attached;

alternatively, $R^{101}$ and $R^{103}$ taken together with the carbons to which they are attached form a 3-membered saturated, unsaturated or aromatic carbocyclic or heterocyclic ring which can optionally be substituted with one or more $R^{114}$ groups;

$R^{104}$ is selected from:
(a) H, (b) $R^{114}$, (c) —C(O)$R^{114}$, (d) —C(O)$OR^{114}$, (e) —C(O)$NR^{114}R^{114}$, (f) —$C_{1-6}$ alkyl-K—$R^{114}$, (g) —$C_{2-6}$ alkenyl-K—$R^{114}$, and (h) —$C_{2-6}$ alkynyl-K—$R^{114}$;

K is selected from:
(a) —C(O)—, (b) —C(O)O—, (c) —C(O)$NR^{114}$—, (d) —C(=$NR^{114}$)—, (e) —C(=$NR^{114}$)O—, (f) —C(=$NR^{114}$)$NR^{114}$—, (g) —OC(O)—, (h) —OC(O)O—, (i) —OC(O)$NR^{114}$—, (j) —$NR^{114}$C(O)—, (k) —$NR^{114}$C(O)O—, (l) —$NR^{114}$C(O)$NR^{114}$—, (m) —$NR^{114}$C(=$NR^{114}$)$NR^{114}$—, and (n) —$S(O)_p$—;

alternatively, $R^{103}$ and $R^{104}$, taken together with the atoms to which they are bonded, form:

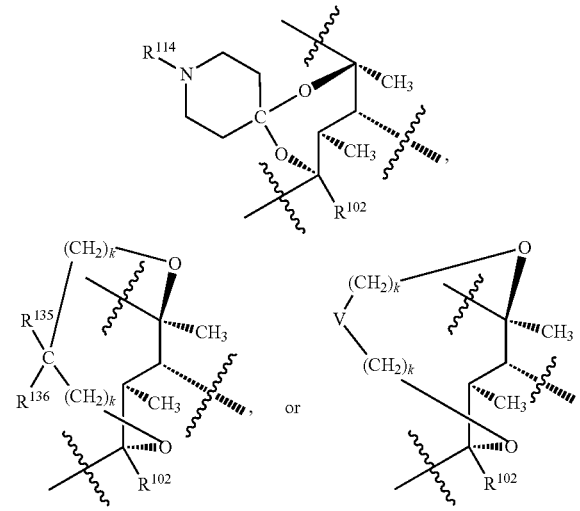

wherein $R^{135}$ and $R^{136}$ are selected from (a) hydrogen, (b) $C_{1-6}$ alkyl, (c) $C_{2-6}$ alkenyl, (d) $C_{2-6}$ alkynyl, (d) $C_{3-14}$ saturated, unsaturated or aromatic carbocycle, (e) 3-14 membered saturated, unsaturated or aromatic heterocycle containing one or more oxygen, nitrogen, or sulfur atoms, (f) F, (g) Br, (h) I, (i) OH, and (j) —$N_3$, wherein (b) through (e) are optionally substituted with one or more $R^{117}$;

alternatively, $R^{135}$ and $R^{136}$ taken together form =O, =S, =$NR^{114}$, =$NOR^{114}$, =$NR^{114}$, and =N—$NR^{114}R^{114}$;

wherein V is selected from (a) —($C_1$-$C_4$-alkyl)-, (b) —($C_4$-alkenyl)-, (c) O, (d) S, and (e) $NR^{114}$, wherein (a) and (b) are optionally further substituted with one or more $R^{117}$;

$R^{105}$ is selected from:
(a) $R^{114}$, (b) —$OR^{114}$, (c) —$NR^{114}R^{114}$, (d) —O—$C_{1-6}$ alkyl-$R^{115}$, (e) —C(O)—$R^{114}$, (f) —C(O)—$C_{1-6}$ alkyl-$R^{115}$, (g) —OC(O)—$R^{114}$, (h) —OC(O)—$C_{1-6}$ alkyl-$R^{115}$, (i) —OC(O)O—$R^{114}$, (j) —OC(O)O—$C_{1-6}$ alkyl-$R^{115}$, (k) —OC(O)$NR^{114}R^{114}$, (l) —OC(O)$NR^{114}$—$C_{1-6}$ alkyl-$R^{115}$, (m) —C(O)—$C_{2-6}$ alkenyl-$R^{115}$, and (n) —C(O)—$C_{2-6}$ alkynyl-$R^{115}$;

alternatively, $R^{104}$ and $R^{105}$, taken together with the atoms to which they are bonded, form

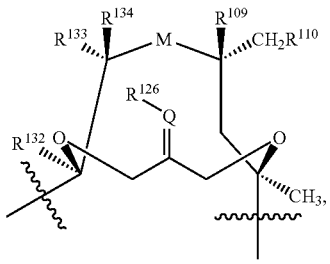

wherein
Q is CH or N, and $R^{126}$ is $-OR^{114}$, $-NR^{114}$ or $R^{114}$;
alternatively, $R^{104}$ and $R^{105}$, taken together with the atoms to which they are bonded, form:

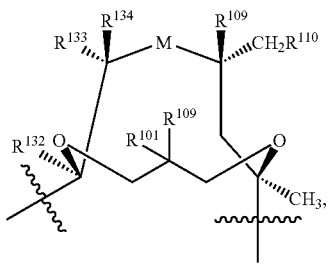

wherein
i) $R^{101}$ is as defined above;
ii) alternatively, $R^{101}$ and $R^{109}$ taken together with the carbon to which they are attached form a carbonyl group;
iii) alternatively, $R^{101}$ and $R^{109}$ taken together form the group $-O(CR^{116}R^{116})_uO-$;
alternatively, $R^{104}$ and $R^{105}$, taken together with the atoms to which they are bonded, form:

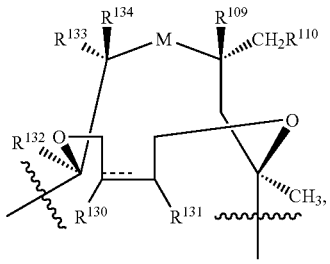

wherein in the preceding structure the dotted line indicates an optional double bond,
i) $R^{130}$ is $-OH$ or $R^{114}$,
ii) $R^{131}$ is $-OH$ or $R^{114}$,
iii) alternatively, $R^{130}$ and $R^{131}$ taken together with the carbons to which they are attached form a 3-7 membered saturated, unsaturated or aromatic carbocyclic or heterocyclic ring which can optionally be substituted with one or more $R^{114}$ groups;
iv) alternatively, $R^{130}$ and the carbon to which it is attached or $R^{131}$ and the carbon to which it is attached are each independently $-C(=O)-$;

alternatively, $R^{105}$, $R^{132}$ and M, taken together with the atoms to which they are attached, form:

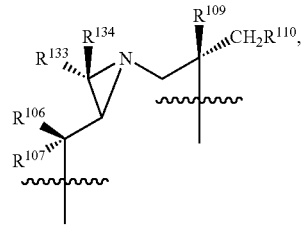

$R^{106}$ is selected from:
(a) $-OR^{114}$, (b) $-C_{1-6}$ alkoxy-$R^{115}$, (c) $-C(O)R^{114}$, (d) $-OC(O)R^{114}$, (e) $-OC(O)OR^{114}$, (f) $-OC(O)NR^{114}R^{114}$, and (g) $NR^{114}R^{114}$;
alternatively, $R^{105}$ and $R^{106}$ taken together with the atoms to which they are attached form a 5-membered ring by attachment to each other through a chemical moiety selected from:
(a) $-OC(R^{115})_2O-$, (b) $-OC(O)O-$, (c) $-OC(O)NR^{114}-$, (d) $-NR^{114}C(O)O-$, (e) $-OC(O)NOR^{114}-$, (f) $-NOR^{114}-C(O)O-$, (g) $-OC(O)NNR^{114}R^{114}-$, (h) $-NNR^{114}R^{114}-C(O)O-$, (i) $-OC(O)C(R^{115})_2-$, (j) $-C(R^{115})_2C(O)O-$, (k) $-OC(S)O-$, (l) $-OC(S)NR^{114}-$, (m) $-NR^{114}C(S)O-$, (n) $-OC(S)NOR^{114}-$, (o) $-NOR^{114}-C(S)O-$, (p) $-OC(S)NNR^{114}R^{114}-$, (q) $-NNR^{114}R^{114}-C(S)O-$, (r) $-OC(S)C(R^{115})_2-$, and (s) $-C(R^{115})_2C(S)O-$;
alternatively, $R^{105}$, $R^{106}$, and $R^{133}$ taken together with the atoms to which they are attached form:

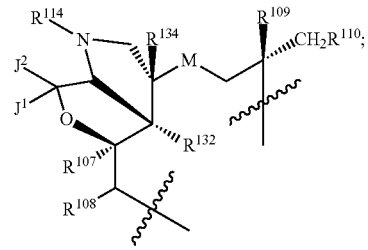

alternatively, M, $R^{105}$, and $R^{106}$ taken together with the atoms to which they are attached form:

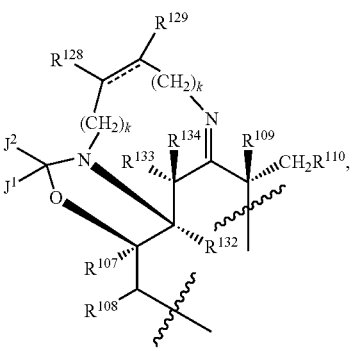

wherein in the preceding structure the dotted line indicates an optional double bond,

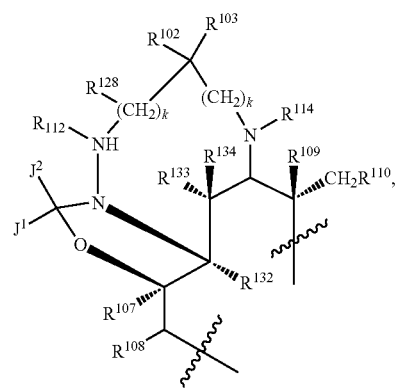

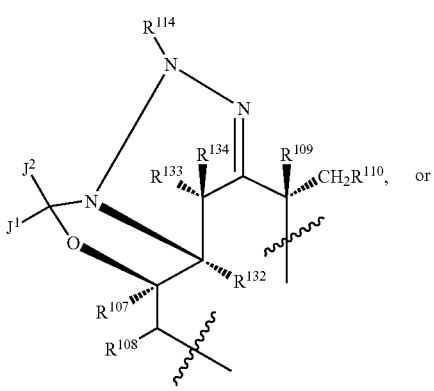

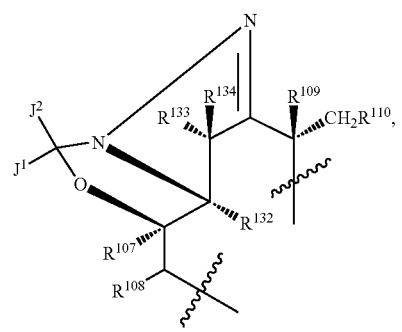

wherein $J^1$ and $J^2$ are selected from hydrogen, Cl, F, Br, I, OH, —$C_{1-6}$ alkyl, and —$O(C_{1-6}$ alkyl) or taken together form =O, =S and =$NR^{114}$, =$NOR^{114}$, =$NR^{114}$, and =N—$NR^{114}R^{114}$;

alternatively, M and $R^{104}$ taken together with the atoms to which they are attached form:

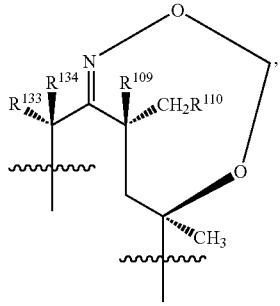

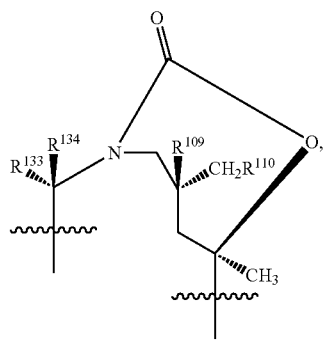

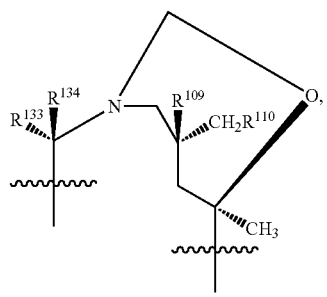

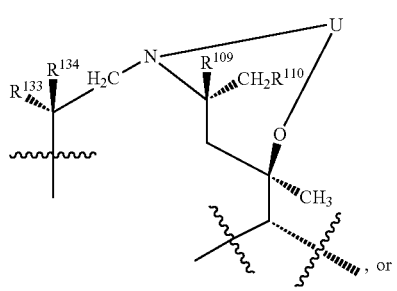

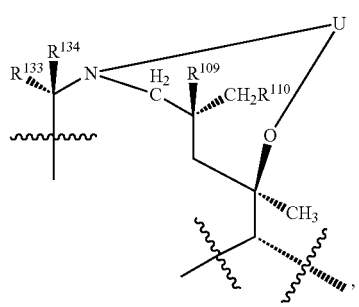

wherein U is selected from (a) —($C_4$-alkyl)- and (b) —($C_4$-alkenyl)-, wherein (a) and (b) are optionally further substituted with one or more $R^{117}$;

alternatively, M and $R^{105}$ are taken together with the atoms to which they are attached to form:

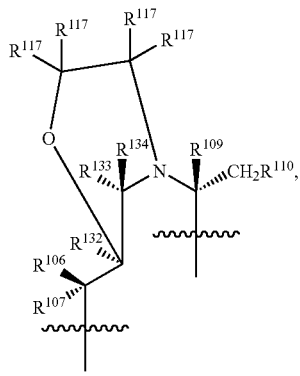

$R^{107}$ is selected from:
(a) H, (b) —$C_{1-4}$ alkyl, (c) —$C_{2-4}$ alkenyl, which can be further substituted with $C_{1-12}$ alkyl or one or more halogens, (d) —$C_{2-4}$ alkynyl, which can be further substituted with $C_{1-12}$ alkyl or one or more halogens, (e) aryl or heteroaryl, which can be further substituted with $C_{1-12}$ alkyl or one or more halogens, (f) —C(O)H, (g) —COOH, (h) —CN, (i) —COO$R^{114}$, (j) —C(O)N$R^{114}R^{114}$, (k) —C(O)$R^{114}$, and (l) —C(O)S$R^{114}$, wherein (b) is further substituted with one or more substituents selected from (aa) —O$R^{114}$, (bb) halogen, (cc) —S$R^{114}$, (dd) $C_{1-12}$ alkyl, which can be further substituted with halogen, hydroxyl, $C_{1-6}$ alkoxy, or amino, (ee) —O$R^{114}$, (ff) —S$R^{114}$, (gg) —N$R^{114}R^{114}$, (hh) —CN, (ii) —NO$_2$, (jj) —NC(O)$R^{114}$, (kk) —COO$R^{114}$, (ll) —N$_3$, (mm) =N—O—$R^{114}$, (nn) =N$R^{114}$, (oo) =N—N$R^{114}R^{114}$, (pp) =N—NH—C(O)$R^{114}$, and (qq) =N—NH—C(O)N$R^{114}R^{114}$;

alternatively $R^{106}$ and $R^{107}$ are taken together with the atom to which they are attached to form an epoxide, a carbonyl, an olefin, or a substituted olefin, or a $C_3$-$C_7$ carbocyclic, carbonate, or carbamate, wherein the nitrogen of said carbamate can be further substituted with a $C_1$-$C_6$ alkyl;

$R^{108}$ is selected from:
(a) $C_{1-6}$ alkyl, (b) $C_{2-6}$ alkenyl, and (c) $C_{2-6}$ alkynyl, wherein any of (a)-(c) optionally is substituted with one or more $R^{114}$ groups;

$R^{112}$ is selected from H, OH, and O$R^{114}$;
$R^{114}$, at each occurrence, independently is selected from:
(a) H, (b) $C_{1-6}$ alkyl, (c) $C_{2-6}$ alkenyl, (d) $C_{2-6}$ alkynyl, (e) $C_{6-10}$ saturated, unsaturated, or aromatic carbocycle, (f) 3-12 membered saturated, unsaturated, or aromatic heterocycle containing one or more heteroatoms selected from nitrogen, oxygen, and sulfur, (g) —C(O)—$C_{1-6}$ alkyl, (h) —C(O)—$C_{2-6}$ alkenyl, (i) —C(O)—$C_{2-6}$ alkynyl, (j) —C(O)—$C_{6-10}$ saturated, unsaturated, or aromatic carbocycle, (k) —C(O)-3-12 membered saturated, unsaturated, or aromatic heterocycle containing one or more heteroatoms selected from nitrogen, oxygen, and sulfur, (l) —C(O)O—$C_{1-6}$ alkyl, (m) —C(O)O—$C_{2-6}$ alkenyl, (n) —C(O)O—$C_{2-6}$ alkynyl, (o) —C(O)O—$C_{6-10}$ saturated, unsaturated, or aromatic carbocycle, (p) —C(O)O-3-12 membered saturated, unsaturated, or aromatic heterocycle containing one or more heteroatoms selected from nitrogen, oxygen, and sulfur, (q) —C(O)N$R^{116}R^{116}$, (r) —N$R^{116}$CO—C2-6 alkyl, (s) —N$R^{116}$CO—$C_{6-10}$ saturated, unsaturated, or aromatic carbocycle, and (t) —N$R^{116}$C(O)-3-12 membered saturated, unsaturated, or aromatic heterocycle containing one or more heteroatoms selected from nitrogen, oxygen, and sulfur wherein any of (b)-(t) optionally is substituted with one or more $R^{115}$ groups,
wherein one or more non-terminal carbon moieties of any of (b)-(d)
optionally is replaced with oxygen, S(O)$_p$, or —N$R^{116}$;

alternatively, N$R^{114}R^{114}$ forms a 3-7 membered saturated, unsaturated or aromatic ring including the nitrogen atom to which the $R^{114}$ groups are bonded and optionally one or more moieties selected from O, S(O)$_p$, N, and N$R^{118}$;

$R^{115}$ is selected from:
(a) $R^{117}$, (b) $C_{1-8}$ alkyl, (c) $C_{2-8}$ alkenyl, (d) $C_{2-8}$ alkynyl, (e) $C_{3-12}$ saturated, unsaturated, or aromatic carbocycle, and (f) 3-12 membered saturated, unsaturated, or aromatic heterocycle containing one or more heteroatoms selected from nitrogen, oxygen, and sulfur,
wherein any of (b)-(f) optionally is substituted with one or more $R^{117}$ groups;

$R^{116}$, at each occurrence, independently is selected from:
(a) H, (b) $C_{1-6}$ alkyl, (c) $C_{2-6}$ alkenyl, (d) $C_{2-6}$ alkynyl, (e) $C_{3-10}$ saturated, unsaturated, or aromatic carbocycle, and (f) 3-10 membered saturated, unsaturated, or aromatic heterocycle containing one or more heteroatoms selected from nitrogen, oxygen, and sulfur,
wherein one or more non-terminal carbon moieties of any of (b)-(d) optionally is replaced with oxygen, S(O)$_p$, or —N$R^{114}$, wherein any of (b)-(f) optionally is substituted with one or more moieties selected from:
(aa) carbonyl, (bb) formyl, (cc) F, (dd) Cl, (ee) Br, (ff) I, (gg) CN, (hh) N$_3$, (ii) NO$_2$, (jj) O$R^{118}$, (kk) —S(O)$_p R^{118}$, (ll) —C(O)$R^{118}$, (mm) —C(O)O$R^{118}$, (nn) —OC(O)$R^{118}$, (oo) —C(O)N$R^{118}R^{118}$, (pp) —OC(O)N$R^{118}R^{118}$, (qq) —C(=N$R^{118}$)$R^{118}$, (rr) —C($R^{118}$)($R^{118}$)O$R^{118}$, (ss) —C($R^{118}$)$_2$OC(O)$R^{118}$, (tt) —C($R^{118}$)(O$R^{118}$)(CH$_2$)$_r$N$R^{118}R^{118}$, (uu) —N$R^{118}R^{118}$; (vv) —N$R^{118}$O$R^{118}$, (ww) —N$R^{118}$C(O)$R^{118}$, (xx) —N$R^{118}$C(O)O$R^{118}$, (yy) —N$R^{118}$C(O)N$R^{118}R^{118}$, (zz) —N$R^{118}$S(O)$_r R^{118}$, (ab) —C(O$R^{118}$)(O$R^{118}$)$R^{118}$, (ac) —C($R^{118}$)$_2$N$R^{118}R^{118}$, (ad) =N$R^{118}$, (ae) —C(S)N$R^{118}R^{118}$, (af) —N$R^{118}$C(S)$R^{118}$, (ag) —OC(S)N$R^{118}R^{118}$, (ah) —N$R^{118}$C(S)O$R^{118}$, (ai) —N$R^{118}$C(S)N$R^{118}R^{118}$, (aj) —SC(O)$R^{118}$, (ak) $C_{1-8}$ alkyl, (al) $C_{2-8}$ alkenyl, (am) $C_{2-8}$ alkynyl, (an) $C_{1-8}$ alkoxy, (ao) $C_{1-8}$ alkylthio, (ap) $C_{1-8}$ acyl, (aq) saturated, unsaturated, or aromatic $C_{3-10}$ carbocycle, and (ar) saturated, unsaturated, or aromatic 3-10 membered heterocycle containing one or more heteroatoms selected from nitrogen, oxygen, and sulfur;

alternatively, N$R^{116}R^{116}$ forms a 3-10 membered saturated, unsaturated or aromatic ring including the nitrogen atom to which the $R^{116}$ groups are attached and optionally one or more moieties selected from O, S(O)$_p$, N, and N$R^{118}$;

alternatively, C$R^{116}R^{116}$ forms a carbonyl group;

$R^{117}$, at each occurrence, is selected from:
(a) H, (b) =O, (c) F, (d) Cl, (e) Br, (f) I, (g) $(CR^{116}R^{116})_rCF_3$, (h) $(CR^{116}R^{116})_rCN$, (i) $(CR^{116}R^{116})_rNO_2$, (j) $(CR^{116}R^{116})_rNR^{116}(CR^{116}R^{116})_rR^{119}$, (k) $(CR^{116}R^{116})_rOR^{119}$, (l) $(CR^{116}R^{116})_rS(O)_p(CR^{116}R^{116})_rR^{119}$, (m) $(CR^{116}R^{116})_rC(O)(CR^{116}R^{116})_rR^{119}$, (n) $(CR^{116}R^{116})_rOC(O)(CR^{116}R^{116})_rR^{119}$, (o) $(CR^{116}R^{116})_rSC(O)(CR^{116}R^{116})_rR^{119}$, (p) $(CR^{116}R^{116})_rC(O)O(CR^{116}R^{116})_rR^{119}$, (q) $(CR^{116}R^{116})_rNR^{116}C(O)(CR^{116}R^{116})_rR^{119}$, (r) $(CR^{116}R^{116})_rC(O)NR^{116}(CR^{116}R^{116})_rR^{119})$, (s) $(CR^{116}R^{116})_rC(=NR^{116})(CR^{116}R^{116})_rR^{119}$, (t) $(CR^{116}R^{116})_rC(=NNR^{116}R^{116})(CR^{116}R^{116})_rR^{119}$, (u) $(CR^{116}R^{116})_rC(=NNR^{116}C(O)R^{116})(CR^{116}R^{116})_rR^{119}$, (v) $(CR^{116}R^{116})_rC(=NOR^{119})(CR^{116}R^{116})_rR^{119}$, (w) $(CR^{116}R^{116})_rNR^{116}C(O)O(CR^{116}R^{116})_rR^{119}$, (x) $(CR^{116}R^{116})_rOC(O)NR^{116}(CR^{116}R^{116})_rR^{119}$, (y) $(CR^{116}R^{116})_rNR^{116}C(O)NR^{116}(CR^{116}R^{116})_rR^{116}$, (z) $(CR^{116}R^{116})_rNR^{116}S(O)_p(CR^{116}R^{116})_rR^{119}$, (aa) $(CR^{116}R^{116})_rS(O)_pNR^{116}(CR^{116}R^{116})_rR^{119}$, (bb) $(CR^{116}R^{116})_rNR^{116}S(O)_pNR^{116}(CR^{116}R^{116})_rR^{119}$, (cc) $(CR^{116}R^{116})_rNR^{116}R^{116}$, (dd) $C_{1-6}$ alkyl, (ee) $C_{2-6}$ alkenyl, (ff) $C_{2-6}$ alkynyl, (gg) $(CR^{116}R^{116})_r$—$C_{3-10}$ saturated, unsaturated, or aromatic carbocycle, and (hh) $(CR^{116}R^{116})_r$-3-10 membered saturated, unsaturated, or aromatic heterocycle containing one or more heteroatoms selected from nitrogen, oxygen, and sulfur,
wherein any of (dd)-(hh) optionally is substituted with one or more $R^{119}$ groups;
alternatively, two $R^{117}$ groups form —$O(CH_2)_uO$—;

$R^{118}$ is selected from:
(a) H, (b) $C_{1-6}$ alkyl, (c) $C_{2-6}$ alkenyl, (d) $C_{2-6}$ alkynyl, (e) $C_{3-10}$ saturated, unsaturated, or aromatic carbocycle, (f) 3-10 membered saturated, unsaturated, or aromatic heterocycle containing one or more heteroatoms selected from -nitrogen, oxygen, and sulfur, (g) —C(O)—$C_{1-6}$ alkyl, (h) —C(O)—$C_{1-6}$ alkenyl, (i) —C(O)—$C_{1-6}$ alkynyl, (j) —C(O)—$C_{3-10}$ saturated, unsaturated, or aromatic carbocycle, and (k) —C(O)-3-10 membered saturated, unsaturated, or aromatic heterocycle containing one or more heteroatoms selected from nitrogen, oxygen, and sulfur,
wherein any of (b)-(k) optionally is substituted with one or more moieties selected from: (aa) H, (bb) F, (cc) Cl, (dd) Br, (ee) I, (ff) CN, (gg) $NO_2$, (hh) OH, (ii) $NH_2$, (jj) $NH(C_{1-6}$ alkyl), (kk) $N(C_{1-6}$ alkyl$)_2$, (ll) $C_{1-6}$ alkoxy, (mm) aryl, (nn) substituted aryl, (oo) heteroaryl, (pp) substituted heteroaryl, and (qq) $C_{1-6}$ alkyl, optionally substituted with one or more moieties selected from -aryl, substituted aryl, heteroaryl, substituted heteroaryl, F, Cl, Br, I, CN, $NO_2$, and OH;

$R^{119}$, at each occurrence, independently is selected from:
(a) $R^{120}$, (b) $C_{1-6}$ alkyl, (c) $C_{2-6}$ alkenyl, (d) $C_{2-6}$ alkynyl, (e) $C_{3-10}$ saturated, unsaturated, or aromatic carbocycle, and (f) 3-10 membered saturated, unsaturated, or aromatic heterocycle containing one or more heteroatoms selected from -nitrogen, oxygen, and sulfur;

$R^{120}$, at each occurrence, independently is selected from:
(a) H, (b) =O, (c) F, (d) Cl, (e) Br, (f) I, (g) $(CR^{116}R^{116})_rCF_3$, (h) $(CR^{116}R^{116})_rCN$, (i) $(CR^{116}R^{116})_rNO_2$, (j) $(CR^{116}R^{116})_rNR^{116}R^{116}$, (k) $(CR^{116}R^{116})_rOR^{114}$, (l) $(CR^{116}R^{116})_rS(O)_pR^{116}$, (m) $(CR^{116}R^{116})_rC(O)R^{116}$, (n) $(CR^{116}R^{116})_rC(O)OR^{116}$, (o) $(CR^{116}R^{116})_rOC(O)R^{116}$, (p) $(CR^{116}R^{116})_rNR^{116}C(O)R^{116}$, (q) $(CR^{116}R^{116})_rC(O)NR^{116}R^{116}$, (r) $(CR^{116}R^{116})_rC(=NR^{116})R^{116}$, (s) $(CR^{116}R^{116})_rNR^{116}C(O)NR^{116}R^{116}$, (t) $(CR^{116}R^{116})_rNR^{116}S(O)_pR^{116}$, (u) $(CR^{116}R^{116})_rS(O)_pNR^{116}R^{116}$, (v) $(CR^{116}R^{116})_rNR^{116}S(O)_pR^{116}$, (w) $C_{1-6}$ alkyl, (x) $C_{2-6}$ alkenyl, (y) $C_{2-6}$ alkynyl, (z) $(CR^{116}R^{116})_r$—$C_{3-10}$ saturated, unsaturated, or aromatic carbocycle, and (aa) $(CR^{116}R^{116})_r$-3-10 membered saturated, unsaturated, or aromatic heterocycle containing one or more heteroatoms selected from -nitrogen, oxygen, and sulfur,
wherein any of (w)-(aa) optionally is substituted with one or more moieties selected from: $R^{116}$, F, Cl, Br, I, CN, $NO_2$, —$OR^{116}$, —$NH_2$, —$NH(C_{1-6}$ alkyl), —$N(C_{1-6}$ alkyl$)_2$, $C_{1-6}$ alkoxy, $C_{1-6}$ alkylthio, and $C_{1-6}$ acyl;

$R^{121}$, at each occurrence, independently is selected from:
(a) H, (b) —$OR^{118}$, (c) —O—$C_{1-6}$ alkyl-$OC(O)R^{118}$, (d) —O—$C_{1-6}$ alkyl-$OC(O)OR^{118}$, (e) —O—$C_{1-6}$alkyl-$OC(O)NR^{118}R^{118}$, (f) —O—$C_{1-6}$ alkyl-$C(O)NR^{118}R^{118}$, (g) —O—$C_{1-6}$ alkyl-$NR^{118}C(O)R^{118}$, (h) —O—$C_{1-6}$ alkyl-$NR^{118}C(O)OR^{118}$, (i) —O—$C_{1-6}$ alkyl-$NR^{118}C(O)NR^{118}R^{118}$, (j) —O—$C_{1-6}$ alkyl-$NR^{118}C(=N(H)NR^{118}R^{118}$, (k) —O—$C_{1-6}$ alkyl-$S(O)_pR^{118}$, (l) —O—$C_{2-6}$ alkenyl-$OC(O)R^{118}$, (m) —O—$C_{2-6}$ alkenyl-$OC(O)OR^{118}$, (n) —O—$C_{2-6}$ alkenyl-$OC(O)NR^{118}R^{118}$, (o) —O—$C_{2-6}$ alkenyl-$C(O)NR^{118}R^{118}$, (p) —O—$C_{2-6}$ alkenyl-$NR^{118}C(O)R^{118}$, (q) —O—$C_{2-6}$ alkenyl-$NR^{118}C(O)OR^{118}$, (r) —O—$C_{2-6}$ alkenyl-$NR^{118}C(O)NR^{118}R^{118}$, (s) —O—$C_{2-6}$ alkenyl-$NR^{118}C(=N(H)NR^{118}R^{118}$, (t) —O—$C_{2-6}$ alkenyl-$S(O)_pR^{118}$, (u) —O—$C_{2-6}$ alkynyl-$OC(O)R^{118}$, (v) —O—$C_{2-6}$ alkynyl-$OC(O)OR^{118}$, (w) —O—$C_{2-6}$ alkynyl-$OC(O)NR^{118}R^{118}$, (x) —O—$C_{2-6}$ alkynyl-$C(O)NR^{118}R^{118}$, (y) —O—$C_{2-6}$ alkynyl-$NR^{118}C(O)R^{118}$, (z) —O—$C_{2-6}$ alkynyl-$NR^{118}C(O)OR^{118}$, (aa) —O—$C_{2-6}$ alkynyl-$NR^{118}C(O)NR^{118}R^{118}$, (bb) —O—$C_{2-6}$ alkynyl-$NR^{118}C(=N(H)NR^{118}R^{118}$, (cc) —O—$C_{2-6}$ alkynyl-$S(O)_pR^{118}$; and (dd) —$NR^{118}R^{118}$;
alternatively, two $R^{121}$ groups taken together form =O, =$NOR^{118}$, or =$NNR^{118}R^{118}$;

$R^{109}$ is H or F;

$R^{127}$ is $R^{114}$, a monosaccharide or disaccharide (including amino sugars and halo sugar(s)), —$(CH_2)_n$—(O—$CH_2CH_2$—)$_m$—O$(CH_2)_pCH_3$, or —$(CH_2)_n$—(O—$CH_2CH_2$—)$_m$—OH;

$R^{128}$ is $R^{114}$;
$R^{129}$ is $R^{114}$;
$R^{110}$ is $R^{114}$;

alternatively, $R^{109}$ and $R^{110}$ taken together with the carbons to which they are attached form:

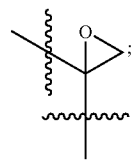

alternatively, $R^{128}$ and $R^{129}$ together with the carbons to which they are attached form a 3-6 membered saturated, unsaturated or aromatic carbocyclic or heterocyclic ring which can optionally be substituted with one or more $R^{114}$ groups;

387

$R^{132}$, $R^{133}$, and $R^{134}$ are each independently selected from: (a) H, (b) F, (c) Cl, (d) Br, (e) —$OR^{114}$, (f) —$SR^{114}$, (g) —$NR^{114}R^{114}$, and (h) $C_{1-6}$ alkyl, wherein (h) optionally is substituted with one or more $R^{115}$ groups;

alternatively, $R^{132}$ and $R^{133}$ taken together form a carbon-carbon double bond;

alternatively, $R^{133}$ and $R^{134}$ taken together form =O, =S, =$NOR^{114}$, =$NR^{114}$, and =N—$NR^{114}R^{114}$;

alternatively, $R^{105}$ and $R^{134}$ taken together with the carbons to which they are attached form a 3-membered ring, said ring optionally containing an oxygen or nitrogen atom, and said ring being optionally substituted with one or more $R^{114}$ groups;

alternatively, when M is a carbon moiety, $R^{134}$ and M taken together form a carbon-carbon double bond;

k, at each occurrence is 0, 1, or 2;

m, at each occurrence is 0, 1, 2, 3, 4, or 5;

n, at each occurrence is 1, 2, or 3;

p at each occurrence is 0, 1, or 2;

r at each occurrence is 0, 1, or 2;

t at each occurrence is 0, 1, or 2; and u at each occurrence is 1, 2, 3, or 4.

17. The compound according to claim 16, or a pharmaceutically acceptable salt, ester, or N-oxide thereof, wherein T is selected from:

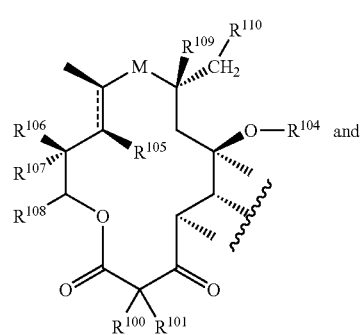

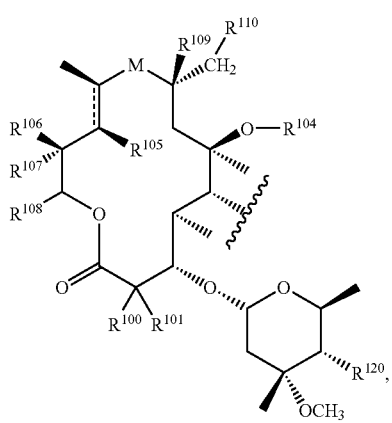

where the dotted lines indicate optional double bonds.

388

18. The compound according to claim 16, or a pharmaceutically acceptable salt, ester, or N-oxide thereof, wherein T is selected from:

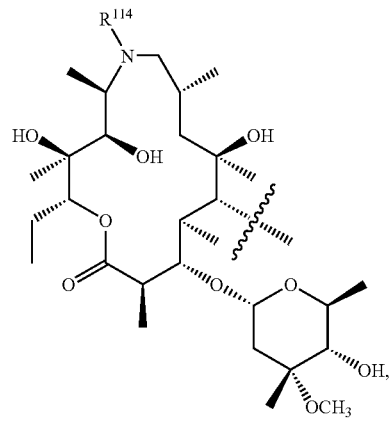

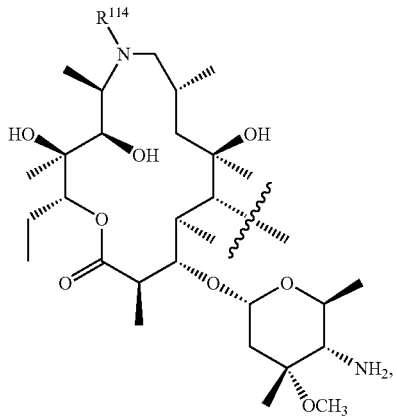

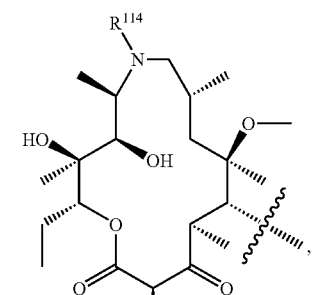

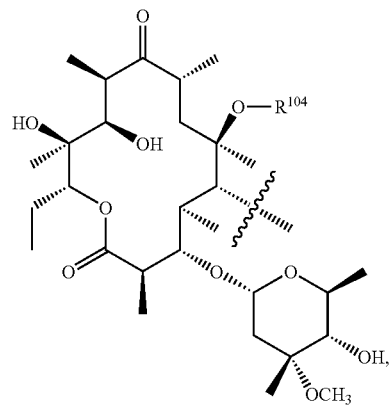

389
-continued
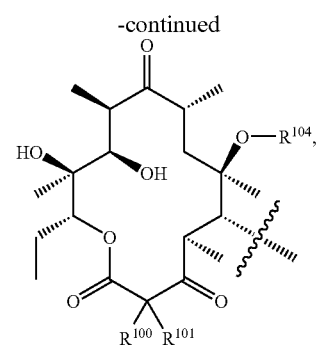
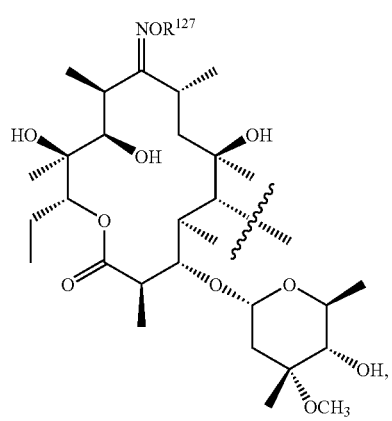
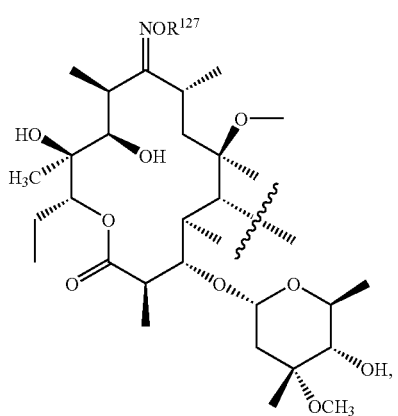
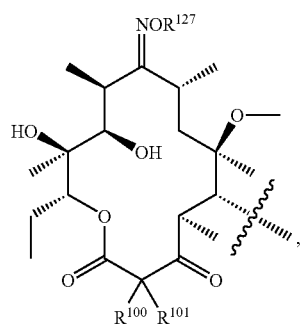
390
-continued
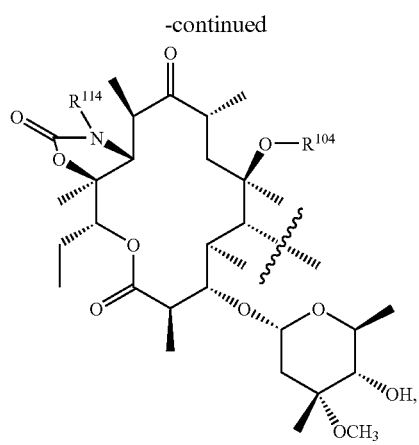
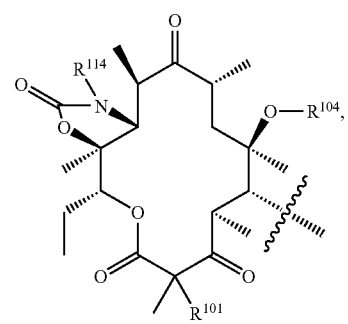
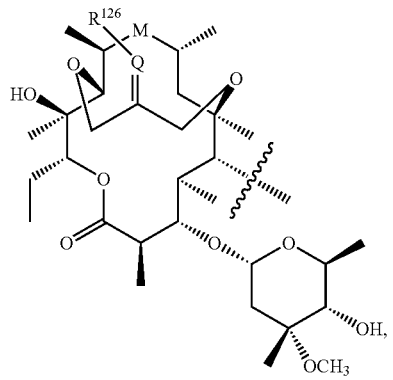
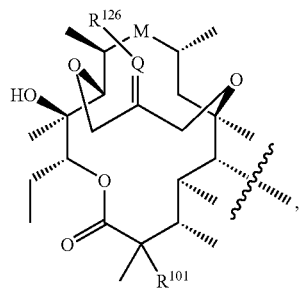

-continued
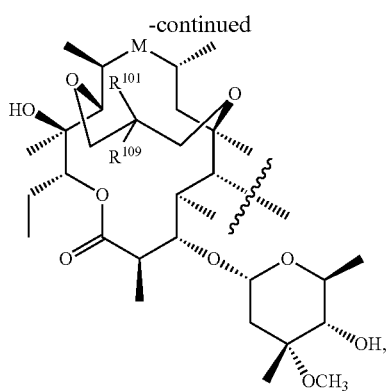
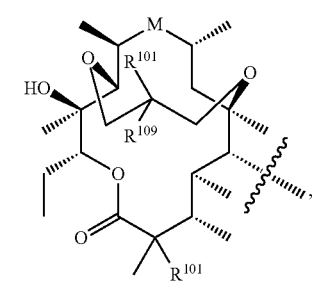
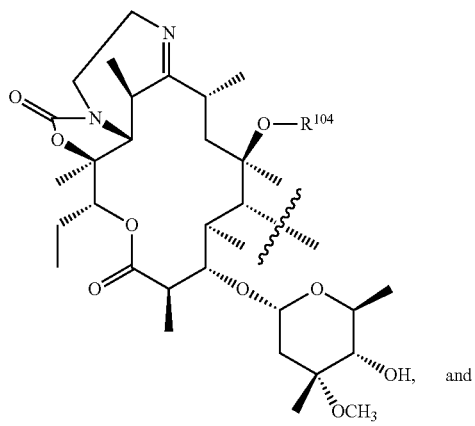
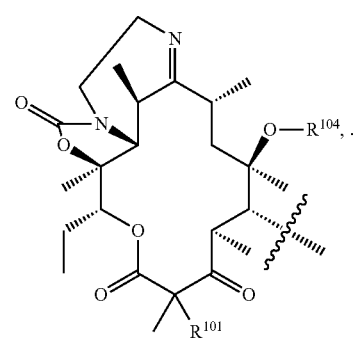
19. A compound according to claim 1, or a pharmaceutically acceptable salt, ester, or N-oxide thereof, wherein T is selected from T1 through T33:
T1
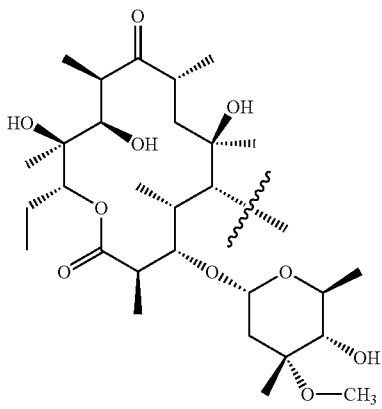
T2
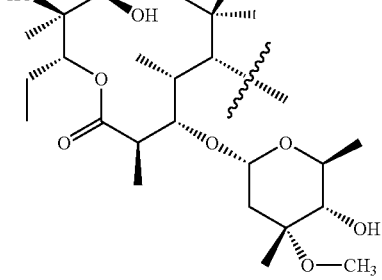
T3
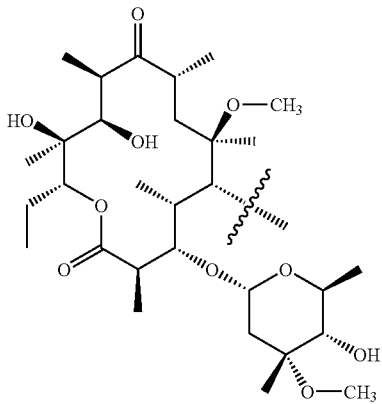
T4
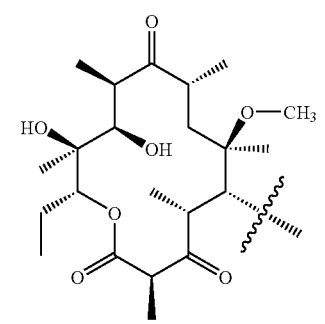

393
-continued
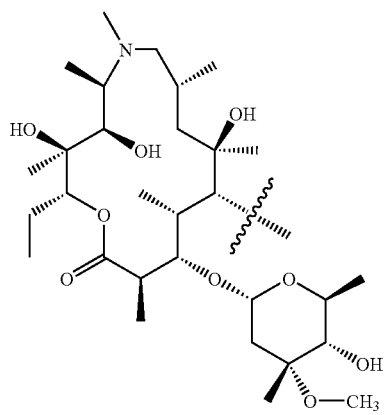
T5
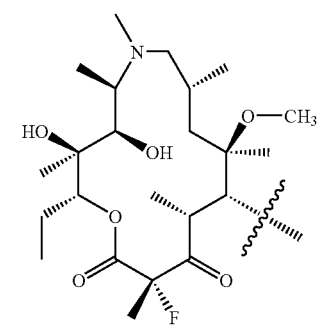
T6
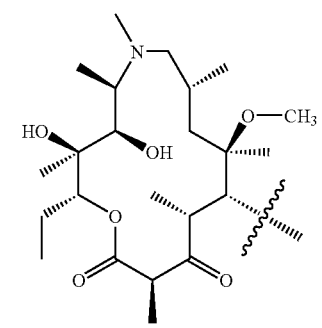
T7
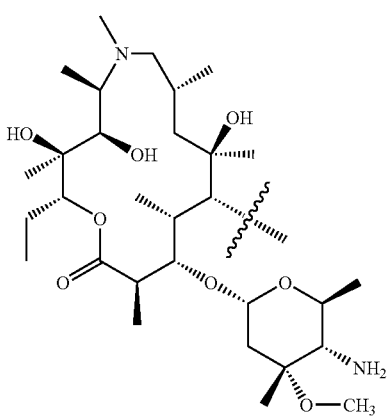
T8
394
-continued
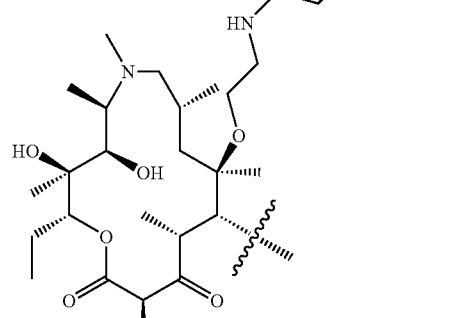
T9
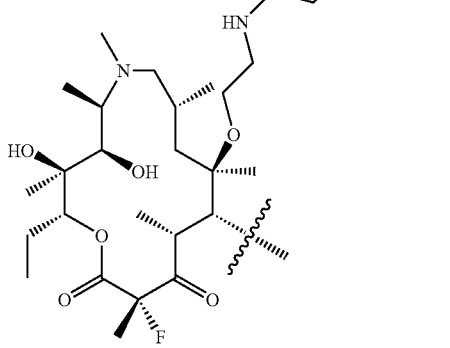
T10
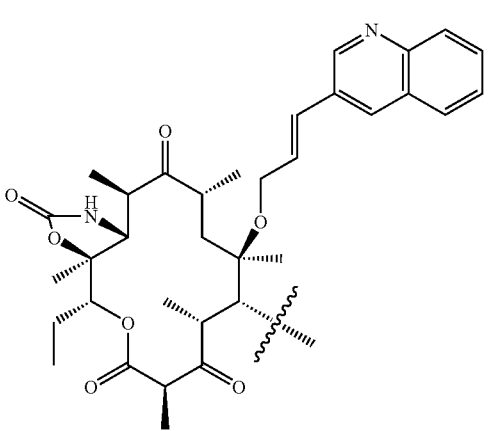
T11
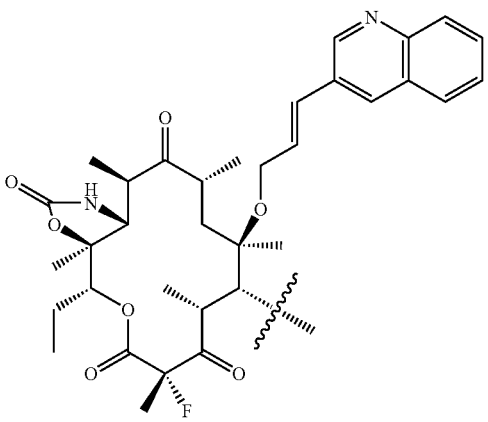
T12

T13
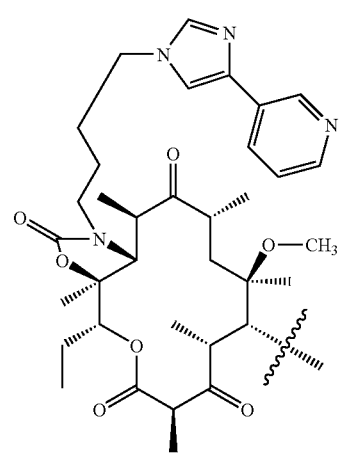
T14
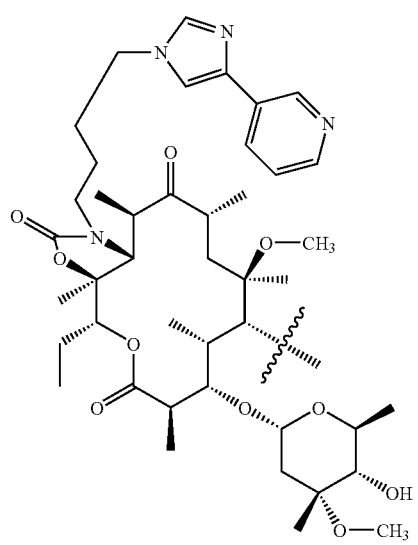
T15
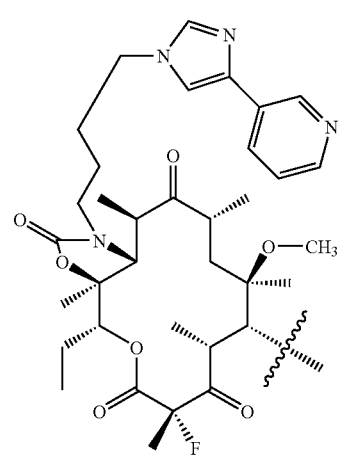
T16
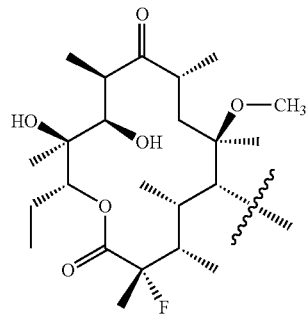
T17
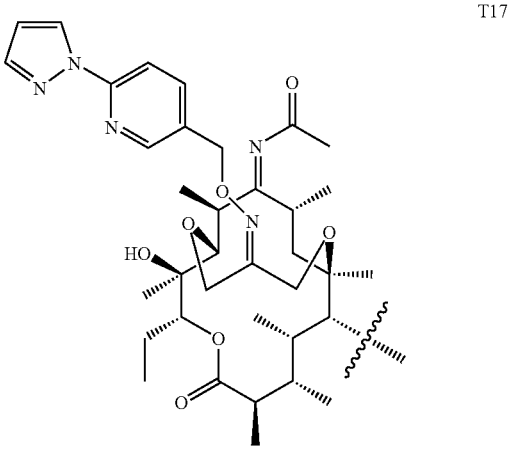
T18
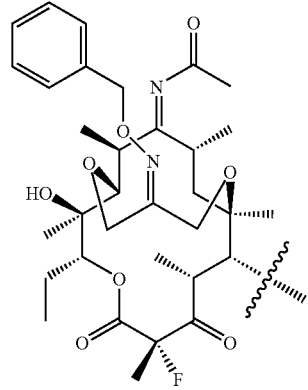
T19
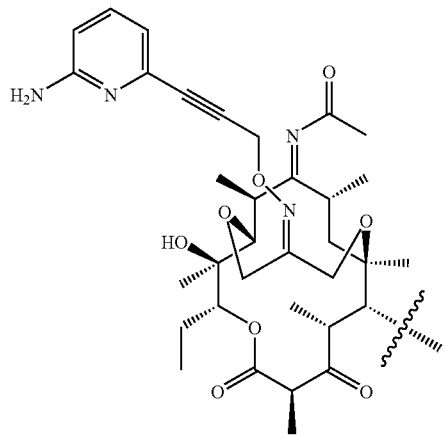

397
-continued
T20
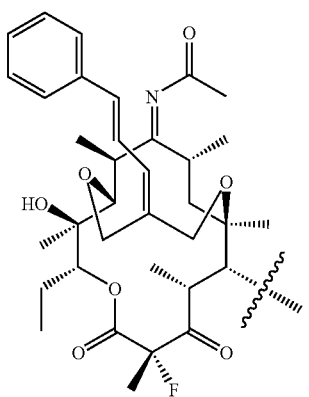
T21
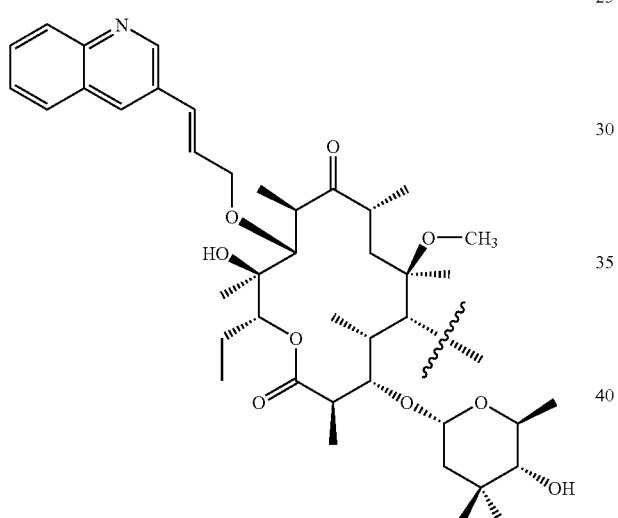
T22
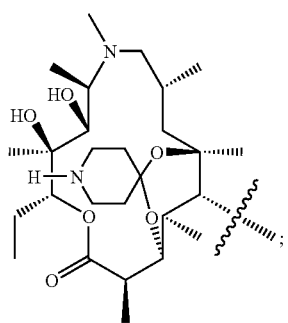
398
-continued
T23
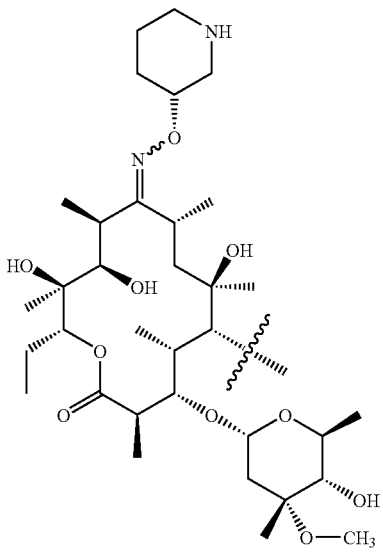
T24
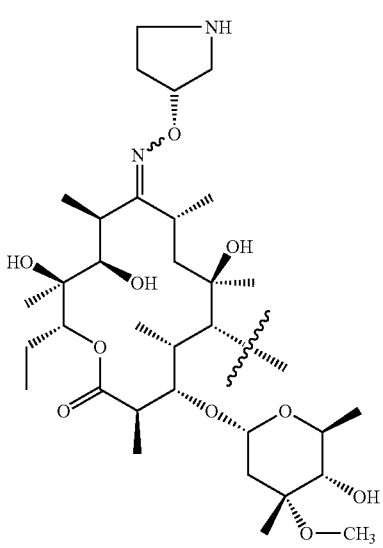
T25
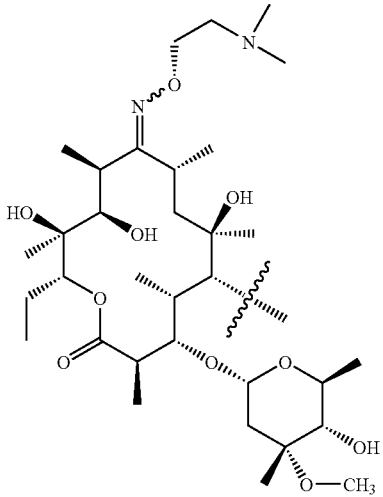

399
-continued
400
-continued
T26
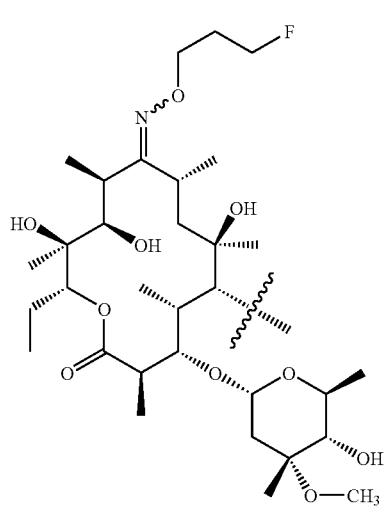
T29
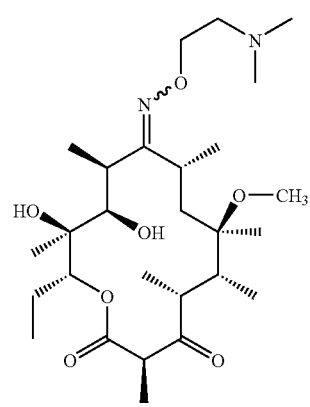
T27
T30
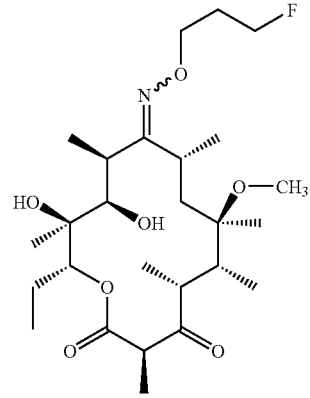
T28
T31
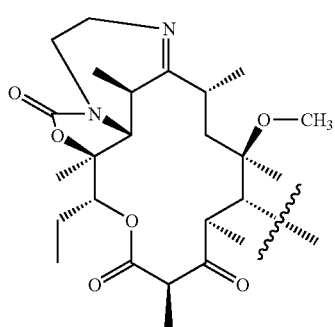

| | |
|---|---|
| T32 | 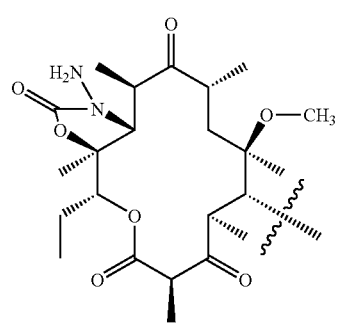 |
| T33 | 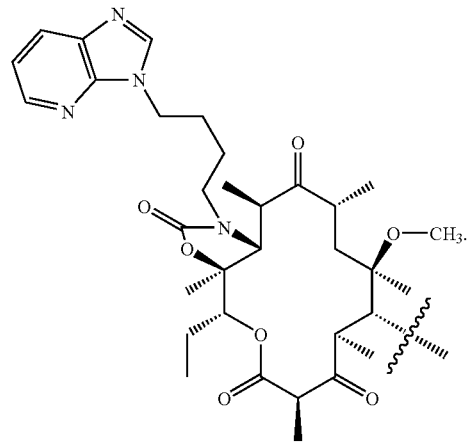 |
20. A compound selected from:
| Compound No. | Structure |
|---|---|
| 101 | 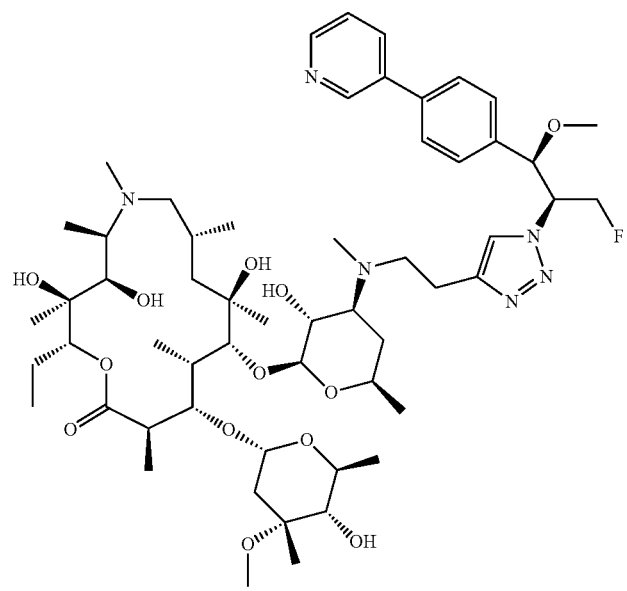 |

| Compound No. | Structure |
|---|---|
| 102 | 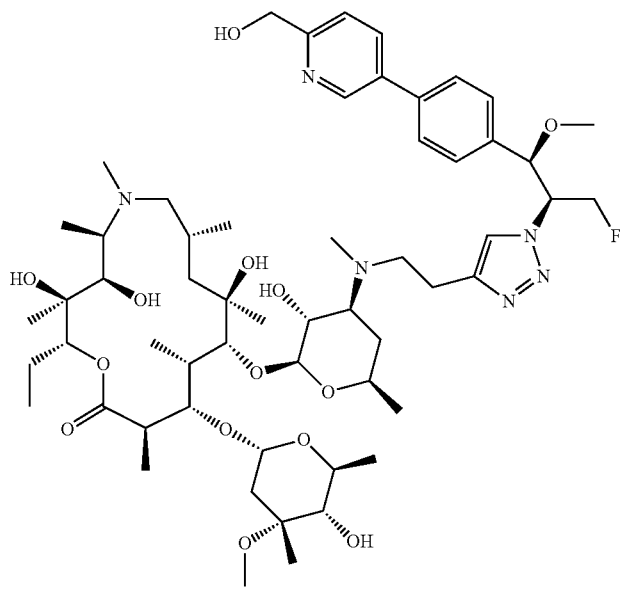 |
| 103 | 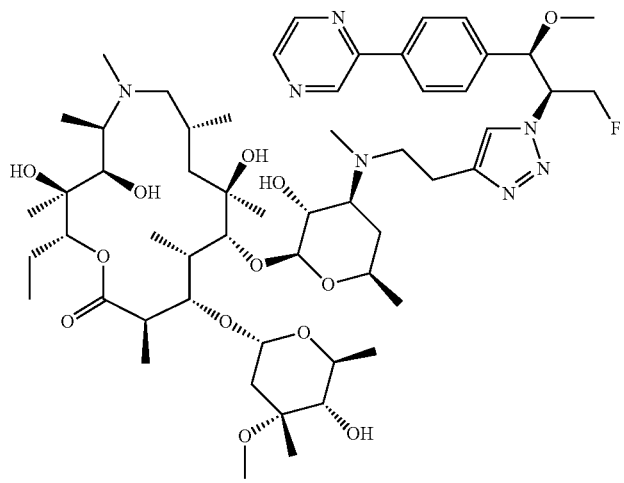 |
| 104 | 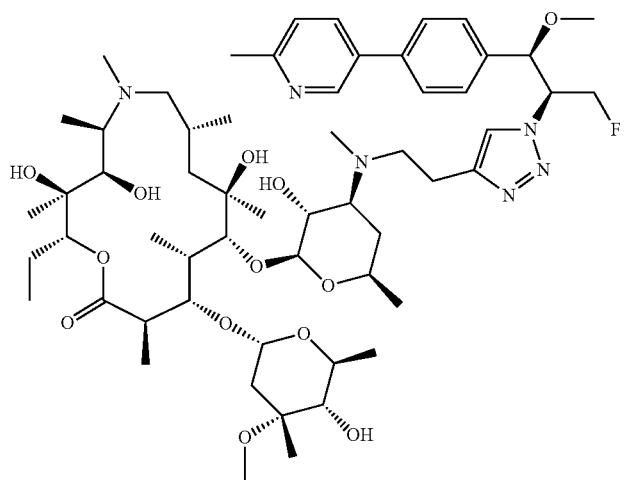 |

-continued
| Compound No. | Structure |
|---|---|
| 105 | 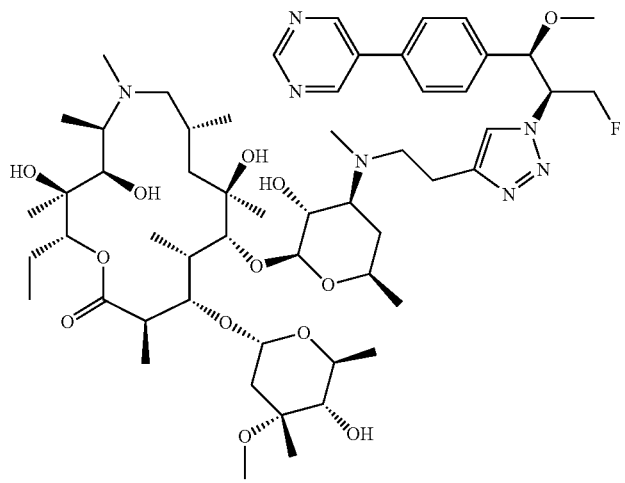 |
| 106 | 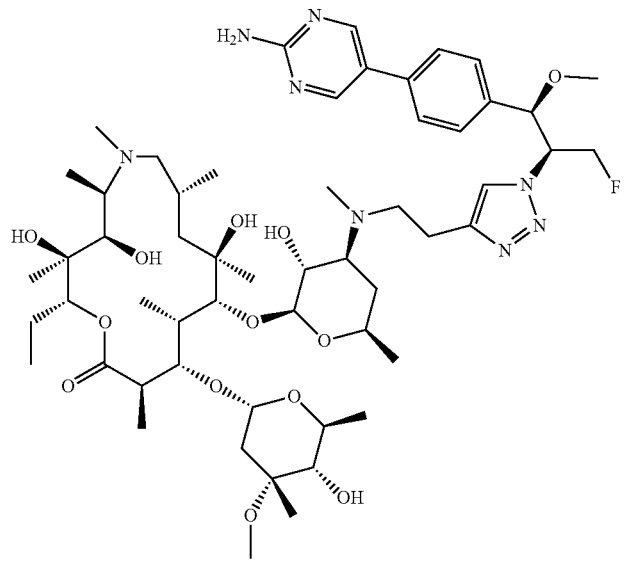 |
| 107 | 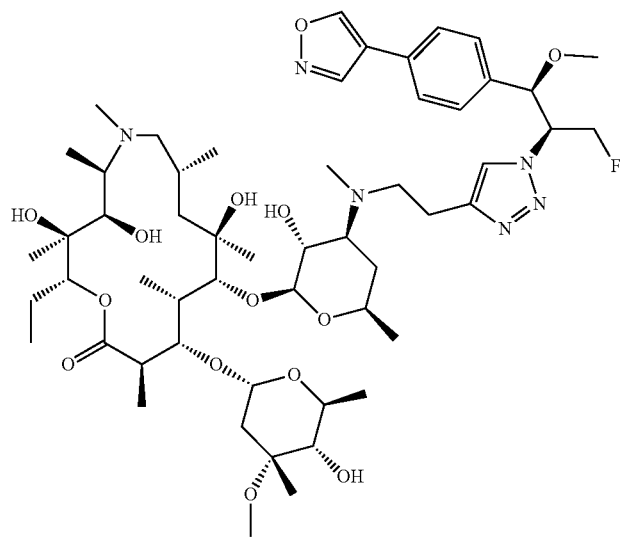 |

-continued
| Compound No. | Structure |
|---|---|
| 108 | 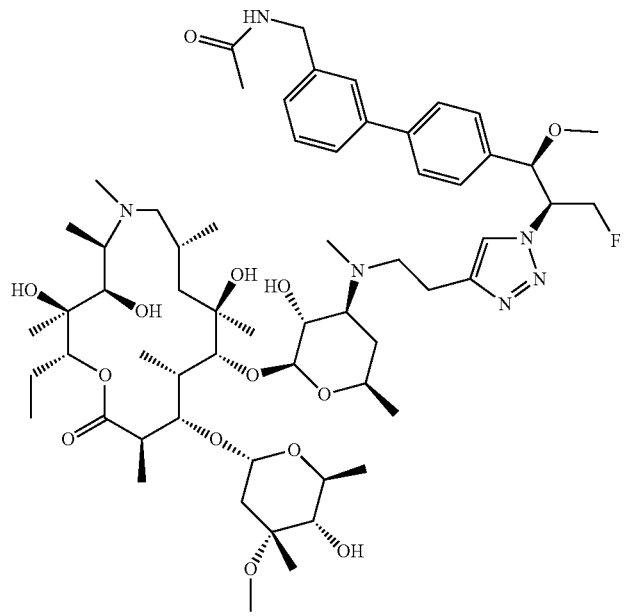 |
| 109 | 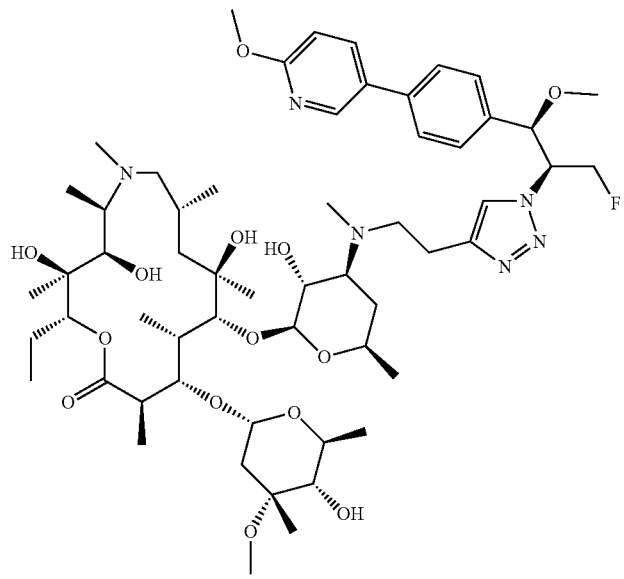 |

-continued
| Compound No. | Structure |
|---|---|
| 110 | 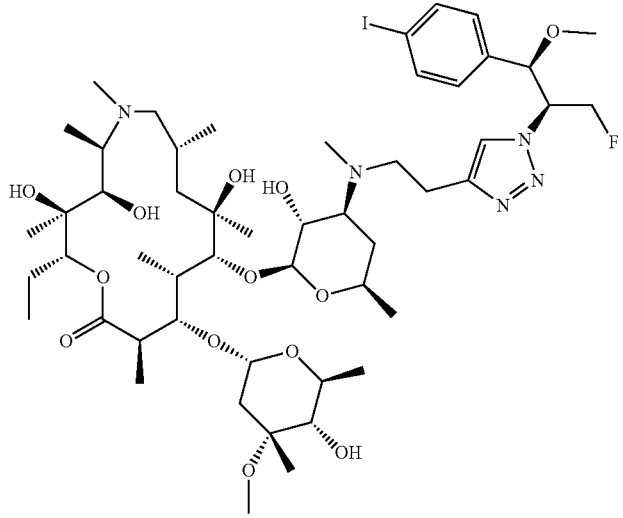 |
| 111 | 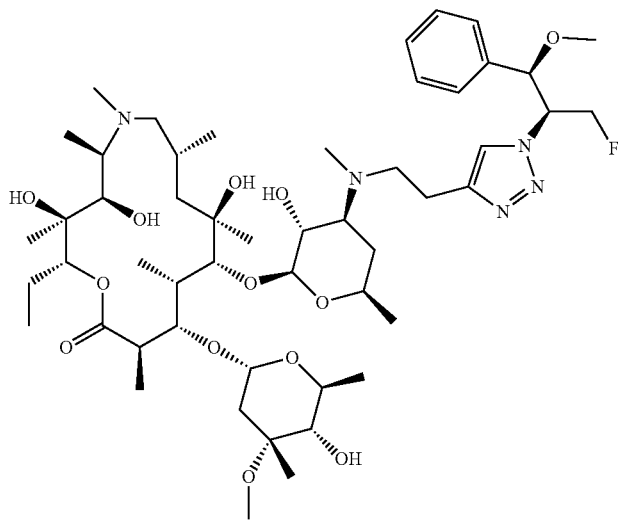 |
| 112 | 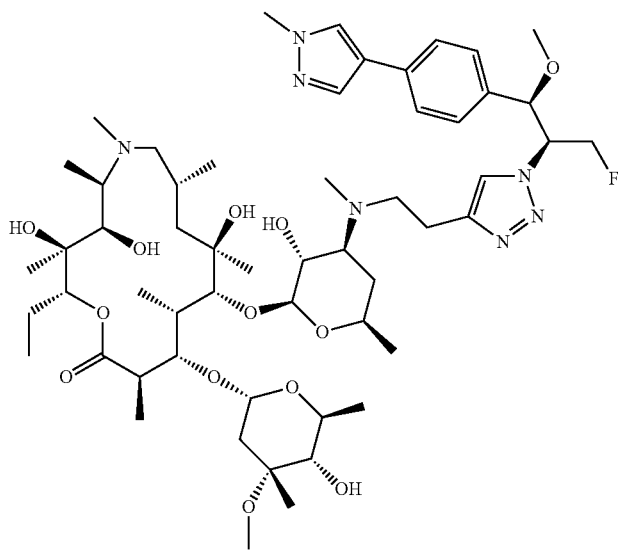 |

-continued
| Compound No. | Structure |
|---|---|
| 113 | 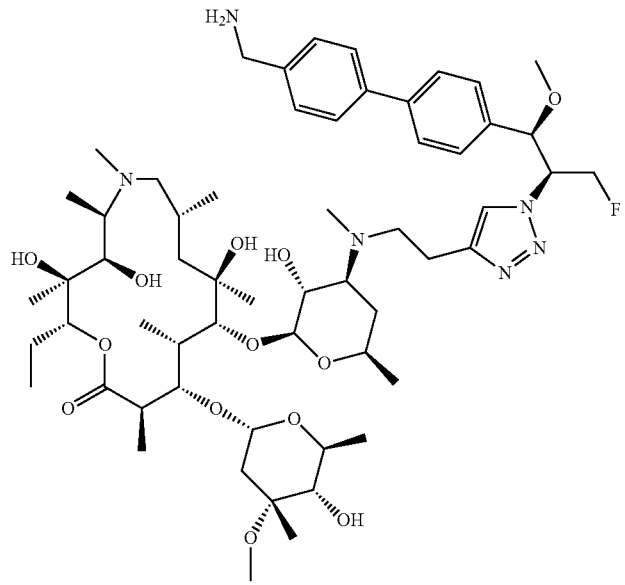 |
| 114 | 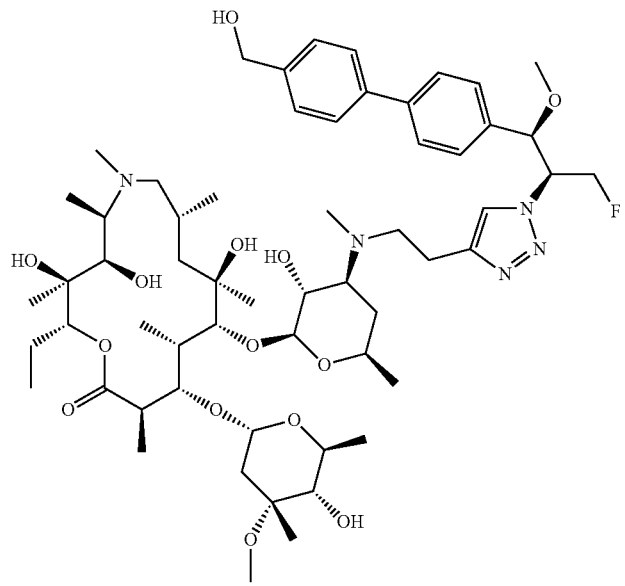 |
| 115 | 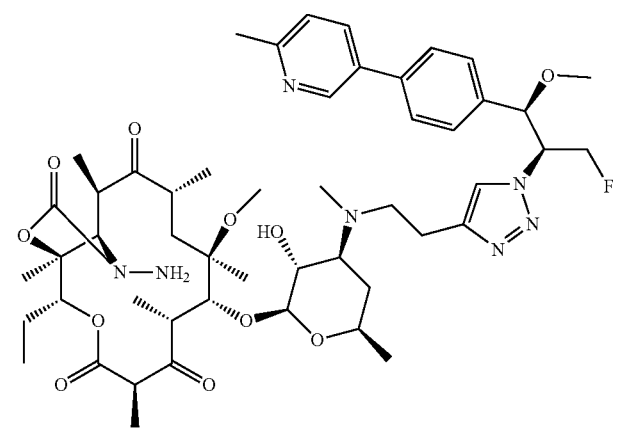 |

-continued
| Compound No. | Structure |
|---|---|
| 116 | 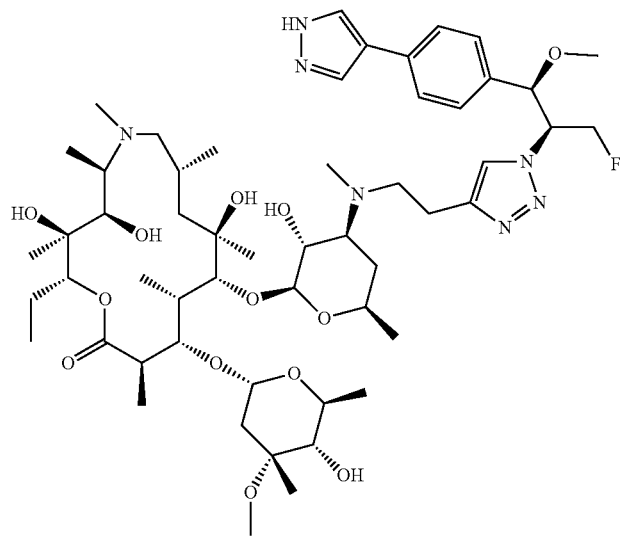 |
| 117 | 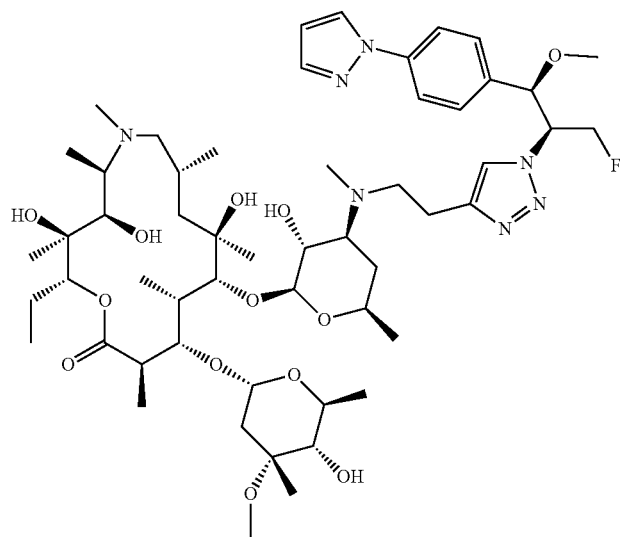 |
| 118 | 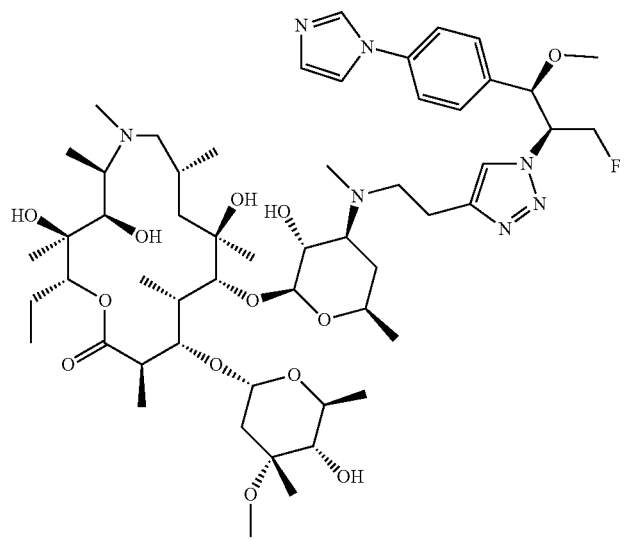 |

-continued
| Compound No. | Structure |
|---|---|
| 119 | 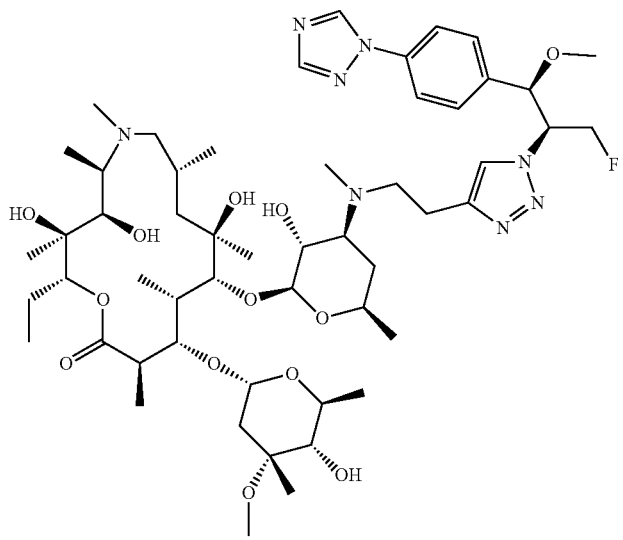 |
| 120 | 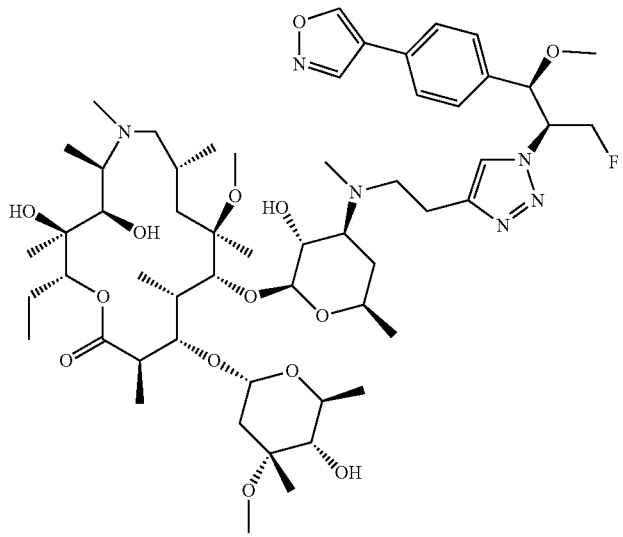 |

-continued
| Compound No. | Structure |
|---|---|
| 121 | 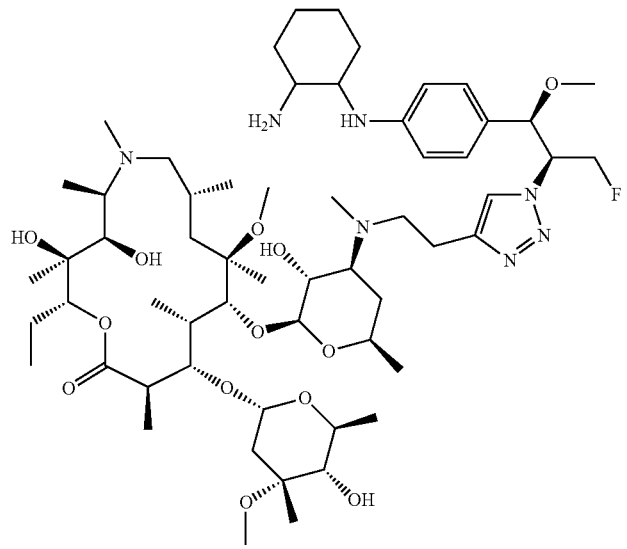 |
| 122 | 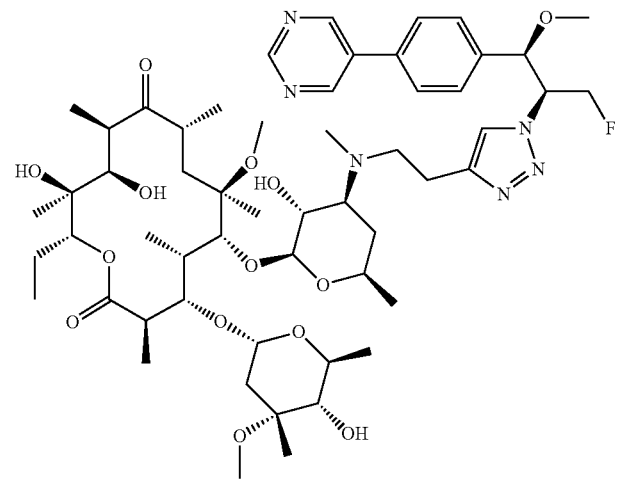 |
| 123 | 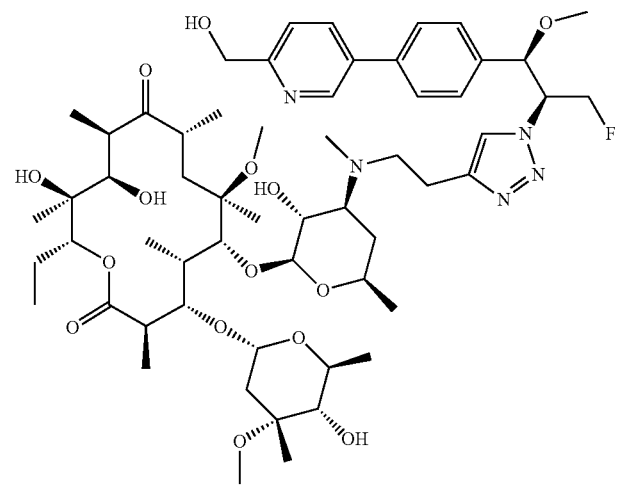 |

| Compound No. | Structure |
|---|---|
| 124 | 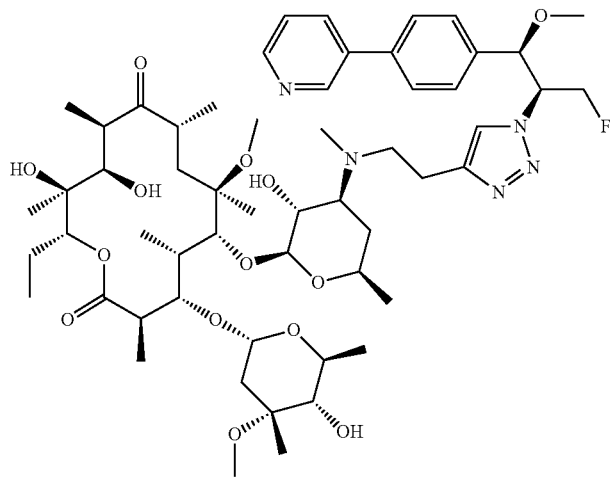 |
| 125 | 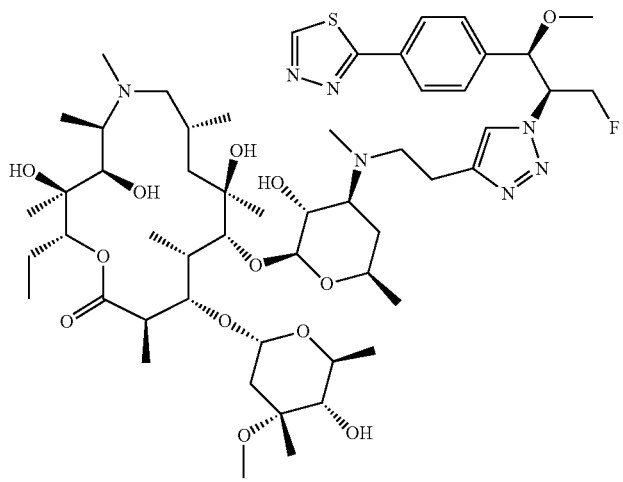 |
| 126 | 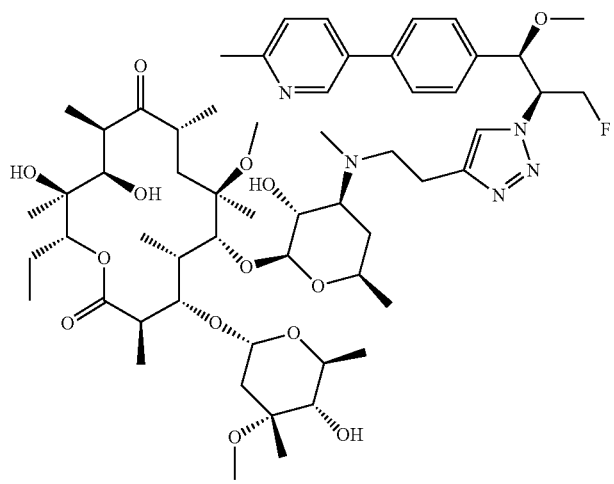 |

| Compound No. | Structure |
|---|---|
| 127 | 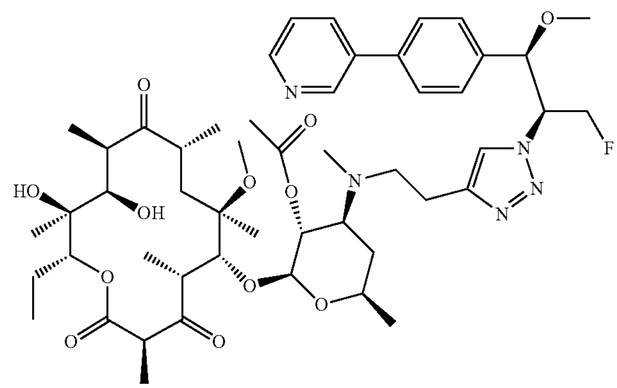 |
| 128 | 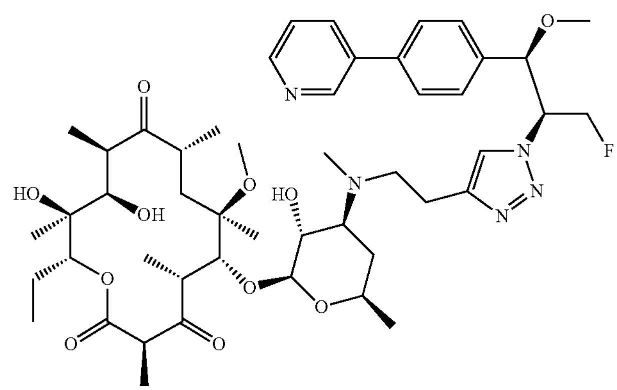 |
| 129 | 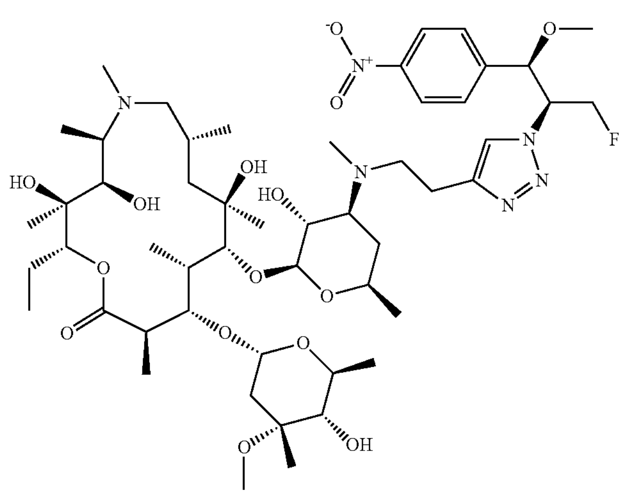 |

-continued
| Compound No. | Structure |
|---|---|
| 130 | 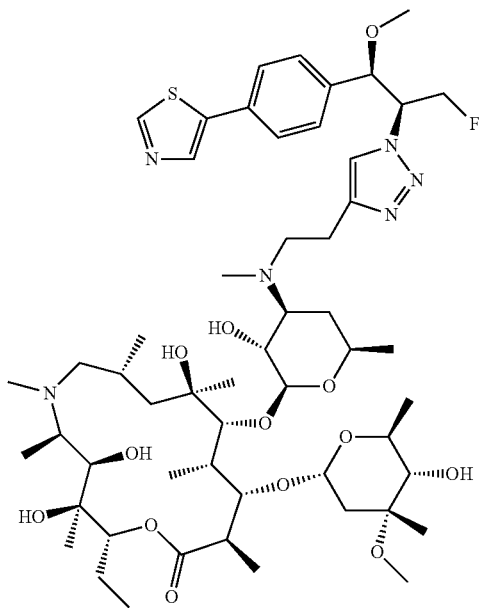 |
| 131 | 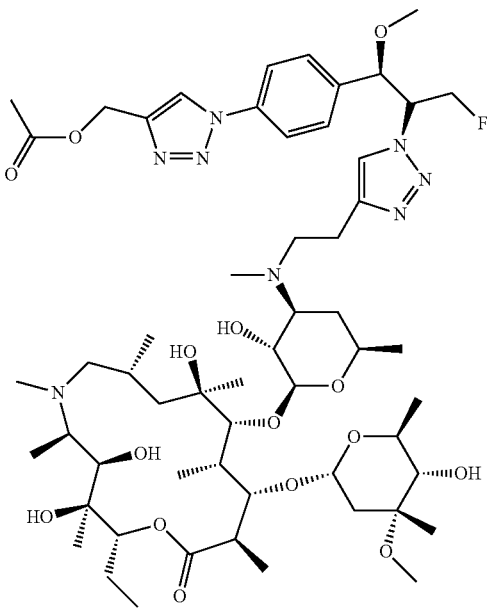 |

-continued

| Compound No. | Structure |
|---|---|
| 132 | 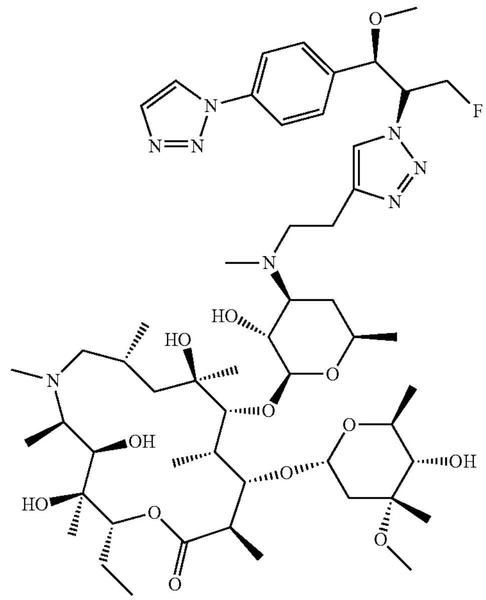 |
| 133 | 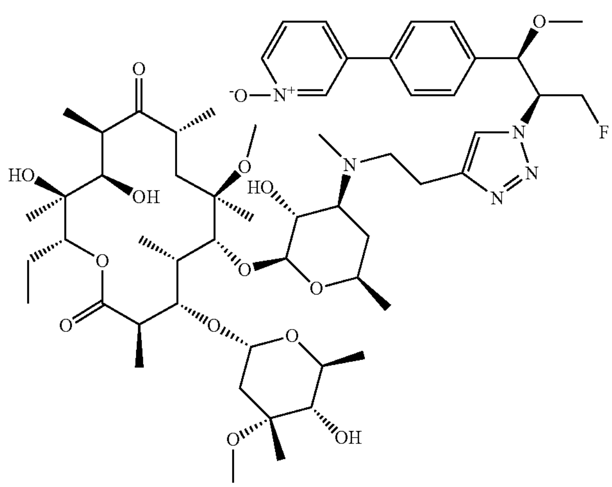 |
| 134 | 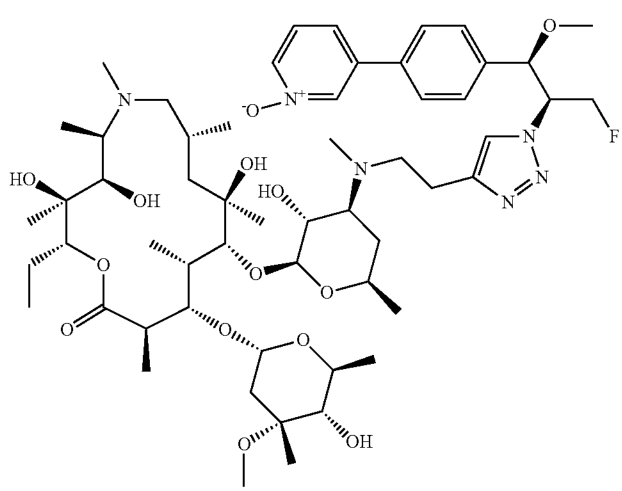 |

-continued
| Compound No. | Structure |
|---|---|
| 135 | 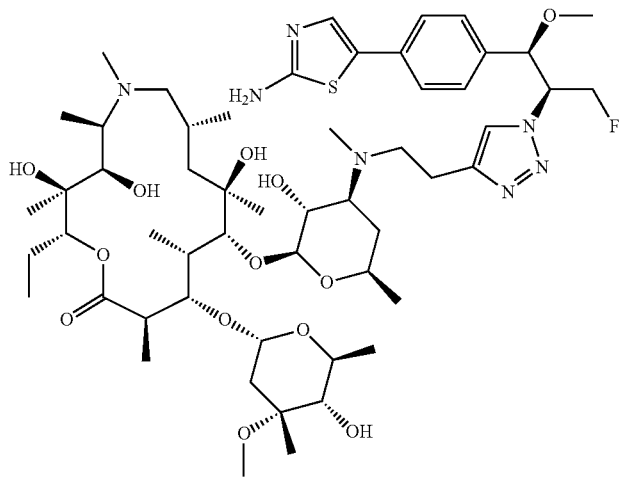 |
| 136 | 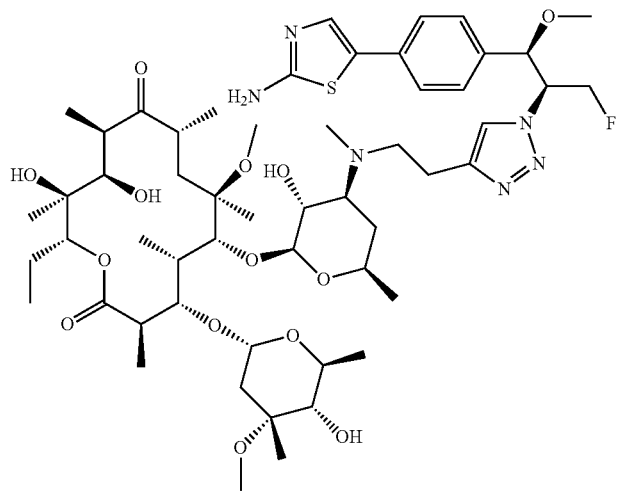 |
| 137 | 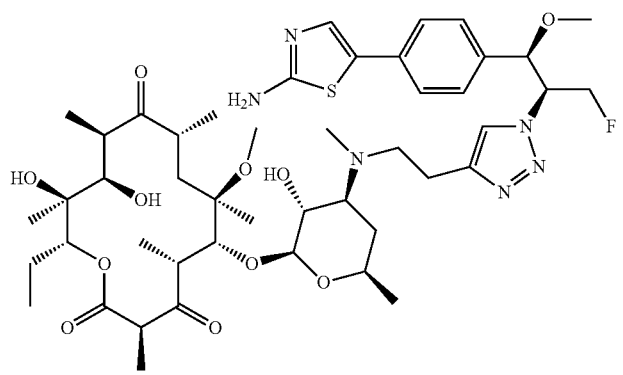 |

| Compound No. | Structure |
|---|---|
| 138 | 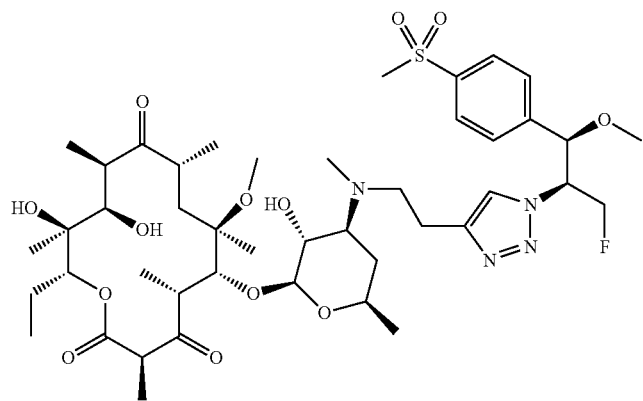 |
| 139 | 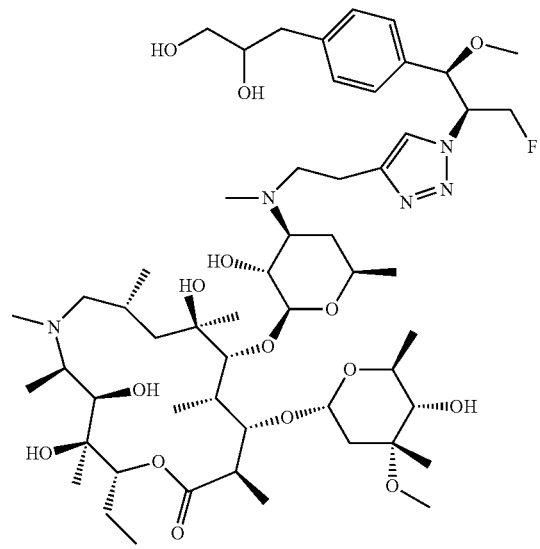 |
| 140 | 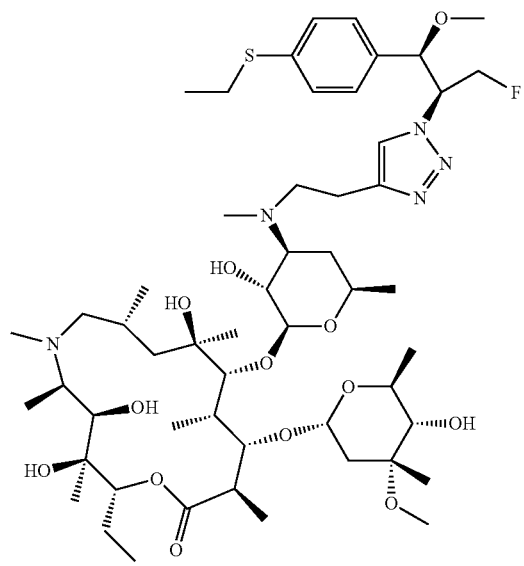 |

-continued
| Compound No. | Structure |
|---|---|
| 141 | 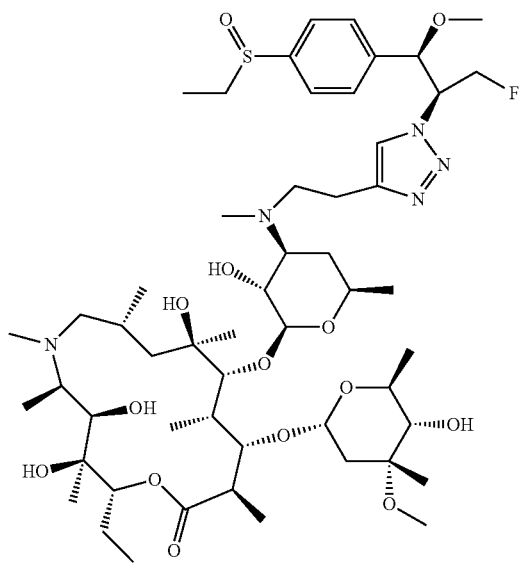 |
| 142 | 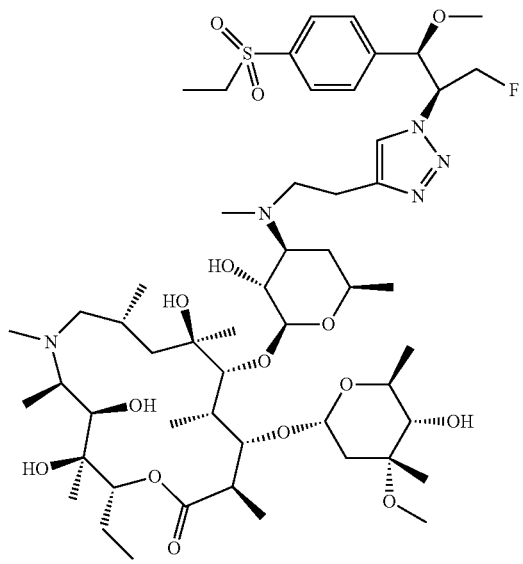 |

| Compound No. | Structure |
|---|---|
| 143 | 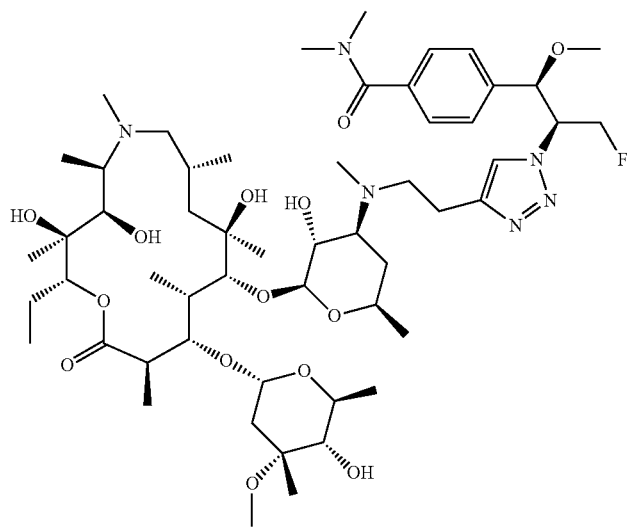 |
| 144 | 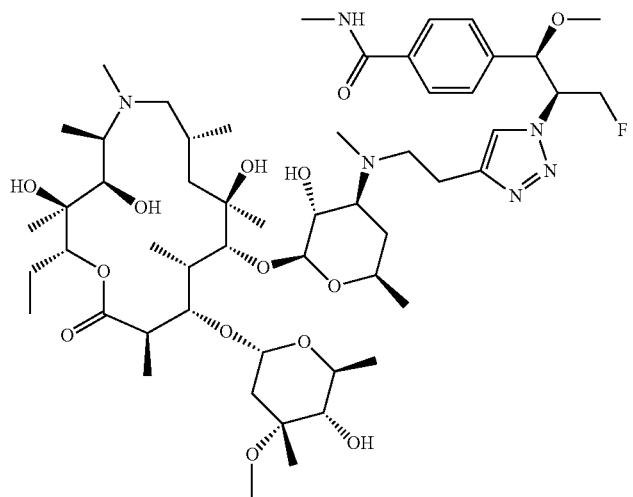 |
| 145 | 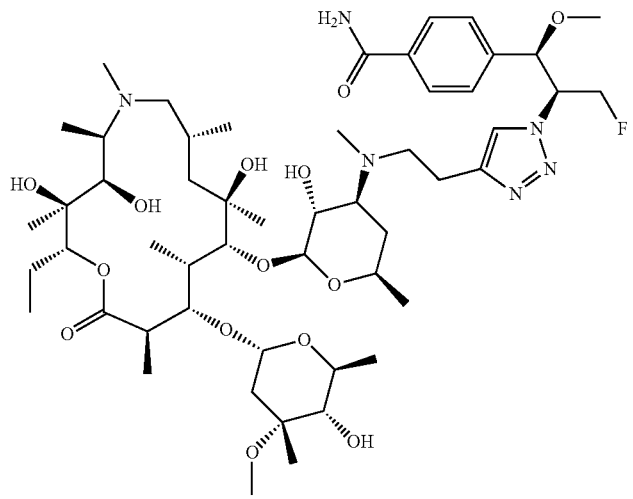 |

| Compound No. | Structure |
|---|---|
| 146 | 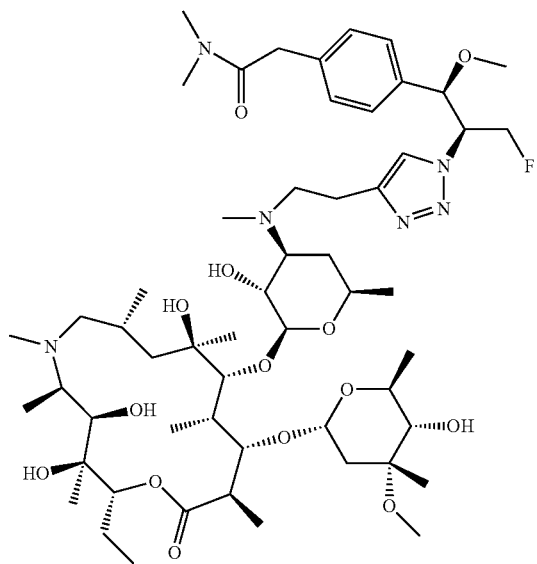 |
| 147 | 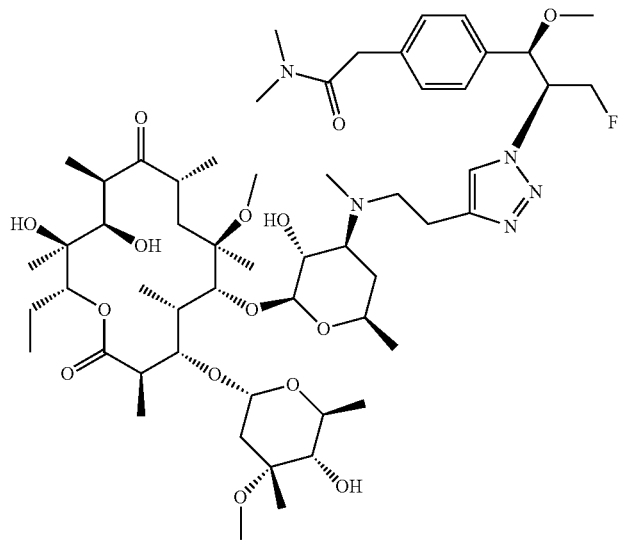 |

-continued
| Compound No. | Structure |
|---|---|
| 148 | 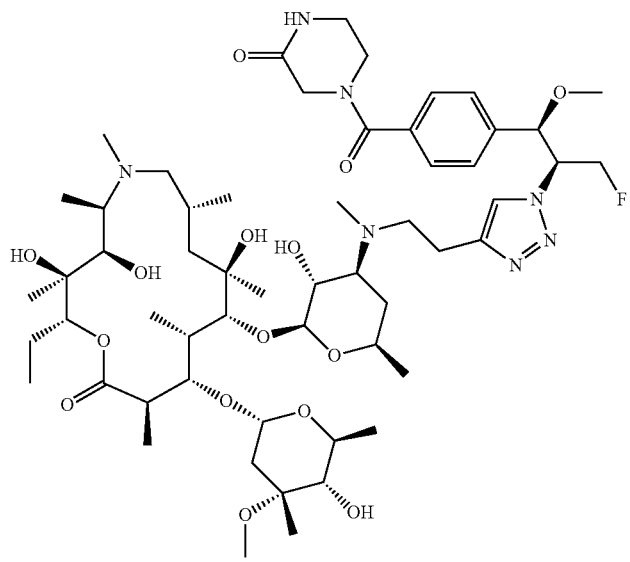 |
| 149 | 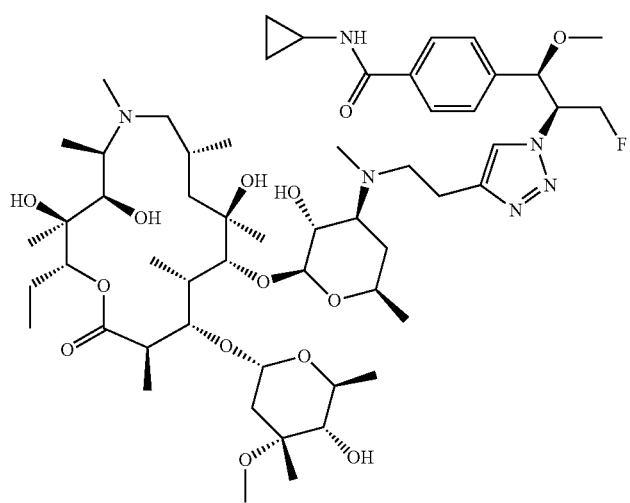 |
| 150 | 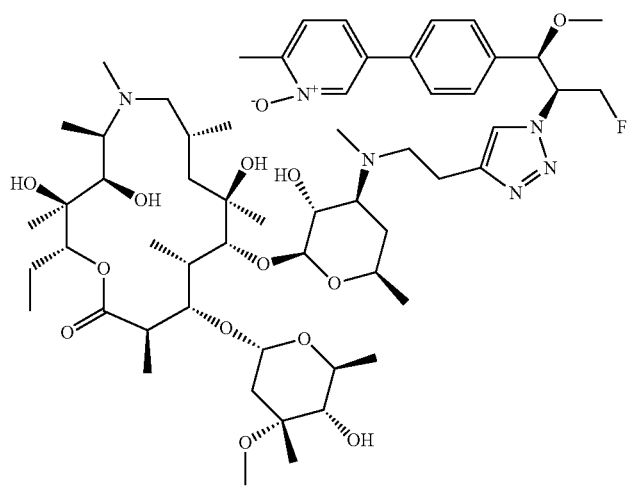 |

| Compound No. | Structure |
|---|---|
| 151 | 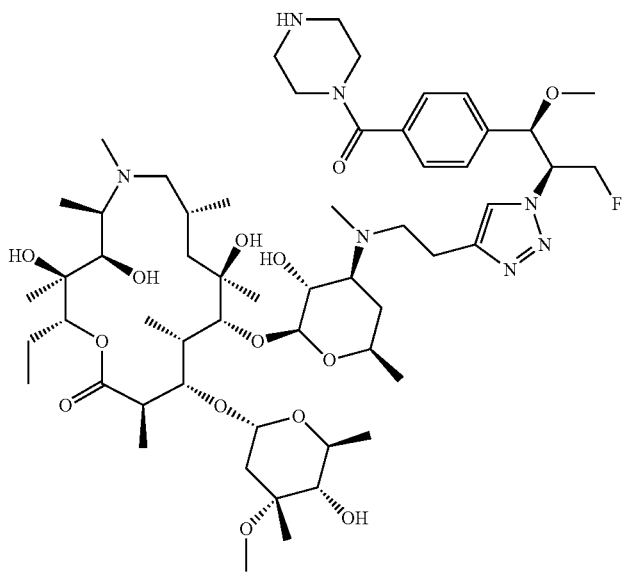 |
| 152 | 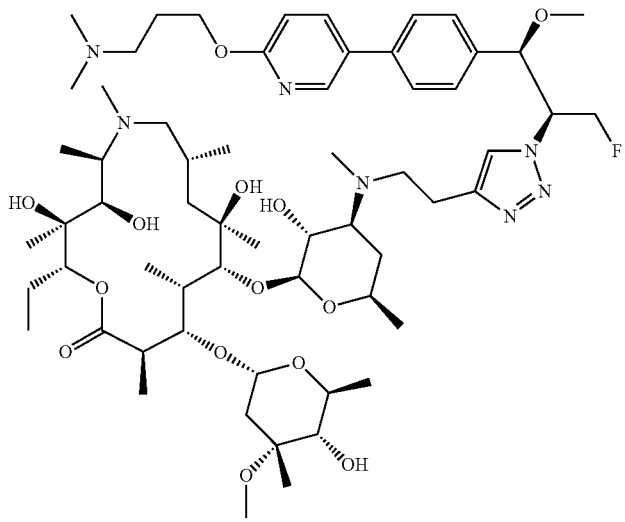 |

-continued
| Compound No. | Structure |
|---|---|
| 153 | 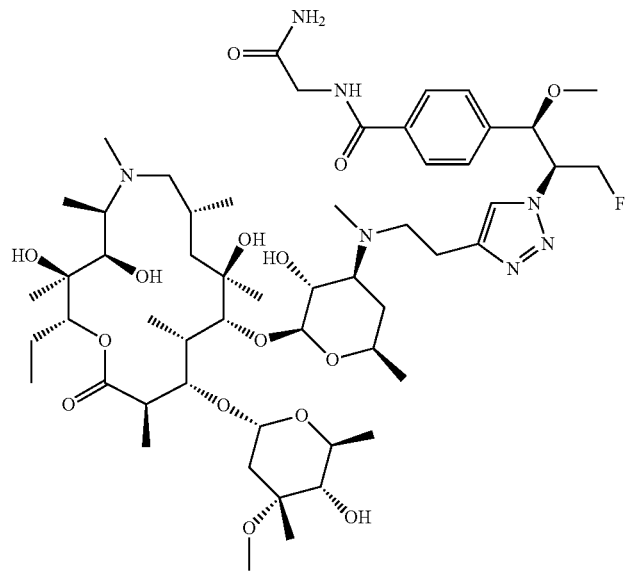 |
| 154 | 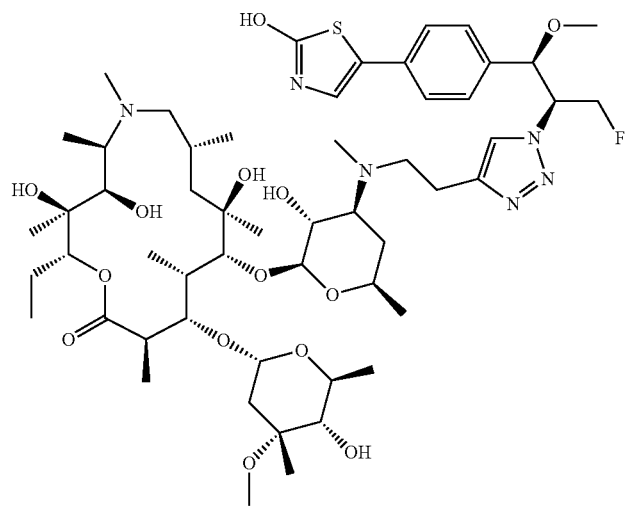 |
| 155 | 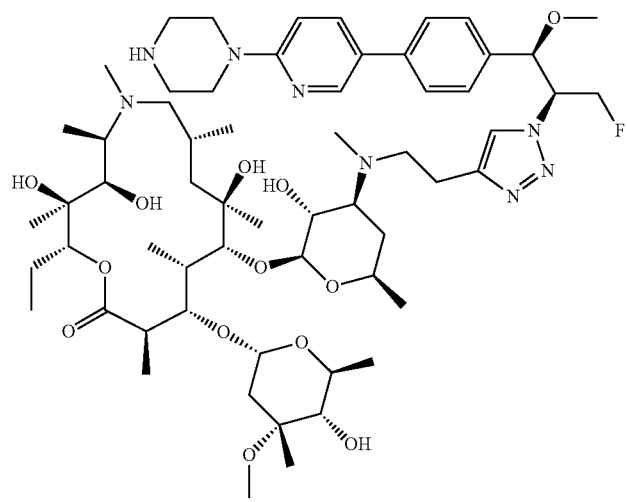 |

| Compound No. | Structure |
|---|---|
| 156 | 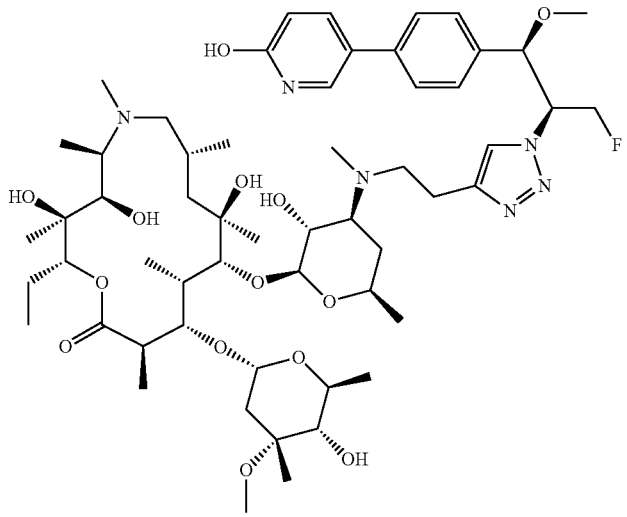 |
| 157 | 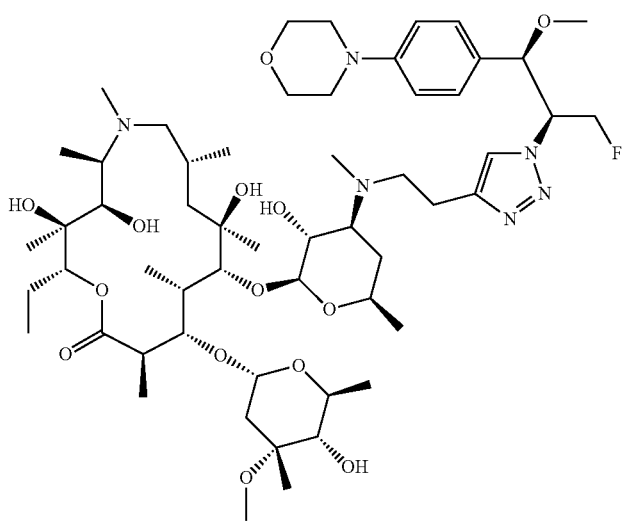 |
| 158 | 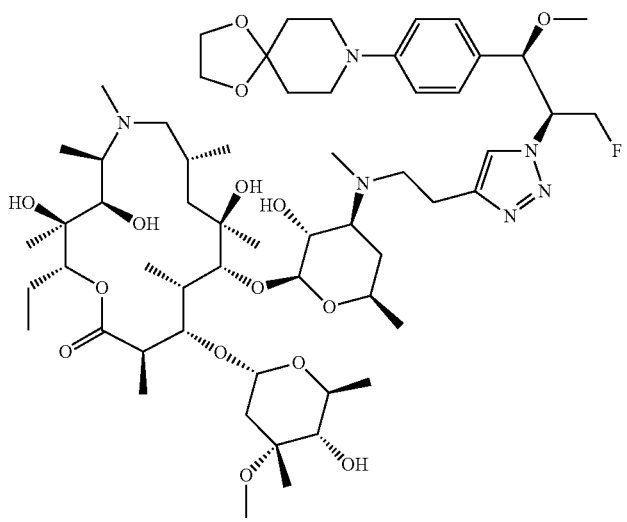 |

| Compound No. | Structure |
|---|---|
| 159 | 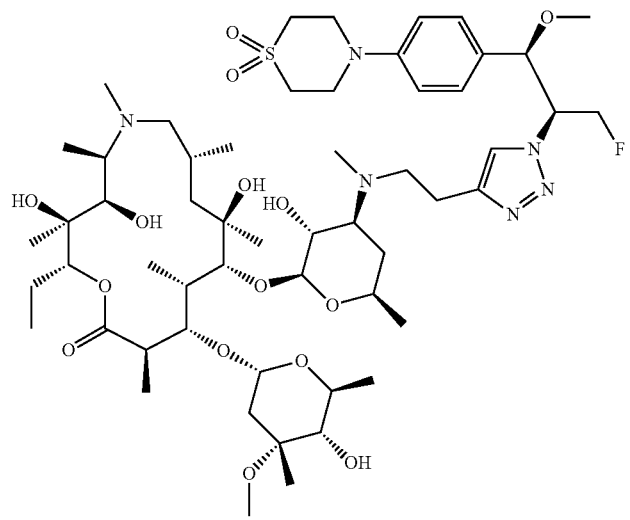 |
| 160 | 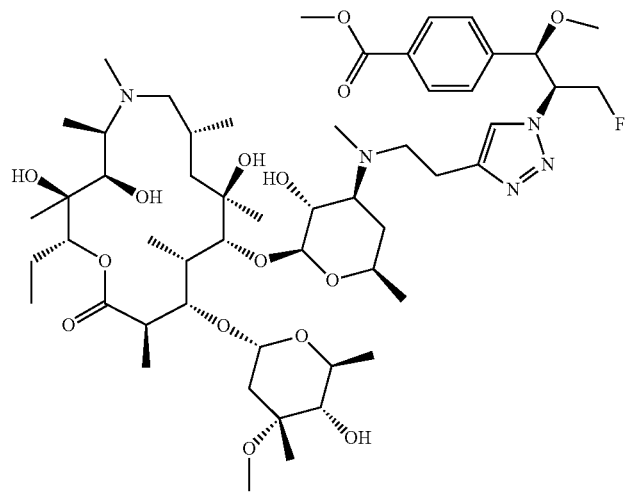 |
| 161 | 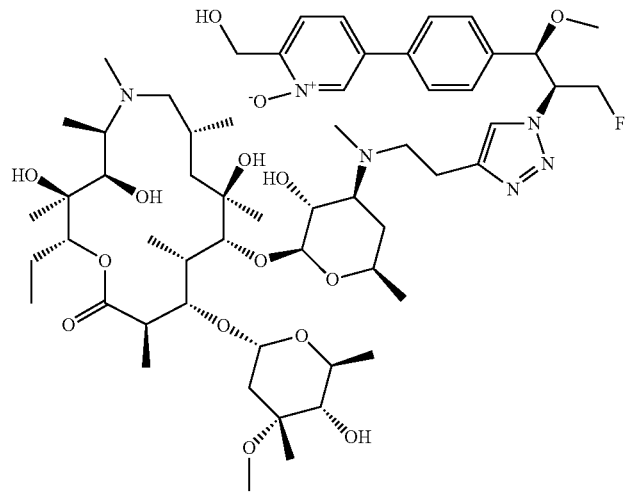 |

| Compound No. | Structure |
|---|---|
| 162 | *(chemical structure)* |
| 163 | *(chemical structure)* |
| 164 | *(chemical structure)* |

| Compound No. | Structure |
|---|---|
| 165 | 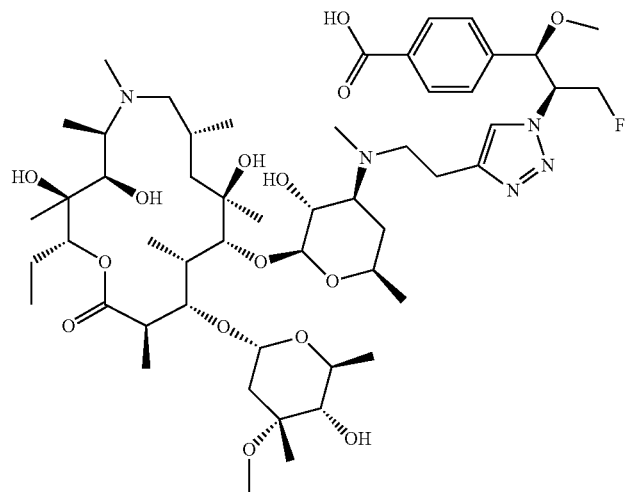 |
| 166 | 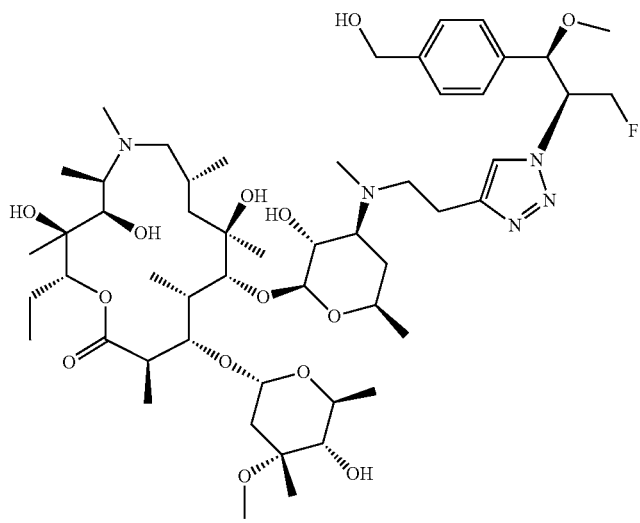 |
| 167 | 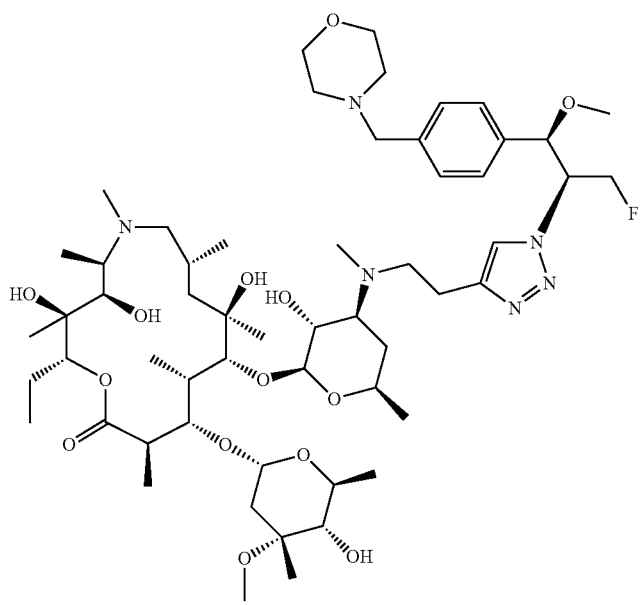 |

-continued
| Compound No. | Structure |
|---|---|
| 168 | 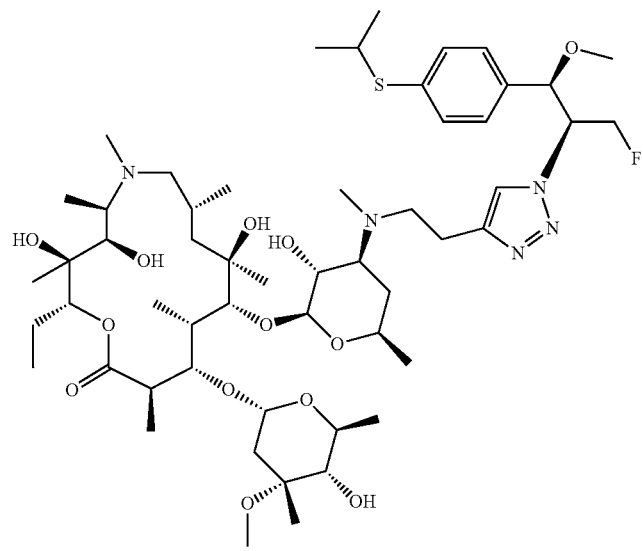 |
| 169 | 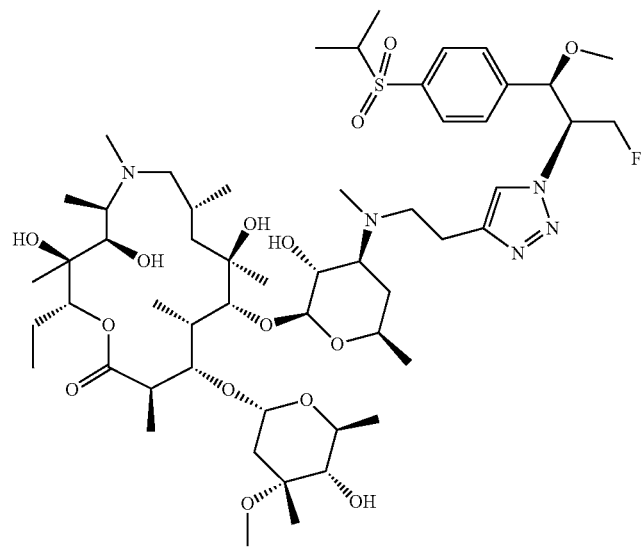 |

| Compound No. | Structure |
|---|---|
| 170 | 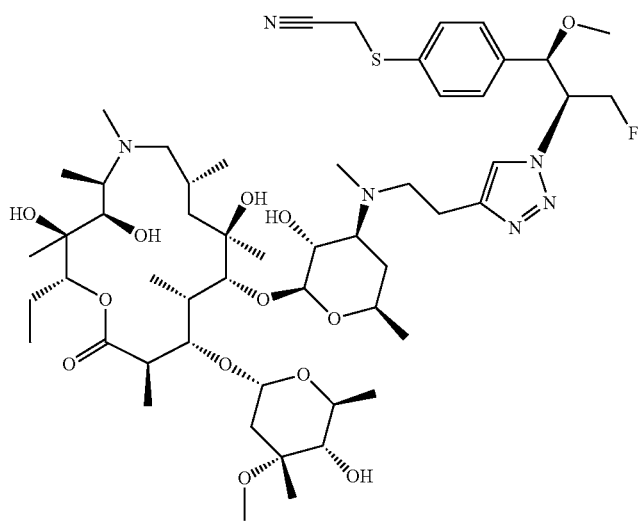 |
| 171 | 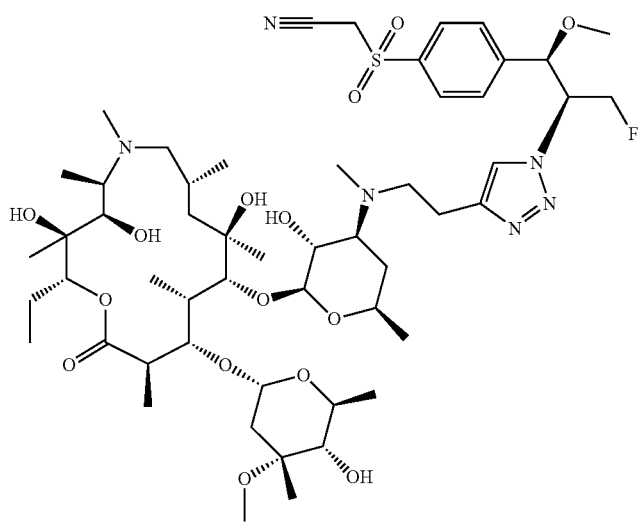 |
| 172 | 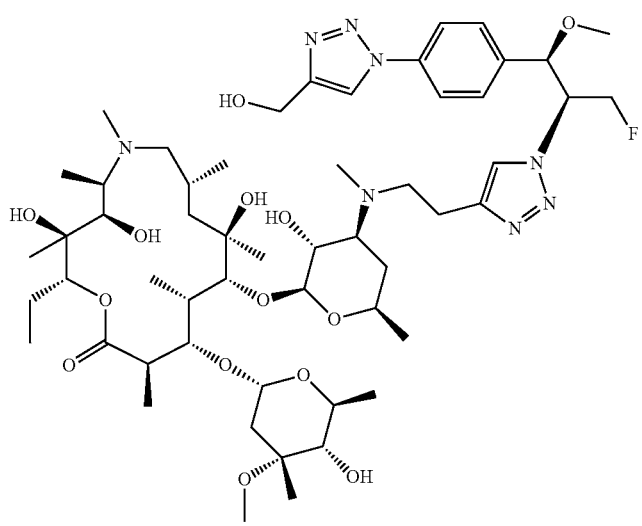 |

| Compound No. | Structure |
|---|---|
| 173 | 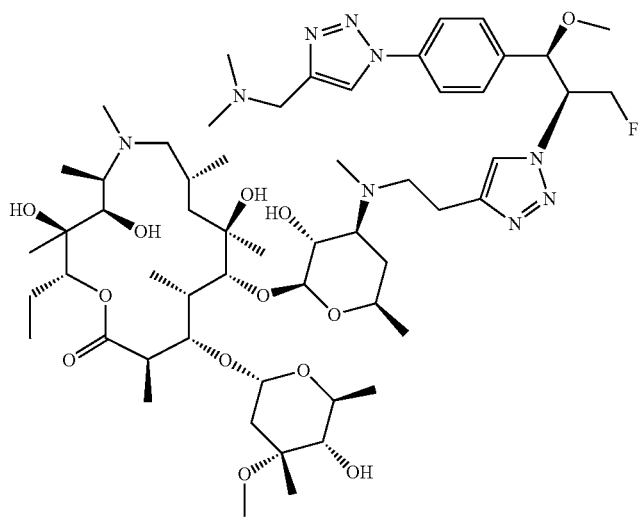 |
| 174 | 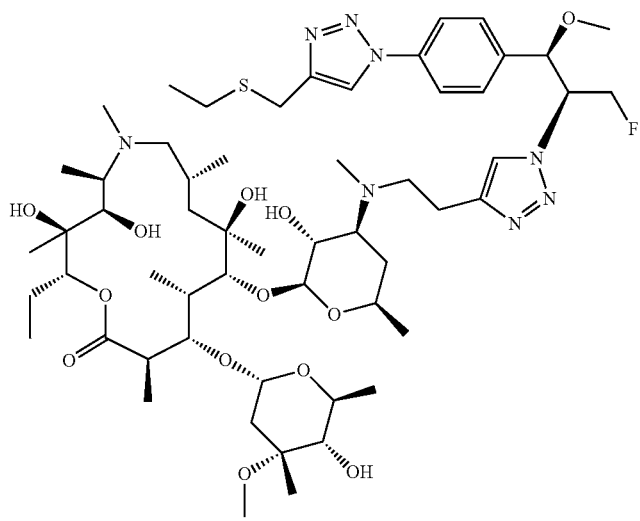 |
| 175 | 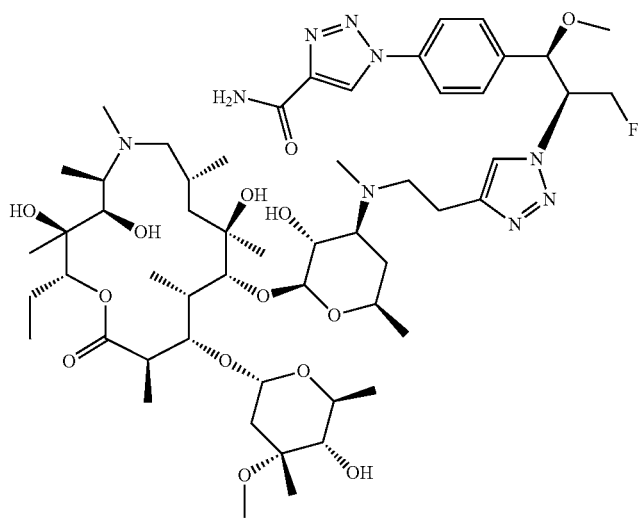 |

| Compound No. | Structure |
|---|---|
| 176 | 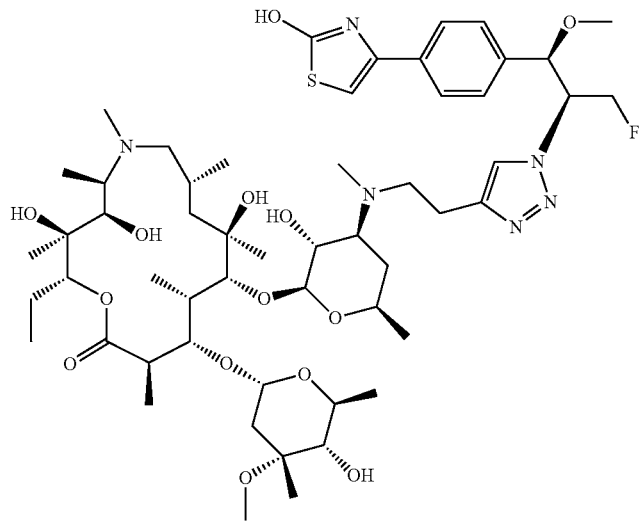 |
| 177 | 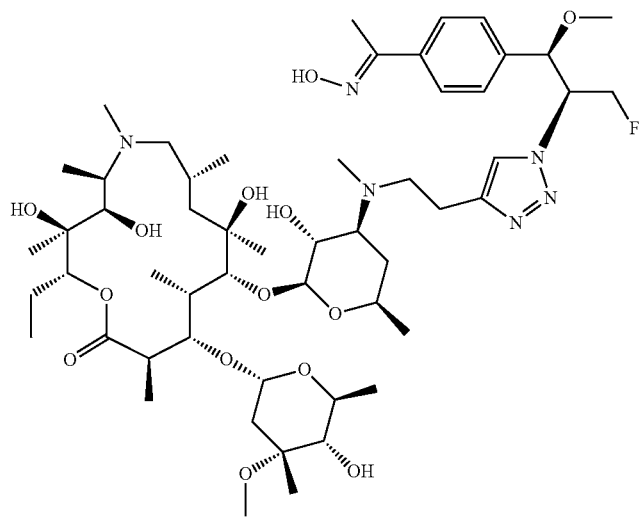 |
| 178 | 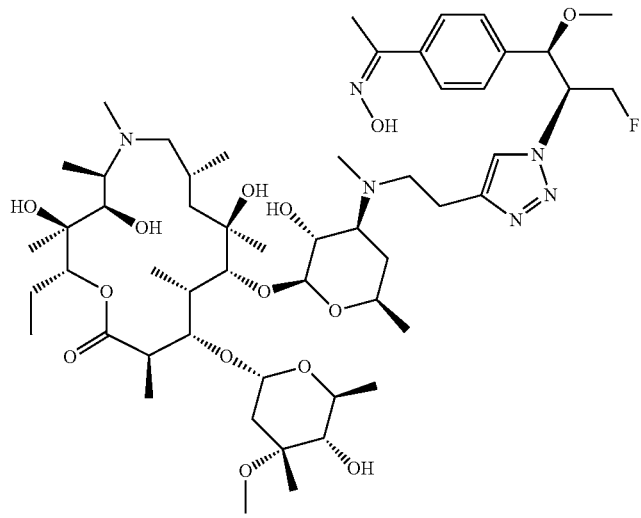 |

| Compound No. | Structure |
|---|---|
| 179 | 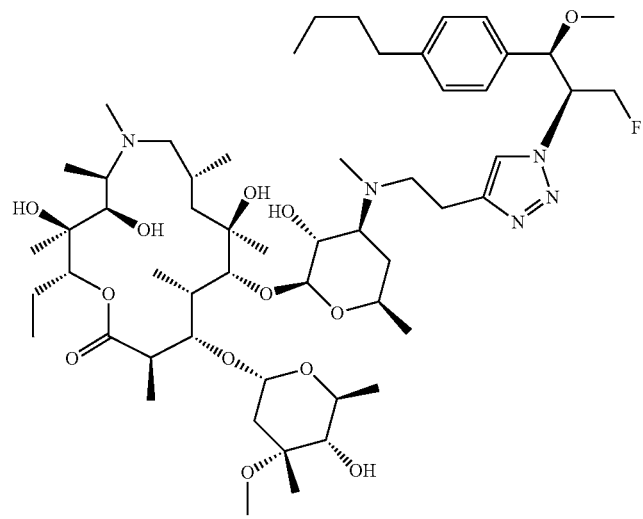 |
| 180 | 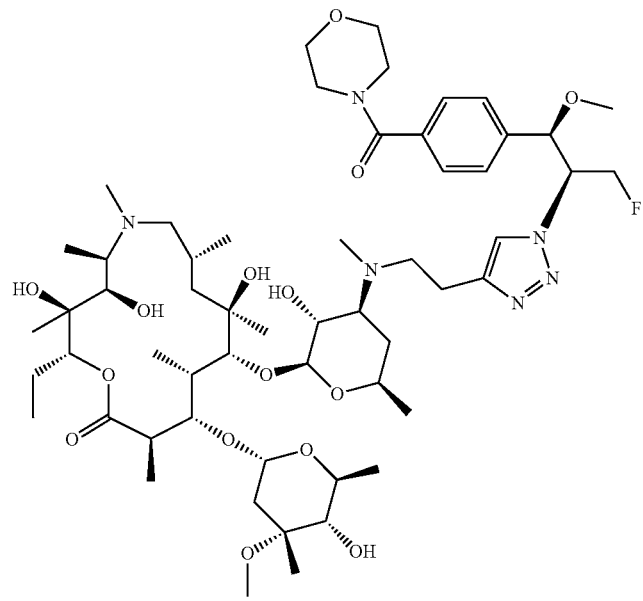 |

| Compound No. | Structure |
|---|---|
| 181 | 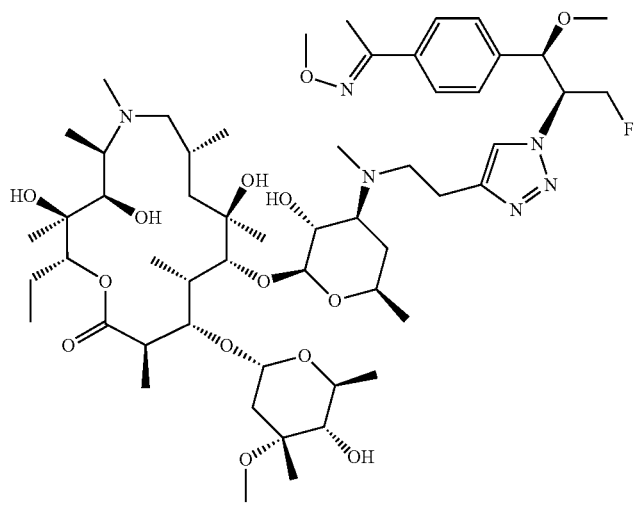 |
| 182 | 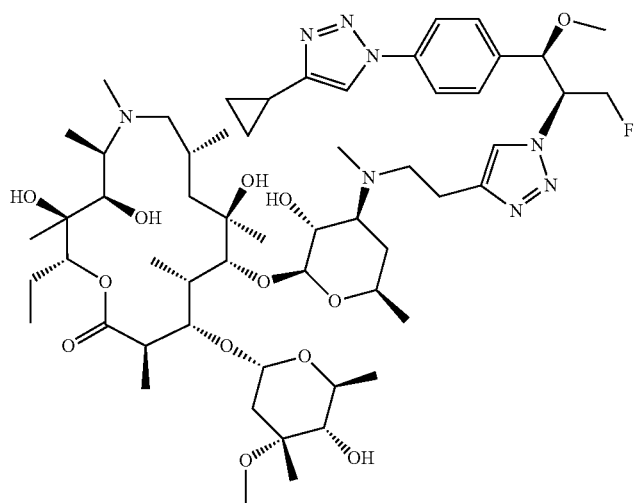 |
| 183 | 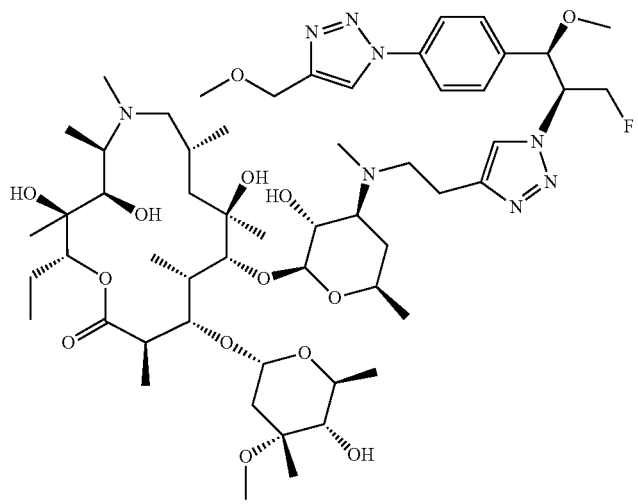 |

-continued
| Compound No. | Structure |
|---|---|
| 184 | 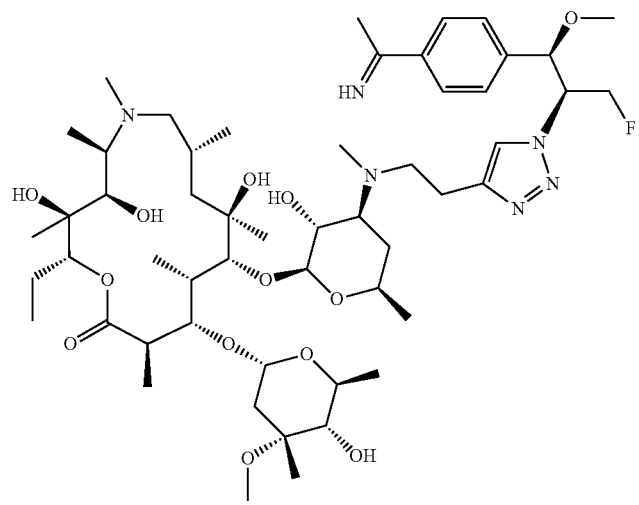 |
| 185 | 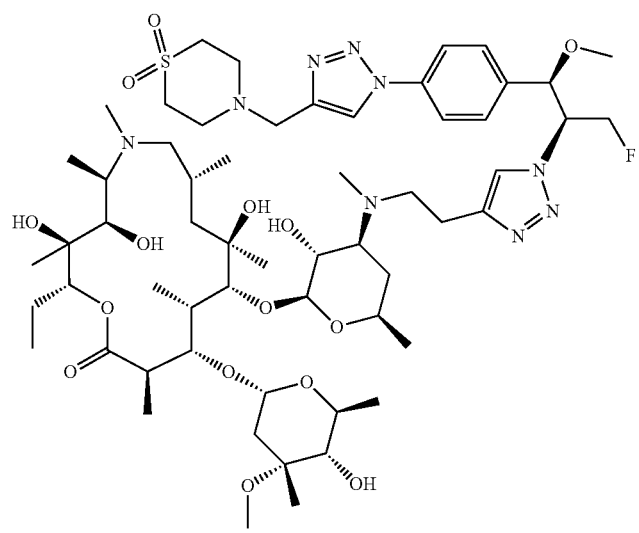 |
| 186 | 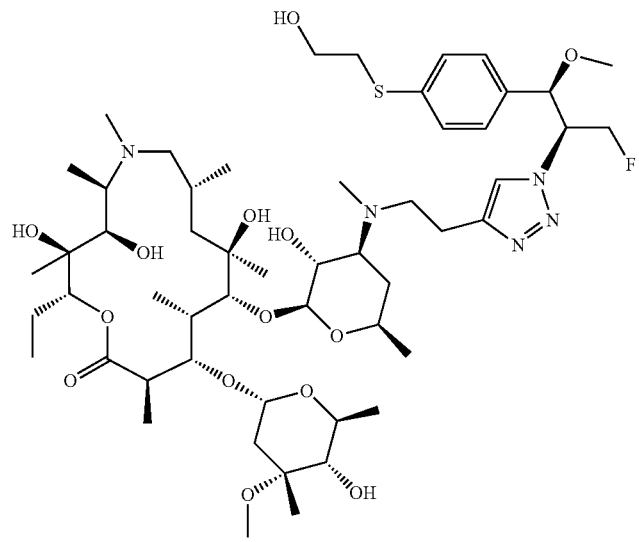 |

| Compound No. | Structure |
|---|---|
| 187 | (chemical structure) |
| 188 | (chemical structure) |

| Compound No. | Structure |
|---|---|
| 189 | 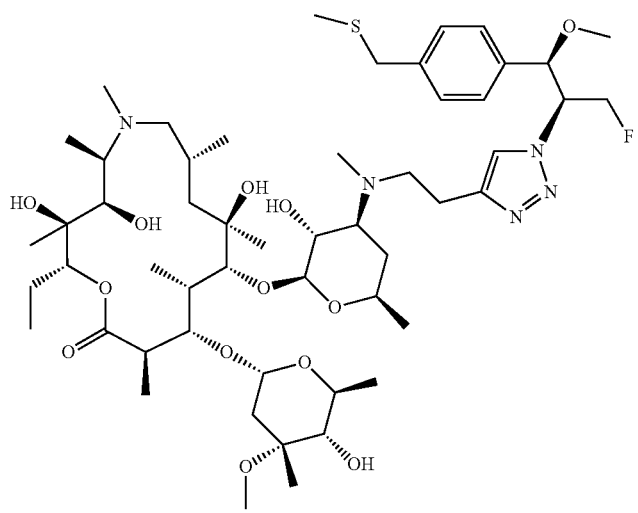 |
| 190 | 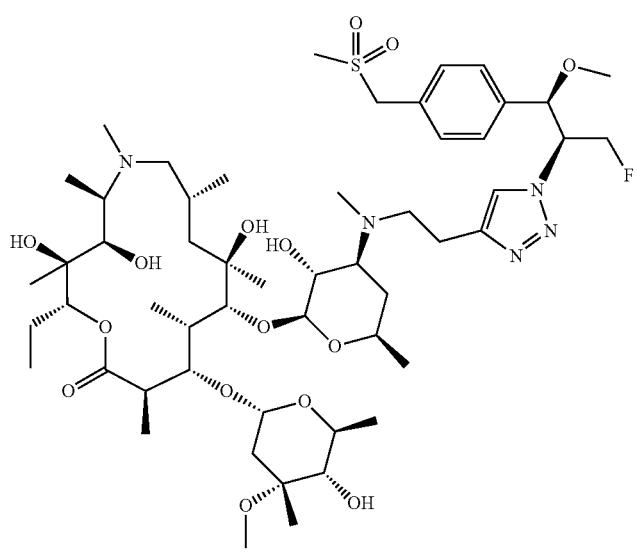 |
| 191 | 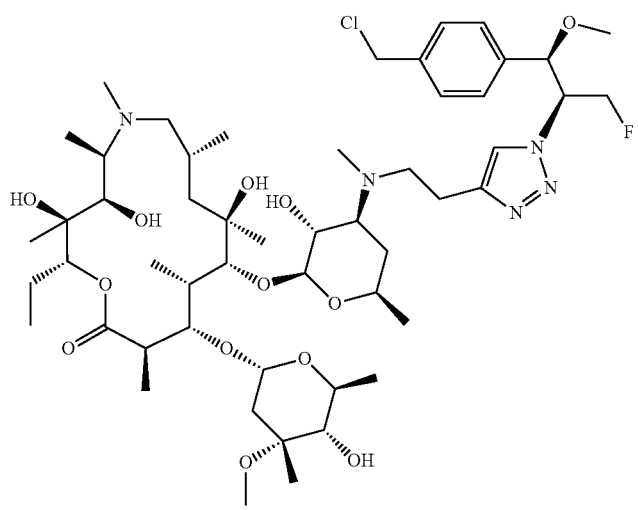 |

| Compound No. | Structure |
|---|---|
| 192 | 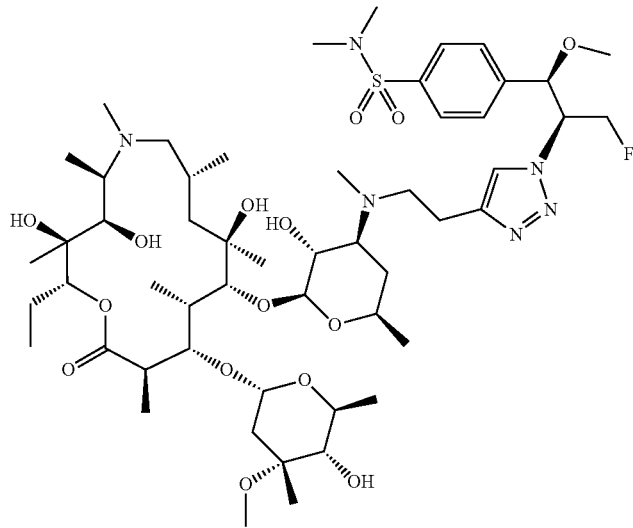 |
| 193 | 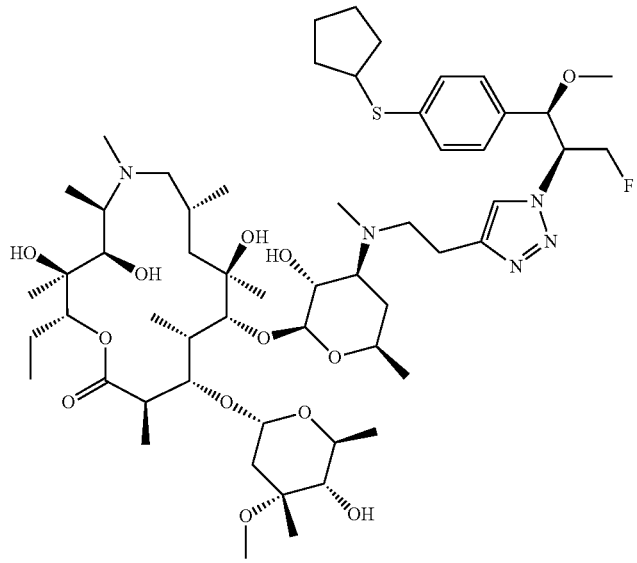 |

-continued
| Compound No. | Structure |
|---|---|
| 194 | 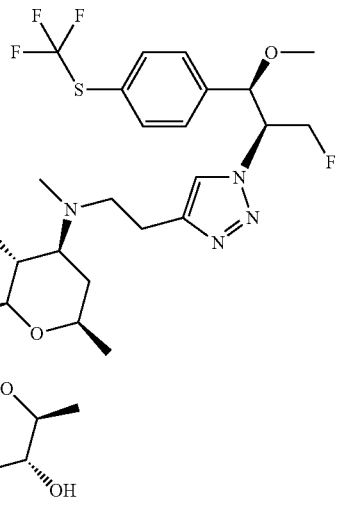 |
| 195 | 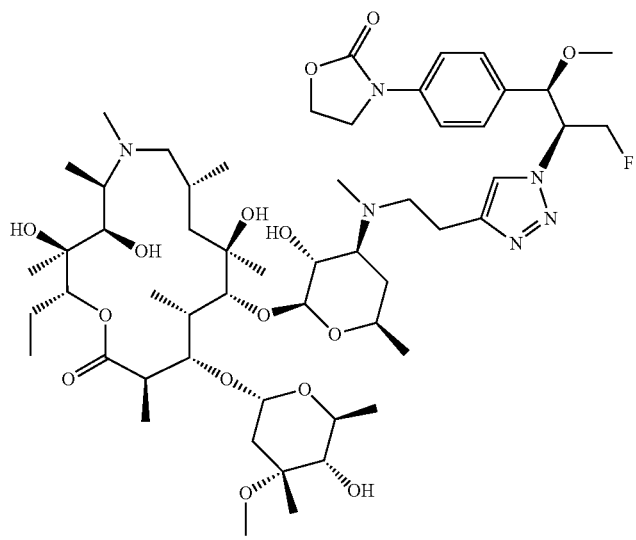 |
| 196 | 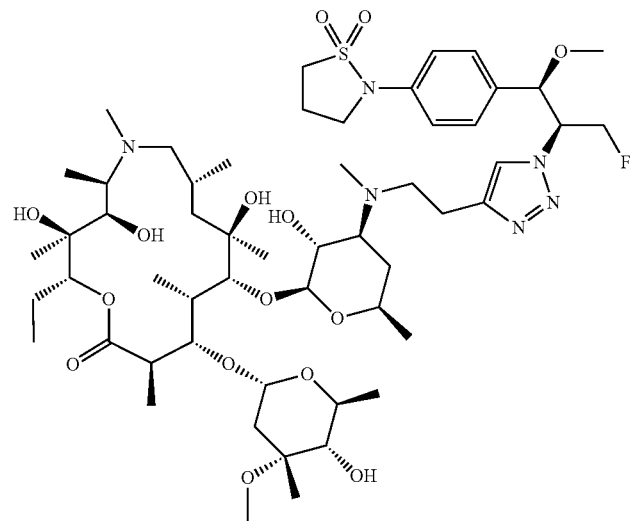 |

| Compound No. | Structure |
|---|---|
| 197 | 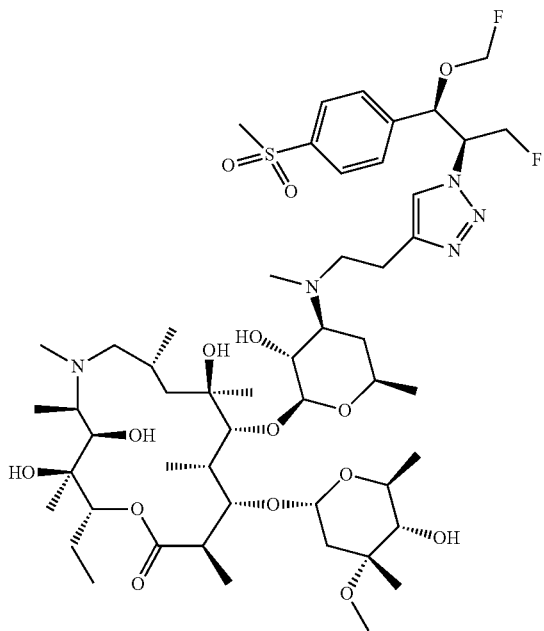 |
| 198 | 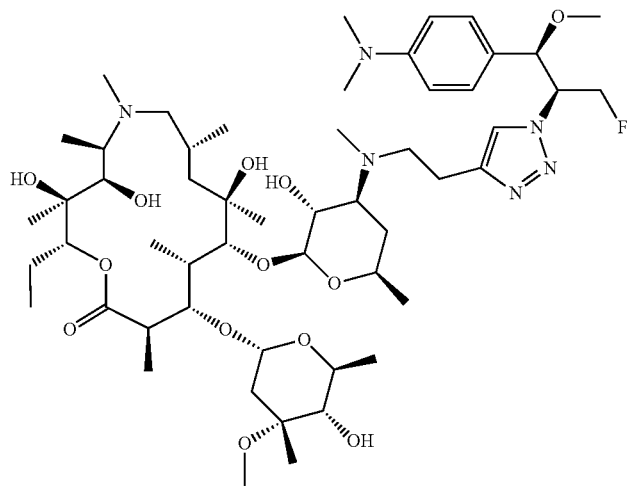 |

-continued

| Compound No. | Structure |
|---|---|
| 199 | 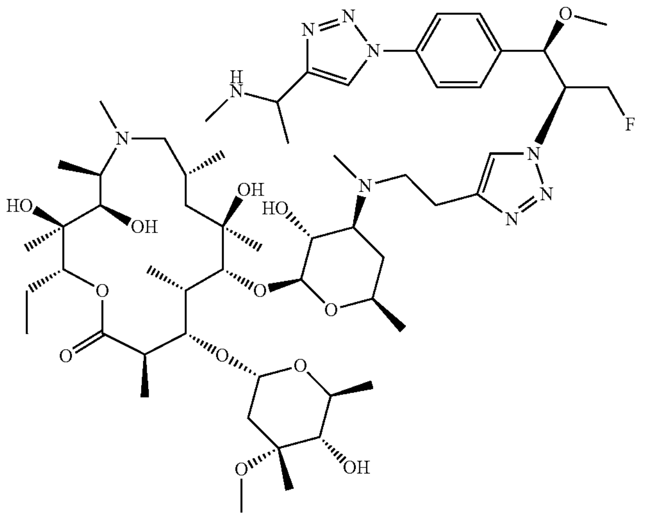 |
| 200 | 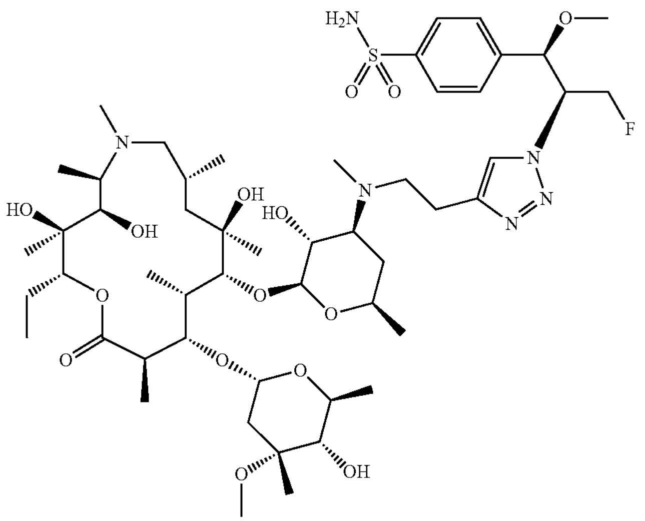 |
| 201 | 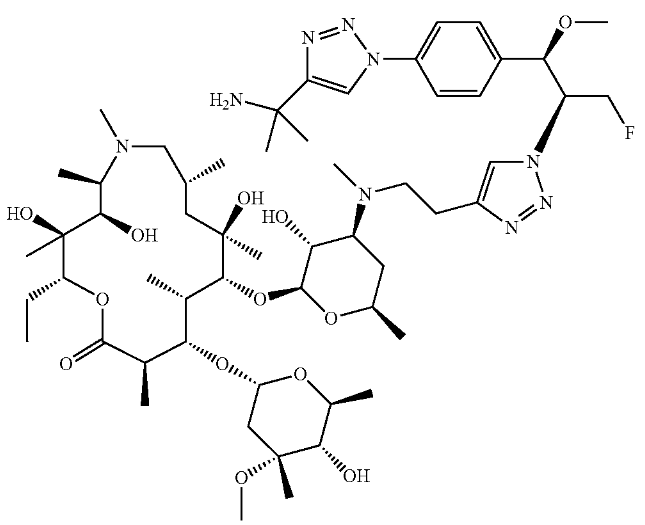 |

-continued
| Compound No. | Structure |
|---|---|
| 202 | 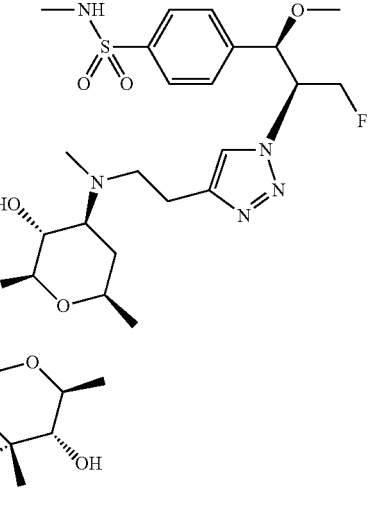 |
| 203 | 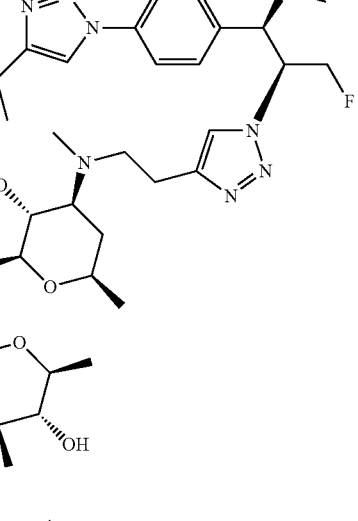 |
| 204 | 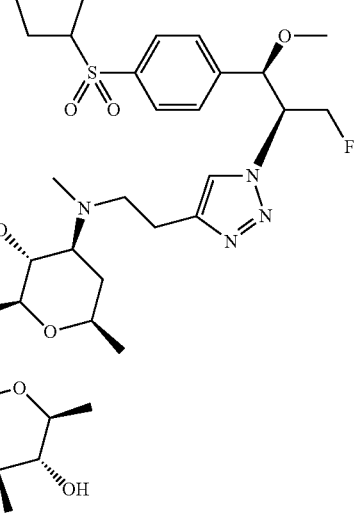 |

| Compound No. | Structure |
|---|---|
| 205 | 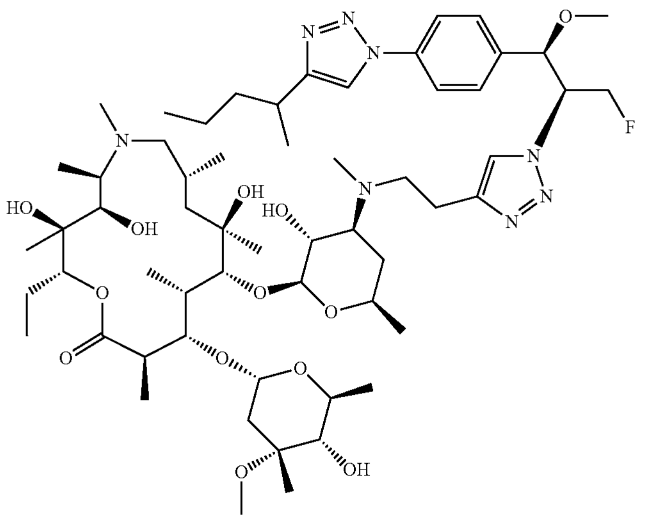 |
| 206 | 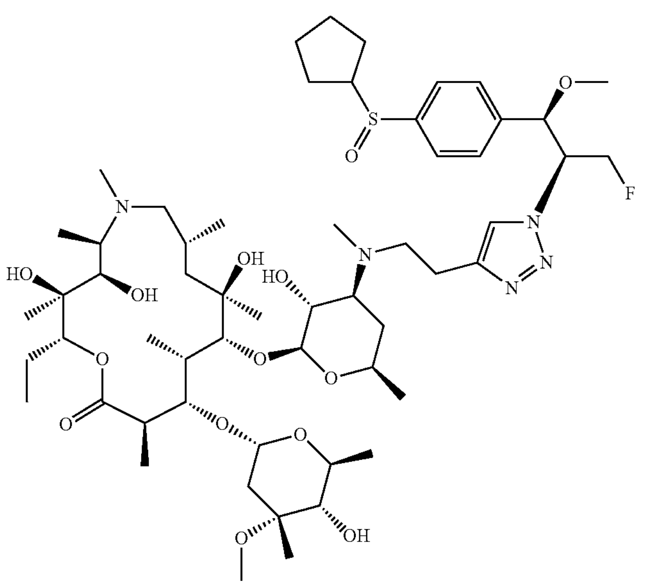 |

| Compound No. | Structure |
|---|---|
| 207 | 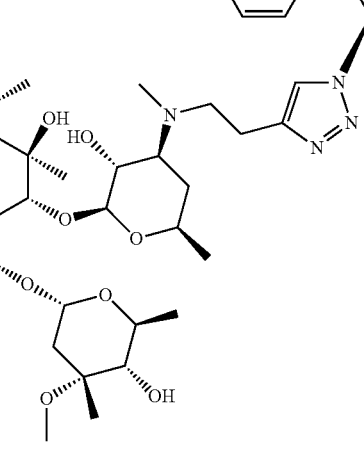 |
| 208 | 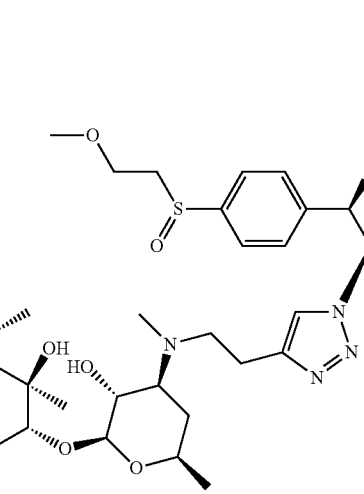 |

| Compound No. | Structure |
|---|---|
| 209 | 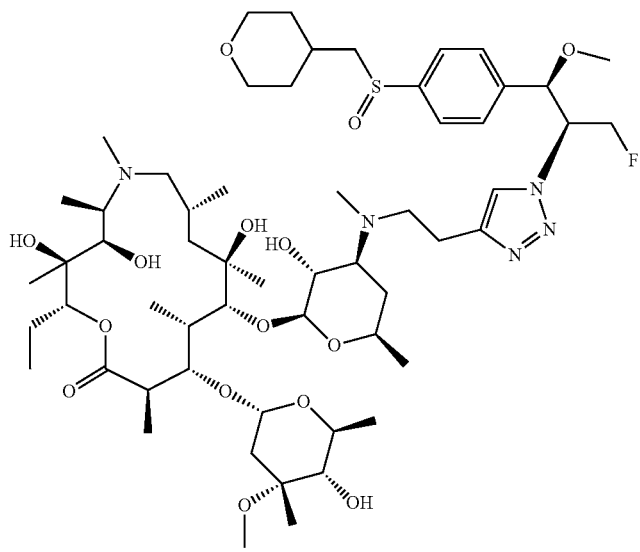 |
| 210 | 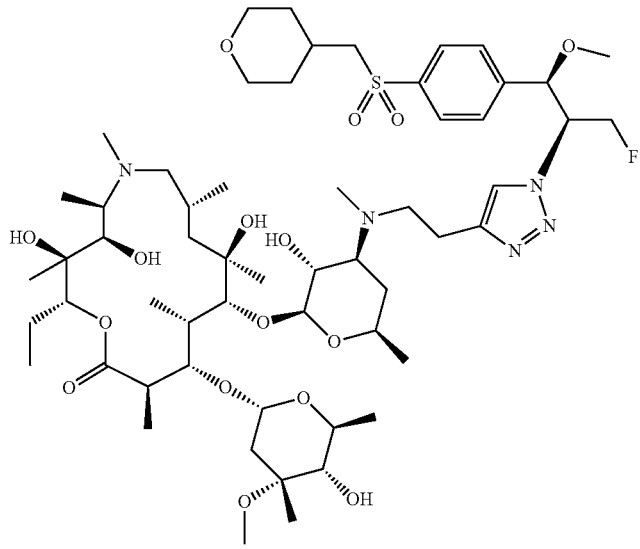 |

-continued
| Compound No. | Structure |
|---|---|
| 211 | 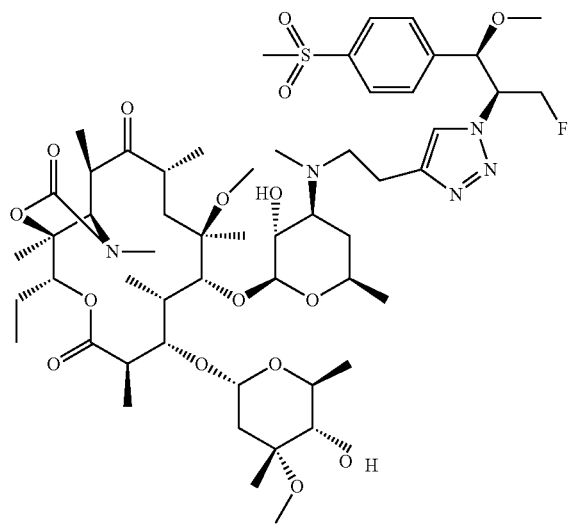 |
| 212 | 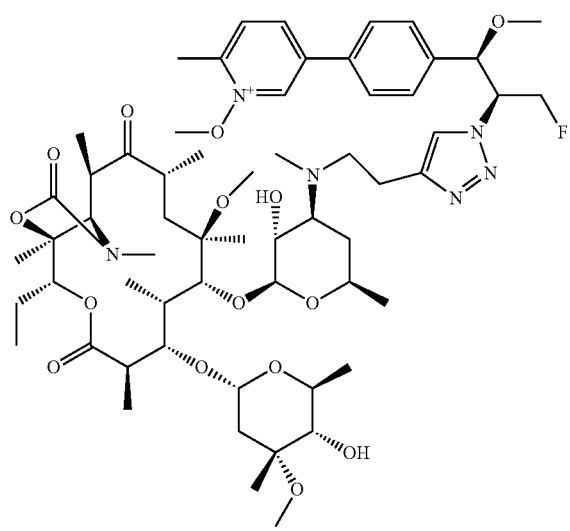 |
| 213 | 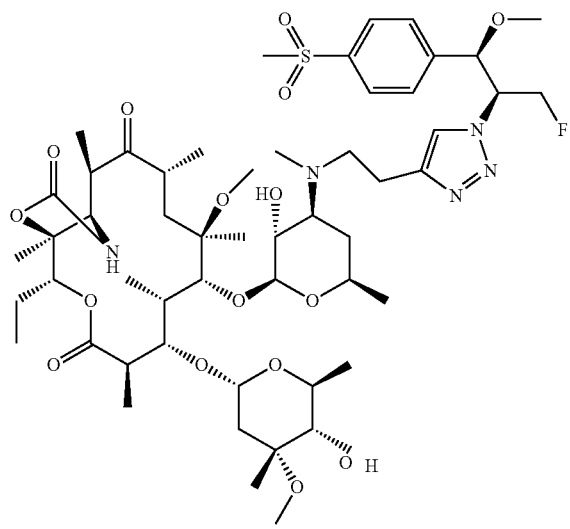 |

-continued
| Compound No. | Structure |
|---|---|
| 214 | 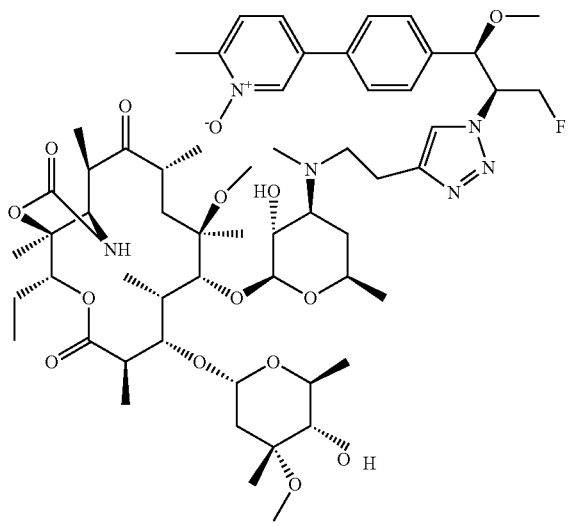 |
| 215 | 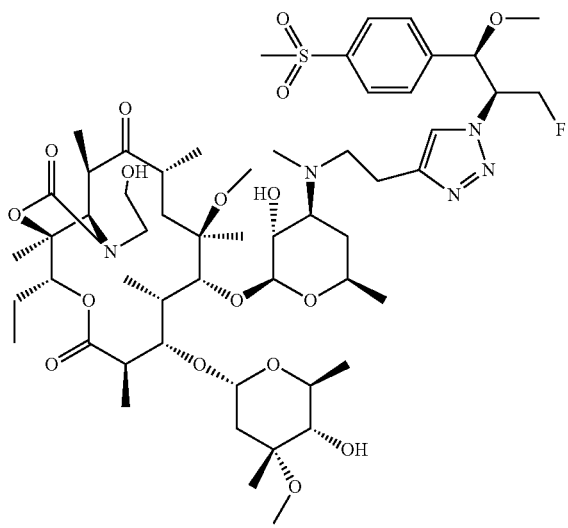 |
| 216 | 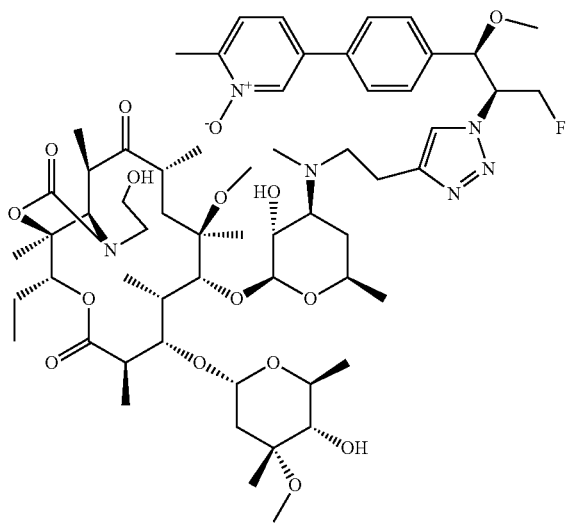 |

| Compound No. | Structure |
|---|---|
| 217 | 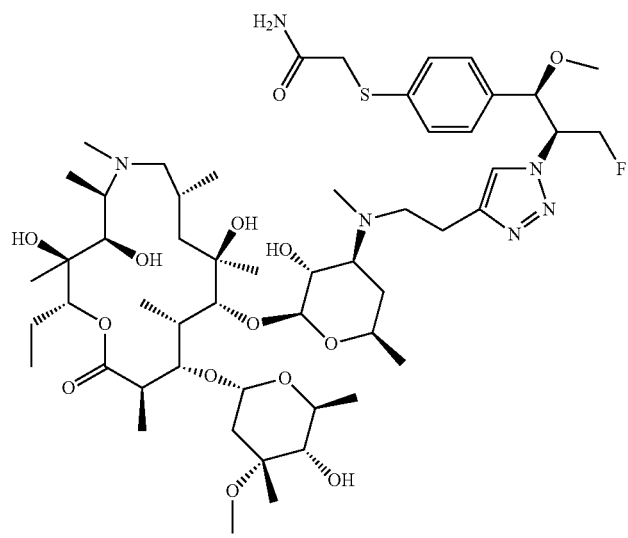 |
| 218 | 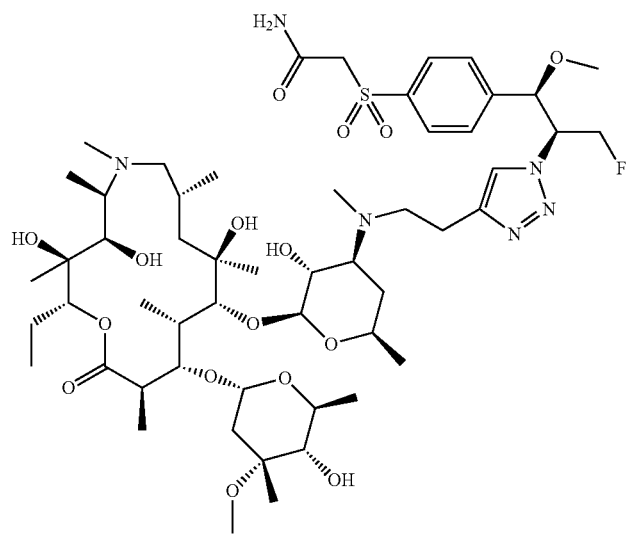 |
| 219 | 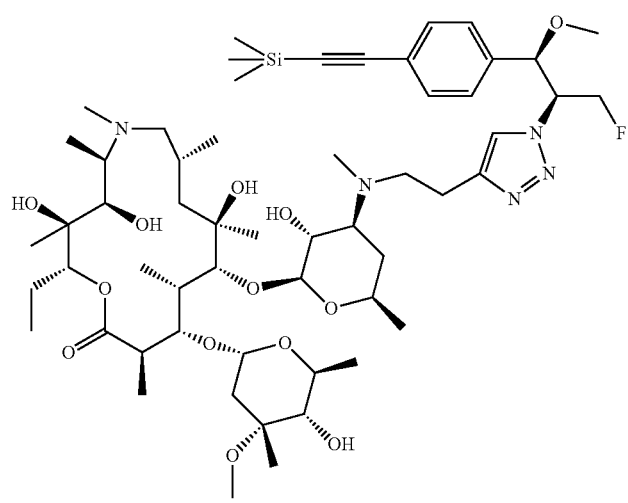 |

-continued
| Compound No. | Structure |
|---|---|
| 220 | 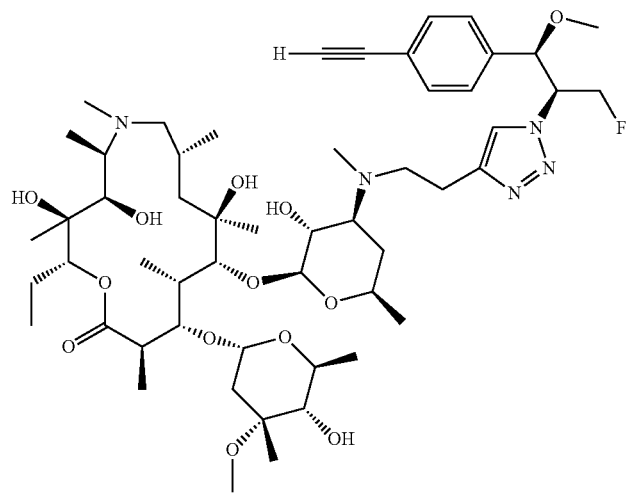 |
| 221 | 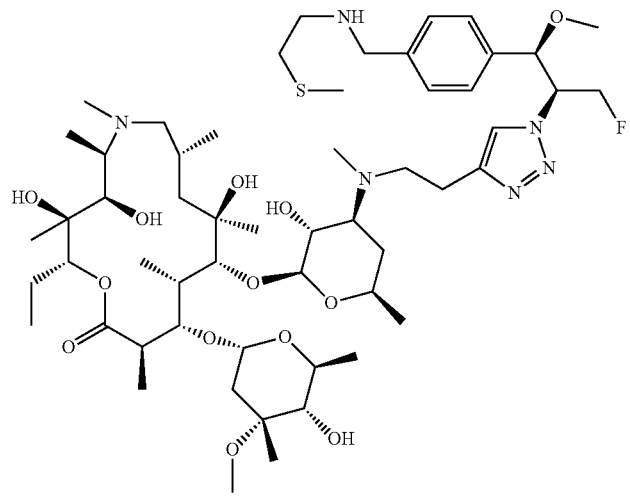 |
| 222 | 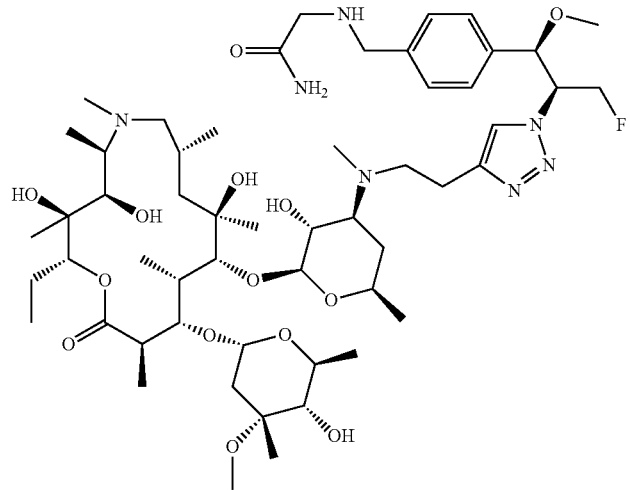 |

| Compound No. | Structure |
|---|---|
| 223 | 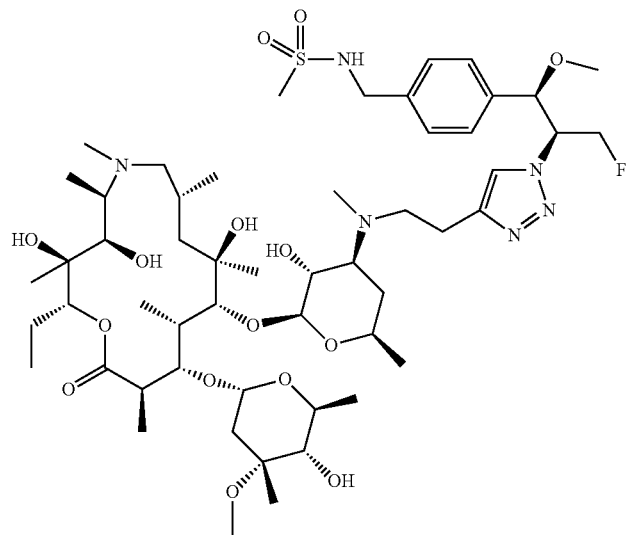 |
| 224 | 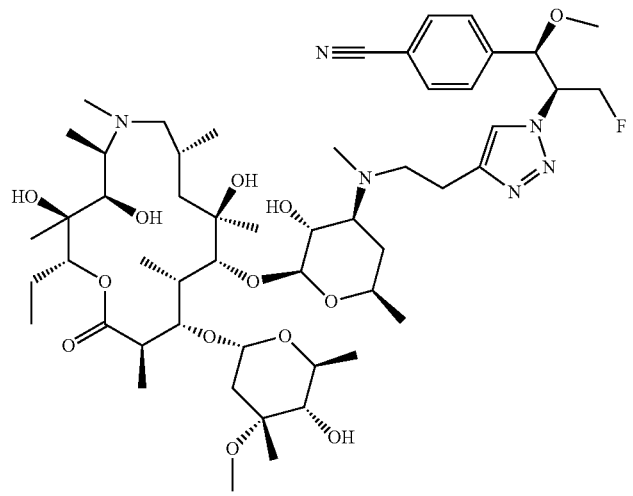 |
| 225 | 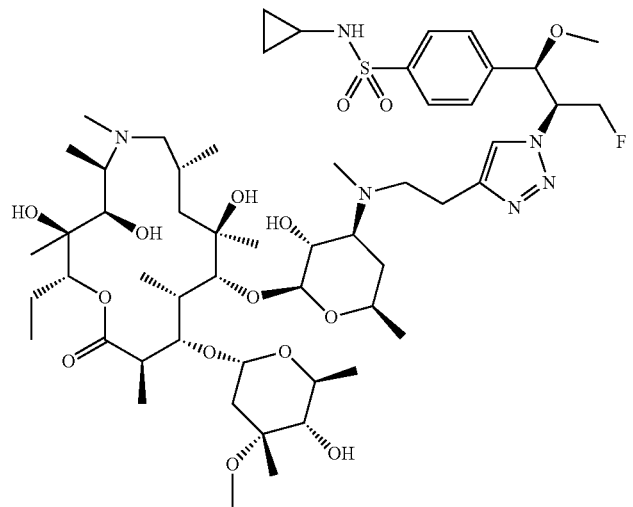 |

-continued
| Compound No. | Structure |
|---|---|
| 226 | 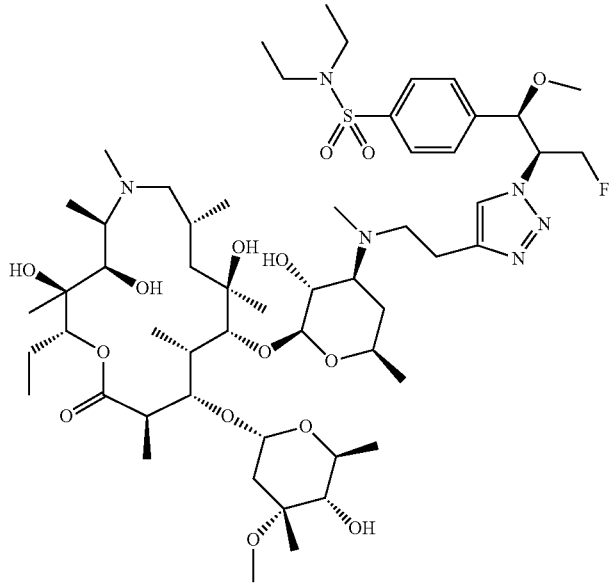 |
| 227 | 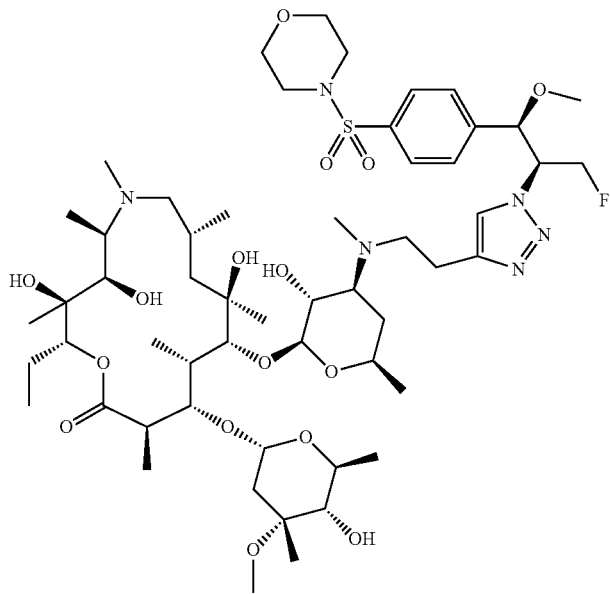 |

| Compound No. | Structure |
|---|---|
| 228 | 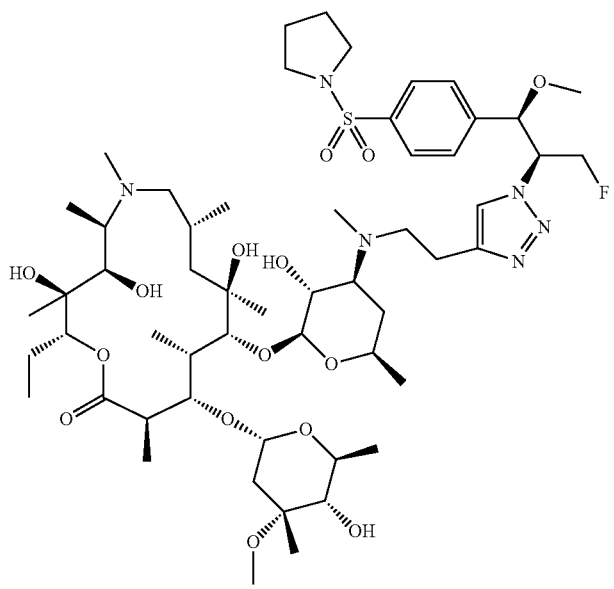 |
| 229 | 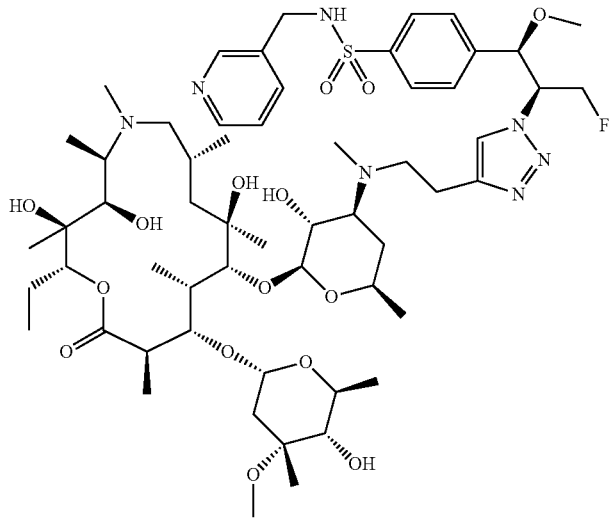 |

-continued
| Compound No. | Structure |
| --- | --- |
| 230 | 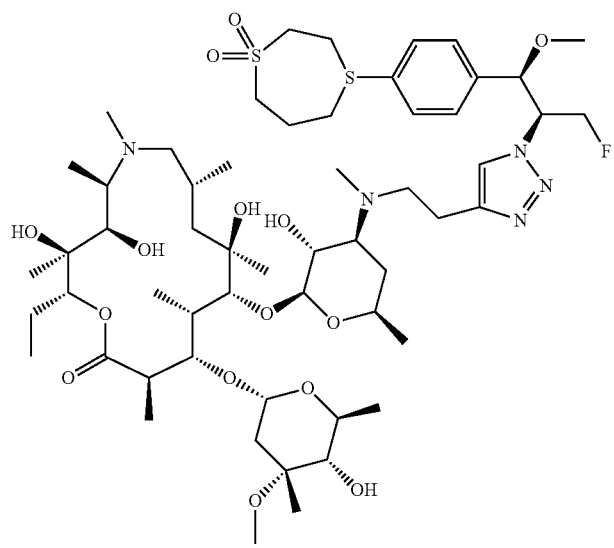 |
| 231 | 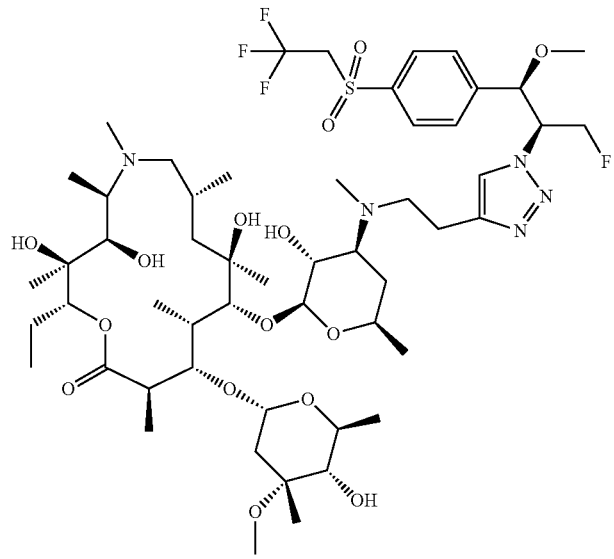 |

-continued
| Compound No. | Structure |
|---|---|
| 232 | 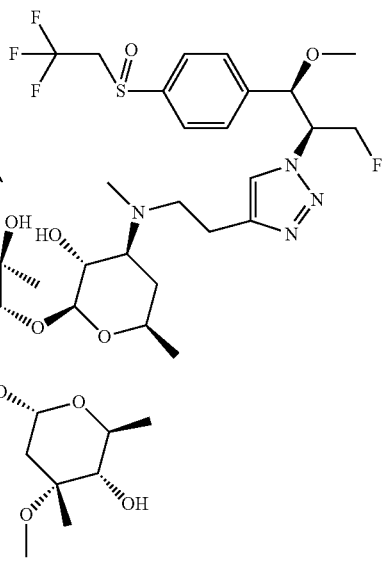 |
| 233 | 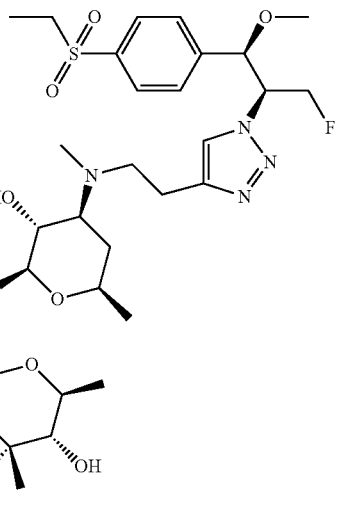 |
| 234 | 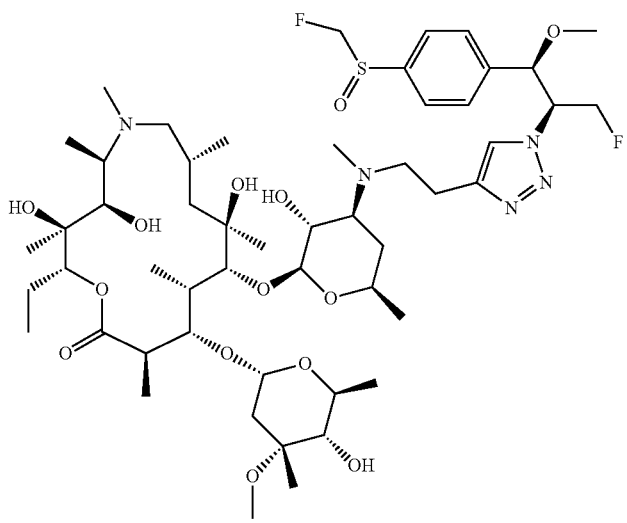 |

-continued
| Compound No. | Structure |
|---|---|
| 235 | 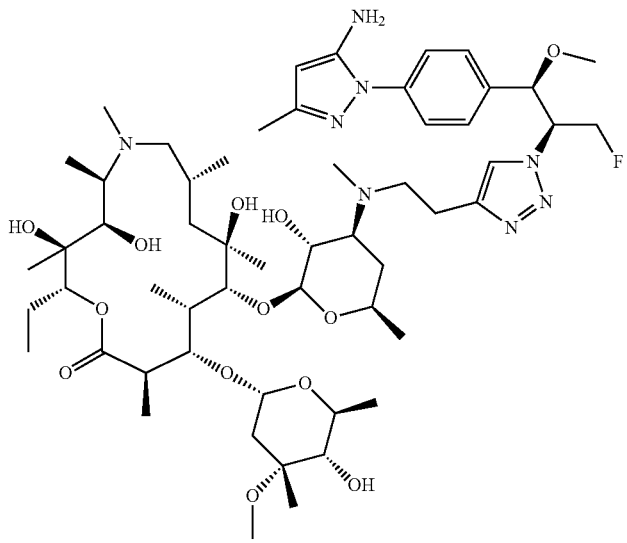 |
| 236 | 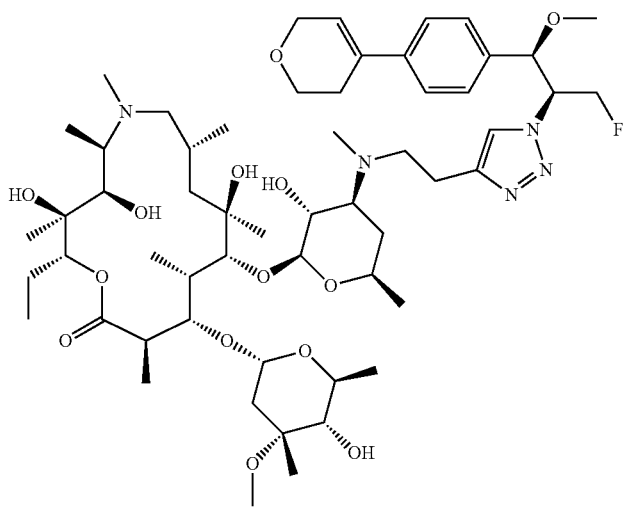 |
| 237 | 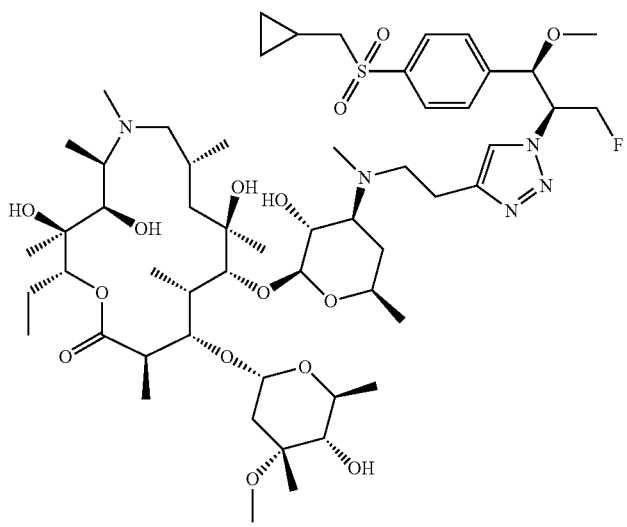 |

| Compound No. | Structure |
|---|---|
| 238 | 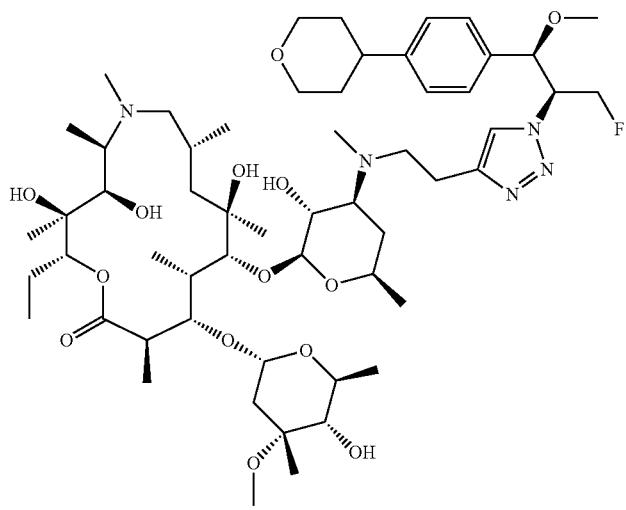 |
| 239 | 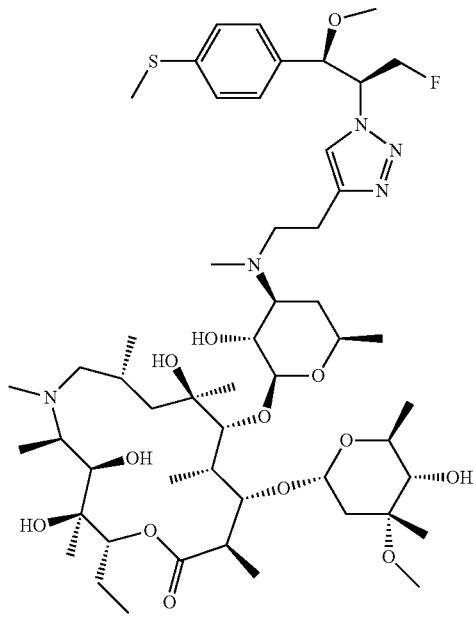 |

-continued
| Compound No. | Structure |
|---|---|
| 240 | 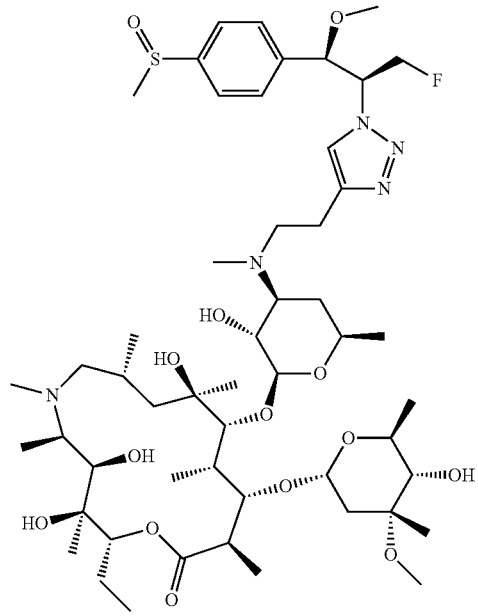 |
| 241 | 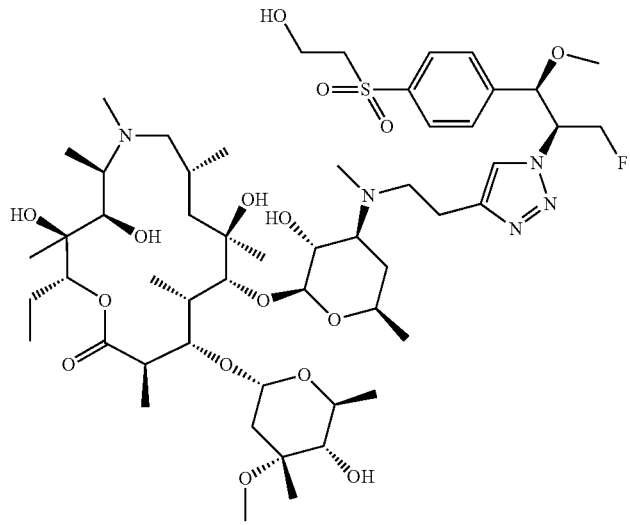 |

-continued
| Compound No. | Structure |
|---|---|
| 242 | 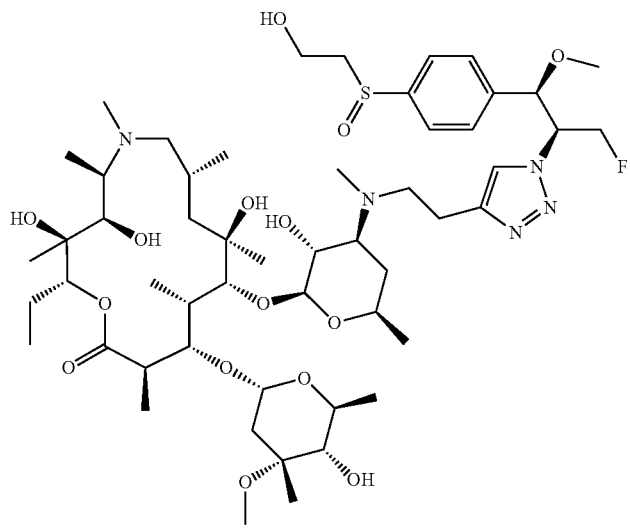 |
| 243 | 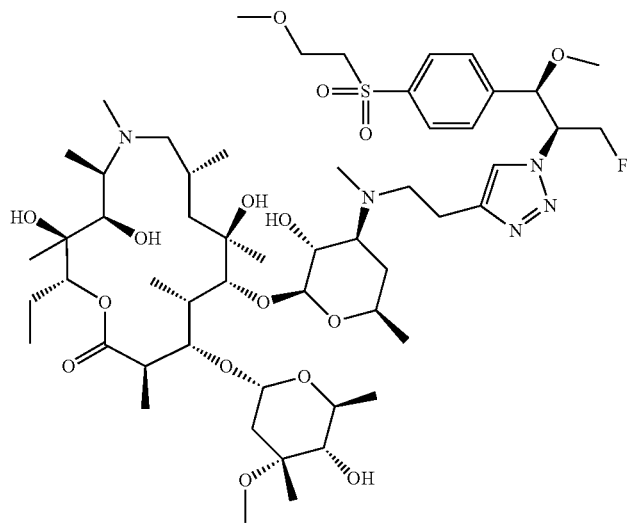 |
| 244 | 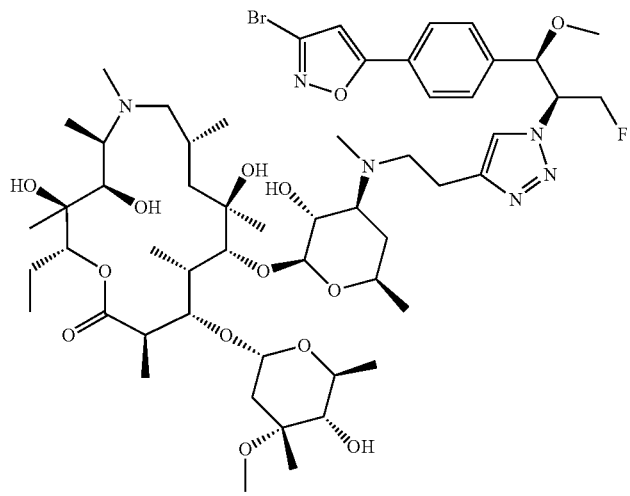 |

| Compound No. | Structure |
|---|---|
| 245 | 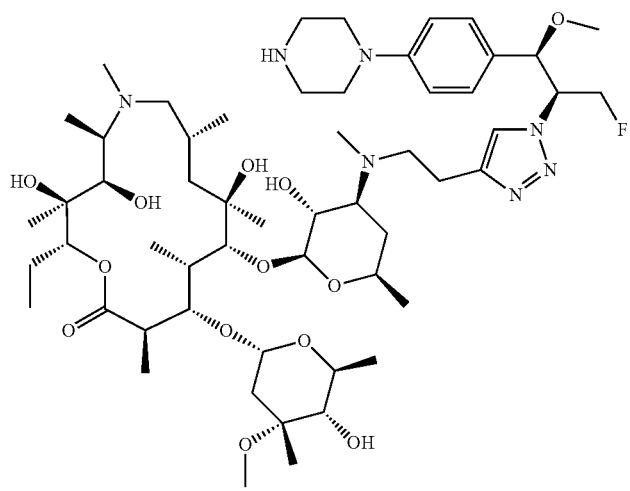 |
| 246 | 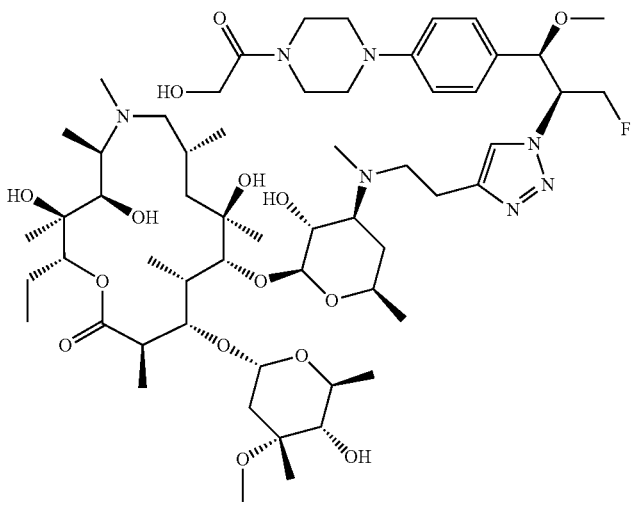 |
| 247 | 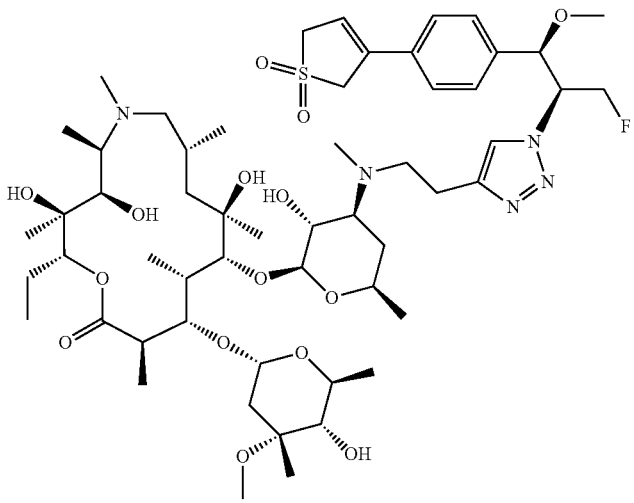 |

| Compound No. | Structure |
|---|---|
| 248 | 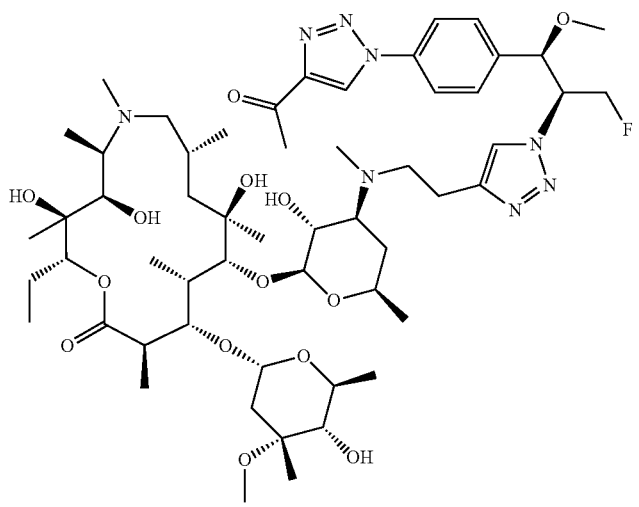 |
| 249 | 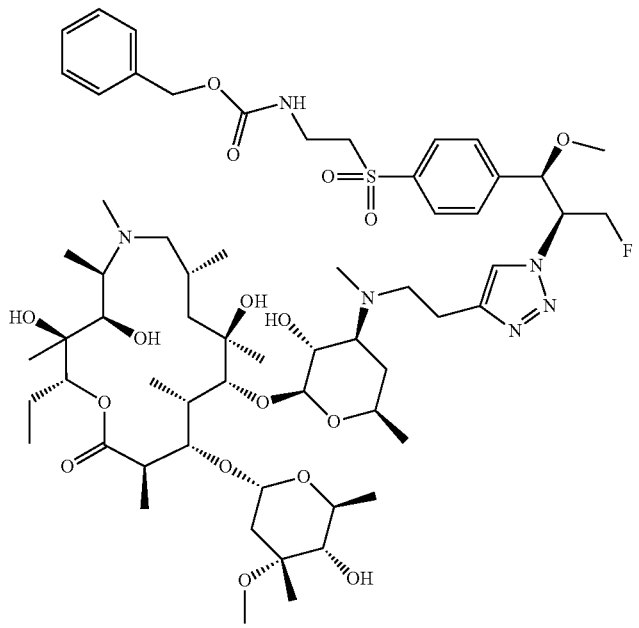 |

| Compound No. | Structure |
|---|---|
| 250 | 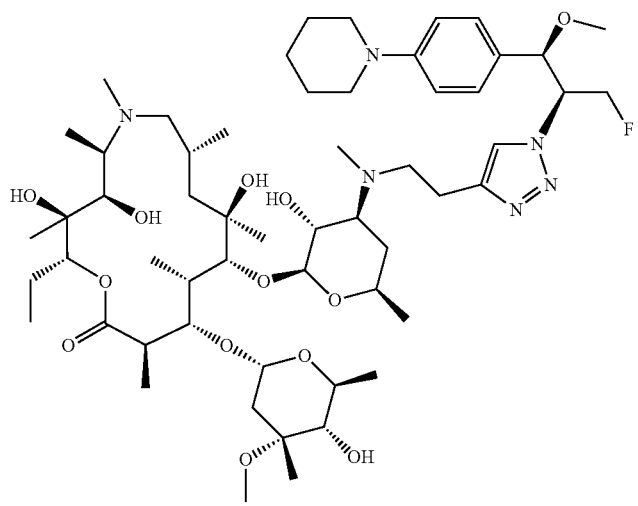 |
| 251 | 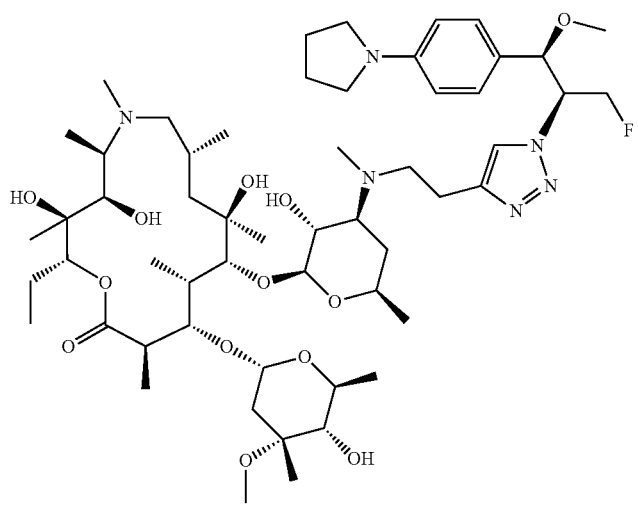 |
| 252 | 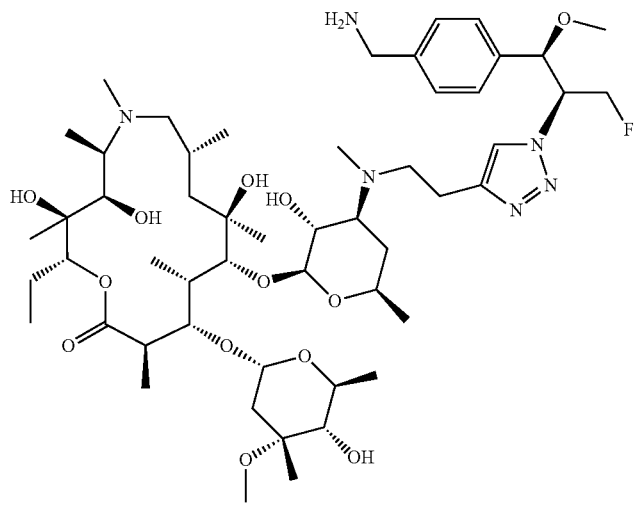 |

-continued
| Compound No. | Structure |
|---|---|
| 253 | 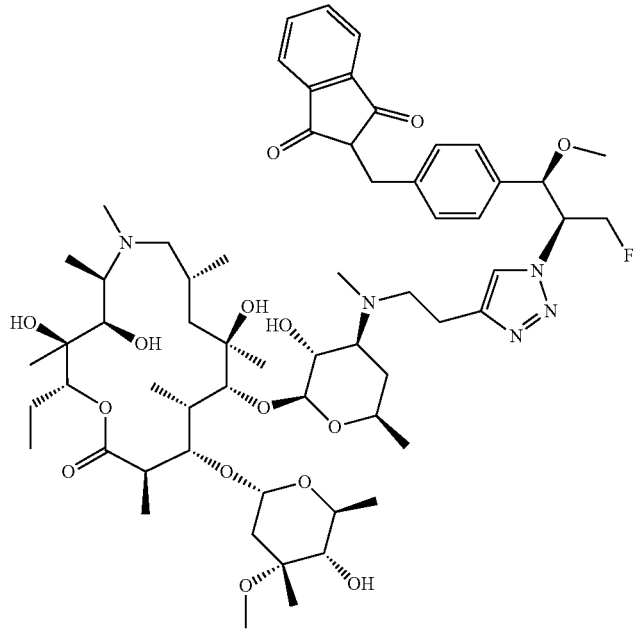 |
| 254 | 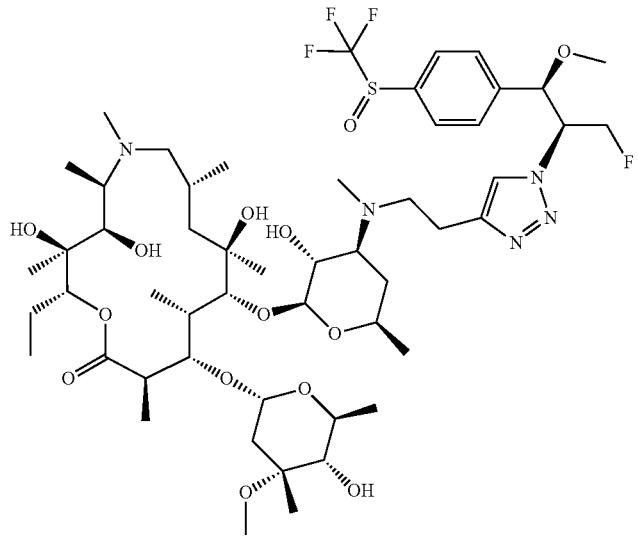 |

-continued
| Compound No. | Structure |
|---|---|
| 255 | 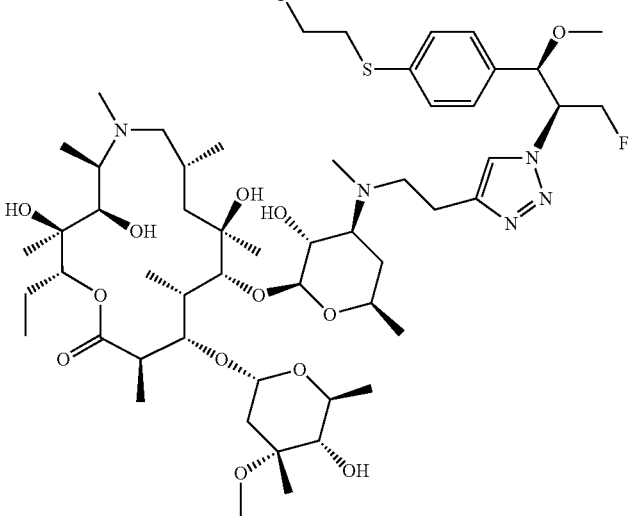 |
| 256 | 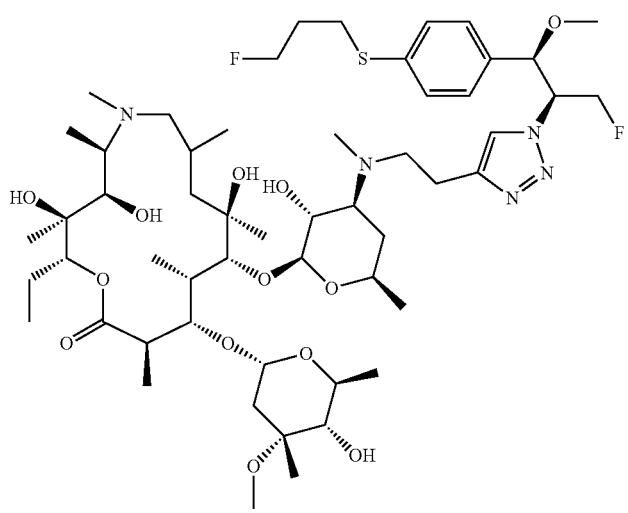 |
| 257 | 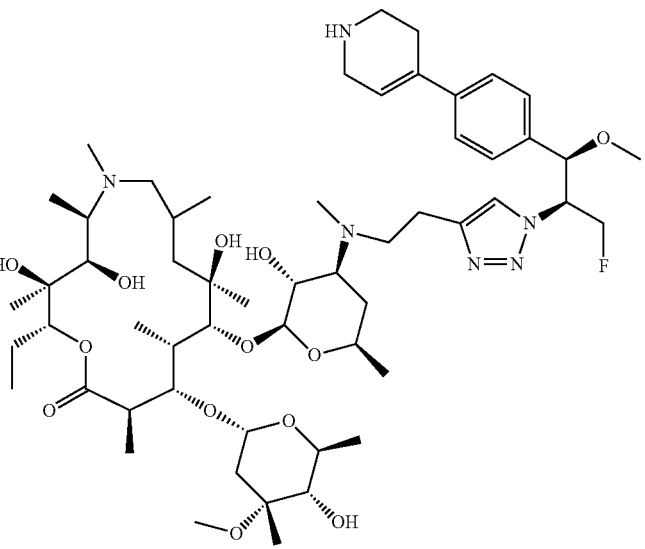 |

-continued
| Compound No. | Structure |
|---|---|
| 258 | 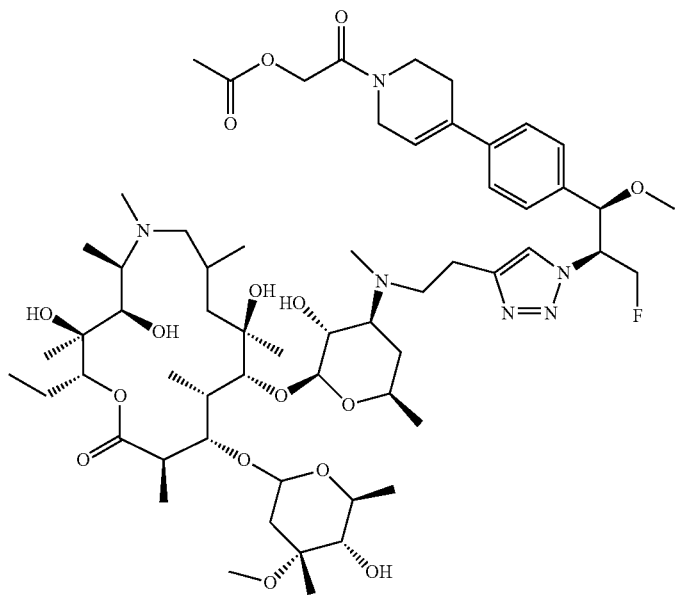 |
| 259 | 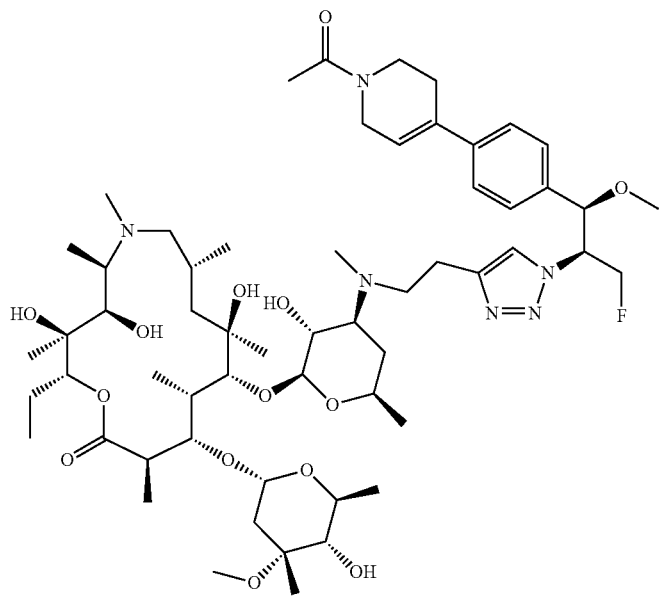 |

-continued
| Compound No. | Structure |
|---|---|
| 260 | 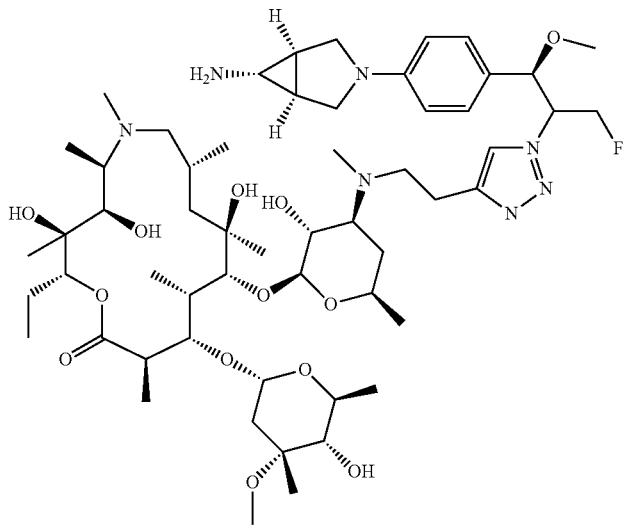 |
| 261 | 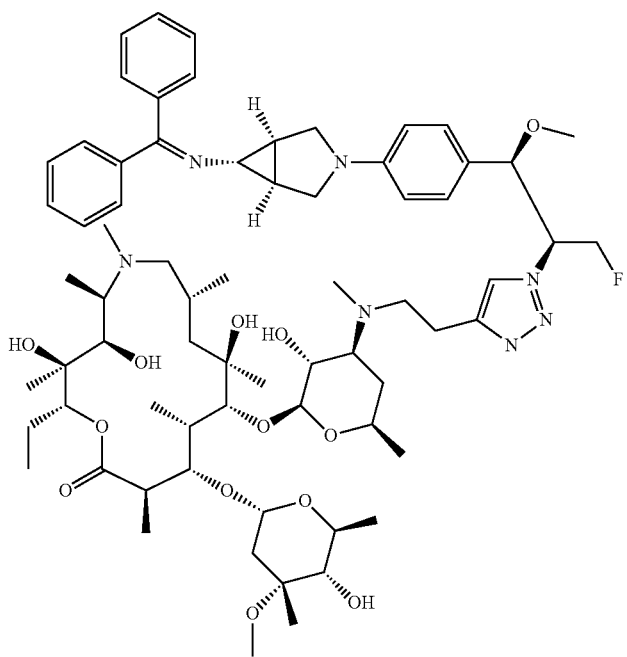 |

| Compound No. | Structure |
|---|---|
| 262 | 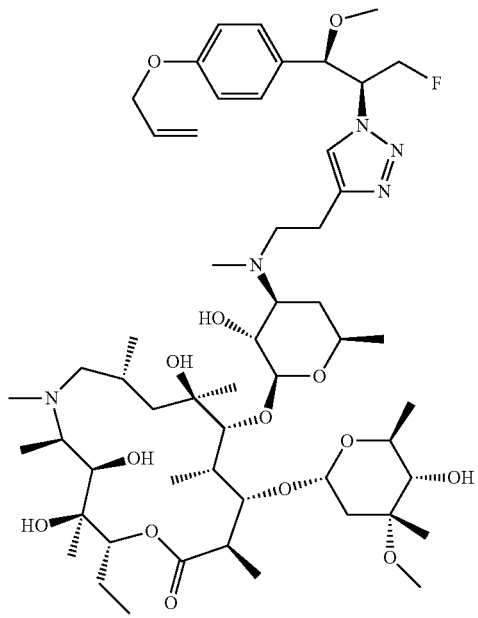 |
| 263 | 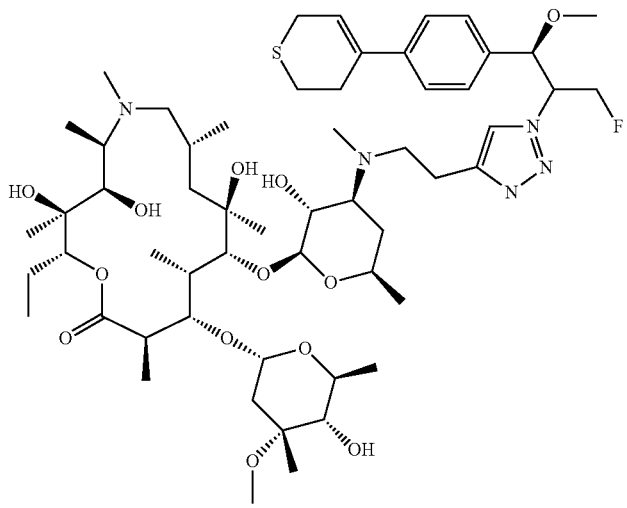 |

| Compound No. | Structure |
|---|---|
| 264 | 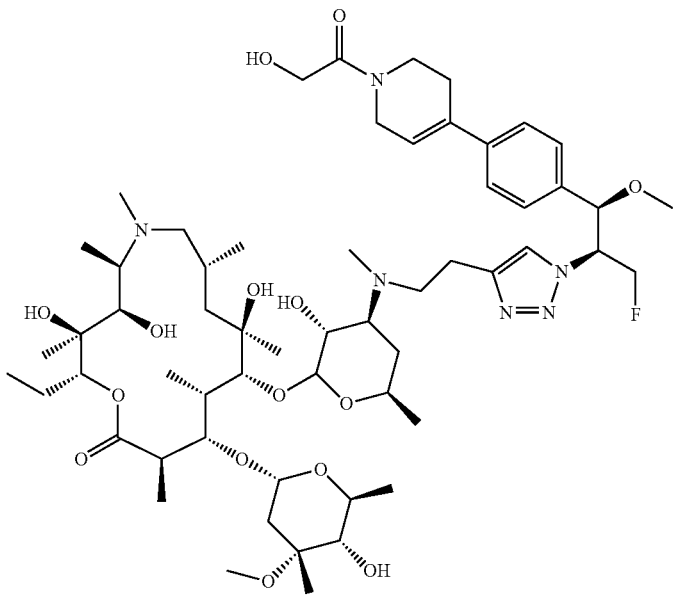 |
| 265 | 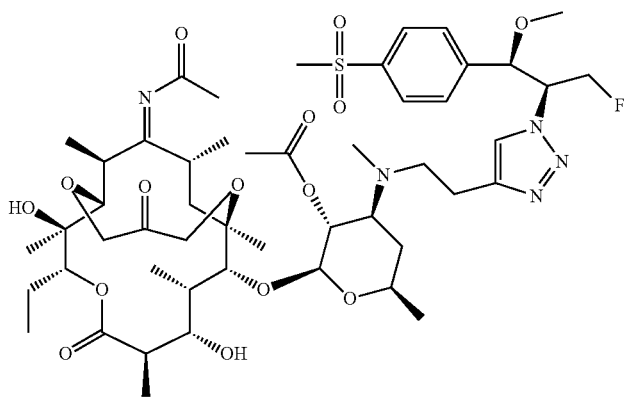 |
| 266 | 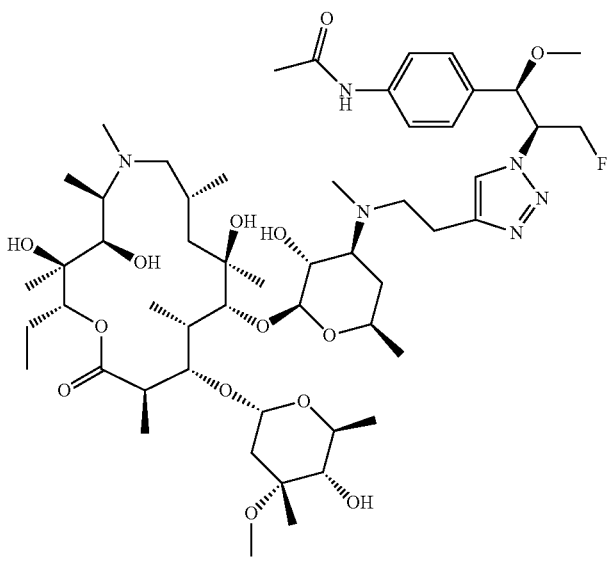 |

| Compound No. | Structure |
|---|---|
| 267 | 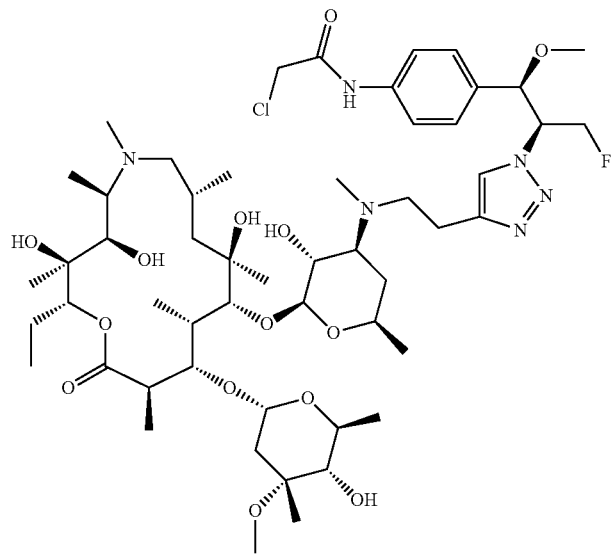 |
| 268 | 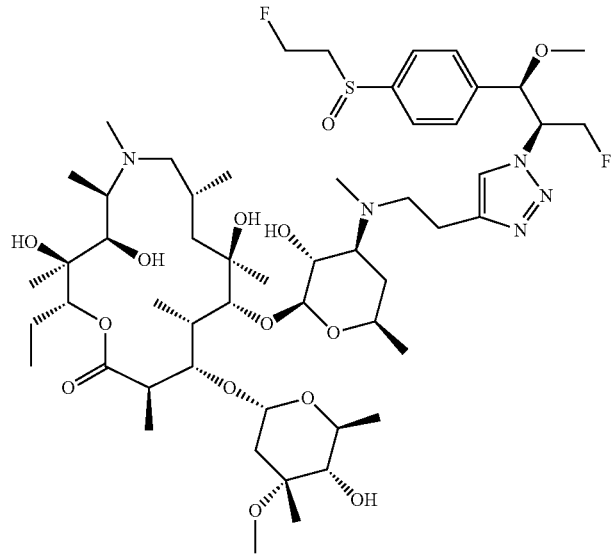 |

-continued

| Compound No. | Structure |
|---|---|
| 269 | 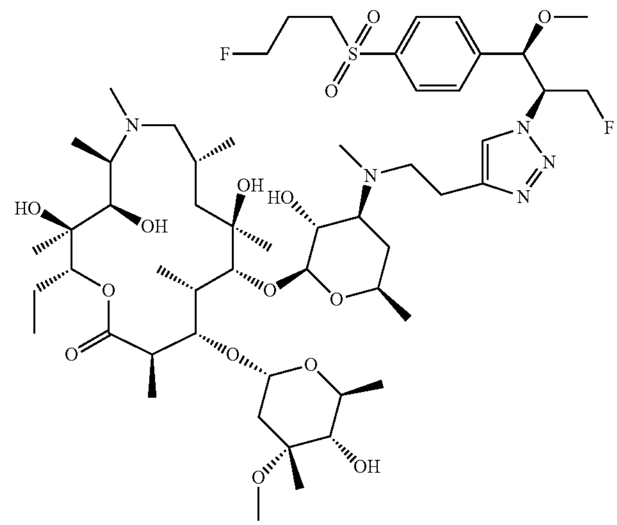 |
| 270 | 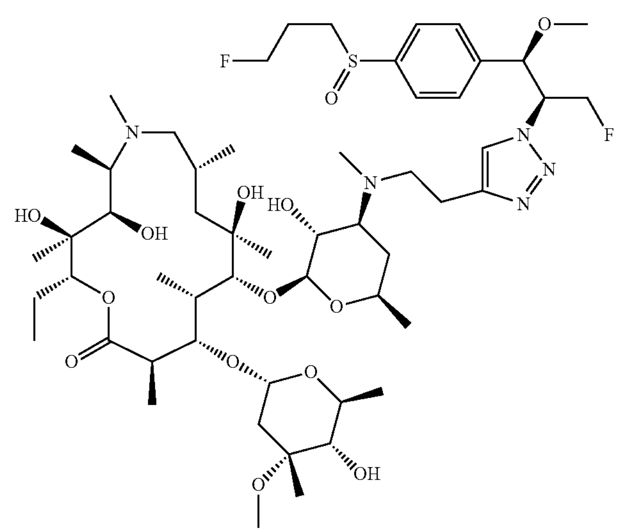 |

| Compound No. | Structure |
|---|---|
| 271 | 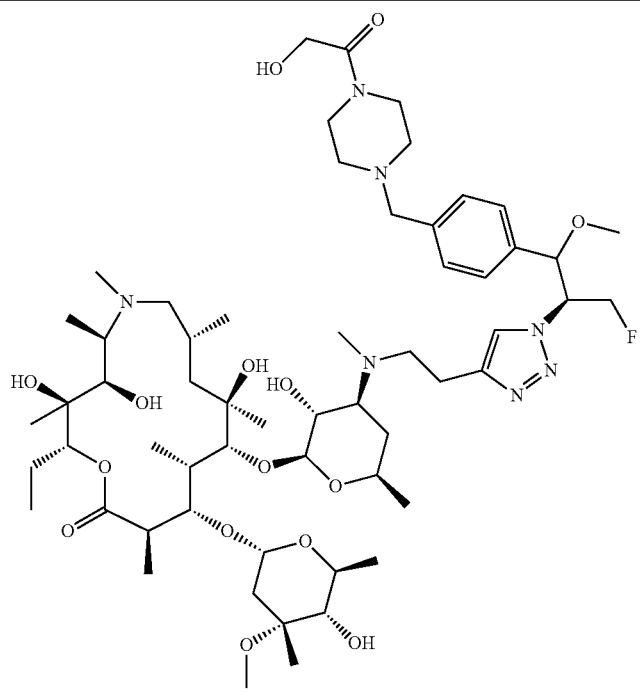 |
| 272 | 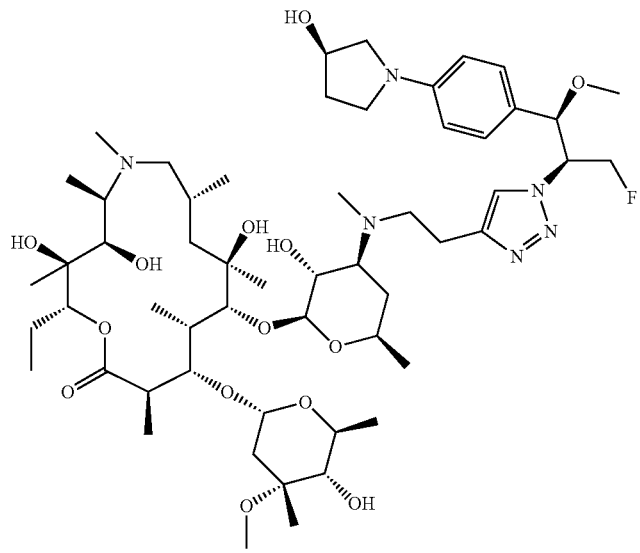 |

| Compound No. | Structure |
|---|---|
| 273 | 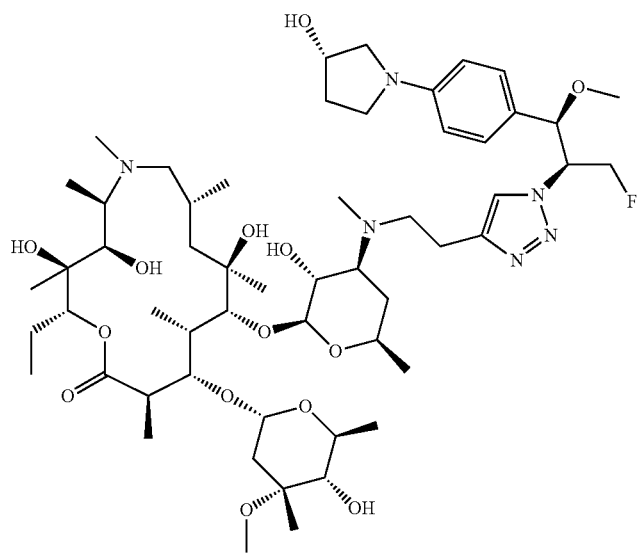 |
| 274 | 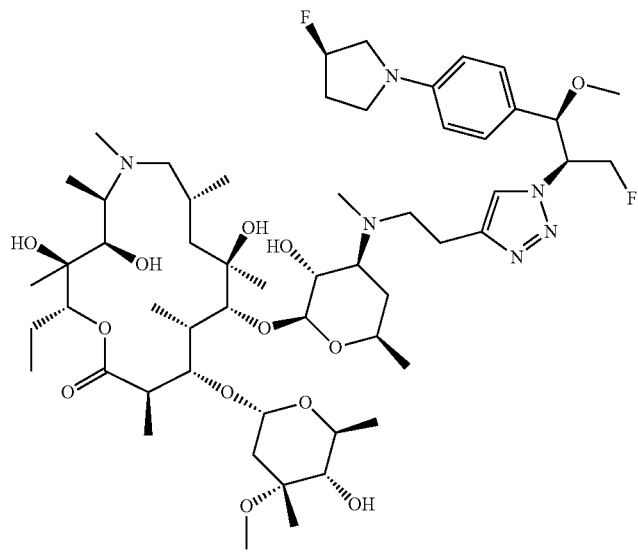 |

-continued
| Compound No. | Structure |
|---|---|
| 275 | 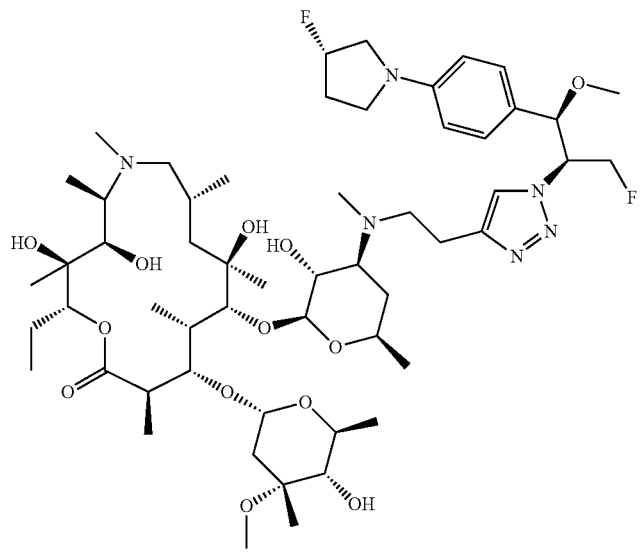 |
| 276 | 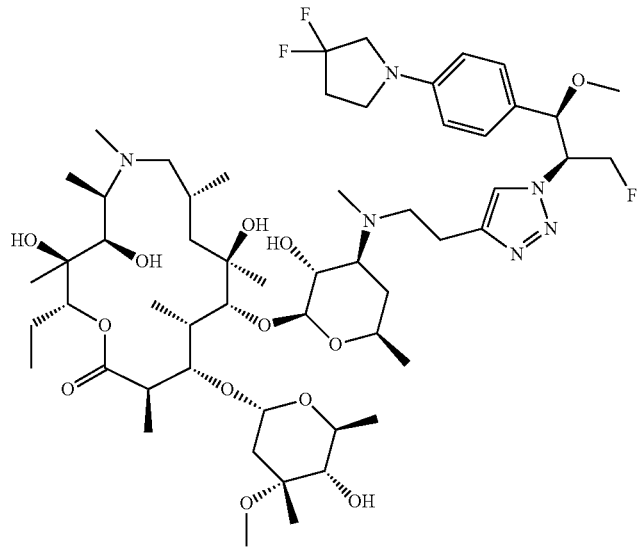 |

| Compound No. | Structure |
|---|---|
| 277 | 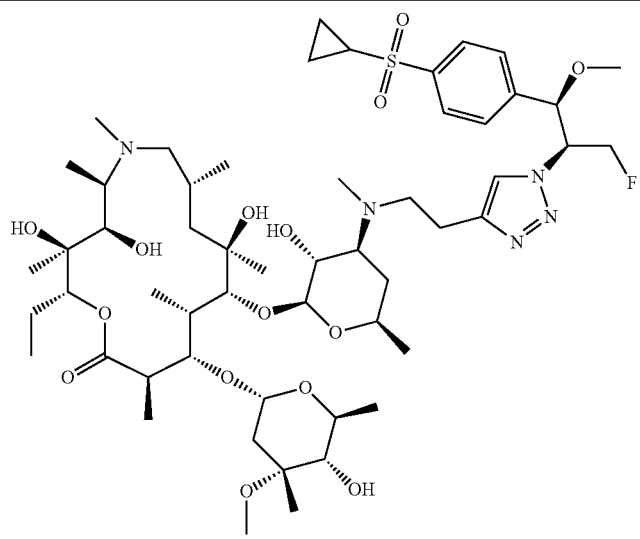 |
| 278 | 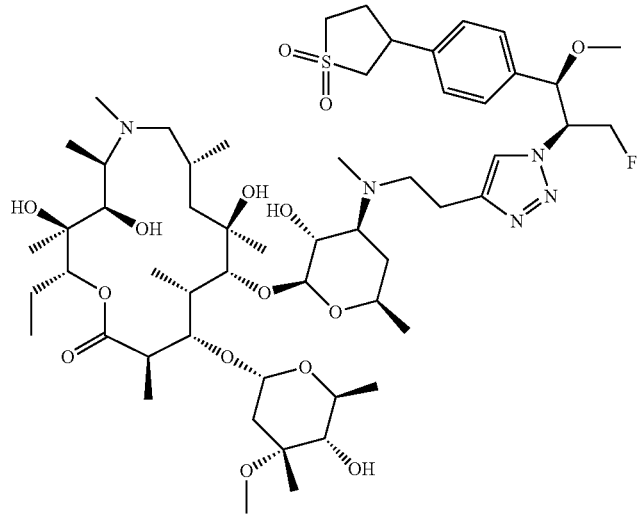 |
| 279 | 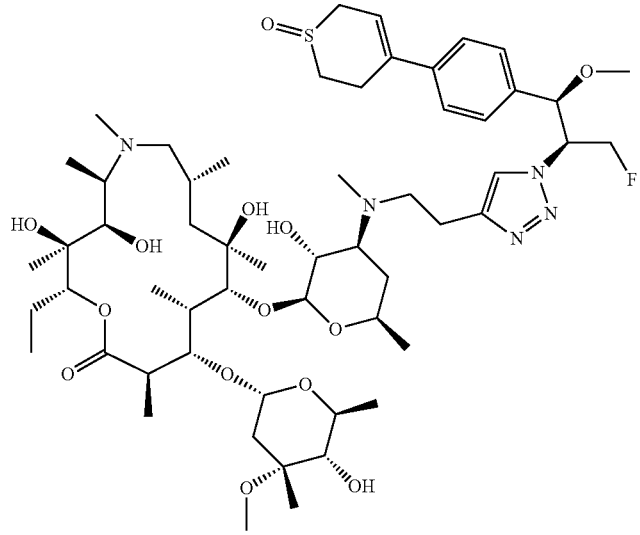 |

| Compound No. | Structure |
|---|---|
| 280 | 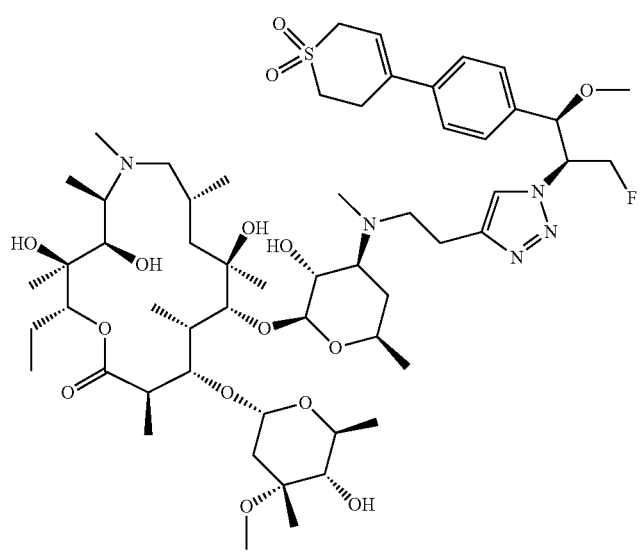 |
| 281 | 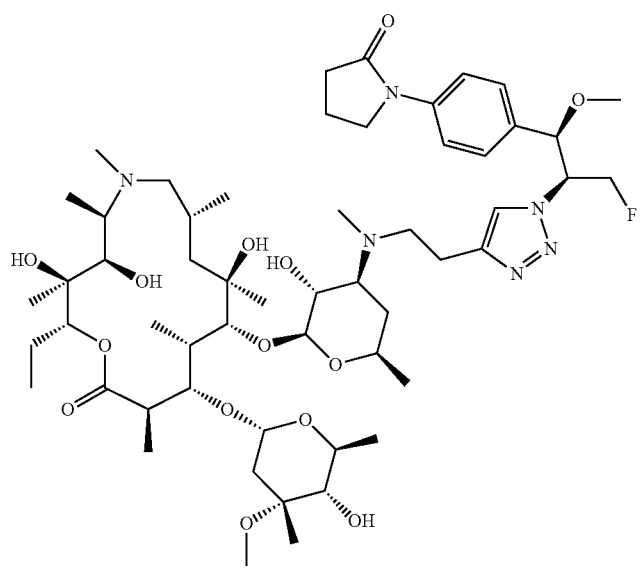 |

| Compound No. | Structure |
| --- | --- |
| 282 | 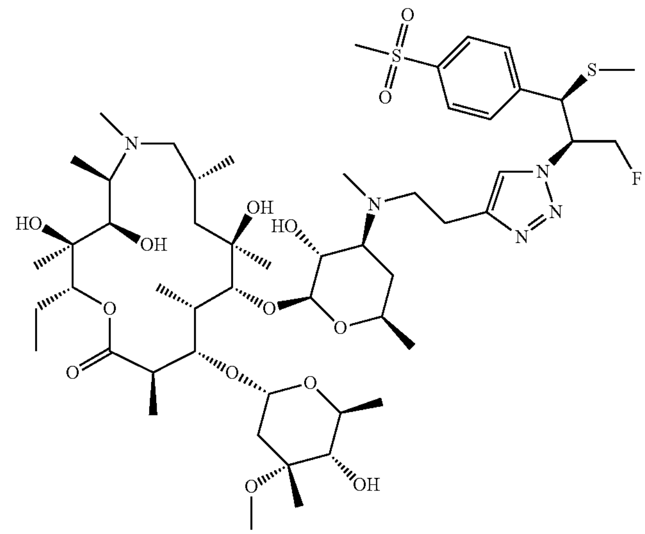 |
| 283 | 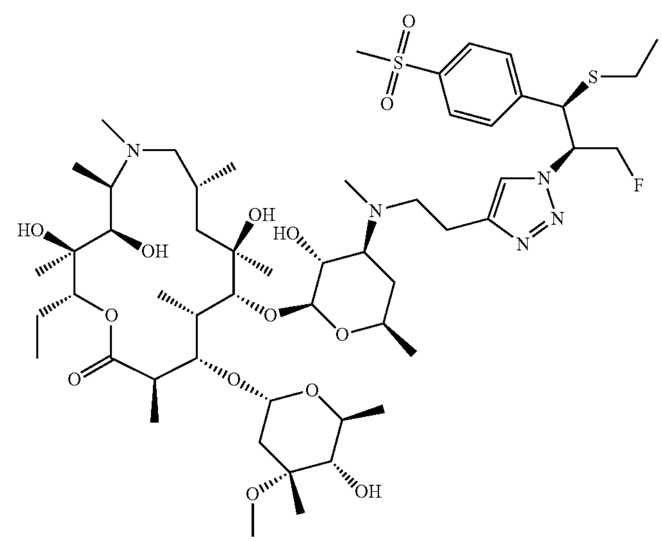 |
| 284 | 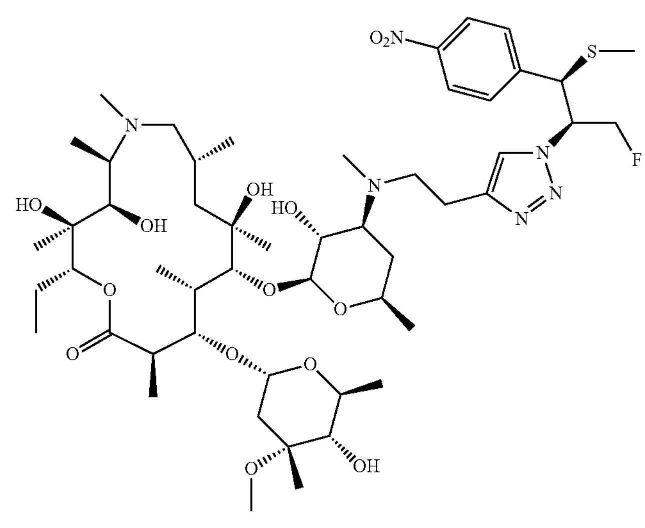 |

-continued

| Compound No. | Structure |
|---|---|
| 285 | 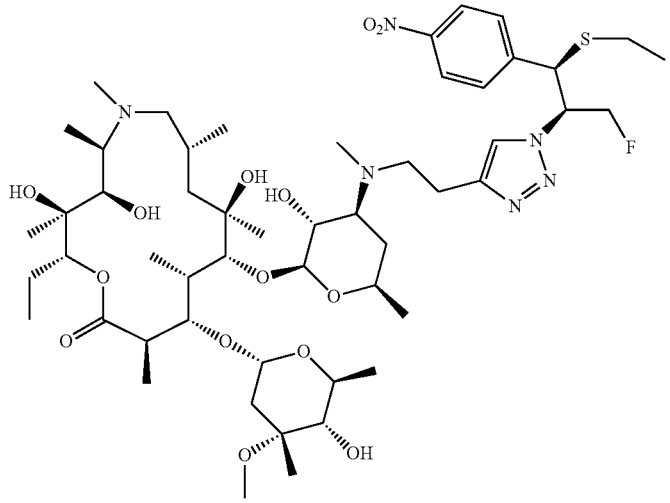 |

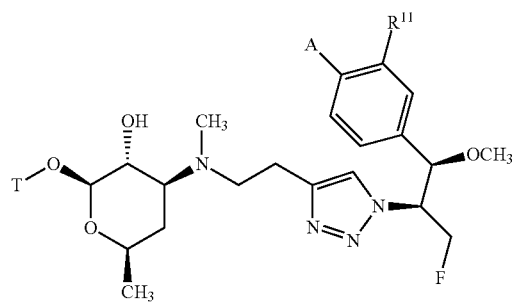

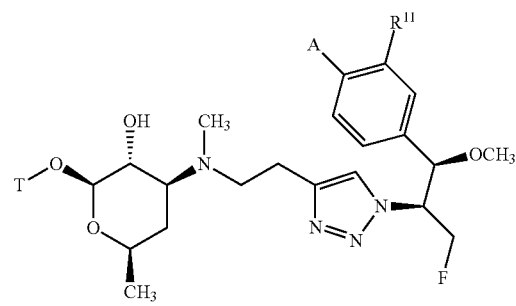

| Compound | T | A | R¹¹ | Compound | T | A | R¹¹ |
|---|---|---|---|---|---|---|---|
| 1000a | T1 | H | H | 1003h | T4 | HC≡CCH₂— | F |
| 1000b | T1 | H | F | 1004a | T1 | cyclohexyl | H |
| 1000c | T2 | H | H | | | | |
| 1000d | T2 | H | F | | | | |
| 1000e | T3 | H | H | | | | |
| 1000f | T3 | H | F | | | | |
| 1000g | T4 | H | H | 1004b | T1 | cyclohexyl | F |
| 1000h | T4 | H | F | | | | |
| 1001a | T1 | CH₃CH₂CH₂— | H | | | | |
| 1001b | T1 | CH₃CH₂CH₂— | F | | | | |
| 1001c | T2 | CH₃CH₂CH₂— | H | | | | |
| 1001d | T2 | CH₃CH₂CH₂— | F | 1004c | T2 | cyclohexyl | H |
| 1001e | T3 | CH₃CH₂CH₂— | H | | | | |
| 1001f | T3 | CH₃CH₂CH₂— | F | | | | |
| 1001g | T4 | CH₃CH₂CH₂— | H | | | | |
| 1001h | T4 | CH₃CH₂CH₂— | F | | | | |
| 1002a | T1 | CH₂=CHCH₂— | H | | | | |
| 1002b | T1 | CH₂=CHCH₂— | F | 1004d | T2 | cyclohexyl | F |
| 1002c | T2 | CH₂=CHCH₂— | H | | | | |
| 1002d | T2 | CH₂=CHCH₂— | F | | | | |
| 1002e | T3 | CH₂=CHCH₂— | H | | | | |
| 1002f | T3 | CH₂=CHCH₂— | F | 1004e | T3 | cyclohexyl | H |
| 1002g | T4 | CH₂=CHCH₂— | H | | | | |
| 1002h | T4 | CH₂=CHCH₂— | F | | | | |
| 1003a | T1 | HC≡CCH₂— | H | | | | |
| 1003b | T1 | HC≡CCH₂— | F | | | | |
| 1003c | T2 | HC≡CCH₂— | H | 1004f | T3 | cyclohexyl | F |
| 1003d | T2 | HC≡CCH₂— | F | | | | |
| 1003e | T3 | HC≡CCH₂— | H | | | | |
| 1003f | T3 | HC≡CCH₂— | F | | | | |
| 1003g | T4 | HC≡CCH₂— | H | | | | |

547

-continued

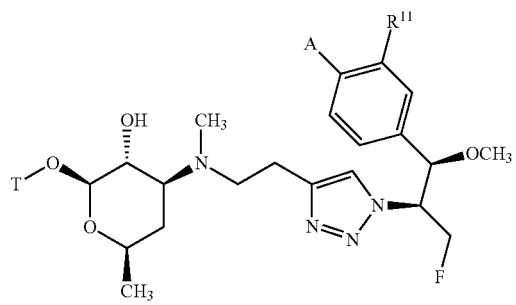

| Compound | T | A | R11 |
|---|---|---|---|
| 1004g | T4 | cyclohexyl | H |
| 1004h | T4 | cyclohexyl | F |
| 1005a | T1 | cyclohexenyl | H |
| 1005b | T1 | cyclohexenyl | F |
| 1005c | T2 | cyclohexenyl | H |
| 1005d | T2 | cyclohexenyl | F |
| 1005e | T3 | cyclohexenyl | H |
| 1005f | T3 | cyclohexenyl | F |
| 1005g | T4 | cyclohexenyl | H |
| 1005h | T4 | cyclohexenyl | F |
| 1006a | T1 | phenyl | H |
| 1006b | T1 | phenyl | F |
| 1006c | T2 | phenyl | H |

548

-continued

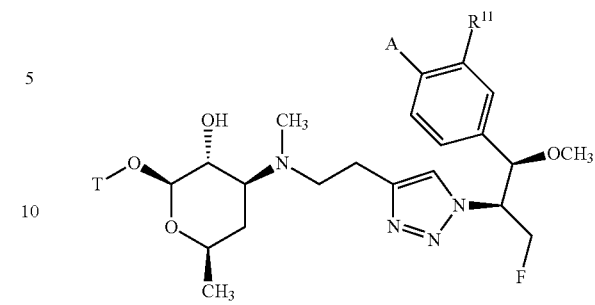

| Compound | T | A | R11 |
|---|---|---|---|
| 1006d | T2 | phenyl | F |
| 1006e | T3 | phenyl | H |
| 1006f | T3 | phenyl | F |
| 1006g | T4 | phenyl | H |
| 1006h | T4 | phenyl | F |
| 1007a | T1 | pyrrolidinyl | H |
| 1007b | T1 | pyrrolidinyl | F |
| 1007c | T2 | pyrrolidinyl | H |
| 1007d | T2 | pyrrolidinyl | F |
| 1007e | T3 | pyrrolidinyl | H |
| 1007f | T3 | pyrrolidinyl | F |
| 1007g | T4 | pyrrolidinyl | H |
| 1007h | T4 | pyrrolidinyl | F |

| | 549 -continued | | | | 550 -continued | | |
|---|---|---|---|---|---|---|---|
| 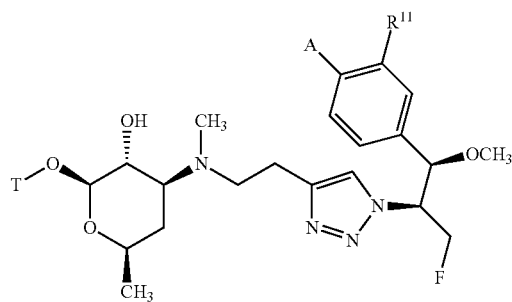 | | | | | 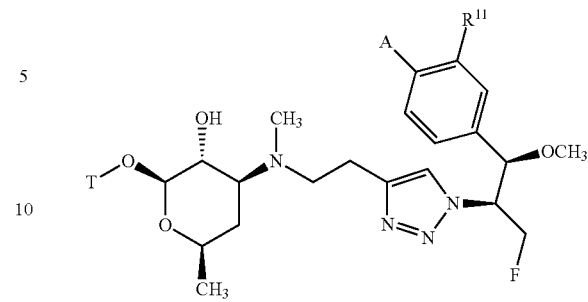 | | |
| Compound | T | A | R11 | Compound | T | A | R11 |
| 1008a | T1 | cyclopentadienyl | H | 1009f | T3 | furan-3-yl | F |
| 1008b | T1 | cyclopentadienyl | F | 1009g | T4 | furan-3-yl | H |
| 1008c | T2 | cyclopentadienyl | H | 1009h | T4 | furan-3-yl | F |
| 1008d | T2 | cyclopentadienyl | F | 1010a | T1 | morpholinyl | H |
| 1008e | T3 | cyclopentadienyl | H | 1010b | T1 | morpholinyl | F |
| 1008f | T3 | cyclopentadienyl | H | 1010c | T2 | morpholinyl | H |
| 1008g | T4 | cyclopentadienyl | H | 1010d | T2 | morpholinyl | F |
| 1008h | T4 | cyclopentadienyl | F | 1010e | T3 | morpholinyl | H |
| 1009a | T1 | furan-3-yl | H | 1010f | T3 | morpholinyl | F |
| 1009b | T1 | furan-3-yl | F | 1010g | T4 | morpholinyl | H |
| 1009c | T2 | furan-3-yl | H | 1010h | T4 | morpholinyl | F |
| 1009d | T2 | furan-3-yl | F | 1011a | T1 | tetrahydropyridinyl | H |
| 1009e | T3 | furan-3-yl | H | 1011b | T1 | tetrahydropyridinyl | F |

551
-continued

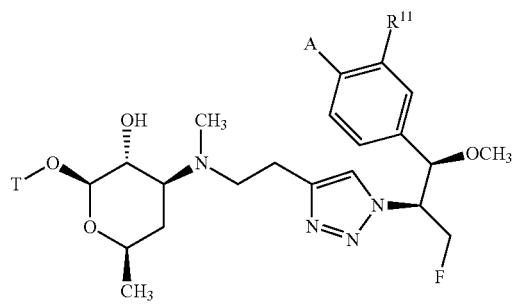

| Compound | T | A | R11 |
|---|---|---|---|
| 1011c | T2 | N-methyl dihydropyridine | H |
| 1011d | T2 | N-methyl dihydropyridine | F |
| 1011e | T3 | N-methyl dihydropyridine | H |
| 1011f | T3 | N-methyl dihydropyridine | F |
| 1011g | T4 | N-methyl dihydropyridine | H |
| 1011h | T4 | N-methyl dihydropyridine | F |
| 1012a | T1 | 1,3,5-triazinyl | H |
| 1012b | T1 | 1,3,5-triazinyl | F |
| 1012c | T2 | 1,3,5-triazinyl | H |
| 1012d | T2 | 1,3,5-triazinyl | F |
| 1012e | T3 | pyrazinyl | H |
| 1012f | T3 | pyrazinyl | F |

552
-continued

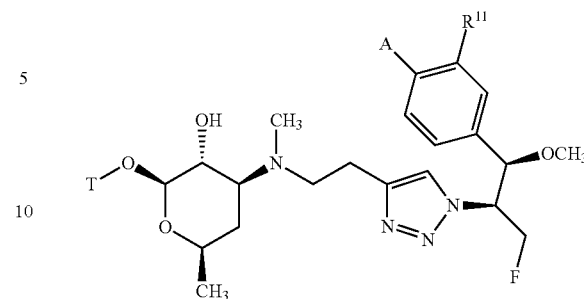

| Compound | T | A | R11 |
|---|---|---|---|
| 1012g | T4 | pyrimidinyl | H |
| 1012h | T4 | pyrimidinyl | F |
| 1013a | T1 | cyclooctyl | H |
| 1013b | T1 | cyclooctyl | F |
| 1013c | T2 | cyclooctyl | H |
| 1013d | T2 | cyclooctyl | F |
| 1013e | T3 | cyclooctyl | H |
| 1013f | T3 | cyclooctyl | F |
| 1013g | T4 | cyclooctyl | H |
| 1013h | T4 | naphthyl | F |

553
-continued

554
-continued

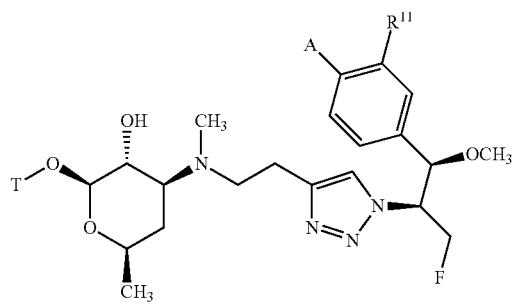

| Compound | T | A | R¹¹ |
|---|---|---|---|
| 10140a | T1 | (spiro cyclohexane-cyclopentene, methyl) | H |
| 1014b | T1 | (spiro) | F |
| 1014c | T2 | (spiro) | H |
| 1014d | T2 | (spiro) | F |
| 1014e | T3 | (spiro) | H |
| 1014f | T3 | (spiro) | F |
| 1014g | T4 | (spiro) | H |
| 1014h | T4 | (spiro) | F |
| 1015a | T1 | (naphthyl) | H |
| 1015b | T1 | (naphthyl) | F |
| 1015c | T2 | (naphthyl) | H |

| Compound | T | A | R¹¹ |
|---|---|---|---|
| 1015d | T2 | (naphthyl) | F |
| 1015e | T3 | (naphthyl) | H |
| 1015f | T3 | (naphthyl) | F |
| 1015g | T4 | (naphthyl) | H |
| 1015h | T4 | (naphthyl) | F |
| 1016a | T1 | HO— | H |
| 1016b | T1 | HO— | F |
| 1016c | T2 | HO— | H |
| 1016d | T2 | HO— | F |
| 1016e | T3 | HO— | H |
| 1016f | T3 | HO— | F |
| 1016g | T4 | HO— | H |
| 1016h | T4 | HO— | F |
| 1017a | T1 | HS— | H |
| 1017b | T1 | HS— | F |
| 1017c | T2 | HS— | H |
| 1017d | T2 | HS— | F |
| 1017e | T3 | HS— | H |
| 1017f | T3 | HS— | F |
| 1017g | T4 | HS— | H |
| 1017h | T4 | HS— | F |
| 1018a | T1 | F | H |
| 1018b | T1 | F | F |
| 1018c | T2 | F | H |
| 1018d | T2 | F | F |
| 1018e | T3 | F | H |
| 1018f | T3 | F | F |
| 1018g | T4 | F | H |
| 1018h | T4 | F | F |
| 1019a | T1 | Cl | H |
| 1019b | T1 | Cl | F |
| 1019c | T2 | Cl | H |
| 1019d | T2 | Cl | F |
| 1019e | T3 | Cl | H |
| 1019f | T3 | Cl | F |

-continued

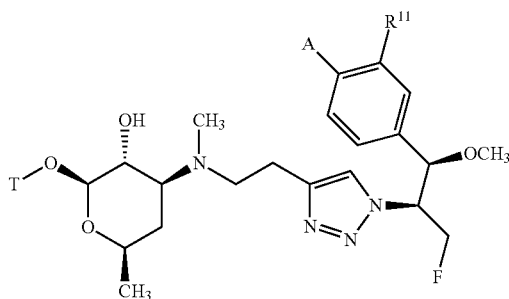

| Compound | T | A | R[11] |
|---|---|---|---|
| 1019g | T4 | Cl | H |
| 1019h | T4 | Cl | F |
| 1020a | T1 | Br | H |
| 1020b | T1 | Br | F |
| 1020c | T2 | Br | H |
| 1020d | T2 | Br | F |
| 1020e | T3 | Br | H |
| 1020f | T3 | Br | F |
| 1020g | T4 | Br | H |
| 1020h | T4 | Br | F |
| 1021a | T1 | I | H |
| 1021b | T1 | I | F |
| 1021c | T2 | I | H |
| 1021d | T2 | I | F |
| 1021e | T3 | I | H |
| 1021f | T3 | I | F |
| 1021g | T4 | I | H |
| 1021h | T4 | I | F |
| 1022a | T1 | $F_3C-$ | H |
| 1022b | T1 | $F_3C-$ | F |
| 1022c | T2 | $F_3C-$ | H |
| 1022d | T2 | $F_3C-$ | F |
| 1022e | T3 | $F_3C-$ | H |
| 1022f | T3 | $F_3C-$ | F |
| 1022g | T4 | $F_3C-$ | H |
| 1022h | T4 | $F_3C-$ | F |
| 1023a | T1 | NC— | H |
| 1023b | T1 | NC— | F |
| 1023c | T2 | NC— | H |
| 1023d | T2 | NC— | F |
| 1023e | T3 | NC— | H |
| 1023f | T3 | NC— | F |
| 1023g | T4 | NC— | H |
| 1023h | T4 | NC— | F |
| 1024a | T1 | $N_3-$ | H |
| 1024b | T1 | $N_3-$ | F |
| 1024c | T2 | $N_3-$ | H |
| 1024d | T2 | $N_3-$ | F |
| 1024e | T3 | $N_3-$ | H |
| 1024f | T3 | $N_3-$ | F |
| 1024g | T4 | $N_3-$ | H |
| 1024h | T4 | $N_3-$ | F |
| 1025a | T1 | $NO_2-$ | H |
| 1025b | T1 | $NO_2-$ | F |
| 1025c | T2 | $NO_2-$ | H |
| 1025d | T2 | $NO_2-$ | F |
| 1025e | T3 | $NO_2-$ | H |
| 1025f | T3 | $NO_2-$ | F |
| 1025g | T4 | $NO_2-$ | H |
| 1025h | T4 | $NO_2-$ | F |
| 1026a | T1 | $(CH_3)_2N-$ | H |
| 1026b | T1 | $(CH_3)_2N-$ | F |
| 1026c | T2 | $(CH_3)_2N-$ | H |
| 1026d | T2 | $(CH_3)_2N-$ | F |
| 1026e | T3 | $(CH_3)_2N-$ | H |
| 1026f | T3 | $(CH_3)_2N-$ | F |
| 1026g | T4 | $(CH_3)_2N-$ | H |
| 1026h | T4 | $(CH_3)_2N-$ | F |
| 1027a | T1 | $CH_3O-$ | H |
| 1027b | T1 | $CH_3O-$ | F |
| 1027c | T2 | $CH_3O-$ | H |
| 1027d | T2 | $CH_3O-$ | F |
| 1027e | T3 | $CH_3O-$ | H |

-continued

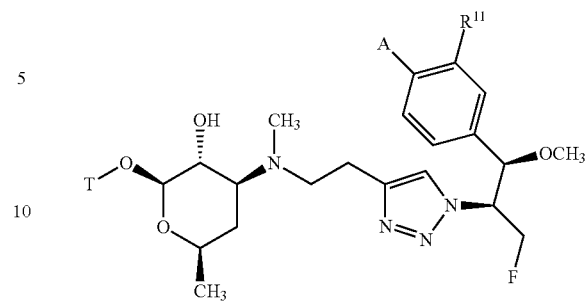

| Compound | T | A | R[11] |
|---|---|---|---|
| 1027f | T3 | $CH_3O-$ | F |
| 1027g | T4 | $CH_3O-$ | H |
| 1027h | T4 | $CH_3O-$ | F |
| 1028a | T1 | $CH_3S-$ | H |
| 1028b | T1 | $CH_3S-$ | F |
| 1028c | T2 | $CH_3S-$ | H |
| 1028d | T2 | $CH_3S-$ | F |
| 1028e | T3 | $CH_3S-$ | H |
| 1028f | T3 | $CH_3S-$ | F |
| 1028g | T4 | $CH_3S-$ | H |
| 1028h | T4 | $CH_3S-$ | F |
| 1029a | T1 | $CH_3S(=O)-$ | H |
| 1029b | T1 | $CH_3S(=O)-$ | F |
| 1029c | T2 | $CH_3S(=O)-$ | H |
| 1029d | T2 | $CH_3S(=O)-$ | F |
| 1029e | T3 | $CH_3S(=O)-$ | H |
| 1029f | T3 | $CH_3S(=O)-$ | F |
| 1029g | T4 | $CH_3S(=O)-$ | H |
| 1029h | T4 | $CH_3S(=O)-$ | F |
| 1030a | T1 | $CH_3S(=O)_2-$ | H |
| 1030b | T1 | $CH_3S(=O)_2-$ | F |
| 1030c | T2 | $CH_3S(=O)_2-$ | H |
| 1030d | T2 | $CH_3S(=O)_2-$ | F |
| 1030e | T3 | $CH_3S(=O)_2-$ | H |
| 1030f | T3 | $CH_3S(=O)_2-$ | F |
| 1030g | T4 | $CH_3S(=O)_2-$ | H |
| 1030h | T4 | $CH_3S(=O)_2-$ | F |
| 1031a | T1 | $HC(=O)-$ | H |
| 1031b | T1 | $HC(=O)-$ | F |
| 1031c | T2 | $HC(=O)-$ | H |
| 1031d | T2 | $HC(=O)-$ | F |
| 1031e | T3 | $HC(=O)-$ | H |
| 1031f | T3 | $HC(=O)-$ | F |
| 1031g | T4 | $HC(=O)-$ | H |
| 1031h | T4 | $HC(=O)-$ | F |
| 1032a | T1 | $CH_3C(=O)-$ | H |
| 1032b | T1 | $CH_3C(=O)-$ | F |
| 1032c | T2 | $CH_3C(=O)-$ | H |
| 1032d | T2 | $CH_3C(=O)-$ | F |
| 1032e | T3 | $CH_3C(=O)-$ | H |
| 1032f | T3 | $CH_3C(=O)-$ | F |
| 1032g | T4 | $CH_3C(=O)-$ | H |
| 1032h | T4 | $CH_3C(=O)-$ | F |
| 1033a | T1 | $CH_3OC(=O)-$ | H |
| 1033b | T1 | $CH_3OC(=O)-$ | F |
| 1033c | T2 | $CH_3OC(=O)-$ | H |
| 1033d | T2 | $CH_3OC(=O)-$ | F |
| 1033e | T3 | $CH_3OC(=O)-$ | H |
| 1033f | T3 | $CH_3OC(=O)-$ | F |
| 1033g | T4 | $CH_3OC(=O)-$ | H |
| 1033h | T4 | $CH_3OC(=O)-$ | F |
| 1034a | T1 | $CH_3COO-$ | H |
| 1034b | T1 | $CH_3COO-$ | F |
| 1034c | T2 | $CH_3COO-$ | H |
| 1034d | T2 | $CH_3COO-$ | F |
| 1034e | T3 | $CH_3COO-$ | H |
| 1034f | T3 | $CH_3COO-$ | F |
| 1034g | T4 | $CH_3COO-$ | H |
| 1034h | T4 | $CH_3COO-$ | F |
| 1035a | T1 | $CH_3OCOO-$ | H |
| 1035b | T1 | $CH_3OCOO-$ | F |
| 1035c | T2 | $CH_3OCOO-$ | H |
| 1035d | T2 | $CH_3OCOO-$ | F |

557
-continued

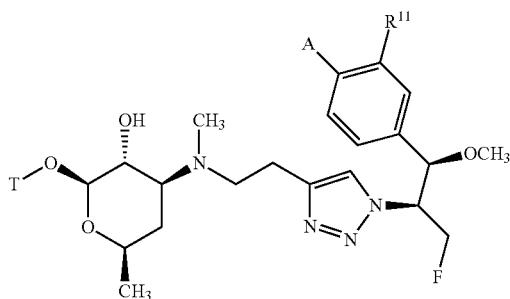

| Compound | T | A | R[11] |
|---|---|---|---|
| 1035e | T3 | CH3OCOO— | H |
| 1035f | T3 | CH3OCOO— | F |
| 1035g | T4 | CH3OCOO— | H |
| 1035h | T4 | CH3OCOO— | F |
| 1036a | T1 | CH3C(=O)S— | H |
| 1036b | T1 | CH3C(=O)S— | F |
| 1036c | T2 | CH3C(=O)S— | H |
| 1036d | T2 | CH3C(=O)S— | F |
| 1036e | T3 | CH3C(=O)S— | H |
| 1036f | T3 | CH3C(=O)S— | F |
| 1036g | T4 | CH3C(=O)S— | H |
| 1036h | T4 | CH3C(=O)S— | F |
| 1037a | T1 | CH3C(=O)NH— | H |
| 1037b | T1 | CH3C(=O)NH— | F |
| 1037c | T2 | CH3C(=O)NH— | H |
| 1037d | T2 | CH3C(=O)NH— | F |
| 1037e | T3 | CH3C(=O)NH— | H |
| 1037f | T3 | CH3C(=O)NH— | F |
| 1037g | T4 | CH3C(=O)NH— | H |
| 1037h | T4 | CH3C(=O)NH— | F |
| 1038a | T1 | CH3NHC(=O)— | H |
| 1038b | T1 | CH3NHC(=O)— | F |
| 1038c | T2 | CH3NHC(=O)— | H |
| 1038d | T2 | CH3NHC(=O)— | F |
| 1038e | T3 | CH3NHC(=O)— | H |
| 1038f | T3 | CH3NHC(=O)— | F |
| 1038g | T4 | CH3NHC(=O)— | H |
| 1038h | T4 | CH3NHC(=O)— | F |
| 1039a | T1 | CH3C(=NOH)— | H |
| 1039b | T1 | CH3C(=NOH)— | F |
| 1039c | T2 | CH3C(=NOH)— | H |
| 1039d | T2 | CH3C(=NOH)— | F |
| 1039e | T3 | CH3C(=NOH)— | H |
| 1039f | T3 | CH3C(=NOH)— | F |
| 1039g | T4 | CH3C(=NOH)— | H |
| 1039h | T4 | CH3C(=NOH)— | F |
| 1040a | T1 | CH3C[=N—N(CH3)2]— | H |
| 1040b | T1 | CH3C[=N—N(CH3)2]— | F |
| 1040c | T2 | CH3C[=N—N(CH3)2]— | H |
| 1040d | T2 | CH3C[=N—N(CH3)2]— | F |
| 1040e | T3 | CH3C[=N—N(CH3)2]— | H |
| 1040f | T3 | CH3C[=N—N(CH3)2]— | F |
| 1040g | T4 | CH3C[=N—N(CH3)2]— | H |
| 1040h | T4 | CH3C[=N—N(CH3)2]— | F |
| 1041a | T1 | 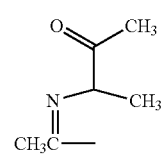 | H |
| 1041b | T1 | 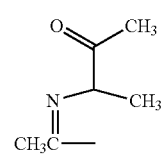 | F |

558
-continued

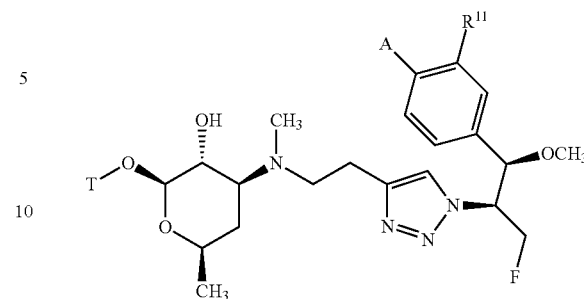

| Compound | T | A | R[11] |
|---|---|---|---|
| 1041c | T2 | 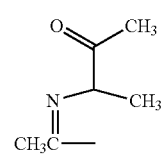 | H |
| 1041d | T2 | 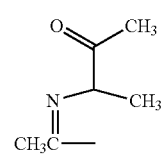 | F |
| 1041e | T3 | 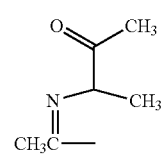 | H |
| 1041f | T3 | 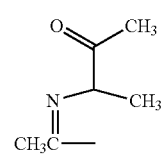 | F |
| 10410g | T4 | 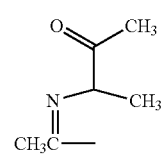 | H |
| 1041h | T4 | 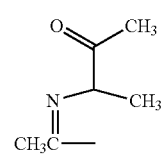 | F |
| 1042a | T1 | CH3C[=N—OCH3]— | H |
| 1042b | T1 | CH3C[=N—OCH3]— | F |
| 1042c | T2 | CH3C[=N—OCH3]— | H |
| 1042d | T2 | CH3C[=N—OCH3]— | F |
| 1042e | T3 | CH3C[=N—OCH3]— | H |
| 1042f | T3 | CH3C[=N—OCH3]— | F |
| 1042g | T4 | CH3C[=N—OCH3]— | H |
| 1042h | T4 | CH3C[=N—OCH3]— | F |
| 1043a | T1 | CH3OC(=O)NH— | H |
| 1043b | T1 | CH3OC(=O)NH— | F |
| 1043c | T2 | CH3OC(=O)NH— | H |
| 1043d | T2 | CH3OC(=O)NH— | F |
| 1043e | T3 | CH3OC(=O)NH— | H |
| 1043f | T3 | CH3OC(=O)NH— | F |
| 1043g | T4 | CH3OC(=O)NH— | H |
| 1043h | T4 | CH3OC(=O)NH— | F |

559
-continued

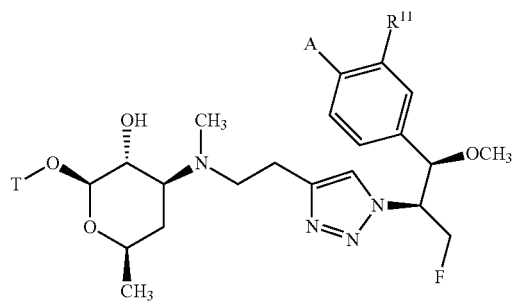

| Compound | T | A | R[11] |
|---|---|---|---|
| 1044a | T1 | CH₃NHC(=O)O— | H |
| 1044b | T1 | CH₃NHC(=O)O— | F |
| 1044c | T2 | CH₃NHC(=O)O— | H |
| 1044d | T2 | CH₃NHC(=O)O— | F |
| 1044e | T3 | CH₃NHC(=O)O— | H |
| 1044f | T3 | CH₃NHC(=O)O— | F |
| 1044g | T4 | CH₃NHC(=O)O— | H |
| 1044h | T4 | CH₃NHC(=O)O— | F |
| 1045a | T1 | CH₃NHC(=O)NH— | H |
| 1045b | T1 | CH₃NHC(=O)NH— | F |
| 1045c | T2 | CH₃NHC(=O)NH— | H |
| 1045d | T2 | CH₃NHC(=O)NH— | F |
| 1045e | T3 | CH₃NHC(=O)NH— | H |
| 1045f | T3 | CH₃NHC(=O)NH— | F |
| 1045g | T4 | CH₃NHC(=O)NH— | H |
| 1045h | T4 | CH₃NHC(=O)NH— | F |
| 1046a | T1 | CH₃S(=O)₂NH— | H |
| 1046b | T1 | CH₃S(=O)₂NH— | F |
| 1046c | T2 | CH₃S(=O)₂NH— | H |
| 1046d | T2 | CH₃S(=O)₂NH— | F |
| 1046e | T3 | CH₃S(=O)₂NH— | H |
| 1046f | T3 | CH₃S(=O)₂NH— | F |
| 1046g | T4 | CH₃S(=O)₂NH— | H |
| 1046h | T4 | CH₃S(=O)₂NH— | F |
| 1047a | T1 | CH₃NHS(=O)₂— | H |
| 1047b | T1 | CH₃NHS(=O)₂— | F |
| 1047c | T2 | CH₃NHS(=O)₂— | H |
| 1047d | T2 | CH₃NHS(=O)₂— | F |
| 1047e | T3 | CH₃NHS(=O)₂— | H |
| 1047f | T3 | CH₃NHS(=O)₂— | F |
| 1047g | T4 | CH₃NHS(=O)₂— | H |
| 1047h | T4 | CH₃NHS(=O)₂— | F |
| 1048a | T1 | NH₂— | H |
| 1048b | T1 | NH₂— | F |
| 1048c | T2 | NH₂— | H |
| 1048d | T2 | NH₂— | F |
| 1048e | T3 | NH₂— | H |
| 1048f | T3 | NH₂— | F |
| 1048g | T4 | NH₂— | H |
| 1048h | T4 | NH₂— | F |
| 1049a | T1 | (CH₃)₂N— | H |
| 1049b | T1 | (CH₃)₂N— | F |
| 1049c | T2 | (CH₃)₂N— | H |
| 1049d | T2 | (CH₃)₂N— | F |
| 1049e | T3 | (CH₃)₂N— | H |
| 1049f | T3 | (CH₃)₂N— | F |
| 1049g | T4 | (CH₃)₂N— | H |
| 1049h | T4 | (CH₃)₂N— | F |
| 1050a | T1 | (CH₃)₃Si— | H |
| 1050b | T1 | (CH₃)₃Si— | F |
| 10450c | T2 | (CH₃)₃Si— | H |
| 1050d | T2 | (CH₃)₃Si— | F |
| 1050e | T3 | (CH₃)₃Si— | H |
| 1050f | T3 | (CH₃)₃Si— | F |
| 1050g | T4 | (CH₃)₃Si— | H |
| 1050h | T4 | (CH₃)₃Si— | F |
| 1051a | T1 | (CH₃O)₃Si— | H |
| 1051b | T1 | (CH₃O)₃Si— | F |
| 1051c | T2 | (CH₃O)₃Si— | H |
| 1051d | T2 | (CH₃O)₃Si— | F |
| 1051e | T3 | (CH₃O)₃Si— | H |
| 1051f | T3 | (CH₃O)₃Si— | F |

560
-continued

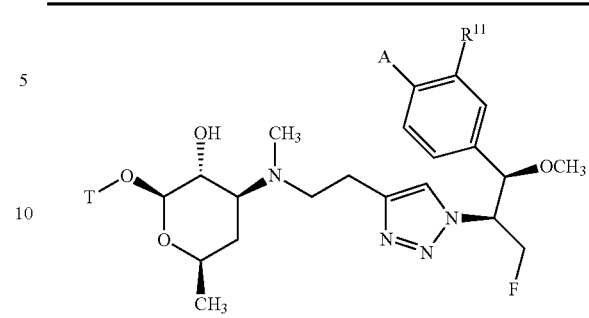

| Compound | T | A | R[11] |
|---|---|---|---|
| 1051g | T4 | (CH₃O)₃Si— | H |
| 1051h | T4 | (CH₃O)₃Si— | F |

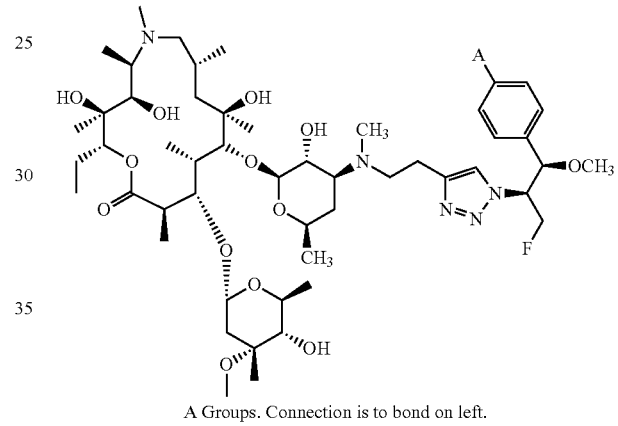

A Groups. Connection is to bond on left.

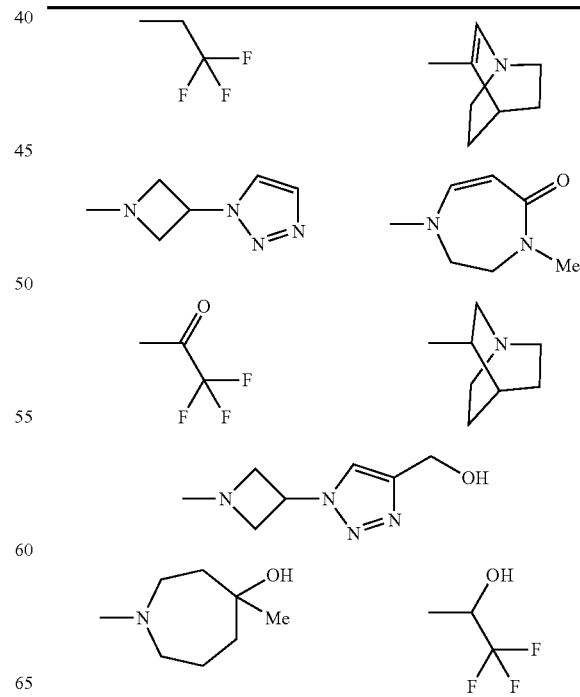

561 562
-continued -continued
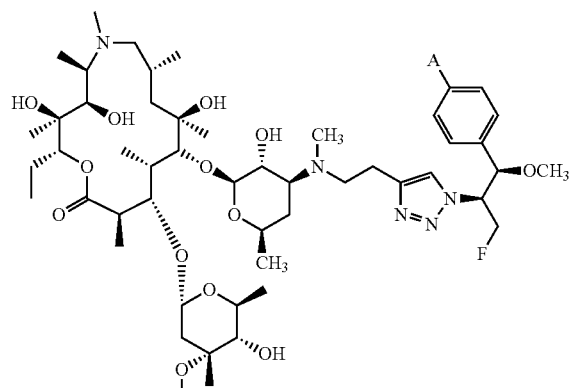
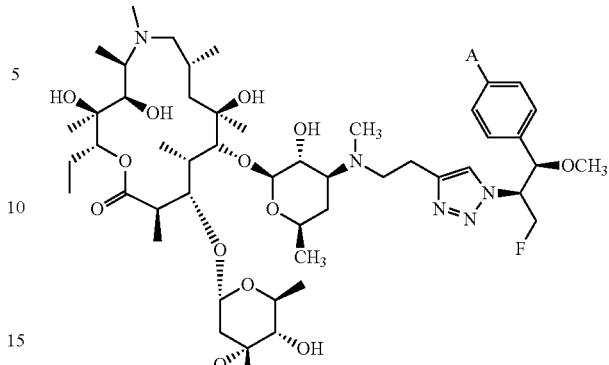
A Groups. Connection is to bond on left.　　A Groups. Connection is to bond on left.
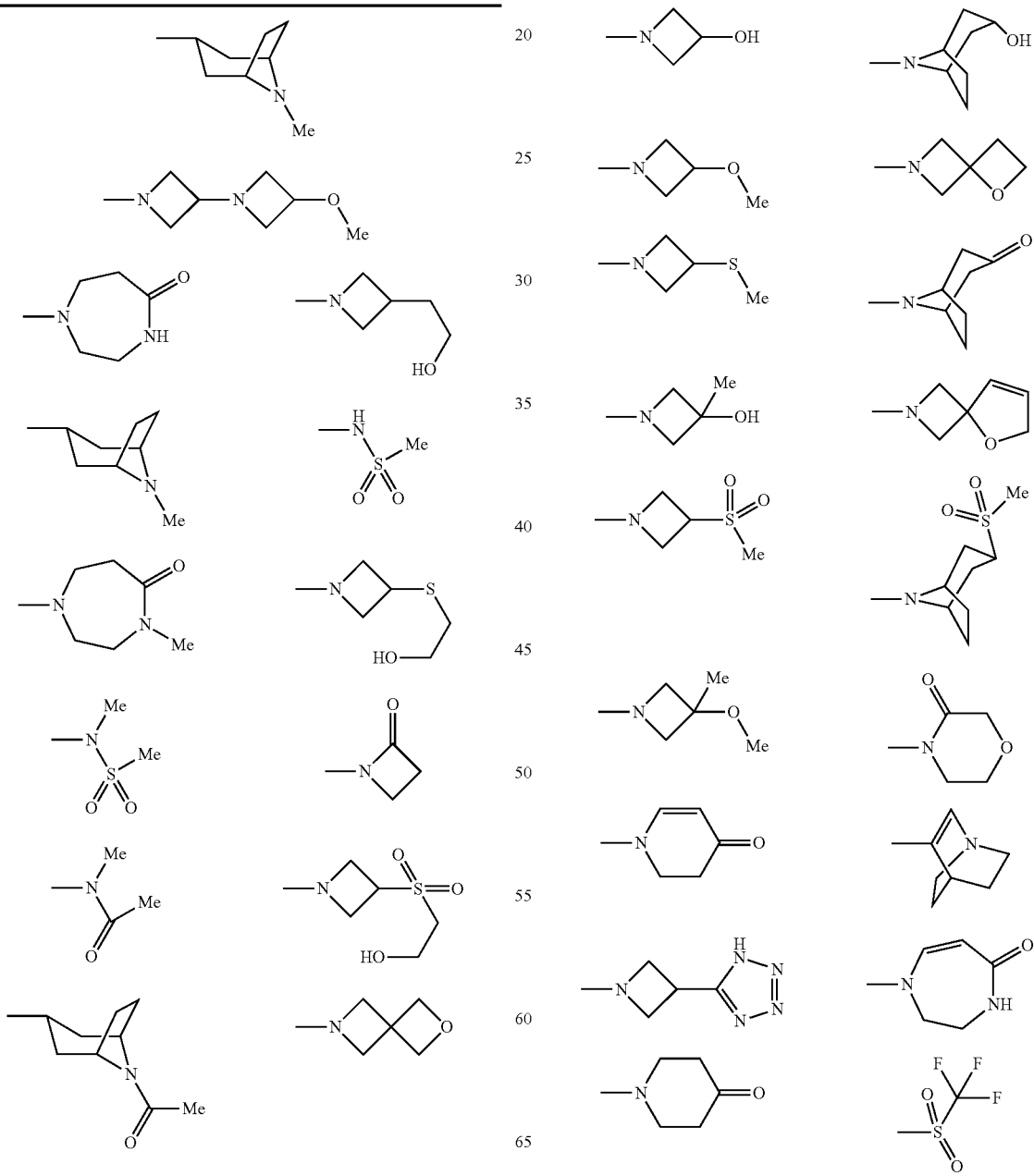

| 563 | 564 |
|---|---|
| -continued | -continued |
| 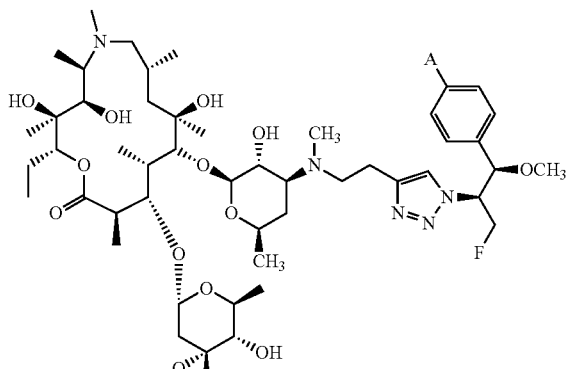 | 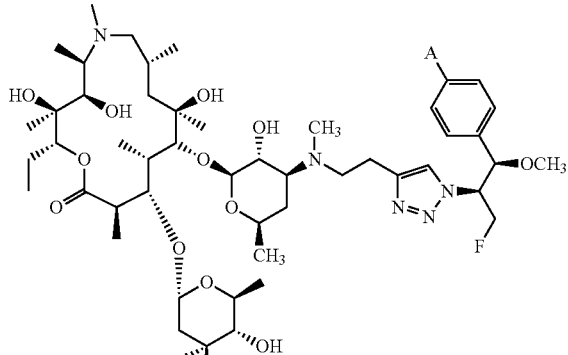 |
| A Groups. Connection is to bond on left. | A Groups. Connection is to bond on left. |
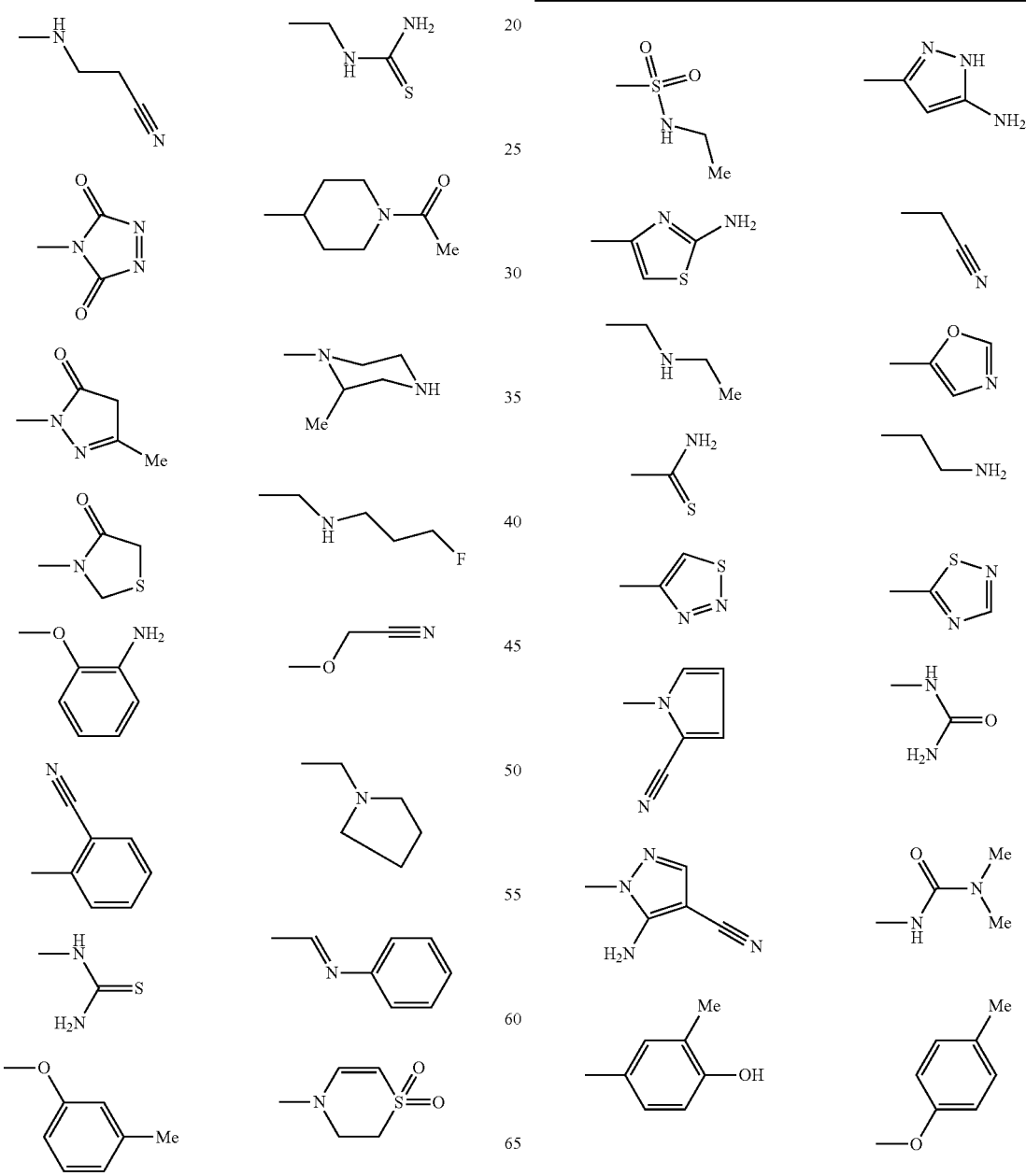

565 -continued | 566 -continued
---|---
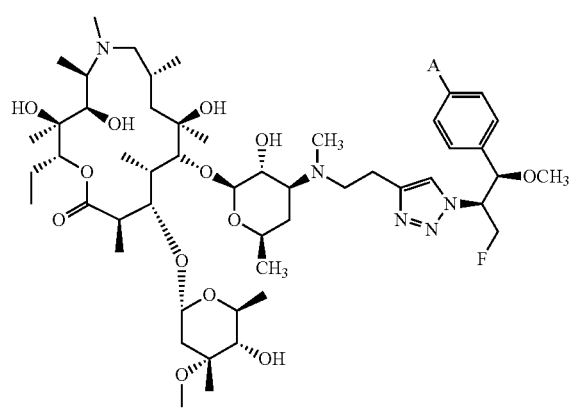
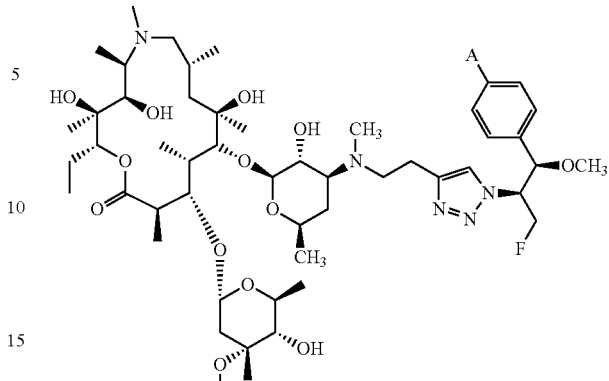
A Groups. Connection is to bond on left.
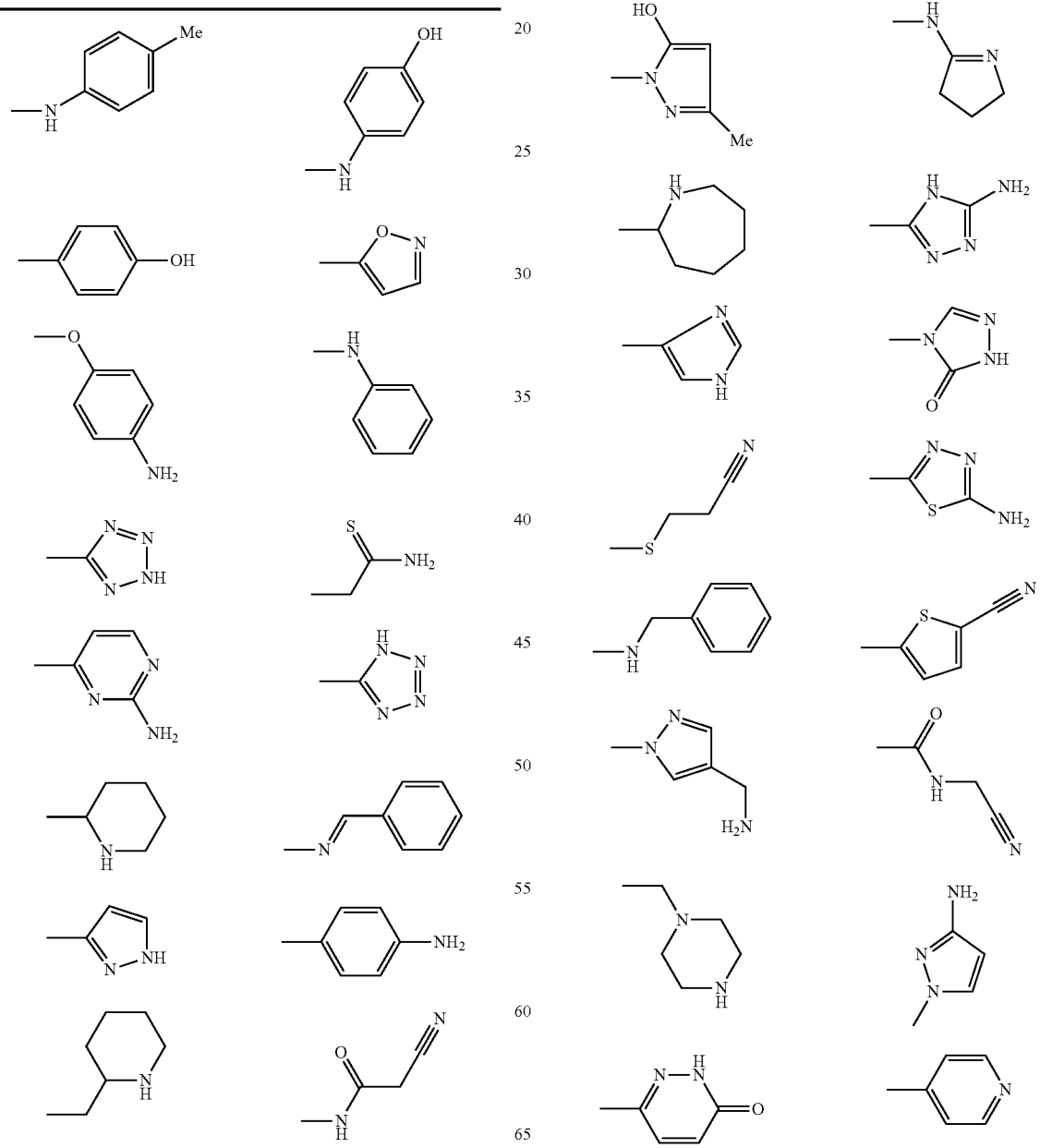

567 -continued | 568 -continued
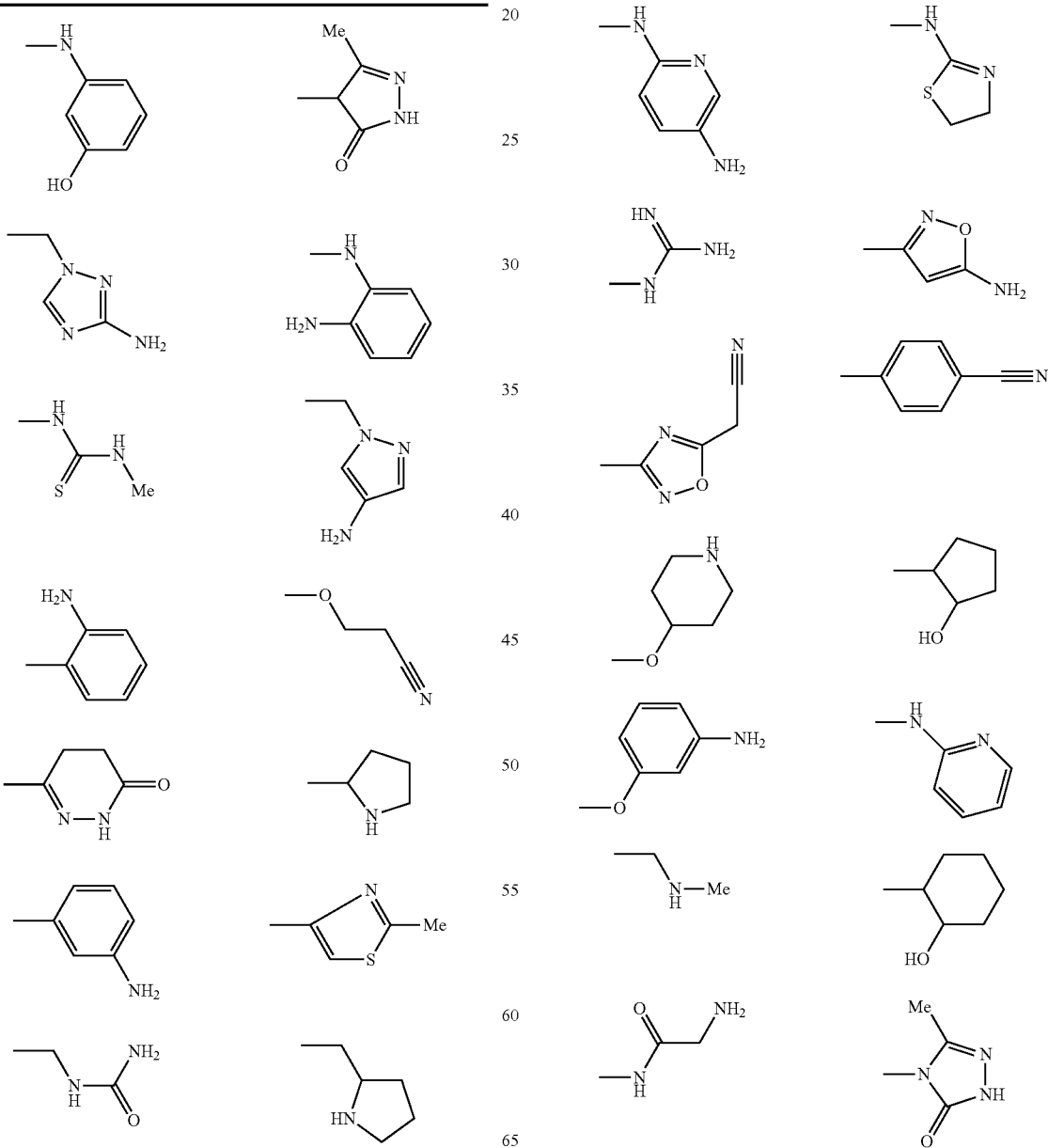
A Groups. Connection is to bond on left.

569
-continued
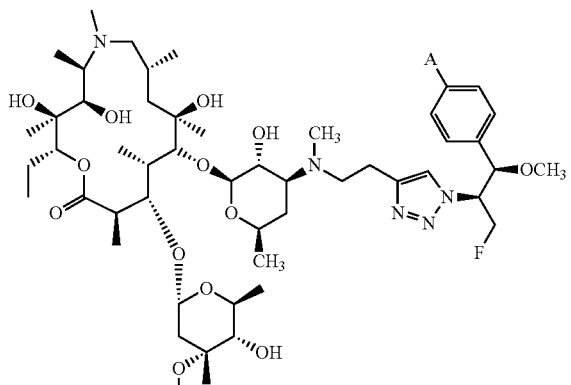
A Groups. Connection is to bond on left.
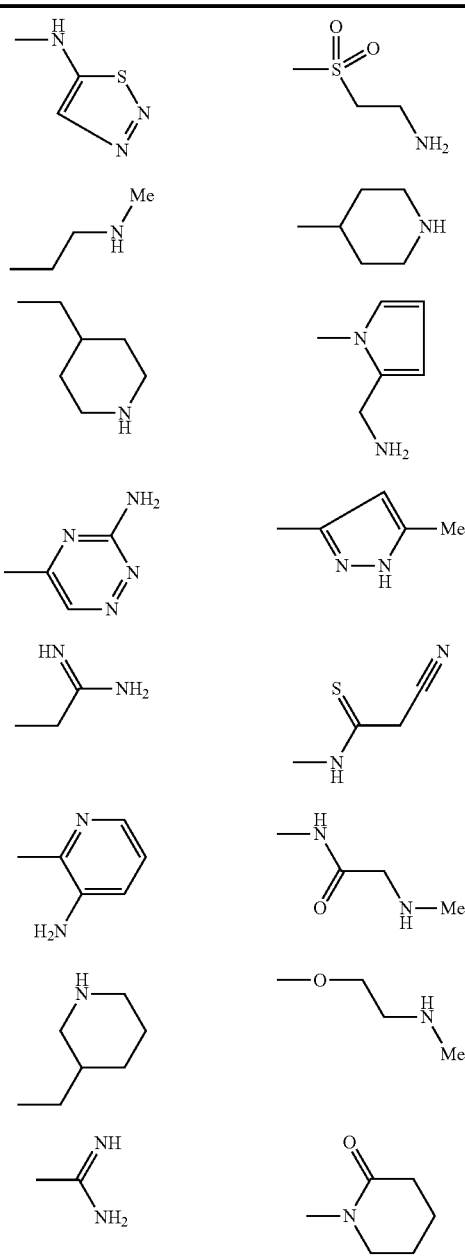
570
-continued
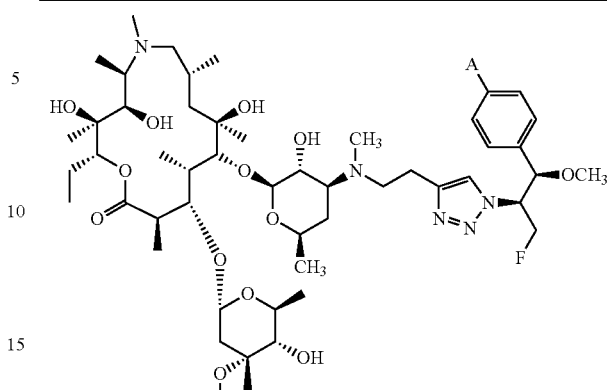
A Groups. Connection is to bond on left.
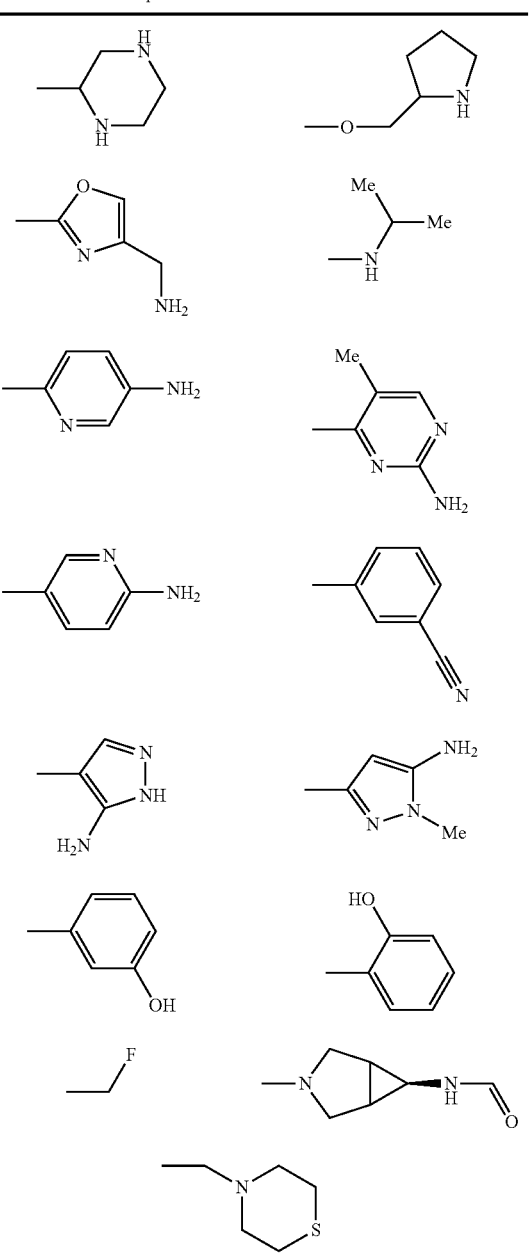

571
-continued
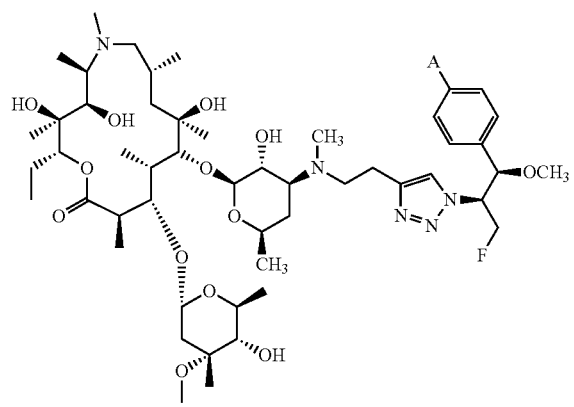
A Groups. Connection is to bond on left.
572
-continued
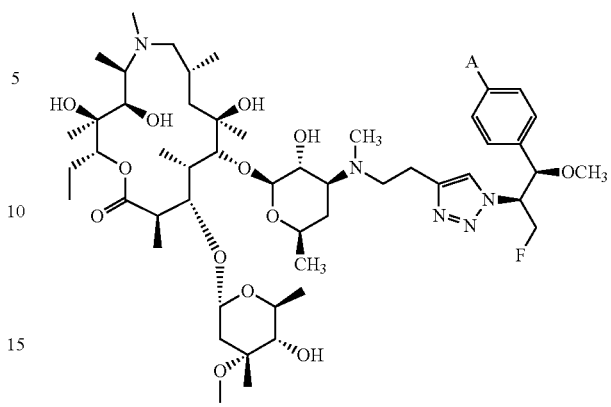
A Groups. Connection is to bond on left.
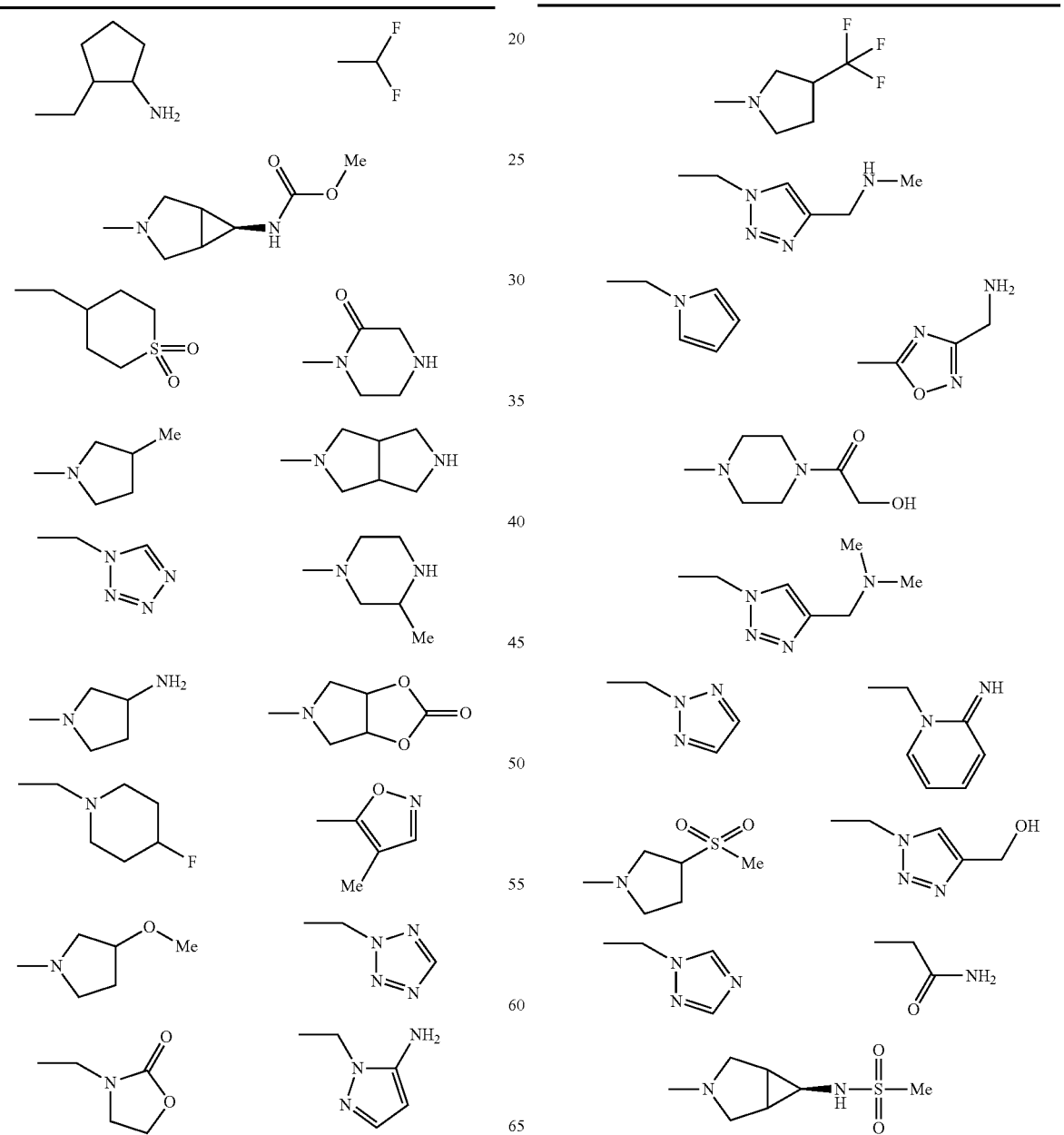

573 -continued
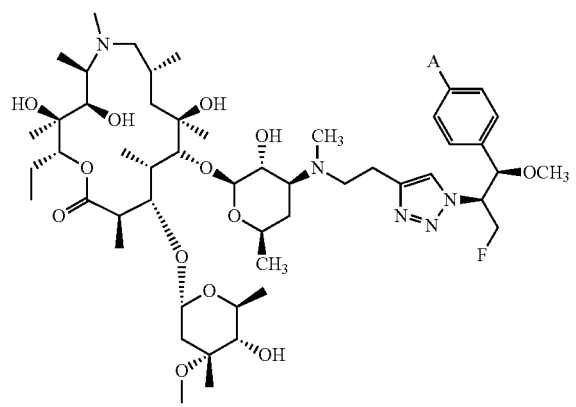
574 -continued
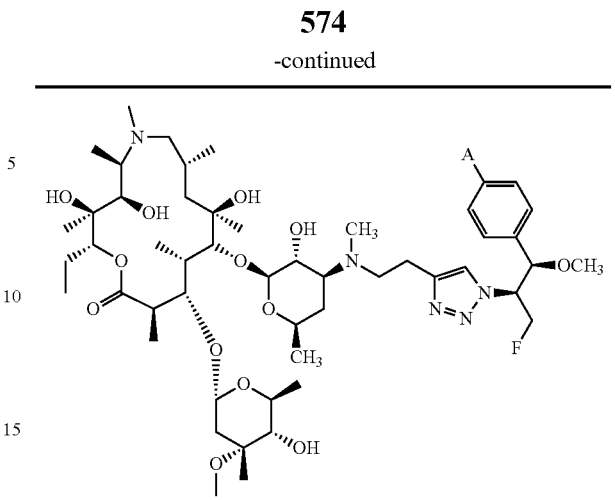
A Groups. Connection is to bond on left.
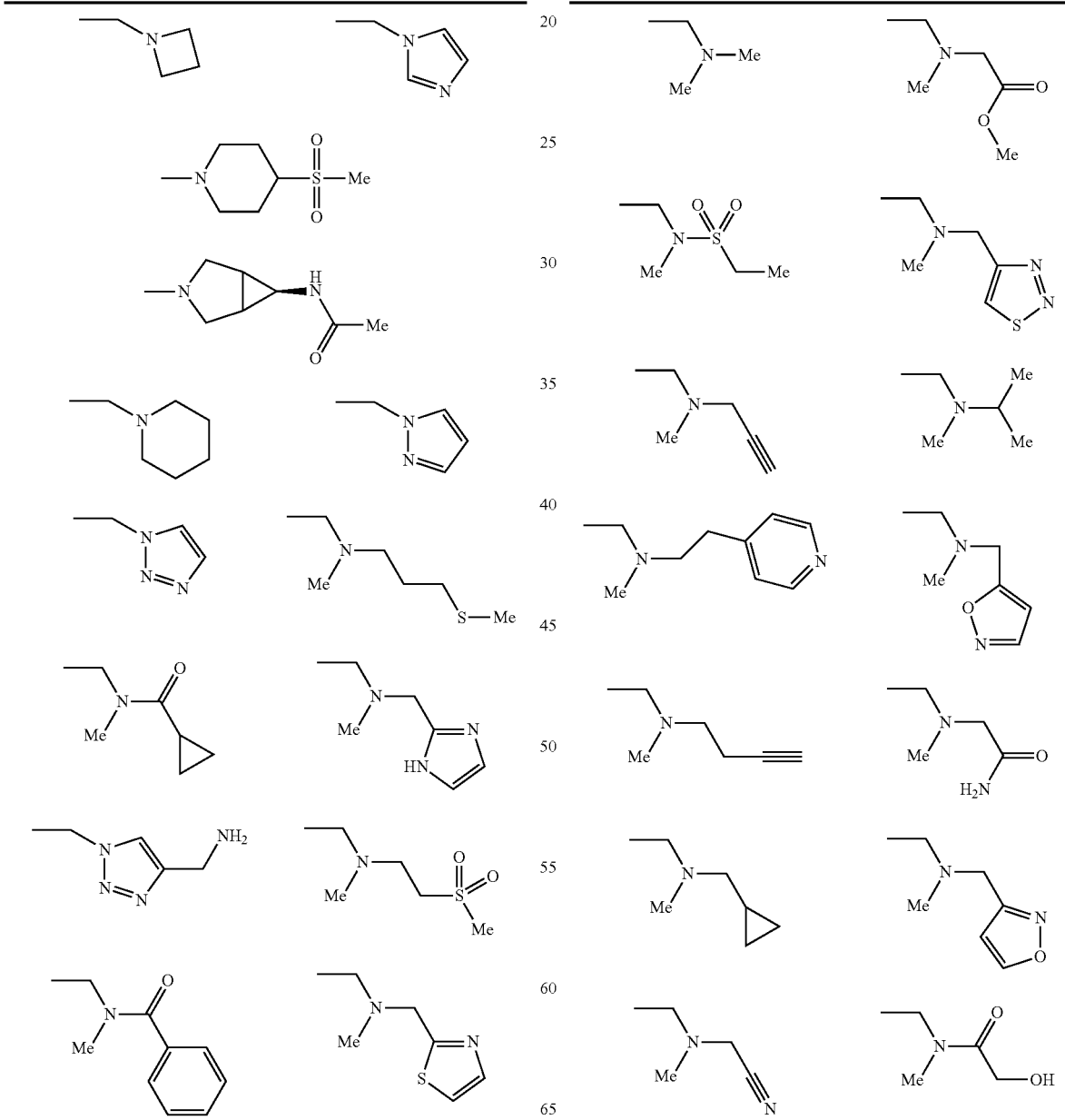

575
-continued
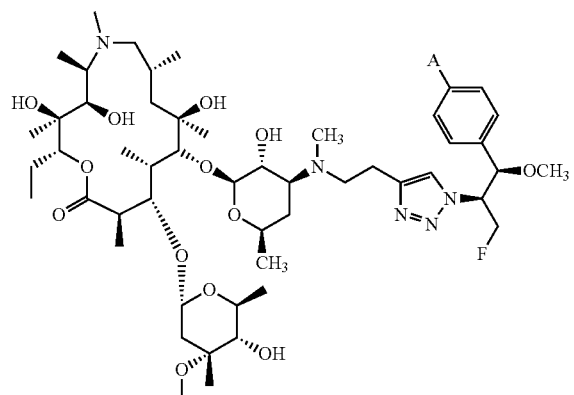
A Groups. Connection is to bond on left.
576
-continued
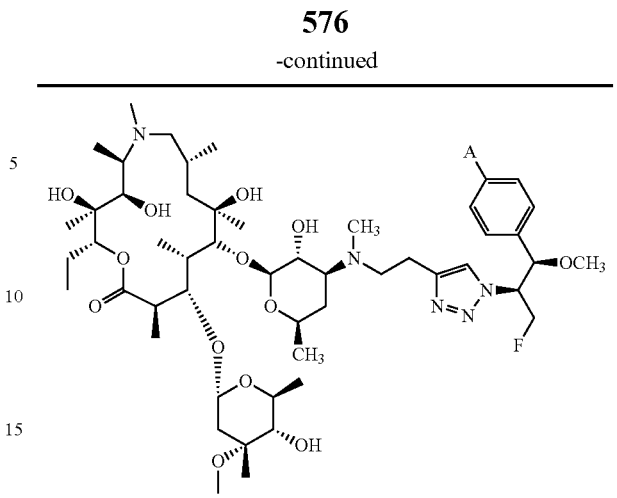
A Groups. Connection is to bond on left.
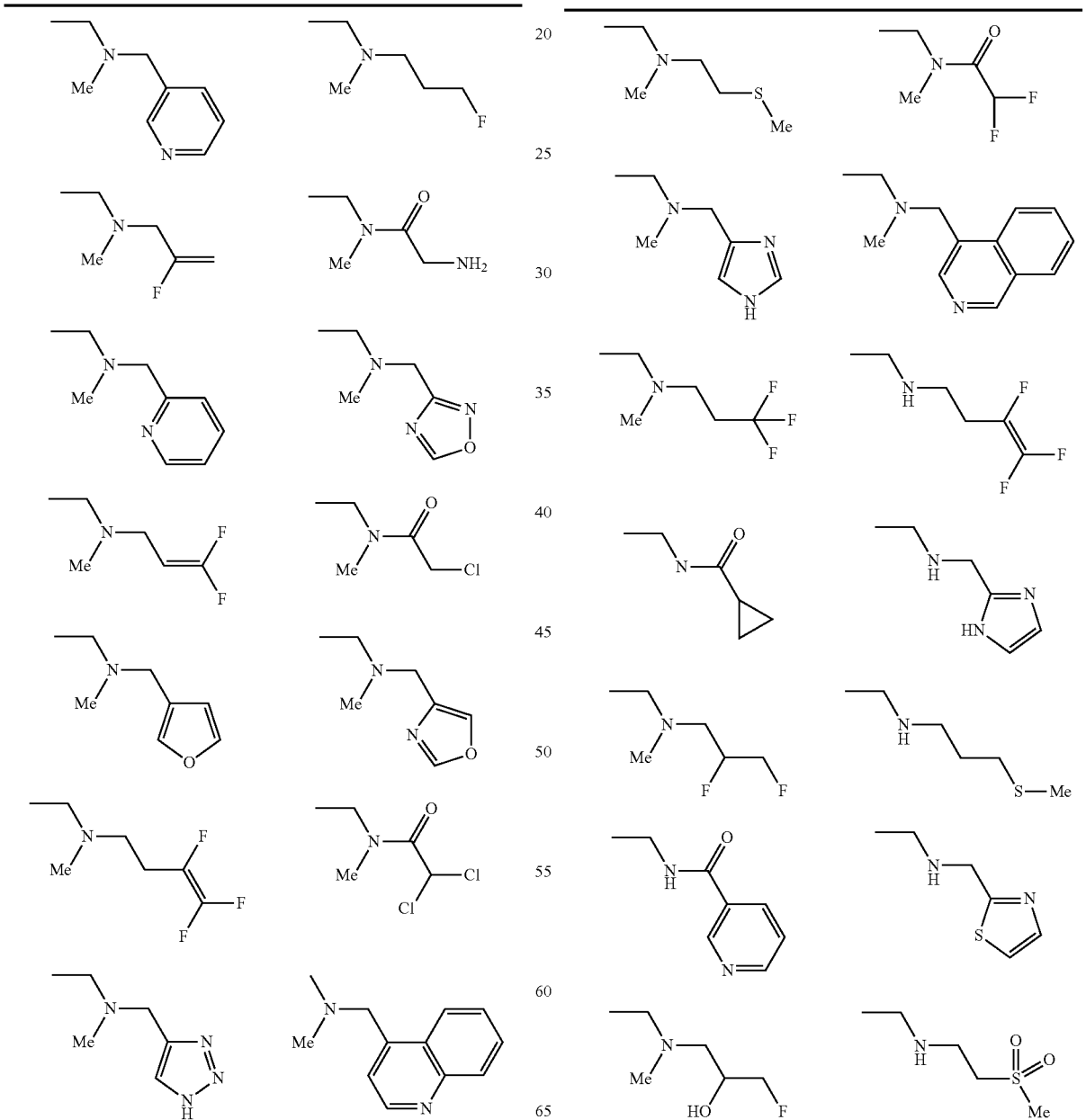

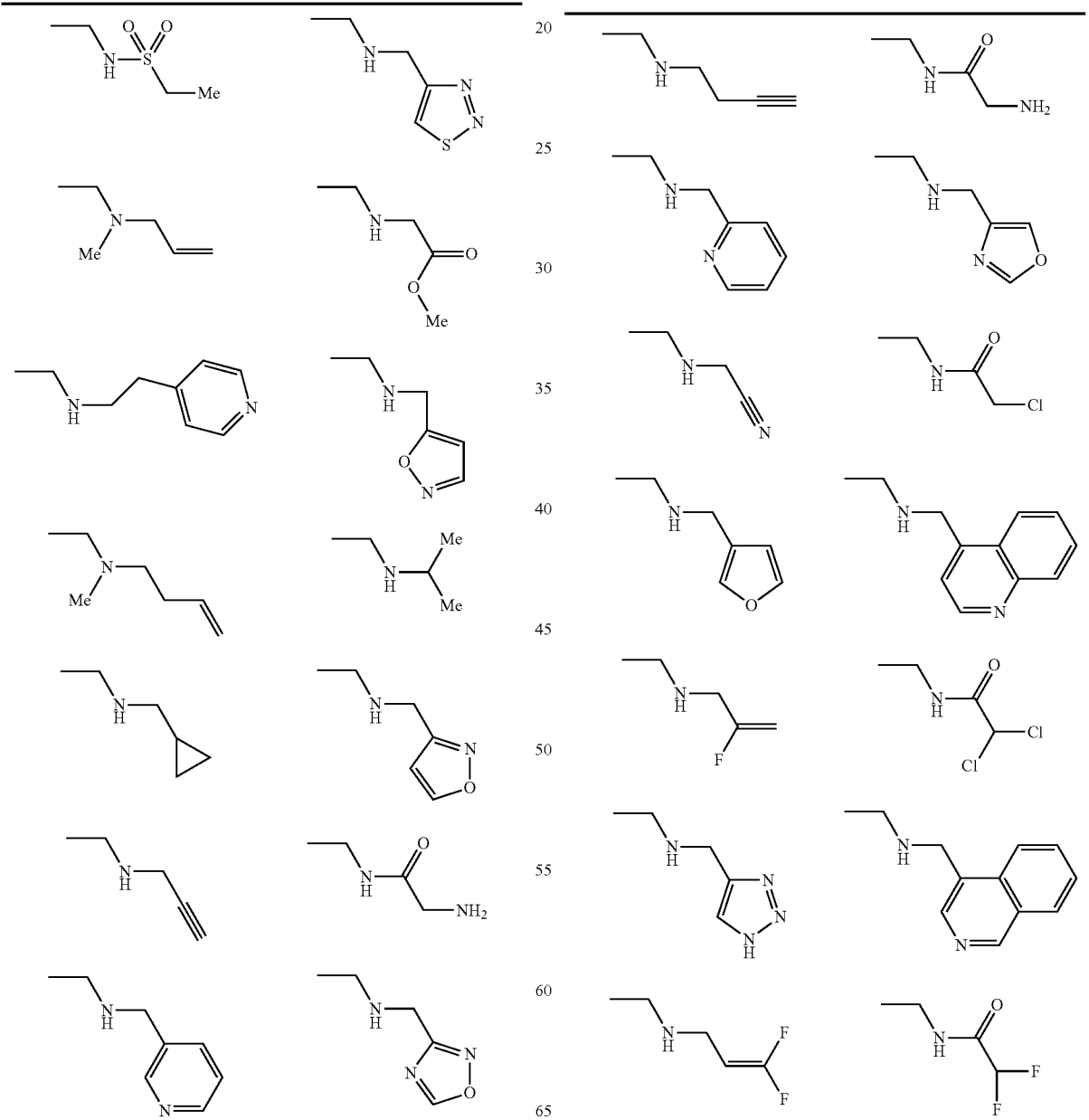

579
580
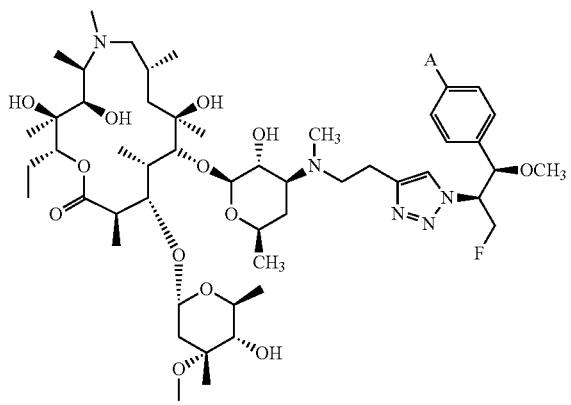
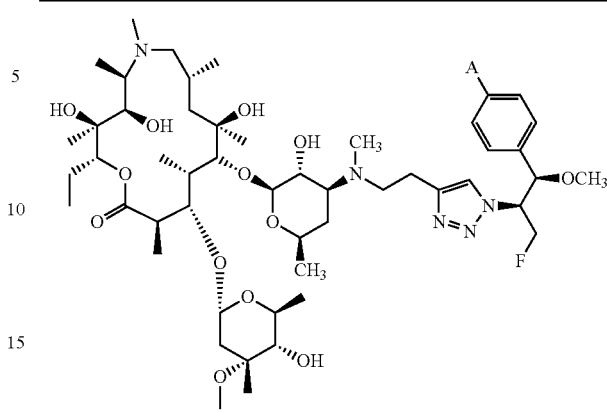
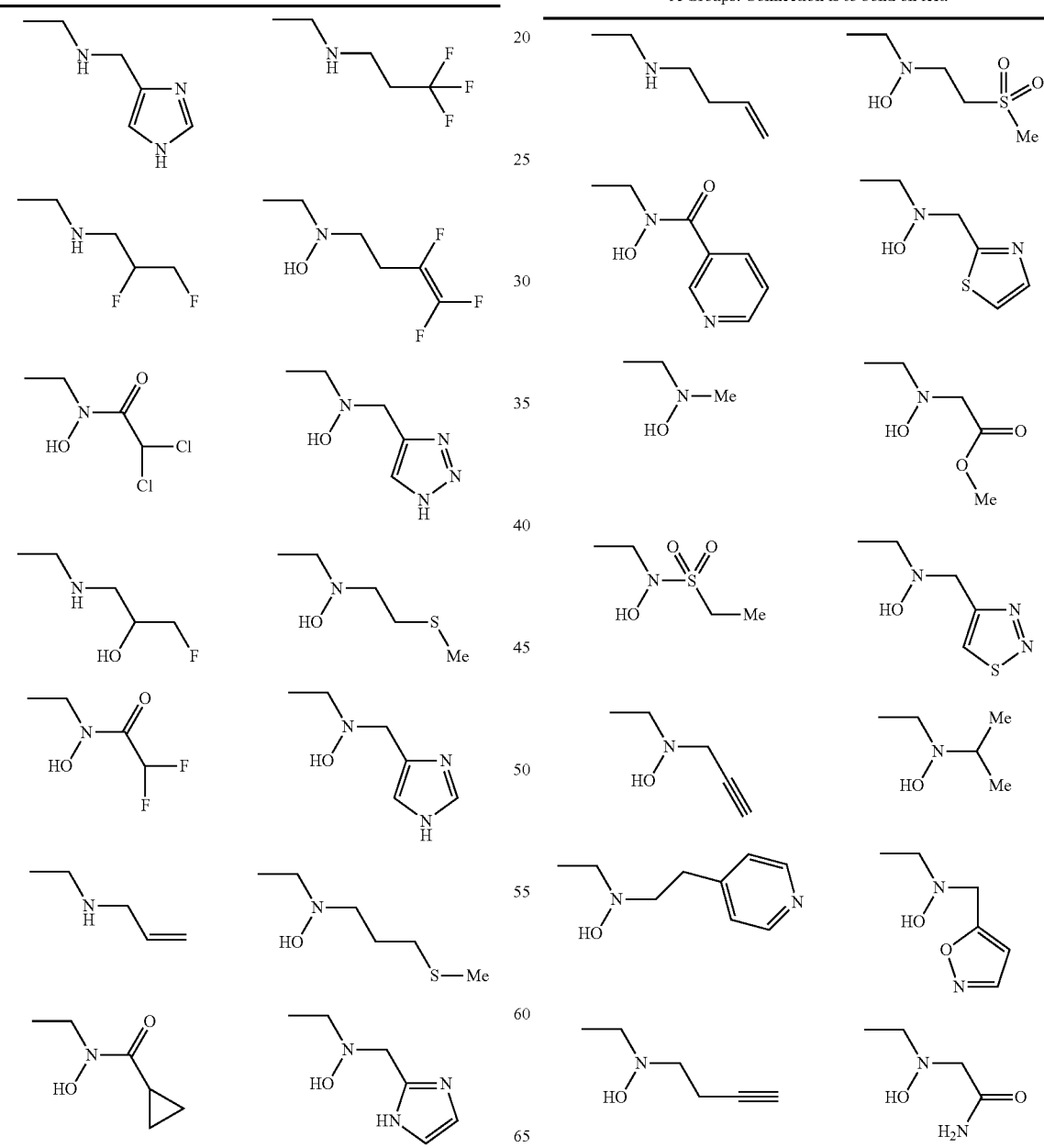
A Groups. Connection is to bond on left.

581 -continued
582 -continued
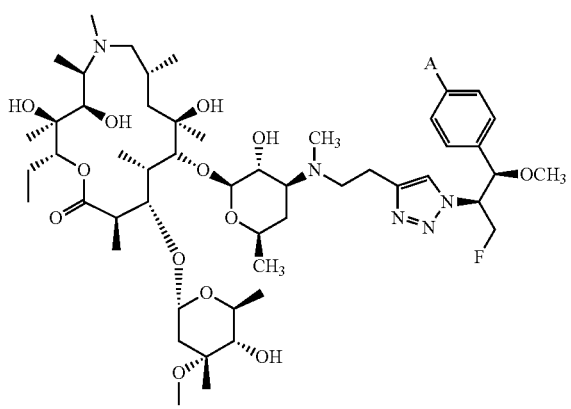
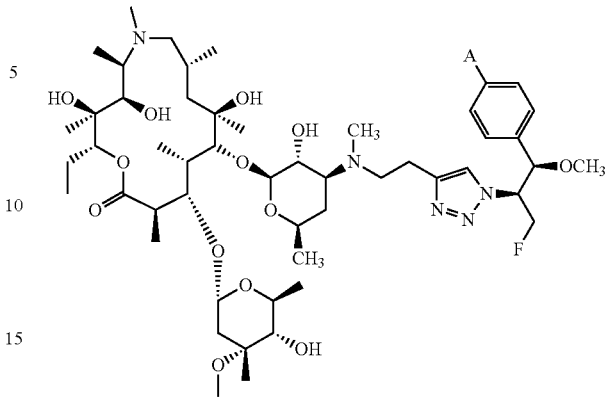
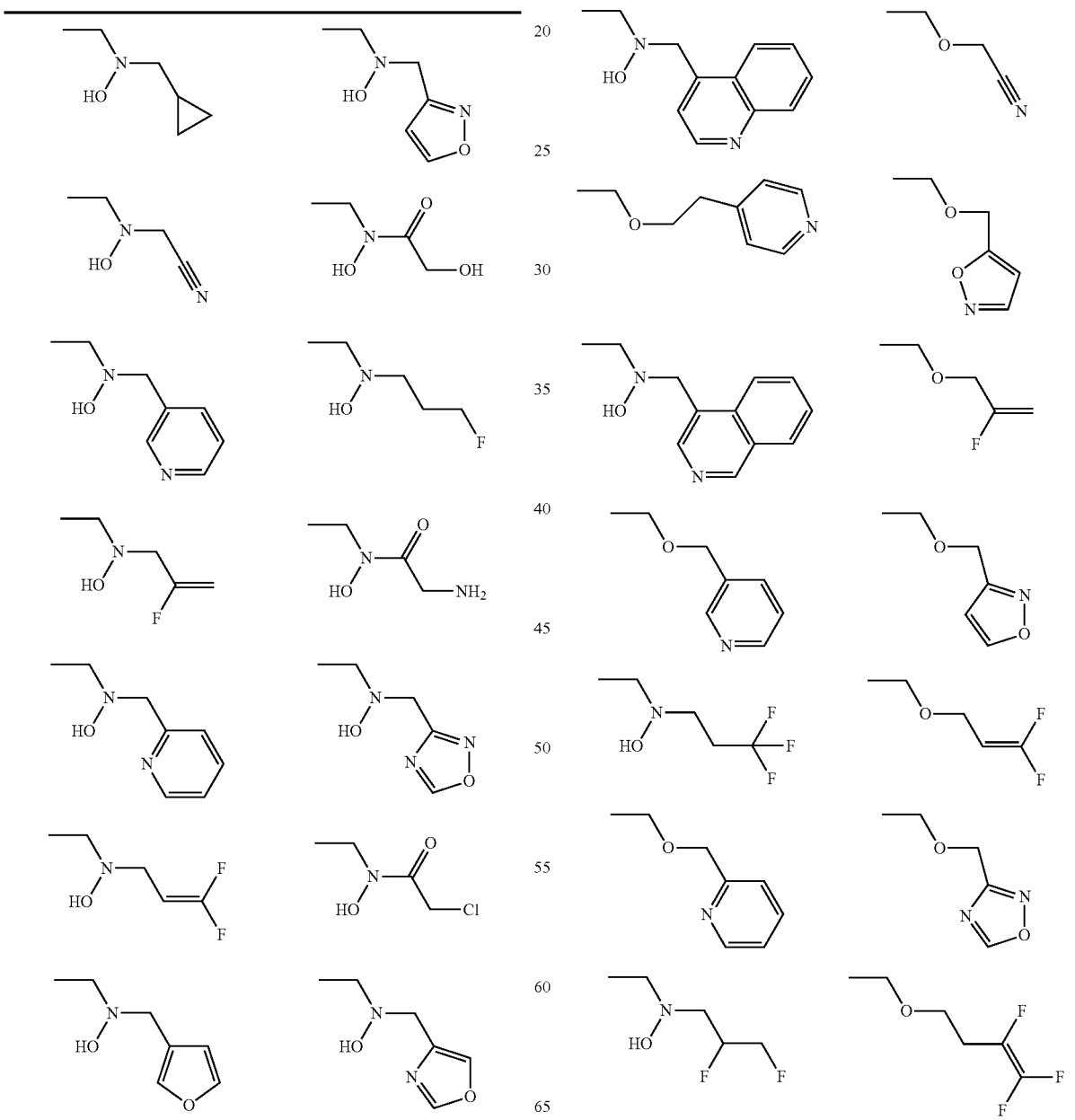

| 583 | 584 |
|---|---|
| -continued | -continued |
| 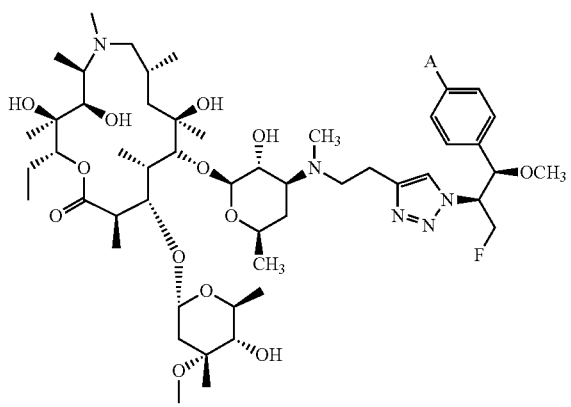 | 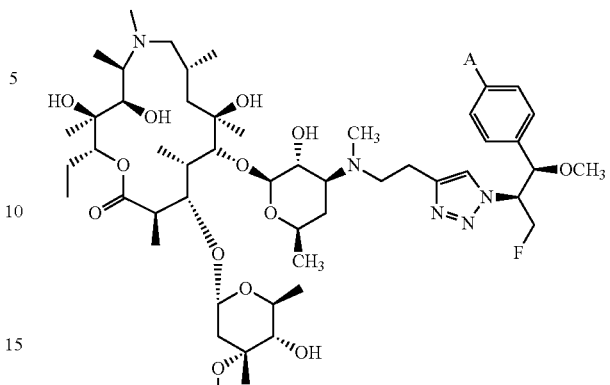 |
| A Groups. Connection is to bond on left. | A Groups. Connection is to bond on left. |
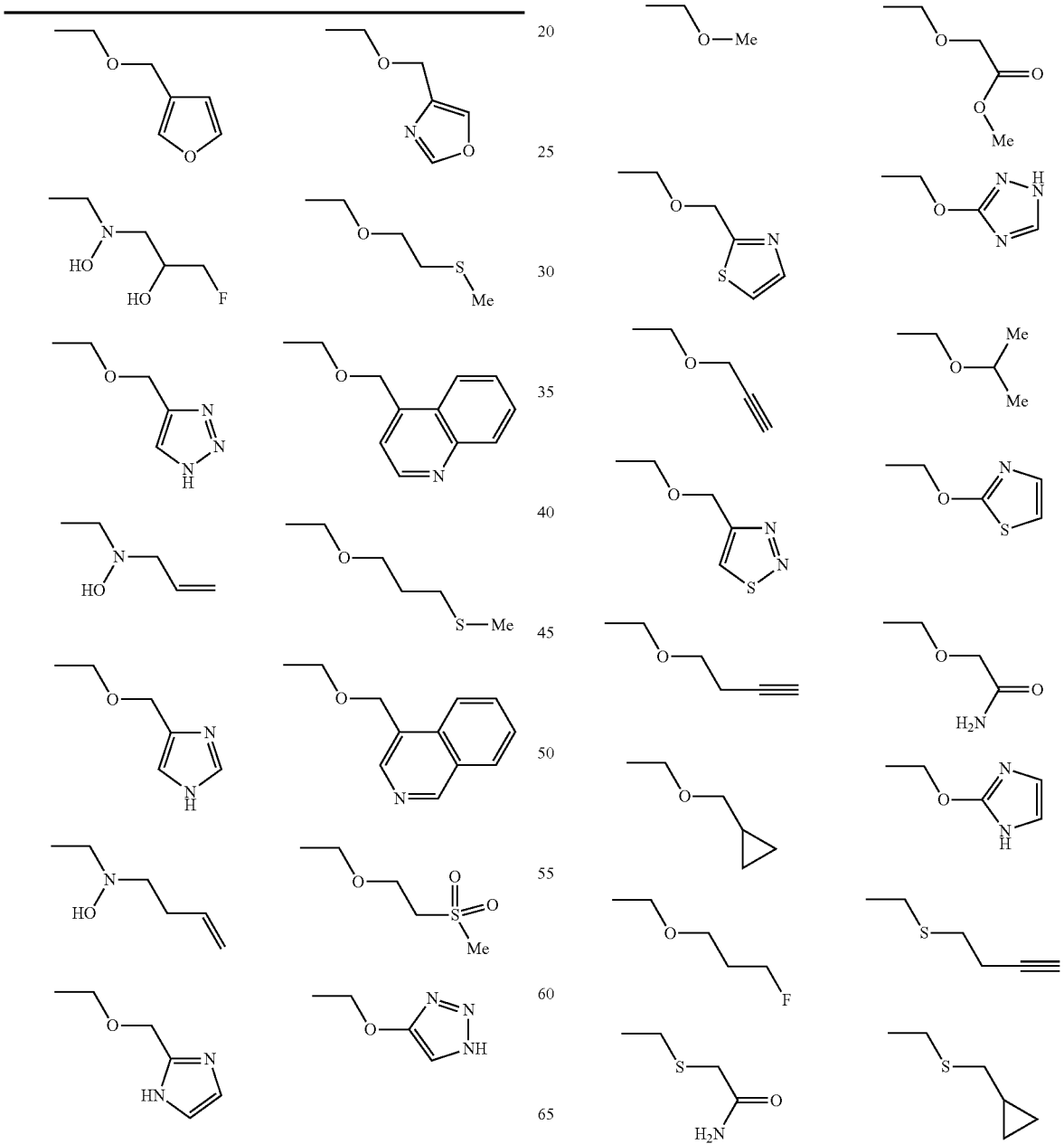

585
-continued
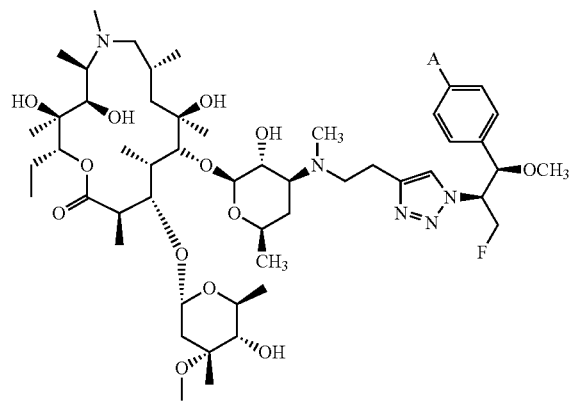
A Groups. Connection is to bond on left.
586
-continued
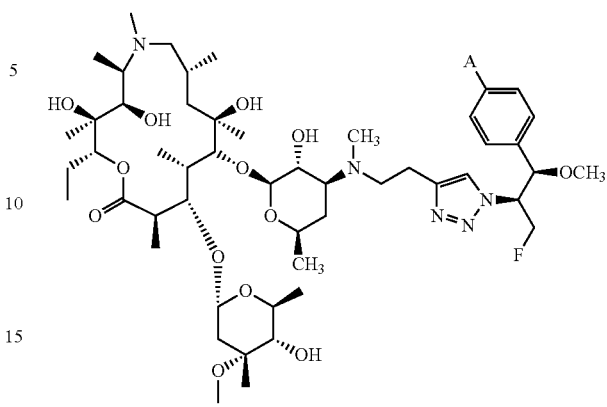
A Groups. Connection is to bond on left.
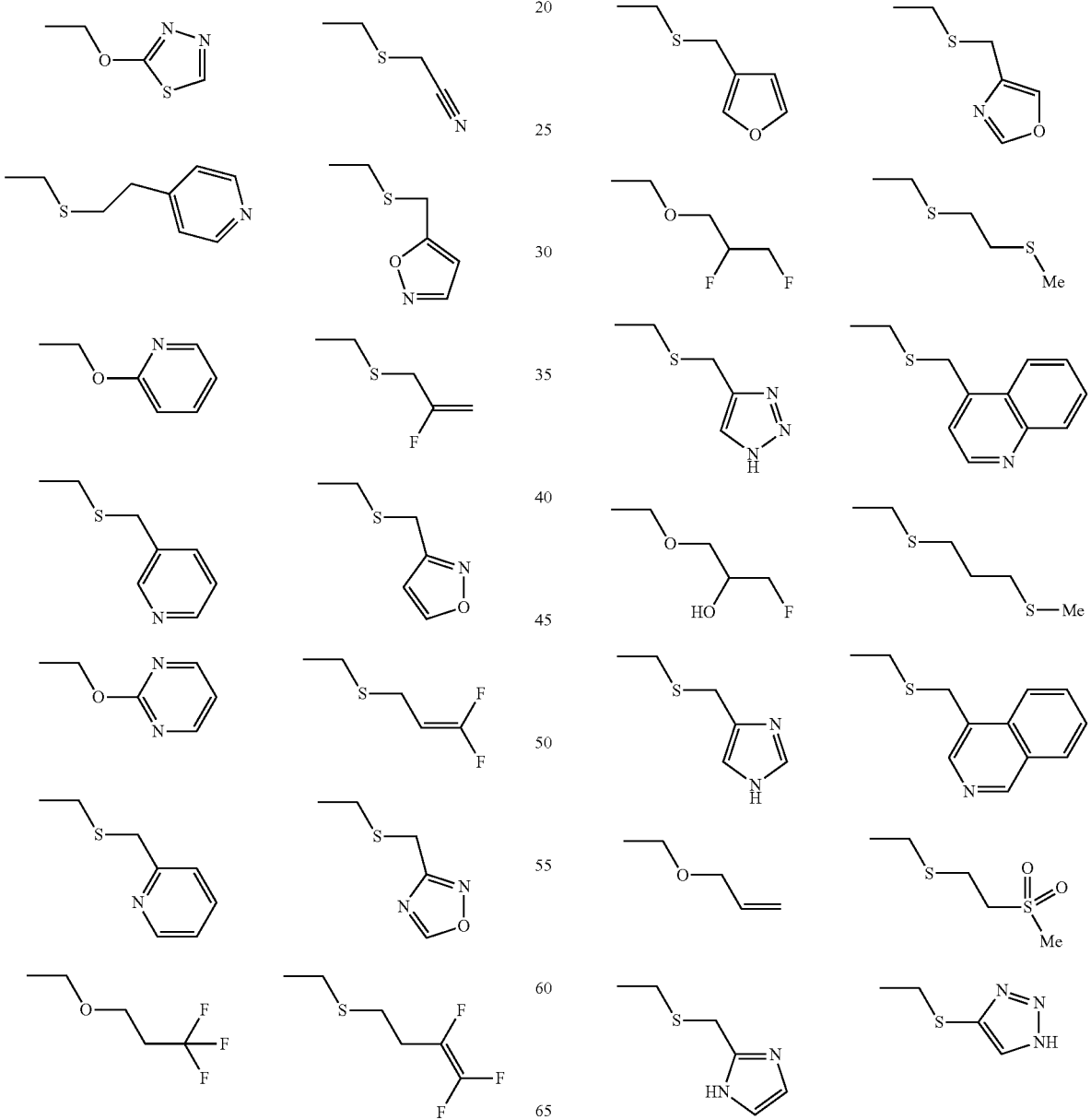

587
-continued
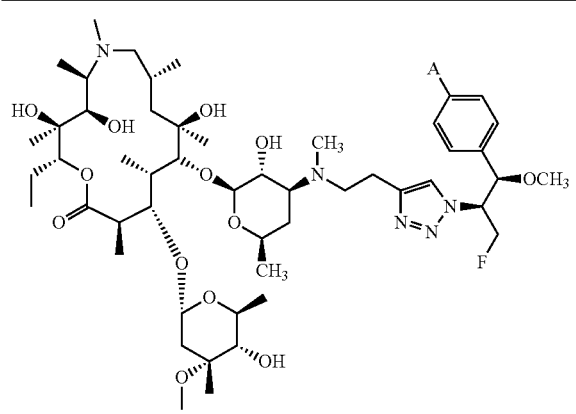
A Groups. Connection is to bond on left.
588
-continued
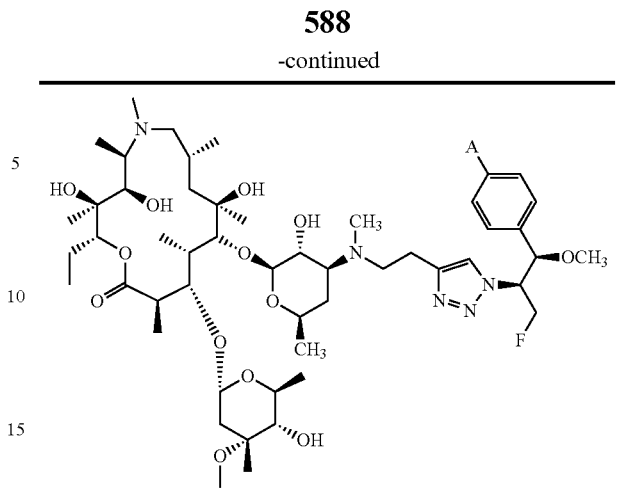
A Groups. Connection is to bond on left.
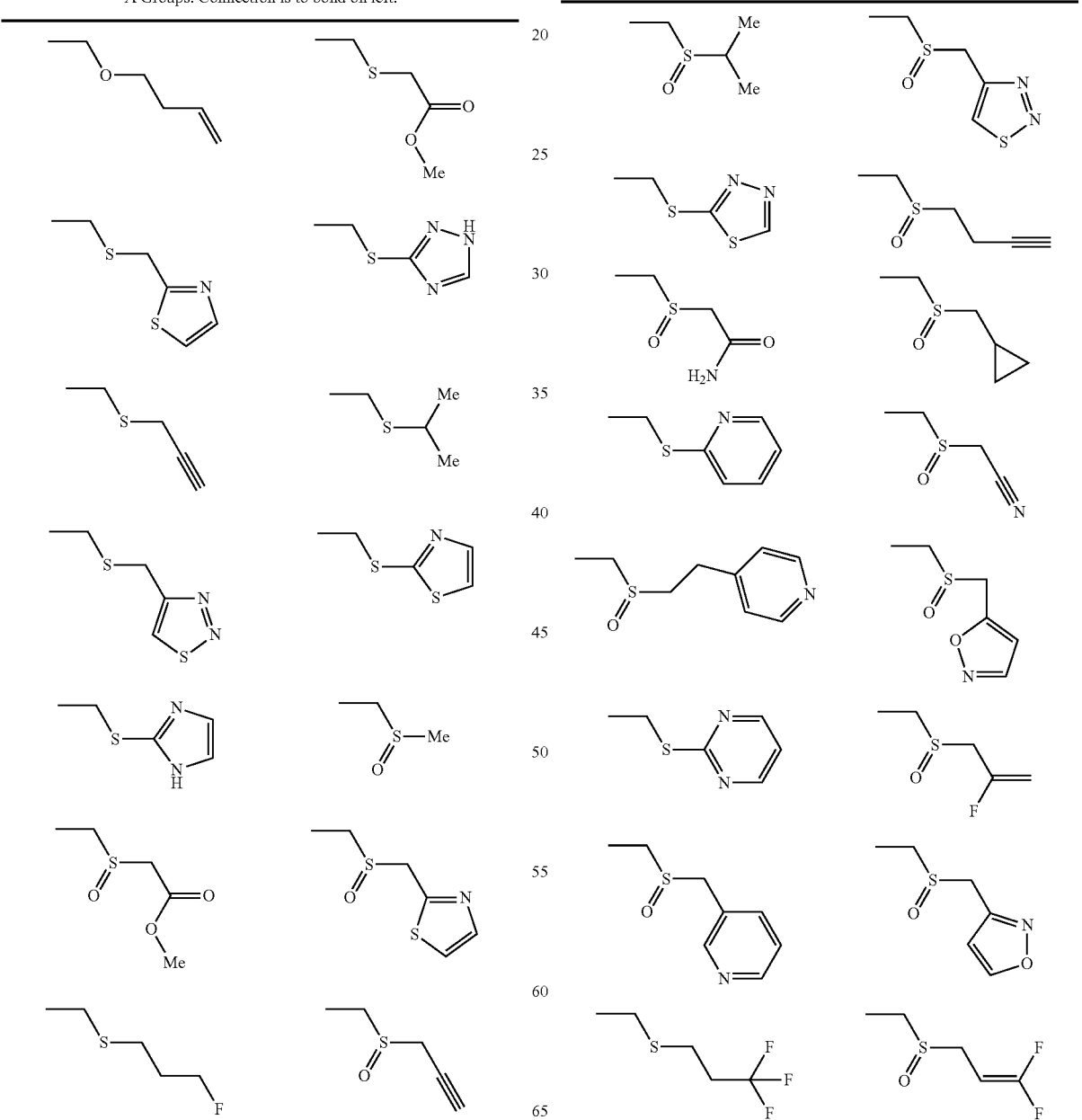

589 -continued
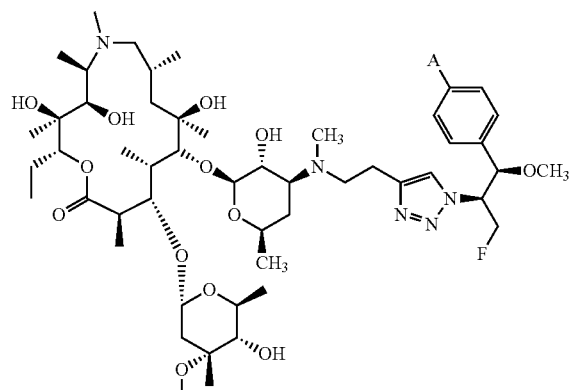
A Groups. Connection is to bond on left.
590 -continued
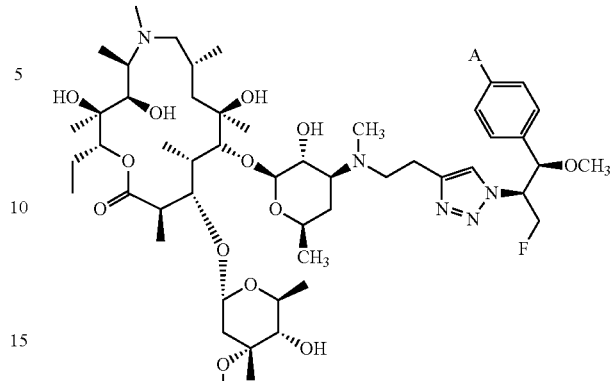
A Groups. Connection is to bond on left.
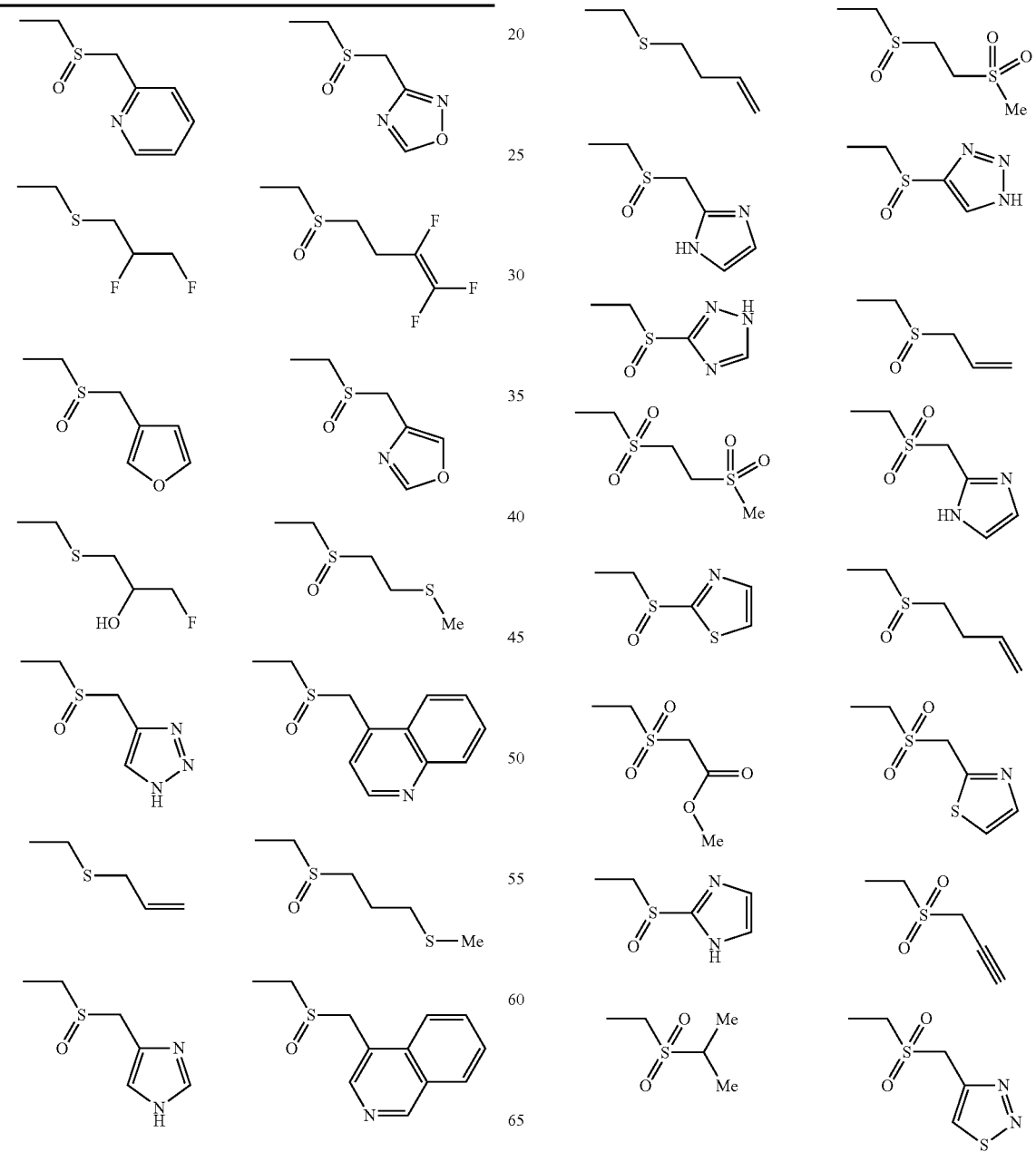

591
-continued
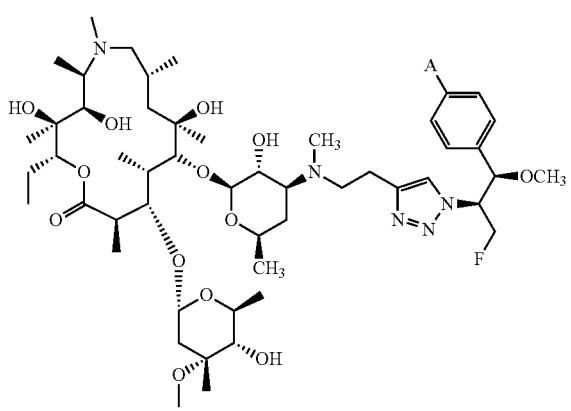
592
-continued
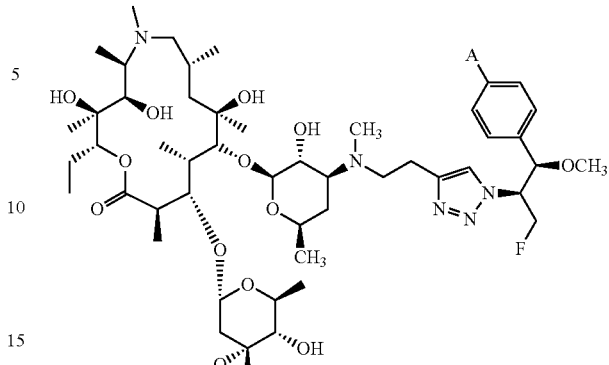
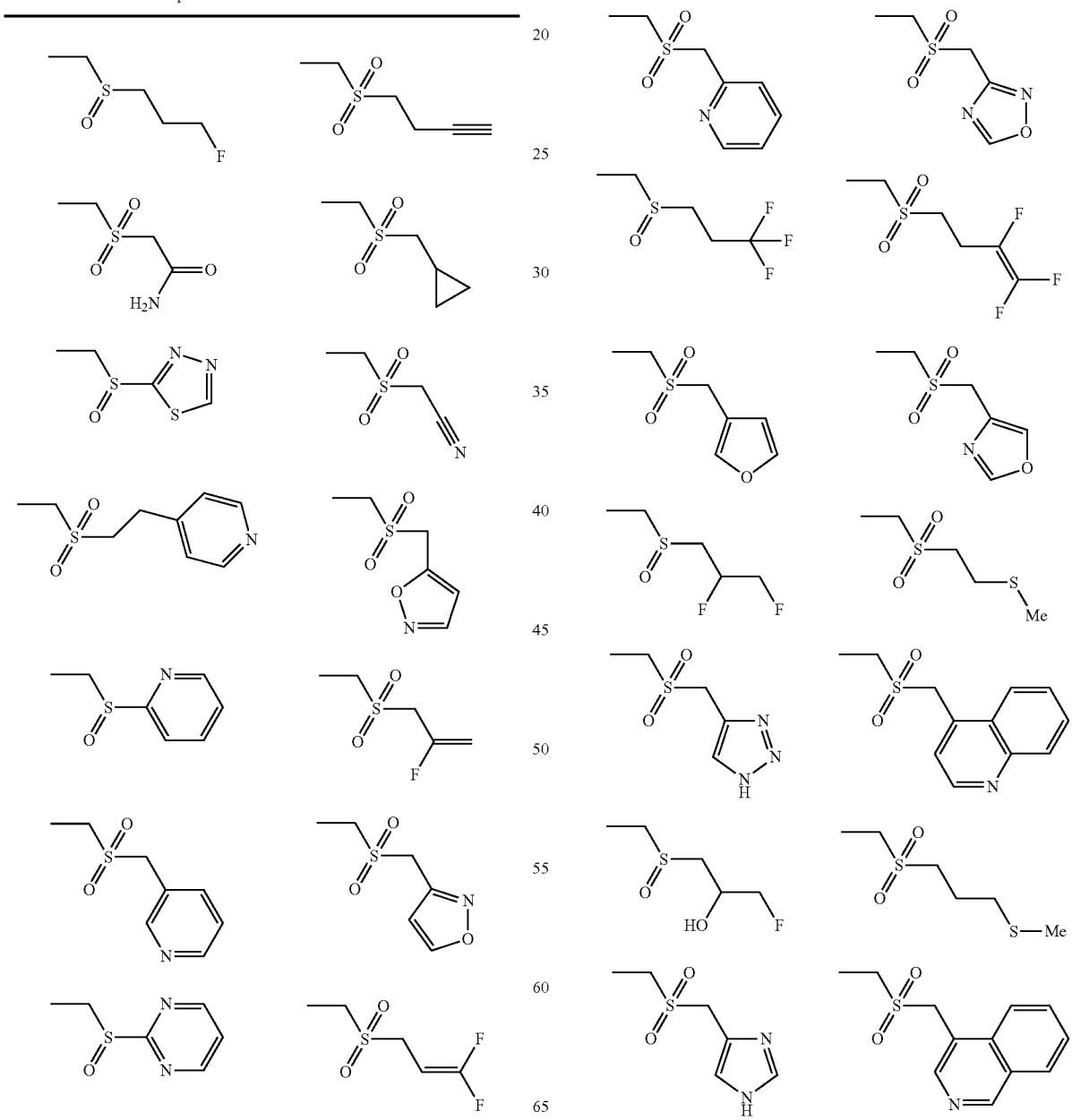

593
-continued
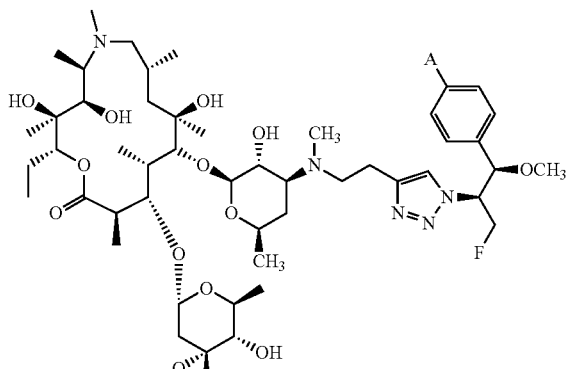
A Groups. Connection is to bond on left.
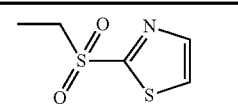 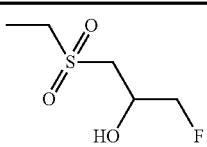
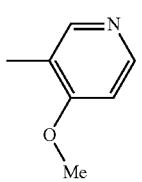 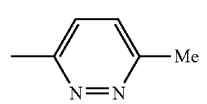
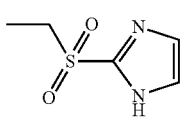 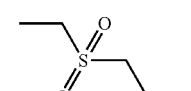
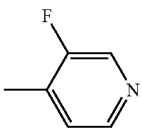 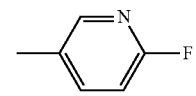
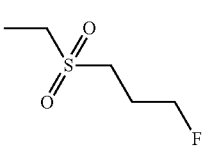 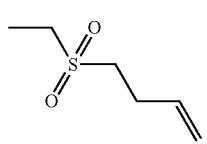
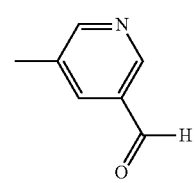 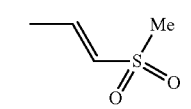
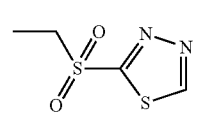 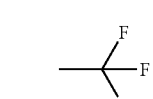
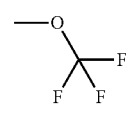 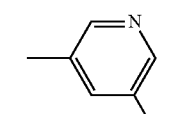
594
-continued
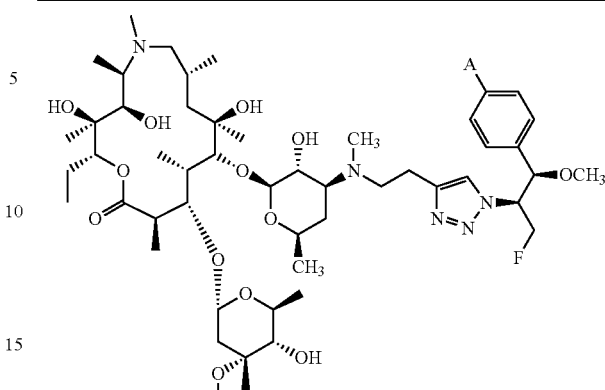
A Groups. Connection is to bond on left.
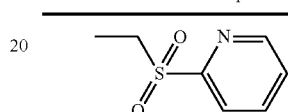
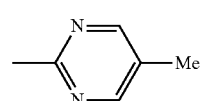
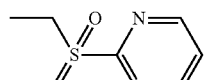 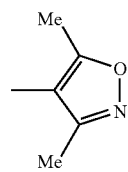
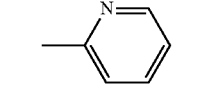 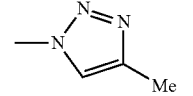
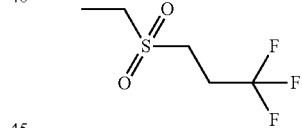 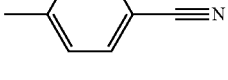
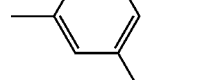 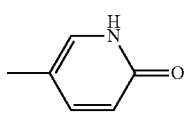
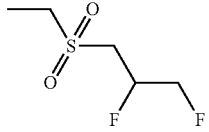 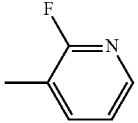
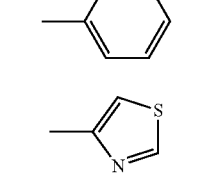 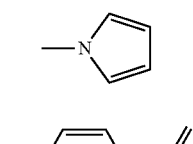

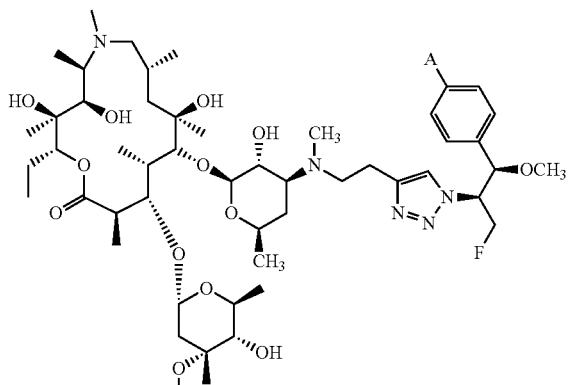
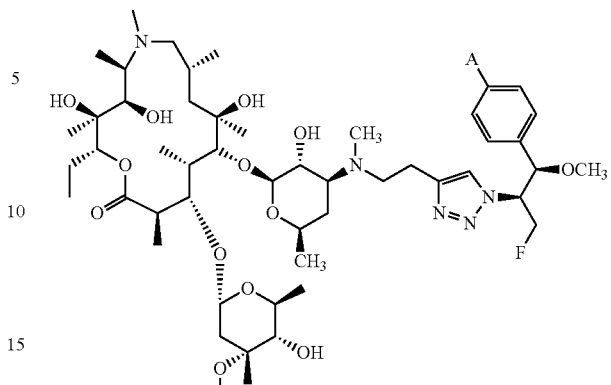
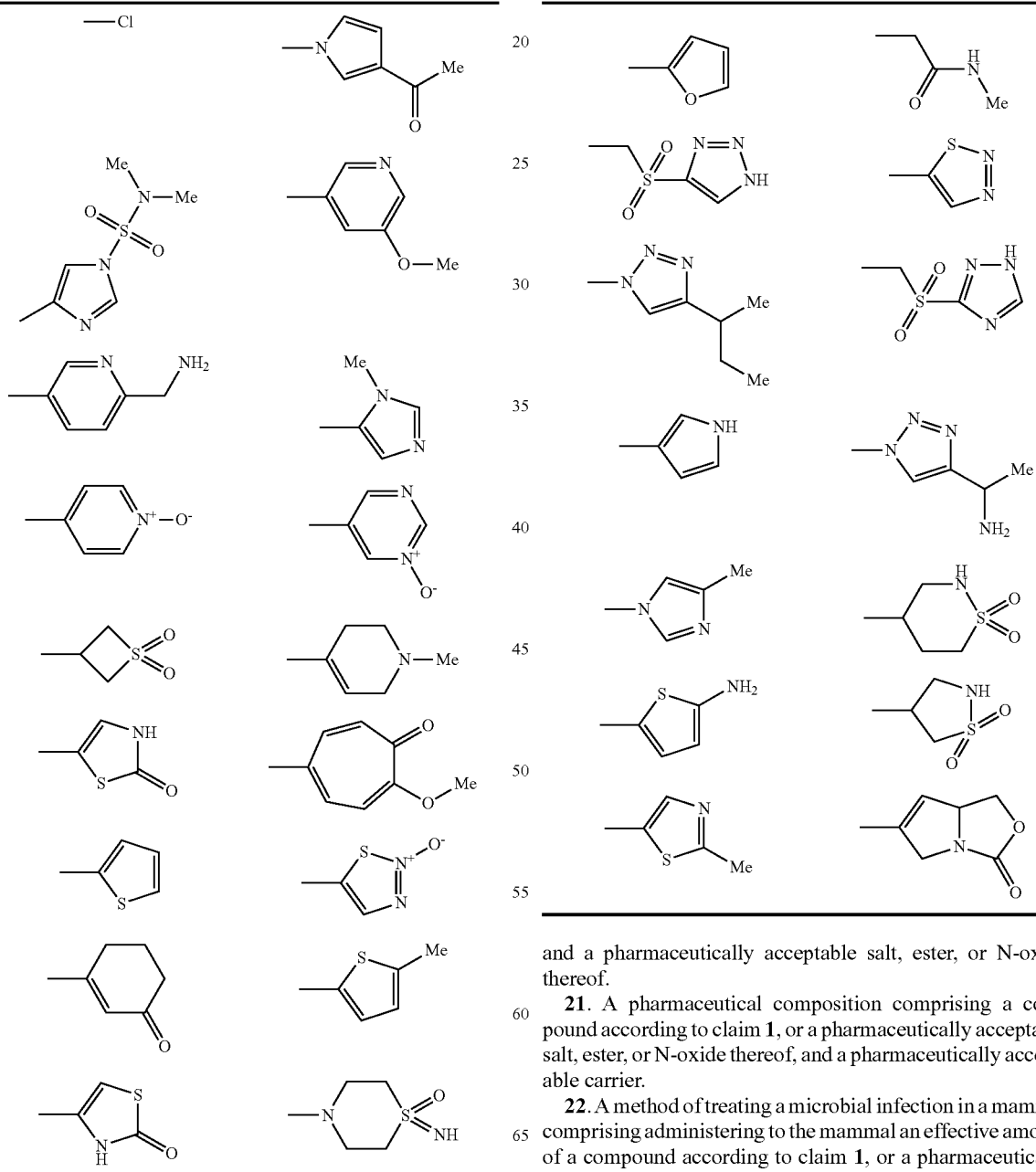

and a pharmaceutically acceptable salt, ester, or N-oxide thereof.

21. A pharmaceutical composition comprising a compound according to claim 1, or a pharmaceutically acceptable salt, ester, or N-oxide thereof, and a pharmaceutically acceptable carrier.

22. A method of treating a microbial infection in a mammal comprising administering to the mammal an effective amount of a compound according to claim 1, or a pharmaceutically acceptable salt, ester, or N-oxide thereof.

23. The method according to claim 22 wherein the compound is administered orally, parenterally, or topically.

24. A medical device containing a compound, or a pharmaceutically acceptable salt, ester, or N-oxide thereof, according to claim 1.

25. The medical device according to claim 24, wherein the device is a stent.

* * * * *